(12) United States Patent
Bladh et al.

(10) Patent No.: US 8,163,724 B2
(45) Date of Patent: Apr. 24, 2012

(54) GLUCOCORTICOSTEROIDS, PROCESSES FOR THEIR PREPARATION, PHARMACEUTICAL COMPOSITIONS CONTAINING THEM AND THEIR USE IN THERAPY

(75) Inventors: Håkan Bladh, Lund (SE); Frank Burkamp, Lund (SE); Balint Gabos, Lund (SE); Peter Hansen, Lund (SE); Svetlana Ivanova, Lund (SE); Karolina Lawitz, Lund (SE)

(73) Assignee: AstraZeneca AB, Sodertalje (SE)

( * ) Notice: Subject to any disclaimer, the term of this patent is extended or adjusted under 35 U.S.C. 154(b) by 524 days.

(21) Appl. No.: 12/245,275

(22) Filed: Oct. 3, 2008

(65) Prior Publication Data

US 2009/0286835 A1 Nov. 19, 2009

Related U.S. Application Data

(60) Provisional application No. 60/977,416, filed on Oct. 4, 2007.

(51) Int. Cl.
*A61K 31/58* (2006.01)
*C07J 71/00* (2006.01)
(52) U.S. Cl. .......................................... 514/176; 540/52
(58) Field of Classification Search .................... 540/52; 514/176
See application file for complete search history.

(56) References Cited

U.S. PATENT DOCUMENTS

| | | | |
|---|---|---|---|
| 3,072,639 A | 1/1963 | Hirschmann et al. | |
| 3,129,218 A | 4/1964 | Fried et al. | |
| 3,364,203 A | 1/1968 | Beard et al. | |
| 3,471,477 A | 10/1969 | Fried | |
| 3,704,295 A | 11/1972 | Clinton | |
| 4,242,334 A | 12/1980 | Stache et al. | |
| 4,377,575 A | 3/1983 | Stache et al. | |
| 4,820,700 A | 4/1989 | Brattsand et al. | |
| 2010/0256103 A1 | 10/2010 | Burkamp et al. | |
| 2010/0256104 A1 | 10/2010 | Burkamp et al. | |
| 2010/0256105 A1 | 10/2010 | Burkamp et al. | |
| 2010/0261690 A1 | 10/2010 | Burkamp et al. | |

FOREIGN PATENT DOCUMENTS

| | | |
|---|---|---|
| DE | 27 27 367 | 6/1977 |
| EP | 0000471 | 2/1979 |
| GB | 933867 | 8/1963 |
| JP | 60-067495 | 4/1985 |
| WO | WO-94/25478 A1 | 11/1994 |
| WO | WO-97/22596 A1 | 6/1997 |
| WO | WO-97/30035 A1 | 8/1997 |
| WO | WO-97/32856 A1 | 9/1997 |
| WO | WO-98/13354 A1 | 4/1998 |
| WO | WO-99/02166 A1 | 1/1999 |
| WO | WO-00/40529 A1 | 7/2000 |
| WO | WO-00/41669 A2 | 7/2000 |
| WO | WO-01/92224 A1 | 12/2001 |
| WO | WO-02/04434 A1 | 1/2002 |
| WO | WO-02/08213 A1 | 1/2002 |
| WO | WO 02/088167 | 11/2002 |
| WO | WO-02/088169 A2 | 11/2002 |
| WO | WO-2004/052912 A1 | 6/2004 |
| WO | WO-2005/028495 A1 | 3/2005 |
| WO | WO-2005/063777 A1 | 7/2005 |
| WO | WO 2006/108572 | 10/2006 |
| WO | WO-2007/054974 A2 | 5/2007 |
| WO | WO-2009/044200 A1 | 4/2009 |
| WO | WO-2009/082342 A1 | 7/2009 |
| WO | WO-2009/108118 A1 | 9/2009 |
| WO | WO-2010/114471 A1 | 10/2010 |
| WO | WO-2010/114472 A1 | 10/2010 |
| WO | WO-2010/114473 A1 | 10/2010 |
| WO | WO-2010/114476 A1 | 10/2010 |

OTHER PUBLICATIONS

Tomlinson, J.E.M., et al., "Efficacy of low and high dose inhaled corticosteroid in smokers versus non-smokers with mild asthma," *Thorax* (2005), vol. 60, pp. 282-287.

Bodor et al. "Novel soft steroids: effects on cell growth in vitro and on wound healing in the mouse" Steroids 56(8):434-439 (1991).

Hirschmann et al. "Synthesis and Structure of Steroidal 4-Pregneno[3,2-c]-pyrazoles. A Novel Class of Potent Anti-Inflammatory Steroids" Journal of American Chemical Society 85(1):120-122 (1963).

Hoyte et al. "Iodinated and Fluorinated Steroid 2'-Aryl-[3,2-c]pyrazoles as Potential Glucocorticoid Receptor Imaging Agents" Steroids 63(11):595-602 (1998).

Hoyte et al. "Synthesis of halogen-substituted pyridyl and pyrimidyl derivatives of [3,2-c]pyrazolo corticosteroids: Strategies for the development of glucocorticoid receptor mediated imaging agents" Journal of Medicinal Chemistry 45(24): 5397-5405 (2002).

Kahn et al. "Microwave-enhanced nucleophilic fluorination in the synthesis of fluoropyridyl derivatives of [3,2-c]pyrazolo-corticosteroids, potential glucocorticoid receptor-mediated imaging agents" Bioorganic & Medicinal Chemistry Letters 16(13): 3454-3458 (2006).

(Continued)

*Primary Examiner* — Barbara P Badio

(57) ABSTRACT

The present invention provides compounds of formula (I)

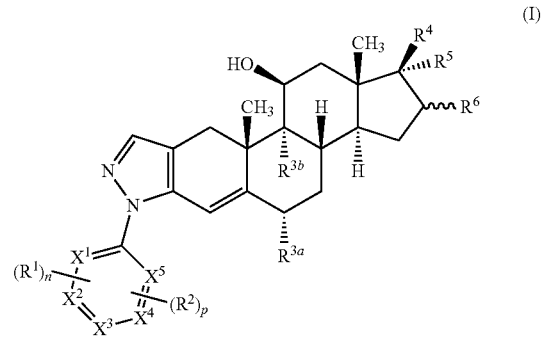

wherein n, p, $R^1$, $R^2$, $X^1$, $X^2$, $X^3$, $X^4$, $X^5$, $R^{3a}$, $R^{3b}$, $R^4$, $R^5$ and $R^6$ are as defined in the specification, a process for their preparation, pharmaceutical compositions containing them and their use in therapy.

19 Claims, No Drawings

OTHER PUBLICATIONS

Loftsson et al. "The pharmacokinetics and transdermal delivery of loteprednol etabonate and related soft steroids" Advance Drug Delivery Reviews 14(2-3):293-299 (1994).
Chemical & Pharmaceutical Bulletin (1986), 34(4), 1613-1618.
Journal of the American Chemical Society (1964), 86(8), 1520-1527.
Journal of Medicinal Chemistry (1975), 18(2), 168-172.
Bulletin de la Société Chimique de France (1969), (4), 1256-1266.
Journal of Medicinal Chemistry (1964), 7(3), 352-355.
Steroids 68 (2003) 177-191.
Merck Index 14th Edition Merck & Co. NJ USA 2006 Monograph No. 0000634.

GLUCOCORTICOSTEROIDS, PROCESSES FOR THEIR PREPARATION, PHARMACEUTICAL COMPOSITIONS CONTAINING THEM AND THEIR USE IN THERAPY

The present invention relates to compounds having glucocorticosteroid receptor agonist activity, processes for their preparation, pharmaceutical compositions containing them and their therapeutic use, particularly for the treatment of inflammatory and allergic conditions.

Glucocorticosteroids (GCs) that have anti-inflammatory properties are known and are widely used for the treatment of diseases such as inflammatory arthritides (e.g. rheumatoid arthritis, ankylosing spondylitis and psoriatic arthropathy), other rheumatoid diseases such as systemic lupus erythematosis, scleroderma, vascutitides including temporal arteritis and polyarteritis nodosa, inflammatory bowel disease such as Crohns disease and ulcerative colitis, lung diseases such as asthma and chronic obstructive airways disease, as well as many other conditions such as polymyalgia rheumatica. GCs have also been used very extensively for their immunosuppressive properties in the prevention and treatment of transplant rejection. Finally GCs have been used for their anti-tumour effects in a number of malignancies.

GCs act via specific glucocorticoid receptors (GR) that are members of the nuclear receptor superfamily. Ligand binding promotes receptor dimerisation, DNA binding, and transcriptional activation. This mechanism of GC action is well defined in vitro and is critical for regulation of the hypothalamic-pituitary-adrenal axis, gluconeogenesis as well as transcription of anti-inflammatory genes such as mitogen-activated protein kinase phosphatase-1 (MKP-1) and secretory leukocyte protease inhibitor (SLPI) in vivo. Ligand-bound receptor is also able to suppress gene transcription in a dimerisation-independent manner by interfering with the activity of transcription factors, such as AP-1 and NFkB, which are critically involved in the inflammatory reaction.

After ligand binding, the GR translocates from the cytoplasm of the cell to the nucleus and binds to glucocorticoid response elements in regulator regions of target genes. The activated GR then recruits co-factors, including the glucocorticoid receptor interacting protein 1 (GRIP-1) and steroid receptor co-activator 1 (SRC1). These accessory proteins bind to the receptor and link the GR with the general transcription machinery to drive transcription of target genes.

Glucocorticoid effects on transcription may be mediated by both the direct binding of activated GR to target DNA, homodimerisation and recruitment of co-activators (known as "transactivation") but also by GR interfering with other transcription factor function, including AP-1 and NFkB, by complexing with these other transcription factors and preventing them from binding to their target genes leading to repression of the genes normally upregulated by AP-1 or NFkB (known as "transrepression"). These two modes of receptor activity are dissociable and negative effects on NFkB activity can be retained in the absence of transactivation. It appears that transrepression is largely responsible for mediating the therapeutically desirable anti-inflammatory activity of the GR. Interestingly, the $IC_{50}$ for inhibition of AP-1 or NFkB (0.04 nM) is lower than the $EC_{50}$ for activation of target genes (5 nM) and yet high doses of GCs are frequently required to treat patients with inflammatory disease. One explanation is that cytokines expressed at the site of inflammation may induce relative glucocorticoid resistance, for instance by activating AP-1 or NFkB. This is of importance as many pro-inflammatory cytokines signal by activation of NFkB and a major anti-inflammatory action of GCs is thought to be mediated by opposing NFkB action.

Published Japanese Patent Application No. 60067495 describes certain pregnenopyrazoles as anti-inflammatory agents.

There has now been found a new series of glucocorticosteroids having a long duration of action which have potential for once daily administration.

In accordance with the present invention, there is therefore provided a compound of formula

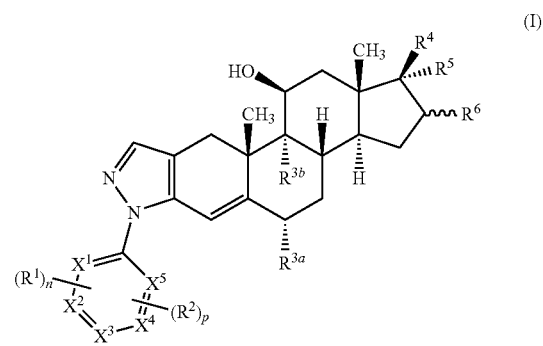

(I)

wherein
$X^1, X^2, X^3, X^4$ and $X^5$ each independently represent CH or a nitrogen atom, provided that no more than two of $X^1, X^2, X^3, X^4$ and $X^5$ may simultaneously represent a nitrogen atom;

n and p each independently represent 0 or 1;

$R^1$ represents a halogen atom or a methyl or a methoxy group;

$R^2$ represents a halogen atom, —C(O)OCH$_3$, —C(O)—S—CH$_2$CN, —C(O)—S—CH$_3$, —C(O)-heterocyclyl, —SO$_2$CH$_3$, a $C_2$-$C_6$ alkenyl group, or a methyl group optionally substituted by halogen, hydroxyl, methoxy, —OCH$_2$CH=CH$_2$ or —NR$^7$R$^8$;

$R^{3a}$ represents a hydrogen atom or methyl group and $R^{3b}$ represents a hydrogen or fluorine atom;

$R^4$ represents —C(O)—S—C(O)N(CH$_3$)$_2$, —C(O)CH$_2$Cl, —C(O)—Y—CH(R$^{11}$)—R$^9$ or —C(O)—CH(R$^{11}$)—Y—R$^9$;

$R^5$ represents hydroxyl, —OCH$_2$SCH$_3$, —O—C(O)—R$^{10}$, —O—C(O)—NH—R$^{10}$, —O—C(O)—O—R$^{10}$ or —O—C(O)—S—R$^{10}$;

$R^6$ represents a hydrogen or a halogen atom or a methyl group, and when $R^5$ is other than a hydroxyl group, $R^6$ may additionally represent a hydroxyl group;

$R^7$ and $R^8$ each independently represent a hydrogen atom, or a $C_1$-$C_3$ alkyl or a $C_1$-$C_3$ hydroxyalkyl group, or $R^7$ and $R^8$ together with the nitrogen atom to which they are attached form a 3- to 8-membered saturated or partially saturated heterocyclic ring optionally containing a further ring heterogroup selected from nitrogen, $S(O)_m$ and oxygen, the heterocyclic ring being optionally substituted by at least one substituent selected from hydroxyl, $C_1$-$C_3$ alkyl and $C_1$-$C_3$ hydroxyalkyl;

m is 0, 1 or 2;

Y represents an oxygen or sulphur atom or a group >NH;

$R^9$ represents hydrogen, halogen, cyano, —S—CN, —C(O)N(R$^{12}$)$_2$, $C_1$-$C_6$ alkoxycarbonyl, $C_1$-$C_6$ alkylcarbonyl (optionally substituted by —OC(O)CH$_3$), $C_1$-$C_6$ alkylcarbonyloxy, $C_1$-$C_6$ alkoxy, $C_1$-$C_6$ alkylthio, —C(O)—S—$C_1$-$C_6$ alkyl, —C(=CH$_2$)—O—CH$_2$OCH$_3$, $C_1$-$C_6$ alkyl, $C_2$-$C_6$ alkenyl, $C_2$-$C_6$ alkynyl or $C_3$-$C_7$ cycloalkyl, the latter four groups being optionally substituted by one or more substituents independently selected from halogen, hydroxyl, cyano, hydroxymethyl, $C_1$-$C_4$ alkoxy and $C_1$-$C_4$ alkylcarbonyloxy;

$R^{10}$ represents $C_1$-$C_6$ alkyl (optionally substituted by halogen, $C_1$-$C_4$ alkoxy, $C_1$-$C_4$ alkylcarbonyloxy or $C_3$-$C_7$ cycloalkyl) or a 3- to 10-membered saturated or unsaturated carbocyclic or heterocyclic ring system which ring system may be optionally substituted by at least one substituent selected from halogen, carboxyl, hydroxyl, oxo, nitro, cyano, mercapto, $C_1$-$C_6$ alkyl, $C_2$-$C_6$ alkenyl, $C_1$-$C_6$ haloalkyl, $C_1$-$C_6$ hydroxyalkyl, $C_1$-$C_6$ alkoxy, $C_1$-$C_6$ haloalkoxy, $C_1$-$C_6$ alkylthio, $C_1$-$C_6$ alkylsulphinyl, $C_1$-$C_6$ alkylsulphonyl, $C_1$-$C_6$ alkylcarbonyl, $C_1$-$C_6$ alkylcarbonyloxy, $C_1$-$C_6$ alkoxycarbonyl, amino (—$NH_2$), carboxamido (—$CONH_2$), (mono) $C_1$-$C_6$ alkylamino, (di) $C_1$-$C_6$ alkylamino and phenyl;

$R^{11}$ represents a hydrogen atom or a methyl group; and
each $R^{12}$ independently represents a hydrogen atom or a methyl group;

provided that when $R^4$ represents —$C(O)CH_2OH$, —$C(O)CH_2OC(O)C_2H_5$ or —$C(O)CH_2Cl$, $X^1$, $X^2$, $X^3$, $X^4$ and $X^5$ each represent CH and $R^5$ represents —O—C(O)—$R^{10}$ where $R^{10}$ represents $C_1$-$C_6$ alkyl, then at least one of $R^1$ and $R^2$ is present;

or a pharmaceutically acceptable salt thereof.

In one aspect of the invention, there is provided a compound of formula

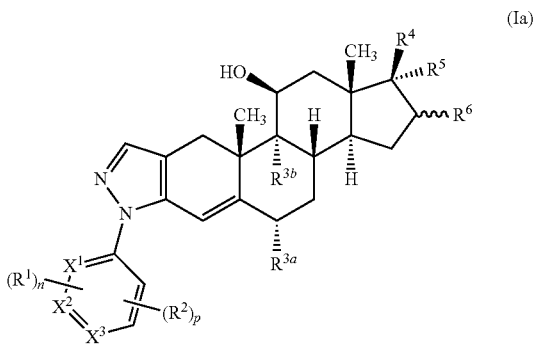

(Ia)

wherein
$X^1$, $X^2$ and $X^3$ each represent CH or, alternatively, one of $X^1$, $X^2$ and $X^3$ may additionally represent a nitrogen atom;

n and p each independently represent 0 or 1;

$R^1$ represents a halogen atom or a methyl or a methoxy group;

$R^2$ represents —$CO_2CH_3$, a halogen atom, or a methyl group optionally substituted by a hydroxyl or a —$NR^7R^8$ group;

$R^{3a}$ represents a hydrogen atom and $R^{3b}$ represents a hydrogen or fluorine atom;

$R^4$ represents —$C(O)CH_2OH$ or —$C(O)$—Y—$CH_2R^9$;

$R^5$ represents a group —O—C(O)—$R^{10}$, —O—C(O)—NH—$R^{10}$, —O—C(O)—O—$R^{10}$ or —O—C(O)—S—$R^{10}$;

$R^6$ represents a hydrogen or halogen atom or a hydroxyl or a methyl group;

$R^7$ and $R^8$ each independently represent a hydrogen atom, or a $C_1$-$C_3$ alkyl or a $C_1$-$C_3$ hydroxyalkyl group, or $R^7$ and $R^8$ together with the nitrogen atom to which they are attached form a 3- to 8-membered saturated or partially saturated heterocyclic ring optionally containing a further ring heterogroup selected from nitrogen, $S(O)_m$ and oxygen, the heterocyclic ring being optionally substituted by at least one substituent selected from hydroxyl, $C_1$-$C_3$ alkyl and $C_1$-$C_3$ hydroxyalkyl;

m is 0, 1 or 2;

Y represents an oxygen or sulphur atom or a group >NH;

$R^9$ represents a hydrogen or a halogen atom or a methyl or a cyano group; and $R^{10}$ represents a 5- to 10-membered saturated or unsaturated carbocyclic or heterocyclic ring system optionally substituted by at least one substituent selected from halogen, carboxyl, hydroxyl, oxo, nitro, cyano, mercapto, $C_1$-$C_6$ alkyl, $C_2$-$C_6$ alkenyl, $C_1$-$C_6$ haloalkyl, $C_1$-$C_6$ hydroxyalkyl, $C_1$-$C_6$ alkoxy, $C_1$-$C_6$ haloalkoxy, $C_1$-$C_6$ alkylthio, $C_1$-$C_6$ alkylsulphinyl, $C_1$-$C_6$ alkylsulphonyl, $C_1$-$C_6$ alkylcarbonyl, $C_1$-$C_6$ alkylcarbonyloxy, $C_1$-$C_6$ alkoxycarbonyl, amino (—$NH_2$), carboxamido (—$CONH_2$), (mono) $C_1$-$C_6$ alkylamino, (di) $C_1$-$C_6$ alkylamino and phenyl; or a pharmaceutically acceptable salt thereof.

In the context of the present specification, unless otherwise stated, an alkyl, alkenyl or alkynyl substituent group or an alkyl, alkenyl or alkynyl moiety in a substituent group may be linear or branched. Examples of $C_1$-$C_6$ alkyl groups/moieties include methyl, ethyl, propyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, tert-butyl, n-pentyl, isopentyl, neopentyl and n-hexyl. Examples of $C_2$-$C_6$ alkenyl groups/moieties include ethenyl, propenyl, 1-butenyl, 2-butenyl, 1-pentenyl, 1-hexenyl, 1,3-butadienyl, 1,3-pentadienyl, 1,4-pentadienyl and 1-hexadienyl. Examples of $C_2$-$C_6$ alkynyl groups/moieties include ethynyl, propynyl, 1-butynyl, 2-butynyl, 1-pentynyl and 1-hexynyl. Similarly, an alkylene group/moiety may be linear or branched. Examples of $C_1$-$C_6$ alkylene groups/moieties include methylene, ethylene, n-propylene, n-butylene, n-pentylene, n-hexylene, 1-methylethylene, 2-methylethylene, 1,2-dimethylethylene, 1-ethylethylene, 2-ethylethylene, 1-, 2- or 3-methylpropylene and 1-, 2- or 3-ethylpropylene. A $C_1$-$C_6$ haloalkyl or $C_1$-$C_6$ haloalkoxy substituent group/moiety will comprise at least one halogen atom, e.g. one, two, three, four or five halogen atoms, examples of which include trifluoromethyl, trifluoromethoxy or pentafluoroethyl. A $C_1$-$C_6$ hydroxyalkyl substituent group/moiety will comprise at least one hydroxyl group, e.g. one, two, three or four hydroxyl groups, examples of which include —$CH_2OH$, —$CH_2CH_2OH$, —$CH_2CH_2CH_2OH$, —$CH(OH)CH_2OH$, —$CH(CH_3)OH$ and —$CH(CH_2OH)_2$. The alkyl groups in a di-$C_1$-$C_6$ alkylamino group/moiety may be the same as, or different from, one another. In the definition of $R^{10}$, the saturated or unsaturated 3- to 10-membered carbocyclic or heterocyclic ring system may have alicyclic or aromatic properties. An unsaturated ring system will be partially or fully unsaturated. When $R^2$ represents —C(O)-heterocyclyl, the term "heterocyclyl" refers to saturated heterocyclic rings, for example rings containing from 3 to 10 ring atoms, up to four of which are selected from oxygen, nitrogen and sulphur. Particular examples of heterocyclyl moieties include morpholinyl, azetidinyl, pyrrolidinyl, piperidinyl and piperazinyl. For the avoidance of doubt, it should be understood that the definitions of the heterocyclic groups/moieties in formula (I) are not intended to include unstable structures or any O—O, O—S or S—S bonds and that a substituent, if present, may be attached to any suitable ring atom.

When any chemical moiety or group in formula (I) is described as being optionally substituted, it will be appreciated that the moiety or group may be either unsubstituted or substituted by one or more of the specified substituents. It will be appreciated that the number and nature of substituents will be selected so as to avoid sterically undesirable combinations.

In formula (I), $X^1, X^2, X^3, X^4$ and $X^5$ each represent CH (so as to form a phenyl ring) or, alternatively, one or two of $X^1$, $X^2, X^3, X^4$ and $X^5$ may additionally represent a nitrogen atom (e.g. to form a pyridyl, pyrazinyl or pyridazinyl ring).

In an embodiment of the invention, $X^1, X^2, X^3, X^4$ and $X^5$ each represent CH.

In another embodiment, one of $X^1, X^2, X^3, X^4$ and $X^5$ represents a nitrogen atom and the others represent CH.

In a further embodiment, either $X^2$ and $X^3$ each represent a nitrogen atom and $X^1, X^4$ and $X^5$ each represent CH, or, $X^3$ and $X^4$ each represent a nitrogen atom and $X^1, X^2$ and $X^5$ each represent CH, or, $X^1$ and $X^4$ each represent a nitrogen atom and $X^2, X^3$ and $X^5$ each represent CH, or, $X^2$ and $X^5$ each represent a nitrogen atom and $X^1, X^3$ and $X^4$ each represent CH.

In an embodiment of the invention n is 1 and p is 0 or 1.

Thus, in one aspect, $X^1, X^2, X^3, X^4$ and $X^5$ each represent CH, n is 1 and p is 0.

In another aspect, $X^1, X^2, X^3, X^4$ and $X^5$ each represent CH, n is 1 and p is 1.

In still another aspect, $X^1, X^2, X^3, X^4$ and $X^5$ each independently represent CH or a nitrogen atom, provided that at least one and not more than two of $X^1, X^2, X^3, X^4$ and $X^5$ simultaneously represent a nitrogen atom, n is 0 and p is 0.

In yet another aspect, $X^1, X^2, X^3, X^4$ and $X^5$ each independently represent CH or a nitrogen atom, provided that only one of $X^1, X^2, X^3, X^4$ and $X^5$ represents a nitrogen atom, n is 1 and p is 0.

$R^1$ represents a halogen atom (e.g. fluorine, chlorine, bromine or iodine) or a methyl or a methoxy group.

In an embodiment of the invention, $R^1$ represents a fluorine, chlorine or bromine atom, particularly a fluorine atom.

In another embodiment, $R^1$ represents a methyl group.

In a further embodiment, when n is 1 and $X^3$ represents CH, $X^3$ is substituted by $R^1$ $R^2$ represents a halogen atom (e.g. fluorine, chlorine, bromine or iodine), —C(O)OCH$_3$, —C(O)—S—CH$_2$CN, —C(O)—S—CH$_3$, —C(O)-heterocyclyl, —SO$_2$CH$_3$, a $C_2$-$C_6$ or $C_2$-$C_4$ alkenyl (e.g. ethenyl) group, or a methyl group optionally substituted by halogen (e.g. fluorine, chlorine, bromine or iodine), hydroxyl, methoxy, —OCH$_2$CH=CH$_2$ or —NR$^7$R$^8$.

In one embodiment, $R^2$ represents —C(O)OCH$_3$, —C(O)—S—CH$_2$CN, —C(O)—S—CH$_3$, —C(O)-morpholinyl, —SO$_2$CH$_3$, ethenyl, or a methyl group optionally substituted by halogen (e.g. fluorine, chlorine or bromine), hydroxyl, methoxy or —OCH$_2$CH=CH$_2$.

In another embodiment, $R^2$ represents a methyl group substituted by one hydroxyl group, i.e. —CH$_2$OH.

In an embodiment of the invention $R^{3a}$ and $R^{3b}$ each represent a hydrogen atom.

In another embodiment of the invention $R^{3a}$ represents a hydrogen atom and $R^{3b}$ represents a fluorine atom.

$R^4$ represents —C(O)—S—C(O)N(CH$_3$)$_2$, —C(O)CH$_2$Cl, —C(O)—Y—CH(R$^{11}$)—R$^9$ or —C(O)—CH(R$^{11}$)—Y—R$^9$;

In an embodiment of the invention, $R^4$ represents —C(O)—Y—CH(R$^{11}$)—R$^9$ or —C(O)—CH(R$^{11}$)—Y—R$^9$.

$R^5$ represents hydroxyl, —OCH$_2$SCH$_3$, —O—C(O)—R$^{10}$, —O—C(O)—NH—R$^{10}$, —O—C(O)—O—R$^{10}$ or —O—C(O)—S—R$^{10}$, in particular a hydroxyl, —OCH$_2$SCH$_3$, O—C(O)—R$^{10}$ or —O—C(O)—O—R$^{10}$ group.

In an embodiment of the invention, $R^5$ represents —O—C(O)—R$^{10}$.

$R^6$ represents a hydrogen or a halogen (e.g. fluorine, chlorine, bromine or iodine) atom or a methyl group, and when $R^5$ is other than a hydroxyl group, $R^6$ may additionally represent a hydroxyl group.

In one embodiment, $R^5$ represents a —O—C(O)—R$^{10}$ group and $R^6$ represents a hydrogen atom.

$R^7$ and $R^8$ each independently represent a hydrogen atom, or a $C_1$-$C_3$ alkyl (methyl, ethyl, n-propyl or isopropyl) or a $C_1$-$C_3$ hydroxyalkyl (e.g. hydroxymethyl, —(CH$_2$)$_2$OH, —(CH$_2$)$_3$OH or —CH(CH$_2$OH)$_2$) group, or $R^7$ and $R^8$ together with the nitrogen atom to which they are attached form a 3- to 8-membered, preferably 5- to 6-membered, saturated or partially saturated heterocyclic ring optionally containing a further ring heterogroup selected from nitrogen, $S(O)_m$ and oxygen, the heterocyclic ring being optionally substituted by at least one substituent, e.g. one, two, three or four substituents independently, selected from hydroxyl, $C_1$-$C_3$ alkyl (methyl, ethyl, n-propyl or isopropyl) and $C_1$-$C_3$ hydroxyalkyl (e.g. hydroxymethyl, —(CH$_2$)$_2$OH, —(CH$_2$)$_3$OH or —CH(CH$_2$OH)$_2$).

Examples of 3- to 8-membered saturated or partially saturated heterocyclic rings include morpholine, azetidine, pyrrolidine, piperidine, piperazine, 3-pyrroline, isoindoline, tetrahydroquinoline and thiomorpholine.

In one embodiment, $R^7$ and $R^8$ each independently represent a hydrogen atom or a $C_1$-$C_2$ alkyl (particularly ethyl) or $C_2$-$C_3$ hydroxyalkyl group.

In another embodiment, $R^7$ and $R^8$ together with the nitrogen atom to which they are attached form a 5- to 6-membered saturated or partially saturated heterocyclic ring optionally containing a further ring heterogroup selected from nitrogen, $S(O)_m$ and oxygen, the heterocyclic ring being optionally substituted by one or two substituents independently selected from hydroxyl, $C_1$-$C_3$ alkyl and $C_1$-$C_3$ hydroxyalkyl.

In yet another embodiment, $R^7$ and $R^8$ together with the nitrogen atom to which they are attached form a 5- to 6-membered saturated heterocyclic ring optionally containing a further ring heterogroup selected from nitrogen, sulphur and oxygen (e.g. pyyrrolidinyl, piperidinyl, piperazinyl, thiomorpholinyl or morpholinyl), the heterocyclic ring being optionally substituted by one or two substituents independently selected from hydroxyl, $C_1$-$C_3$ alkyl and $C_1$-$C_3$ hydroxyalkyl.

In a still further embodiment, $R^7$ and $R^8$ together with the nitrogen atom to which they are attached form a 5- to 6-membered saturated heterocyclic ring optionally containing a further ring heterogroup selected from nitrogen, sulphur and oxygen, the heterocyclic ring being optionally substituted by one or two substituents independently selected from hydroxyl, methyl and hydroxymethyl.

In an embodiment of the invention, m is 0.

Y represents an oxygen or sulphur atom or a group>NH, particularly an oxygen or sulphur atom.

$R^9$ represents hydrogen, halogen (e.g. fluorine, chlorine, bromine or iodine), cyano, —S—CN, —C(O)N(R$^{12}$)$_2$, $C_1$-$C_6$, or $C_1$-$C_4$, or $C_1$-$C_2$ alkoxycarbonyl, $C_1$-$C_6$, or $C_1$-$C_4$, or $C_1$-$C_2$ alkylcarbonyl (optionally substituted by —OC(O) CH$_3$), $C_1$-$C_6$, or $C_1$-$C_4$, or $C_1$-$C_2$ alkylcarbonyloxy, $C_1$-$C_6$, or $C_1$-$C_4$, or $C_1$-$C_2$ alkoxy, $C_1$-$C_6$, or $C_1$-$C_4$, or $C_1$-$C_2$ alkylthio, —C(O)—S—$C_1$-$C_6$, or $C_1$-$C_4$, or $C_1$-$C_2$ alkyl, —C(=CH$_2$)—O—CH$_2$OCH$_3$, $C_1$-$C_6$, or $C_1$-$C_4$, or $C_1$-$C_2$ alkyl, $C_2$-$C_6$ or $C_2$-$C_4$ alkenyl, $C_2$-$C_6$ or $C_2$-$C_4$ alkynyl or $C_3$-$C_7$, or $C_5$-$C_6$, cycloalkyl, the latter four groups being optionally substituted by one or more (e.g. one, two, three or four) substituents independently selected from halogen (e.g. fluorine, chlorine, bromine or iodine), hydroxyl, cyano, hydroxymethyl, $C_1$-$C_4$, or $C_1$-$C_2$, alkoxy and $C_1$-$C_4$, or $C_1$-$C_2$, alkylcarbonyloxy.

In an embodiment of the invention, $R^9$ represents hydrogen, halogen (particularly fluorine), cyano, —S—CN, —C(O)N($R^{12}$)$_2$, $C_1$-$C_2$ alkoxycarbonyl, $C_1$-$C_2$ alkylcarbonyl (optionally substituted by —OC(O)CH$_3$), $C_1$-$C_2$ alkylcarbonyloxy, $C_1$-$C_2$ alkoxy, $C_1$-$C_2$ alkylthio, —C(O)—S—$C_1$-$C_2$ alkyl, —C(=CH$_2$)—O—CH$_2$OCH$_3$, $C_1$-$C_6$, or $C_1$-$C_4$, or $C_1$-$C_2$ alkyl, $C_2$-$C_4$ alkenyl, $C_2$-$C_4$ alkynyl or $C_3$-$C_6$ cycloalkyl, the latter four groups being optionally substituted by one or more (e.g. one, two, three or four) substituents independently selected from halogen (particularly fluorine or chlorine), hydroxyl, cyano, hydroxymethyl, $C_1$-$C_4$ alkoxy (particularly methoxy) and $C_1$-$C_4$ alkylcarbonyloxy (particularly methylcarbonyloxy).

In another embodiment of the invention, $R^9$ represents hydrogen, halogen (particularly fluorine), cyano, methyl and hydroxymethyl.

$R^{10}$ represents $C_1$-$C_6$, or $C_1$-$C_4$, or $C_1$-$C_2$ alkyl (optionally substituted by at least one substituent, e.g. one, two, three or four substituents independently, selected from halogen (such as fluorine, chlorine, bromine or iodine), $C_1$-$C_4$, or $C_1$-$C_2$, alkoxy, $C_1$-$C_4$, or $C_1$-$C_2$, alkylcarbonyloxy and $C_3$-$C_7$, or $C_5$-$C_6$, cycloalkyl), or a 3- to 10-membered (e.g. 3-, 4-, 5- or 6- to 7-, 8-, 9- or 10-membered) saturated or unsaturated carbocyclic or heterocyclic ring system optionally substituted by at least one substituent (e.g. one, two, three or four substituents independently) selected from halogen (e.g. fluorine, chlorine, bromine or iodine), carboxyl, hydroxyl, oxo, nitro, cyano, mercapto, $C_1$-$C_6$, or $C_1$-$C_4$, or $C_1$-$C_2$ alkyl, $C_2$-$C_6$ or $C_2$-$C_4$ alkenyl, $C_1$-$C_6$, or $C_1$-$C_4$, or $C_1$-$C_2$ haloalkyl, $C_1$-$C_6$, or $C_1$-$C_4$, or $C_1$-$C_2$ hydroxyalkyl, $C_1$-$C_6$, or $C_1$-$C_4$, or $C_1$-$C_2$ alkoxy, $C_1$-$C_6$, or $C_1$-$C_4$, or $C_1$-$C_2$ haloalkoxy, $C_1$-$C_6$, or $C_1$-$C_4$, or $C_1$-$C_2$ alkylthio, $C_1$-$C_6$, or $C_1$-$C_4$, or $C_1$-$C_2$ alkylsulphinyl, $C_1$-$C_6$, or $C_1$-$C_4$, or $C_1$-$C_2$ alkylsulphonyl, $C_1$-$C_6$, or $C_1$-$C_4$, or $C_1$-$C_2$ alkylcarbonyl, $C_1$-$C_6$, or $C_1$-$C_4$, or $C_1$-$C_2$ alkylcarbonyloxy, $C_1$-$C_6$, or $C_1$-$C_4$, or $C_1$-$C_2$ alkoxycarbonyl, amino, carboxamido, (mono) $C_1$-$C_6$, or $C_1$-$C_4$, or $C_1$-$C_2$ alkylamino, (di) $C_1$-$C_6$, or $C_1$-$C_4$, or $C_1$-$C_2$ alkylamino and phenyl.

In another embodiment, $R^{10}$ represents $C_1$-$C_4$, or $C_1$-$C_3$, or $C_1$-$C_2$ alkyl (optionally substituted by at least one substituent, e.g. one, two, three or four substituents independently, selected from halogen (particularly fluorine), $C_1$-$C_2$, alkoxy, $C_1$-$C_2$, alkylcarbonyloxy or $C_5$-$C_6$ cycloalkyl) or a 3- to 10-membered saturated or unsaturated carbocyclic or heterocyclic ring system optionally substituted as hereinbefore defined.

The heterocyclic ring system will comprise at least one ring heteroatom selected from nitrogen, sulphur and oxygen.

Examples of saturated or unsaturated 3- to 10-membered carbocyclic or heterocyclic ring systems that may be used, which may be monocyclic or polycyclic (e.g. bicyclic) in which the two or more rings are fused, include one or more (in any combination) of cyclopropyl, cyclobutyl, cyclopentyl, cyclohexyl, bicyclo[2.2.1]heptyl, cyclopentenyl, cyclohexenyl, phenyl, pyrrolidinyl, piperidinyl, piperazinyl, morpholinyl, thiomorpholinyl, tetrahydrofuranyl, diazabicyclo[2.2.1]hept-2-yl, naphthyl, benzofuranyl, benzothienyl, benzodioxolyl, quinolinyl, oxazolyl, thiadiazolyl (e.g. 1,2,3-thiadiazolyl), 2,3-dihydrobenzofuranyl, tetrahydropyranyl, pyrazolyl, pyrazinyl, thiazolidinyl, indanyl, thienyl, isoxazolyl, pyridazinyl, pyrrolyl, furanyl, thiazolyl, indolyl, imidazolyl, pyrimidinyl, benzimidazolyl, triazolyl, tetrazolyl and pyridinyl. Preferred ring systems include thiadiazolyl, furanyl, thiazolyl, cyclopropyl, cyclobutyl, imidazolyl, oxazolyl, triazolyl, isoxazolyl, thienyl, tetrahydrofuranyl, tetrahydropyranyl and pyrrolyl.

Preferred substituents on the 3- to 10-membered saturated or unsaturated carbocyclic or heterocyclic ring system include alkyl, alkoxy and cyano substituent groups.

In an embodiment of the invention, $R^{10}$ represents a 3-, 4- or 5- to 6-, 7- or 8-membered saturated or unsaturated carbocyclic or heterocyclic ring system optionally substituted by one, two, three or four substituents independently selected from halogen, carboxyl, hydroxyl, oxo, nitro, cyano, mercapto, $C_1$-$C_6$, or $C_1$-$C_4$, or $C_1$-$C_2$ alkyl, $C_2$-$C_6$ or $C_2$-$C_4$ alkenyl, $C_1$-$C_6$, or $C_1$-$C_4$, or $C_1$-$C_2$ haloalkyl, $C_1$-$C_6$, or $C_1$-$C_4$, or $C_1$-$C_2$ hydroxyalkyl, $C_1$-$C_6$, or $C_1$-$C_4$, or $C_1$-$C_2$ alkoxy, $C_1$-$C_6$, or $C_1$-$C_4$, or $C_1$-$C_2$ haloalkoxy, $C_1$-$C_6$, or $C_1$-$C_4$, or $C_1$-$C_2$ alkylthio, $C_1$-$C_6$, or $C_1$-$C_4$, or $C_1$-$C_2$ alkylsulphinyl, $C_1$-$C_6$, or $C_1$-$C_4$, or $C_1$-$C_2$ alkylsulphonyl, $C_1$-$C_6$, or $C_1$-$C_4$, or $C_1$-$C_2$ alkylcarbonyl, $C_1$-$C_6$, or $C_1$-$C_4$, or $C_1$-$C_2$ alkylcarbonyloxy, $C_1$-$C_6$, or $C_1$-$C_4$, or $C_1$-$C_2$ alkoxycarbonyl, amino, carboxamido, (mono) $C_1$-$C_6$, or $C_1$-$C_4$, or $C_1$-$C_2$ alkylamino, (di) $C_1$-$C_6$, or $C_1$-$C_4$, or $C_1$-$C_2$ alkylamino and phenyl.

In a further embodiment, $R^{10}$ represents a 5- to 6-membered unsaturated carbocyclic or heterocyclic ring system optionally substituted by one, two, three or four substituents independently selected from halogen, carboxyl, hydroxyl, oxo, nitro, cyano, mercapto, $C_1$-$C_4$ alkyl, $C_2$-$C_4$ alkenyl, $C_1$-$C_4$ haloalkyl, $C_1$-$C_4$ hydroxyalkyl, $C_1$-$C_4$ alkoxy, $C_1$-$C_4$ haloalkoxy, $C_1$-$C_4$ alkylthio, $C_1$-$C_4$ alkylsulphinyl, $C_1$-$C_4$ alkylsulphonyl, $C_1$-$C_4$ alkylcarbonyl, $C_1$-$C_4$ alkylcarbonyloxy, $C_1$-$C_4$ alkoxycarbonyl, amino, carboxamido, (mono) $C_1$-$C_4$ alkylamino, (di) $C_1$-$C_4$ alkylamino and phenyl.

In a still further embodiment, $R^{10}$ represents a 5- to 6-membered unsaturated heterocyclic ring system optionally substituted by one or two substituents independently selected from halogen, carboxyl, hydroxyl, oxo, nitro, cyano, mercapto, $C_1$-$C_4$ alkyl, $C_1$-$C_4$ haloalkyl, $C_1$-$C_4$ hydroxyalkyl, $C_1$-$C_4$ alkoxy, amino, carboxamido, (mono) $C_1$-$C_4$ alkylamino, (di) $C_1$-$C_4$ alkylamino and phenyl.

In yet another embodiment, $R^{10}$ represents a 5- to 6-membered unsaturated heterocyclic ring system optionally substituted by one or two $C_1$-$C_4$ alkyl substituents.

In a further aspect, $R^{10}$ represents a 3- to 6-membered saturated or unsaturated carbocyclic or heterocyclic ring system such as a thiadiazolyl, furanyl, thiazolyl, cyclopropyl, cyclobutyl, imidazolyl, oxazolyl, triazolyl, isoxazolyl, thienyl, tetrahydrofuranyl, tetrahydropyranyl or pyrrolyl ring, the ring system being optionally substituted by at least one substituent (e.g. one, two, three or four, preferably one or two, substituents independently) selected from cyano, $C_1$-$C_4$ alkyl (particularly methyl) and $C_1$-$C_4$ alkoxy (particularly methoxy).

In another embodiment, $R^{10}$ represents either $C_1$-$C_4$, or $C_1$-$C_3$, or $C_1$-$C_2$ alkyl optionally substituted by $C_1$-$C_2$, alkoxy (e.g. methoxymethyl), or a cyclopropyl or furanyl ring.

Examples of compounds of the invention include:
(1R,3aS,3bS,10R,10bS,11S,12aS)-1-{[(Fluoromethyl)thio]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 4-methyl-1,3-thiazole-5-carboxylate;

(1R,3aS,3bS,10aR,10bS,11S,12aS)-1-{[(Cyanomethyl)thio]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 4-methyl-1,3-thiazole-5-carboxylate;

(1R,3aS,3bS,10aR,10bS,11S,12aS)-1-[(Ethylthio)carbonyl]-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 4-methyl-1,3-thiazole-5-carboxylate;

(1R,3aS,3bS,10aR,10bS,11S,12aS)-1-{[(Fluoromethyl)thio]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 4-methyl-1,2,3-thiadiazole-5-carboxylate;

(1R,3aS,3bS,10aR,10bS,11S,12aS)-1-[(Ethylthio)carbonyl]-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 4-methyl-1,2,3-thiadiazole-5-carboxylate;

(1R,3aS,3bS,10aR,10bS,11S,12aS)-1-{[(Cyanomethyl)thio]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 4-methyl-1,2,3-thiadiazole-5-carboxylate;

(1R,3aS,3bS,10aR,10bS,11S,12aS)-1-{[(Cyanomethyl)thio]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 2-furoate;

(1R,3aS,3bS,10aR,10bS,11S,12aS)-1-{[(Fluoromethyl)thio]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 2-furoate;

Cyanomethyl(1R,3aS,3bS,10aR,10bS,11S,12aS)-7-(4-fluorophenyl)-11-hydroxy-10a,12a-dimethyl-1-{[(4-methyl-1,3-thiazol-5-yl)carbonyl]oxy}-1,2,3,3a,3b,4,5,7,10,10a,10b,11,12,12a-tetradecahydrocyclopenta[5,6]naphtho[1,2-f]indazole-1-carboxylate;

(1R,3aS,3bS,10aR,10bS,11S,12aS)-1-{[(Cyanomethyl)thio]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl propionate;

(1R,3aS,3bS,10aR,10bS,11S,12aS)-7-(4-Fluorophenyl)-11-hydroxy-1-{[(2-methoxy-2-oxoethyl)thio]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl propanoate;

(1R,3aS,3bS,10aR,10bS,11S,12aS)-1-{[(1-Cyanoethyl)thio]carbonyl}-7-(4-fluoro-phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl propanoate;

(1R,3aS,3bS,10aR,10bS,11S,12aS)-1-{[(2-Amino-2-oxoethyl)thio]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl propanoate;

(1R,3aS,3bS,10aR,10bS,11S,12aS)-7-(4-Fluorophenyl)-11-hydroxy-1-{[(methoxy-methyl)thio]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl propanoate;

(1R,3aS,3bS,10aR,10bS,11S,12aS)-7-(4-Fluorophenyl)-11-hydroxy-1-{[(2-hydroxyethyl)thio]carbonyl}-10a,12a-dimethyl-1,2,3,3a,3b,4,5,7,10,10a,10b,11,12,12a-tetradecahydropcyclopenta[5,6]naphtho[1,2-f]indazol-1-yl propanoate;

(1R,3aS,3bS,10aR,10bS,11S,12aS)-1-{[(2-Cyanoethyl)thio]carbonyl}-7-(4-fluoro-phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl propanoate;

(1R,3aS,3bS,10aR,10bS,11S,12aS)-7-(4-Fluorophenyl)-11-hydroxy-10a,12a-dimethyl-1-{[(2-oxopropyl)thio]carbonyl}-1,2,3,3a,3b,4,5,7,10,10a,10b,11,12,12a-tetradecahydrocyclopenta[5,6]naphtho[1,2-f]indazol-1-yl propanoate;

(1R,3aS,3bS,10aR,10bS,11S,12aS)-7-(4-Fluorophenyl)-11-hydroxy-1-{[(4-hydroxy-but-2-yn-1-yl)thio]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl propanoate;

(1R,3aS,3bS,10aR,10bS,11S,12aS)-1-{[(Fluoromethyl)thio]carbonyl}-7-(4-fluoro-phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl propanoate;

(1R,3aS,3bS,10aR,10bS,11S,12aS)-7-(4-fluorophenyl)-11-hydroxy-10a,12a-dimethyl-1-[(prop-2-yn-1-ylthio)carbonyl]-1,2,3,3a,3b,4,5,7,10,10a,10b,11,12,12a-tetradecaphydrocyclopenta[5,6]naphtho[1,2-f]indazol-1-yl propanoate;

(1R,3aS,3bS,10aR,10bS,11S,12aS)-7-(4-Fluorophenyl)-11-hydroxy-10a,12a-dimethyl-1-[(methylthio)carbonyl]-1,2,3,3a,3b,4,5,7,10,10a,10b,11,12,12a-tetradecahydropcyclopenta[5,6]naphtho[1,2-f]indazol-1-yl propanoate;

(1R,3aS,3bS,10R,10bS,11S,12aS)-1-({[2-(Dimethylamino)-2-oxoethyl]thio}carbonyl)-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl propanoate;

(1R,3aS,3bS,10aR,10bS,11S,12aS)-7-(4-Fluorophenyl)-11-hydroxy-10a,12a-dimethyl-1-[(prop-2-en-1-ylthio)carbonyl]-1,2,3,3a,3b,4,5,7,10,10a,10b,11,12,12a-tetradecahydropcyclopenta[5,6]naphtho[1,2-f]indazol-1-yl propanoate;

(1R,3aS,3bS,10R,10bS,11S,12aS)-7-(4-Fluorophenyl)-11-hydroxy-1-{[(3-hydroxy-propyl)thio]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl propanoate;

(1R,3aS,3bS,10aR,10bS,11S,12aS)-1-{[(Cyclopropylmethyl)thio]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl propanoate;

(1R,3aS,3bS,10aR,10bS,11S,12aS)-1-{[(2-Fluoroethyl)thio]carbonyl}-7-(4-fluoro-phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl propanoate;

(1R,3aS,3bS,10aR,10bS,11S,12aS)-1-{[(Cyanomethyl)thio]carbonyl}-7-(4-fluoro-phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl fluoroacetate;

(1R,3aS,3bS,10aR,10bS,11S,12aS)-1-{[(Fluoromethyl)thio]carbonyl}-7-(4-fluoro-phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl fluoroacetate;

(1R,3aS,3bS,10aR,10bS,11S,12aS)-1-{[(Cyanomethyl)thio]carbonyl}-7-(4-fluoro-phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl (acetyloxy)acetate;

(1R,3aS,3bS,10aR,10bS,11S,12aS)-1-{[(Cyanomethyl)thio]carbonyl}-7-(4-fluoro-phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl methoxyacetate;

(1R,3aS,3bS,10aR,10bS,11S,12aS)-7-(4-Fluorophenyl)-11-hydroxy-1-{[(4-hydroxy-but-2-yn-1-yl)thio]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl methoxyacetate;

(1R,3aS,3bS,10aR,10bS,11S,12aS)-7-(4-Fluorophenyl)-11-hydroxy-1-{[(2-hydroxy-ethyl)thio]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl methoxyacetate;

(1R,3aS,3bS,10aR,10bS,11S,12aS)-7-(4-Fluorophenyl)-11-hydroxy-10a,12a-dimethyl-1-{[(2-oxopropyl)thio]carbonyl}-1,2,3,3a,3b,4,5,7,10,10a,10b,11,12,12a-tetradecahydrocyclopenta[5,6]naphtho[1,2-f]indazol-1-yl methoxyacetate;

(1R,3aS,3bS,10aR,10bS,11S,12aS)-1-{[(Fluoromethyl)thio]carbonyl}-7-(4-fluoro-phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl methoxyacetate;

(1R,3aS,3bS,10aR,10bS,11S,12aS)-1-{[(Cyanomethyl)thio]carbonyl}-7-(4-fluoro-phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl cyclopropanecarboxylate;

(1R,3aS,3bS,10aR,10bS,11S,12aS)-7-(4-Fluorophenyl)-11-hydroxy-1-{[(2-hydroxy-ethyl)thio]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl cyclopropanecarboxylate;

(1R,3aS,3bS,10aR,10bS,11S,12aS)-7-(4-Fluorophenyl)-11-hydroxy-1-{[(4-hydroxybut-2-yn-1-yl)thio]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl cyclopropanecarboxylate;

(1R,3aS,3bS,10aR,10bS,11S,12aS)-1-{[(Fluoromethyl)thio]carbonyl}-7-(4-fluoro-phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl cyclopropanecarboxylate;

(1R,3aS,3bS,10aR,10bS,11S,12aS)-1-{[(Cyanomethyl)thio]carbonyl}-7-(4-fluorophenyl)-11-hydroxy-10a,12a-dimethyl-1,2,3,3a,3b,4,5,7,10,10a,10b,11,12,12a-tetradecahydropcyclopenta[5,6]naphtho[1,2-f]indazol-1-yl 1,3-thiazole-2-carboxylate;

(1R,3aS,3bS,10aR,10bS,11S,12aS)-7-(4-Fluorophenyl)-11-hydroxy-1-{[(2-hydroxy-ethyl)thio]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl 1,3-thiazole-2-carboxylate;

(1R,3aS,3bS,10aR,10bS,11S,12aS)-7-(4-Fluorophenyl)-11-hydroxy-1-{[(4-hydroxy-but-2-yn-1-yl)thio]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl 1,3-thiazole-2-carboxylate;

(1R,3aS,3bS,10aR,10bS,11S,12aS)-1-{[(Fluoromethyl)thio]carbonyl}-7-(4-fluoro-phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 1,3-thiazole-2-carboxylate;

(1R,3aS,3bS,10aR,10bS,11S,12aS)-1-{[(Cyanomethyl)thio]carbonyl}-7-(4-fluoro-phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 1,3-oxazole-4-carboxylate;

(1R,3aS,3bS,10aR,10bS,11S,12aS)-7-(4-Fluorophenyl)-11-hydroxy-1-{[(2-hydroxy-ethyl)thio]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl 1,3-oxazole-4-carboxylate;

(1R,3aS,3bS,10aR,10bS,11S,12aS)-1-{[(Fluoromethyl)thio]carbonyl}-7-(4-fluoro-phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 1,3-oxazole-4-carboxylate;

(1R,3aS,3bS,10aR,10bS,11S,12aS)-7-(4-Fluorophenyl)-11-hydroxy-10a,12a-dimethyl-1-{[(2-oxopropyl)thio]carbonyl}-1,2,3,3a,3b,4,5,7,10,10a,10b,11,12,12a-tetradecahydropcyclopenta[5,6]naphtho[1,2-f]indazol-1-yl 1,3-oxazole-4-carboxylate;

(1R,3aS,3bS,10aR,10bS,11S,12aS)-1-{[(Cyanomethyl)thio]carbonyl}-7-(4-fluoro-phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 1-methyl-1H-1,2,3-triazole-4-carboxylate;

(1R,3aS,3bS,10aR,10bS,11S,12aS)-1-{[(Fluoromethyl)thio]carbonyl}-7-(4-fluoro-phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 1-methyl-1H-1,2,3-triazole-4-carboxylate;

(1R,3aS,3bS,10aR,10bS,11S,12aS)-7-(4-Fluorophenyl)-11-hydroxy-1-{[(2-hydroxy-ethyl)thio]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl 1-methyl-1H-1,2,3-triazole-4-carboxylate;

(1R,3aS,3bS,10aR,10bS,11S,12aS)-1-{[(Cyanomethyl)thio]carbonyl}-7-(4-fluoro-phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-3-carboxylate;

(1R,3aS,3bS,10aR,10bS,11S,12aS)-1-{[(Fluoromethyl)thio]carbonyl}-7-(4-fluoro-phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-3-carboxylate;

(1R,3aS,3bS,10aR,10bS,11S,12aS)-7-(4-Fluorophenyl)-11-hydroxy-1-{[(2-hydroxy-ethyl)thio]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl furan-3-carboxylate;

(1R,3aS,3bS,10aR,10bS,11S,12aS)-1-{[(Cyanomethyl)sulfanyl]carbonyl}-7-(4-fluoro-phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 2-methylfuran-3-carboxylate;

(1R,3aS,3bS,10aR,10bS,11S,12aS)-1-{[(Fluoromethyl)thio]carbonyl}-7-(4-fluorophenyl)-11-hydroxy-10a,12a-dimethyl-1,2,3,3a,3b,4,5,7,10,10a,10b,11,12,12a-tetradecahydropcyclopenta[5,6]naphtho[1,2-f]indazol-1-yl 2-methylfuran-3-carboxylate;

(1R,3aS,3bS,10aR,10bS,11S,12aS)-7-(4-Fluorophenyl)-11-hydroxy-1-{[(2-hydroxy-ethyl)thio]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl 2-methylfuran-3-carboxylate;

(1R,3aS,3bS,10aR,10bS,11S,12aS)-1-{[(Cyanomethyl)thio]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 3-methylfuran-2-carboxylate;

(1R,3aS,3bS,10aR,10bS,11S,12aS)-1-{[(Fluoromethyl)thio]carbonyl}-7-(4-fluorophenyl)-11-hydroxy-10a,12a-dimethyl-1,2,3,3a,3b,4,5,7,10,10a,10b,11,12,12a-tetradecaphydrocyclopenta[5,6]naphtho[1,2-f]indazol-1-yl 3-methylfuran-2-carboxylate;

(1R,3aS,3bS,10aR,10bS,11S,12aS)-7-(4-Fluorophenyl)-11-hydroxy-1-{[(2-hydroxy-ethyl)thio]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl 3-methylfuran-2-carboxylate;

(1R,3aS,3bS,10aR,10bS,11S,12aS)-1-{[(Cyanomethyl)thio]carbonyl}-7-(4-fluorophenyl)-11-hydroxy-10a,12a-dimethyl-1,2,3,3a,3b,4,5,7,10,10a,10b,11,12,12a-tetradecahydropcyclopenta[5,6]naphtho[1,2-f]indazol-1-yl isoxazole-5-carboxylate;

(1R,3aS,3bS,10aR,10bS,11S,12aS)-1-{[(Fluoromethyl)thio]carbonyl}-7-(4-fluorophenyl)-11-hydroxy-10a,12a-dimethyl-1,2,3,3a,3b,4,5,7,10,10a,10b,11,12,12a-tetradecahydropcyclopenta[5,6]naphtho[1,2-f]indazol-1-yl isoxazole-5-carboxylate;

(1R,3aS,3bS,10aR,10bS,11S,12aS)-7-(4-Fluorophenyl)-11-hydroxy-1-{[(2-hydroxy-ethyl)thio]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl isoxazole-5-carboxylate;

(1R,3aS,3bS,10aR,10bS,11S,12aS)-1-{[(Cyanomethyl)thio]carbonyl}-7-(4-fluorophenyl)-11-hydroxy-10a,12a-dimethyl-1,2,3,3a,3b,4,5,7,10,10a,10b,11,12,12a-tetradecahydropcyclopenta[5,6]naphtho[1,2-f]indazol-1-yl 3-methoxypropanoate;

(1R,3aS,3bS,10aR,10bS,11S,12aS)-1-{[(Fluoromethyl)thio]carbonyl}-7-(4-fluorophenyl)-11-hydroxy-10a,12a-dimethyl-1,2,3,3a,3b,4,5,7,10,10a,10b,11,12,12a-tetradecahydropcyclopenta[5,6]naphtho[1,2-f]indazol-1-yl 3-methoxypropanoate;

(1R,3aS,3bS,10aR,10bS,11S,12aS)-7-(4-Fluorophenyl)-11-hydroxy-10a,12a-dimethyl-1-[(methylthio)carbonyl]-1,2,3,3a,3b,4,5,7,10,10a,10b,11,12,12a-tetradecahydropcyclopenta[5,6]naphtho[1,2-f]indazol-1-yl furan-2-carboxylate;

Cyanomethyl(1R,3aS,3bS,10aR,10bS,11S,12aS)-7-(4-fluorophenyl)-1-[(furan-2-ylcarbonyl)oxy]-11-hydroxy-10a,12a-dimethyl-1,2,3,3a,3b,4,5,7,10,10a,10b,11,12,12a-tetradecahydrocyclopenta[5,6]naphtho[1,2-f]indazole-1-carboxylate;

Methyl(1R,3aS,3bS,10aR,10bS,11S,12aS)-7-(4-fluorophenyl)-1-[(furan-2-yl-carbonyl)oxy]-11-hydroxy-10a,12a-dimethyl-1,2,3,3a,3b,4,5,7,10,10a,10b,11,12,12a-tetradecahydrocyclopenta[5,6]naphtho[1,2-f]indazole-1-carboxylate;

S-(Cyanomethyl)(1R,3aS,3bS,10aR,10bS,11S,12aS)-1-[(ethoxycarbonyl)oxy]-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazole-1-carbothioate;

S-(Cyanomethyl)(1R,3aS,3bS,10aR,10bS,11S,12aS)-7-(4-fluorophenyl)-11-hydroxy-10a,12a-dimethyl-1-{[(1-methylethoxy)carbonyl]oxy}-1,2,3,3a,3b,4,5,7,10,10a,10b,11,12,12a-tetradecahydrocyclopenta[5,6]naphtho[1,2-f]indazole-1-carbothioate;

(1R,3aS,3bS,10aR,10bS,11S,12aS)-7-(4-Fluorophenyl)-11-hydroxy-10a,12a-dimethyl-1-(methylcarbamoyl)-1,2,3,3a,3b,4,5,7,10,10a,10b,11,12,12a-tetradehydropcyclopenta[5,6]naphtho[1,2-f]indazol-1-yl furan-2-carboxylate;

(1R,3aS,3bS,10aR,10bS,11S,12aS)-7-(4-Fluorophenyl)-1,11-dihydroxy-N,10a,12a-trimethyl-1,2,3,3a,3b,4,5,7,10,10a,10b,11,12,12a-tetradecahydrocyclopenta[5,6]naphtho[1,2-f]indazole-1-carboxamide;

(1R,3aS,10aR,10bS,11S,12aS)-7-(3-Bromophenyl)-1-{[(fluoromethyl)thio]carbonyl}-11-hydroxy-10a,12a-dimethyl-1,2,3,3a,3b,4,5,7,10,10a,10b,11,12,12a-tetradecaphydrocyclopenta[5,6]naphtho[1,2-f]indazol-1-yl furan-2-carboxylate;

(1R,10aR,11S,12aS)-7-(3-Ethenylphenyl)-1-{[(fluoromethyl)thio]carbonyl}-11-hydroxy-10a,12a-dimethyl-1,2,3,3a,3b,4,5,7,10,10a,10b,11,12,12a-tetradecahydropcyclopenta[5,6]naphtho[1,2-f]indazol-1-yl furan-2-carboxylate;

(1R,3aS,3bS,10aR,10bS,11S,12aS)-1-{[(Cyanomethyl)thio]carbonyl}-7-[4-fluoro-3-(methoxymethyl)phenyl]-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-7-[4-Fluoro-3-(methoxymethyl)phenyl]-1-{[(fluoromethyl)thio]carbonyl}-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-1-{[(Cyanomethyl)thio]carbonyl}-7-[4-fluoro-3-(fluoromethyl)phenyl]-11-hydroxy-10a,12a-dimethyl-1,2,3,3a,3b,4,5,7,10,10a,10b,11,12,12a-tetradecahydrocyclopenta[5,6]naphtho[1,2-]indazol-1-yl furan-2-carboxylate;

(1R,3aS,3bS,10aR,10bS,11S,12aS)-7-[4-Fluoro-3-(fluoromethyl)phenyl]-1-{[(fluoromethyl)thio]carbonyl}-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-1-{[(Cyanomethyl)thio]carbonyl}-7-{4-fluoro-3-[(prop-2-en-1-yloxy)methyl]phenyl}-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-7-{4-Fluoro-3-[(prop-2-en-1-yloxy)methyl]phenyl}-11-hydroxy-10a,12a-dimethyl-1-(methylcarbamoyl)-1,2,3,3a,3b,4,5,7,10,10a,10b,11,12,12a-tetradecahydrocyclopenta[5,6]naphtho[1,2-f]indazol-1-yl furan-2-carboxylate;

Cyanomethyl(1R,3aS,3bS,10aR,10bS,11S,12aS)-7-[4-fluoro-3-(hydroxymethyl)phenyl]-1-[(furan-2-ylcarbonyl)oxy]-11-hydroxy-10a,12a-dimethyl-1,2,3,3a,3b,4,5,7,10,10a,10b,11,12,12a-tetradecahydrocyclopenta[5,6]naphtho[1,2-f]indazole-1-carboxylate;

(1R,3aS,3bS,10R,10bS,11S,12aS)-1-{[(Cyanomethyl)thio]carbonyl}-7-[4-fluoro-3-(hydroxymethyl)phenyl]-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-7-[4-Fluoro-3-(hydroxymethyl)phenyl]-1-{[(fluoromethyl)thio]carbonyl}-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-7-(4-Fluorophenyl)-11-hydroxy-10a,12a-dimethyl-1-({[(methylsulfanyl)methyl]sulfanyl}carbonyl)-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-7-(4-Fluorophenyl)-11-hydroxy-10a,12a-dimethyl-1-{[(thiocyanatomethyl)sulfanyl]carbonyl}-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-1-{[(2,3-Dihydroxypropyl)sulfanyl]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-7-(4-Fluorophenyl)-11-hydroxy-1-{[(3-methoxypropyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-1-{[(3-Cyanopropyl)sulfanyl]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-1-({[3-(Acetyloxy)-2-oxopropyl]sulfanyl}carbonyl)-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-7-(4-fluorophenyl)-11-hydroxy-1-({[2-(methoxymethoxy)prop-2-en-1-yl]sulfanyl}carbonyl)-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-7-(4-Fluorophenyl)-11-hydroxy-10a,12a-dimethyl-1-{[(2-oxopropyl)sulfanyl]carbonyl}-1,2,3,3a,3b,4,5,7,10,10a,10b,12,12a-tetradecahydrocyclopenta[5,6]naphtho[1,2-f]indazol-1-yl furan-2-carboxylate;

(1R,3aS,3bS,10aR,10bS,11S,12aS)-1-{[(2-Amino-2-oxoethyl)sulfanyl]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-7-(4-fluorophenyl)-11-hydroxy-1-{[(2-hydroxyethyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-7-(4-Fluorophenyl)-11-hydroxy-1-{[(3-hydroxypropyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-7-(4-Fluorophenyl)-11-hydroxy-1-{[(methoxymethyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-1-({[(Acetyloxy)methyl]sulfanyl}carbonyl)-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-1-({[2-(Acetyloxy)ethyl]sulfanyl}carbonyl)-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl propanoate;

(1R,3aS,3bS,10aR,10bS,11S,12aS)-7-(4-Fluorophenyl)-11-hydroxy-1-{[(2-hydroxypropyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl propanoate;

(1R,3aS,3bS,10aR,10bS,11S,12aS)-1-{[(Cyanomethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl propanoate;

(1R,3aS,3bS,10aR,10bS,11S,12aS)-7-(6-Fluoropyridin-3-yl)-11-hydroxy-1-{[(methoxymethyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl propanoate;

(1R,3aS,3bS,10R,10bS,11S,12aS)-1-{[(Fluoromethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl propanoate;

(1R,3aS,3bS,10aR,10bS,11S,12aS)-1-{[(Fluoromethyl)thio]carbonyl}-11-hydroxy-10a,12a-dimethyl-7-[3-(morpholin-4-ylcarbonyl)phenyl]-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10R,10bS,11S,12aS)-1-{[(Cyanomethyl)thio]carbonyl}-7-(2,4-difluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-1-{[(Cyanomethyl)thio]carbonyl}-7-(3,5-difluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-1-{[(Cyanomethyl)thio]carbonyl}-7-(3,4-difluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

Ethyl (1R,3aS,3bS,10aR,10bS,11S,12aS)-7-(4-fluorophenyl)-1,11-dihydroxy-10a,12a-dimethyl-1,2,3,3a,3b,4,5,7,10,10a,10b,11,12,12a-tetradecahydrocyclopenta[5,6]naphtho[1,2-f]indazole-1-carboxylate;

Cyanomethyl(1R,3aS,3bS,10aR,10bS,11S,12aS)-1-[(furan-2-ylcarbonyl)oxy]-11-hydroxy-10a,12a-dimethyl-7-pyridin-2-yl-1,2,3,3a,3b,4,5,7,10,10a,10b,11,12a-tetradecahydrocyclopenta[5,6]naphtho[1,2-f]indazole-1-carboxylate;

(1R,3aS,3bS,10aR,10bS,11S,12aS)-1-{[(Cyanomethyl)sulfanyl]carbonyl}-11-hydroxy-10a,12a-dimethyl-7-[4-(methylsulfonyl)phenyl]-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-7-(3,5-Difluorophenyl)-1-{[(dimethylcarbamoyl)sulfanyl]carbonyl}-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-1-{[(Fluoromethyl)sulfanyl]carbonyl}-11-hydroxy-7-[3-(methoxycarbonyl)phenyl]-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-1-{[(Cyanomethyl)sulfanyl]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl acetate;

(1R,3aS,3bS,10aR,10bS,11S,12aS)-1-{[(Fluoromethyl)sulfanyl]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl acetate;

(1R,3aS,3bS,10aR,10bS,11S,12aS)-1-{[(Cyanomethyl)sulfanyl]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 2-methylpropanoate;

(1R,3aS,3bS,10aR,10bS,11S,12aS)-1-{[(Cyanomethyl)sulfanyl]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 3-methylbutanoate;

(1R,3aS,3bS,10aR,10bS,11S,12aS)-1-{[(Cyanomethyl)sulfanyl]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl cyclobutanecarboxylate;

(1R,3aS,3bS,10aR,10bS,11S,12aS)-1-{[(Cyanomethyl)sulfanyl]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl cyclopentylacetate;

(1R,3aS,3bS,10aR,10bS,11S,12aS)-1-{[(Cyanomethyl)sulfanyl]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl thiophene-2-carboxylate;

(1R,3aS,3bS,10aR,10bS,11S,12aS)-1-{[(Cyanomethyl)sulfanyl]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 5-methylisoxazole-3-carboxylate;

(Methylsulfanyl)methyl(1R,3aS,3bS,10aR,10bS,11S,12aS)-7-(4-fluorophenyl)-1,11-dihydroxy-10a,12a-dimethyl-1,2,3,3a,3b,4,5,7,10,10a,10b,11,12,12a-tetradecahydrocyclopenta[5,6]naphtho[1,2-f]indazole-1-carboxylate;

(1R,3aS,3bS,10aR,10bS,11S,12aS)-7-(4-Fluorophenyl)-11-hydroxy-10a,12a-dimethyl-1-({[(methylsulfanyl)methyl]sulfanyl}carbonyl)-1,2,3,3a,3b,4,5,7,10,10a,10b,11,12,12a-tetradecahydrocyclopenta[5,6]naphtho[1,2-f]indazol-1-yl acetate;

(Methylsulfanyl)methyl(1R,3aS,3bS,10aR,10bS,11S,12aS)-1-(acetyloxy)-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazole-1-carboxylate;

(Methylsulfanyl)methyl(1R,3aS,3bS,10aR,10bS,11S,12aS)-7-(4-fluorophenyl)-11-hydroxy-10a,12a-dimethyl-1-[(methylsulfanyl)methoxy]-1,2,3,3a,3b,4,5,7,10,10a,10b,11,12,12a-tetradecahydrocyclopenta[5,6]naphtho[1,2-f]indazole-1-carboxylate;

2-(Ethylsulfanyl)-2-oxoethyl(1R,3aS,3bS,10R,10bS,11S,12aS)-1-(acetyloxy)-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazole-1-carboxylate;

(1R,3aS,3bS,10aR,10bS,11S,12aS)-7-(4-Fluorophenyl)-11-hydroxy-1-(hydroxyacetyl)-10a,12a-dimethyl-1,2,3,3a,3b,4,5,7,10,10a,10b,11,12,12a-tetradecahydrocyclopenta[5,6]naphtho[1,2-f]indazol-1-yl acetate;

(1R,3aS,3bS,10aR,10bS,11S,12aS)-1-[(Acetylsulfanyl)acetyl]-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl acetate;

(1R,3aS,3bS,10aR,10bS,11S,12aS)-7-(4-Fluorophenyl)-11-hydroxy-10a,12a-dimethyl-1-[(methylsulfanyl)acetyl]-1,2,3,3a,3b,4,5,7,10,10a,10b,11,12,12a-tetradecahydrocyclopenta[5,6]naphtho[1,2-f]indazol-1-yl acetate;

S-(Fluoromethyl)(1R,3aS,3bS,10aR,10bS,11S,12aS)-7-(4-fluorophenyl)-11-hydroxy-10a,12a-dimethyl-1-[(methylsulfanyl)methoxy]1,2,3,3a,3b,4,5,7,10,10a,10b,11,12,12a-tetradecahydrocyclopenta[5,6]naphtho[1,2-f]indazole-1-carbothioate;

(1R,3aS,3bS,10aR,10bS,11S,12aS)-1-{[(Cyanomethyl)sulfanyl]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl tetrahydro-2H-pyran-4-carboxylate;

(1R,3aS,3bS,10aR,10bS,11S,12aS)-7-(4-Fluorophenyl)-11-hydroxy-1-{[(2-hydroxyethyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl tetrahydro-2H-pyran-4-carboxylate;

(1R,3aS,3bS,10aR,10bS,11S,12aS)-1-{[(Cyanomethyl)sulfanyl]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl (2R)-tetrahydrofuran-2-carboxylate;

(1R,3aS,3bS,10aR,10bS,11S,12aS)-7-(4-Fluorophenyl)-11-hydroxy-1-{[(2-hydroxyethyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl tetrahydrofuran-2-carboxylate;

(1R,3aS,3bS,10aR,10bS,11S,12aS)-7-(4-Fluorophenyl)-11-hydroxy-10a,12a-dimethyl-1-(thiocyanatoacetyl)-1,2,3,3a,3b,4,5,7,10,10a,10b,11,12,12a-tetradecahydrocyclopenta[5,6]naphtho[1,2-f]indazol-1-yl acetate;

(1R,3aS,3bS,10aR,10bS,11S,12aS)-1-[(Ethylsulfanyl)acetyl]-7-(4-fluoro phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl acetate;

(1R,3aS,3bS,10aR,10bS,11S,12aS)-1-{[(Cyanomethyl)sulfanyl]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 2-methyltetrahydrofuran-2-carboxylate;

(1R,3aS,3bS,10aR,10bS,11S,12aS)-1-(Chloroacetyl)-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl acetate;

(1R,3aS,3bS,10aR,10bS,11S,12aS)-7-(4-Fluorophenyl)-11-hydroxy-10a,12a-dimethyl-1-[(methyldisulfanyl)acetyl]-1,2,3,3a,3b,4,5,7,10,10a,10b,11,12,12a-tetradecahydrocyclopenta[5,6]naphtho[1,2-f]indazol-1-yl acetate;

(1R,3aS,3bS,10aR,10bS,11S,12aS)-1-{[(Cyanomethyl)sulfanyl]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 1-methoxycyclopropanecarboxylate;

(1R,3aS,3bS,10aR,10bS,11S,12aS)-1-{[(Cyanomethyl)sulfanyl]carbonyl}-7-(4-fluorophenyl)-11-hydroxy-10a,12a-dimethyl 1,2,3,3a,3b,4,5,7,10,10a,10b,11,12,12a-tetradecahydrocyclopenta[5,6]naphtho[1,2-f]indazol-1-yl tetrahydro-2H-pyran-2-carboxylate;

(1R,3aS,3bS,10aR,10bS,11S,12aS)-1-{[(Fluoromethyl)sulfanyl]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl (2R)-tetrahydrofuran-2-carboxylate;

(1R,3aS,3bS,10aR,10bS,11S,12aS)-1-{[(Cyanomethyl)sulfanyl]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl tetrahydro-2H-pyran-3-carboxylate;

(1R,3aS,3bS,10aR,10bS,11S,12aS)-7-[4-Fluoro-3-(hydroxymethyl)phenyl]-1-{[(fluoromethyl)thio]carbonyl}-11-hydroxy-10a,12a-dimethyl-1,2,3,3a,3b, 4,5,7,10,10a,10b,11,12,12a-tetradecahydrocyclopenta[5,6]naphtho[1,2-f]indazol-1-yl cyclopropanecarboxylate;

(1R,3aS,3bS,10aR,10bS,11S,12aS)-1-{[(Cyanomethyl)thio]carbonyl}-7-[4-fluoro-3-(hydroxymethyl)phenyl]-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl methoxyacetate;

(1R,2R,3aS,3bS,10aR,10bS,11S,12aS)-1-{[(Cyanomethyl)thio]carbonyl}-7-(4-fluorophenyl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-1-{[(Cyanomethyl)sulfanyl]carbonyl}-7-[4-fluoro-3-(hydroxymethyl)phenyl]-11-hydroxy-10a,12a-dimethyl-1,2,3,3a,3b, 4,5,7,10,10a,10b,11,12,12a-tetradecahydrocyclopenta[5,6]naphtho[1,2-f]indazol-1-yl cyclopropanecarboxylate;

Cyanomethyl(1R,3aS,3bS,10aR,10bS,11S,12aS)-1-[(cyclopropylcarbonyl)oxy]-7-[4-fluoro-3-(hydroxymethyl)phenyl]-11-hydroxy-10a,12a-dimethyl-1,2,3,3a,3b,4,5,7,10,10a,10b,11,12,12a-tetradecahydrocyclopenta[5,6]naphtho[1,2-f]indazole-1-carboxylate;

(1R,3aS,3bS,10aR,10bS,11S,12aS)-1-{[(Cyanomethyl)sulfanyl]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 1-cyanocyclopropane carboxylate;

(1R,3aS,3bS,10aR,10bS,11S,12aS)-1-{[(Cyanomethyl)sulfanyl]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl tetrahydrofuran-3-carboxylate;

(1R,3aS,3bS,10aR,10bS,11S,12aS)-1-{[(Fluoromethyl)sulfanyl]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl tetrahydrofuran-3-carboxylate;

(1R,3aS,3bS,10aR,10bS,11S,12aS)-1-{[(Fluoromethyl)sulfanyl]carbonyl}-11-hydroxy-10a,12a-dimethyl-7-pyridin-2-yl-1,2,3,3a,3b,4,5,7,10,10a,10b,11,12,12a-tetradecahydrocyclopenta[5,6]naphtho[1,2-f]indazol-1-yl cyclopropane carboxylate;

(1R,3aS,3bS,10aR,10bS,11S,12aS)-7-(5-Chloropyridin-2-yl)-1-{[(fluoromethyl)sulfanyl]carbonyl}-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl cyclopropane carboxylate;

Cyanomethyl(1R,3aS,3bS,10aR,10bS,11S,12aS)-1-[(cyclopropylcarbonyl)oxy]-11-hydroxy-10a,12a-dimethyl-7-pyridin-2-yl-1,2,3,3a,3b,4,5,7,10,10a,10b,11,12,12a-tetradecahydrocyclopenta[5,6]naphtho[1,2-f]indazole-1-carboxylate;

(1R,3aS,3bS,10aR,10bS,11S,12aS)-1-{[(Cyanomethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl cyclopropanecarboxylate;

(1R,3aS,3bS,10aR,10bS,11S,12aS)-7-(6-Fluoropyridin-3-yl)-11-hydroxy-10a,12a-dimethyl-1-[(methylsulfanyl)carbonyl]-1,2,3,3a,3b,4,5,7,10,10a,10b,11,12,12a-tetradecahydrocyclopenta[5,6]naphtho[1,2-f]indazol-1-yl cyclopropanecarboxylate;

(1R,3aS,3bS,10aR,10bS,11S,12aS)-7-(6-Fluoropyridin-3-yl)-11-hydroxy-1-{[(methoxymethyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl cyclopropanecarboxylate;

(1R,3aS,3bS,10aR,10bS,11S,12aS)-7-(6-Fluoropyridin-3-yl)-11-hydroxy-1-{[(2-hydroxyethyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl cyclopropanecarboxylate;

(1R,3aS,3bS,10aR,10bS,11S,12aS)-1-{[(Cyanomethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl methoxyacetate;

(1R,3aS,3bS,10aR,10bS,11S,12aS)-7-(6-Fluoropyridin-3-yl)-11-hydroxy-10a,12a-dimethyl-1-[(methylsulfanyl)carbonyl]-1,2,3,3a,3b,4,5,7,10,10a,10b,11,12,12a-tetradecahydrocyclopenta[5,6]naphtho[1,2-f]indazol-1-yl methoxyacetate;

(1R,3aS,3bS,10aR,10bS,11S,12aS)-7-(6-Fluoropyridin-3-yl)-11-hydroxy-1-{[(methoxymethyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl methoxyacetate;

(1R,3aS,3bS,10aR,10bS,11S,12aS)-7-(6-Fluoropyridin-3-yl)-11-hydroxy-1-{[(2-hydroxyethyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl methoxyacetate;

(1R,3aS,3bS,10aR,10bS,11S,12aS)-1-{[(Cyanomethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 1,3-oxazole-4-carboxylate;

(1R,3aS,3bS,10aR,10bS,11S,12aS)-7-(6-Fluoropyridin-3-yl)-11-hydroxy-10a,12a-dimethyl-1-[(methylsulfanyl)carbonyl]-1,2,3,3a,3b,4,5,7,10,10a,10b,11,12,12a-tetradecahydrocyclopenta[5,6]naphtho[1,2-f]indazol-1-yl 1,3-oxazole-4-carboxylate;

(1R,3aS,3bS,10aR,10bS,11S,12aS)-7-(6-Fluoropyridin-3-yl)-11-hydroxy-1-{[(2-hydroxyethyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl 1,3-oxazole-4-carboxylate;

(1R,3aS,3bS,10aR,10bS,11S,12aS)-7-(6-Fluoropyridin-3-yl)-11-hydroxy-1-{[(methoxymethyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl 1,3-oxazole-4-carboxylate;

S-(Cyanomethyl)(1R,3aS,3bS,10aR,10bS,11S,12aS)-7-(6-fluoropyridin-3-yl)-1,11-dihydroxy-10a,12a-dimethyl-1,2,3,3a,3b,4,5,7,10,10a,10b,11,12,12a-tetradecahydrocyclopenta[5,6]naphtho[1,2-f]indazole-1-carbothioate;

S-Methyl(1R,3aS,3bS,10aR,10bS,11S,12aS)-7-(6-fluoropyridin-3-yl)-1,11-dihydroxy-10a,12a-dimethyl-1,2,3,3a,3b,4,5,7,10,10a,10b,11,12,12a-tetradecahydrocyclopenta[5,6]naphtho[1,2-f]indazole-1-carbothioate;

(1R,3aS,3bS,10aR,10bS,11S,12aS)-1-{[(Cyanomethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-7-(6-Fluoropyridin-3-yl)-11-hydroxy-10a,12a-dimethyl-1-[(methylsulfanyl)carbonyl]-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-7-(6-Fluoropyridin-3-yl)-11-hydroxy-1-{[(2-hydroxyethyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-1-{[(Fluoromethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-1-{[(Fluoromethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl methoxyacetate;

(1R,3aS,3bS,10aR,10bS,11S,12aS)-1-{[(Fluoromethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl acetate;

(1R,3aS,3bS,10aR,10bS,11S,12aS)-7-(6-Fluoropyridin-3-yl)-11-hydroxy-10a,12a-dimethyl-1-[(methylsulfanyl)carbonyl]-1,2,3,3a,3b,4,5,7,10,10a,10b,11,12,12a-tetradecahydrocyclopenta[5,6]naphtho[1,2-f]indazol-1-yl acetate;

(1R,3aS,3bS,10aR,10bS,11S,12aS)-1-{[(Cyanomethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl acetate;

(1R,3aS,3bS,10aR,10bS,11S,12aS)-1-{[(Cyanomethyl)sulfanyl]carbonyl}-7-(3-{[(cyanomethyl)sulfanyl]carbonyl}-4-fluorophenyl)-11-hydroxy-10a,12a-dimethyl-1,2,3a,3b,4,5,7,10,10a,10b,11,12,12a-tetradecahydrocyclopenta[5,6]naphtho[1,2-f]indazol-1-yl propanoate;

(1R,3aS,3bS,10aR,10bS,11S,12aS)-7-{4-Fluoro-3-[(methylsulfanyl)carbonyl]phenyl}-11-hydroxy-10a,12a-dimethyl-1-[(methylsulfanyl)carbonyl]-1,2,3,3a,3b,4,5,7,10,10a,10b,11,12,12a-tetradecahydrocyclopenta[5,6]naphtho[1,2-f]indazol-1-yl propanoate;

(1R,3aS,3bS,10aR,10bS,11S,12aS)-1-{[(Cyanomethyl)thio]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 1-methyl-1H-pyrrole-2-carboxylate;

(1R,3aS,3bS,10aR,10bS,11BS,12aS)-1-{[(Fluoromethyl)thio]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 1-methyl-1H-pyrrole-2-carboxylate;

(1R,3aS,3bS,10aR,10bS,11S,12aS)-7-(4-Fluorophenyl)-11-hydroxy-1-{[(2-hydroxyethyl)thio]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl 1-methyl-1H-pyrrole-2-carboxylate;

(1R,3aS,3bS,10aR,10bS,11S,12aS)-1-{[(Fluoromethyl)thio]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl cyclopropanecarboxylate;

S-(Fluoromethyl)(1R,3aS,3bS,10aR,10bS,11S,12aS)-7-(6-fluoropyridin-3-yl)-1,11-dihydroxy-10a,12a-dimethyl-1,2,3,3a,3b,4,5,7,10,10a,10b,11,12,12a-tetradecahydrocyclopenta[5,6]naphtho[1,2-f]indazole-1-carbothioate;

(1R,3aS,3bS,10aR,10bS,11S,12aS)-1-{[(Fluoromethyl)thio]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 1,3-oxazole-4-carboxylate;

(1R,3aS,3bS,10aR,10bS,11S,12aS)-7-(6-Fluoropyridin-3-yl)-11-hydroxy-1-{[(methoxymethyl)thio]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl acetate;

(1R,3aS,3bS,10aR,10bS,11S,12aS)-7-(6-Fluoropyridin-3-yl)-11-hydroxy-1-{[(2-hydroxyethyl)thio]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl acetate;

Cyanomethyl(1R,3aS,3bS,10aR,10bS,11S,12aS)-1-[(cyclopropylcarbonyl)oxy]-11-hydroxy-10a,12a-dimethyl-7-(2-methylpyridin-4-yl)-1,2,3,3a,3b,4,5,7,10,10a,10b,11,12,12a-tetradecahydrocyclopenta[5,6]naphtho[1,2-f]indazole-1-carboxylate;

Cyanomethyl(1R,3aS,3bS,10aR,10bS,11S,12aS)-1-[(cyclopropylcarbonyl)oxy]-11-hydroxy-10a,12a-dimethyl-7-pyridin-2-yl-1,2,3,3a,3b,4,5,7,10,10a,10b,11,12,12a-tetradecahydrocyclopenta[5,6]naphtho[1,2-f]indazole-1-carboxylate;

Cyanomethyl(1R,3aS,3bS,10aR,10bS,11S,12aS)-1-[(cyclopropylcarbonyl)oxy]-11-hydroxy-10a,12a-dimethyl-7-pyridazin-4-yl-1,2,3,3a,3b,4,5,7,10,10a,10b,11,12,12a-tetradecahydrocyclopenta[5,6]naphtho[1,2-f]indazole-1-carboxylate;

(1R,3aS,3bS,10aR,10bS,11S,12aS)-1-{[(Cyanomethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl (2R)-tetrahydrofuran-2-carboxylate;

(1R,3aS,3bS,10aR,10bS,11S,12aS)-7-(6-Fluoropyridin-3-yl)-11-hydroxy-1-{[(2-hydroxyethyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl (2R)-tetrahydrofuran-2-carboxylate;

(1R,3aS,3bS,10aR,10bS,11S,12aS)-1-{[(Fluoromethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl (2R)-tetrahydrofuran-2-carboxylate;

(1R,3aS,3bS,10aR,10bS,11S,12aS)-7-(6-Fluoropyridin-3-yl)-11-hydroxy-10a,12a-dimethyl-1-[(methylsulfanyl)carbonyl]-1,2,3,3a,3b,4,5,7,10,10a,10b,11,12,12a-tetradecahydrocyclopenta[5,6]naphtho[1,2-f]indazol-1-yl (2R)-tetrahydrofuran-2-carboxylate;

(1R,3aS,3bS,10aR,10bS,11S,12aS)-1-{[(Cyanomethyl)sulfanyl]carbonyl}-11-hydroxy-10a,12a-dimethyl-7-pyrazin-2-yl-1,2,3,3a,3b,4,5,7,10,10a,10b,11,12,12a-tetradecahydrocyclopenta[5,6]naphtho[1,2-f]indazol-1-yl cyclopropanecarboxylate;

(1R,3aS,3bS,10aR,10bS,11S,12aS)-11-Hydroxy-1-{[(2-hydroxyethyl)sulfanyl]carbonyl}-10a,12a-dimethyl-7-pyrazin-2-yl-1,2,3,3a,3b,4,5,7,10,10a,10b,11,12,12a-tetradecahydrocyclopenta[5,6]naphtho[1,2-f]indazol-1-yl cyclopropane carboxylate;

(1R,3aS,3bS,10aR,10bS,11S,12aS)-1-{[(Cyanomethyl)sulfanyl]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 1-methyl-1H-imidazole-4-carboxylate;

(1R,3aS,3bS,10aR,10bS,11S,12aS)-1-{[(Cyanomethyl)sulfanyl]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 1-methyl-1H-imidazole-2-carboxylate;

(1R,3aS,3bS,10aS,10bR,11S,12aS)-1-{[(Cyanomethyl)sulfanyl]carbonyl}-10b-fluoro-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aS,10bR,11S,12aS)-1-{[(Fluoromethyl)sulfanyl]carbonyl}-10b-fluoro-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aS,10bR,11S,12aS)-1-{[(Cyanomethyl)sulfanyl]carbonyl}-10b-fluoro-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl cyclopropanecarboxylate;

(1R,3aS,3bS,10aS,10bR,11S,12aS)-1-{[(Fluoromethyl)sulfanyl]carbonyl}-10b-fluoro-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl cyclopropanecarboxylate;

(1R,3aS,3bS,10aS,10bR,11S,12aS)-1-{[(Cyanomethyl)sulfanyl]carbonyl}-10b-fluoro-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl methoxyacetate;

(1R,3aS,3bS,10aS,10bR,11S,12aS)-1-{[(Fluoromethyl)sulfanyl]carbonyl}-10b-fluoro-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl methoxyacetate;

(1R,3aS,3bS,10aS,10bR,11S,12aS)-1-{[(Cyanomethyl)sulfanyl]carbonyl}-10b-fluoro-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl propanoate;

(1R,3aS,3bS,10aS,10bR,11S,12aS)-1-{[(Fluoromethyl)sulfanyl]carbonyl}-10b-fluoro-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl propanoate;

(1R,3aS,3bS,10aS,10bR,11S,12aS)-1-{[(Cyanomethyl)sulfanyl]carbonyl}-10b-fluoro-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 1,3-oxazole-4-carboxylate;

(1R,3aS,3bS,10aS,10bR,11S,12aS)-1-{[(Fluoromethyl)sulfanyl]carbonyl}-10b-fluoro-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 1,3-oxazole-4-carboxylate;

(1R,3aS,3bS,10aS,10bR,11S,12aS)-1-{[(Cyanomethyl)sulfanyl]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl propanoate;

(1R,3aS,3bS,10aS,10bR,11S,12aS)-1-{[(Fluoromethyl)sulfanyl]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl propanoate;

(1R,3aS,3bS,10aS,10bR,11S,12aS)-1-{[(Cyanomethyl)sulfanyl]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl methoxyacetate;

(1R,3aS,3bS,10aS,10bR,11S,12aS)-1-{[(Fluoromethyl)sulfanyl]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl methoxyacetate;

(1R,3aS,3bS,10aS,10bR,11S,12aS)-1-{[(Cyanomethyl)sulfanyl]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl cyclopropanecarboxylate;

(1R,3aS,3bS,10aS,10bR,11S,12aS)-1-{[(Fluoromethyl)sulfanyl]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl cyclopropanecarboxylate;

(1R,3aS,3bS,10aS,10bR,11S,12aS)-1-{[(Cyanomethyl)sulfanyl]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 1,3-oxazole-4-carboxylate;

(1R,3aS,3bS,10aS,10bR,11S,12aS)-1-{[(Fluoromethyl)sulfanyl]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 1,3-oxazole-4-carboxylate;

(1R,3aS,3bS,10aS,10bR,11S,12aS)-1-{[(Cyanomethyl)sulfanyl]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aS,10bR,11S,12aS)-1-{[(Fluoromethyl)sulfanyl]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,5S,10aR,10bS,11S,12aS)-1-{[(Cyanomethyl)sulfanyl]carbonyl}-7-(4-fluorophenyl)-11-hydroxy-5,10a,12a-trimethyl-1,2,3,3a,3b,4,5,7,10,10a,10b,11,12,12a-tetradecahydrocyclopenta[5,6]naphtho[1,2-f]indazol-1-yl propanoate;

(1R,3aS,3bS,5S,10aR,10bS,11S,12aS)-1-{[(Fluoromethyl)sulfanyl]carbonyl}-7-(4-fluorophenyl)-11-hydroxy-5,10a,12a-trimethyl-1,2,3,3a,3b,4,5,7,10,10a,10b,11,12,12a-tetradecahydrocyclopenta[5,6]naphtho[1,2-f]indazol-1-yl propanoate;

(1R,3aS,3bS,5S,10aR,10bS,11S,12aS)-1-{[(Cyanomethyl)sulfanyl]carbonyl}-7-(4-fluorophenyl)-11-hydroxy-5,10a,12a-trimethyl-1,2,3,3a,3b,4,5,7,10,10a,10b,11,12,12a-tetradecahydrocyclopenta[5,6]naphtho[1,2-f]indazol-1-yl methoxyacetate;

(1R,3aS,3bS,5S,10aR,10bS,11S,12aS)-1-{[(Fluoromethyl)sulfanyl]carbonyl}-7-(4-fluorophenyl)-11-hydroxy-5,10a,12a-trimethyl-1,2,3,3a,3b,4,5,7,10,10a,10b,11,12, 12a-tetradecahydrocyclopenta[5,6]naphtho[1,2-f]
indazol-1-yl methoxyacetate;
(1R,3aS,3bS,5S,10aR,10bS,11S,12aS)-1-{[(Cyanomethyl)
sulfanyl]carbonyl}-7-(4-fluorophenyl)-11-hydroxy-5,
10a,12a-trimethyl-1,2,3,3a,3b,4,5,7,10,10a,10b,11,12,
12a-tetradecahydrocyclopenta[5,6]naphtho[1,2-f]
indazol-1-yl cyclopropanecarboxylate;
(1R,3aS,3bS,5S,10aR,10bS,11S,12aS)-1-{[(Fluoromethyl)
sulfanyl]carbonyl}-7-(4-fluorophenyl)-11-hydroxy-5,
10a,12a-trimethyl-1,2,3,3a,3b,4,5,7,10,10a,10b,11,12,
12a-tetradecahydrocyclopenta[5,6]naphtho[1,2-f]
indazol-1-yl cyclopropanecarboxylate;
(1R,3aS,3bS,5S,10aR,10bS,11S,12aS)-1-{[(Cyanomethyl)
sulfanyl]carbonyl}-7-(4-fluorophenyl)-11-hydroxy-5,
10a,12a-trimethyl-1,2,3,3a,3b,4,5,7,10,10a,10b,11,12,
12a-tetradecahydrocyclopenta[5,6]naphtho[1,2-f]
indazol-1-yl furan-2-carboxylate;
(1R,3aS,3bS,5S,10aR,10bS,11S,12aS)-1-{[(Fluoromethyl)
sulfanyl]carbonyl}-7-(4-fluorophenyl)-11-hydroxy-5,
10a,12a-trimethyl-1,2,3,3a,3b,4,5,7,10,10a,10b,11,12,
12a-tetradecahydrocyclopenta[5,6]naphtho[1,2-f]
indazol-1-yl furan-2-carboxylate;
and pharmaceutically acceptable salts of any one thereof.

It should be noted that each of the chemical compounds listed above represents a particular and independent aspect of the invention.

The present invention further provides a process for the preparation of a compound of formula (I) or a pharmaceutically acceptable salt thereof as defined above which comprises reacting a compound of formula (II)

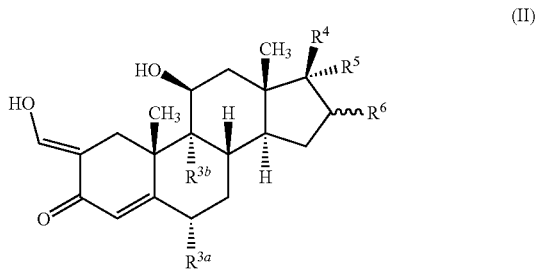

(II)

wherein $R^{3a}$, $R^{3b}$, $R^4$, $R^5$ and $R^6$ are as defined in formula (I), with a compound of formula (III) or an acid addition salt (e.g. hydrochloride salt) thereof

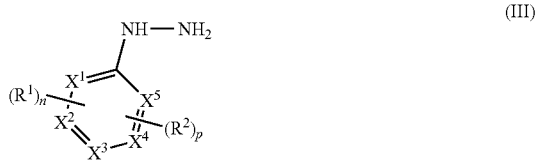

(III)

wherein n, p, $R^1$, $R^2$, $X^1$, $X^2$, $X^3$, $X^4$ and $X^5$ are as defined in formula (I), and optionally thereafter carrying out one or more of the following procedures:
  converting a compound of formula (I) into another compound of formula (I)
  removing any protecting groups
  forming a pharmaceutically acceptable salt.

The above process is conveniently carried out in the presence of an organic solvent such as acetic acid/water mixture at room temperature (20° C.) or, alternatively, in the presence of an organic solvent such as ethanol at a temperature in the range from room temperature (20° C.) to 90° C. Preferably, the reaction is carried out in the presence of a base, e.g. an alkali metal acetate such as potassium acetate.

The compounds of formula (II) may be prepared by reacting a compound of formula (IV)

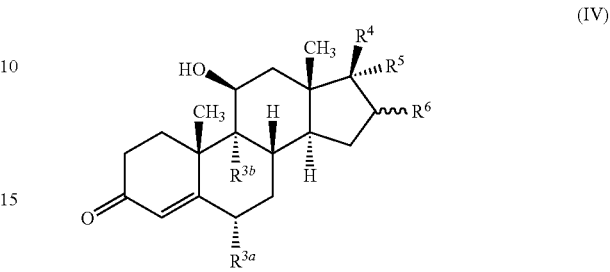

(IV)

wherein $R^{3a}$, $R^{3b}$, $R^4$, $R^5$ and $R^6$ are as defined in formula (II), with methyl or ethyl formate in the presence of a base such as sodium hydride, in a manner analogous to the method described in the journal article by Wuest, F et al., *Steroids*, 68 (2003), 177-191. Compounds of formulae (III) and (IV) are either commercially available, are well known in the literature or may be prepared easily using known techniques.

It will be appreciated by those skilled in the art that in the processes of the present invention certain functional groups such as hydroxyl or amino groups in the reagents may need to be protected by protecting groups. Thus, the preparation of the compounds of formula (I) may involve, at an appropriate stage, the removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', 3$^{rd}$ edition, T. W. Greene and P. G. M. Wuts, Wiley-Interscience (1999).

The compounds of formula (I) above may be converted to a pharmaceutically acceptable salt thereof, preferably an acid addition salt such as a hydrochloride, hydrobromide, trifluoroacetate, sulphate, phosphate, acetate, fumarate, maleate, tartrate, lactate, citrate, pyruvate, succinate, oxalate, methanesulphonate or p-toluenesulphonate.

The compounds of formula (I) and pharmaceutically acceptable salts thereof may exist in solvated, for example hydrated, as well as unsolvated forms, and the present invention encompasses all such solvated forms.

Compounds of formula (I) are capable of existing in stereoisomeric forms. It will be understood that the invention encompasses the use of all geometric and optical isomers (including atropisomers) of the compounds of formula (I) and mixtures thereof including racemates. The use of tautomers and mixtures thereof also form an aspect of the present invention. Enantiomerically pure forms are particularly desired.

The compounds of formula (I) and their pharmaceutically acceptable salts have activity as pharmaceuticals, in particular as modulators of glucocorticoid receptor activity, and thus may be used in the treatment of:
1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fuingal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus;

2. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia greata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

3. eyes: blepharitis; conjunctivitis, including perennial and vernal allergic conjunctivitis; iritis; anterior and posterior uveitis; choroiditis; autoimmune, degenerative or inflammatory disorders affecting the retina; ophthalmitis including sympathetic ophthalmitis; sarcoidosis; infections including viral, fungal, and bacterial;

4. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

5. allograft rejection: acute and chronic following, for example, transplantation of kidney, heart, liver, lung, bone marrow, skin or cornea or following blood transfusion; or chronic graft versus host disease;

6. other auto-immune and allergic disorders including rheumatoid arthritis, irritable bowel syndrome, systemic lupus erythematosus, multiple sclerosis, Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome and Sazary syndrome;

7. oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and, 8. infectious diseases: virus diseases such as genital warts, common warts, plantar warts, hepatitis B, hepatitis C, herpes simplex virus, molluscum contagiosum, variola, human immunodeficiency virus (HIV), human papilloma virus (HPV), cytomegalovirus (CMV), varicella zoster virus (VZV), rhinovirus, adenovirus, coronavirus, influenza, para-influenza; bacterial diseases such as tuberculosis and mycobacterium avium, leprosy; other infectious diseases, such as fungal diseases, chlamydia, candida, aspergillus, cryptococcal meningitis, pneumocystis carnii, cryptosporidiosis, histoplasmosis, toxoplasmosis, trypanosome infection and leishmaniasis.

Thus, the present invention provides a compound of formula (I) or a pharmaceutically acceptable salt thereof as hereinbefore defined for use in therapy.

In a further aspect, the present invention provides the use of a compound of formula (I) or a pharmaceutically acceptable salt thereof as hereinbefore defined in the manufacture of a medicament for use in therapy.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

In particular, the compounds of the invention (including pharmaceutically acceptable salts) may be used in the treatment of asthma {such as bronchial, allergic, intrinsic, extrinsic or dust asthma, particularly chronic or inveterate asthma (for example late asthma or airways hyper-responsiveness)}, chronic obstructive pulmonary disease (COPD) or allergic rhinitis.

The invention also provides a method of treating, or reducing the risk of, an obstructive airways disease or condition (e.g. asthma or COPD) which comprises administering to a patient in need thereof a therapeutically effective amount of a compound of formula (I) or a pharmaceutically acceptable salt thereof as hereinbefore defined.

For the above-mentioned therapeutic uses the dosage administered will, of course, vary with the compound employed, the mode of administration, the treatment desired and the disorder indicated. For example, the daily dosage of the compound of the invention, if inhaled, may be in the range from 0.05 micrograms per kilogram body weight (µg/kg) to 100 micrograms per kilogram body weight (µg/kg). Alternatively, if the compound is administered orally, then the daily dosage of the compound of the invention may be in the range from 0.01 micrograms per kilogram body weight (µg/kg) to 100 milligrams per kilogram body weight (mg/kg).

The compounds of formula (I) and pharmaceutically acceptable salts thereof may be used on their own but will generally be administered in the form of a pharmaceutical composition in which the formula (I) compound/salt (active ingredient) is in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I) or a pharmaceutically acceptable salt thereof as hereinbefore defined in association with a pharmaceutically acceptable adjuvant, diluent or carrier.

The invention further provides a process for the preparation of a pharmaceutical composition of the invention which comprises mixing a compound of formula (I) or a pharmaceutically acceptable salt thereof as hereinbefore defined with a pharmaceutically acceptable adjuvant, diluent or carrier.

The pharmaceutical compositions may be administered topically (e.g. to the skin or to the lung and/or airways) in the form, e.g., of creams, solutions, suspensions, heptafluoroalkane (HFA) aerosols and dry powder formulations, for example, formulations in the inhaler device known as the Turbuhaler®; or systemically, e.g. by oral administration in the form of tablets, capsules, syrups, powders or granules; or by parenteral administration in the form of a sterile solution, suspension or emulsion for injection (including intravenous, subcutaneous, intramuscular, intravascular or infusion); or by rectal administration in the form of suppositories.

Dry powder formulations and pressurized HFA aerosols of the compounds of the invention (that is, compounds of formula (I) and pharmaceutically acceptable salts thereof) may be administered by oral or nasal inhalation. For inhalation, the compound is desirably finely divided. The finely divided compound preferably has a mass median diameter of less than 10 micrometres (μm), and may be suspended in a propellant mixture with the assistance of a dispersant, such as a $C_8$-$C_{20}$ fatty acid or salt thereof, (for example, oleic acid), a bile salt, a phospholipid, an alkyl saccharide, a perfluorinated or polyethoxylated surfactant, or other pharmaceutically acceptable dispersant.

The compounds of the invention may also be administered by means of a dry powder inhaler. The inhaler may be a single or a multi dose inhaler, and may be a breath actuated dry powder inhaler.

One possibility is to mix the finely divided compound of the invention with a carrier substance, for example, a mono-, di- or polysaccharide, a sugar alcohol, or another polyol. Suitable carriers are sugars, for example, lactose, glucose, raffinose, melezitose, lactitol, maltitol, trehalose, sucrose, mannitol; and starch. Alternatively the finely divided compound may be coated by another substance. The powder mixture may also be dispensed into hard gelatine capsules, each containing the desired dose of the active compound.

Another possibility is to process the finely divided powder into spheres which break up during the inhalation procedure. This spheronized powder may be filled into the drug reservoir of a multidose inhaler, for example, that known as the Turbuhaler® in which a dosing unit meters the desired dose which is then inhaled by the patient. With this system the active ingredient, with or without a carrier substance, is delivered to the patient.

For oral administration the compound of the invention may be admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum and titanium dioxide. Alternatively, the tablet may be coated with a suitable polymer dissolved in a readily volatile organic solvent.

For the preparation of soft gelatine capsules the compound of the invention may be admixed with, for example, a vegetable oil or polyethylene glycol. Hard gelatine capsules may contain granules of the compound using either the abovementioned excipients for tablets. Also liquid or semisolid formulations of the compound of the invention may be filled into hard gelatine capsules.

Liquid preparations for oral application may be in the form of syrups or suspensions, for example, solutions containing the compound of the invention, the balance being sugar and a mixture of ethanol, water, glycerol and propylene glycol. Optionally such liquid preparations may contain colouring agents, flavouring agents, saccharine and/or carboxymethylcellulose as a thickening agent or other excipients known to those skilled in art.

The compounds of the invention (that is, compounds of formula (I) and pharmaceutically acceptable salts thereof) may also be administered in conjunction with other compounds used for the treatment of the above conditions.

The invention therefore further relates to combination therapies wherein a compound of the invention or a pharmaceutical composition or formulation comprising a compound of the invention is administered concurrently or sequentially or as a combined preparation with another therapeutic agent or agents, for the treatment of one or more of the conditions listed.

In particular, for the treatment of the inflammatory diseases such as (but not restricted to) rheumatoid arthritis, osteoarthritis, asthma, allergic rhinitis, chronic obstructive pulmonary disease (COPD), psoriasis, and inflammatory bowel disease, the compounds of the invention may be combined with the following agents: non-steroidal anti-inflammatory agents (hereinafter NSAIDs) including non-selective cyclo-oxygenase COX-1/COX-2 inhibitors whether applied topically or systemically (such as piroxicam, diclofenac, propionic acids such as naproxen, flurbiprofen, fenoprofen, ketoprofen and ibuprofen, fenamates such as mefenamic acid, indomethacin, sulindac, azapropazone, pyrazolones such as phenylbutazone, salicylates such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticosteroids (whether administered by topical, oral, intramuscular, intravenous, or intra-articular routes); methotrexate; leflunomide; hydroxychloroquine; d-penicillamine; auranofin or other parenteral or oral gold preparations; analgesics; diacerein; intra-articular therapies such as hyaluronic acid derivatives; and nutritional supplements such as glucosamine.

The present invention still further relates to the combination of a compound of the invention together with a cytokine or agonist or antagonist of cytokine function, (including agents which act on cytokine signalling pathways such as modulators of the SOCS system) including alpha-, beta-, and gamma-interferons; insulin-like growth factor type I (IGF-1); interleukins (IL) including IL1 to 17, and interleukin antagonists or inhibitors such as anakinra; tumour necrosis factor alpha (TNF-α) inhibitors such as anti-TNF monoclonal antibodies (for example infliximab; adalimumab, and CDP-870) and TNF receptor antagonists including immunoglobulin molecules (such as etanercept) and low-molecular-weight agents such as pentoxyfylline.

In addition the invention relates to a combination of a compound of the invention with a monoclonal antibody targeting B-Lymphocytes (such as CD20 (rituximab), MRA-aIL16R and T-Lymphocytes, CTLA4-Ig, HuMax Il-15).

The present invention still further relates to the combination of a compound of the invention with a modulator of chemokine receptor function such as an antagonist of CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and CX$_3$CR1 for the C—X$_3$—C family.

The present invention further relates to the combination of a compound of the invention with an inhibitor of matrix metalloprotease (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11) and MMP-9 and MMP-12, including agents such as doxycycline.

The present invention still further relates to the combination of a compound of the invention and a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; a N-(5-substituted)-thiophene-2-alkylsulfonamide; 2,6-di-tert-butylphenolhydrazones; a methoxytetrahydropyrans such as Zeneca ZD-2138; the compound SB-210661; a pyridinyl-substituted 2-cyanonaphthalene compound such as L-739,010; a 2-cyanoquinoline compound such as L-746,530; or an indole or quinoline compound such as MK-591, MK-886, and BAY x 1005.

The present invention further relates to the combination of a compound of the invention and a receptor antagonist for leukotrienes (LT) B4, LTC4, LTD4, and LTE4 selected from the group consisting of the phenothiazin-3-1s such as L-651, 392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY x 7195.

The present invention still further relates to the combination of a compound of the invention and a phosphodiesterase (PDE) inhibitor such as a methylxanthanine including theophylline and aminophylline; a selective PDE isoenzyme inhibitor including a PDE4 inhibitor an inhibitor of the isoform PDE4D, or an inhibitor of PDE5.

The present invention further relates to the combination of a compound of the invention and a histamine type 1 receptor antagonist such as cetirizine, loratadine, desloratadine, fexofenadine, acrivastine, terfenadine, astemizole, azelastine, levocabastine, chlorpheniramine, promethazine, cyclizine, or mizolastine; applied orally, topically or parenterally.

The present invention still further relates to the combination of a compound of the invention and a proton pump inhibitor (such as omeprazole) or a gastroprotective histamine type 2 receptor antagonist.

The present invention further relates to the combination of a compound of the invention and an antagonist of the histamine type 4 receptor.

The present invention still further relates to the combination of a compound of the invention and an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride or ethylnorepinephrine hydrochloride.

The present invention further relates to the combination of a compound of the invention and an anticholinergic agents including muscarinic receptor (M1, M2, and M3) antagonist such as atropine, hyoscine, glycopyrrrolate, ipratropium bromide, tiotropium bromide, oxitropium bromide, pirenzepine or telenzepine.

The present invention still further relates to the combination of a compound of the invention and a beta-adrenoreceptor agonist (including beta receptor subtypes 1-4) such as isoprenaline, salbutamol, formoterol, salmeterol, terbutaline, orciprenaline, bitolterol mesylate, or pirbuterol, or a chiral enantiomer thereof.

The present invention further relates to the combination of a compound of the invention and a chromone, such as sodium cromoglycate or nedocromil sodium.

The present invention still further relates to the combination of a compound of the invention with a glucocorticoid, such as flunisolide, triamcinolone acetonide, beclomethasone dipropionate, budesonide, fluticasone propionate, ciclesonide or mometasone furoate.

The present invention further relates to the combination of a compound of the invention with an agent that modulates a nuclear hormone receptor such as PPARs.

The present invention still further relates to the combination of a compound of the invention together with an immunoglobulin (Ig) or Ig preparation or an antagonist or antibody modulating Ig function such as anti-IgE (for example omalizumab).

The present invention further relates to the combination of a compound of the invention and another systemic or topically-applied anti-inflammatory agent, such as thalidomide or a derivative thereof, a retinoid, dithranol or calcipotriol.

The present invention still further relates to the combination of a compound of the invention and combinations of aminosalicylates and sulfapyridine such as sulfasalazine, mesalazine, balsalazide, and olsalazine; and immunomodulatory agents such as the thiopurines.

The present invention further relates to the combination of a compound of the invention together with an antibacterial agent such as a penicillin derivative, a tetracycline, a macrolide, a beta-lactam, a fluoroquinolone, metronidazole, an inhaled aminoglycoside; an antiviral agent including acyclovir, famciclovir, valaciclovir, ganciclovir, cidofovir, amantadine, rimantadine, ribavirin, zanamavir and oseltamavir; a protease inhibitor such as indinavir, nelfinavir, ritonavir, and saquinavir; a nucleoside reverse transcriptase inhibitor such as didanosine, lamivudine, stavudine, zalcitabine or zidovudine; or a non-nucleoside reverse transcriptase inhibitor such as nevirapine or efavirenz.

The present invention still further relates to the combination of a compound of the invention and a cardiovascular agent such as a calcium channel blocker, a beta-adrenoceptor blocker, an angiotensin-converting enzyme (ACE) inhibitor, an angiotensin-2 receptor antagonist; a lipid lowering agent such as a statin or a fibrate; a modulator of blood cell morphology such as pentoxyfylline; thrombolytic, or an anticoagulant such as a platelet aggregation inhibitor.

The present invention further relates to the combination of a compound of the invention and a CNS agent such as an antidepressant (such as sertraline), an anti-Parkinsonian drug (such as deprenyl, L-dopa, ropinirole, pramipexole, a MAOB inhibitor such as selegine and rasagiline, a comP inhibitor such as tasmar, an A-2 inhibitor, a dopamine reuptake inhibitor, an NMDA antagonist, a nicotine agonist, a dopamine agonist or an inhibitor of neuronal nitric oxide synthase), or an anti-Alzheimer's drug such as donepezil, rivastigmine, tacrine, a COX-2 inhibitor, propentofylline or metrifonate.

The present invention still further relates to the combination of a compound of the invention and an agent for the treatment of acute or chronic pain, such as a centrally or peripherally-acting analgesic (for example an opioid or derivative thereof), carbamazepine, phenyloin, sodium valproate, amitryptiline or other anti-depressant agent-s, paracetamol, or a non-steroidal anti-inflammatory agent.

The present invention further relates to the combination of a compound of the invention together with a parenterally or topically-applied (including inhaled) local anaesthetic agent such as lignocaine or a derivative thereof.

A compound of the present invention can also be used in combination with an anti-osteoporosis agent including a hormonal agent such as raloxifene, or a biphosphonate such as alendronate.

The present invention still further relates to the combination of a compound of the invention together with a: (i) tryptase inhibitor; (ii) platelet activating factor (PAF) antagonist; (iii) interleukin converting enzyme (ICE) inhibitor; (iv) IMPDH inhibitor; (v) adhesion molecule inhibitors including VLA-4 antagonist; (vi) cathepsin; (vii) kinase inhibitor such as an inhibitor of tyrosine kinase (such as Btk, Itk, Jak3 or MAP, for example Gefitinib or Imatinib mesylate), a serine/threonine kinase (such as an inhibitor of a MAP kinase such as p38, JNK, protein kinase A, B or C, or IKK), or a kinase involved in cell cycle regulation (such as a cylin dependent kinase); (viii) glucose-6 phosphate dehydrogenase inhibitor; (ix) kinin-$B_1$.- or $B_2$.-receptor antagonist; (x) anti-gout agent, for example colchicine; (xi) xanthine oxidase inhibitor, for example allopurinol; (xii) uricosuric agent, for example probenecid, sulfinpyrazone or benzbromarone; (xiii) growth hormone secretagogue; (xiv) transforming growth factor (TGFβ); (xv) platelet-derived growth factor (PDGF); (xvi) fibroblast growth factor for example basic fibroblast growth factor (bFGF); (xvii) granulocyte macrophage colony stimulating factor (GM-CSF); (xviii) capsaicin cream; (xix) tachykinin $NK_1$. or $NK_3$. receptor antagonist such as NKP-608C, SB-233412 (talnetant) or D-4418; (xx) elastase inhibitor such as UT-77 or ZD-0892; (xxi) TNF-alpha converting enzyme inhibitor (TACE); (xxii) induced nitric oxide synthase (iNOS) inhibitor; (xxiii) chemoattractant receptor-homologous molecule expressed on TH2 cells, (such as a CRTH2 antagonist); (xxiv) inhibitor of P38; (xxv) agent modulating the function of Toll-like receptors (TLR), (xxvi) agent modulating the activity of purinergic receptors such as P2x7; (xxvii) inhibitor of transcription factor activation such as NFkB, API, or STATS; or (xxviii) a glucocorticoid receptor agonist.

In a further aspect the present invention provides a combination (for example for the treatment of COPD, asthma or allergic rhinitis) of a compound of formula (I) or a pharmaceutically acceptable salt thereof as hereinbefore defined and one or more agents independently selected from:

a non-steroidal glucocorticoid receptor (GR-receptor) agonist;

a selective $β_2$ adrenoceptor agonist (such as metaproterenol, isoproterenol, isoprenaline, albuterol, salbutamol, formoterol, salmeterol, terbutaline, orciprenaline, bitolterol mesylate, pirbuterol or indacaterol);

a phosphodiesterase inhibitor (such as a PDE4 inhibitor);

a protease inhibitor (such as a neutrophil elastase or matrix metalloprotease MMP-12 inhibitor);

a glucocorticoid;

an anticholinergic agent;

a modulator of chemokine receptor function (such as a CCR1 receptor antagonist); and an inhibitor of kinase function (such as the kinases p38 or IKK).

The invention also provides a pharmaceutical product comprising, in combination, a preparation of a first active ingredient which is a compound of formula (I) or a pharmaceutically acceptable salt thereof as hereinbefore defined, and a preparation of a second active ingredient which is a non-steroidal glucocorticoid receptor (GR-receptor) agonist;

a selective $β_2$ adrenoceptor agonist;

a phosphodiesterase inhibitor;

a protease inhibitor;

a glucocorticoid;

an anticholinergic agent;

a modulator of chemokine receptor function; or an inhibitor of kinase function;

for simultaneous, sequential or separate use in therapy.

In another aspect, the invention provides a kit comprising a preparation of a first active ingredient which is a compound of formula (I) or a pharmaceutically acceptable salt thereof as hereinbefore defined, and a preparation of a second active ingredient which is a non-steroidal glucocorticoid receptor (GR-receptor) agonist;

a selective $β_2$ adrenoceptor agonist;

a phosphodiesterase inhibitor;

a protease inhibitor;

a glucocorticoid;

an anticholinergic agent;

a modulator of chemokine receptor function; or an inhibitor of kinase function;

and instructions for the simultaneous, sequential or separate administration of the preparations to a patient in need thereof.

A compound of the invention can also be used in combination with an existing therapeutic agent for the treatment of cancer, for example suitable agents include:

(i) an antiproliferative/antineoplastic drug or a combination thereof, as used in medical oncology, such as an alkylating agent (for example cis-platin, carboplatin, cyclophosphamide, nitrogen mustard, melphalan, chlorambucil, busulphan or a nitrosourea); an antimetabolite (for example an antifolate such as a fluoropyrimidine like 5-fluorouracil or tegafur, raltitrexed, methotrexate, cytosine arabinoside, hydroxyurea, gemcitabine or paclitaxel); an antitumour antibiotic (for example an anthracycline such as adriamycin, bleomycin, doxorubicin, daunomycin, epirubicin, idarubicin, mitomycin-C, dactinomycin or mithramycin); an antimitotic agent (for example a vinca alkaloid such as vincristine, vinblastine, vindesine or vinorelbine, or a taxoid such as taxol or taxotere); or a topoisomerase inhibitor (for example an epipodophyllotoxin such as etoposide, teniposide, amsacrine, topotecan or a camptothecin);

(ii) a cytostatic agent such as an antioestrogen (for example tamoxifen, toremifene, raloxifene, droloxifene or iodoxyfene), an oestrogen receptor down regulator (for example fulvestrant), an antiandrogen (for example bicalutamide, flutamide, nilutamide or cyproterone acetate), a LHRH antagonist or LHRH agonist (for example goserelin, leuprorelin or buserelin), a progestogen (for example megestrol acetate), an aromatase inhibitor (for example as anastrozole, letrozole, vorazole or exemestane) or an inhibitor of 5α-reductase such as finasteride;

(iii) an agent which inhibits cancer cell invasion (for example a metalloproteinase inhibitor like marimastat or an inhibitor of urokinase plasminogen activator receptor function);

(iv) an inhibitor of growth factor function, for example: a growth factor antibody (for example the anti-erbb2 antibody trastuzumab, or the anti-erbb1 antibody cetuximab [C225]), a farnesyl transferase inhibitor, a tyrosine kinase inhibitor or a serine/threonine kinase inhibitor, an inhibitor of the epidermal growth factor family (for example an EGFR family tyrosine kinase inhibitor such as N-(3-chloro-4-fluorophenyl)-7-methoxy-6-(3-morpholinopropoxy)quinazolin-4-amine (gefitinib, AZD 1839), N-(3-ethynylphenyl)-6,7-bis(2-methoxyethoxy)quinazolin-4-amine (erlotinib, OSI-774) or 6-acrylamido-N-(3-chloro-4-fluorophenyl)-7-(3-morpholinopropoxy)quinazolin-4-amine (CI 1033)), an inhibitor of the platelet-derived growth factor family, or an inhibitor of the hepatocyte growth factor family;

(v) an antiangiogenic agent such as one which inhibits the effects of vascular endothelial growth factor (for example the anti-vascular endothelial cell growth factor antibody bevacizumab, a compound disclosed in WO 97/22596, WO 97/30035, WO 97/32856 or WO 98/13354), or a compound that works by another mechanism (for example linomide, an inhibitor of integrin αvβ3 function or an angiostatin);

(vi) a vascular damaging agent such as combretastatin A4, or a compound disclosed in WO 99/02166, WO 00/40529, WO 00/41669, WO 01/92224, WO 02/04434 or WO 02/08213;

(vii) an agent used in antisense therapy, for example one directed to one of the targets listed above, such as ISIS 2503, an anti-ras antisense;

(viii) an agent used in a gene therapy approach, for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; or (ix) an agent used in an immunotherapeutic approach, for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

The present invention will now be further explained by reference to the following illustrative examples in which the following abbreviations are used:

| | |
|---|---|
| EtOAc | ethyl acetate |
| HCl | hydrochloric acid |
| H$_2$S | hydrogen sulphide |
| CH$_2$Cl$_2$ | dichloromethane (DCM) |
| DMF | N,N-dimethylformamide |
| NaH | sodium hydride |
| MgSO$_4$ | magnesium sulphate |
| NaNO$_2$ | sodium nitrite |
| K$_2$CO$_3$ | potassium carbonate |
| SnCl$_2$ | tin (II) chloride |
| NaOH | sodium hydroxide |
| Na$_2$SO$_4$ | sodium sulphate |
| NH$_4$Cl | ammonium chloride |
| DIEA | diisopropylethylamine |
| DME | dimethyl ether |
| DMSO | dimethylsulfoxide |
| EtOH | ethanol |
| THF | tetrahydrofuran |
| TFA | trifluoroacetic acid |
| HCl | hydrochloric acid |
| NaHCO$_3$ | sodium hydrogen carbonate |
| Et$_3$N | triethylamine |
| MeOH | methanol |
| MeCN/CH$_3$CN | acetonitrile |
| EDTA | ethylenediaminetetraacetic acid |
| conc. | concentrated |
| rt | room temperature |
| h | hours |
| min | minutes |
| M | molar |
| MS | mass spectrometry |
| APCI | atmospheric chemical ionisation method |
| ESI | electron spray ionisation method |
| NMR | nuclear magnetic resonance |
| SCX | solid phase extraction with a sulfonic acid sorbent |
| HPLC | high performance liquid chromatography |
| LC-MS | liquid chromatography with mass spectrometry detection |

GENERAL METHODS

NMR spectra were recorded on a Varian Mercury-VX 300 MHz instrument or a Varian Inova 400 MHz instrument. The central peaks of chloroform-d (H 7.26 ppm), acetone-d$_6$ (H 2.05 ppm), acetonitrile-d$_3$ ($\delta_H$ 1.94 ppm) or DMSO-d$_6$ (H 2.50 ppm) were used as internal references.

The following method was used for LC/MS analysis:
Instrument Agilent 1100; Column Waters Symmetry 2.1×30 mm; Mass APCI; Flow rate 0.7 mL/min; Wavelength 254 nm; Solvent A: water+0.1% TFA; Solvent B: acetonitrile+0.1% TFA; Gradient 15-95%/B 2.7 min, 95% B 0.3 min.

Column chromatography was carried out using silica gel (0.040-0.063 mm, Merck). For preparative HPLC either a Kromasil® KR-100-5-C18 column (250×20 mm, Akzo Nobel) and mixtures of acetonitrile/water (0.1% TFA) at a flow rate of 10 ml/min or a XTerra® Prep MS C$_{18}$ OBD™ Column, 5 μm, 19×50 mm (acetonitrile/water/0.1% NH$_3$) at a flow rate of 20 ml/min was used. UV=254 nm or 220 nm was used for detection.

Unless stated otherwise, starting materials were commercially available. All solvents and commercial reagents were of laboratory grade and were used as received.

Intermediate 1

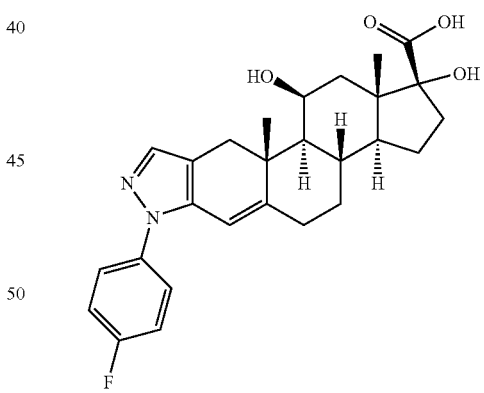

(1R,3aS,3bS,10aR,10bS,11S,12aS)-7-(4-Fluorophenyl)-1,11-dihydroxy-10a,12a-dimethyl-1,2,3,3a,3b,4,5,7,10,10a,10b,11,12,12a-tetradecahydrocyclopenta[5,6]naphtho[1,2-f]indazole-1-carboxylic Acid In a 100 ml round-bottomed flask 1-[(1R,3aS,3bS,10aR,10bS,11S,12aS)-7-(4-fluorophenyl)-1,11-dihydroxy-10a,12a-dimethyl-1,2,3,3a,3b,4,5,7,10,10a,10b,11,12,12a-tetradecahydrocyclopenta[5,6]naphtho[1,2-f]indazol-1-yl]-2-hydroxyethanone (*Steroids* 2003 (68) 177-191) (0.48 g, 1 mmol) was dissolved in MeOH (40 ml). NaOH (6 ml, 1M, 6 mmol) was added and the mixture was stirred vigorously for 6 hours at room temperature in an open vessel. The reaction was monitored by LC-MS. When the reaction was completed the solution was neutralised by the addition of 1M HCl (6 ml, 6 mmol) and the MeOH was removed in vacuo. Water was added to the precipitate (15 ml) and the mixture was stirred for 5 minutes. The solid was then collected by filtration and dried to give 0.4 g (86%) of the desired compound.

$^1$H NMR (400 MHz, CDCl$_3$) δ 7.53 (1H, s); 7.46 (2H, m); 7.19 (2H, t); 6.02 (1H, s); 4.55 (1H, m); 3.03 (1H, d); 2.76-2.65 (2H, m); 2.57-2.48 (2H, m); 2.31 (1H, d); 2.07-1.94 (2H, m); 1.94-1.84 (2H, m); 1.81-1.66 (3H, m); 1.52-1.42 (1H, m); 1.34 (3H, s); 1.28-1.22 (1H, m); 1.18-1.12 (1H, m); 1.11 (3H, s). APCI-MS m/z: 467 [MH$^+$].

Intermediate 2

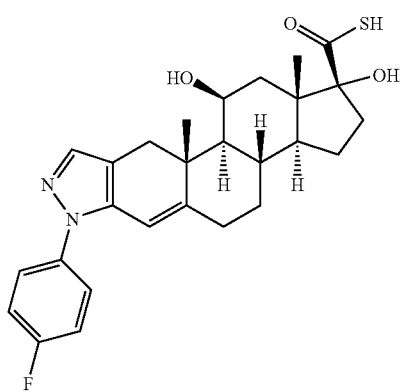

(1R,3aS,3bS,10aR,10bS,11S,12aS)-7-(4-Fluorophenyl)-1,11-dihydroxy-10a,12a-dimethyl-1,2,3,3a,3b,4, 5,7,10,10a,10b,11,12,12a-tetradecahydrocyclopenta [5,6]naphtho[1,2-f]indazole-1-carbothioic S-acid In a 25 ml round-bottomed flask was added Intermediate 1 (0.2 g, 0.43 mmol) and 1,1-carbonyldiimidazole (0.139 g, 0.86 mmol) in DMF (3 ml) to give a yellow solution. The solution was stirred over night at room temperature. H$_2$S (g) was bubbled through the solution for 5 minutes, a colour change from yellow to green was observed. The mixture was then stirred for 30 minutes. The reaction mixture was poured into 1M HCl (15 ml). The solid formed was isolated by filtration, washed with water and dried to give 0.2 g of the crude compound. APCI-MS m/z: 483 [MH$^+$].

Intermediate 3

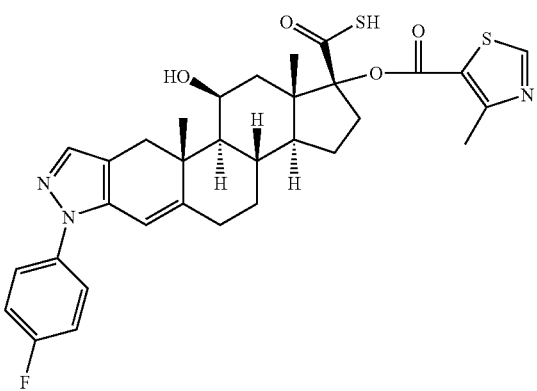

(1R,3aS,3bS,10aR,10bS,11S,12aS)-7-(4-Fluorophenyl)-11-hydroxy-10a,12a-dimethyl-1-{[(4-methyl-1, 3-thiazol-5-yl)carbonyl]oxy}-1,2,3,3a,3b,4,5,7,10, 10a,10b,11,12,12a-tetradecahydrocyclopenta[5,6] naphtho[1,2-f]indazole-1-carbothioic S-acid Intermediate 2 (0.09 g, 0.19 mmol) and triethylamine (0.09 ml, 0.65 mmol) was dissolved in CH$_2$Cl$_2$ (5 ml) to give a yellow solution. The solution was stirred under argon and cooled in an ice-water bath. To this solution was added a solution of 4-methylthiazole-5-carbonyl chloride (0.090 g, 0.56 mmol) in CH$_2$Cl$_2$ (1 ml). The solution was stirred at this temperature for 15 minutes and was then allowed to reach room temperature during 30 minutes. The solution was cooled again in an ice-water bath and diethylamine (0.192 ml, 1.86 mmol) was added. The reaction was allowed to proceed until the formation of the title compound was completed. The crude reaction mixture was partitioned between 1M HCl (15 ml) and CH$_2$Cl$_2$ (10 ml). The organic phase was collected and the aqueous phase was extracted with another portion of CH$_2$Cl$_2$ (10 ml). The combined organic phases were washed with brine, and were finally dried over Na$_2$SO$_4$. Filtration and evaporation gave 0.14 g of a mixture of the expected product and the diethylamide of the excess thiazole acid chloride. The mixture was used in the next step without further purification. APCI-MS m/z: 608 [MH$^+$].

Intermediate 4

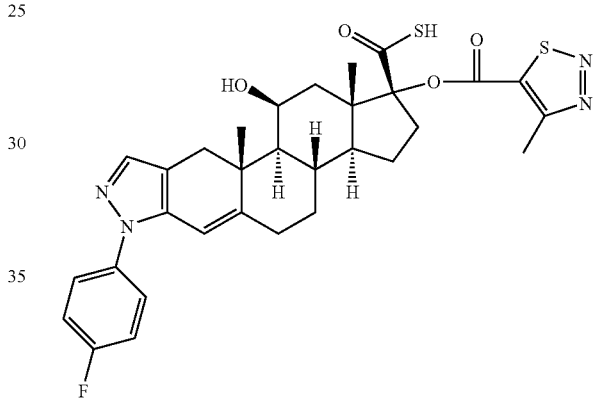

(1R,3aS,3bS,10aR,10bS,11S,12aS)-7-(4-fluorophenyl)-11-hydroxy-10a,12a-dimethyl-1-{[(4-methyl-1, 2,3-thiadiazol-5-yl)carbonyl]oxy}-1,2,3,3a,3b,4,5,7, 10,10a,10b,11,12,12a-tetradecahydrocyclopenta[5,6] naphtho[1,2-f]indazole-1-carbothioic S-acid The compound was prepared according to the procedure for Intermediate 3, starting from Intermediate 2. APCI-MS m/z: 609 [MH$^+$].

Intermediate 5

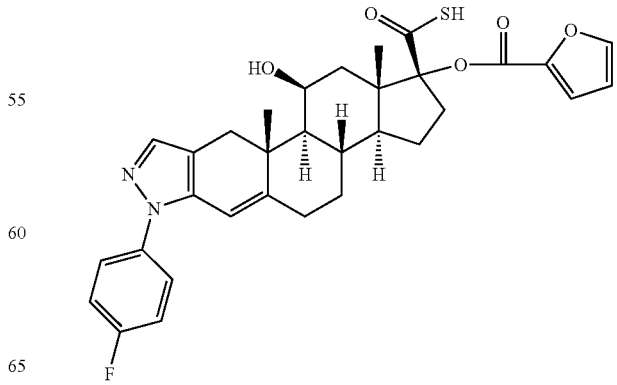

(1R,3aS,3bS,10aR,10bS,11S,12aS)-7-(4-Fluorophenyl)-1-(2-furoyloxy)-11-hydroxy-10a,12a-dimethyl-1,2,3,3a,3b,4,5,7,10,10a,10b,11,12,12a tetradecahydrocyclopenta[5,6]naphtho[1,2-f]indazole-1-carbothioic S-acid The compound was prepared according to the procedure for Intermediate 3, starting from Intermediate 2. APCI-MS m/z: 577 [MH⁺].

Intermediate 6

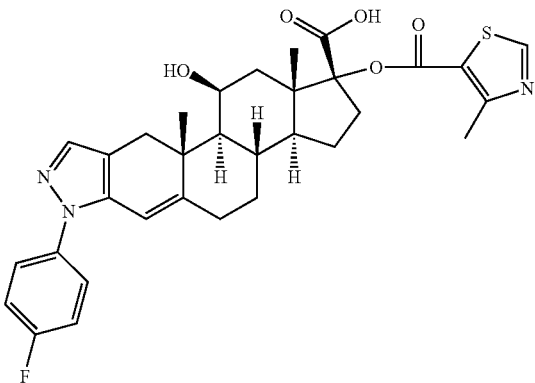

(1R,3aS,3bS,10aR,10bS,11S,12aS)-7-(4-Fluorophenyl)-11-hydroxy-10a,12a-dimethyl-1-{[(4-methyl-1,3-thiazol-5-yl)carbonyl]oxy}-1,2,3,3a,3b,4,5,7,10,10a,10b,11,12,12a-tetradecahydrocyclopenta[5,6]naphtho[1,2-f]indazole-1-carboxylic Acid Intermediate 1 (80 mg, 0.17 mmol) and triethylamine (0.1 ml, 0.72 mmol) was dissolved in CH$_2$Cl$_2$ (10 ml) to give a yellow solution. 4-Methylthiazole-5-carbonyl chloride (83 mg, 0.51 mmol) was added and the solution was cooled on an ice bath under argon. The solution was stirred for 20 minutes at this temperature and diethylamine (0.2 ml, 1.94 mmol) was added. The obtained mixture was stirred in an ice bath for 20 minutes until the formation of the desired product was completed. The crude mixture was diluted with CH$_2$Cl$_2$ (20 ml) and washed with 1M HCl (15 ml) and brine (15 ml) and finally dried over Na$_2$SO$_4$. Filtration and evaporation gave 0.15 g of the crude product as an oil which was purified by preparative HPLC (CH$_3$CN/water, TFA) to give 30 mg of pure material.

$^1$H NMR (400 MHz, CDCl$_3$) δ 8.82 (1H, s); 7.53 (1H, s); 7.46 (2H, m); 7.19 (2H, t); 6.06 (1H, s); 4.62 (1H, m); 3.14-2.98 (2H, m); 2.84-2.73 (5H, m); 2.60-2.42 (2H, m); 2.32 (1H, d); 2.20-1.96 (4H, m); 1.96-1.82 (2H, m); 1.81-1.70 (1H, m); 1.61-1.48 (1H, m); 1.36 (3H, s); 1.30 (1H, dd); 1.21-1.10 (4H, m). APCI-MS m/z: 592 [MH⁺].

Intermediate 7

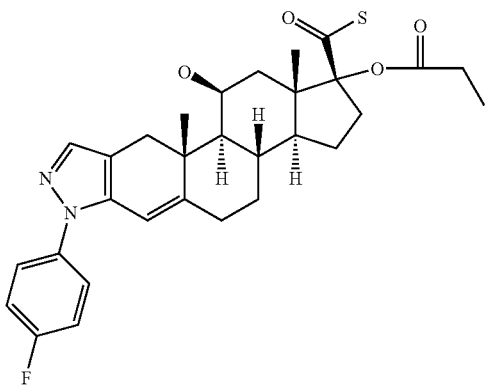

(1R,3aS,3bS,10aR,10bS,11S,12aS)-7-(4-Fluorophenyl)-1-propanoyloxy-11-hydroxy-10a,12a-dimethyl-1,2,3,3a,3b,4,5,7,10,10a,10b,11,12,12a-tetradecahydrocyclopenta[5,6]naphtho[1,2-f]indazole-1-carbothioic S-acid The compound was prepared according to the procedure for Intermediate 3, starting from Intermediate 2. APCI-MS m/z: 539 [MH⁺].

Intermediate 8

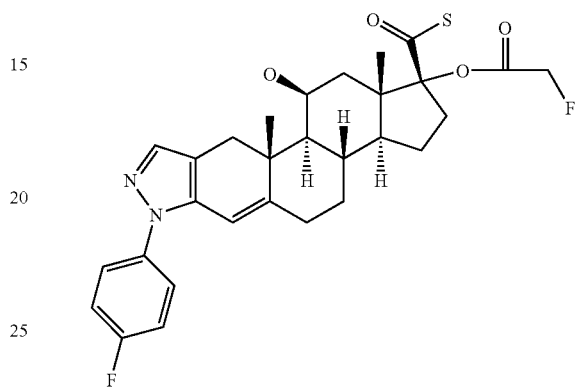

(1R,3aS,3bS,10aR,10bS,11S,12aS)-1-[(fluoroacetyl)oxy]-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazole-1-carbothioic S-acid The compound was prepared according to the procedure for Intermediate 3, starting from Intermediate 2. APCI-MS m/z: 543 [MH⁺].

Intermediate 9

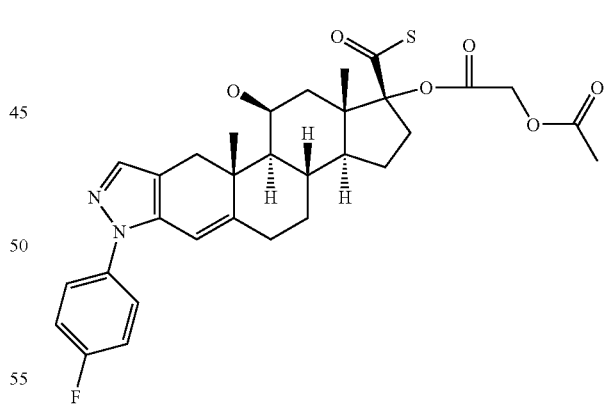

(1R,3aS,3bS,10aR,10bS,11S,12aS)-1-1{[(acetyloxy)acetyl]oxy}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazole-1-carbothioic S-acid The compound was prepared according to the procedure for Intermediate 3, starting from Intermediate 2. APCI-MS m/z: 583 [MH⁺].

Intermediate 10

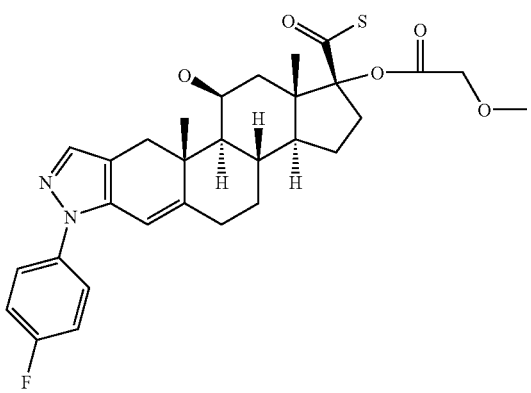

(1R,3aS,3bS,10aR,10bS,11S,12aS)-7-(4-fluorophenyl)-11-hydroxy-1-[(methoxyacetyl)oxy]-10a,12a-dimethyl-1,2,3,3a,3b,4,5,7,10,10a,10b,11,12,12a-tetradecahydrocyclopenta[5,6]naphtho[1,2-f]indazole-1-carbothioic S-acid The compound was prepared according to the procedure for Intermediate 3, starting from Intermediate 2. APCI-MS m/z: 555 [MH⁺].

Intermediate 11

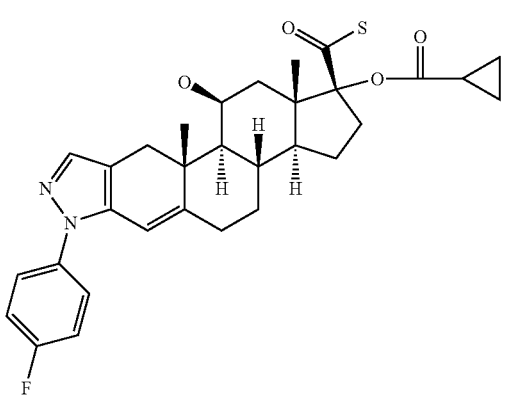

(1R,3aS,3bS,10aR,10bS,11S,12aS)-1-[(cyclopropylcarbonyl)oxy]-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazole-1-carbothioic S-acid The compound was prepared according to the procedure for Intermediate 3, starting from Intermediate 2. APCI-MS m/z: 551 [MH⁺].

Intermediate 12

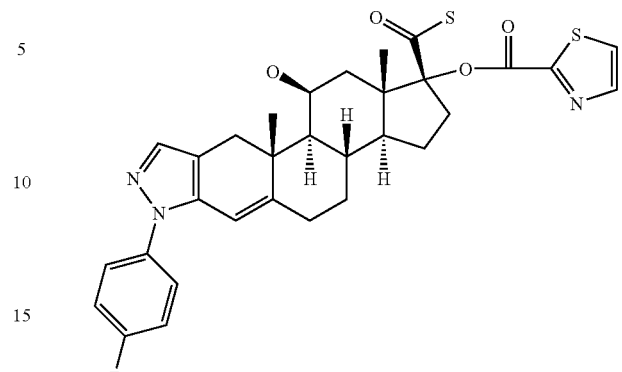

(1R,3aS,3bS,10aR,10bS,11S,12aS)-7-(4-fluorophenyl)-11-hydroxy-10a,12a-dimethyl-1-[(1,3-thiazol-2-ylcarbonyl)oxy]-1,2,3,3a,3b,4,5,7,10,10a,10b,11,12,12a-tetradecahydrocyclopenta[5,6]naphtho[1,2-f]indazole-1-carbothioic S-acid The compound was prepared according to the procedure for Intermediate 3, starting from Intermediate 2 APCI-MS m/z: 594 [MH⁺].

Intermediate 13

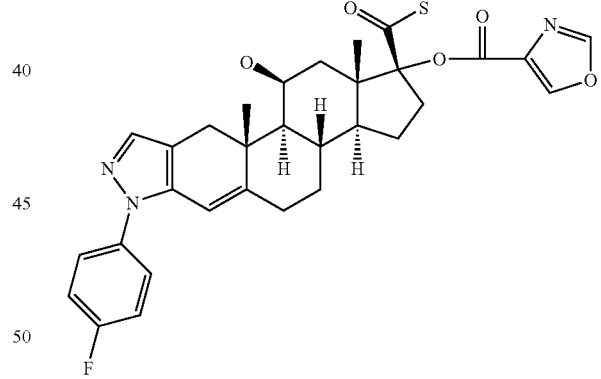

(1R,3aS,3bS,10aR,10bS,11S,12aS)-7-(4-fluorophenyl)-11-hydroxy-10a,12a-dimethyl-1-[(1,3-oxazol-4-ylcarbonyl)oxy]-1,2,3,3a,3b,4,5,7,10,10a,10b,11,12,12a-tetradecahydrocyclopenta[5,6]naphtho[1,2-f]indazole-1-carbothioic S-acid The compound was prepared according to the procedure for Intermediate 3, starting from Intermediate 2. APCI-MS m/z: 578 [MH⁺].

Intermediate 14

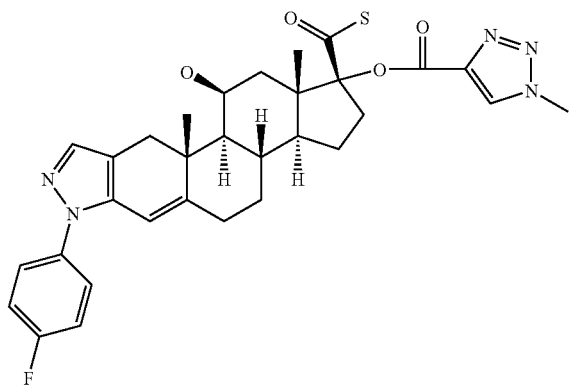

(1R,3aS,3bS,10aR,10bS,11S,12aS)-7-(4-fluorophenyl)-11-hydroxy-10a,12a-dimethyl-1-{[(1-methyl-1H-1,2,3-triazol-4-yl)carbonyl]oxy}-1,2,3,3a,3b,4,5,7,10,10a,b,11,12,12a-tetradecahydrocyclopenta[5,6]naphtho[1,2-f]indazole-1-carbothioic S-acid The compound was prepared according to the procedure for Intermediate 3, starting from Intermediate 2. APCI-MS m/z: 592 [MH+].

Intermediate 15

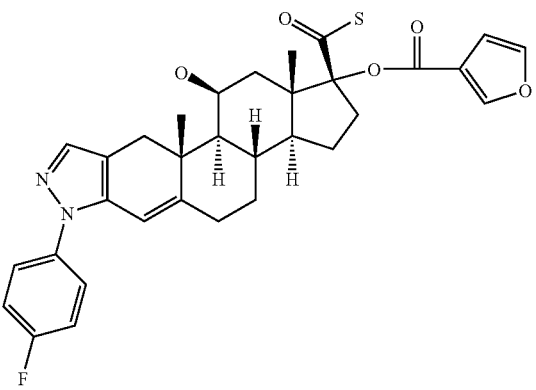

(1R,3aS,3bS,10aR,10bS,11S,12aS)-7-(4-fluorophenyl)-1-[(furan-3-ylcarbonyl)oxy]-1-hydroxy-10a,12a-dimethyl-1,2,3,3a,3b,4,5,7,10,10a,10b,11,12,12a-tetradecahydrocyclopenta[5,6]naphtho[1,2-f]indazole-1-carbothioic S-acid The compound was prepared according to the procedure for Intermediate 3, starting from Intermediate 2. APCI-MS m/z: 577 [MH+].

Intermediate 16

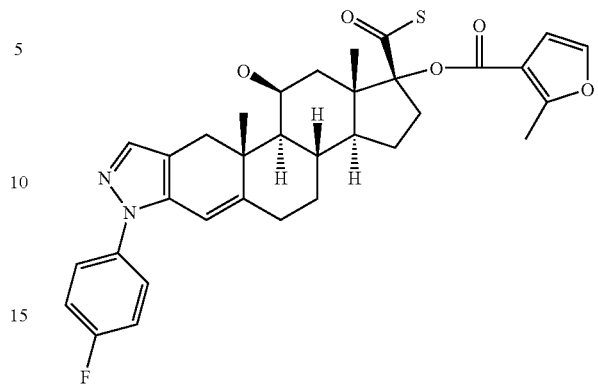

(1R,3aS,3bS,10aR,10bS,11S,12aS)-7-(4-fluorophenyl)-11-hydroxy-10a,12a-dimethyl-1-{[(2-methylfuran-3-yl)carbonyl]oxy}-1,2,3,3a,3b,4,5,7,10,10a,10b,11,12,12a-tetradecahydrocyclopenta[5,6]naphtho[1,2-f]indazole-1-carbothioic S-acid The compound was prepared according to the procedure for Intermediate 3, starting from Intermediate 2. APCI-MS m/z: 591 [MH+].

Intermediate 17

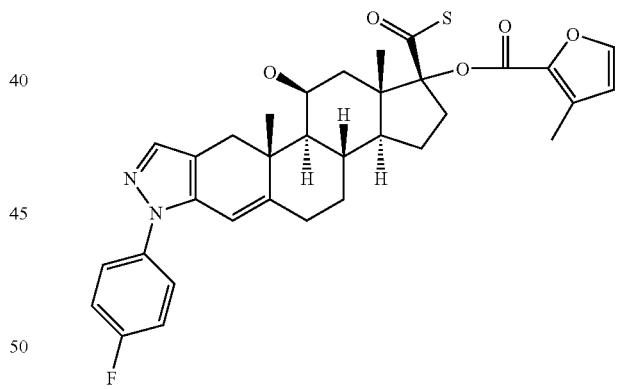

(1R,3aS,3bS,10aR,10bS,11S,12aS)-7-(4-fluorophenyl)-11-hydroxy-10a,12a-dimethyl-1-{[(3-methylfuran-2-yl)carbonyl]oxy}-1,2,3,3a,3b,4,5,7,11,10a,10b,11,12,12a-tetradecahydrocyclopenta[5,6]naphtho[1,2-f]indazole-1-carbothioic S-acid The compound was prepared according to the procedure for Intermediate 3, starting from Intermediate 2. APCI-MS m/z: 591 [MH+].

Intermediate 18

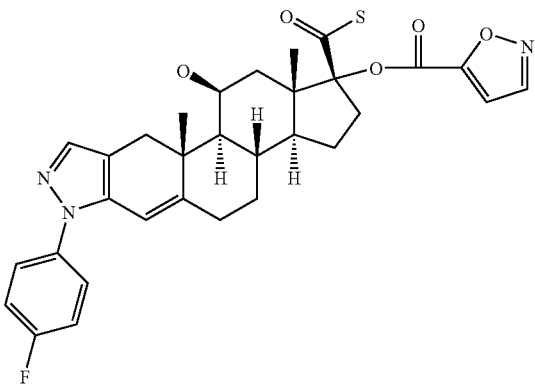

(1R,3aS,3bS,10aR,10bS,11S,12aS)-7-(4-fluorophe-
nyl)-11-hydroxy-1-[(isoxazol-5-ylcarbonyl)oxy]-
10a,12a-dimethyl-1,2,3,3a,3b,4,5,7,10,10a,10b,11,
12,12a-tetradecahydrocyclopenta[5,6]naphtho[1,2-f]
indazole-1-carbothioic S-acid The compound was prepared according to the procedure for Intermediate 3, starting from Intermediate 2. APCI-MS m/z: 578 [MH$^+$].

Intermediate 19

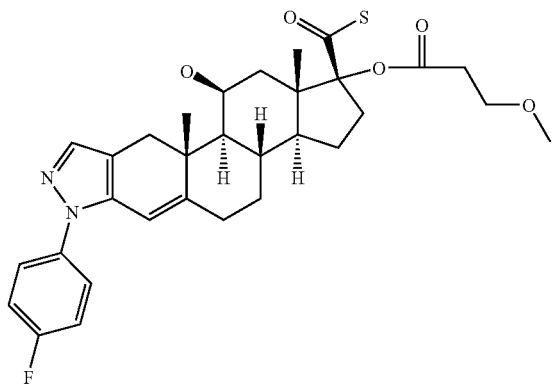

(1R,3aS,3bS,10aR,10bS,11S,12aS)-7-(4-fluorophe-
nyl)-11-hydroxy-1-[(3-methoxypropanoyl)oxy]-10a,
12a-dimethyl-1,2,3,3a,3b,4,5,7,10,10a,10b,11,12,
12a-tetradecahydrocyclopenta[5,6]naphtho[1,2-f]
indazole-1-carbothioic S-acid The compound was prepared according to the procedure for Intermediate 3, starting from Intermediate 2. APCI-MS m/z: 569 [MH$^+$].

Intermediate 20

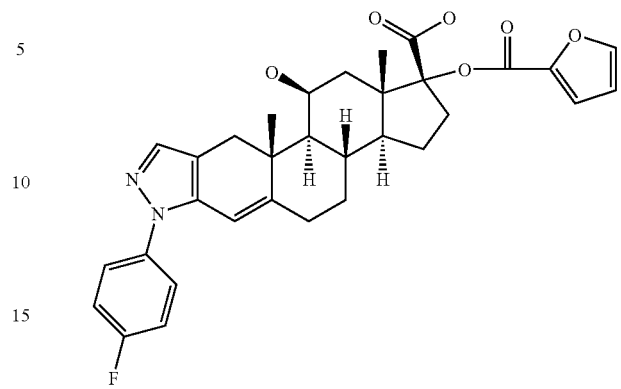

(1R,3aS,3bS,10aR,10bS,11S,12aS)-7-(4-fluorophe-
nyl)-1-[(furan-2-ylcarbonyl)oxy]-11-hydroxy-10a,
12a-dimethyl-1,2,3,3a,3b,4,5,7,10,10a,10b,11,12,
12a-tetradecahydrocyclopenta[5,6]naphtho[1,2-f]
indazole-1-carboxylic Acid The compound was prepared according to the procedure for Intermediate 6, starting from Intermediate 1. APCI-MS m/z: 561 [MH$^+$].

Intermediate 21

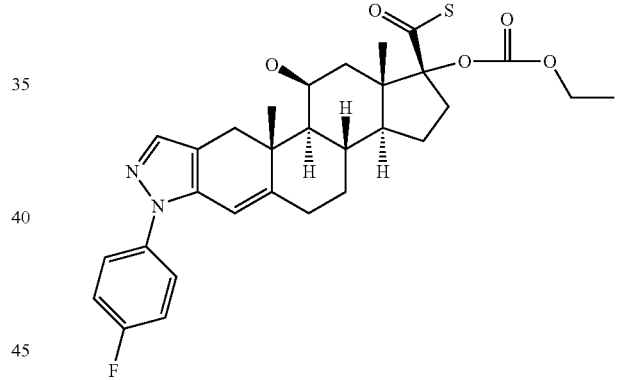

(1R,3aS,3bS,10aR,10bS,11S,12aS)-1-[(ethoxycarbo-
nyl)oxy]-7-(4-fluorophenyl)-11-hydroxy-10a,12a-
dimethyl-1,2,3,3a,3b,4,5,7,10,10a,10b,11,12,12a-
tetradecahydrocyclopenta[5,6]naphtho[1,2-f]
indazole-1-carbothioic S-acid In a 25 mL round-bottomed flask was dissolved Intermediate 2 (0.05 g, 0.10 mmol) and triethylamine (0.058 mL, 0.41 mmol) in DCM (10 mL) was added to give a yellow solution. The mixture was stirred at room temperature and ethyl carbonochloridate (0.030 mL, 0.31 mmol) dissolved in DCM (1 ml) was added in one portion. The mixture was stirred in a sealed flask for 15 minutes, N$_1$-ethyl-N$_2$,N$_2$-dimethylethane-1,2-diamine (0.098 mL, 0.62 mmol) was added, and the solution was stirred for another 15 minutes. The reaction mixture was diluted with DCM (20 ml) in a separation funnel and was washed with 2M HCl (2 times 20 ml), and brine (20 ml), and was then dried over Na$_2$SO$_4$. Filtration and evaporation gave 56 mg (90%) of a yellow solid. APCI-MS m/z: 555 [MH$^+$].

Intermediate 22

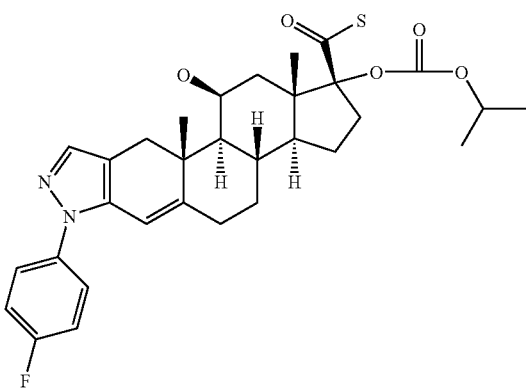

(1R,3aS,3bS,10aR,10bS,11S,12aS)-7-(4-fluorophenyl)-11-hydroxy-10a,12a-dimethyl-1-f{[(1-methylethoxy)carbonyl]oxy}-1,2,3,3a,3b,4,5,7,10a,10b,11,12,12a-tetradecahydrocyclopenta[5,6]naphtho[1,2-f]indazole-1-carbothioic S-acid The compound was prepared according to the procedure described for Intermediate 21, starting from Intermediate 2. APCI-MS m/z: 569 [MH+].

Intermediate 23

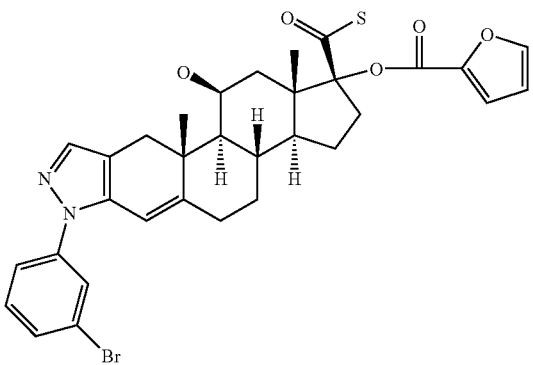

(1R,3aS,3bS,10aR,10bS,11S,12aS)-7-(3-bromophenyl)-1-[(furan-2-ylcarbonyl)oxy]-11-hydroxy-10a,12a-dimethyl-1,2,3,3a,3b,4,5,7,10,10a,10b,11,12,12a-tetradecahydrocyclopenta[5,6]naphtho[1,2-f]indazole-1-carbothioic S-acid The compound was prepared analogous to the procedures described for Intermediate 1, Intermediate 2 and Intermediate 3. APCI-MS m/z: 637 and 639 [MH+].

Intermediate 24

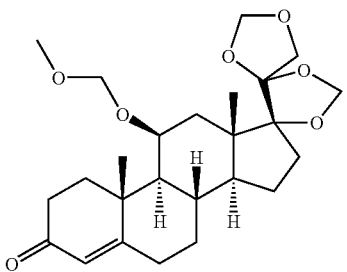

(8S,9S,10R,11S,13S,14S,17R)-11-(methoxymethoxy)-10,13-dimethyl-1,6,7,8,9,10,11,12,13,14,15,16-dodecahydrodispiro[cyclopenta[a]phenanthrene-17,4'-[1,3]dioxolane-5',4''-[1,3]dioxolan]-3(2H)-one In a 250 mL round-bottomed flask was added Hydrocortisone (2.5 g, 6.90 mmol) in DCM (100 mL) to give a colorless suspension. The mixture was vigorously stirred, and formaldehyde solution (37%, 40 ml, 532.34 mmol) was added followed by conc. hydrochloric acid (40 ml, 487.10 mmol). The flask was sealed and stirred vigorously for 6 hours at room temperature. LC-MS showed complete disappearance of the starting material, and formation of mainly one product. The mixture was transferred to a separation funnel, and the phases were separated. The organic phase was collected, and the aqueous phase was extracted with another portion of DCM. The combined organic phases were washed with $H_2O$, sat $NaHCO_3$, and brine. The organic was dried $Na_2SO_4$ and filtered. Filtration through a silica plug, eluting with EtOAc:Heptane=1:1, followed by removal of the solvent in vacuo gave 3.2 g of crude product which was used as such without any further purification. APCI-MS m/z: 449 [MH+].

Intermediate 25

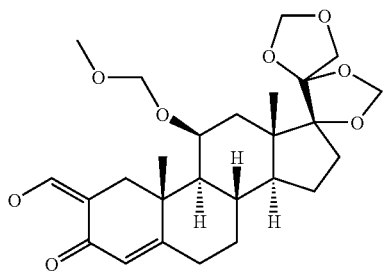

(2Z,8S,9S,10R,11S,13S,14S,17R)-2-(hydroxymethylidene)-11-(methoxymethoxy)-10,13-dimethyl-1,6,7,8,9,10,11,12,13,14,15,16-dodecahydrodispiro[cyclopenta[a]phenanthrene-17,4'-[1,3]dioxolane-5',4''-[1,3]dioxolan]-3(2H)-one In a 250 mL round-bottomed flask was added Intermediate 24 (3.2 g, 7.91 mmol) and ethyl formate (2.5 mL, 30.71 mmol) in Toluene (20 ml) to give a colorless solution. Sodium hydride dispersion (55-60% in oil, 0.7 g, 16.04 mmol) was added and the mixture was stirred for approximately 1 hour whilst the colour turned into deep brown. The crude material was poured into 1M HCl (100 ml) in a separation funnel. EtOAc (100 ml) was added and the phases were separated. The organic phase was extracted with 1M NaOH (4 times 50 ml). The combined aqueous phases were washed with EtOAc (50 ml), acidified with 2M HCl (120 ml) and extracted into EtOAc (2 times 60 ml). The combined organic phases were washed with brine (50 ml) and dried over $Na_2SO_4$. Filtration and evaporation of the solvent in vacuo gave 2.1 g of a yellow solid. APCI-MS m/z: 477 [MH+].

Intermediate 26

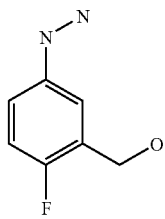

2-fluoro-5-hydrazinylphenyl)methanol (5-amino-2-fluorophenyl)methanol (6.7 g, 47.47 mmol) was dissolved in conc. hydrochloric acid (37%, 70 mL) at room temperature. The solution was cooled to approximately −5° C. and sodium nitrite (3.44 g, 49.84 mmol), dissolved in water (10 ml), was added dropwise over 5 minutes. After stirring for an additional 5 minutes, a solution of Tin(II) chloride dihydrate (23.56 g, 104.43 mmol) in 30 ml of conc. HCl was added dropwise while keeping the temperature below 0° C. After stirring for an additional 40 minutes, 4N NaOH was added (approximately 500 ml) to adjust the pH to approximately 14 and the product was extracted with EtOAc (6 times 100 mL). The combined organic phases were washed with brine and dried over $K_2CO_3$. After filtration and evacuation of the solvent 4.86 g of a dark solid was obtained which was used as such without any further purification. APCI-MS m/z: 157 [MH+].

Intermediate 27

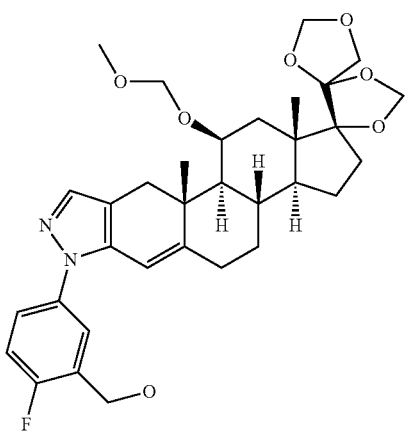

{2-fluoro-5-[(1R,3aS,3bS,10aR,10bS,11S,12aS)-11-(methoxymethoxy)-10a,12a-dimethyl-2,3,3a,3b,4,5,10,10a,10b,11,12,12a-dodecahydro-7H-dispiro[cyclopenta[5,6]naphtho[1,2-f]indazole-1,4'-[1,3]dioxolane-5',4"-[1,3]dioxolan]-7-yl]phenyl}methanol In a round-bottomed flask was suspended Intermediate 25 (9.86 g, 20.69 mmol), Intermediate 26 (3.23 g, 20.69 mmol) and potassium acetate (2.05 g; 20.7 mmol) in acetic acid (45 ml). Water (15.00 ml) was added and the dark solution was stirred 1 h at 25° C. LC-MS confirmed complete reaction and water (100 ml) was added to the reaction mixture. Stirring was continued overnight, the suspension was filtered and the brown solid was washed with water and dried on the sinter to yield 12.6 g of a brown solid which was used as such without any further purification. APCI-MS m/z: 597 [MH+].

Intermediate 28

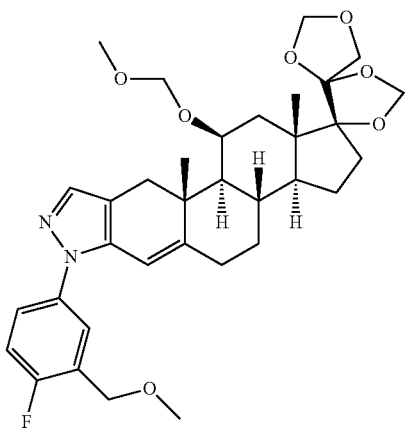

(1R,3aS,3bS,10aR,10bS,11S,12aS)-7-[4-fluoro-3-(methoxymethyl)phenyl]-11-(methoxymethoxy)-10a,12a-dimethyl-3,3a,3b,4,5,7,10a,10b,11,12,12a-dodecahydro-2H-dispiro[cyclopenta[5,6]naphtho[1,2-f]indazole-1,4'-[1,3]dioxolane-5',4"-[1,3]dioxolane]

In a 25 mL round-bottomed flask was added Intermediate 27 (312 mg, 0.52 mmol) and sodium hydride dispersion (55-60% in oil, 45.6 mg, 1.05 mmol) in DMF (5 mL) to give a brown suspension. The mixture was stirred in a sealed flask for 15 minutes. Iodomethane (0.130 mL, 2.09 mmol) was added, and the mixture was stirred for another 30 minutes. The mixture was partitioned between EtOAc (20 ml) and water (20 ml). The organic phase was collected and the aqueous phase was extracted with another portion of EtOAc (15 ml). The combined organic phases were washed with water (2 times 15 ml) and brine (15 ml). The organic phase was dried over $Na_2SO_4$. Filtration and evaporation gave an oil (0.35 g) which was purified on silica (Heptane:EtOAc=3:1 to 2:1), giving 0.19 g of an orange semi-solid. APCI-MS m/z: 611 [MH+].

Intermediate 29

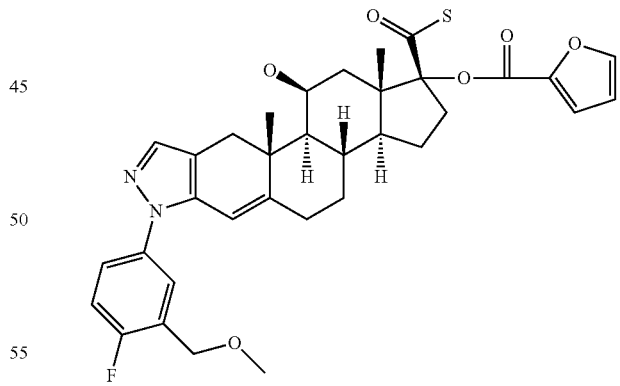

(1R,3aS,3bS,10aR,10bS,11S,12aS)-7-[4-fluoro-3-(methoxymethyl)phenyl]-1-[(furan-2-ylcarbonyl)oxy]-11-hydroxy-10a,12a-dimethyl-1,2,3,3a,3b,4,5,7,10,10a,10b,11,12,12a-tetradecahydrocyclopenta[5,6]naphtho[1,2-f]indazole-1-carbothioic S-acid The compound was prepared according to the descriptions in *Steroids* 2003 (68) 177-191 and according to the preparation of Intermediate 1, 2 and 3, starting from Intermediate 28. APCI-MS m/z: 621 [MH+].

Intermediate 30

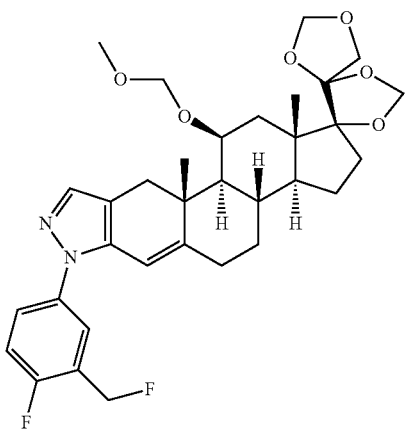

(1R,3aS,3bS,10aR,10bS,11S,12aS)-7-[4-fluoro-3-(fluoromethyl)phenyl]-11-(methoxymethoxy)-10a,12a-dimethyl-3,3a,3b,4,5,7,10,10a,10b,11,12a-dodecahydro-2H-dispiro[cyclopenta[5,6]naphtho[1,2-f]indazole-1,4'-[1,3]dioxolane-5',4"-[1,3]dioxolane]

In a 50 mL round-bottomed flask was dissolved Intermediate 27 (375 mg, 0.63 mmol) in DCM (10 mL) to give a brown solution. Diethylaminosulfurtrifluoride (DAST, 0.108 mL, 0.82 mmol) was added at room temperature in one portion, and the mixture was stirred in a sealed flask for 30 minutes. The reaction was quenched by carefully adding water to the reaction mixture. The crude reaction mixture was diluted with DCM (30 ml), and was washed with water (20 ml) and brine (10 ml). The organic phase was dried over Na$_2$SO$_4$. Filtration and evaporation of the solvent gave a semi-solid, which was purified on silica (Heptane:EtOAC=3:1 to 2:1), giving 130 mg of the desired product as an orange solid. APCI-MS m/z: 599 [MH$^+$].

Intermediate 31

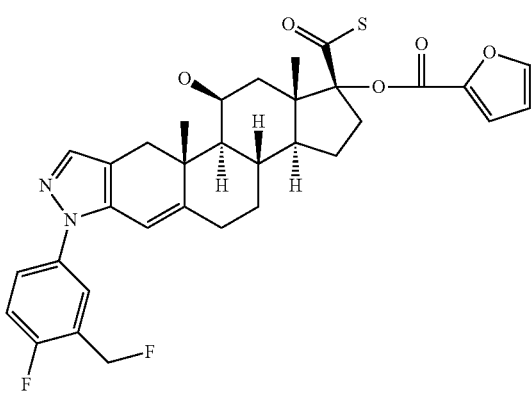

(1R,3aS,3bS,10aR,10bS,11S,12aS)-7-[4-fluoro-3-(fluoromethyl)phenyl]-1-[(furan-2-ylcarbonyl)oxy]-11-hydroxy-10a,12a-dimethyl-1,2,3,3a,3b,4,5,7,10,10a,10b,11,12,12a-tetradecahydrocyclopenta[5,6]naphtho[1,2-f]indazole-1-carbothioic S-acid The compound was prepared according to the descriptions in Steroids 2003 (68) 177-191 and according to the preparation of Intermediate 1, 2 and 3, starting from Intermediate 30. APCI-MS m/z: 609 [MH$^+$].

Intermediate 32

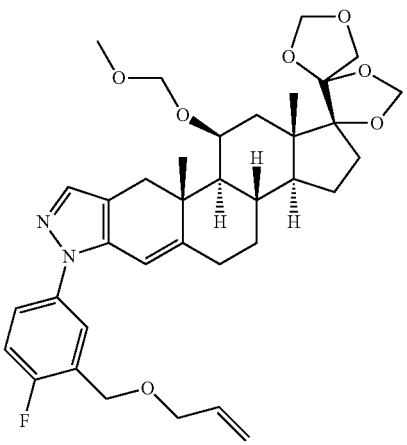

(1R,3aS,3bS,10aR,10bS,11S,12aS)-7-{4-fluoro-3-[(prop-2-en-1-yloxy)methyl]phenyl}-11-(methoxymethoxy)-10a,12a-dimethyl-3,3a,3b,4,5,7,10,10a,10b,11,12,12a-dodecahydro-2H-dispiro[cyclopenta[5,6]naphtho[1,2-f]indazole-1,4'-[1,3]-dioxolane-5',4"-[1,3]dioxolane]

In a 25 mL round-bottomed flask was dissolved Intermediate 27 (490 mg, 0.82 mmol) in DMF (5 mL) and sodium hydride dispersion (55-60% in oil, 90 mg, 2.05 mmol) was added to give a brown suspension. The flask was sealed an the mixture was stirred at room temperature for 20 minutes. 3-bromoprop-1-ene (0.208 mL, 2.46 mmol) was added, and the mixture was stirred for another 20 minutes. The reaction was stopped by carefully adding 1 ml of water to the mixture and it was partitioned between EtOAc (20 ml) and water (20 ml). The organic phase was collected and the aqueous phase was extracted with another portion of EtOAc (15 ml). The combined organic phases were washed with water (2×15 ml) and brine (15 ml) and dried over Na$_2$SO$_4$. Filtration and evaporation of the solvent gave an oil, which was purified on silica (Heptane:EtOAc=3:1 to 2:1). The product containing phases were evaporated in vacuo, giving 0.3 g of an orange dry film. APCI-MS m/z: 637 [MH$^+$].

Intermediate 33

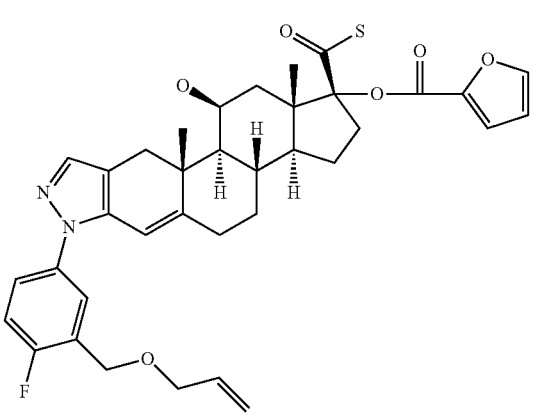

(1R,3aS,3bS,10aR,10bS,11S,12aS)-7-{4-fluoro-3-[(prop-2-en-1-yloxy)methyl]phenyl}-1-[(furan-2-ylcarbonyl)oxy]-11-hydroxy-10a,12a-dimethyl-1,2,3,3a,3b,4,5,7,10,10a,10b,11,12,12a-tetradecahydrocyclopenta[5,6]naphtho[1,2-f]indazole-1-carbothioic S-acid The compound was prepared according to the descriptions in *Steroids* 2003 (68) 177-191 and according to the preparation of Intermediate 1, 2 and 3, starting from Intermediate 32. APCI-MS m/z: 647 [MH+].

Intermediate 34

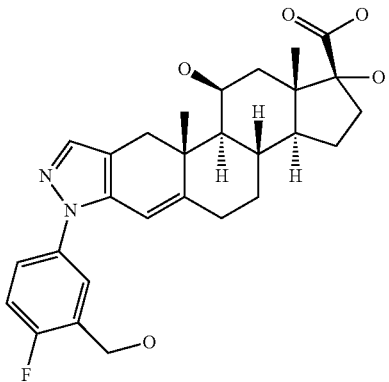

(1R,3aS,3bS,10aR,10bS,11S,12aS)-7-[4-fluoro-3-(hydroxymethyl)phenyl]-1,11-dihydroxy-10a,12a-dimethyl-1,2,3,3a,3b,4,5,7,10,10a,10b,11,12,12a-tetradecahydrocyclopenta[5,6]naphtho[1,2-f]indazole-1-carboxylic Acid The compound was prepared according to the descriptions in *Steroids* 2003 (68) 177-191 and according to the preparation of Intermediate 1, starting from Intermediate 27. APCI-MS m/z: 497 [MH+].

Intermediate 35

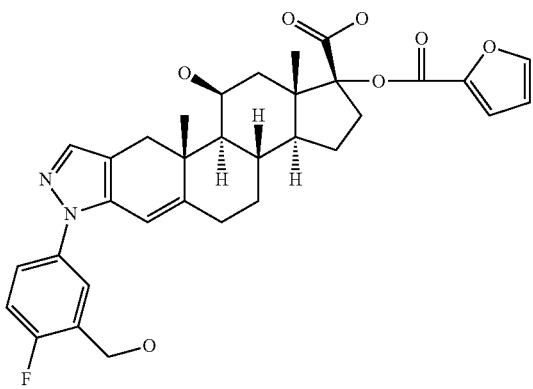

(1R,3aS,3bS,10aR,10bS,11S,12aS)-7-[4-fluoro-3-(hydroxymethyl)phenyl]-1-[(furan-2-ylcarbonyl)oxy]-11-hydroxy-10a,12a-dimethyl-1,2,3,3a,3b,4,5,7,10,10a,10b,11,12,12a-tetradecahydrocyclopenta[5,6]naphtho[1,2-f]indazole-1-carboxylic Acid In a 25 mL round-bottomed flask Intermediate 34 (0.08 g, 0.16 mmol) was dissolved in DCM (8 mL) and triethylamine (0.082 g, 0.81 mmol) was added followed by a solution of furan-2-carbonyl chloride (0.064 mL, 0.64 mmol) in DCM (1 ml), and the mixture was stirred for 20 minutes at room temperature. $N_1$-ethyl-$N_2,N_2$-dimethylethane-1,2-diamine (0.152 mL, 0.97 mmol) was added, and the mixture was stirred for another 20 minutes. DCM was removed in vacuo, and the oily residue was redissolved in acetonitrile (8.00 mL). Sodium hydroxide (1M, 1.9 mL, 1.90 mmol) was added and the mixture was heated at 40° C. for 1-2 hours, monitoring the hydrolysis by LC-MS. Acetonitrile was removed in vacuo, and the residue was partitioned between EtOAc (20 ml) and 1M HCl (20 ml). The organic phase was collected and the aqueous phase was extracted with another portion of EtOAc (20 ml). The combined organic phases were washed with 1M HCl (10 ml) and brine (10 ml) and dried over $Na_2SO_4$. Filtration and evaporation gave 0.11 g of a yellow film that contained a mixture of the product and furane-2-carboxylic acid. APCI-MS m/z: 591 [MH+].

Intermediate 36

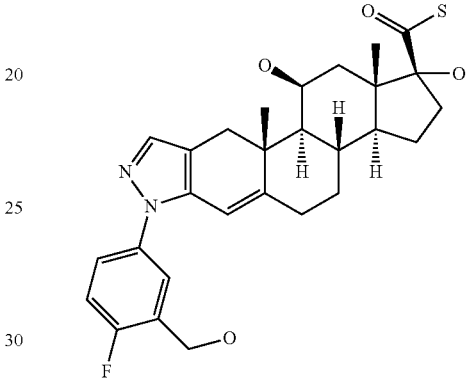

(1R,3aS,3bS,10aR,10bS,11S,12aS)-7-[4-fluoro-3-(hydroxymethyl)phenyl]-1,11-dihydroxy-10a,12a-dimethyl-1,2,3,3a,3b,4,5,7,10,10a,10b,11,12,12a-tetradecahydrocyclopenta[5,6]naphtho[1,2-f]indazole-1-carbothioic S-acid In a 10 mL round-bottomed flask was dissolved Intermediate 34 (0.087 g, 0.18 mmol) and carbonyldiimidazole (0.057 g, 0.35 mmol) in DMF (1.5 mL). The mixture was stirred in a sealed flask overnight. $H_2S$ was bubbled through the solution for 1 minute and 1M NaOH (2 ml) was added. The mixture was stirred for 5 minutes and it was subsequently poured into 1M HCl (20 ml), extracted with EtOAc (2 times 15 ml) and the combined aqueous phases were washed with water (2 times 15 ml) and brine (10 ml) and dried over $Na_2SO_4$. Filtration and evaporation of the solvent gave 76 mg (85%) of an orange semi-solid which was taken on as such in the next step. APCI-MS m/z: 513 [MH+].

Intermediate 37

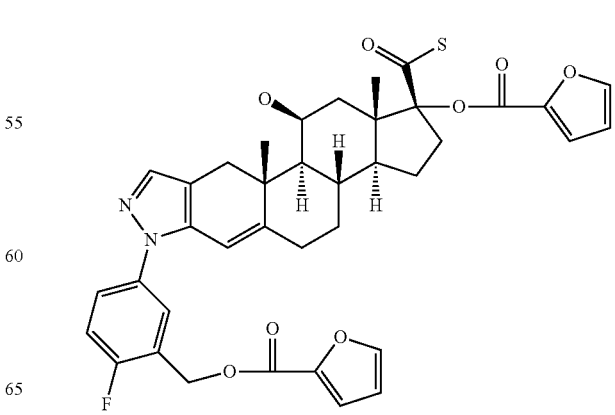

(1R,3aS,3bS,10aR,10bS,11S,12aS)-7-(4-fluoro-3-{[(furan-2-ylcarbonyl)oxy]methyl}phenyl)-1-[(furan-2-ylcarbonyl)oxy]-11-hydroxy-10a,12a-dimethyl-1,2,3,3a,3b,4,5,7,10,10a,10b,11,12,12a-tetradecahydrocyclopenta[5,6]naphtho[1,2-f]indazole-1-carbothioic S-acid In a 25 mL round-bottomed flask was dissolved Intermediate 36 (0.076 g, 0.15 mmol) and triethylamine (0.103 mL, 0.74 mmol) in DCM (8 mL). To the stirred mixture was added a solution of furan-2-carbonyl chloride (0.045 mL, 0.46 mmol) in DCM (1 ml) and stirring was continued for an additional 15 minutes. $N_1$-ethyl-$N_2$,$N_2$-dimethylethane-1,2-diamine (0.140 mL, 0.89 mmol) was added, and the mixture was stirred for another 15 minutes. The mixture was diluted with 20 ml DCM in a separation funnel and the solution was washed with 1M HCl (2×15 ml), and brine (10 ml). The organic phase was dried over $Na_2SO_4$, filtered and evaporated to give 91 mg of an orange semi-solid which was taken on as such in the next step. APCI-MS m/z: 701 [MH+].

Intermediate 38

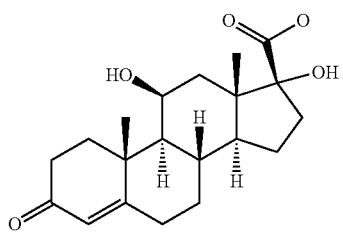

(8S,9S,10R,11S,13S,14S,17R)-11,17-dihydroxy-10,13-dimethyl-3-oxo-2,3,6,7,8,9,10,11,12,13,14,15,16,17-tetradecahydro-1H-cyclopenta[a]phenanthrene-17-carboxylic Acid A solution of orthoperiodic acid (21.4 g, 94 mmol) in water (80 ml) was added to a solution of (8S,9S,10R,11S,13S,14S,17R)-11,17-dihydroxy-17-(2-hydroxyacetyl)-10,13-dimethyl-6,7,8,9,10,11,12,13,14,15,16,17-dodecahydro-1H-cyclopenta[a]phenanthren-3(2H)-one (Hydrocortisone, 17.0 g, 46.9 mmol) in THF (350 ml), and the reaction mixture was stirred at room temperature in an open flask for 2 hours. Then the mixture was poured onto ice. After the ice had molten, the mixture was extracted with ethyl acetate (3 times 150 ml). Evaporation of the solvent gave a white solid, which was dissolved in aqueous NaOH (1 M, 150 ml). The solution was washed with ethyl acetate, and acidified with conc. aqueous HCl. The precipitate formed was collected by filtration, and dried on the sinter overnight to afford the target compound as an off-white powder (15.51 g, 95%).

$^1$H NMR (400 MHz, DMSO-$d_6$) δ 12.20 (s, 1H), 5.55 (s, 1H), 4.74 (s, 1H), 4.24 (s, 2H), 2.43 (m, 3H), 2.18 (m, 2H), 2.09 (m, 1H), 2.00-1.44 (m, 6H), 1.37 (s, 3H), 1.31-1.15 (m, 1H), 0.98 (m, 1H), 0.89 (s, 3H), 0.83 (d, 1H).

Intermediate 39

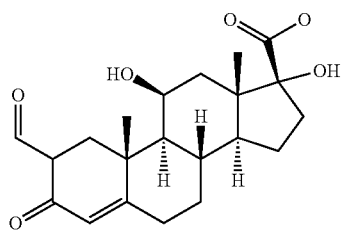

(8S,9S,10R,11S,13S,14S,17R)-2-formyl-11,17-dihydroxy-10,13-dimethyl-3-oxo-2,3,6,7,8,9,10,11,12,13,14,15,16,17-tetradecahydro-1H-cyclopenta[a]phenanthrene-17-carboxylic Acid To a stirred suspension of sodium hydride (5.73 g, 143.5 mmol, 60% suspension in mineral oil) in THF (100 ml) under argon was added Intermediate 38 (5.00 g, 14.35 mmol) in small portions. After 5 minutes ethyl formate (58.4 ml, 717.5 mmol) was added and stirring was continued at room temperature overnight. The mixture was quenched with formic acid to afford a thick suspension and aqueous NaOH solution (2M, 50 ml) was added. The mixture was stirred at room temperature for 10 min, the layers were separated, the aqueous layer was acidified with aqueous conc. HCl and extracted with ethyl acetate (3 times 50 ml). The combined organic phases were dried with sodium sulfate, filtered and the solvent evaporated under reduced pressure to afford the target compound as a yellow solid (5.65 g).

$^1$H NMR (400 MHz, DMSO-$d_6$) δ 5.56 (s, 1H), 4.26 (m, 2H), 2.54-2.37 (m, 2H), 2.29-2.11 (m, 2H), 1.96-1.78 (m, 2H), 1.77-1.43 (m, 6H), 1.34-1.20 (m, 1H), 1.25 (s, 3H), 1.09-0.85 (m, 1H), 0.89 (s, 3H). APCI-MS m/z: 377 [MH+].

Intermediate 40

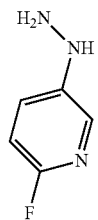

2-Fluoro-5-hydrazinylpyridine

A solution of sodium nitrite (345 mg, 5.00 mmol) in water (2.5 ml) was added dropwise to a vigorously stirred solution of 6-fluoropyridin-3-amine (561 mg, 5 mmol) in 6N hydrochloric acid (5 ml) at 0° C. The mixture was stirred at 0° C. for 1 hour, then a solution of tin (II) chloride dihydrate (2.82 g, 12.5 mmol) in 6N hydrochloric acid (5 ml) was added dropwise whilst adding small pieces of ice to keep the inner temperature below 5° C. The formation of a foamy layer was observed during the addition and stirring was continued at 0° C. for 3 h. The mixture was made alkaline (pH=14) by addition of 40% aqueous solution of potassium hydroxide and extracted with ethyl acetate (5 times 15 ml). The combined organic extracts were dried over sodium sulfate, the drying agent was filtered off and the solvent was removed under reduced pressure to afford 250 mg (39%) of the target compound as a pale-yellow solid.

$^1$H NMR (400 MHz, DMSO-$d_6$) δ 7.69 (t, 1H), 7.35 (ddd, 1H), 6.93 (dd, 1H), 5.90 (s, 3H).

Intermediate 41

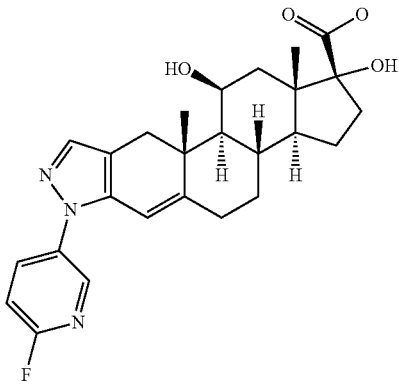

(1R,3aS,3bS,10aR,10bS,11S,12aS)-7-(6-fluoropyridin-3-yl)-1,11-dihydroxy-10a,12a-dimethyl-1,2,3,3a,3b,4,5,7,10,10a,10b,11,12,12a-tetradecahydrocyclopenta[5,6]naphtho[1,2-f]indazole-1-carboxylic Acid To a stirred solution of Intermediate 39 (376 mg, 1.0 mmol) in acetic acid (8 ml) and water (2 ml) was added Intermediate 40 (127 mg, 1.0 mmol). The mixture was stirred overnight. Evaporation of solvent afforded a dark oil (574 mg), containing traces of acetic acid. APCI-MS m/z: 468 [MH$^+$].

Intermediate 42

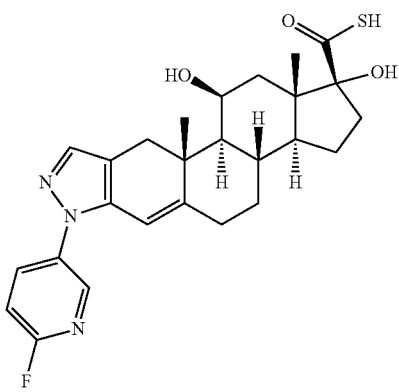

(1R,3aS,3bS,10aR,10bS,11S,12aS)-7-(6-fluoropyridin-3-yl)-1,11-dihydroxy-10a,12a-dimethyl-1,2,3,3a,3b,4,5,7,10,10a,10b,11,12,12a-tetradecahydrocyclopenta[5,6]naphtho[1,2-f]indazole-1-carbothioic S-acid Intermediate 41 (574 mg, 1.23 mmol) was dissolved in DMF (5 ml), and di(1H-imidazol-1-yl)methanone (498 mg, 3.07 mmol) was added. The mixture was stirred at room temperature for 3 hours. Hydrogen sulfide was bubbled through the stirred solution for 5 minutes and stirring was continued for 10 min. in a sealed flask. The mixture was poured into a mixture of ice (50 g) and hydrochloric acid (10 ml, 2 M). The precipitate was collected by filtration and dried on the sinter to afford 460 mg (77%) of the desired compound. APCI-MS m/z: 484 [MH$^+$].

Intermediate 43

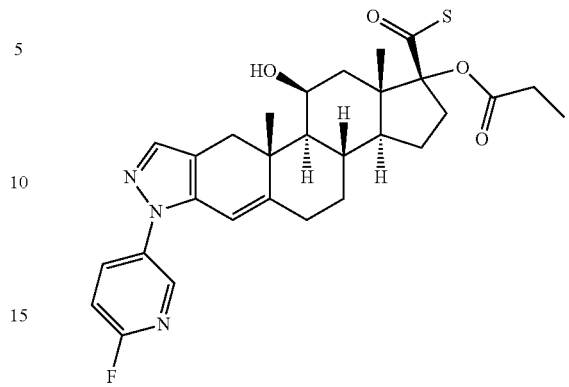

(1R,3aS,3bS,10aR,10bS,11S,12aS)-7-(6-fluoropyridin-3-yl)-11-hydroxy-10a,12a-dimethyl-1-(propanoyloxy)-1,2,3,3a,3b,4,5,7,10,10a,10b,11,12,12a-tetradecahydrocyclopenta[5,6]naphtho[1,2-f]indazole-1-carbothioic S-acid A stirred solution of Intermediate 42 (460 mg, 0.95 mmol) and triethylamine (337 mg, 461 µl, 3.33 mmol) in dichloromethane (10 ml) was cooled to 0° C. under argon and a solution of propionyl chloride (264 mg, 2.85 mmol) in dichloromethane (5 ml) was added. The mixture was stirred at 0° C. for 1 hour. N1,N1,N2-trimethylethane-1,2-diamine (686 mg, 607 µl, 4.76 mmol) was added and stirring was continued at 0° C. for 40 min. The reaction mixture was quenched by addition of hydrochloric acid (1 M, 20 ml), and diluted with dichloromethane (50 ml). The layers were separated, the organic layer was washed with water (20 ml) and dried over sodium sulfate. Filtration of the drying agent followed by evaporation of the solvent in vacuo gave 346 mg (67%) of the target compound that was used as such without further purification. APCI-MS m/z: 540 [MH$^+$].

Intermediate 44

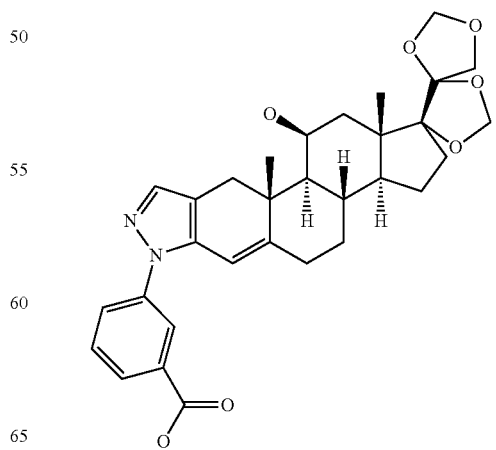

3-[(1S,3aR,3bR,10aS,10bR,11R,12aR)-11-hydroxy-10a,12a-dimethyl-2,3,3a,3b,4,5,10,10a,10b,11,12,12a-dodecahydro-7H-dispiro[cyclopenta[5,6]naph-tho[1,2-f]indazole-1,4'-[1,3]dioxolane-5',4"-[1,3]dioxolan]-7-yl]benzoic Acid (8S,9S,10R,11S,13S,14S,17R)-11-hydroxy-10,13-dimethyl-3-oxo-1,2,3,6,7,8,9,10,11,12,13,14,15,16-tetradecahydrodispiro[cyclopenta[a]phenanthrene-17,4'-[1,3]dioxolane-5',4"-[1,3]dioxolane]-2-carbaldehyde (*Steroids* 2003, (68), 177-191) (1.4 g, 3.24 mmol) was dissolved in ethanol (10 ml) and water (1 ml). 3-hydrazinobenzoic acid (0.493 g, 3.24 mmol) and potassium acetate (0.491 g, 5 mmol) were added to give a brown solution which was stirred for 1 hour at room temperature. The mixture was poured into a separation funnel containing 1M HCl (200 ml) and was extracted with DCM (3 times 150 ml). The combined organic phases were washed with water (2 times 100 ml) and 1M NaOH. The organic phase was washed with brine, dried over $Na_2SO_4$, filtered and the solvent was evaporated to give 1.9 g of a brownish foam. The crude product was purified on a silica gel column (Heptane:EtOAc=1:1) and the product containing fractions were evaporated under reduced pressure to yield 1.5 g of the desired compound. APCI-MS m/z: 549 [MH$^+$].

Intermediate 45

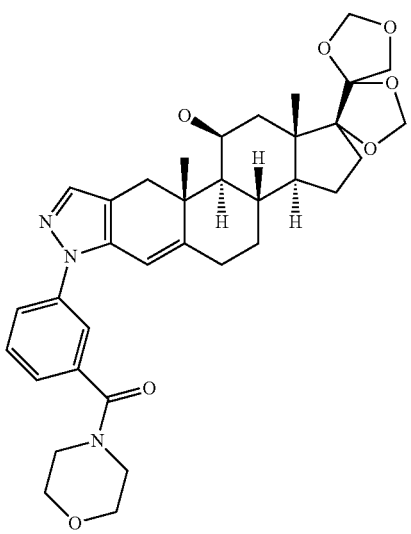

(1S,3aR,3bR,10aS,10bR,11R,12aR)-10a,12a-dimethyl-7-[3-(morpholin-4-ylcarbonyl)phenyl]-3,3a,3b,4,5,7,10,10a,10b,11,12,12a-dodecahydro-2H-dispiro[cyclopenta[5,6]naphtho[1,2-f]indazole-1,4'-[1,3]dioxolane-5',4"-[1,3]-dioxolan]-11-ol In a 25 ml round-bottomed flask Intermediate 44 (500 mg, 0.91 mmol), 1H-benzo[d][1,2,3]triazol-1-ol (0.123 g, 0.91 mmol) and N,N'-methanediylidenedipropan-2-amine (DIC, 0.115 g, 0.91 mmol) were dissolved in DMF (5 mL) to give a colorless solution. Morpholine (0.170 g, 1.95 mmol) was added ten minutes later and the reaction mixture was stirred for 3 hours at room temperature. DMF was removed in vacuo and the residue was redissolved in MeCN and purified using a preparative HPLC column ($CH_3CN$/water). The product containing fractions were freeze-dried to give 450 mg of the desired compound. APCI-MS m/z: 618 [MH$^+$].

Intermediate 46

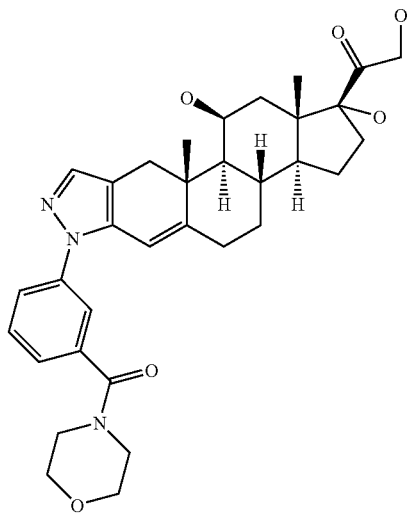

1-{(1R,3aS,3bS,10aR,10bS,11S,12aS)-1,11-dihydroxy-10a,12a-dimethyl-7-[3-(morpholin-4-ylcarbonyl)phenyl]-1,2,3,3a,3b,4,5,7,10,10a,10b,11,12,12a-tetradecahydrocyclopenta[5,6]naphtho[1,2-f]indazol-1-yl}-2-hydroxyethanone Intermediate 45 (0.45 g, 0.73 mmol) was weighed into a 20 mL vial and formic acid (6 mL, 1.59 mmol) in water (5 mL) was added to give a brown suspension. The mixture was heated at 90° C. and monitored by LC-MS. After approximately 90 minutes the starting materials were consumed and the mixture was allowed to cool to room temperature and partitioned between EtOAc (30 ml) and water (30 ml). The organic phase was collected and the aqueous phase was extracted with another portion of EtOAc (20 ml). The combined organic phases were washed with water (2 times 20 ml) and 1M NaOH until the water phase showed an alkaline pH. The organic phase was subsequently washed with brine (15 ml), dried over $Na_2SO_4$, filtered and the solvent removed in vacuo to give 0.18 g of crude material as a brown solid which was taken on as such in the next step. APCI-MS m/z: 576 [MH$^+$].

Intermediate 47

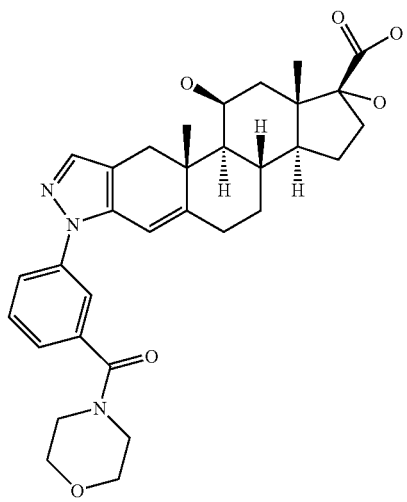

(1S,3aR,3bR,10aS,10bR,11R,12aR)-1,11-dihydroxy-10a,12a-dimethyl-7-[3-(morpholin-4-ylcarbonyl)phenyl]-1,2,3,3a,3b,4,5,7,10,10a,10b,11,12,12a-tetradecahydrocyclopenta[5,6]naphtho[1,2-f]indazole-1-carboxylic Acid The compound was prepared from Intermediate 46 according to the procedure for Intermediate 1. APCI-MS m/z: 562 [MH⁺].

Intermediate 48

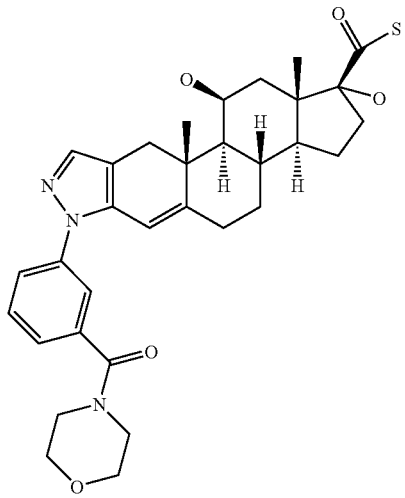

(Morpholin-4-ylcarbonyl)phenyl]-1,2,3,3a,3b,4,5,7,10,10(1S,3aR,3bR,10aS,10bR,11R,12aR)-1,11-dihydroxy-10a,12a-dimethyl-7-[3-a,10b,11,12,12a-tetradecahydrocyclopenta[5,6]naphtho[1,2-f]indazole-1-carbothioic S-acid The compound was prepared from Intermediate 47 according to the procedure for Intermediate 2. APCI-MS m/z: 578 [MH⁺].

Intermediate 49

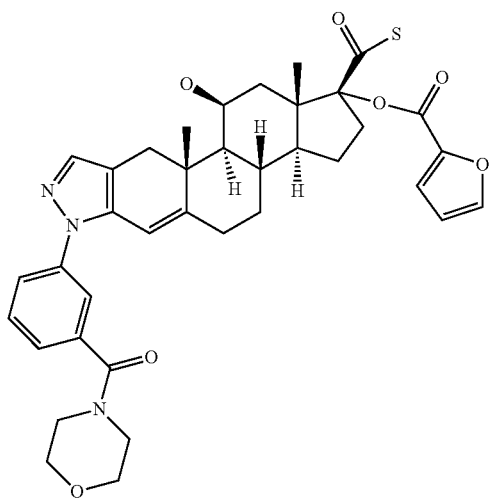

(1S,3aR,3bR,10aS,10bR,11R,12aR)-1-[(furan-2-ylcarbonyl)oxy]-11-hydroxy-10a,12a-dimethyl-7-[3-(morpholin-4-ylcarbonyl)phenyl]-1,2,3,3a,3b,4,5,7,10,10a,10b,11,12,12a-tetradecahydrocyclopenta[5,6]naphtho[1,2-f]indazole-1-carbothioic S-acid The compound was prepared from Intermediate 48 and 2-furoyl chloride according to the procedure for Intermediate 3. APCI-MS m/z: 672 [MH⁺].

Intermediate 50

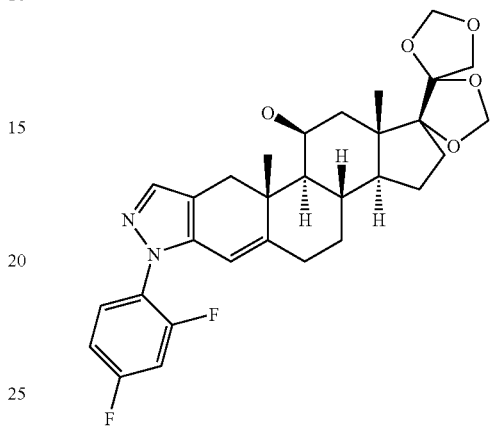

(1S,3aR,3bR,10aS,10bR,11R,12aR)-7-(2,4-difluorophenyl)-10a,12a-dimethyl-3,3a,3b,4,5,7,10,10a,10b,11,12,12a-dodecahydro-2H-dispiro[cyclopenta[5,6]naphtho[1,2-f]indazole-1,4'-[1,3]-dioxolane-5',4''-[1,3]-dioxolan]-11-ol (8S,9S,10R,11S,13S,14S,17R)-11-hydroxy-10,13-dimethyl-3-oxo-1,2,3,6,7,8,9,10,11,12,13,14,15,16-tetradecahydrodispiro[cyclopenta[a]phenanthrene-17,4'-[1,3]dioxolane-5',4''-[1,3]dioxolane]-2-carbaldehyde (*Steroids* 2003, (68), 177-191) (400 mg, 0.92 mmol) was dissolved in ethanol (10 ml) and water (1 ml). (2,4-difluorophenyl)hydrazine hydrochloride (167 mg, 0.92 mmol) and potassium acetate (160 mg, 1.63 mmol)) were added and the mixture was heated under microwave irradiation at 90° C. for 20 minutes. The mixture was partitioned between EtOAc (10 ml) and water (10 ml). The organic phase was washed with water (2 times 10 ml) and brine (5 ml) and was dried over Mg₂SO₄. Filtration followed by evaporation of the solvent gave 297 mg of the crude compound which was used as such without further purification. APCI-MS m/z: 541 [MH⁺].

Intermediate 51

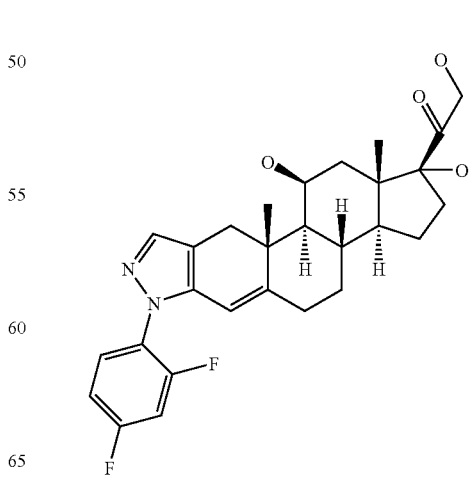

1-[(1S,3aR,3bR,10aS,10bR,11R,12aR)-7-(2,4-difluorophenyl)-1,11-dihydroxy-10a,12a-dimethyl-1,2,3,3a,3b,4,5,7,10,10a,10b,11,12,12a-tetradecahydrocyclopenta[5,6]naphtho[1,2-f]indazol-1-yl]-2-hydroxyethanone The compound was prepared from Intermediate 50 according to the procedure for Intermediate 46. APCI-MS m/z: 499 [MH+].

Intermediate 52

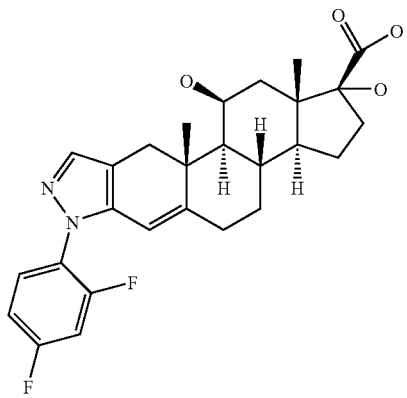

(1S,3aR,3bR,10aS,10bR,11R,12aR)-7-(2,4-difluorophenyl)-1,11-dihydroxy-10a,12a-dimethyl-1,2,3,3a,3b,4,5,7,10,10a,10b,11,12,12a-tetradecahydrocyclopenta[5,6]naphtho[1,2-f]indazole-1-carboxylic Acid The compound was prepared from Intermediate 51 according to the procedure for Intermediate 1 APCI-MS m/z: 485 [MH+].

Intermediate 53

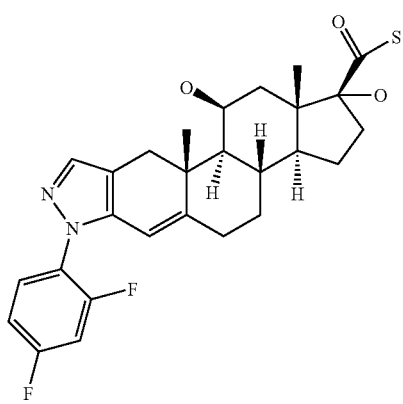

(1S,3aR,3bR,10aS,10bR,11R,12aR)-7-(2,4-difluorophenyl)-1,11-dihydroxy-10a,12a-dimethyl-1,2,3,3a,3b,4,5,7,10,10a,10b,11,12,12a-tetradecahydrocyclopenta[5,6]naphtho[1,2-f]indazole-1-carbothioic S-acid The compound was prepared from Intermediate 52 according to the procedure for Intermediate 2. APCI-MS m/z: 501 [MH+].

Intermediate 54

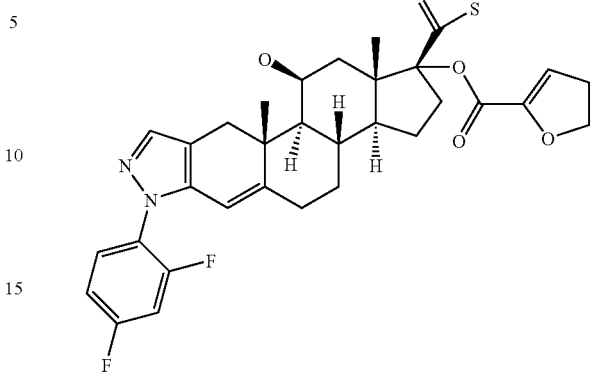

(1R,3aS,3bS,10aR,10bS,11S,12aS)-7-(2,4-difluorophenyl)-1-[(furan-2-ylcarbonyl)oxy]-11-hydroxy-10a,12a-dimethyl-2,3,3a,3b,4,5,7,10,10a,10b,11,12,12a-tetradecahydrocyclopenta[5,6]naphtho[1,2-f]indazole-1-carbothioic S-acid The compound was prepared from Intermediate 53 and 2-furoyl chloride according to the procedure for Intermediate 3. APCI-MS m/z: 595 [MH+].

Intermediate 55

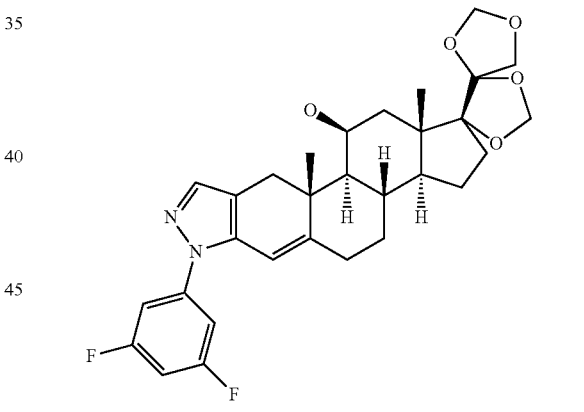

(1R,3aS,3bS,10aR,10bS,11S,12aS)-7-(3,5-difluorophenyl)-10a,12a-dimethyl-3,3a,3b,4,5,7,10,10a,10b,11,12,12a-dodecahydro-2H-dispiro[cyclopenta[5,6]naphtho[1,2-f]indazole-1,4'-[1,3]-dioxolane-5',4"-[1,3]dioxolan]-11-ol The compound was prepared from (8S,9S,10R,11S,13S,14S,17R)-11-hydroxy-10,13-dimethyl-3-oxo-1,2,3,6,7,8,9,10,11,12,13,14,15,16-tetradecahydrodispiro[cyclopenta[a]phenanthrene-17,4'-[1,3]dioxolane-5',4"[1,3]dioxolane]-2-carbaldehyde and (3,5-difluorophenyl)hydrazine according to the procedure for Intermediate 50. APCI-MS m/z: 541 [MH+].

Intermediate 56

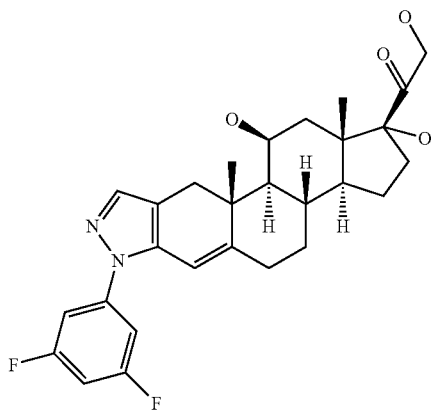

1[(1R,3aS,3bS,10aR,10bS,11S,12aS)-7-(3,5-difluorophenyl)-1,11-dihydroxy-10a,12a-dimethyl-1,2,3,3a,3b,4,5,7,10,10a,10b,11,12,12a-tetradecahydrocyclopenta[5,6]naphtho[1,2-f]indazol-1-yl]-2-hydroxyethanone The compound was prepared from Intermediate 55 according to the procedure for Intermediate 46. APCI-MS m/z: 499 [MH⁺].

Intermediate 57

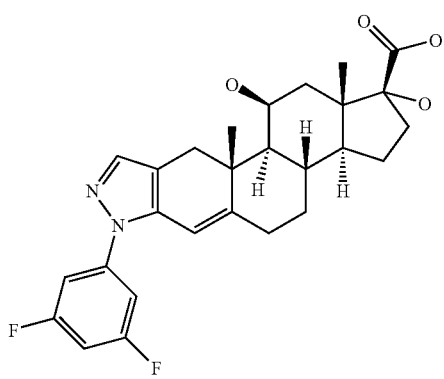

(1R,3aS,3bS,10aR,10bS,11S,12aS)-7-(3,5-difluorophenyl)-1,11-dihydroxy-10a,12a-dimethyl-1,2,3,3a,3b,4,5,7,10,10a,10b,11,12,12a-tetradecahydrocyclopenta[5,6]naphtho[1,2-f]indazole-1-carboxylic Acid The compound was prepared from Intermediate 56 according to the procedure for Intermediate 1. APCI-MS m/z: 485 [MH⁺].

Intermediate 58

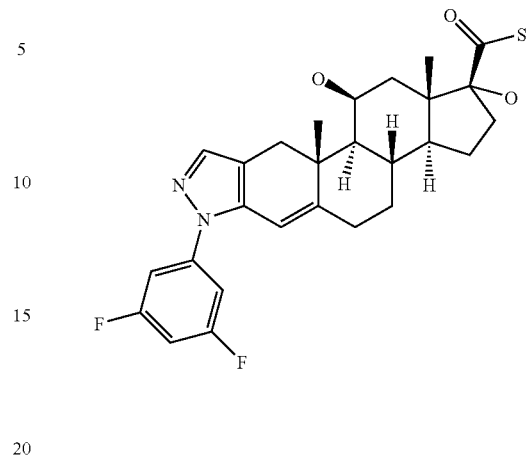

(1S,3aR,3bR,10aS,10bR,11R,12aR)-7-(3,5-difluorophenyl)-1,11-dihydroxy-10a,12a-dimethyl-1,2,3,3a,3b,4,5,7,10,10a,10b,11,12,12a-tetradecahydrocyclopenta[5,6]naphtho[1,2-f]indazole-1-carbothioic S-acid The compound was prepared from Intermediate 57 according to the procedure for Intermediate 2. APCI-MS m/z: 501 [MH⁺].

Intermediate 59

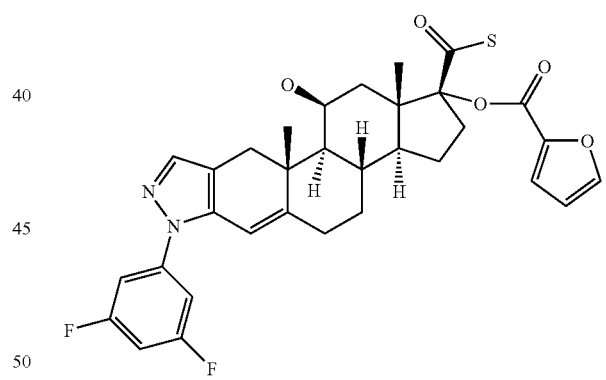

(1S,3aR,3bR,10aS,10bR,11R,12aR)-7-(3,5-difluorophenyl)-1-[(furan-2-ylcarbonyl)oxy]-11-hydroxy-10a,12a-dimethyl-1,2,3,3a,3b,4,5,7,10,10a,10b,11,12,12a-tetradecahydrocyclopenta[5,6]naphtho[1,2-f]indazole-1-carbothioic S-acid The compound was prepared from Intermediate 58 and 2-furoyl chloride according to the procedure for Intermediate 3. APCI-MS m/z: 595 [MH⁺].

Intermediate 60

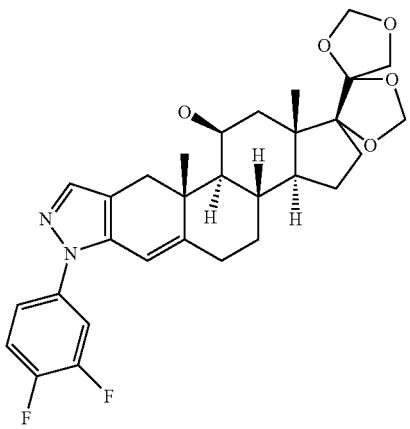

(1S,3aR,3bR,10aS,10bR,11R,12aR)-7-(3,4-difluorophenyl)-10a,12a-dimethyl-3,3a,3b,4,5,7,10,10a, 10b,11,12,12a-dodecahydro-2H-dispiro[cyclopenta [5,6]naphtho[1,2-f]indazole-1,4'-[1,3]dioxolane-5', 4''-[1,3]-dioxolan]-11-ol The compound was prepared from (8S,9S,10R,11S,13S, 14S,17R)-11-hydroxy-10,13-dimethyl-3-oxo-1,2,3,6,7,8,9, 10,11,12,13,14,15,16-tetradecahydrodispiro[cyclopenta[a] phenanthrene-17,4'-[1,3]dioxolane-5',4''-[1,3]dioxolane]-2-carbaldehyde and (3,4-difluorophenyl)hydrazine according to the procedure for Intermediate 50. APCI-MS m/z: 541 [MH$^+$].

Intermediate 61

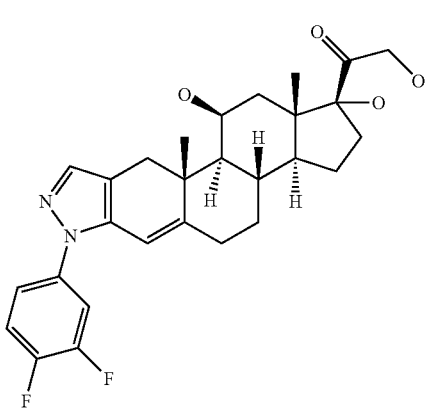

1-[(1S,3aR,3bR,10aS,10bR,11R,12aR)-7-(3,4-difluorophenyl)-1,11-dihydroxy-10a,12a-dimethyl-1,2, 3,3a,3b,4,5,7,10,10a,10b,11,12,12a-tetradecahydrocyclopenta[5,6]naphtho[1,2-f]indazol-1-yl]-2-hydroxyethanone The compound was prepared from Intermediate 60 according to the procedure for Intermediate 46. APCI-MS m/z: 499 [MH$^+$].

Intermediate 62

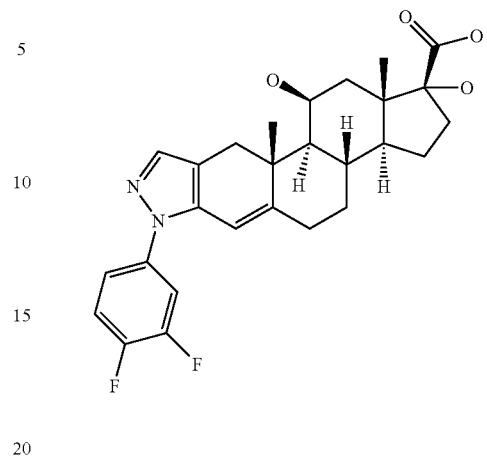

(1R,3aS,3bS,10aR,10bS,11S,12aS)-7-(3,4-difluorophenyl)-1,11-dihydroxy-10a,12a-dimethyl-1,2,3, 3a,3b,4,5,7,10,10a,10b,11,12,12a-tetradecahydrocyclopenta[5,6]naphtho[1,2-f]indazole-1-carboxylic Acid The compound was prepared from Intermediate 61 according to the procedure for Intermediate 1. APCI-MS m/z: 485 [MH$^+$].

Intermediate 63

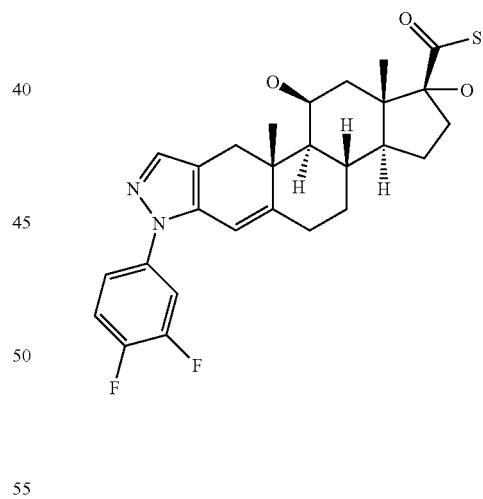

(1S,3aR,3bR,10aS,10bR,11R,12aR)-7-(3,4-difluorophenyl)-1,11-dihydroxy-10a,12a-dimethyl-1,2,3, 3a,3b,4,5,7,10,10a,10b,11,12,12a-tetradecahydrocyclopenta[5,6]naphtho[1,2-f]indazole-1-carbothioic S-acid The compound was prepared from Intermediate 62 according to the procedure for Intermediate 2. APCI-MS m/z: 501 [MH$^+$].

Intermediate 64

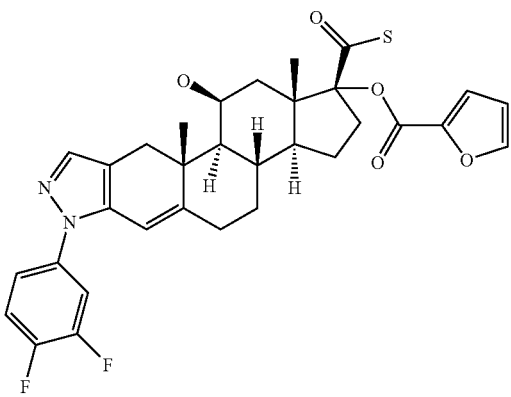

(1S,3aR,3bR,10aS,10bR,11R,12aR)-7-(3,4-difluorophenyl)-1-[(furan-2-ylcarbonyl)oxy]-11-hydroxy-10a,12a-dimethyl-1,2,3,3a,3b,4,5,7,10,10a,10b,11,12,12a-tetradecahydrocyclopenta[5,6]naphtho[1,2]-indazole-1-carbothioic S-acid The compound was prepared from Intermediate 63 and 2-furoyl chloride according to the procedure for Intermediate 3 APCI-MS m/z: 595 [MH⁺].

Intermediate 66

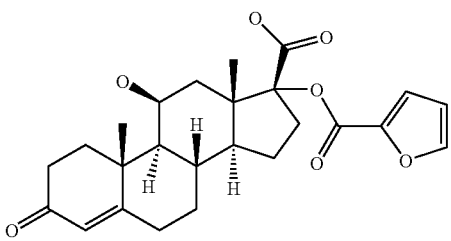

(8S,9S,10R,11S,13S,14S,17R)-17-(furan-2-carbonyloxy)-11-hydroxy-10,13-dimethyl-3-oxo-2,3,6,7,8,9,10,11,12,13,14,15,16,17-tetradecahydro-1H-cyclopenta[a]phenanthrene-17-carboxylic Acid The compound was prepared from Intermediate 38 and 2-furoyl chloride according to the procedure for Intermediate 3. APCI-MS m/z: 443 [MH⁺].

Intermediate 67

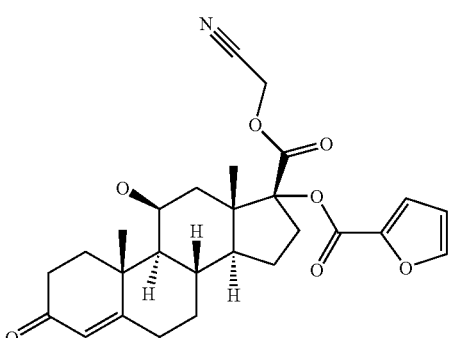

(8S,9S,10R,11S,13S,14S,17R)-17-((cyanomethoxy)carbonyl)-11-hydroxy-10,13-dimethyl-3-oxo-2,3,6,7,8,9,10,11,12,13,14,15,16,17-tetradecahydro-1H-cyclopenta[a]phenanthren-17-yl furan-2-carboxylate The compound was prepared from Intermediate 66 and bromoacetonitrile according to the procedure for Example 9. APCI-MS m/z: 482 [MH⁺].

Intermediate 68

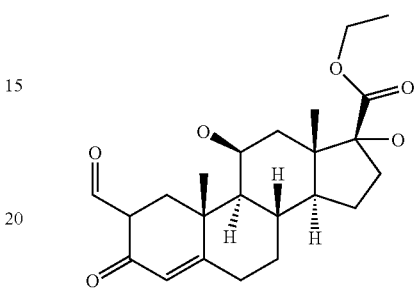

(8S,9S,10R,11S,13S,14S,17R)-ethyl 2-formyl-11,17-dihydroxy-10,13-dimethyl-3-oxo-2,3,6,7,8,9,10,11,12,13,14,15,16,17-tetradecahydro-1H-cyclopenta[a]phenanthrene-17-carboxylate Intermediate 67 (2 g, 4.15 mmol) was dissolved in toluene (20 ml) using a microwave vial and 55% NaH in oil (1.5 g, 36.6 mmol) was added under argon. Ethyl formate (1.6 ml, 20 mmol) was added. After the hydrogen evolution had ceased the vial was heated under microwave irradiation at 45° C. for 60 minutes. The mixture was partitioned between water and EtOAc. The organic phase was washed with brine, dried with MgSO₄, filtered and evaporated in vacuo. The crude product was used in the next step without further purification. APCI-MS m/z: 405 [MH⁺].

Intermediate 69

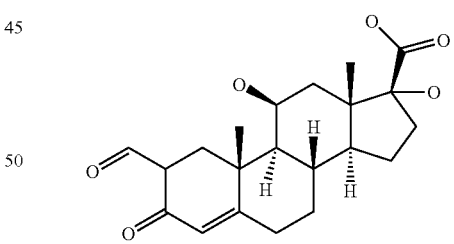

(8S,9S,10R,11S,13S,14S,17R)-2-formyl-11,17-dihydroxy-10,13-dimethyl-3-oxo-2,3,6,7,8,9,10,11,12,13,14,15,16,17-tetradecahydro-1H-cyclopenta[a]phenanthrene-17-carboxylic Acid The compound was prepared from Intermediate 66 according to the procedure for Intermediate 68. The crude mixture containing Intermediate 69 and Intermediate 70 was purified using a HPLC Kromasil® column (CH₃CN/water) and the product containing fractions were freeze-dried, giving 1.2 g of the desired compound. APCI-MS m/z: 377 [MH⁺].

Intermediate 70

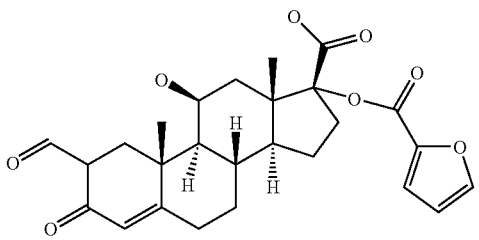

(8alpha,9beta,10alpha,11alpha,13alpha,14beta, 17beta)-2-formyl-17-[(furan-2-ylcarbonyl)oxy]-11-hydroxy-3-oxoandrost-4-ene-17-carboxylic Acid The compound was prepared from Intermediate 66 according to the procedure for Intermediate 68. The crude mixture containing Intermediate 69 and Intermediate 70 was purified using a HPLC Kromasil® column (CH$_3$CN/water) and the product containing fractions were freeze-dried, giving 0.4 g of the desired compound. APCI-MS m/z: 471 [MH$^+$].

Intermediate 71

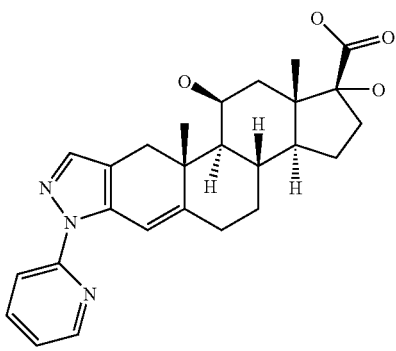

(1S,3aR,3bR,10aS,10bR,11R,12aR)-7-pyridin-1,11-dihydroxy-10a,12a-dimethyl-1,2,3,3a,3b,4,5,7,10,10a,10b,11,12,12a-tetradecahydrocyclopenta[5,6]naphtho[1,2-f]indazole-1-carboxylic Acid The compound was prepared from Intermediate 69 according to the procedure for Intermediate 50. APCI-MS m/z: 450 [MH$^+$].

Intermediate 72

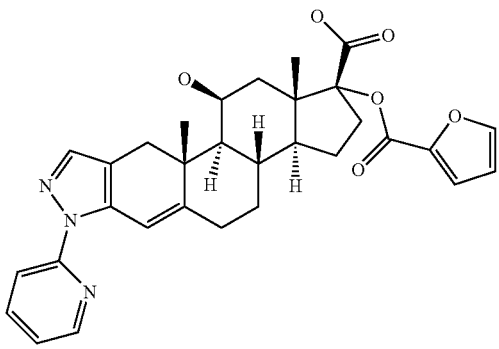

(1S,3aR,3bR,10aS,10bR,11R,12aR)-1-[(furan-2-ylcarbonyl)oxy]-11-hydroxy-10a,12a-dimethyl-7-pyridin-2-yl-1,2,3,3a,3b,4,5,7,10,10a,10b,11,12,12a-tetradecahydrocyclopenta[5,6]naphtho[1,2-f]indazole-1-carboxylic Acid The compound was prepared from Intermediate 71 and 2-furoyl chloride according to the procedure for Intermediate 6. APCI-MS m/z: 544 [MH$^+$].

Intermediate 73

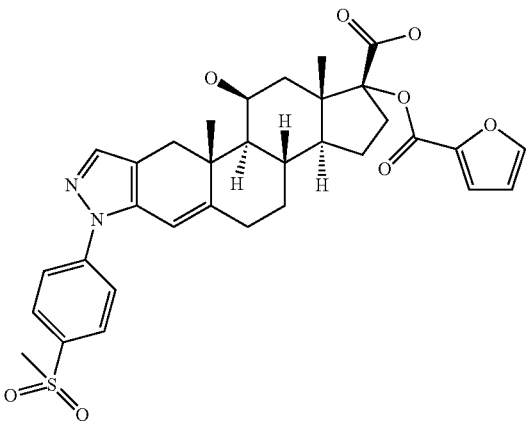

(1S,3aR,3bR,10aS,10bR,11R,12aR)-1-[(furan-2-ylcarbonyl)oxy]-11-hydroxy-10a,12a-dimethyl-7-[4-(methylsulfonyl)phenyl]1,2,3,3a,3b,4,5,7,10,10a,10b,11,12,12a-tetradecahydrocyclopenta[5,6]naphtho[1,2-f]indazole-1-carboxylic Acid The compound was prepared from Intermediate 70 and 4-hydrazinophenyl-methylsulfone according to the procedure for Intermediate 50. APCI-MS m/z: 621 [MH$^+$].

Intermediate 74

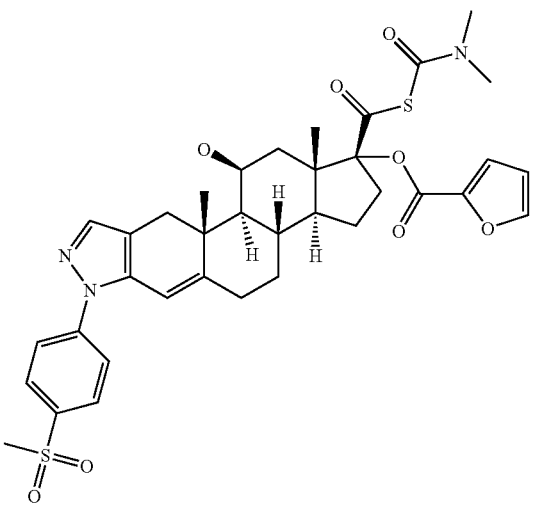

(1R,3aS,3bS,10aR,10bS,11S,12aS)-7-4-(methylsul-fonyl)phenyl]-1-{[[(dimethylcarbamoyl)sulfanyl]carbonyl}-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate Intermediate 73 (80 mg, 0.13 mmol), dimethylcarbamoyl chloride (31.9 mg, 0.26 mmol) in acetone (1.5 mL) was treated with triethylamine (39 μl, 0.28 μmol), sodium iodide (19.3 mg, 0.13 mmol) and water (20 μl). The mixture was stirred for 4 hours at room temperature, the solvent was removed in vacuo and the resulting residue was redissolved in EtOAc, washed with aqueous sodium hydrogen carbonate and the organic phase was dried over sodium sulphate, filtered and the solvent was removed under reduced pressure, giving 58 mg of the desired compound which was used without further purification. APCI-MS m/z: 708 [MH$^+$].
Intermediate 75

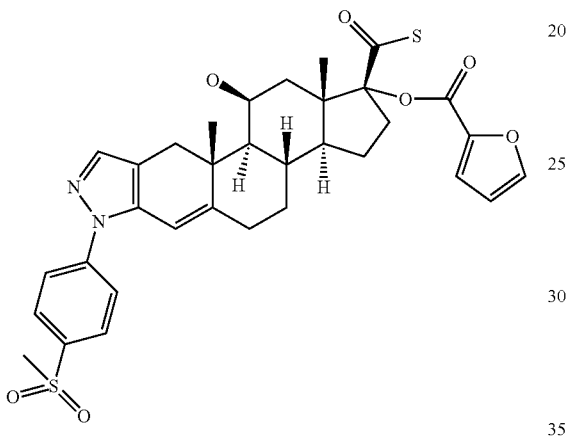

(1S,3aR,3bR,10aS,10bR,11R,12aR)-1-[(furan-2-ylcarbonyl)oxy]-11-hydroxy-10a,12a-dimethyl-7-[4-(methylsulfonyl)phenyl]-1,2,3,3a,3b,4,5,7,10,10a,10b,11,12,12a-tetradecahydrocyclopenta[5,6]naphtho[1,2-f]indazole-1-carbothioic S-acid A solution of Intermediate 74 (58 mg, 0.082 mmol) in N,N-dimethylacetamide (2 ml) was treated with sodium hydrogen sulfide monohydrate (28 mg, 0.5 mmol). The reaction was heated under microwave irradiation at 70° C. for 30 minutes. On completion the mixture was poured into cold 1 M aqueous HCl and the resulting yellowish precipitate was filtered and dried on the sinter in air to yield 34 mg of the desired compound which was used without further purification. APCI-MS m/z: 637 [MH$^+$].
Intermediate 76

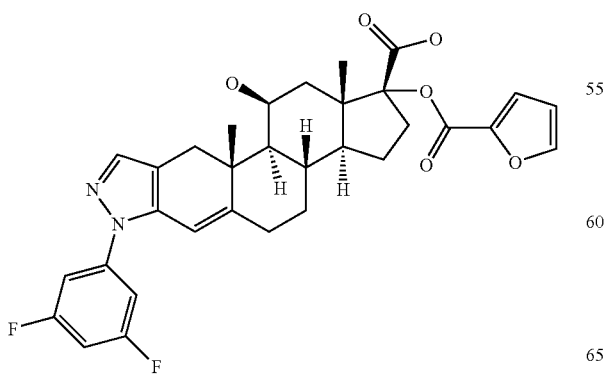

(1S,3aR,3bR,10aS,10bR,11R,12aR)-1-[(furan-2-ylcarbonyl)oxy]-11-hydroxy-7-(3,5-difluorophenyl)-10a,12a-dimethyl-1,2,3,3a,3b,4,5,7,10,10a,10b,11,12,12a-tetradecahydrocyclopenta[5,6]naphtho[1,2-f]indazole-1-carbothioic S-acid The compound was prepared from Intermediate 57 and 2-furoyl chloride according to the procedure for Intermediate 6. APCI-MS m/z: 579 [MH$^+$].
Intermediate 77

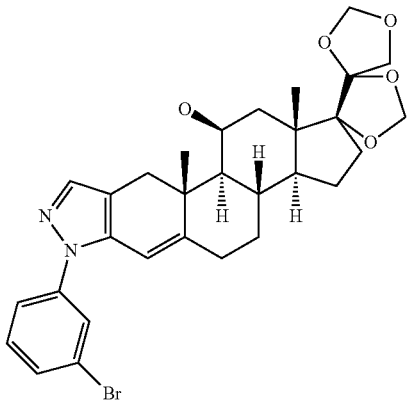

(1S,3aR,3bR,10aS,10bR,11R,12aR)-7-(3-bromophenyl)-10a,12a-dimethyl-3,3a,3b,4,5,7,10,10a,10b,11,12,12a-dodecahydro-2H-dispiro[cyclopenta[5,6]naphtho[1,2-f]indazole-1,4'-[1,3]-dioxolane-5'',4''-[1,3]-dioxolan]-11-ol The compound was prepared according to the procedure for Intermediate 44 using 3-bromophenylhydrazine hydrochloride. APCI-MS m/z: 583 and 585 [MH$^+$].
Intermediate 78

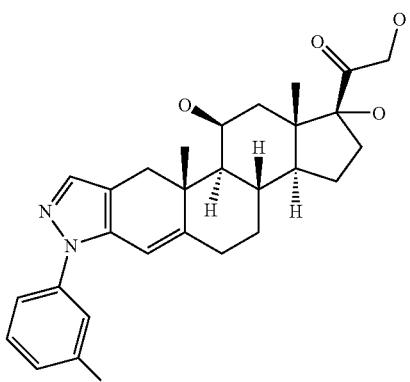

1-[(1S,3aR,3bR,10aS,10bR,11R,12aR)-7-(3-bromophenyl)-1,11-dihydroxy-10a,12a-dimethyl-1,2,3,3a,3b,4,5,7,10,10a,10b,11,12,12a-tetradecahydrocyclopenta[5,6]naphtho[1,2-f]indazol-1-yl]-2-hydroxyethanone The compound was prepared from Intermediate 77 according to the procedure for Intermediate 46. APCI-MS m/z: 541 and 543 [MH$^+$].

Intermediate 79

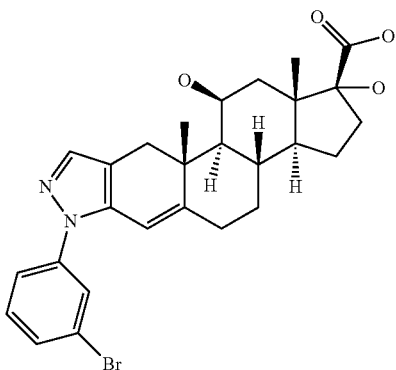

(1R,10aR,11S,12aS)-7-(3-bromophenyl)-1,11-dihydroxy-10a,12a-dimethyl-1,2,3,3a,3b,4,5,7,10,10a,10b,11,12,12a-tetradecahydrocyclopenta[5,6]naphtho[1,2-f]indazole-1-carboxylic Acid The compound was prepared from Intermediate 78 according to the procedure for Intermediate 1. APCI-MS m/z: 527 and 529 [MH⁺].

Intermediate 80

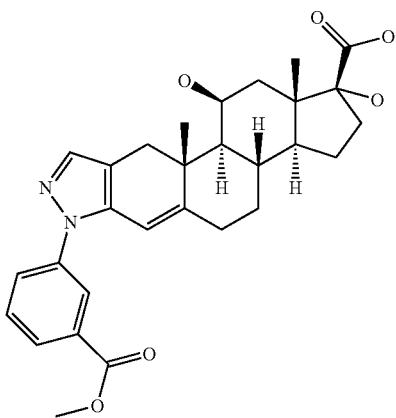

(1S,3aR,3bR,10aS,10bR,11R,12aR)-1,11-dihydroxy-7-[3-(methoxycarbonyl)phenyl]-10a,12a-dimethyl-1,2,3,3a,3b,4,5,7,10,10a,10b,11,12,12a-tetradecahydrocyclopenta[5,6]naphtho[1,2-f]indazole-1-carboxylic Acid In a stainless-steel high-pressure reactor were placed Intermediate 79 (410 mg, 0.78 mmol), palladium acetate (9 mg, 0.04 mmol), 1,3-bis(diphenylphosphino)propane (50 mg, 0.12 mmol) and N,N-diisopropylethylamine (0.136 ml, 0.78 mmol) in DMF (3 ml) and methanol (3 ml). The reaction mixture was degassed with carbon monoxide under vigorous stirring, pressurized at 6.5 atmospheres carbon monoxide and heated at 110° C. overnight. The reaction mixture was allowed to reach room temperature and the pressure was reduced to 1 atmosphere. The reaction mixture was concentrated in vacuo and the residue was partitioned between EtOAc and water. The organic phase was washed with water and brine, dried over Na₂SO₄ and concentrated in vacuo. The obtained residue was purified on silica gel (EtOAc:Heptane=1:4) to give 300 mg of the desired product. APCI-MS m/z: 507 [MH⁺].

Intermediate 81

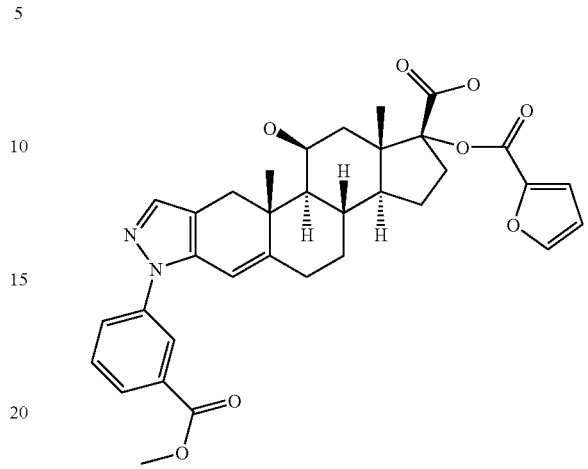

(1S,3aR,3bR,10aS,10bR,11R,12aR)-1-[(furan-2-ylcarbonyl)oxy]-11-hydroxy-7-[3-(methoxycarbonyl)phenyl]-10a,12a-dimethyl-1,2,3,3a,3b,4,5,7,10,10a,10b,11,12,12a-tetradecahydrocyclopenta[5,6]naphtho[1,2-f]indazole-1-carbothioic S-acid The compound was prepared from Intermediate 80 and 2-furoyl chloride according to the procedure for Intermediate 6. APCI-MS m/z: 601 [MH⁺].

Intermediate 82

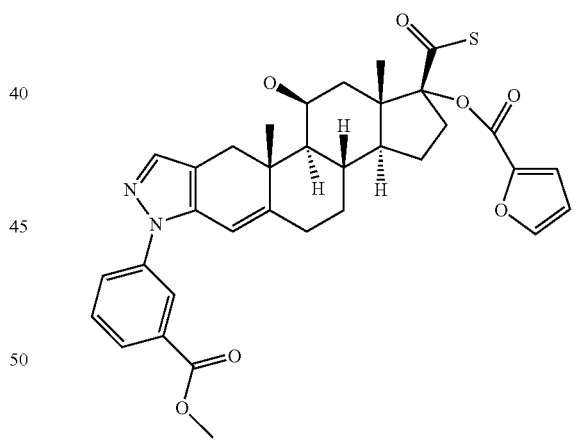

(1S,3aR,3bR,10aS,10bR,11R,12aR)-1-[(furan-2-ylcarbonyl)oxy]-11-hydroxy-7-[3-(methoxycarbonyl)phenyl]-10a,12a-dimethyl-1,2,3,3a,3b,4,5,7,10,10a,10b,11,12,12a-tetradecahydrocyclopenta[5,6]naphtho[1,2-f]indazole-1-carbothioic S-acid In a 25 mL round-bottomed flask was added Intermediate 81 (0.3 g, 0.5 mmol) and diethyl chlorophophate (0.2 g, 1.16 mmol) in THF (5 mL) to give a yellow solution. The solution was stirred overnight at room temperature and H₂S (g) was bubbled through the solution for 5 minutes. A colour change from yellow to green was observed and the mixture was stirred for another 30 minutes at the same temperature. The reaction mixture was poured into 1M HCl (15 ml) and the solid formed was isolated by filtration, washed with water and dried on the sinter in air to give 0.12 g of the desired compound which was used as such. APCI-MS m/z: 617 [MH$^+$].

Intermediate 83

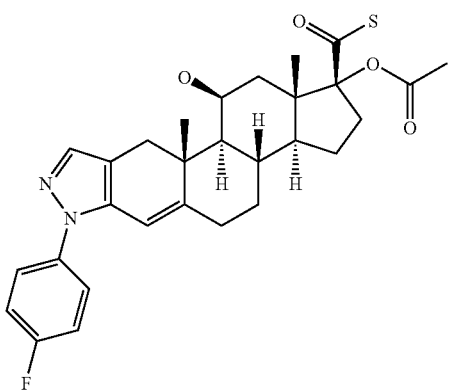

(1R,3aS,3bS,10aR,10bS,11S,12aS)-1-(acetyloxy)-7-(4-fluorophenyl)-11-hydroxy-10a,12a-dimethyl-1,2,3,3a,3b,4,5,7,10,10a,10b,11,12,12a-tetradecahydro-cyclopenta[5,6]naphtho[1,2-f]indazole-1-carbothioic S-acid Intermediate 2 (0.2 g, 0.41 mmol) was dissolved in DCM (8 ml) and triethylamine (0.230 ml, 1.66 mmol) was added at room temperature. The mixture was stirred for 3 min. before acetyl chloride (0.088 ml, 1.24 mmol) in DCM (1 ml) was added portionwise and the mixture was stirred for 15 min. N$_1$-ethyl-N$_2$,N$_2$-dimethylethane-1,2-diamine (0.325 ml, 2.07 mmol) was added and the mixture was stirred for another 20 min. The mixture was diluted with DCM (20 ml), washed with 2N HCl (2 times 20 ml), brine and dried over sodium sulfate. Filtration and evaporation of the solvent under reduced pressure gave 0.217 mg of crude product which was used as such without further purification. APCI-MS m/z: 525 [MH$^+$].

Intermediate 84

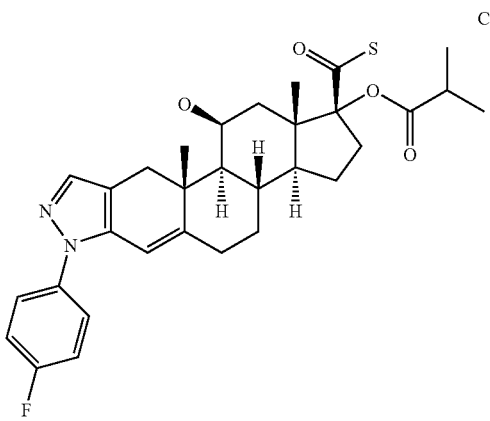

(1R,3aS,3bS,10aR,10bS,11S,12aS)-7-(4-fluorophenyl)-11-hydroxy-10a,12a-dimethyl-1-[(2-methylpropanoyl)oxy]1,2,3,3a,3b,4,5,7,10,11a,10b,11,12,12a-tetradecahydrocyclopenta[5,6]naphtho[1,2-f]indazole-1-carbothioic S-acid The compound was prepared from Intermediate 2 and isobutyryl chloride according to the procedure for Intermediate 83. APCI-MS m/z: 553 [MH$^+$].

Intermediate 85

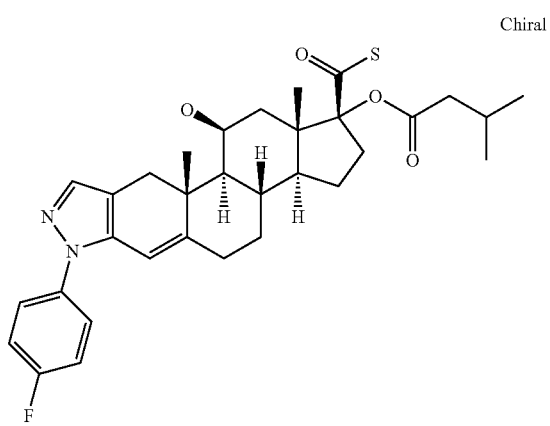

(1R,3aS,3bS,10aR,10bS,11S,12aS)-7-(4-fluorophenyl)-11-hydroxy-10a,12a-dimethyl-1-[(3-methylbutanoyl)oxy]-1,2,3,3a,3b,4,5,7,10,10a,10b,11,12,12a-tetradecahydrocyclopenta[5,6]naphtho[1,2-f]indazole-1-carbothioic S-acid The compound was prepared from Intermediate 2 and 3-methyl butyryl chloride according to the procedure for Intermediate 83. APCI-MS m/z: 567 [MH$^+$].

Intermediate 86

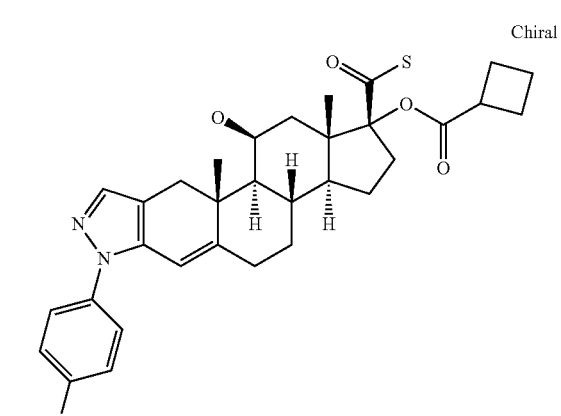

(1R,3aS,3bS,10aR,10bS,11S,12aS)-1-[(cyclobutylcarbonyl)oxy]-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazole-1-carbothioic S-acid The compound was prepared from Intermediate 2 and cyclobutanecarbonyl chloride according to the procedure for Intermediate 83. APCI-MS m/z: 565 [MH$^+$].

Intermediate 87

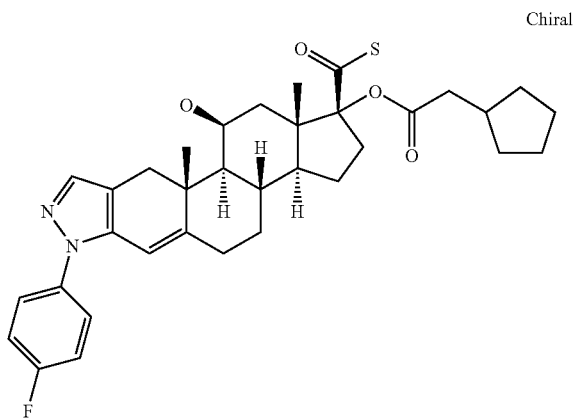

(1R,3aS,3bS,10aR,10bS,11S,12aS)-1[(cyclopenty-lacetyl)oxy]-7-(4-fluorophenyl)-11-hydroxy-10a,
12a-dimethyl-1,2,3,3a,3b,4,5,7,10,10a,10b,11,12,
12a-tetradecahydrocyclopenta[5,6]naphtho[1,2-f]
indazole-1-carbothioic S-acid The compound was prepared from Intermediate 2 and cyclopentylacetyl chloride according to the procedure for Intermediate 83. APCI-MS m/z: 593 [MH+].

Intermediate 88

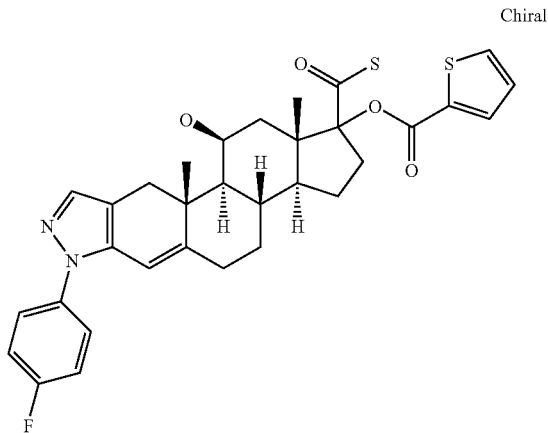

(1R,3aS,3bS,10aR,10bS,11S,12aS)-7-(4-fluorophe-nyl)-11-hydroxy-10a,12a-dimethyl-1-[(thiophen-2-ylcarbonyl)oxy]-1,2,3,3a,3b,4,5,7,10,10a,10b,11,12,
12a-tetradecahydrocyclopenta[5,6]naphtho[1,2-f]
indazole-1-carbothioic S-acid The compound was prepared from Intermediate 2 and thiophene-2-carbonyl chloride according to the procedure for Intermediate 83. APCI-MS m/z: 593 [MH+].

Intermediate 89

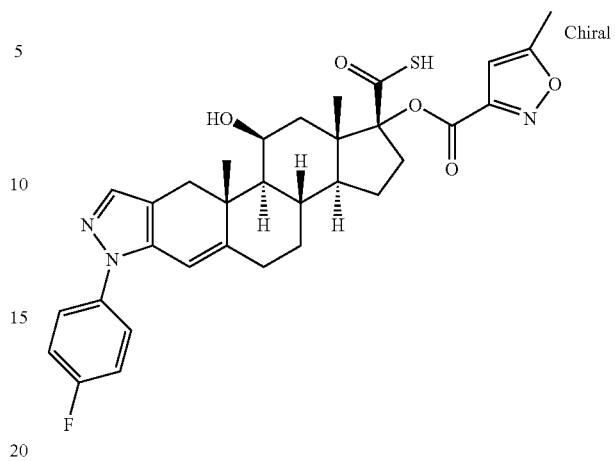

(1R,3aS,3bS,10aR,10bS,11S,12aS)-7-(4-fluorophe-nyl)-11-hydroxy-10a,12a-dimethyl-1-{[(5-methyl-isoxazol-3-yl)carbonyl]oxy}-1,2,3,3a,3b,4,5,7,10,
10a,10b,11,12,12a-tetradecahydrocyclopenta[5,6]
naphtho[1,2-f]indazole-1-carbothioic S-acid The compound was prepared from Intermediate 2 and 5-methyl-isoxazole-3 carbonyl chloride according to the procedure for Intermediate 83. APCI-MS m/z: 592 [MH+].

Intermediate 90

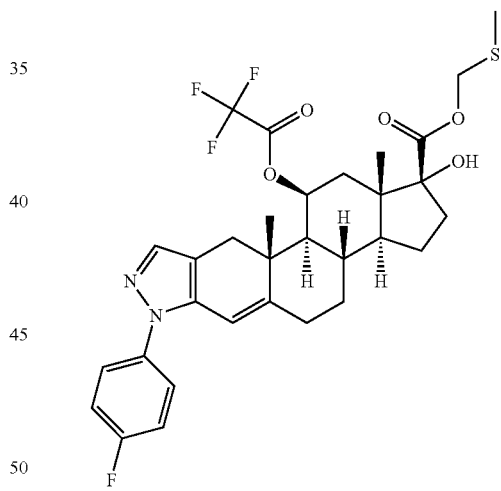

(Methylsulfanyl)methyl(1R,3aS,3bS,10aR,10bS,11S,
12aS)-7-(4-fluoro phenyl)-1-hydroxy-10a,12a-dim-ethyl-11-[(trifluoroacetyl)oxy]-1,2,3,3a,3b,4,5,7,10,
10a,10b,11,12,12a-tetradecahydro cyclopenta[5,6]
naphtho[1,2-f]indazole-1-carboxylate Example 117 (0.87 g, 1.65 mmol) was stirred for 20 min. in pyridine (8 ml) at −20° C. and 2,2,2-trifluoroacetic anhydride (0.256 ml, 1.82 mmol) was added dropwise. The cooling bath was removed and the mixture was left stirring overnight. The solvent was evaporated under reduced pressure and the residue was partitioned between 1N HCl (50 ml) and EtOAc (50 ml). The phases were separated and the organic phase was washed with brine (20 ml), dried over $Na_2SO_4$ and purified on a preparative HPLC column ($CH_3CN$/water) to give after freeze-drying of the product containing fractions 170 mg of the title compound. APCI-MS m/z: 623 [MH+].

Intermediate 91

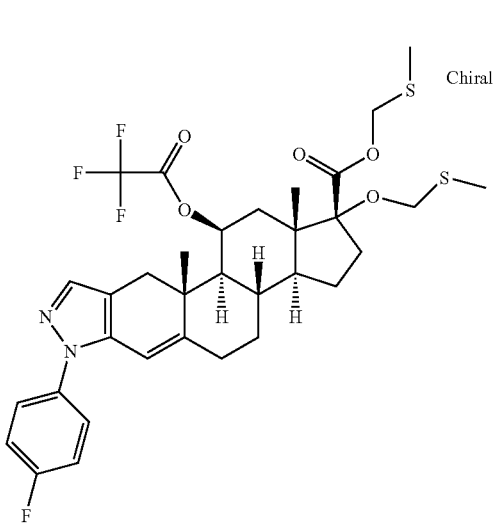

(Methylsulfanyl)methyl(1R,3aS,3bS,10aR,10bS,11S, 12aS)-7-(4-fluorophenyl)-10a,12a-dimethyl-1-[(methylsulfanyl)methoxy]-11-[(trifluoroacetyl)oxy]-1,2, 3,3a,3b,4,5,7,10a,10b,11,12,12a-tetradecahydrocyclopenta[5,6]naphtho[1,2-f] indazole-1-carboxylate Intermediate 90 (0.16 g, 0.26 mmol) was dissolved in a mixture containing DMSO (3 ml) and acetic anhydride (3 ml). The solution was stirred for 72 hours under an atmosphere of argon. After removal of the solvent in vacuo, acetonitrile (1 ml) and water (200 µl) were added and the mixture was purified on a preparative HPLC column (CH$_3$CN/water) to give after freeze drying of the product containing fractions 120 mg of the title compound. APCI-MS m/z: 683 [MH+].

Intermediate 92

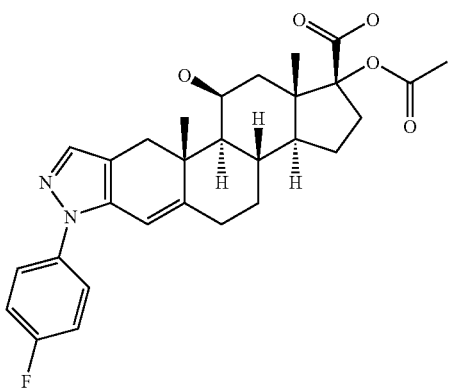

(1S,3aR,3bR,10aS,10bR,11R,12aR)-1-(acetyloxy)-7-(4-fluorophenyl)-11-hydroxy-10a,12a-dimethyl-1,2, 3,3a,3b,4,5,7,10,10a,10b,11,12,12a-tetradecahydrocyclopenta[5,6]naphtho[1,2-f]indazole-1-carboxylic Acid The compound was prepared from Intermediate 1 and acetyl chloride according to the procedure for Intermediate 83. APCI-MS m/z: 509 [MH+].

Intermediate 93

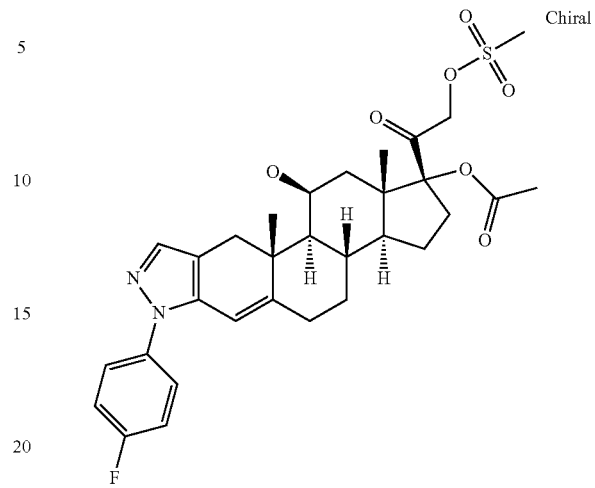

(1R,3aS,3bS,10aR,10bS,11S,12aS)-7-(4-fluorophenyl)-11-hydroxy-10a,12a-dimethyl-1-{[(methlsulfonyl)oxy]acetyl}-1,2,3,3a,3b,4,5,7,10,10a,10b,11,12, 12a-tetradecahydrocyclopenta[5,6]naphtho[1,2-f] indazol-1-yl acetate Methanesulfonyl chloride (0.018 ml, 0.23 mmol) was added to a solution of Intermediate 92 (0.06 g, 0.11 mmol) in pyridine (1.5 ml) while cooling in an ice-bath. The mixture was stirred at 4° C. for 240 min. and was subsequently poured into ice-water (30 ml) and extracted with EtOAc (20 ml). The organic phase was washed successively with 1N HCl and brine, dried over sodium sulfate, filtered and concentrated under reduced pressure to give 90 mg of a mixture which was purified on a preparative HPLC column (CH$_3$CN/water) to give after freeze drying of the product containing fractions 45 mg of the title compound.

$^1$H NMR (400 MHz, DMSO-d6) δ 7.52 (m, 2H), 7.49 (s, 1H), 7.35 (m, 2H), 6.15 (s, 1H), 4.96 (dd, 2H), 4.59 (d, 1H), 4.41 (d, 1H), 3.25 (s, 3H), 2.98 (d, 1H), 2.86 (m, 1H), 2.70 (d, 1H), 2.42 (m, 1H), 2.29 (m, 1H), 2.06 (s 3H), 2.02 (m, 2H), 1.91 (m, 3H), 1.78 (m, 1H), 1.69 (m, 1H), 1.42 (m, 1H), 1.29 (d, 1H), 1.26 (s, 3H), 1.04 (m, 1H), 0.90 (s, 3H). APCI-MS m/z: 601 [MH+].

Intermediate 94

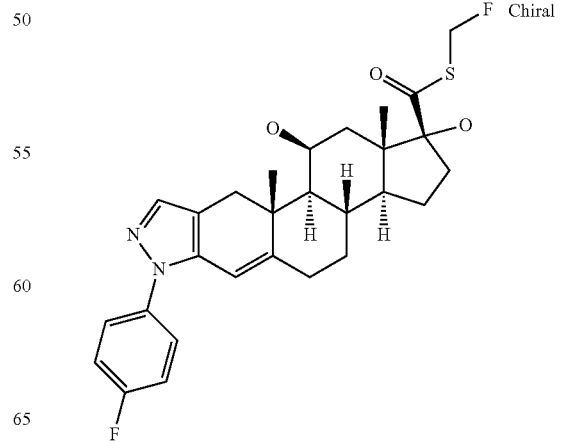

S-(fluoromethyl)(1R,3aS,3bS,10aR,10bS,11S,12aS)-7-(4-fluorophenyl)-1,11-dihydroxy-10a,12a-dimethyl-1,2,3,3a,3b,4,5,7,10,10a,10b,11,12,12a-tetradecahydrocyclopenta[5,6]naphtho[1,2-f]indazole-1-carbothioate To a solution of Intermediate 2 (0.62 g, 1.28 mmol) in acetonitrile (10 ml), triethylamine (0.534 ml, 3.85 mmol) was added followed by 0.65 ml of a 45% solution of bromofluoromethane in DCM. The resulting solution was heated under reflux for 1 hour and cooled to room temperature. The solvent was evaporated under reduced pressure and the residue redissolved in EtOAc (15 ml), washed with 1N HCl, and brine and dried over $Na_2SO_4$. Purification on silica gel (EtOAC/Heptane=4:1), collection of the product containing fractions and evaporation of the combined fractions yielded 330 mg of the target compound. APCI-MS m/z: 515 [MH+].

Intermediate 95

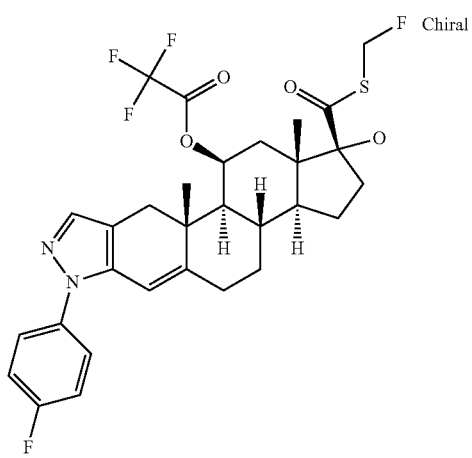

(1R,3aS,3bS,10aR,10bS,11S,12aS)-1-{[(fluoromethyl)sulfanyl]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-11-yl trifluoroacetate Intermediate 94 (0.33 g, 0.64 mmol) was stirred for 20 min. in pyridine (3 ml) at −20° C. and 2,2,2-trifluoroacetic anhydride (0.1 ml, 0.71 mmol) was added dropwise and stirring was continued for 180 min. The solvent was evaporated under reduced pressure and the residue was partitioned between 1N HCl (50 ml) and EtOAc (50 ml). The phases were separated and the organic phase was washed with brine and dried over $Na_2SO_4$. After filtration and evaporation under reduced pressure the obtained mixture was purified on a preparative HPLC column ($CH_3CN$/water) and the product containing fractions were freeze-dried to give 87 mg of the title compound. APCI-MS m/z: 611 [MH+].

Intermediate 96

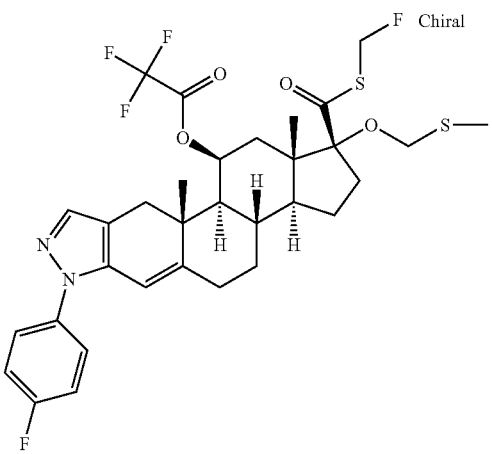

(1R,3aS,3bS,10aR,10bS,11S,12aS)-1-{[(fluoromethyl)sulfanyl]carbonyl}-7-(4-fluorophenyl)-10a,12a-dimethyl-1-[(methylsulfanyl)methoxy]-1,2,3,3a,3b,4,5,7,10,10a,10b,11,12,12a-tetradecahydrocyclopenta[5,6]naphtho[1,2-f]indazol-11-yl trifluoroacetate Intermediate 95 (0.084 g, 0.14 mmol) was dissolved in a mixture containing DMSO (0.5 ml) and acetic anhydride (0.5 ml). The solution was stirred for 48 hours under an atmosphere of argon. After evaporation under reduced pressure the residue was purified on a preparative HPLC column ($CH_3CN$/water) and the product containing fractions were freeze-dried to give 5 mg of the title compound. APCI-MS m/z: 671 [MH+].

Intermediate 97

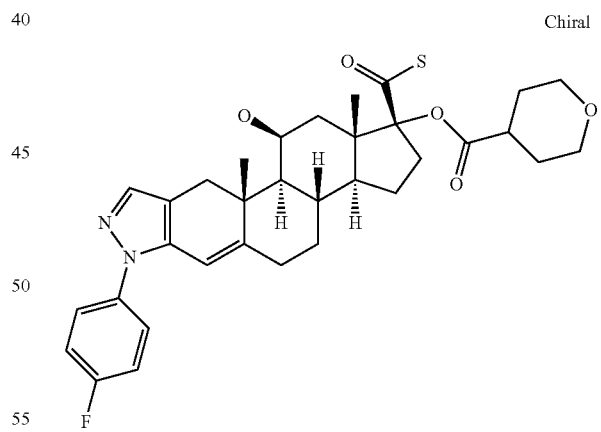

(1R,3aS,3bS,10aR,10bS,11S,12aS)-1-{[(cyanomethyl)sulfanyl]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl tetrahydro-2H-pyran-4-carboxylate The compound was prepared from Intermediate 2 and tetrahydro-2H-pyran-4-carbonyl chloride according to the procedure for Intermediate 83. APCI-MS m/z: 595 [MH+].

Intermediate 98

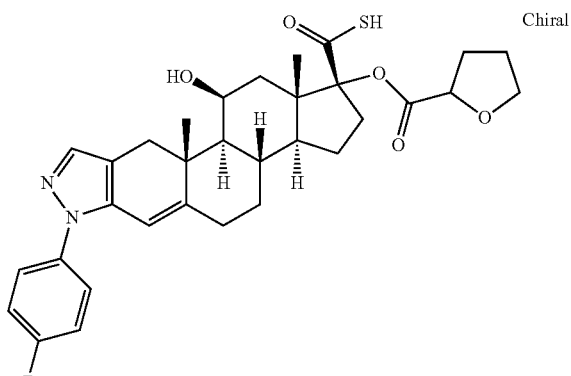

(1R,3aS,3bS,10aR,10bS,11S,12aS)-7-(4-fluorophenyl)-11-hydroxy-10a,12a-dimethyl-1-[(tetrahydrofuran-2-ylcarbonyl)oxy]-1,2,3,3a,3b,4,5,7,10,10a,11,12,12a-tetradecahydrocyclopenta[5,6]naphtho[1,2-f]indazole-1-carbothioic S-acid The compound was prepared from Intermediate 2 and tetrahydrofuran-2-carbonyl chloride (J. Chem. Soc, Perkin Trans. 1, 2002, 571-576) according to the procedure for Intermediate 83. APCI-MS m/z: 581 [MH$^+$].

Intermediate 99

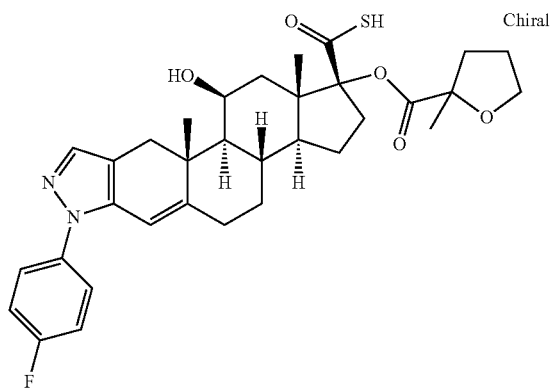

(1R,3aS,3bS,10aR,10bS,11S,12aS)-7-(4-fluorophenyl)-11-hydroxy-10a,12a-dimethyl-1-{[(2-methyltetrahydrofuran-2-yl)carbonyl]oxy}-1,2,3,3a,3b,4,5,7,10,10a,10b,11,12,12a-tetradecahydrocyclopenta[5,6]naphtho[1,2-f]indazole-1-carbothioic S-acid The compound was prepared from Intermediate 2 and racemic 2-methyltetrahydrofuran-2-carbonyl chloride according to the procedure for Intermediate 83. APCI-MS m/z: 595 [MH$^+$].

Intermediate 100

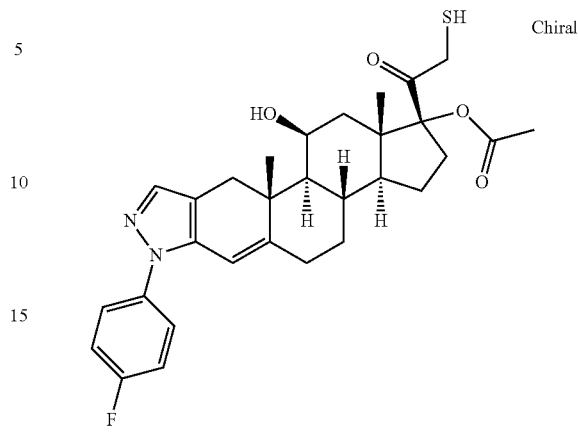

(1R,3aS,3bS,10aR,10bS,11S,12aS)-7-(4-fluorophenyl)-11-hydroxy-10a,12a-dimethyl-1-(sulfanylacetyl)-1,2,3,3a,3b,4,5,7,10,10a,10b,11,12,12a-tetradecahydrocyclopenta[5,6]naphtho[1,2-f]indazol-1-yl acetate Hydrazine hydrate (0.09 ml, 1.85 mmol) was added to a solution of Example 123 (0.02 g, 0.03 mmol) in THF (10 ml). The mixture was stirred for 40 min. at −30° C., diluted with ice-water (20 ml) and extracted with EtOAc (30 ml). The organic extract was washed successively with 1N HCl and brine, dried and concentrated in vacuo. The obtained residue was purified on a preparative HPLC column (CH$_3$CN/water) to give 11 mg of the title compound. APCI-MS m/z: 539 [MH$^+$].

Intermediate 101

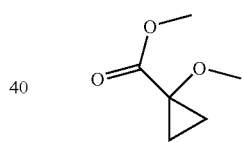

Methyl 1-methoxycyclopropanecarboxylate

According to WO 2005/014577 methyl 1-hydroxycyclopropanecarboxylate (1.01 g, 8.70 mmol) was dissolved under argon in THF (10 ml) and cooled using an ice-bath. Sodium hydride (60%, 0.52 g, 13.00 mmol) was added portionwise followed by iodomethane (1 ml, 16.06 mmol) and the mixture was stirred for 18 hours at room temperature. The mixture was quenched with saturated solution of NH$_4$Cl (20 ml) and extracted with EtOAc. The organic extracts were combined, dried, filtered and evaporated in vacuo to give 620 mg of the crude product which was used as such.

$^1$H NMR (400 MHz, CDCl$_3$) δ 3.76 (s, 3H), 3.43 (s, 3H), 1.25-1.17 (b, 4H),

Intermediate 102

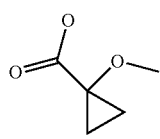

1-methoxycyclopropanecarboxylic Acid

According to WO 2005/014577 Intermediate 101 (0.62 g, 4.76 mmol) was dissolved in THF (10 ml) and 7 ml of 5M NaOH was added. After stirring for 16 hours the mixture was acidified with conc. HCl whilst cooling the reaction in an ice-bath. The product was extracted with EtOAc, dried, filtered and evaporated in vacuo to give 436 mg of the desired product.

$^{13}$C-NMR (DMSO-d6) δ 15.30, 56.2, 60.2, 174.14

Intermediate 103

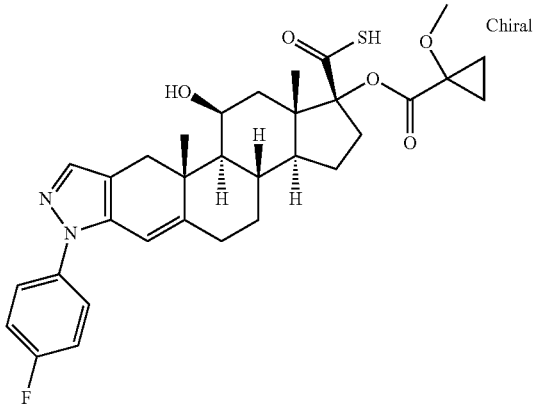

(1R,3aS,3bS,10aR,10bS,11S,12aS)-7-(4-fluorophenyl)-11-hydroxy-1-{[(1-methoxycyclopropyl)carbonyl]oxy}-10a,12a-dimethyl-1,2,3,3a,3b,4,5,7,10,10a,10b,11,12,12a-tetradecahydrocyclopenta[5,6]naphtho[1,2-f]indazole-1-carbothioic S-acid The compound was prepared from Intermediate 2 and 1-methoxycyclopropane carbonyl chloride (generated in situ from Intermediate 102 and excess thionyl chloride in toluene at 80° C. for 15 min) according to the procedure for Intermediate 83. APCI-MS m/z: 581 [MH$^+$].

Intermediate 104

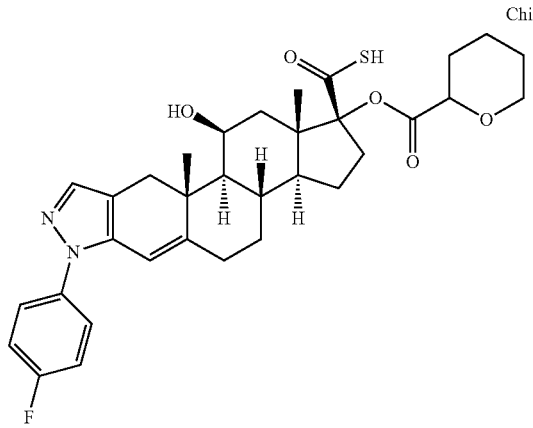

(1R,3aS,3bS,10aR,10bS,11S,12aS)-7-(4-fluorophenyl)-11-hydroxy-10a,12a-dimethyl-1-[(tetrahydro-2H-pyran-2-ylcarbonyl)oxy]-1,2,3,3a,3b,4,5,7,10,10a,10b,11,12,12a-tetradecahydrocyclopenta[5,6]naphtho[1,2-f]indazole-1-carbothioic S-acid The compound was prepared from Intermediate 2 and tetrahydro-2H-pyran-2-carbonyl chloride according to the procedure for Intermediate 83. APCI-MS m/z: 595 [MH$^+$].

Intermediate 105

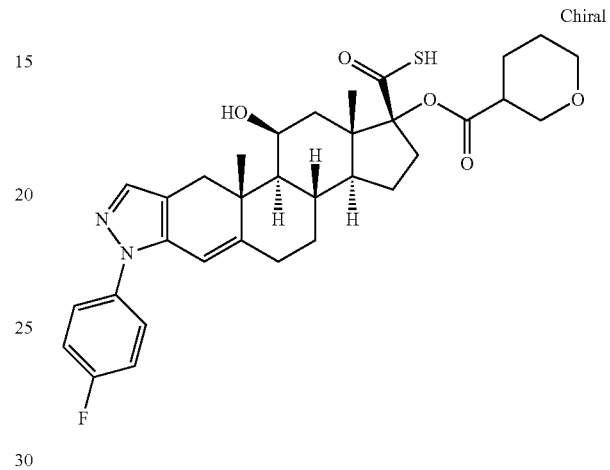

(1R,3aS,3bS,10aR,10bS,11S,12aS)-7-(4-fluorophenyl)-11-hydroxy-10a,12a-dimethyl-1-[(tetrahydro-2H-pyran-3-ylcarbonyl)oxy]-1,2,3,3a,3b,4,5,7,10,10a,10b,11,12,12a-tetradecahydrocyclopenta[5,6]naphtho[1,2-f]indazole-1-carbothioic S-acid The compound was prepared from Intermediate 2 and tetrahydro-2H-pyran-3-carbonyl chloride according to the procedure for Intermediate 83.

$^1$H NMR (500 MHz, DMSO-d$_6$) δ 7.51 (2H, m), 7.46 (1H, s), 7.35 (2H, m), 6.12 (1H, d), 4.57 (1H, s), 4.36 (1H, m), 4.11 (1H, m), 4.06 (1H, d), 3.96 (1H, d), 3.86 (1H, m), 3.43 (1H, m), 2.94 (1H, d), 2.80 (1H, dd), 2.65 (1H, d), 2.51 (1H, m), 2.43 (1H, m), 2.29 (1H, m), 1.94-1.84 (5H, m), 1.82-1.71 (2H, m), 1.63-1.53 (3H, m), 1.49-1.43 (2H, m), 1.37 (1H, m), 1.22 (3H, s), 1.15 (1H, dd), 1.03 (1H, m), 0.89 (3H, s).

APCI-MS m/z: 595 [MH$^+$].

Intermediate 106

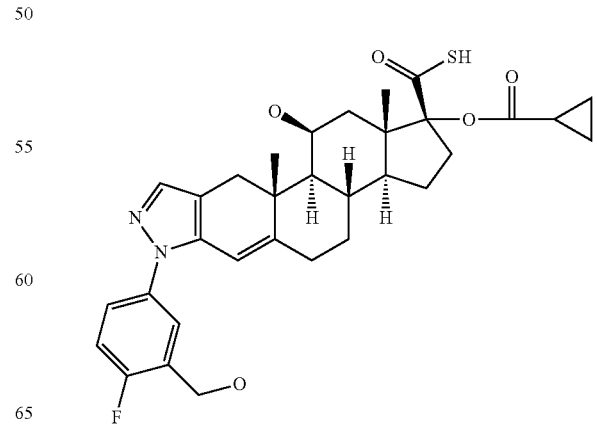

(1R,3aS,3bS,10aR,10bS,11S,12aS)-1-[(cyclopropyl-
carbonyl)oxy]-7-[4-fluoro-3-(hydroxymethyl)phe-
nyl]-11-hydroxy-10a,12a-dimethyl-1,2,3,3a,3b,4,5,7,
10,10a,10b,11,12,12a-tetradecahydrocyclopenta[5,6]
naphtho[1,2-f]indazole-1-carbothioic S-acid In a 25 mL round-bottomed flask was dissolved Intermediate 36 (0.27 g, 0.53 mmol) and triethylamine (0.2 mL, 1.43 mmol) in DCM (8 mL) to give an orange solution. A solution of cyclopropanecarbonyl chloride (0.110 g, 1.05 mmol) in DCM (1 ml) was added and the mixture was stirred for 15 minutes. $N_1$-ethyl-$N_2$,$N_2$-dimethylethane-1,2-diamine (0.248 mL, 1.58 mmol) was added, and the mixture was stirred for another 15 minutes. The mixture was diluted with 20 ml DCM in a separation funnel, and the obtained solution was washed with 1M HCl (2 times 15 ml), and brine (10 ml). The organic solution was dried over $Na_2SO_4$. Filtration and evaporation gave 270 mg of an orange semi-solid, which was used in the subsequent step without purification. APCI-MS m/z: 581 [MH$^+$].

Intermediate 107

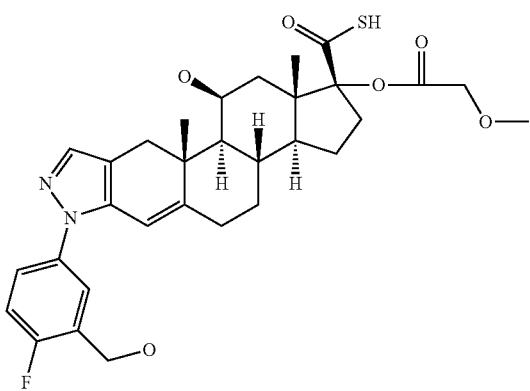

(1R,3aS,3bS,10aR,10bS,11S,12aS)-7-[4-fluoro-3-
(hydroxymethyl)phenyl]-11-hydroxy-1-[(methoxy-
acetyl)oxy]-10a,12a-dimethyl-1,2,3,3a,3b,4,5,7,10,
10a,10b,11,12,12a-tetradecahydrocyclopenta[5,6]
naphtho[1,2-f]indazole-1-carbothioic S-acid In a 100 mL round-bottomed flask was dissolved Intermediate 36 (0.27 g, 0.53 mmol) and triethylamine (0.183 mL, 1.32 mmol) in DCM (8 mL) to give a orange solution. 2-methoxyacetyl chloride (0.074 g, 0.68 mmol) diluted in DCM (1 ml) was added dropwise to the stirred solution. After 10 minutes, $N_1$-ethyl-$N_2$,$N_2$-dimethylethane-1,2-diamine (0.248 mL, 1.58 mmol) was added, and the mixture was stirred for another 10 minutes. The crude mixture was diluted with 20 ml DCM in a separation funnel and washed with 1M HCl (20 ml), and brine (15 ml), and finally dried over $Na_2SO_4$. Filtration and evaporation of the solvent gave 270 mg of the product as a brownish film which was used as such without purification. APCI-MS m/z: 585 [MH$^+$].

Intermediate 108

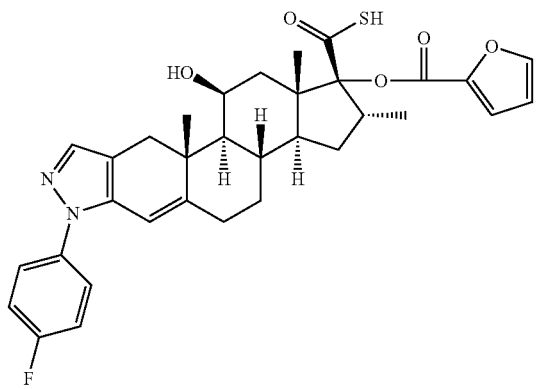

(1R,2R,3aS,3bS,10aR,10bS,11S,12aS)-7-(4-fluo-
rophenyl)-1-[(furan-2-ylcarbonyl)oxy]-11-hydroxy-
2,10a,12a-trimethyl-1,2,3,3a,3b,4,5,7,10,10a,10b,11,
12,12a-tetradecahydrocyclopenta[5,6]naphtho[1,2-f]
indazole-1-carbothioic S-acid The compound was prepared according to the procedure for the preparation of Intermediate 3, starting from 16-a-Methyl-hydrocortisone (*Steroids* 2003 (68) 177-191). APCI-MS m/z: 591 [MH$^+$].

Intermediate 109

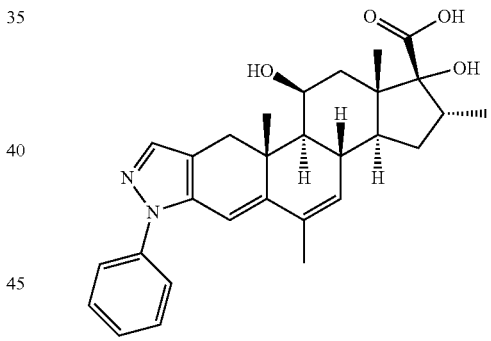

(1R,2R,3aS,3bS,10aR,10bS,11S,12aS)-1,11-dihy-
droxy-2,5,10a,12a-tetramethyl-7-phenyl-1,2,3,3a,3b,
7,10,10a,10b,11,12,12a-dodecahydrocyclopenta[5,6]
naphtho[1,2-f]indazole-1-carboxylic Acid In a 50 mL round-bottomed flask was dissolved (11β,16α)-21-(Acetyloxy)-11,17-dihydroxy-6,16-dimethyl-2'-phenyl-2'H-pregna-2,4,6-trieno[3,2-c]pyrazol-20-one (also known as Cortivazol) (0.1 g, 0.19 mmol) in MeOH (10 mL) to give a colorless solution. 1M sodium hydroxide (1.2 mL, 1.20 mmol) was added, and the mixture was stirred in an open flask overnight. The solution was acidified by the addition of 1M HCl (1.3 ml), MeOH was removed in vacuo after which the product precipitated as a white solid which was filtered, washed with water and dried in air on the sinter to give 85 mg of the desired product as a white solid. APCI-MS m/z: 475 [MH$^+$].

Intermediate 110

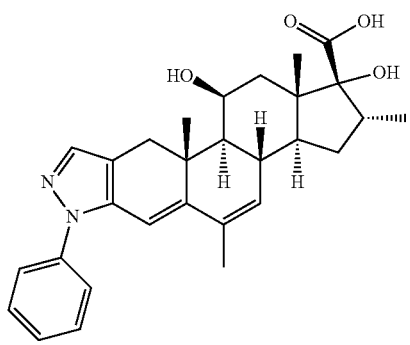

(1R,2R,3aS,3bS,10aR,10bS,11S,12aS)-1,11-dihydroxy-2,5,10a,12a-tetramethyl-7-phenyl-1,2,3,3a,3b,7,10,10a,10b,11,12,12a-dodecahydrocyclopenta[5,6]naphtho[1,2-f]indazole-1-carbothioic S-acid The compound was prepared according to the procedure described for Intermediate 2, starting from Intermediate 109. APCI-MS m/z: 491 [MH$^+$].

Intermediate 111

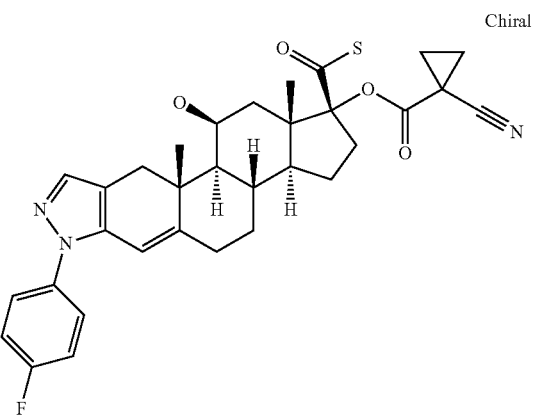

(1R,3aS,3bS,10aR,10bS,11S,12aS)-{[(1-cyanocyclopropyl)carbonyl]oxy}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazole-1-carbothioic S-acid The compound was prepared according to the procedure for Intermediate 3, starting from Intermediate 2 and 1-cyanocyclopropanecarbonyl chloride (generated in situ from 1-cyanocyclopropanecarboxylic acid and excess thionyl chloride in toluene at 80° C. for 15 min.). APCI-MS m/z: 576 [MH$^+$].

Intermediate 112

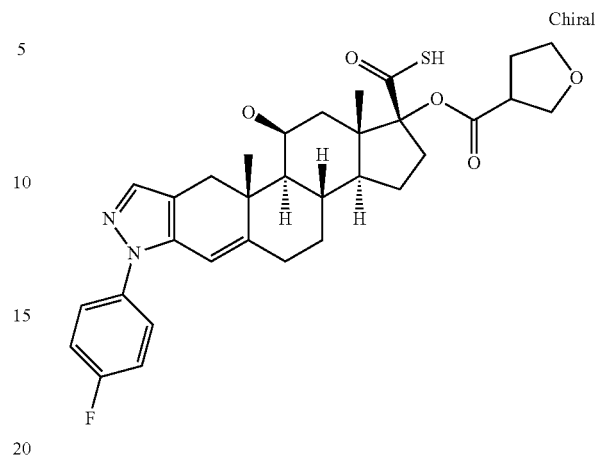

(1R,3aS,3bS,10aR,10bS,11S,12aS)-7-(4-fluorophenyl)-11-hydroxy-10a,12a-dimethyl-1-[(tetrahydrofuran-3-ylcarbonyl)oxy]-1,2,3,3a,3b,4,5,7,10,10a,10b,11,12,12a-tetradecahydrocyclopenta[5,6]naphtho[1,2-f]indazole-1-carbothioic S-acid The compound was prepared according to the procedure for Intermediate 3, starting from Intermediate 2 and rac.-tetrahydrofuran-3-carbonyl chloride (generated in situ from racemic tetrahydrofuran-3-carboxylic acid and excess thionyl chloride in toluene at 80° C. for 15 min). APCI-MS m/z: 581 [MH$^+$].

Intermediate 113

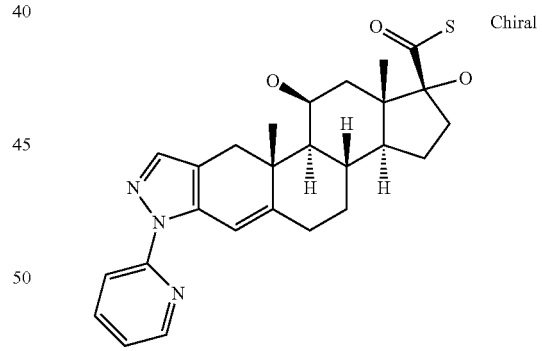

(1R,3aS,3bS,10aR,10bS,11S,12aS)-1,11-dihydroxy-10a,12a-dimethyl-7-pyridin-2-yl-1,2,3,3a,3b,4,5,7,10,10a,10b,11,12,12a-tetradecahydrocyclopenta[5,6]naphtho[1,2-f]indazole-1-carbothioic S-acid The compound was prepared from Intermediate 71 according to the procedure for Intermediate 36. APCI-MS m/z: 466 [MH$^+$].

Intermediate 114

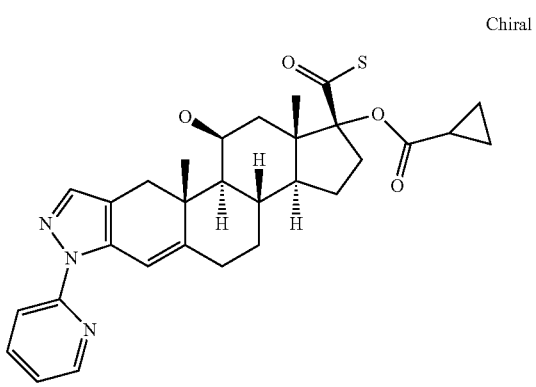

(1R,3aS,3bS,10aR,10bS,11S,12aS)-1-[(cyclopropyl-carbonyl)oxy]-11-hydroxy-10a,12a-dimethyl-7-pyridin-2-yl-1,2,3,3a,3b,4,5,7,10,10a,10b,11,12,12a-tetradecahydrocyclopenta[5,6]naphtho[1,2-f]indazole-1-carbothioic S-acid The compound was prepared according to the procedure for Intermediate 3, starting from Intermediate 113 and cyclopropanecarbonyl chloride. APCI-MS m/z: 534 [MH+].

Intermediate 115

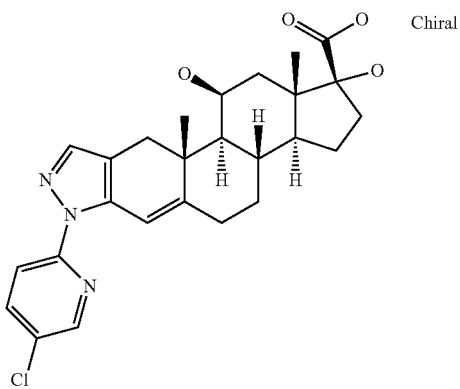

(1R,3aS,3bS,10aR,10bS,11S,12aS)-7-(5-chloropyridin-2-yl)-1,11-dihydroxy-10a,12a-dimethyl-1,2,3,3a,3b,4,5,7,10,10a,10b,11,12,12a-tetradecahydrocyclopenta[5,6]naphtho[1,2-f]indazole-1-carboxylic Acid The compound was prepared from Intermediate 39 and 5-chloro-2-hydrazinopyridine according to the procedure for Intermediate 27. APCI-MS m/z: 484 [MH+].

Intermediate 116

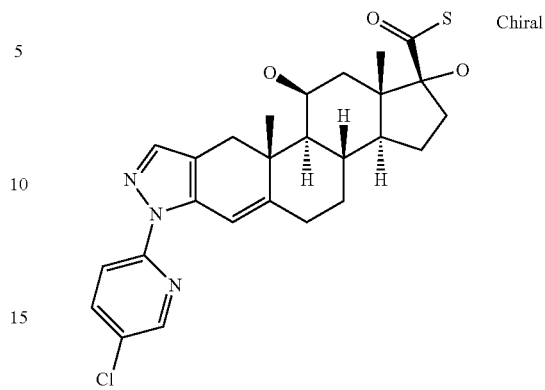

(1R,3aS,3bS,10aR,10bS,11S,12aS)-7-(5-chloropyridin-2-yl)-1,11-dihydroxy-10a,12a-dimethyl-1,2,3,3a,3b,4,5,7,10,10a,10b,11,12,12a-tetradecahydrocyclopenta[5,6]naphtho[1,2-f]indazole-1-carbothioic S-acid The compound was prepared from Intermediate 115 according to the procedure for Intermediate 36. APCI-MS/z: 500 [MH+].

Intermediate 117

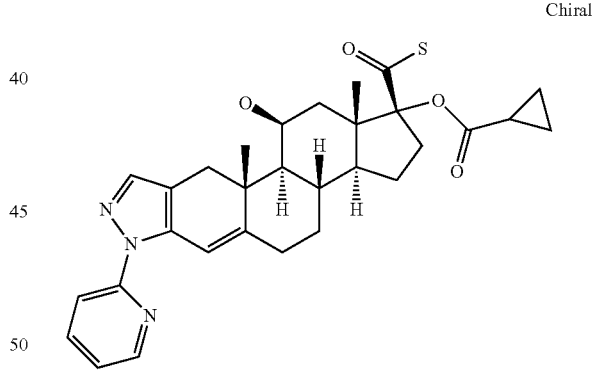

(1R,3aS,3bS,10aR,10bS,11S,12aS)-1-[(Cyclopropyl-carbonyl)oxy]-11-hydroxy-10a,12a-dimethyl-7-pyridin-2-yl-1,2,3,3a,3b,4,5,7,10,10a,10b,11,12,12a-tetradecahydrocyclopenta[5,6]naphtho[1,2-f]indazole-1-carboxylic Acid The compound was prepared according to the procedure for Intermediate 6, starting from Intermediate 71 and cyclopropanecarbonyl chloride APCI-MS m/z: 534 [MH+].

Intermediate 118

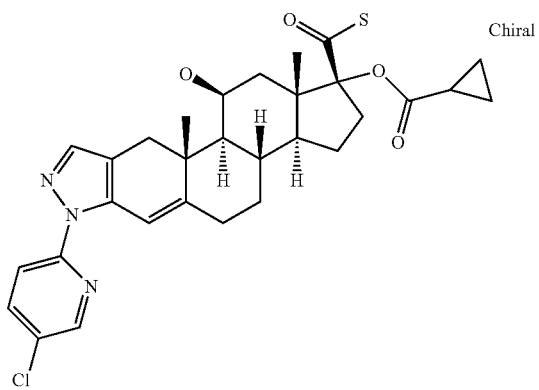

(1R,3aS,3bS,10aR,10bS,11S,12aS)-7-(5-chloropyridin-2-yl)-1-[(cyclopropylcarbonyl)oxy]-11-hydroxy-10a,12a-dimethyl-1,2,3,3a,3b,4,5,7,10,10a,10b,11,12,12a-tetradecahydrocyclopenta[5,6]naphtho[1,2-f]indazole-1-carbothioic S-acid The compound was prepared according to the procedure for Intermediate 3, starting from Intermediate 116 and cyclopropanecarbonyl chloride APCI-MS m/z: 569 [MH⁺].

Intermediate 119

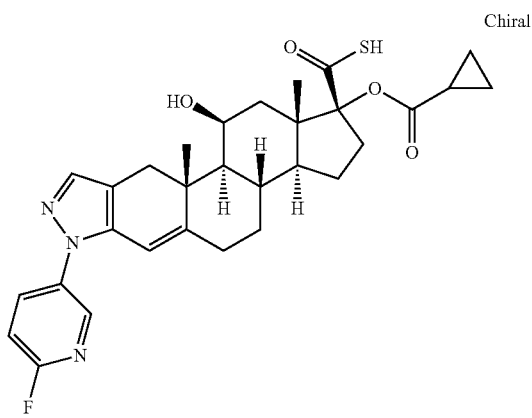

(1R,3aS,3bS,10aR,10bS,11S,12aS)-1-[(cyclopropylcarbonyl)oxy]-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazole-1-carbothioic S-acid The compound was prepared from Intermediate 42 and cyclopropanecarbonyl chloride according to the procedure described for Intermediate 43. APCI-MS m/z: 552 [MH⁺].

Intermediate 120

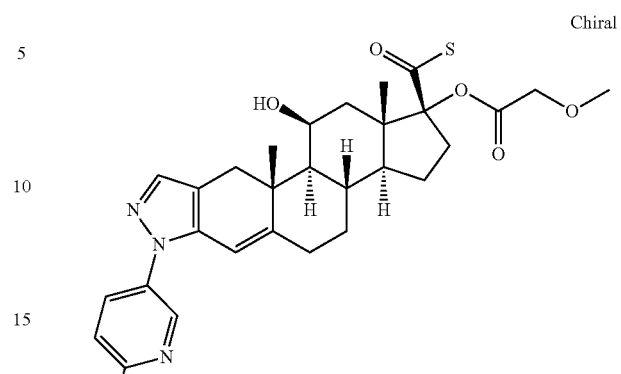

(1R,3aS,3bS,10aR,10bS,11S,12aS)-7-(6-fluoropyridin-3-yl)-11-hydroxy-1-[(methoxyacetyl)oxy]-10a,12a-dimethyl-1,2,3,3a,3b,4,5,7,10,10a,10b,11,12,12a-tetradecahydrocyclopenta[5,6]naphtho[1,2-f]indazole-1-carbothioic S-acid The compound was prepared from Intermediate 42 and 2-methoxyacetyl chloride according to the procedure described for Intermediate 43. APCI-MS m/z: 556 [MH⁺].

Intermediate 121

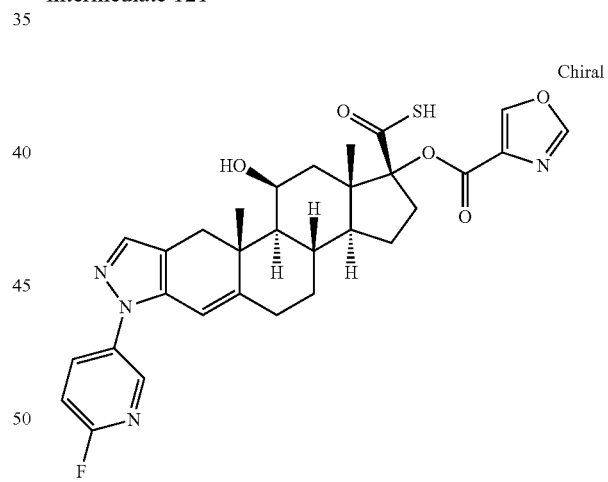

(1R,3aS,3bS,10aR,10bS,11S,12aS)-7-(6-fluoropyridin-3-yl)-11-hydroxy-10a,12a-dimethyl-1-[(1,3-oxazol-4-ylcarbonyl)oxy]-1,2,3,3a,3b,4,5,7,10,10a,10b,1,12,12a-tetradecahydrocyclopenta[5,6]naphtho[1,2-f]indazole-1-carbothioic S-acid The compound was prepared from Intermediate 42 and oxazole-4-carbonyl chloride according to the procedure described in for Intermediate 43 APCI-MS m/z: 579 [MH⁺].

Intermediate 122

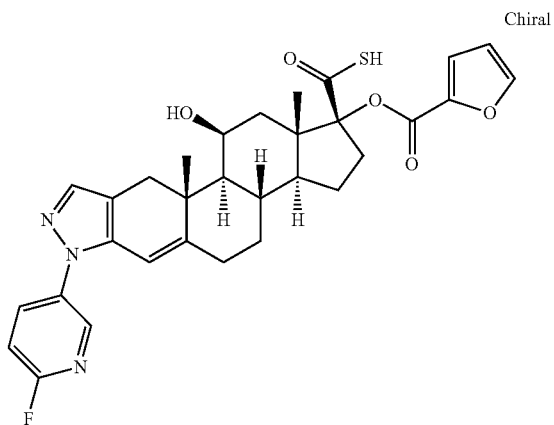

(1R,3aS,3bS,10aR,10bS,11S,12aS)-7-(6-fluoropyridin-3-yl)-1-1[(furan-2-ylcarbonyl)oxy]-11-hydroxy-10a,12a-dimethyl-1,2,3,3a,3b,4,5,7,10,10a,10b,11,12,12a-tetradecahydrocyclopenta[5,6]naphtho[1,2-f]indazole-1-carbothioic S-acid The compound was prepared from Intermediate 42 and furan-2-carbonyl chloride according to the procedure described for Intermediate 43. APCI-MS m/z: 578 [MH+].

Intermediate 123

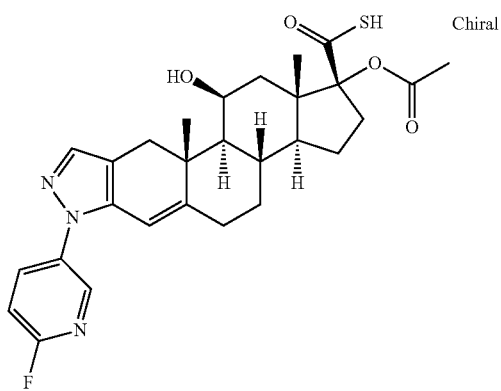

(1R,3aS,3bS,10aR,10bS,11S,12aS)-1-(acetyloxy)-7-(6-fluoropyridin-3-yl)-11-hydroxy-tetradecahydrocyclopenta[5,6]naphtho[1,2-f]indazole-1-carbothioic S-acid The compound was prepared from Intermediate 42 and acetyl chloride according to the procedure described for Intermediate 43. APCI-MS m/z: 526 [MH+].

Intermediate 124

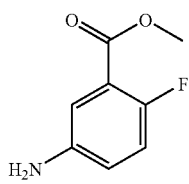

Methyl 5-amino-2-fluorobenzoate

To a stirred solution of methyl 2-fluoro-5-nitrobenzoate (1.96 g, 9.82 mmol) in ethyl is 5 acetate (40 ml) was added tin (II) chloride dihydrate (7.53 g, 33.38 mmol). The mixture was stirred overnight. Then aqueous NaOH solution (1 M, ca. 50 ml) was added to adjust the pH to 9. The layers were separated, the aqueous layer was extracted with ethyl acetate (4 times 20 ml) and the combined organic layers were washed with water and dried with $Na_2SO_4$. Filtration followed by evaporation of the solvent in vacuo afforded a yellowish solid, 1.48 g (90%) which was used in the next step without further purification.

$^1$H NMR (400 MHz, $CDCl_3$) δ 7.21 (dd, 1H), 6.94 (dd, 1H), 6.81 (m, 1H), 3.92 (s, 3H).

Intermediate 125

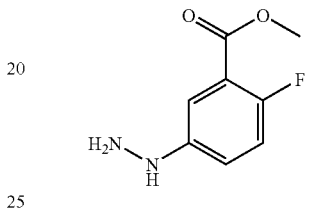

Methyl 2-fluoro-5-hydrazinobenzoate

A stirred suspension of Intermediate 124 (1.484 g, 8.77 mmol) in hydrochloric acid (37%, 10 ml) was cooled to 0° C. using an ice bath. A solution of sodium nitrite (726 mg, 10.5 mmol) in water (2 ml) was added dropwise, so that the temperature did not exceed 5° C. The mixture was stirred at 0° C. for 1 h and subsequently, a solution of tin (II) chloride dihydrate (5.94 g, 26.3 mmol) in a mixture of hydrochloric acid (37%, 5 ml) and water (1 ml) was added dropwise. During the addition the temperature was maintained below 5° C. by cooling via addition of small pieces of ice directly to the reaction mixture. Stirring was continued for 1 hour at 0° C. and the obtained precipitate was collected by filtration, washed with a small amount of water, dissolved in an acetonitrile/water mixture (5:1) and freeze-dried. The title compound was obtained as the hydrochloride-salt as a yellowish solid (1.9 g, 98%).

$^1$H NMR (400 MHz, DMSO-$d_6$) δ 10.16 (br.s, 3H), 8.39 (br.s, 1H), 7.48 (dd, 1H), 7.36-7.22 (m, 2H), 3.86 (s, 3H).

Intermediate 126

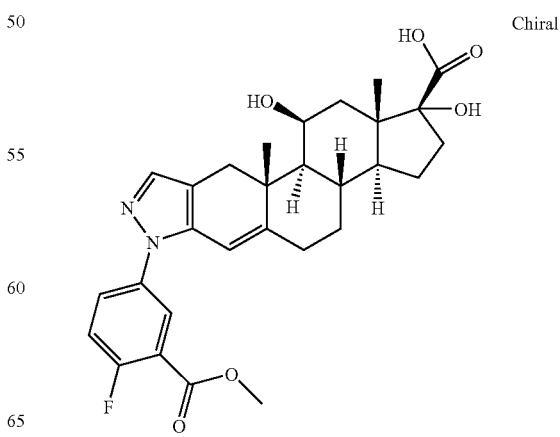

(1R,3aS,3bS,10aR,10bS,11S,12aS)-7-[4-fluoro-3-(methoxycarbonyl)phenyl]-1,11-dihydroxy-10a,12a-dimethyl-1,2,3,3a,3b,4,5,7,10,10a,10b,11,12,12a-tetradecahydrocyclopenta[5,6]naphtho[1,2-f]indazole-1-carboxylic Acid To a stirred solution of Intermediate 39 (376 mg, 1.00 mmol) and sodium acetate (82 mg, 1.00 mmol) in acetic acid (8 ml) and water (2 ml) was added Intermediate 125 (220 mg, 1.00 mmol). The mixture was stirred overnight, then poured into aqueous hydrochloric acid (1 M, 20 ml) and the aqueous layer was extracted with ethyl acetate (3 times 20 ml). The combined organic extracts were dried with $Na_2SO_4$. Filtration followed by evaporation of the solvent afforded a dark oil (927 mg) containing traces of acetic acid and was used as such in the next step. APCI-MS m/z: 525 [$MH^+$].
Intermediate 127

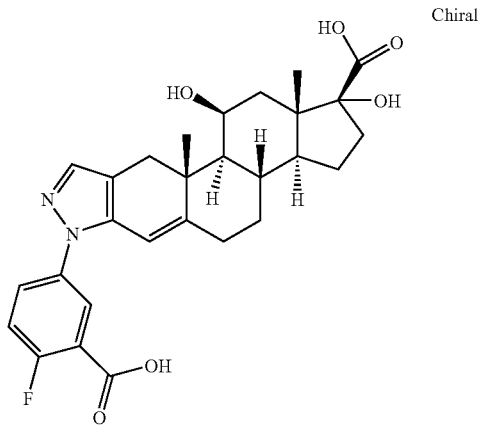

(1R,3aS,3bS,10aR,10bS,11S,12aS)-7-(3-carboxy-4-fluorophenyl)-1,11-dihydroxy-10a,12a-dimethyl-1,2,3,3a,3b,4,5,7,10,10a,10b,11,12,12a-tetradecahydrocyclopenta[5,6]naphtho[1,2-f]indazole-1-carboxylic Acid Intermediate 126 (524 mg, 1.00 mmol) was dissolved in aqueous NaOH (1 M, 20 ml), and stirred at room temperature for 10 min. The solution was acidified with conc. hydrochloric acid to pH 1 and extracted with ethyl acetate. Evaporation of the solvent afforded a dark-yellow solid (380 mg, 74%) which was used as such without further purification. APCI-MS m/z: 511 [$MH^+$].
Intermediate 128

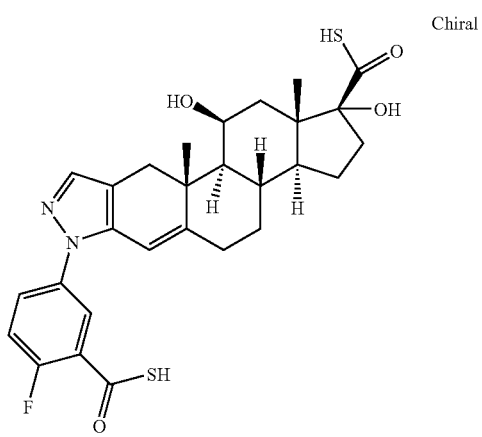

(1R,3aS,3bS,10aR,10bS,11S,12aS)-7-[4-fluoro-3-(sulfanylcarbonyl)phenyl]-1,11-dihydroxy-10a,12a-dimethyl-1,2,3,3a,3b,4,5,7,10a,10b,11,12,12a-tetradecahydrocyclopenta[5,6]naphtho[1,2-f]indazole-1-carbothioic S-acid The compound was prepared from Intermediate 127 according to the procedure described for Intermediate 42. APCI-MS m/z: 543 [$MH^+$].
Intermediate 129

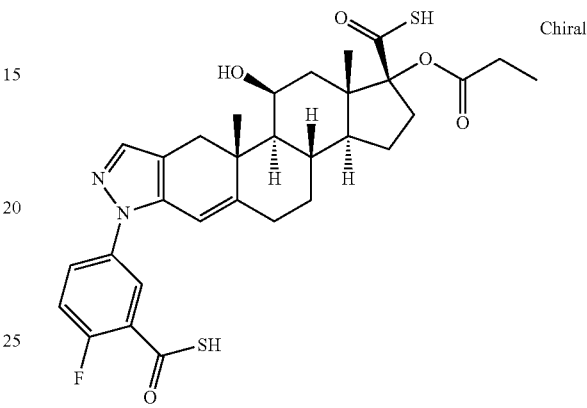

(1R,3aS,3bS,10aR,10bS,11S,12aS)-7-[4-fluoro-3-(sulfanylcarbonyl)phenyl]-11-hydroxy-10a,12a-dimethyl-1-(propanoyloxy)-1,2,3,3a,3b,4,5,7,10,10a,10b,11,12,12a-tetradecahydrocyclopenta[5,6]naphtho[1,2-f]indazole-1-carbothioic S-acid The compound was prepared from Intermediate 128 and propionyl chloride according to the procedure described for Intermediate 43. APCI-MS m/z: 599 [$MH^+$].
Intermediate 130

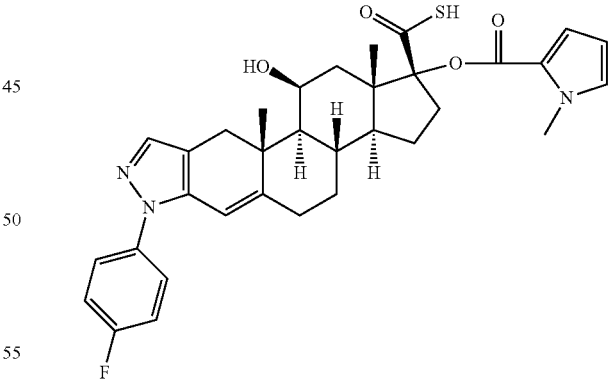

(1R,3aS,3bS,10aR,10bS,11S,12aS)-7-(4-fluorophenyl)-11-hydroxy-10a,12a-dimethyl-1-{[(1-methyl-1H-pyrrol-2-yl)carbonyl]oxy}-1,2,3,3a,3b,4,5,7,10,10a,10b,11,12,12a-tetradecahydrocyclopenta[5,6]naphtho[1,2-f]indazole-1-carbothioic S-acid The compound was prepared according to the procedure for Intermediate 3, starting from Intermediate 2 and 1-methylpyrrole-2-carbonyl chloride. APCI-MS m/z: 590 [$MH^+$].

Intermediate 131

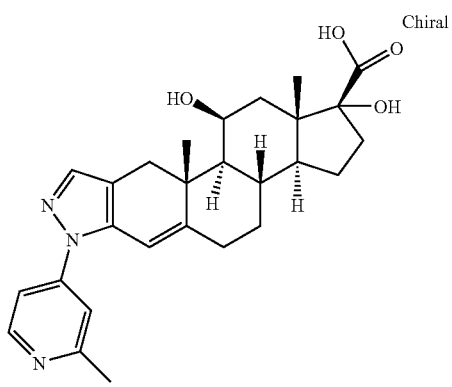

(1R,3aS,3bS,10aR,10bS,11S,12aS)-1,11-Dihydroxy-10a,12a-dimethyl-7-(2-methylpyridin-4-yl)-1,2,3,3a,3b,4,5,7,10,10a,10b,11,12,12a-tetradecahydrocyclopenta[5,6]naphtho[1,2-f]indazole-1-carboxylic Acid The compound was prepared from Intermediate 39 according to the procedure for Intermediate 41. APCI-MS m/z: 464 [MH$^+$].

Intermediate 132

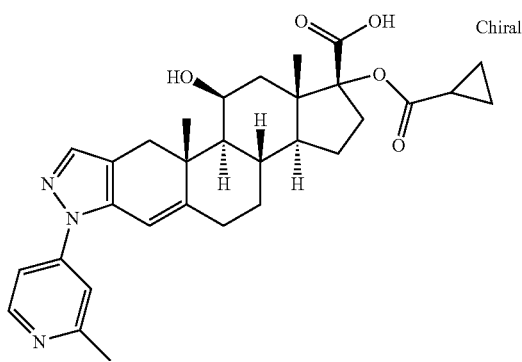

(1R,3aS,3bS,10aR,10bS,11S,12aS)-1-[(Cyclopropyl-carbonyl)oxy]-11-hydroxy-10a,12a-dimethyl-7-(2-methylpyridin-4-yl)-1,2,3,3a,3b,4,5,7,10,10a,10b,11,12,12a-tetradecahydrocyclopenta[5,6]naphtho[1,2-f]indazole-1-carboxylic Acid The compound was prepared from Intermediate 131 and cyclopropanecarbonyl chloride according to the procedure for Intermediate 6. APCI-MS m/z: 532 [MH$^+$].

Intermediate 133

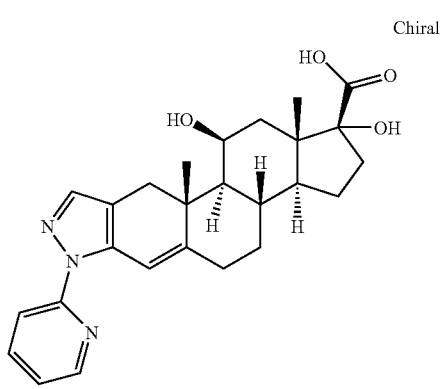

(1R,3aS,3bS,10aR,10bS,11S,12aS)-1,11-Dihydroxy-10a,12a-dimethyl-7-pyridin-2-yl-1,2,3,3a,3b,4,5,7,10,10a,10b,11,12,12a-tetradecahydrocyclopenta[5,6]naphtho[1,2-f]indazole-1-carboxylic Acid The compound was prepared from Intermediate 39 according to the procedure for Intermediate 41. APCI-MS m/z: 450 [MH$^+$].

Intermediate 134

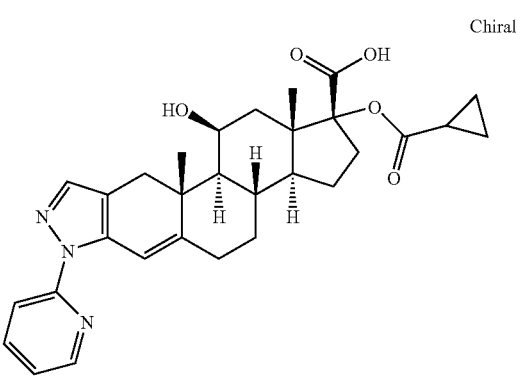

(1R,3aS,3bS,10aR,10bS,11S,12aS)-1-[(Cyclopropyl-carbonyl)oxy]-11-hydroxy-10a,12a-dimethyl-7-pyridin-2-yl-1,2,3,3a,3b,4,5,7,10,10a,10b,11,12,12a-tetradecahydrocyclopenta[5,6]naphtho[1,2-f]indazole-1-carboxylic Acid The compound was prepared from Intermediate 133 and cyclopropanecarbonyl chloride according to the procedure for Intermediate 6. APCI-MS m/z: 518 [MH$^+$].

Intermediate 135

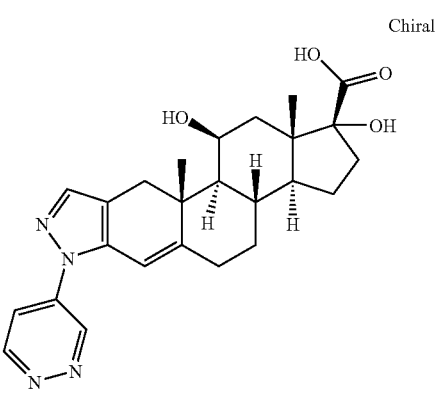

(1R,3aS,3bS,10aR,10bS,11S,12aS)-1,11-Dihydroxy-10a,12a-dimethyl-7-pyridazin-4-yl-1,2,3,3a,3b,4,5,7,10,10a,10b,11,12,12a-tetradecahydrocyclopenta[5,6]naphtho[1,2-f]indazole-1-carboxylic Acid The compound was prepared from Intermediate 39 according to the procedure for Intermediate 41. APCI-MS m/z: 451 [MH$^+$].

Intermediate 136

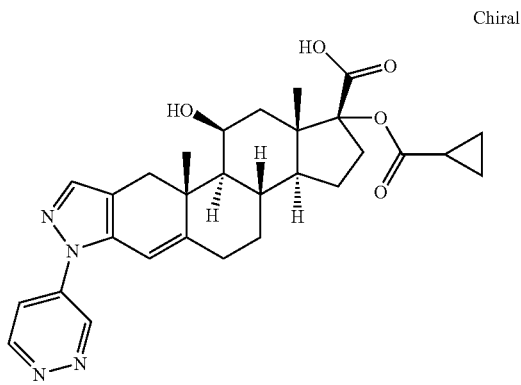

(1R,3aS,3bS,10aR,10bS,11S,12aS)-1-[(Cyclopropyl-carbonyl)oxy]-11-hydroxy-10a,12a-dimethyl-7-pyridazin-4-yl-1,2,3,3a,3b,4,5,7,10,10a,10b,11,12,12a-tetradecahydrocyclopenta[5,6]naphtho[1,2-f]indazole-1-carboxylic Acid The compound was prepared from Intermediate 135 and cyclopropanecarbonyl chloride according to the procedure for Intermediate 6. APCI-MS m/z: 519 [MH⁺].

Intermediate 137

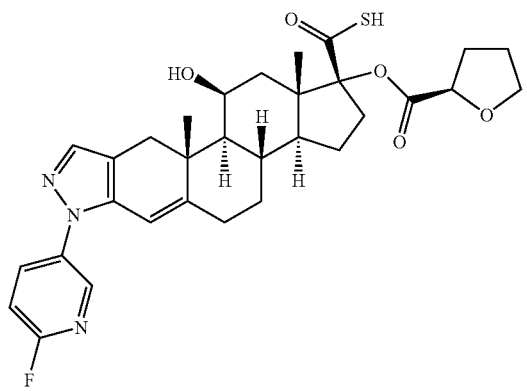

(1R,3aS,3bS,10aR,10bS,11S,12aS)-7-(6-Fluoropyridin-3-yl)-11-hydroxy-10a,12a-dimethyl-1-{[(2R)-tetrahydrofuran-2-ylcarbonyl]oxy}-1,2,3,3a,3b,4,5,7,10,10a,10b,11,12,12a-tetradecahydrocyclopenta[5,6]naphtho[1,2-f]indazole-1-carbothioic S-acid The compound was prepared from Intermediate 42 and (R)-tetrahydrofuran-2-carbonyl chloride (J. Chem. Soc, Perkin Trans. 1, 2002, 571-576) according to the procedure for Intermediate 83. APCI-MS m/z: 582 [MH⁺].

Intermediate 138

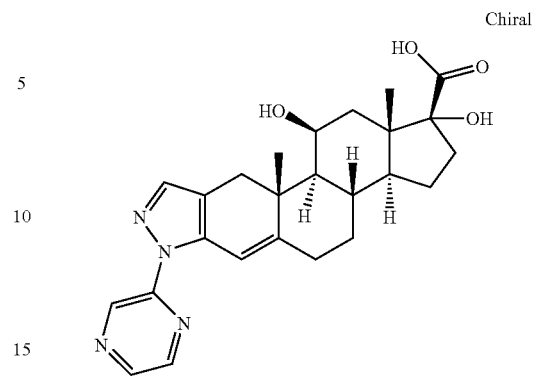

(1R,3aS,3bS,10aR,10bS,11S,12aS)-1,11-Dihydroxy-10a,12a-dimethyl-7-pyrazin-2-yl-1,2,3,3a,3b,4,5,7,10,10a,10b,11,12,12a-tetradecahydrocyclopenta[5,6]naphtho[1,2-f]indazole-1-carboxylic Acid The compound was prepared from Intermediate 39 according to the procedure for Intermediate 41. APCI-MS m/z: 451 [MH⁺].

Intermediate 139

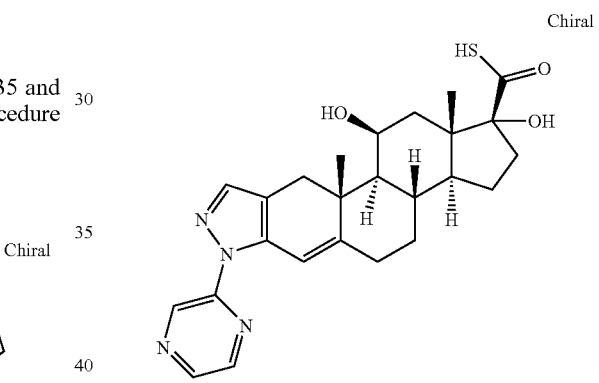

(1R,3aS,3bS,10aR,10bS,11S,12aS)-1,11-Dihydroxy-10a,12a-dimethyl-7-pyrazin-2-yl-1,2,3,3a,3b,4,5,7,10,10a,10b,11,12,12a-tetradecahydrocyclopenta[5,6]naphtho[1,2-f]indazole-1-carbothioic S-acid The compound was prepared from Intermediate 138 according to the procedure for Intermediate 2. APCI-MS m/z: 467 [MH⁺].

Intermediate 140

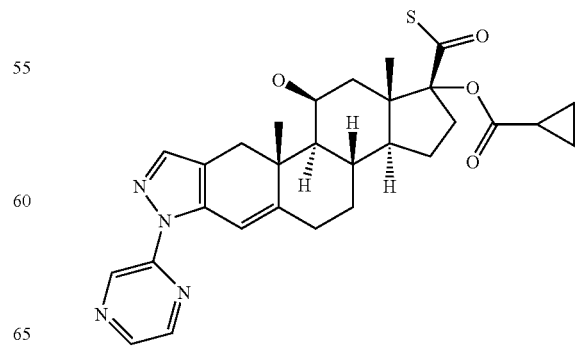

(1R,3aS,3bS,10aR,10bS,11S,12aS)-1-[(Cyclopropyl-
carbonyl)oxy]-11-hydroxy-10a,12a-dimethyl-7-
pyrazin-2-yl-1,2,3,3a,3b,4,5,7,10,10a,10b,11,12,12a-
tetradecahydrocyclopenta[5,6]naphtho[1,2-f]
indazole-1-carbothioic S-acid The compound was prepared from Intermediate 139 and cyclopropanecarbonyl chloride according to the procedure for Intermediate 3. APCI-MS m/z: 535 [MH⁺].

Intermediate 141

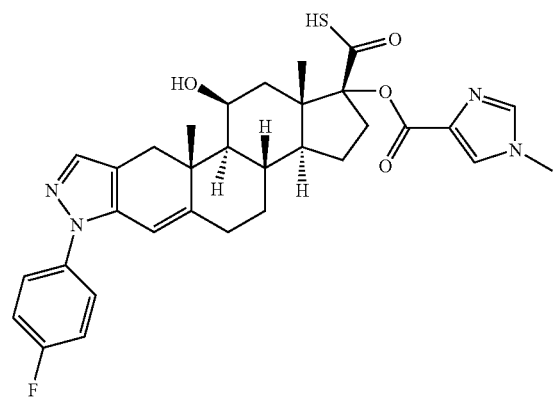

(1R,3aS,3bS,10aR,10bS,11S,12aS)-7-(4-Fluorophe-
nyl)-11-hydroxy-10a,12a-dimethyl-1-{[(1-methyl-
1H-imidazol-4-yl)carbonyl]oxy}-1,2,3,3a,3b,4,5,7,
10,10a,10b,11,12,12a-tetradecahydrocyclopenta[5,6]
naphtho[1,2-f]indazole-1-carbothioic S-acid The compound was prepared from Intermediate 42 and 1-methyl-1H-imidazole-4-carbonyl chloride (J. Chem. Soc, Perkin Trans. 1, 2002, 571-576) according to the procedure for Intermediate 83. APCI-MS m/z: 591 [MH⁺].

Intermediate 142

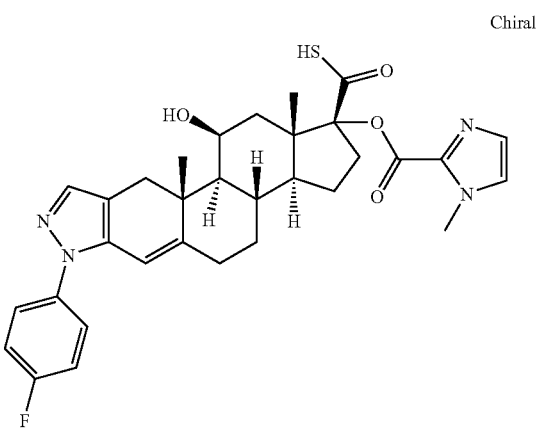

(1R,3aS,3bS,10aR,10bS,11S,12aS)-7-(4-Fluorophe-
nyl)-11-hydroxy-10a,12a-dimethyl-1-{[(1-methyl-
1H-imidazol-2-yl)carbonyl]oxy}-1,2,3,3a,3b,4,5,7,
10,10a,10b,11,12,12a-tetradecahydrocyclopenta[5,6]
naphtho[1,2-f]indazole-1-carbothioic S-acid The compound was prepared from Intermediate 42 and 1-methyl-1H-imidazole-2-carbonyl chloride (J. Chem. Soc, Perkin Trans. 1, 2002, 571-576) according to the procedure for Intermediate 83. APCI-MS m/z: 591 [MH⁺].

Intermediate 143

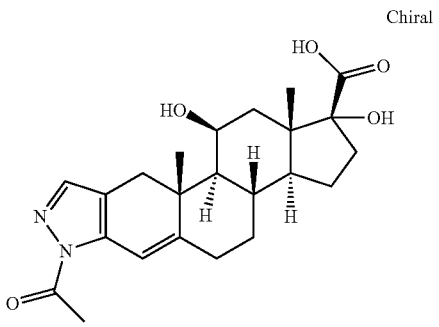

(1R,3aS,3bS,10aR,10bS,11S,12aS)-7-Acetyl-1,11-
dihydroxy-10a,12a-dimethyl-1,2,3,3a,3b,4,5,7,10,
10a,10b,11,12,12a-tetradecahydrocyclopenta[5,6]
naphtho[1,2-f]indazole-1-carboxylic Acid The compound was prepared from Intermediate 39 and acetohydrazide according to the procedure for Intermediate 41. A mixture of isomers was obtained and they were taken on as such. APCI-MS m/z: 415 [MH⁺].

Intermediate 144

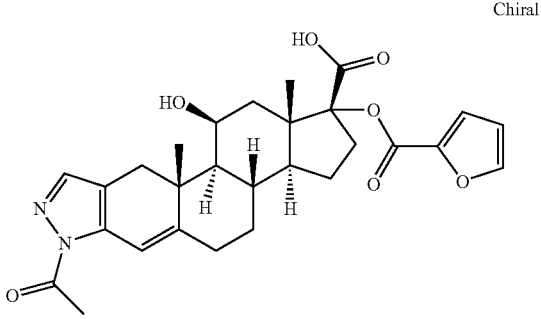

(1R,3aS,3bS,10aR,10bS,11S,12aS)-7-Acetyl-1-[(fu-
ran-2-ylcarbonyl)oxy]-11-hydroxy-10a,12a-dim-
ethyl-1,2,3,3a,3b,4,5,7,10,10a,10b,11,12,12a-tet-
radecahydrocyclopenta[5,6]naphtho[1,2-f]indazole-
1-carboxylic Acid The compound was prepared from Intermediate 143 and furan-2-carbonyl chloride according to the procedure for Intermediate 6. The mixture of isomers was taken on as such. APCI-MS m/z: 509 [MH⁺].

Intermediate 145

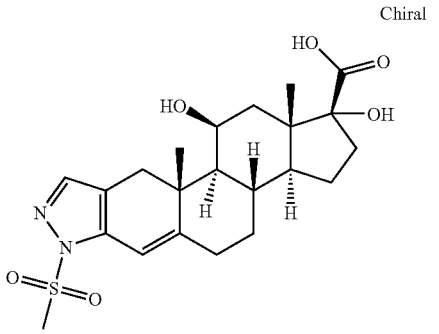

(1R,3aS,3bS,10aR,10bS,11S,12aS)-1,11-Dihydroxy-10a,12a-dimethyl-7-(methylsulfonyl)-1,2,3,3a,3b,4,5,7,10,10a,10b,11,12,12a-tetradecahydrocyclopenta[5,6]naphtho[1,2-f]indazole-1-carboxylic Acid The compound was prepared from Intermediate 39 and methanesulfonohydrazide according to the procedure for Intermediate 41. A mixture of isomers was obtained which was taken on as such. APCI-MS m/z: 451 [MH+].

Intermediate 146

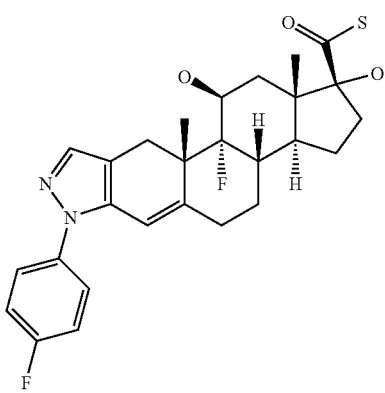

(1R,3aS,3bS,10aS,10bR,11S,12aS)-10b-fluoro-7-(4-fluorophenyl)-1,11-dihydroxy-10a,12a-dimethyl-1,2,3,3a,3b,4,5,7,10,10a,10b,11,12,12a-tetradecahydrocyclopenta[5,6]naphtho[1,2-f]indazole-1-carbothioic S-acid The compound was prepared according to the procedure for Intermediate 38, 39, 41 and 42, starting from commercial 9α-Fluoro-hydrocortisone (Fludrocortisone).
APCI-MS m/z: 501 [MH+].

Intermediate 147

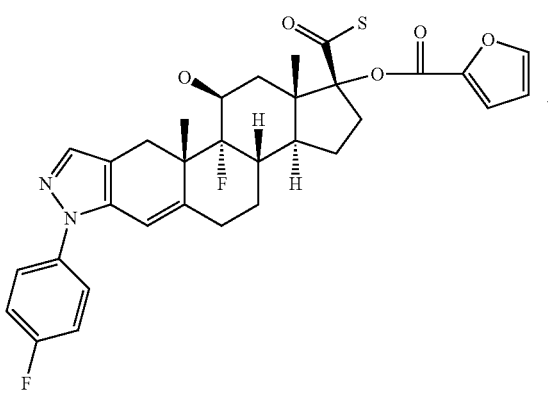

(1R,3aS,3bS,10aS,10bR,11S,12aS)-10b-fluoro-7-(4-fluorophenyl)-1-[(furan-2-ylcarbonyl)oxy]-11-hydroxy-10a,12a-dimethyl-1,2,3,3a,3b,4,5,7,10,10a,10b,11,12,12a-tetradecahydrocyclopenta[5,6]naphtho[1,2-f]indazole-1-carbothioic S-acid The compound was prepared according to the procedure for Intermediate 3, starting from Intermediate 146. APCI-MS m/z: 595 [MH+].

Intermediate 148

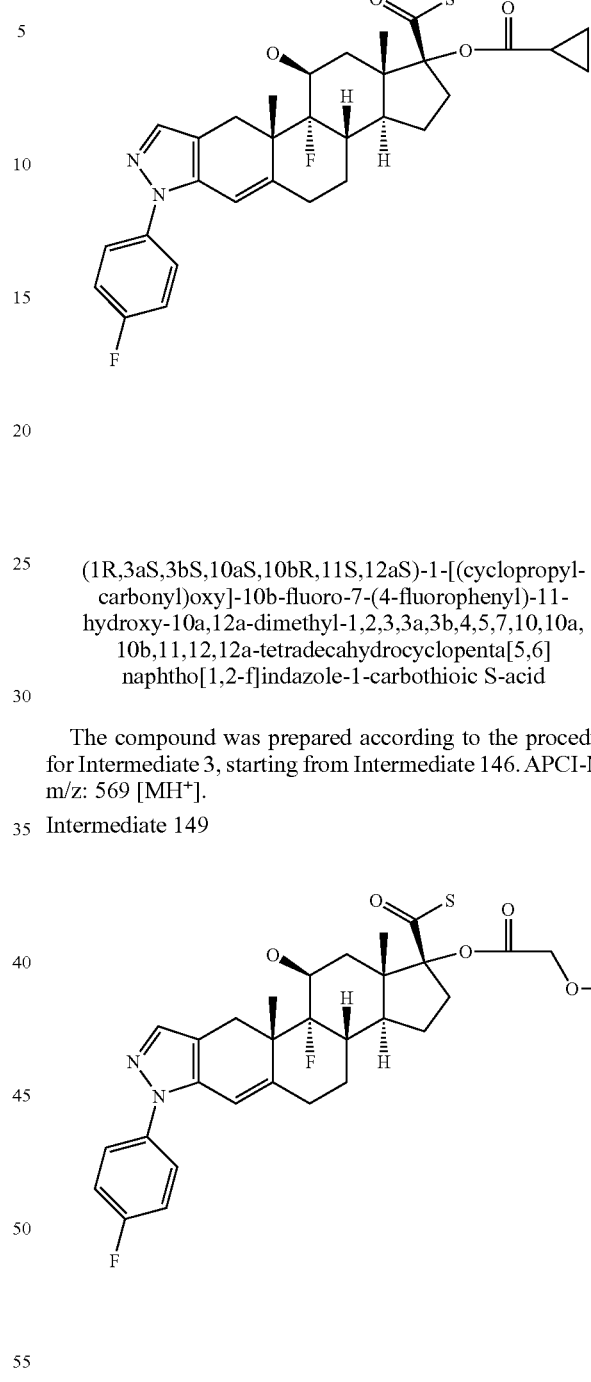

(1R,3aS,3bS,10aS,10bR,11S,12aS)-1-[(cyclopropylcarbonyl)oxy]-10b-fluoro-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazole-1-carbothioic S-acid The compound was prepared according to the procedure for Intermediate 3, starting from Intermediate 146. APCI-MS m/z: 569 [MH+].

Intermediate 149

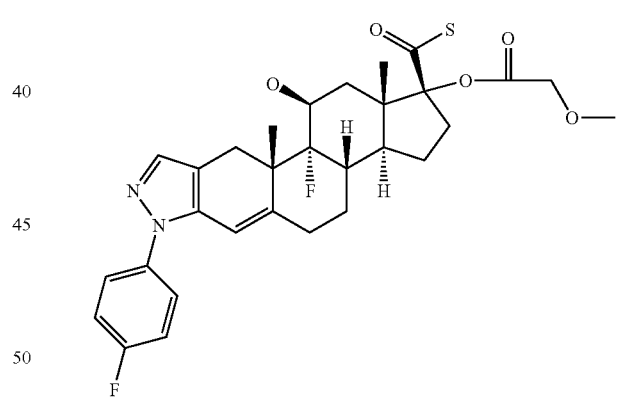

(1R,3aS,3bS,10aS,10bR,11S,12aS)-10b-fluoro-7-(4-fluorophenyl)-11-hydroxy-1-[(methoxyacetyl)oxy]-10a,12a-dimethyl-1,2,3,3a,3b,4,5,7,10,10a,10b,11,12,12a-tetradecahydrocyclopenta[5,6]naphtho[1,2-f]indazole-1-carbothioic S-acid The compound was prepared according to the procedure for Intermediate 3, starting from Intermediate 146. APCI-MS m/z: 573 [MH+].

Intermediate 150

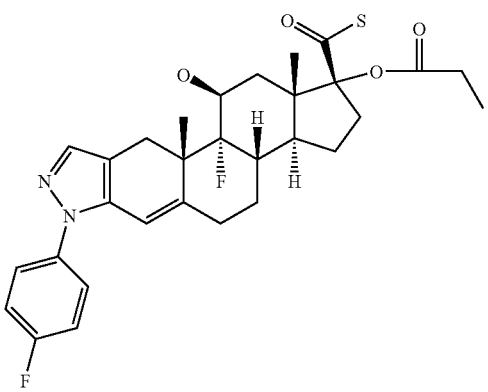

(1R,3aS,3bS,10aS,10bR,11S,12aS)-10b-fluoro-7-(4-fluorophenyl)-11-hydroxy-10a,12a-dimethyl-1-(propanoyloxy)-1,2,3,3a,3b,4,5,7,10,10a,10b,11,12,12a-tetradecahydrocyclopenta[5,6]naphtho[1,2]-indazole-1-carbothioic S-acid The compound was prepared according to the procedure for Intermediate 3, starting from Intermediate 146. APCI-MS m/z: 557 [MH+].

Intermediate 151

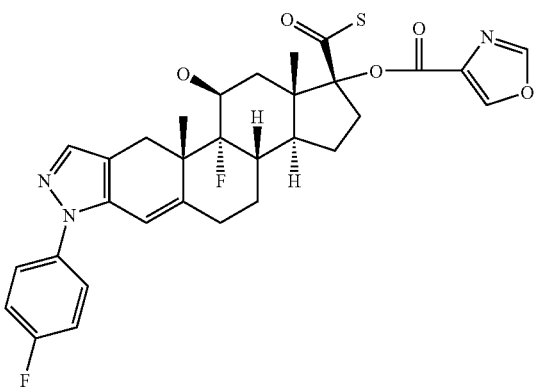

(1R,3aS,3bS,10aS,10bR,11S,12aS)-10b-fluoro-7-(4-fluorophenyl)-11-hydroxy-10a,12a-dimethyl-1-[(1,3-oxazol-4-ylcarbonyl)oxy]-1,2,3,3a,3b,4,5,7,10,10a,10b,11,12,12a-tetradecahydrocyclopenta[5,6]naphtho[1,2-f]indazole-1-carbothioic S-acid The compound was prepared according to the procedure for Intermediate 3, starting from Intermediate 146. APCI-MS m/z: 596 [MH+].

Intermediate 152

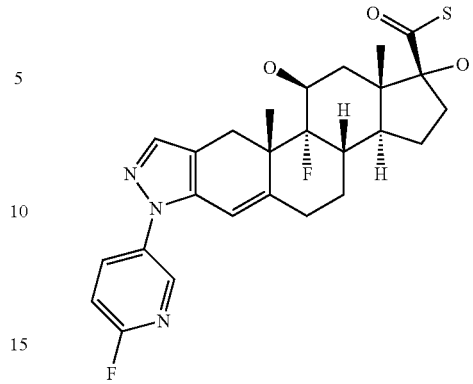

(1R,3aS,3bS,10aS,10bR,11S,12aS)-10b-fluoro-7-(6-fluoropyridin-3-yl)-1,11-dihydroxy-10a,12a-dimethyl-1,2,3,3a,3b,4,5,7,10,10a,10b,11,12,12a-tetradecahydrocyclopenta[5,6]naphtho[1,2-f]indazole-1-carbothioic S-acid The compound was prepared according to the procedure for Intermediate 38, 39, 40, 41 and 42, starting from commercial 9α-Fluoro-hydrocortisone (Fludrocortisone).
APCI-MS m/z: 502 [MH+].

Intermediate 153

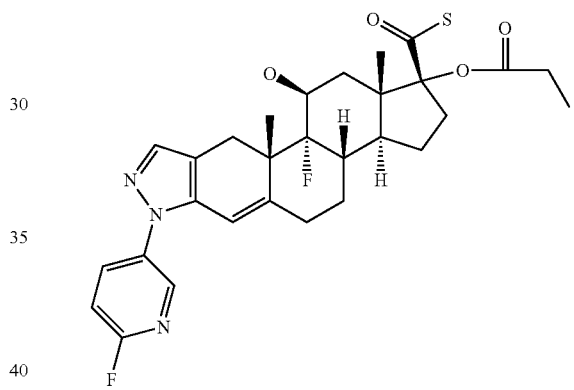

(1R,3aS,3bS,10aS,10bR,11S,12aS)-10b-fluoro-7-(6-fluoropyridin-3-yl)-11-hydroxy-10a,12a-dimethyl-1-(propanoyloxy)-1,2,3,3a,3b,4,5,7,10,10a,10b,11,12,12a-tetradecahydrocyclopenta[5,6]naphtho[1,2-f]indazole-1-carbothioic S-acid The compound was prepared according to the procedure for Intermediate 3, starting from Intermediate 152. APCI-MS m/z: 558 [MH+].

Intermediate 154

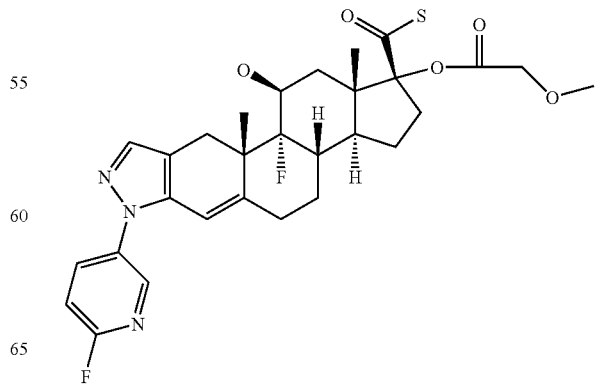

(1R,3aS,3bS,10aS,10bR,11S,12aS)-10b-fluoro-7-(6-fluoropyridin-3-yl)-11-hydroxy-1-[(methoxyacetyl)oxy]-10a,12a-dimethyl-1,2,3,3a,3b,4,5,7,10,10a,10b,11,12,12a-tetradecahydrocyclopenta[5,6]naphtho[1,2-f]indazole-1-carbothioic S-acid The compound was prepared according to the procedure for Intermediate 3, starting from Intermediate 152. APCI-MS m/z: 574 [MH+].

Intermediate 155

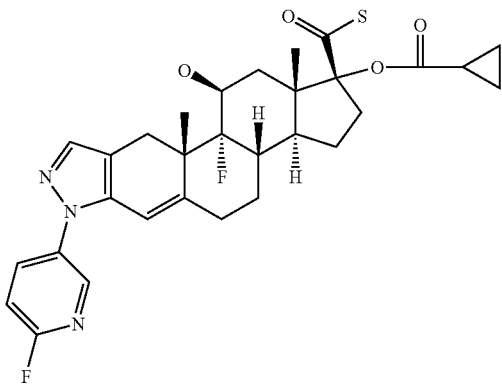

(1R,3aS,3bS,10aS,10bR,11S,12aS)-1-[(cyclopropylcarbonyl)oxy]-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazole-1-carbothioic S-acid The compound was prepared according to the procedure for Intermediate 3, starting from Intermediate 152. APCI-MS m/z: 570 [MH+].

Intermediate 156

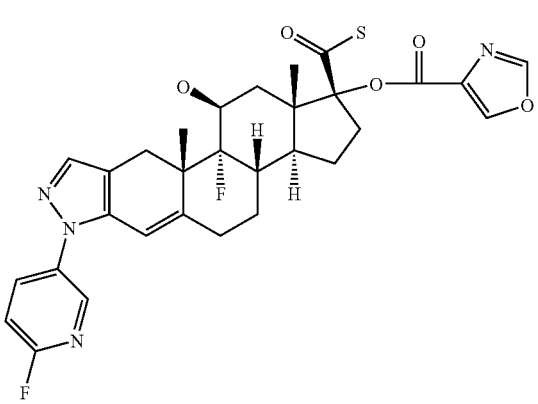

(1R,3aS,3bS,10aS,10bR,11S,12aS)-10b-fluoro-7-(6-fluoropyridin-3-yl)-11-hydroxy-10a,12a-dimethyl-1-[(1,3-oxazol-4-ylcarbonyl)oxy]-1,2,3,3a,3b,4,5,7,10,10a,10b,11,12,12a-tetradecahydrocyclopenta[5,6]naphtho[1,2-f]indazole-1-carbothioic S-acid The compound was prepared according to the procedure for Intermediate 3, starting from Intermediate 152. APCI-MS m/z: 597 [MH+].

Intermediate 157

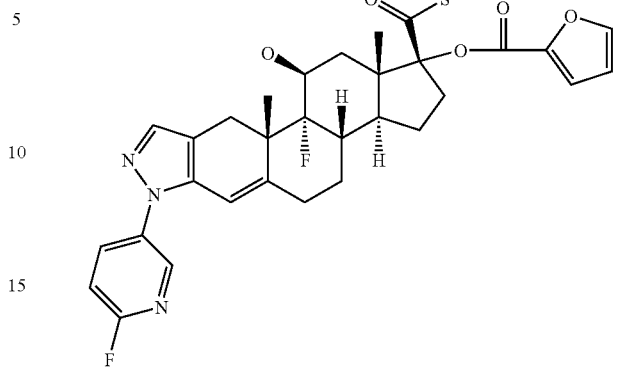

(1R,3aS,3bS,10aS,10bR,11S,12aS)-10b-fluoro-7-(6-fluoropyridin-3-yl)-1-[(furan-2-ylcarbonyl)oxy]-11-hydroxy-10a,12a-dimethyl-1,2,3,3a,3b,4,5,7,10,10a,10b,11,12,12a-tetradecahydrocyclopenta[5,6]naphtho[1,2-f]indazole-1-carbothioic S-acid The compound was prepared according to the procedure for Intermediate 3, starting from Intermediate 152. APCI-MS m/z: 596 [MH+].

Intermediate 158

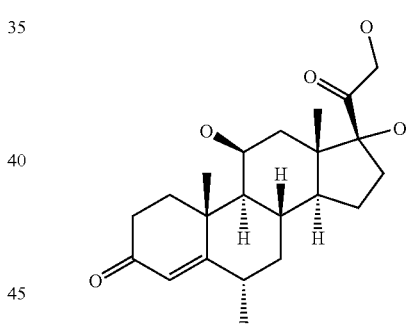

(6S,8S,9S,10R,11S,13S,14S,17R)-11,17-dihydroxy-17-(2-hydroxyacetyl)-6,10,13-trimethyl-6,7,8,9,10,11,12,13,14,15,16,17-dodecahydro-1H-cyclopenta[a]phenanthren-3(2H)-one In a 250 mL round-bottomed flask was suspended (6S,8S,9S,10R,11S,13S,14S,17R)-11,17-dihydroxy-17-(2-hydroxyacetyl)-6,10,13-trimethyl-6,7,8,9,10,11,12,13,14,15,16,17-dodecahydro-3H-cyclopenta[a]phenanthren-3-one (6α-Methyl-Prednisolone, 4.3 g, 11.48 mmol) in EtOAc (80 mL) and the reaction mixture was diluted with ethanol (20.0 mL). Wilkinsons catalyst (1 g, 1.08 mmol) was added and the mixture was hydrogenated for 1 week whilst stirring at room temperature in a hydrogen atmosphere (1 atm). The mixture was filtered and the filtrate was concentrated in vacuo, giving 4.07 g of a light brown solid. The material was used as such without any further purification. APCI-MS m/z: 377 [MH+].

Intermediate 159

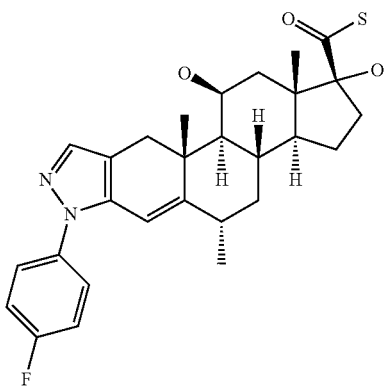

(1R,3aS,3bS,5S,10aR,10bS,11S,12aS)-7-(4-fluorophenyl)-1,11-dihydroxy-5,10a,12a-trimethyl-1,2,3,3a,3b,4,5,7,10,10a,10b,11,12,12a-tetradecahydrocyclopenta[5,6]naphtho[1,2-f]indazole-1-carbothioic S-acid The compound was prepared according to the procedure for Intermediate 38, 39, 41 and 42, starting from Intermediate 158. APCI-MS m/z: 497 [MH+].

Intermediate 160

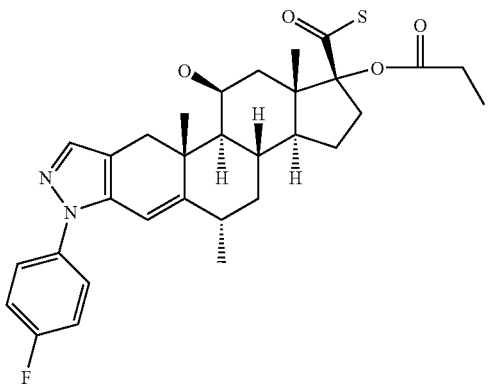

(1R,3aS,3bS,5S,10aR,10bS,1S,12aS)-7-(4-fluorophenyl)-11-hydroxy-5,10a,12a-trimethyl-1-(propanoyloxy)-1,2,3,3a,3b,4,5,7,10,10a,10b,11,12,12a-tetradecahydrocyclopenta[5,6]naphtho[1,2-f]indazole-1-carbothioic S-acid The compound was prepared according to the procedure for Intermediate 3, starting from Intermediate 159. APCI-MS m/z: 553 [MH+].

Intermediate 161

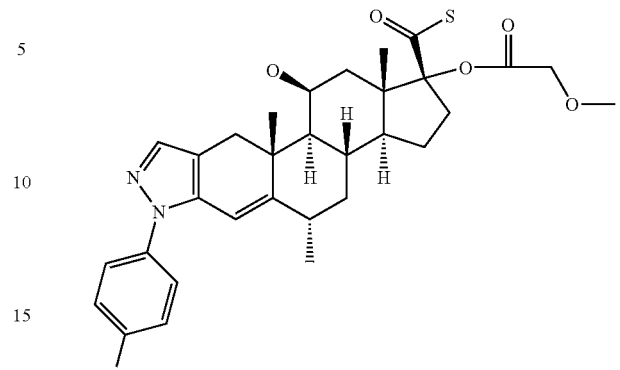

(1R,3aS,3bS,5S,10aR,10bS,11S,12aS)-7-(4-fluorophenyl)-11-hydroxy-1-[(methoxyacetyl)oxy]-5,10a,12a-trimethyl-1,2,3,3a,3b,4,5,7,10,10a,10b,11,12,12a-tetradecahydrocyclopenta[5,6]naphtho[1,2]-indazole-1-carbothioic S-acid The compound was prepared according to the procedure for Intermediate 3, starting from Intermediate 159. APCI-MS m/z: 569 [MH+].

Intermediate 162

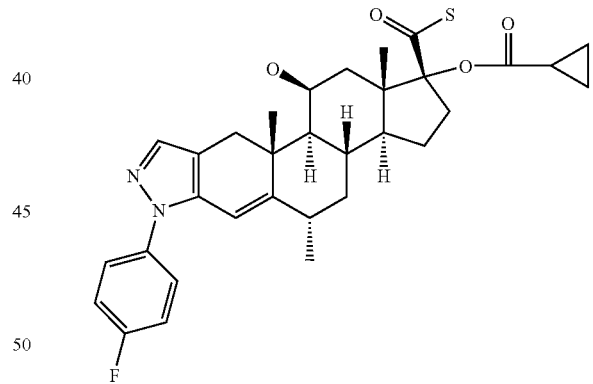

(1R,3aS,3bS,5S,10aR,10bS,11S,12aS)-7-(4-fluorophenyl)-11-hydroxy-1-(cyclopropanoyloxy)-5,10a,12a-trimethyl-1,2,3,3a,3b,4,5,7,10,10a,10b,11,12,12a-tetradecahydrocyclopenta[5,6]naphtho[1,2-f]indazole-1-carbothioic S-acid The compound was prepared according to the procedure for Intermediate 3, starting from Intermediate 159. APCI-MS m/z: 565 [MH+].

Intermediate 163

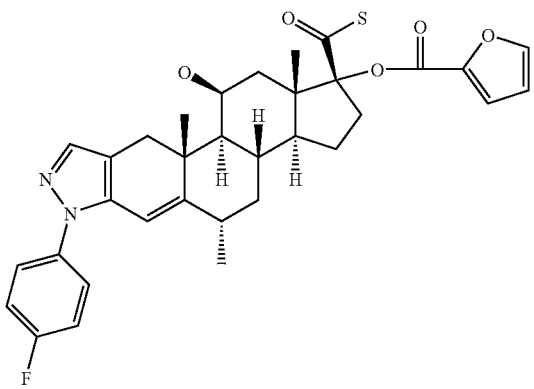

(1R,3aS,3bS,5S,10aR,10bS,11S,12aS)-7-(4-fluorophenyl)-11-hydroxy-1-[(furan-2-ylcarbonyl)oxy]-5,10a,12a-trimethyl-1,2,3,3a,3b,4,5,7,10,10a,10b,11,12,12a-tetradecahydrocyclopenta[5,6]naphtho[1,2-f]indazole-1-carbothioic S-acid The compound was prepared according to the procedure for Intermediate 3, starting from Intermediate 159. APCI-MS m/z: 591 [MH⁺].

Example 1

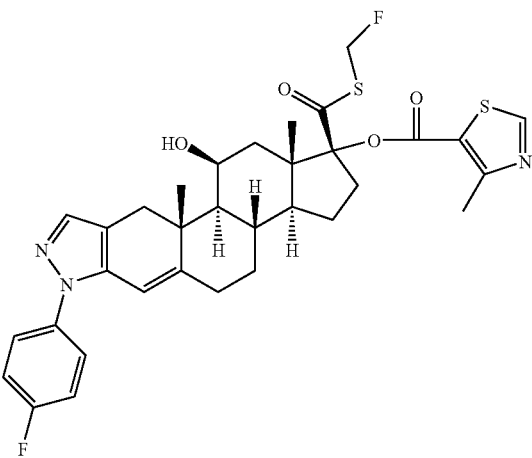

(1R,3aS,3bS,10aR,10bS,11S,12aS)-1-{[(Fluoromethyl)thio]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 4-methyl-1,3-thiazole-5-carboxylate In a 25 ml round-bottomed flask was added Intermediate 3 (0.14 g, 0.14 mmol), NaHCO₃ (0.24 g, 2.86 mmol), bromofluoromethane (0.2 g, 0.64 mmol) to DMF (3 ml) to give a yellow suspension. The mixture was stirred for 20 minutes and partitioned between EtOAc (20 ml) and water (20 ml). The organic phase was collected, and the water phase was extracted with another portion of EtOAc (10 ml). The combined organic phases were washed with water (2 times 15 ml), brine (10 ml), and were finally dried over Na₂SO₄. Filtration and evaporation of the solvent gave a yellow oil. The product was purified on a preparative HPLC column (CH₃CN/water) and the product containing fractions were freeze-dried to give 20 mg of the title compound.

¹H NMR (400 MHz, CDCl₃) δ 8.82 (1H, s); 7.50-7.43 (3H, m); 7.17 (2H, t); 6.09 (1H, s); 6.05-5.65 (2H, m); 4.64 (1H, m); 3.14-3.02 (2H, m); 2.81-2.73 (4H, m); 2.53 (1H, t); 2.30 (1H, d); 2.21-2.03 (4H, m); 2.02-1.95 (1H, m); 1.90-1.82 (1H, m); 1.76-1.68 (1H, m); 1.57-1.47 (1H, m); 1.35 (3H, s); 1.29 (1H, dd); 1.19-1.15 (1H, m); 1.14-1.08 (1H, m); 1.06 (3H, s). APCI-MS m/z: 640 [MH⁺].

Example 2

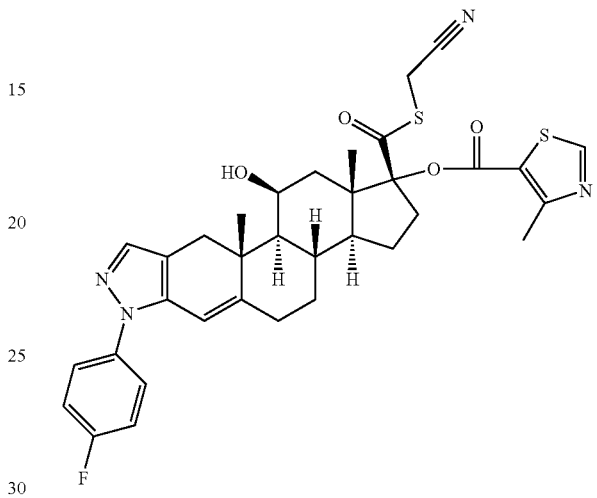

(1R,3aS,3bS,10aR,10bS,11S,12aS)-1-{[(Cyanomethyl)thio]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 4-methyl-1,3-thiazole-5-carboxylate The compound was prepared from Intermediate 3 and bromoacetonitrile according to the procedure for Example 1.

¹H NMR (400 MHz, CDCl₃) δ 8.82 (1H, s); 7.50-7.43 (3H, m); 7.17 (2H, t); 6.09 (1H, s); 4.65 (1H, m); 3.85-3.55 (2H, m); 3.12-3.01 (2H, m); 2.81-2.73 (4H, m); 2.53 (1H, t); 2.30 (1H, d); 2.22-2.02 (4H, m); 2.02-1.95 (1H, m); 1.92-1.82 (1H, m); 1.77-1.66 (1H, m); 1.59-1.47 (1H, m); 1.35 (3H, s); 1.29 (1H, dd); 1.22 (1H, d); 1.17-1.08 (1H, m); 1.07 (3H, s). APCI-MS m/z: 647 [MH⁺].

Example 3

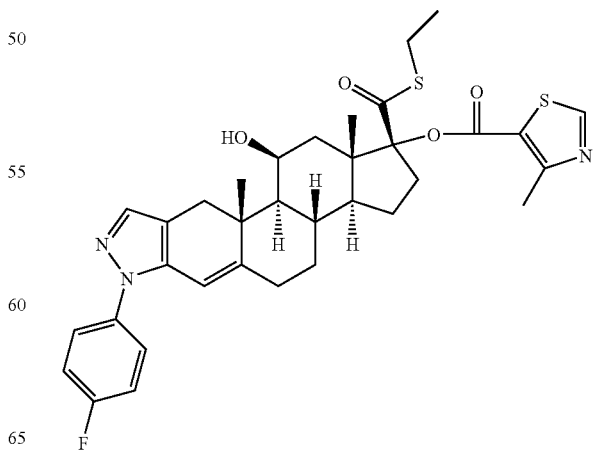

(1R,3aS,3bS,10aR,10bS,11S,12aS)-1-[(Ethylthio)
carbonyl]-7-(4-fluorophenyl)-11-hydroxy-10a,12a-
dimethyl-1,2,3,3a,3b,4,5,7,10,10a,10b,11,12,12a-
tetradecahydrocyclopenta[5,6]naphtho[1,2-f]indazol-
1-yl 4-methyl-1,3-thiazole-5-carboxylate The compound was prepared from Intermediate 3 and iodoethane according to the procedure for Example 1.

$^1$H NMR (400 MHz, CDCl$_3$) δ 8.79 (1H, s); 7.50-7.43 (3H, m); 7.17 (2H, t); 6.09 (1H, s); 4.63 (1H, m); 3.15-3.02 (2H, m); 2.94 (2H, q); 2.81-2.73 (4H, m); 2.52 (1H, t); 2.30 (1H, d); 2.21-1.94 (5H, m); 1.90-1.79 (1H, m); 1.71-1.65 (1H, m); 1.55-1.43 (1H, m); 1.35 (3H, s); 1.32-1.23 (4H, m); 1.18-1.05 (2H, m); 1.03 (3H, s). APCI-MS m/z: 636 [MH$^+$].

Example 4

(1R,3aS,3bS,10aR,10bS,11S,12aS)-1-{[(Fluorom-
ethyl)thio]carbonyl}-7-(4-fluorophenyl)-11-hydroxy-
10a,12a-dimethyl-1,2,3,3a,3b,4,5,7,10,10a,10b,11,
12,12a-tetradecahydrocyclopenta[5,6]naphtho[1,2-f]
indazol-1-yl 4-methyl-1,2,3-thiadiazole-5-
carboxylate The compound was prepared from Intermediate 4 and bromofluoromethane according to the procedure for Example 1.

$^1$H NMR (400 MHz, CDCl$_3$) δ 7.50-7.43 (3H, m); 7.17 (2H, t); 6.09 (1H, s); 6.03-5.67 (2H, m); 4.66 (1H, m); 3.19-3.01 (2H, m); 2.96 (3H, s); 2.79 (1H, d); 2.52 (1H, t); 2.30 (1H, d); 2.20-2.03 (4H, m); 2.03-1.94 (1H, m); 1.94-1.82 (1H, m); 1.72-1.61 (1H, m); 1.60-1.48 (1H, m); 1.35 (3H, s); 1.30 (1H, dd); 1.19 (1H, dd); 1.17-1.08 (1H, m); 1.07 (3H, s). APCI-MS m/z: 641 [MH$^+$].

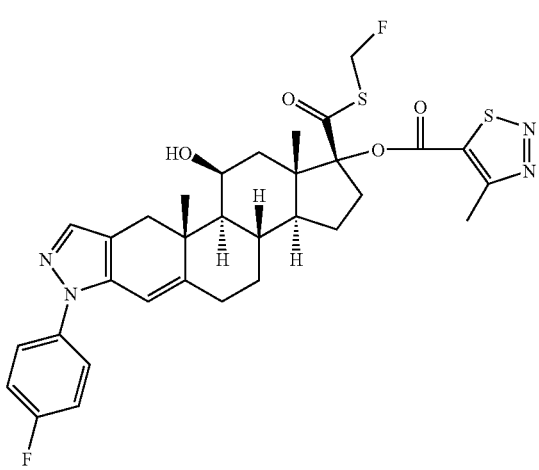

Example 5

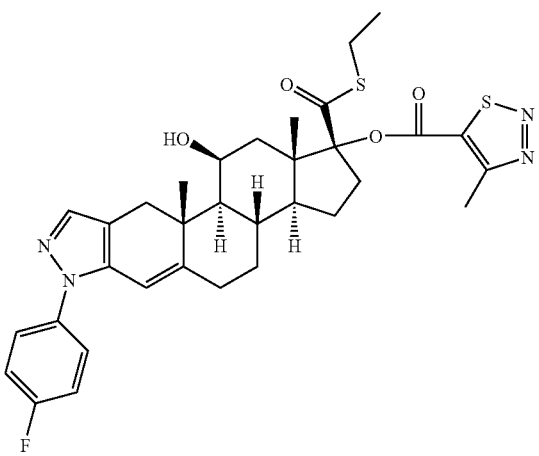

(1R,3aS,3bS,10aR,10bS,11S,12aS)-1-[(Ethylthio)
carbonyl]-7-(4-fluorophenyl)-11-hydroxy-10a,12a-
dimethyl-1,2,3,3a,3b,4,5,7,10,10a,10b,11,12,12a-
tetradecahydrocyclopenta[5,6]naphtho[1,2-f]indazol-
1-yl 4-methyl-1,2,3-thiadiazole-5-carboxylate The compound was prepared from Intermediate 4 and bromoethane according to the procedure for Example 1.

$^1$H NMR (400 MHz, CDCl$_3$) δ 7.50-7.42 (3H, m); 7.17 (2H, t); 6.09 (1H, s); 4.65 (1H, m); 3.17-3.03 (2H, m); 2.99-2.90 (5H, m); 2.79 (1H, d); 2.52 (1H, t); 2.30 (1H, d); 2.20-2.03 (4H, m); 2.03-1.94 (1H, m); 1.92-1.80 (1H, m); 1.70-1.60 (1H, m); 1.58-1.48 (1H, m); 1.35 (3H, s); 1.32-1.22 (2H, m); 1.15 (1H, dd); 1.13-1.06 (1H, m); 1.04 (3H, s). APCI-MS m/z: 637 [MH$^+$].

Example 6

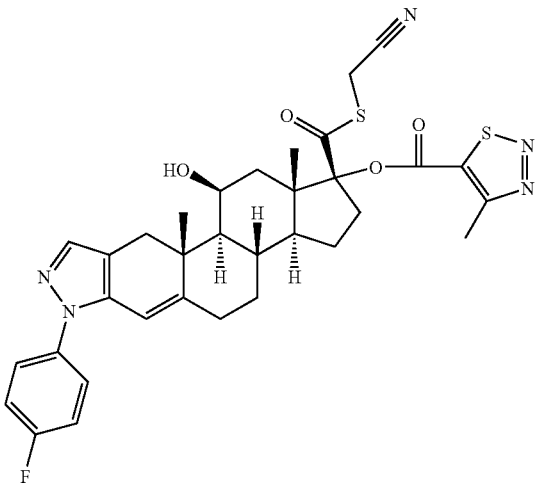

119

(1R,3aS,3bS,10aR,10bS,11S,12aS)-1-{[(Cyanom-
ethyl)thio]carbonyl}-7-(4-fluorophenyl)-11-hydroxy-
10a,12a-dimethyl-1,2,3,3a,3b,4,5,7,10,10a,10b,11,
12,12a-tetradecahydrocyclopenta[5,6]naphtho[1,2-f]
indazol-1-yl 4-methyl-1,2,3-thiadiazole-5-
carboxylate The compound was prepared from Intermediate 4 and bromoacetonitrile according to the procedure for Example 1.

$^1$H NMR (400 MHz, CDCl$_3$) δ 7.50-7.44 (3H, m); 7.17 (2H, t); 6.10 (1H, s); 4.66 (1H, m); 3.71 (2H, m); 3.16-3.02 (2H, m); 2.97 (3H, s); 2.79 (1H, d); 2.52 (1H, t); 2.31 (1H, d); 2.22-2.03 (4H, m); 2.03-1.94 (1H, m); 1.94-1.83 (1H, m); 1.71-1.50 (2H, m); 1.35 (3H, s); 1.33-1.23 (2H, m); 1.17-1.09 (1H, m); 1.08 (3H, s). APCI-MS m/z: 648 [MH$^+$].

Example 7

(1R,3aS,3bS,10aR,10bS,11S,12aS)-1-{[(Cyanom-
ethyl)thio]carbonyl}-7-(4-fluorophenyl)-11-hydroxy-
10a,12a-dimethyl-1,2,3,3a,3b,4,5,7,10,10a,10b,11,
12,12a-tetradecahydrocyclopenta[5,6]naphtho[1,2-f]
indazol-1-yl 2-furoate The compound was prepared from Intermediate 5 and bromoacetonitrile according to the procedure for Example 1.

$^1$H NMR (400 MHz, CDCl$_3$) δ 7.63 (1H, s); 7.50-7.43 (3H, m); 7.24 (1H, s); 7.17 (2H, t); 6.56 (1H, s); 6.09 (1H, s); 4.64 (1H, m); 3.68 (2H, m); 3.10-3.01 (2H, m); 2.78 (1H, d); 2.53 (1H, t); 2.33-2.22 (2H, m); 2.20-2.02 (3H, m); 2.02-1.94 (1H, m); 1.91-1.81 (1H, m); 1.80-1.71 (1H, m); 1.59-1.47 (1H, m); 1.39-1.30 (4H, m); 1.21-1.09 (2H, m); 1.07 (3H, s). APCI-MS m/z: 616 [MH$^+$].

120

Example 8

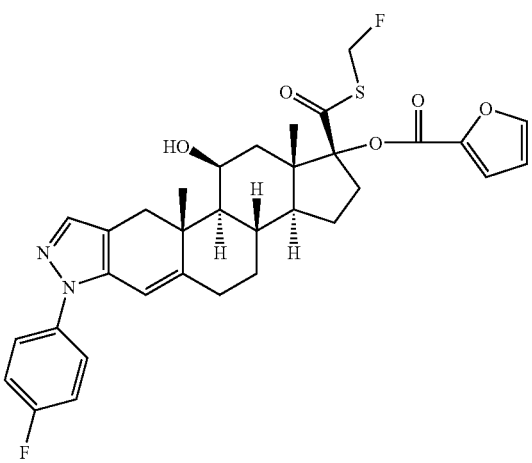

(1R,3aS,3bS,10aR,10bS,11S,12aS)-1-{[(Fluorom-
ethyl)thio]carbonyl}-7-(4-fluorophenyl)-11-hydroxy-
10a,12a-dimethyl-1,2,3,3a,3b,4,5,7,10,10a,10b,11,
12,12a-tetradecahydrocyclopenta[5,6]naphtho[1,2-f]
indazol-1-yl 2-furoate The compound was prepared from Intermediate 5 and bromofluoromethane according to the procedure for Example 1.

$^1$H NMR (400 MHz, CDCl$_3$) δ 7.63 (1H, s); 7.50-7.44 (3H, m); 7.24 (1H, m); 7.17 (2H, m); 6.55 (1H, m); 6.09 (1H, s); 6.07-5.61 (2H, m); 4.63 (1H, m); 3.14-3.02 (2H, m); 2.78 (1H, d); 2.53 (1H, t); 2.34-2.23 (2H, m); 2.19-2.04 (3H, m); 2.02-1.94 (1H, m); 1.90-1.71 (2H, m); 1.59-1.46 (1H, m); 1.38-1.30 (4H, m); 1.20-1.09 (2H, m); 1.06 (3H, s). APCI-MS m/z: 609 [MH$^+$].

Example 9

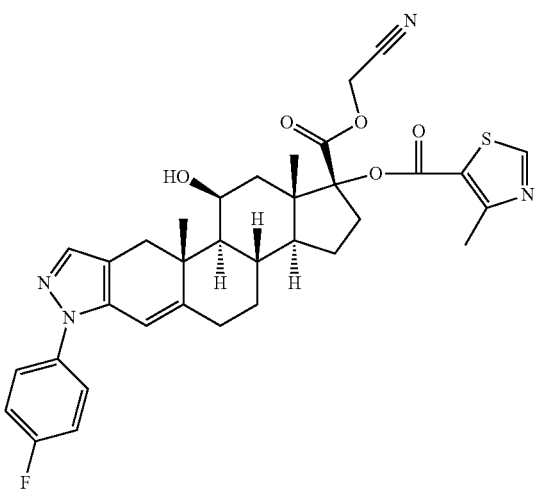

Cyanomethyl(1R,3aS,3bS,10aR,10bS,11S,12aS)-7-(4-fluorophenyl)-11-hydroxy-10a,12a-dimethyl-1-{[(4-methyl-1,3-thiazol-5-yl)carbonyl]oxy}-1,2,3,3a,3b,4,5,7,10,10a,10b,11,12,12a-tetradecahydrocyclopenta[5,6]naphtho[1,2-f]indazole-1-carboxylate In a 5 ml vial was added Intermediate 6 (0.107 g, 0.18 mmol), NaHCO$_3$ (0.17 g, 2.02 mmol), and bromoacetonitrile (0.027 ml, 0.40 mmol) in DMF (2.5 ml) to give a brown suspension that was stirred for 2 hours. The crude reaction mixture was partitioned between EtOAc (20 ml) and water (20 ml). The organic phase was collected and the aqueous phase was extracted with another portion of EtOAc (15 ml). The combined organic phases were washed with water (2×15 ml) and brine (10 ml) and were dried over Na$_2$SO$_4$. Filtration and evaporation gave a yellow oil (0.18 g). This oil was purified on a preparative HPLC column (CH$_3$CN/water) and the product containing fractions were freeze-dried to give 50 mg of the title compound.

$^1$H NMR (400 MHz, CDCl$_3$) δ 8.80 (1H, s); 7.50-7.43 (3H, m); 7.17 (2H, t); 6.10 (1H, s); 4.81 (2H, m); 4.62 (1H, bs); 3.10-2.99 (2H, m); 2.81-2.73 (4H, m); 2.54 (1H, t); 2.31 (1H, d); 2.18-1.95 (4H, m); 1.94-1.81 (2H, m); 1.81-1.70 (1H, m); 1.60-1.50 (1H, m); 1.35 (3H, s); 1.29 (1H, dd); 1.22-1.12 (2H, d); 1.11 (3H, s). APCI-MS m/z: 631 [MH$^+$].

Example 10

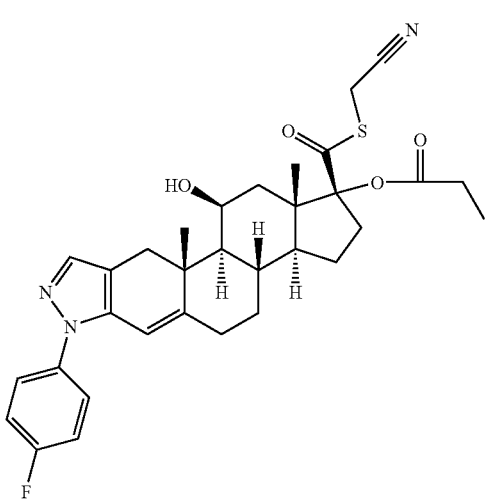

(1R,3aS,3bS,10aR,10bS,11S,12aS)-1-{[(Cyanomethyl)thio]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl propionate The compound was prepared from Intermediate 7 and bromoacetonitrile according to the procedure for Example 1.

$^1$H NMR (400 MHz, CDCl$_3$) δ 7.46 (2H, m), 7.44 (1H, s), 7.17 (2H, t), 6.08 (1H, s), 4.58 (1H, bs), 3.79 (1H, d, AB), 3.57 (1H, d, AB), 3.07-2.92 (2H, m), 2.72 (1H, d), 2.51 (1H, t), 2.39 (2H, dq), 2.29 (1H, d), 2.16-1.92 (5H, m), 1.87-1.77 (1H, m); 1.70-1.60 (1H, m), 1.54-1.41 (1H, m), 1.33 (3H, s), 1.26 (1H, dd), 1.17 (3H, t), 1.13 (2H, m), 1.01 (3H, s). APCI-MS m/z: 578 [MH$^+$].

Example 11

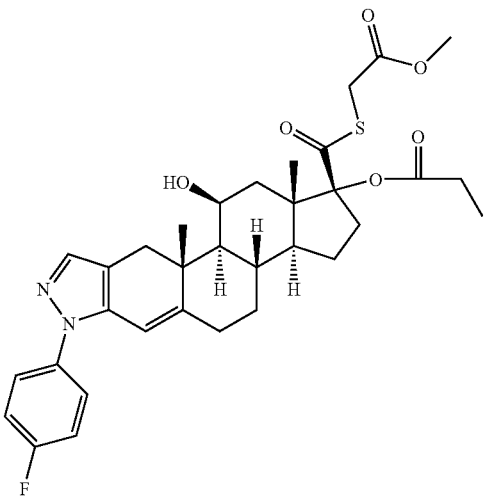

(1R,3aS,3bS,10aR,10bS,11S,12aS)-7-(4-Fluorophenyl)-11-hydroxy-1-{[(2-methoxy-2-oxoethyl)thio]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl propanoate In a 5 mL Vial was dissolved Intermediate 7 (0.035 g, 0.06 mmol) in dioxane (1 mL) to give a yellow solution. N-ethyl-N-isopropylpropan-2-amine (0.026 mL, 0.15 mmol) and methyl 2-bromoacetate (7.45 µL, 0.08 mmol) were added, and the mixture was allowed to stand for 10 minutes. The solution was diluted with CH$_3$CN (1 ml) and water (1 ml), and was then injected into a preparative HPLC column (CH3CN/water). The product containing fraction was freeze-dried to give 20 mg of the desired product as a white solid.

$^1$H NMR (400 MHz, CDCl$_3$) δ 7.47 (2H, m), 7.43 (1H, s), 7.17 (2H, t), 6.08 (1H, s), 4.58 (1H, bs), 3.85 (1H, d, AB), 3.75 (3H, s), 3.59 (1H, d, AB), 3.03 (1H, d), 2.97 (1H, m), 2.73 (1H, d), 2.51 (1H, t), 2.38 (2H, dq), 2.29 (1H, d), 2.18-1.92 (5H, m), 1.87-1.74 (1H, m); 1.70-1.60 (1H, m), 1.50-1.41 (1H, m), 1.33 (3H, s), 1.26 (1H, d), 1.17 (3H, t), 1.13 (2H, m), 1.00 (3H, s). APCI-MS m/z: 611 [MH$^+$].

Example 12

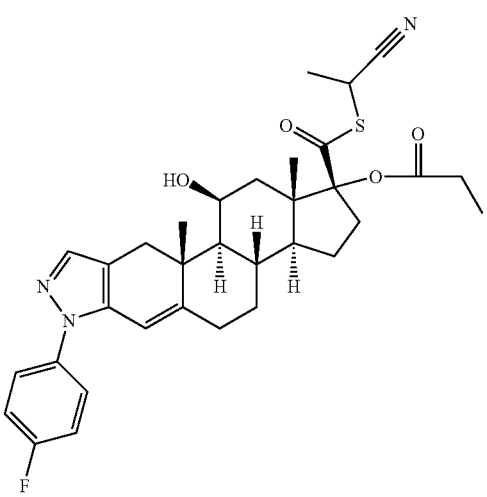

(1R,3aS,3bS,10aR,10bS,11S,12aS)-1-{[(1-Cyanoethyl)thio]carbonyl}-7-(4-fluoro-phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl propanoate The compound was prepared according to the procedure in Example 11, starting from intermediate 7. The product was a mixture of two epimers.

$^1$H NMR (400 MHz, CDCl$_3$) δ 7.46 (2H, m), 7.43 (1H, s), 7.17 (2H, t), 6.08 (1H, s), 4.57 (1H, bs), 4.28 (1H, m), 3.07-2.87 (2H, m), 2.73 (1H, d), 2.51 (1H, t), 2.37 (2H, dq), 2.29 (1H, d), 2.15-1.87 (5H, m), 1.87-1.74 (1H, m); 1.68-1.62 (4H, d), 1.52-1.39 (1H, m), 1.33 (3H, s), 1.26 (1H, m), 1.17 (3H, t), 1.13 (2H, m), 1.01 (3H, s). APCI-MS m/z: 592 [MH$^+$].

Example 13

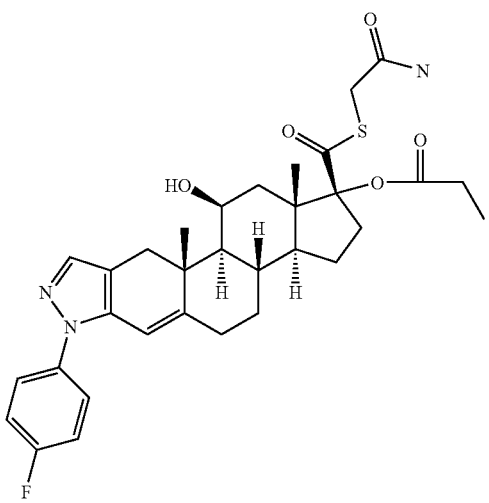

(1R,3aS,3bS,10aR,10bS,11S,12aS)-{[(2-Amino-2-oxoethyl)thio]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl propanoate The compound was prepared according to the procedure in Example 11, starting from intermediate 7 and 2-Bromoacetamide.

$^1$H NMR (400 MHz, CDCl$_3$) δ 7.46 (2H, m), 7.43 (1H, s), 7.17 (2H, t), 6.25 (1H, bs), 6.08 (1H, s), 5.26 (1H, bs), 4.57 (1H, bs), 3.77 (1H, d, AB), 3.48 (1H, d, AB), 3.06-2.96 (2H, m), 2.73 (1H, d), 2.51 (1H, t), 2.40 (2H, dq), 2.29 (1H, d), 2.13 (1H, m), 2.08-1.88 (4H, m), 1.88-1.77 (1H, m); 1.73-1.63 (1H, m), 1.52-1.41 (1H, m), 1.33 (3H, s), 1.28 (1H, m), 1.17 (3H, t), 1.13 (2H, m), 0.97 (3H, s). APCI-MS m/z: 596 [MH$^+$].

Example 14

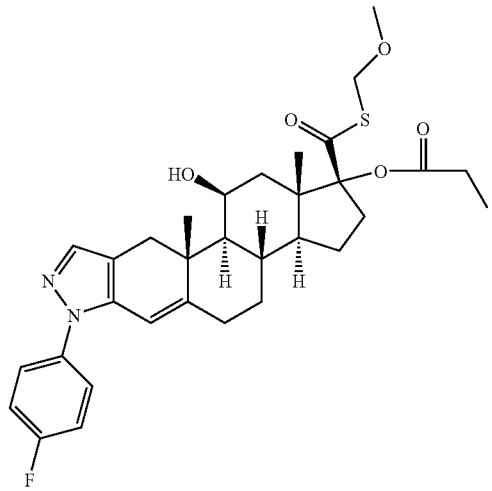

(1R,3aS,3bS,10aR,10bS,11S,12aS)-7-(4-Fluorophenyl)-11-hydroxy-{[(methoxy-methyl)thio]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl propanoate The compound was prepared according to the procedure in Example 11, starting from intermediate 7 and bromomethyl methylether.

$^1$H NMR (400 MHz, CDCl$_3$) δ 7.46 (2H, m), 7.43 (1H, s), 7.17 (2H, t), 6.08 (1H, s), 5.13 (2H, s), 4.56 (1H, bs), 3.32 (3H, s), 3.07-2.96 (2H, m), 2.73 (1H, d), 2.51 (1H, t), 2.39 (2H, dq), 2.29 (1H, d), 2.14 (1H, m), 2.06-1.92 (4H, m), 1.86-1.75 (1H, m); 1.72-1.60 (1H, m), 1.52-1.38 (1H, m), 1.33 (3H, s), 1.28 (1H, m), 1.17 (3H, t), 1.13-1.08 (2H, m), 0.98 (3H, s). APCI-MS m/z: 583 [MH$^+$].

Example 15

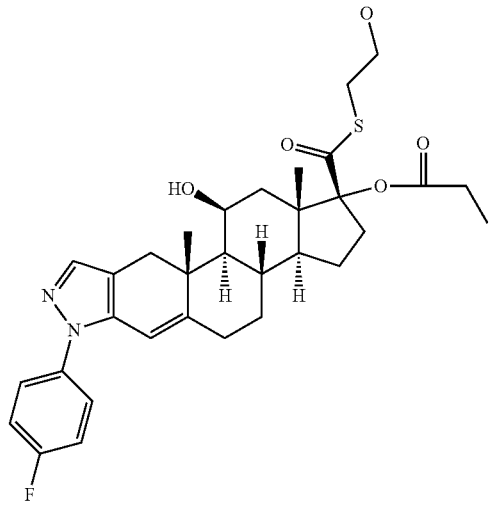

125

(1R,3aS,3bS,10aR,10bS,11S,12aS)-7-(4-Fluorophenyl)-11-hydroxy-1-{[(2-hydroxyethyl)thio]carbonyl}-10a,12a-dimethyl-1,2,3,3a,3b,4,5,7,10,10a,10b,11,12,12a-tetradecahydropcyclopenta[5,6]naphtho[1,2-f]indazol-1-yl propanoate The compound was prepared according to the procedure in Example 11, starting from intermediate 7 and 2-bromoethanol.

$^1$H NMR (400 MHz, CDCl$_3$) δ 7.46 (2H, m), 7.43 (1H, s), 7.17 (2H, t), 6.08 (1H, s), 4.57 (1H, bs), 3.76 (2H, m), 3.24-3.14 (1H, m), 3.12-2.94 (3H, m), 2.73 (1H, d), 2.51 (1H, t), 2.39 (2H, dq), 2.29 (1H, d), 2.14 (1H, m), 2.06-1.88 (5H, m), 1.86-1.76 (1H, m); 1.72-1.60 (1H, m), 1.52-1.38 (1H, m), 1.33 (3H, s), 1.28 (1H, m), 1.17 (3H, t), 1.13-1.08 (2H, m), 0.98 (3H, s). APCI-MS m/z: 583 [MH$^+$].

Example 16

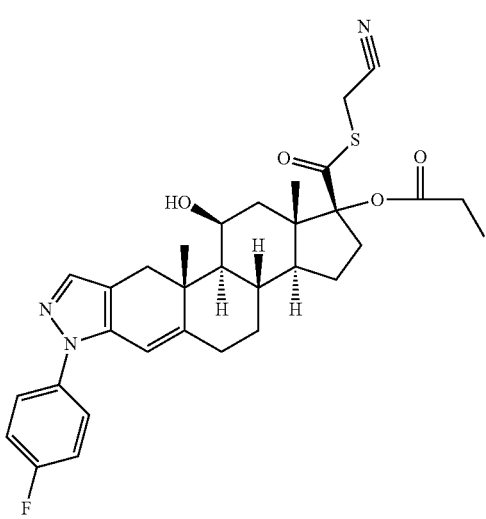

(1R,3aS,3bS,10aR,10bS,11S,12aS)-{[(2-Cyanoethyl)thio]carbonyl}-7-(4-fluoro-phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl propanoate The compound was prepared according to the procedure in Example 11, starting from intermediate 7 and 3-bromopropionitrile.

$^1$H NMR (400 MHz, CDCl$_3$) δ 7.46 (2H, m), 7.43 (1H, s), 7.17 (2H, t), 6.08 (1H, s), 4.57 (1H, bs), 3.23-3.05 (2H, m), 3.05-2.91 (2H, m), 2.78-2.67 (2H, m), 2.67-2.57 (1H, m), 2.51 (1H, t), 2.39 (2H, dq), 2.29 (1H, d), 2.13 (1H, m), 2.07-1.89 (4H, m), 1.86-1.76 (1H, m); 1.72-1.60 (1H, m), 1.50-1.39 (1H, m), 1.33 (3H, s), 1.28 (1H, m), 1.17 (3H, t), 1.13-1.08 (2H, m), 0.98 (3H, s). APCI-MS m/z: 592 [MH$^+$].

Example 17

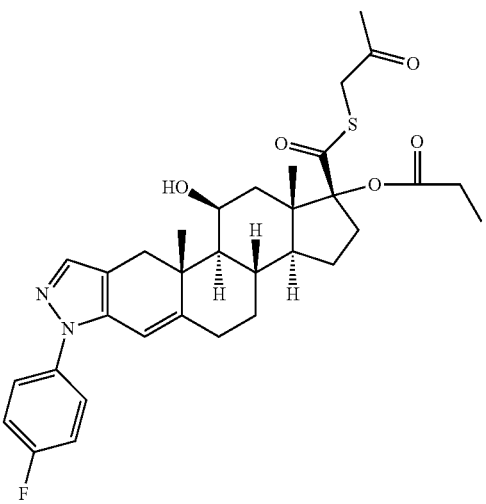

(1R,3aS,3bS,10aR,10bS,11S,12aS)-7-(4-Fluorophenyl)-11-hydroxy-10a,12a-dimethyl-1-{[(2-oxopropyl)thio]carbonyl}-1,2,3,3a,3b,4,5,7,10,10a,10b,11,12,12a-tetradecahydrocyclopenta[5,6]naphtho[1,2-f]indazol-1-yl propanoate The compound was prepared according to the procedure in Example 11, starting from intermediate 7 and 1-chloropropane-2-one.

$^1$H NMR (400 MHz, CDCl$_3$) δ 7.46 (2H, m), 7.43 (1H, s), 7.17 (2H, t), 6.08 (1H, s), 4.57 (1H, bs), 3.80 (1H, d, AB), 3.69 (1H, d, AB), 3.07-2.90 (2H, m), 2.73 (1H, d), 2.52 (1H, t), 2.39 (2H, dq), 2.32-2.24 (4H, m), 2.19-1.91 (5H, m), 1.86-1.73 (1H, m); 1.72-1.60 (1H, m), 1.50-1.39 (1H, m), 1.33 (3H, s), 1.28 (1H, m), 1.17 (3H, t), 1.15-1.10 (2H, m), 0.97 (3H, s). APCI-MS m/z: 595 [MH$^+$].

Example 18

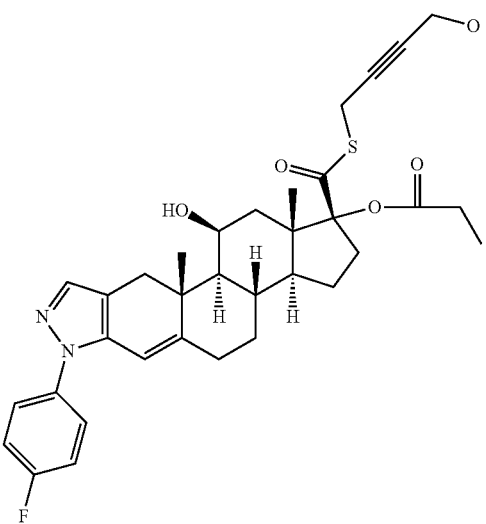

127

(1R,3aS,3bS,10aR,10bS,11S,12aS)-7-(4-Fluorophenyl)-11-hydroxy-1-{[(4-hydroxy-but-2-yn-1-yl)thio]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl propanoate The compound was prepared according to the procedure in Example 11, starting from intermediate 7 and 4-chlorobut-2-yn-1-ol.

$^1$H NMR (400 MHz, CDCl$_3$) δ 7.46 (2H, m), 7.43 (1H, s), 7.17 (2H, t), 6.08 (1H, s), 4.57 (1H, bs), 4.25 (2H, s), 3.68 (2H, m), 3.05-2.93 (2H, m), 2.73 (1H, d), 2.51 (1H, t), 2.39 (2H, dq), 2.29 (1H, d), 2.16-1.90 (6H, m), 1.86-1.75 (1H, m); 1.70-1.59 (1H, m), 1.50-1.39 (1H, m), 1.33 (3H, s), 1.31-1.23 (2H, m), 1.17 (3H, t), 1.15-1.06 (1H, m), 1.00 (3H, s). APCI-MS m/z: 607 [MH$^+$].

Example 19

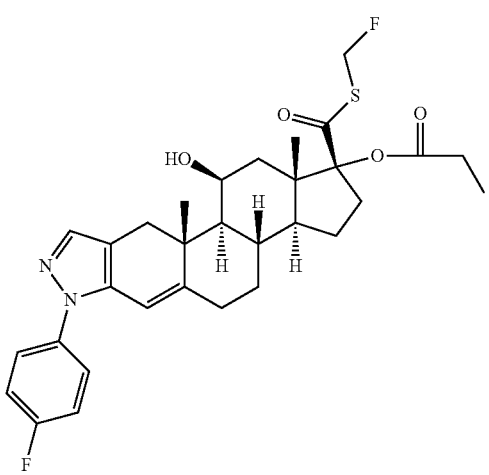

(1R,3aS,3bS,10aR,10bS,11S,12aS)-1-{[(Fluoromethyl)thio]carbonyl}-7-(4-fluoro-phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl propanoate The compound was prepared according to the procedure in Example 11, starting from intermediate 7 and bromofluoromethane.

$^1$H NMR (400 MHz, CDCl$_3$) δ 7.46 (2H, m), 7.43 (1H, s), 7.17 (2H, t), 6.08 (1H, s), 6.05-5.63 (2H, m), 4.57 (1H, m), 3.06-2.95 (2H, m), 2.73 (1H, d), 2.51 (1H, t), 2.39 (2H, dq), 2.29 (1H, d), 2.14 (1H, d), 2.09-1.92 (4H, m), 1.88-1.76 (1H, m); 1.70-1.59 (1H, m), 1.50-1.39 (1H, m), 1.33 (3H, s), 1.27 (1H, d), 1.17 (3H, t), 1.13-1.07 (2H, m), 1.00 (3H, s). APCI-MS m/z: 571 [MH$^+$].

128

Example 20

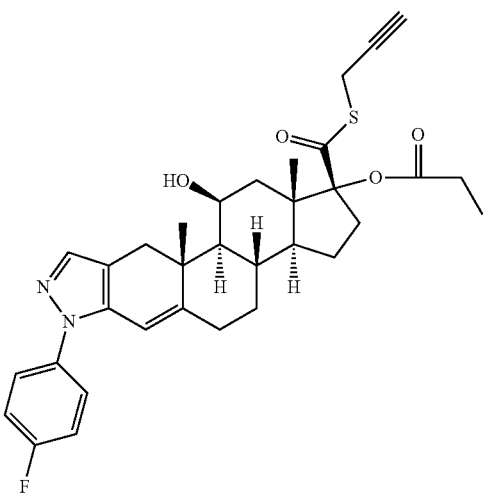

(1R,3aS,3bS,10aR,10bS,11S,12aS)-7-(4-fluorophenyl)-11-hydroxy-10a,12a-dimethyl-1-[(prop-2-yn-1-ylthio)carbonyl]-1,2,3,3a,3b,4,5,7,10,10a,10b,11,12,12a-tetradecaphydrocyclopenta[5,6]naphtho[1,2-f]indazol-1-yl propanoate The compound was prepared according to the procedure in Example 11, starting from intermediate 7 and 3-bromoprop-1-yne.

$^1$H NMR (400 MHz, CDCl$_3$) δ 7.46 (2H, m), 7.43 (1H, s), 7.17 (2H, t), 6.08 (1H, s), 4.57 (1H, m), 3.73 (1H, dd), 3.56 (1H, dd), 3.07-2.93 (2H, m), 2.73 (1H, d), 2.51 (1H, t), 2.38 (2H, dq), 2.29 (1H, d), 2.18 (1H, t), 2.12 (1H, d), 2.08-1.92 (4H, m), 1.85-1.75 (1H, m); 1.68-1.58 (1H, m), 1.51-1.39 (1H, m), 1.33 (3H, s), 1.27 (1H, d), 1.16 (3H, t), 1.13-1.07 (2H, m), 0.99 (3H, s). APCI-MS m/z: 577 [MH$^+$].

Example 21

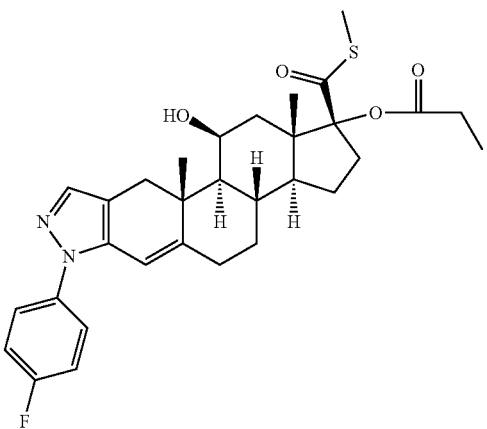

(1R,3aS,3bS,10aR,10bS,11S,12aS)-7-(4-Fluorophenyl)-11-hydroxy-10a,12a-dimethyl-1-[(methylthio)carbonyl]-1,2,3,3a,3b,4,5,7,10,10a,10b,11,12,12a-tetradecahydropcyclopenta[5,6]naphtho[1,2-f]indazol-1-yl propanoate The compound was prepared according to the procedure in Example 11, starting from intermediate 7 and iodomethane.

$^1$H NMR (400 MHz, CDCl$_3$) δ 7.46 (2H, m), 7.43 (1H, s), 7.17 (2H, t), 6.08 (1H, s), 4.57 (1H, bs), 3.06-2.95 (2H, m), 2.73 (1H, d), 2.51 (1H, t), 2.38 (2H, dq), 2.32 (3H, s), 2.29 (1H, d), 2.13 (1H, d), 2.06-1.92 (4H, m), 1.85-1.75 (1H, m); 1.70-1.60 (1H, m), 1.51-1.39 (1H, m), 1.33 (3H, s), 1.27 (1H, d), 1.16 (3H, t), 1.14-1.04 (2H, m), 0.96 (3H, s). APCI-MS m/z: 553 [MH$^+$]

Example 22

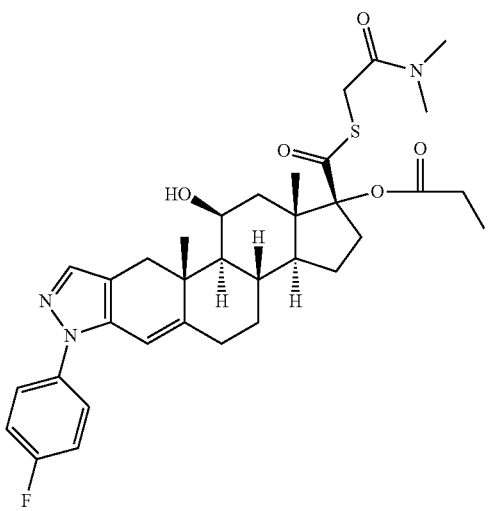

(1R,3aS,3bS,10aR,10bS,11S,12aS)-1-({[2-(Dimethylamino)-2-oxoethyl]thio}carbonyl)-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl propanoate The compound was prepared according to the procedure in Example 11, starting from intermediate 7 and 2-chloro-N,N-dimethylacetamide.

$^1$H NMR (400 MHz, CDCl$_3$) δ 7.46 (2H, m), 7.43 (1H, s), 7.17 (2H, t), 6.08 (1H, s), 4.56 (1H, bs), 3.96 (1H, d), 3.73 (1H, d), 3.10 (3H, s), 3.06-2.95 (2H, m), 2.98 (3H, s), 2.72 (1H, d), 2.51 (1H, t), 2.38 (2H, dq), 2.28 (1H, d), 2.12 (2H, m), 2.07-1.92 (3H, m), 1.85-1.74 (1H, m); 1.69-1.58 (1H, m), 1.50-1.38 (1H, m), 1.35-1.30 (4H, m), 1.26 (1H, d), 1.16 (3H, t), 1.15-1.06 (1H, m), 0.98 (3H, s). APCI-MS m/z: 624 [MH$^+$].

Example 23

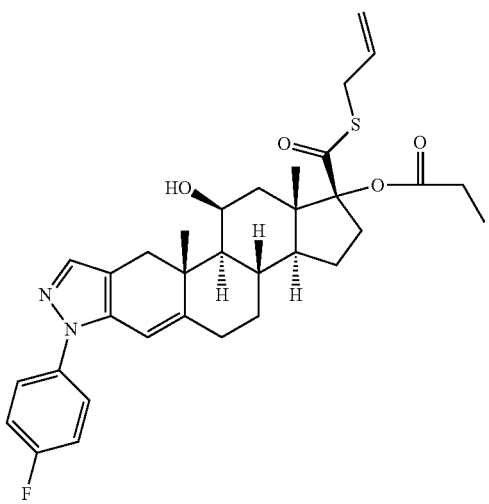

(1R,3aS,3bS,10aR,10bS,11S,12aS)-7-(4-Fluorophenyl)-11-hydroxy-10a,12a-dimethyl-1-[(prop-2-en-1-ylthio)carbonyl]-1,2,3,3a,3b,4,5,7,10,10a,10b,11,12,12a-tetradecahydropcyclopenta[5,6]naphtho[1,2-f]indazol-1-yl propanoate The compound was prepared according to the procedure in Example 11, starting from intermediate 7 and 3-bromoprop-1-ene.

$^1$H NMR (400 MHz, CDCl$_3$) δ 7.46 (2H, m), 7.43 (1H, s), 7.16 (2H, t), 6.08 (1H, s), 5.88-5.73 (1H, m), 5.25 (1H, d), 5.12 (1H, d), 4.56 (1H, bs), 3.57 (2H, m), 3.06-2.95 (2H, m), 2.73 (1H, d), 2.51 (1H, t), 2.37 (2H, dq), 2.29 (1H, d), 2.13 (1H, m), 2.07-1.92 (4H, m), 1.85-1.74 (1H, m); 1.69-1.59 (1H, m), 1.50-1.36 (1H, m), 1.33 (3H, m), 1.27 (1H, d), 1.16 (3H, t), 1.16-1.06 (2H, m), 0.96 (3H, s). APCI-MS m/z: 579 [MH$^+$].

Example 24

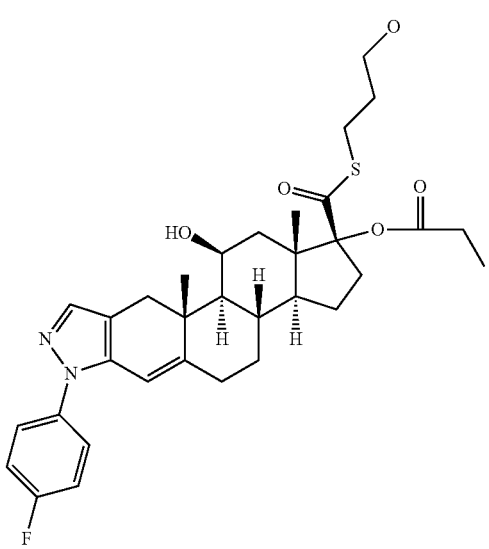

131

(1R,3aS,3bS,10aR,10bS,11S,12aS)-7-(4-Fluorophenyl)-11-hydroxy-1-{[(3-hydroxy-propyl)thio]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl propanoate The compound was prepared according to the procedure in Example 11, starting from intermediate 7 and 3-bromopropan-1-ol.

$^1$H NMR (400 MHz, CDCl$_3$) δ 7.46 (2H, m), 7.43 (1H, s), 7.16 (2H, t), 6.08 (1H, s), 4.56 (1H, bs), 3.67 (2H, q), 3.17-3.07 (1H, m), 3.06-2.93 (3H, m), 2.73 (1H, d), 2.51 (1H, t), 2.37 (2H, dq), 2.29 (1H, d), 2.13 (1H, m), 2.06-1.90 (5H, m), 1.90-1.74 (3H, m); 1.72-1.60 (1H, m), 1.51-1.37 (1H, m), 1.33 (3H, m), 1.27 (1H, d), 1.16 (3H, t), 1.16-1.06 (2H, m), 0.97 (3H, s). APCI-MS m/z: 597 [MH$^+$].

Example 25

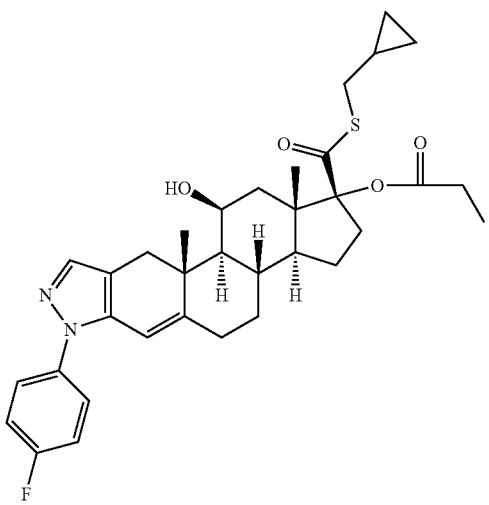

(1R,3aS,3bS,10aR,10bS,11S,12aS)-1-{[(Cyclopropylmethyl)thio]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl propanoate The compound was prepared according to the procedure in Example 11, starting from intermediate 7 and (bromomethyl)cyclopropane.

$^1$H NMR (400 MHz, CDCl$_3$) δ 7.46 (2H, m), 7.43 (1H, s), 7.16 (2H, t), 6.08 (1H, s), 4.56 (1H, bs), 3.08-2.93 (2H, m), 2.87 (2H, dd), 2.73 (1H, d), 2.51 (1H, t), 2.37 (2H, dq), 2.29 (1H, d), 2.13 (1H, m), 2.08-1.91 (4H, m), 1.85-1.72 (1H, m); 1.70-1.58 (1H, m), 1.50-1.38 (1H, m), 1.33 (3H, m), 1.27 (1H, d), 1.16 (3H, t), 1.16-1.06 (2H, m), 1.03-0.95 (1H, m), 0.97 (3H, s), 0.56 (2H, m), 0.25 (2H, m). APCI-MS m/z: 593 [MH$^+$].

132
Example 26

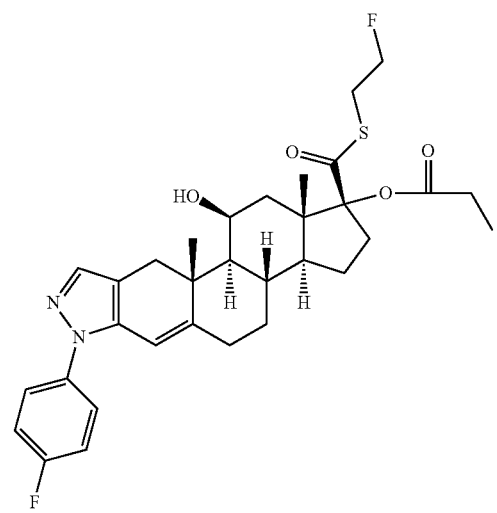

(1R,3aS,3bS,10aR,10bS,11S,12aS)-1-{[(2-Fluoroethyl)thio]carbonyl}-7-(4-fluoro-phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl propanoate The compound was prepared according to the procedure in Example 11, starting from intermediate 7 and 1-Bromo-2-fluoroethane.

$^1$H NMR (400 MHz, CDCl$_3$) δ 7.46 (2H, m), 7.43 (1H, s), 7.16 (2H, t), 6.08 (1H, s), 4.56 (2H, bs), 4.45 (1H, m), 3.26 (1H, t), 3.20 (1H, t), 3.06-2.93 (2H, m), 2.73 (1H, d), 2.51 (1H, t), 2.38 (2H, dq), 2.29 (1H, d), 2.13 (1H, m), 2.06-1.91 (4H, m), 1.85-1.74 (1H, m); 1.70-1.58 (1H, m), 1.50-1.38 (1H, m), 1.33 (3H, m), 1.27 (1H, d), 1.17 (3H, t), 1.16-1.06 (2H, m), 0.96 (3H, s). APCI-MS m/z: 585 [MH$^+$].

Example 27

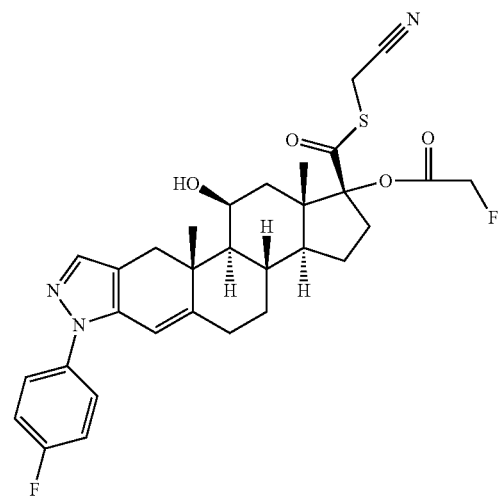

133

(1R,3aS,3bS,10aR,10bS,11S,12aS)-1-{[(Cyanomethyl)thio]carbonyl}-7-(4-fluoro-phenyl)-11-hydroxy-10a,12a-dimethyl-1,2,3,3a,3b,4,5,7,10,10a, 10b,11,12,12a-tetradecahydrocyclopenta[5,6]naphtho[1,2-f]indazol-1-yl fluoroacetate The compound was prepared according to the procedure in Example 11, starting from intermediate 8 and 2-Bromoacetonitrile.

$^1$H NMR (400 MHz, CDCl$_3$) δ 7.46 (2H, m), 7.43 (1H, s), 7.17 (2H, t), 6.08 (1H, s), 4.94 (1H, s), 4.82 (1H, s), 4.57 (1H, bs), 3.79 (1H, d, AB), 3.60 (1H, d, AB), 3.07-2.97 (2H, m), 2.72 (1H, d), 2.52 (1H, t), 2.29 (1H, d), 2.15-1.93 (5H, m), 1.92-1.80 (1H, m); 1.70-1.58 (1H, m), 1.55-1.46 (1H, m), 1.33 (3H, m), 1.27 (1H, d), 1.20-1.07 (2H, m), 1.04 (3H, s).

APCI-MS m/z: 582 [MH$^+$].

Example 28

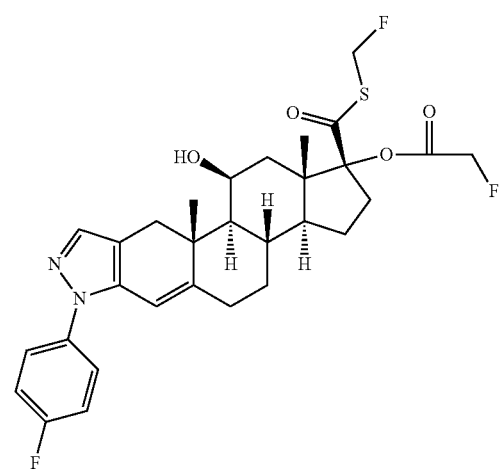

(1R,3aS,3bS,10aR,10bS,11S,12aS)-1-{[(Fluoromethyl)thio]carbonyl}-7-(4-fluoro-phenyl)-11-hydroxy-10a,12a-dimethyl-1,2,3,3a,3b,4,5,7,10,10a, 10b,11,12,12a-tetradecahydrocyclopenta[5,6]naphtho[1,2-f]indazol-1-yl fluoroacetate The compound was prepared according to the procedure in Example 11, starting from intermediate 8 and Bromofluoromethane.

$^1$H NMR (400 MHz, CDCl$_3$) δ 7.46 (2H, m), 7.43 (1H, s), 7.17 (2H, t), 6.08 (1H, s), 6.04-5.66 (2H, m), 4.94 (1H, s), 4.82 (1H, s), 4.57 (1H, bs), 3.12-2.96 (2H, m), 2.72 (1H, d), 2.51 (1H, t), 2.29 (1H, d), 2.15-1.93 (5H, m), 1.91-1.80 (1H, m); 1.70-1.60 (1H, m), 1.55-1.46 (1H, m), 1.33 (3H, m), 1.28 (1H, d), 1.19-1.08 (2H, m), 1.03 (3H, s). APCI-MS m/z: 575 [MH$^+$].

Example 29

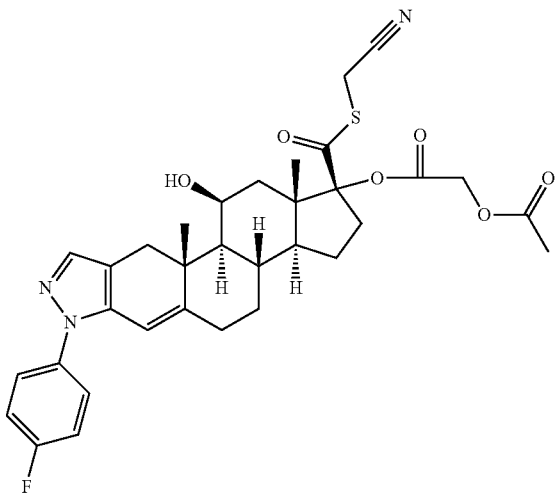

(1R,3aS,3bS,10aR,10bS,11S,12aS)-1-{[(Cyanomethyl)thio]carbonyl}-7-(4-fluoro-phenyl)-11-hydroxy-10a,12a-dimethyl-1,2,3,3a,3b,4,5,7,10,10a, 10b,11,12,12a-tetradecahydrocyclopenta[5,6]naphtho[1,2-f]indazol-1-yl (acetyloxy)acetate The compound was prepared according to the procedure in Example 11, starting from intermediate 9 and 2-Bromoacetonitrile.

$^1$H NMR (400 MHz, CDCl$_3$) δ 7.46 (2H, m), 7.43 (1H, s), 7.17 (2H, t), 6.08 (1H, s), 4.63 (2H, q), 4.57 (1H, bs), 3.79 (1H, d, AB), 3.58 (1H, d, AB), 3.07-2.91 (2H, m), 2.70 (1H, d), 2.51 (1H, t), 2.29 (1H, d), 2.15 (3H, s), 2.10-1.92 (5H, m), 1.91-1.80 (1H, m); 1.67-1.56 (1H, m), 1.55-1.44 (1H, m), 1.33 (3H, m), 1.23 (1H, d), 1.19-1.08 (2H, m), 1.03 (3H, s).

APCI-MS m/z: 622 [MH$^+$].

Example 30

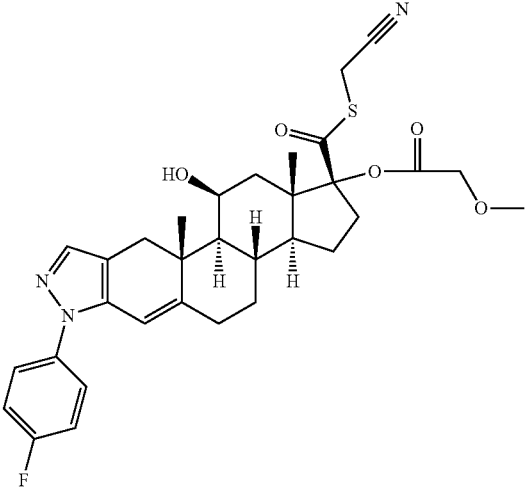

(1R,3aS,3bS,10aR,10bS,11S,12aS)-1-{[(Cyanom-
ethyl)thio]carbonyl}-7-(4-fluoro-phenyl)-11-hy-
droxy-10a,12a-dimethyl-1,2,3,3a,3b,4,5,7,10,10a,
10b,11,12,12a-tetradecahydrocyclopenta[5,6]
naphtho[1,2-f]indazol-1-yl methoxyacetate The compound was prepared according to the procedure in Example 11, starting from intermediate 10 and 2-bromoacetonitrile.

$^1$H NMR (400 MHz, CDCl$_3$) δ 7.46 (2H, m), 7.43 (1H, s), 7.17 (2H, t), 6.09 (1H, s), 4.57 (1H, bs), 4.07 (2H, s), 3.79 (1H, d, AB), 3.58 (1H, d, AB), 3.47 (3H, s), 3.07-2.96 (2H, m), 2.72 (1H, d), 2.51 (1H, t), 2.29 (1H, d), 2.13-1.92 (5H, m), 1.91-1.77 (1H, m); 1.69-1.57 (1H, m), 1.56-1.43 (1H, m), 1.33 (3H, m), 1.27 (1H, d), 1.18-1.06 (2H, m), 1.03 (3H, s). APCI-MS m/z: 594 [MH$^+$].

Example 31

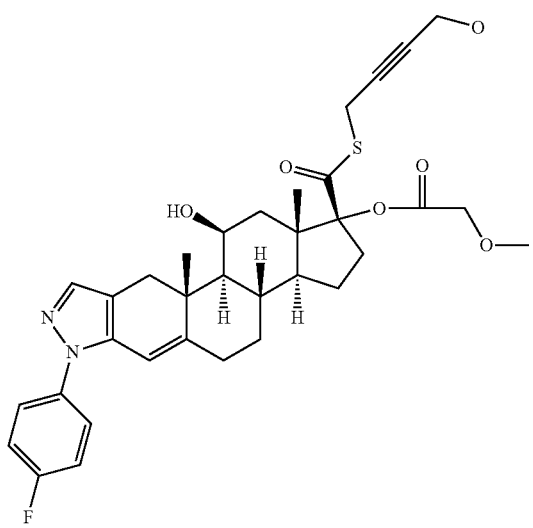

(1R,3aS,3bS,10aR,10bS,11S,12aS)-7-(4-Fluorophe-
nyl)-11-hydroxy-1-{[(4-hydroxy-but-2-yn-1-yl)thio]
carbonyl}-10a,12a-dimethyl-1,2,3,3a,3b,4,5,7,10,
10a,10b,11,12,12a-tetradecahydrocyclopenta[5,6]
naphtho[1,2-f]indazol-1-yl methoxyacetate The compound was prepared according to the procedure in Example 11, starting from intermediate 10 and 4-chlorobut-2-yn-1-ol.

$^1$H NMR (400 MHz, CDCl$_3$) δ 7.46 (2H, m), 7.43 (1H, s), 7.17 (2H, t), 6.08 (1H, s), 4.56 (1H, bs), 4.25 (2H, bs), 4.07 (2H, s), 3.69 (2H, m), 3.46 (3H, s), 3.07-2.96 (2H, m), 2.72 (1H, d), 2.51 (1H, t), 2.29 (1H, d), 2.11-1.91 (5H, m), 1.89-1.76 (1H, m); 1.68-1.58 (1H, m), 1.52-1.40 (1H, m), 1.33 (3H, m), 1.30-1.23 (2H, m), 1.18-1.06 (2H, m), 1.01 (3H, s). APCI-MS m/z: 623 [MH$^+$].

Example 32

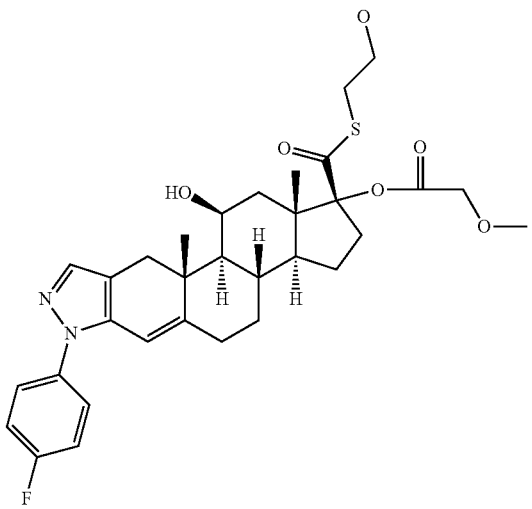

(1R,3aS,3bS,10aR,10bS,11S,12aS)-7-(4-Fluorophe-
nyl)-11-hydroxy-1-{[(2-hydroxy-ethyl)thio]carbo-
nyl}-10a,12a-dimethyl-1,2,3,3a,3b,4,5,7,10a,10b,
11,12,12a-tetradecahydrocyclopenta[5,6]naphtho[1,
2-f]indazol-1-yl methoxyacetate The compound was prepared according to the procedure in Example 11, starting from intermediate 10 and 2-Bromoethanol.

1H NMR (400 MHz, CDCl$_3$) δ 7.46 (2H, m), 7.43 (1H, s), 7.17 (2H, t), 6.08 (1H, s), 4.56 (1H, bs), 4.07 (2H, s), 3.78 (2H, m), 3.47 (3H, s), 3.27-3.15 (1H, m), 3.15-2.96 (3H, m), 2.72 (1H, d), 2.51 (1H, t), 2.29 (1H, d), 2.15-1.94 (5H, m), 1.93-1.76 (1H, m); 1.71-1.58 (1H, m), 1.52-1.40 (1H, m), 1.33 (3H, m), 1.27 (1H, m), 1.20-1.01 (3H, m), 0.99 (3H, s). APCI-MS m/z: 599 [MH$^+$].

Example 33

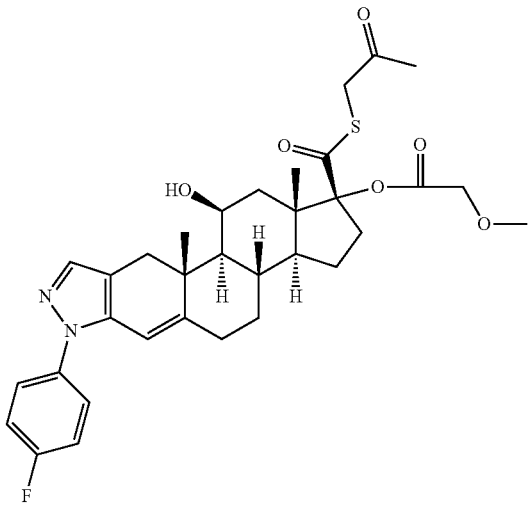

(1R,3aS,3bS,10aR,10bS,11S,12aS)-7-(4-Fluorophenyl)-11-hydroxy-10a,12a-dimethyl-1-{[(2-oxopropyl)thio]carbonyl}-1,2,3,3a,3b,4,5,7,10a,10b,11,12,12a-tetradecahydrocyclopenta[5,6]naphtho[1,2-f]indazol-1-yl methoxyacetate The compound was prepared according to the procedure in Example 11, starting from intermediate 10 and 1-Chloropropane-2-one.

$^1$H NMR (400 MHz, CDCl$_3$) δ 7.46 (2H, m), 7.43 (1H, s), 7.17 (2H, t), 6.08 (1H, s), 4.56 (1H, bs), 4.07 (2H, s), 3.83 (1H, d, AB), 3.70 (1H, d, AB), 3.47 (3H, s), 3.07-2.93 (2H, m), 2.72 (1H, d), 2.51 (1H, t), 2.35-2.24 (4H, m), 2.15-1.94 (5H, m), 1.89-1.76 (1H, m); 1.71-1.58 (1H, m), 1.52-1.40 (1H, m), 1.33 (3H, m), 1.27 (1H, d), 1.20-1.06 (2H, m), 0.99 (3H, s). APCI-MS m/z: 611 [MH$^+$].

Example 34

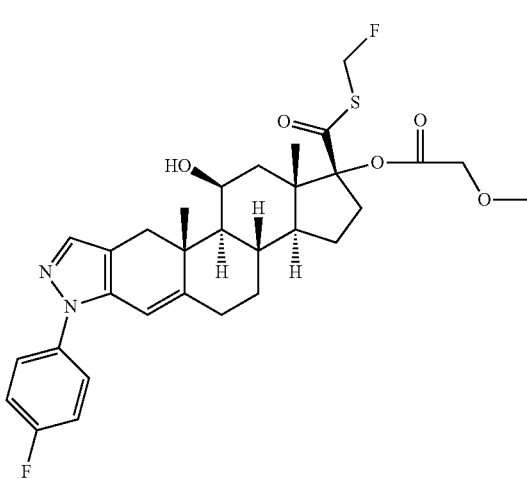

(1R,3aS,3bS,10aR,10bS,11S,12aS)-1-{[(Fluoromethyl)thio]carbonyl}-7-(4-fluoro-phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl methoxyacetate The compound was prepared according to the procedure in Example 11, starting from intermediate 10 and Bromofluoromethane.

$^1$H NMR (400 MHz, CDCl$_3$) δ 7.46 (2H, m), 7.43 (1H, s), 7.17 (2H, t), 6.08 (1H, s), 6.05-5.63 (2H, m), 4.56 (1H, bs), 4.07 (2H, s), 3.47 (3H, s), 3.10-2.96 (2H, m), 2.72 (1H, d), 2.51 (1H, t), 2.29 (1H, d), 2.15-1.92 (5H, m), 1.89-1.76 (1H, m); 1.71-1.58 (1H, m), 1.55-1.41 (1H, m), 1.33 (3H, m), 1.28 (1H, d), 1.18-1.07 (2H, m), 1.01 (3H, s). APCI-MS m/z: 587 [MH$^+$].

Example 35

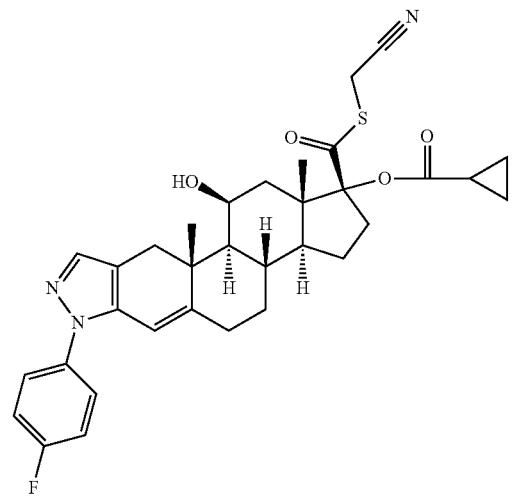

(1R,3aS,3bS,10aR,10bS,11S,12aS)-1-{[(Cyanomethyl)thio]carbonyl}-7-(4-fluoro-Phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl cyclopropanecarboxylate The compound was prepared according to the procedure in Example 11, starting from intermediate 11 and 2-Bromoacetonitrile.

$^1$H NMR (400 MHz, CDCl$_3$) δ 7.46 (2H, m), 7.43 (1H, s), 7.17 (2H, t), 6.09 (1H, s), 4.59 (1H, bs), 3.77 (1H, d, AB), 3.57 (1H, d, AB) 3.07-2.90 (2H, m), 2.73 (1H, d), 2.52 (1H, t), 2.30 (1H, d), 2.14 (1H, m), 2.09-1.92 (4H, m), 1.90-1.78 (1H, m); 1.74-1.61 (2H, m), 1.52-1.40 (1H, m), 1.34 (3H, m), 1.27 (1H, d), 1.19-1.10 (2H, m), 1.10-0.98 (5H, s), 0.98-0.90 (2H, m). APCI-MS m/z: 590 [MH$^+$].

Example 36

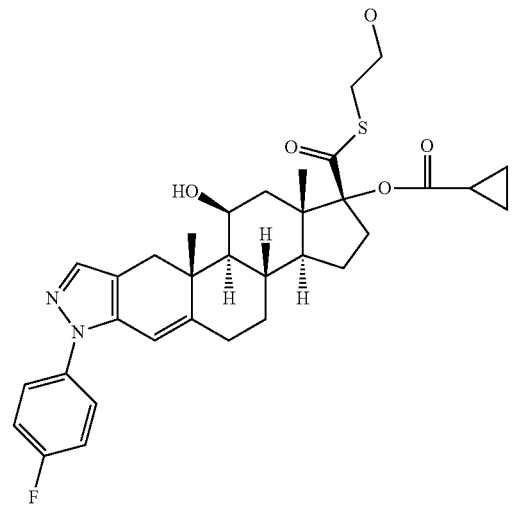

(1R,3aS,3bS,10aR,10bS,11S,12aS)-7-(4-Fluorophenyl)-11-hydroxy-1-{[(2-hydroxy-ethyl)thio]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl cyclopropanecarboxylate The compound was prepared according to the procedure in Example 11, starting from intermediate 11 and 2-Bromoethanol.

¹H NMR (400 MHz, CDCl₃) δ 7.47 (2H, m), 7.43 (1H, s), 7.17 (2H, t), 6.09 (1H, s), 4.58 (1H, bs), 3.75 (2H, m), 3.27-3.18 (1H, m) 3.10-2.93 (3H, m), 2.73 (1H, d), 2.51 (1H, t), 2.30 (1H, d), 2.14 (1H, m), 2.09-1.87 (5H, m), 1.87-1.77 (1H, m); 1.73-1.63 (2H, m), 1.50-1.40 (1H, m), 1.34 (3H, m), 1.28 (1H, d), 1.19-1.09 (2H, m), 1.09-0.99 (2H, s), 0.98 (3H, s), 0.96-0.89 (2H, m). APCI-MS m/z: 595 [MH⁺].

Example 37

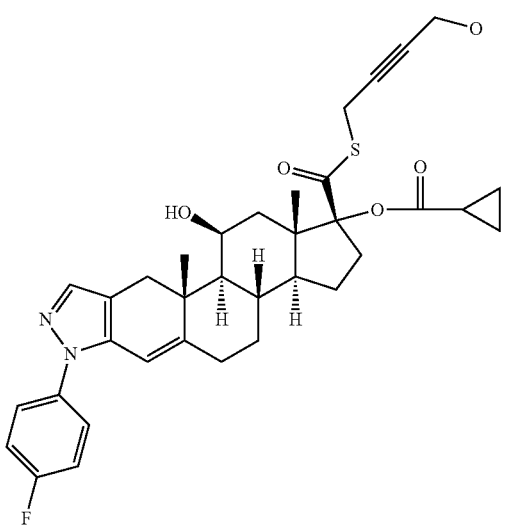

(1R,3aS,3bS,10aR,10bS,11S,12aS)-7-(4-Fluorophenyl)-11-hydroxy-{[(4-hydroxybut-2-yn-1-yl)thio]carbonyl}-10a,12a-dimethyl-1,2,3,3a,3b,4,5,7,10,11a,10b,11,12,12a-tetradecahydrocyclopenta[5,6]naphtho[1,2-f]indazol-1-yl cyclopropanecarboxylate The compound was prepared according to the procedure in Example 11, starting from intermediate 11 and 4-Chlorobut-2-yn-1-ol.

¹H NMR (400 MHz, CDCl₃) δ 7.47 (2H, m), 7.44 (1H, s), 7.17 (2H, t), 6.08 (1H, s), 4.58 (1H, bs), 4.26 (2H, m), 3.74 (1H, dt, AB), 3.61 (1H, dt, AB), 3.06-2.90 (2H, m), 2.74 (1H, d), 2.51 (1H, t), 2.29 (1H, d), 2.17-1.88 (6H, m), 1.87-1.76 (1H, m); 1.73-1.60 (2H, m), 1.52-1.38 (1H, m), 1.34 (3H, m), 1.31-1.23 (2H, m), 1.20-1.10 (1H, m), 1.10-1.02 (2H, m), 1.00 (3H, s), 0.97-0.88 (2H, m). APCI-MS m/z: 619 [MH⁺].

Example 38

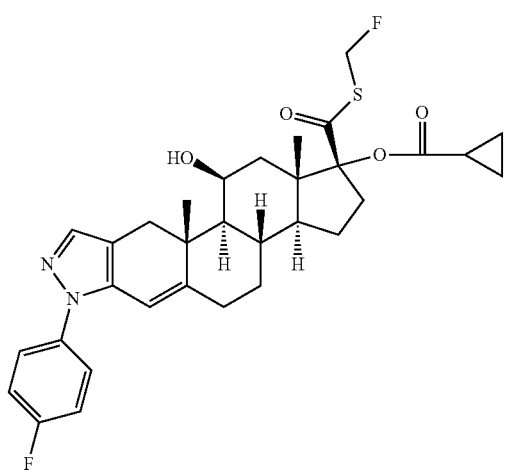

(1R,3aS,3bS,10aR,10bS,11S,12aS)-1-{[(Fluoromethyl)thio]carbonyl}-7-(4-fluoro-phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl cyclopropanecarboxylate The compound was prepared according to the procedure in Example 11, starting from intermediate 11 and Bromofluoromethane.

¹H NMR (400 MHz, CDCl₃) δ 7.47 (2H, m), 7.44 (1H, s), 7.17 (2H, t), 6.08 (1H, s), 6.04-5.62 (2H, m), 4.58 (1H, bs), 3.08-2.92 (2H, m), 2.73 (1H, d), 2.52 (1H, t), 2.30 (1H, d), 2.15 (1H, m), 2.07-1.90 (4H, m), 1.89-1.77 (1H, m); 1.74-1.63 (2H, m), 1.53-1.40 (1H, m), 1.33 (3H, m), 1.28 (1H, m), 1.20-1.02 (4H, m), 1.00 (3H, s), 0.97-0.89 (2H, m). APCI-MS m/z: 583 [MH⁺].

Example 39

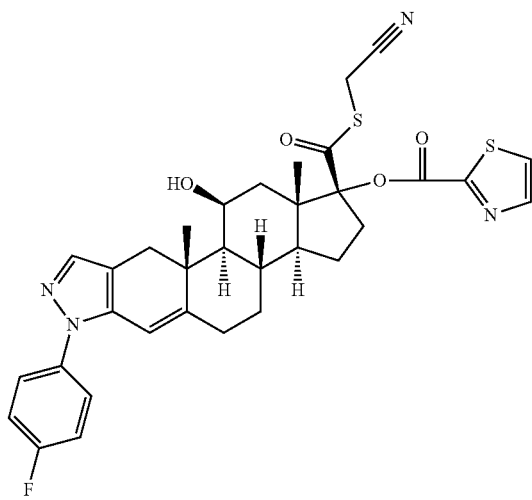

(1R,3aS,3bS,10aR,10bS,11S,12aS)-1-{[(Cyanom-
ethyl)thio]carbonyl}-7-(4-fluorophenyl)-11-hydroxy-
10a,12a-dimethyl-1,2,3,3a,3b,4,5,7,10,10a,10b,11,
12,12a-tetradecahydropcyclopenta[5,6]naphtho[1,2-
f]indazol-1-yl 1,3-thiazole-2-carboxylate The compound was prepared according to the procedure in Example 11, starting from intermediate 12 and 2-Bromoacetonitrile.

$^1$H NMR (400 MHz, CDCl$_3$) δ 8.10 (1H, d), 7.70 (1H, d), 7.47 (2H, m), 7.45 (1H, s), 7.17 (2H, t), 6.08 (1H, s), 4.66 (1H, bs), 3.82 (1H, d, AB), 3.57 (1H, d, AB), 3.16-3.01 (2H, m), 2.78 (1H, d), 2.52 (1H, t), 2.38-2.16 (3H, m), 2.15-2.03 (2H, m), 2.02-1.94 (1H, m), 1.94-1.74 (2H, m); 1.62-1.50 (1H, m), 1.42-1.31 (4H, m), 1.24-1.11 (2H, m), 1.09 (3H, s).

APCI-MS m/z: 633 [MH$^+$].

Example 40

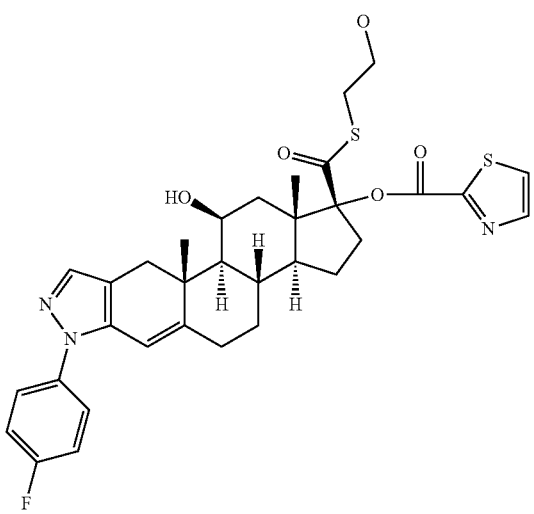

(1R,3aS,3bS,10aR,10bS,11S,12aS)-7-(4-Fluorophe-
nyl)-11-hydroxy-1-{[(2-hydroxy-ethyl)thio]carbo-
nyl}-10a,12a-dimethyl-1,2,3,3a,3b,4,5,7,10,10a,10b,
11,12,12a-tetradecahydrocyclopenta[5,6]naphtho[1,
2-f]indazol-1-yl 1,3-thiazole-2-carboxylate The compound was prepared according to the procedure in Example 11, starting from intermediate 12 and 2-Bromoethanol.

$^1$H NMR (400 MHz, CDCl$_3$) δ 8.10 (1H, d), 7.67 (1H, d), 7.47 (2H, m), 7.44 (1H, s), 7.17 (2H, t), 6.08 (1H, s), 4.65 (1H, bs), 3.78 (2H, m), 3.26-3.01 (4H, m), 2.78 (1H, d), 2.52 (1H, t), 2.42-2.24 (2H, m), 2.24-1.93 (5H, m), 1.93-1.76 (2H, m), 1.62-1.50 (1H, m), 1.46-1.31 (4H, m), 1.26-1.10 (2H, m), 1.06 (3H, s). APCI-MS m/z: 638 [MH$^+$].

Example 41

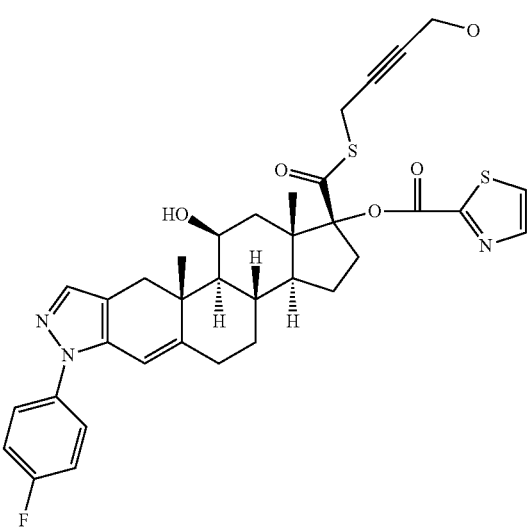

(1R,3aS,3bS,10aR,10bS,11S,12aS)-7-(4-Fluorophe-
nyl)-11-hydroxy-{[(4-hydroxy-but-2-yn-1-yl)thio]
carbonyl}-10a,12a-dimethyl-1,2,3,3a,3b,4,5,7,10,
10a,10b,11,12,12a-tetradecahydrocyclopenta[5,6]
naphtho[1,2-f]indazol-1-yl 1,3-thiazole-2-
carboxylate The compound was prepared according to the procedure in Example 11, starting from intermediate 12 and 4-Chlorobut-2-yn-1-ol.

$^1$H NMR (400 MHz, CDCl$_3$) δ 8.09 (1H, d), 7.68 (1H, d), 7.47 (2H, m), 7.44 (1H, s), 7.16 (2H, t), 6.08 (1H, s), 4.65 (1H, bs), 4.25 (2H, bs), 3.70 (2H, q), 3.17-3.00 (2H, m), 2.78 (1H, d), 2.52 (1H, t), 2.38-2.25 (2H, m), 2.24-2.11 (2H, m), 2.11-2.03 (1H, m), 2.03-1.92 (2H, m), 1.93-1.74 (2H, m), 1.61-1.47 (1H, m), 1.41-1.28 (5H, m), 1.22-1.11 (1H, m), 1.08 (3H, s). APCI-MS m/z: 662 [MH$^+$].

Example 42

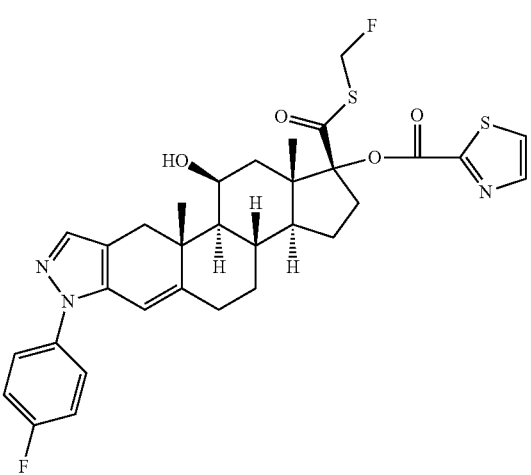

143

(1R,3aS,3bS,10aR,10bS,11S,12aS)-1-{[(Fluoromethyl)thio]carbonyl}-7-(4-fluoro-phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 1,3-thiazole-2-carboxylate The compound was prepared according to the procedure in Example 11, starting from intermediate 12 and Bromofluoromethane.

$^1$H NMR (400 MHz, CDCl$_3$) δ 8.09 (1H, d), 7.68 (1H, d), 7.47 (2H, m), 7.44 (1H, s), 7.17 (2H, t), 6.08 (1H, s), 6.06-5.89 (2H, m), 5.79-5.61 (1H, m), 4.66 (1H, bs), 3.12 (1H, m), 3.05 (1H, d), 2.78 (1H, d), 2.52 (1H, t), 2.40-2.26 (2H, m), 2.26-2.15 (1H, m), 2.15-2.03 (2H, m), 2.03-1.93 (1H, m), 1.93-1.77 (2H, m), 1.60-1.48 (1H, m), 1.39 (1H, m), 1.35 (3H, s), 1.21-1.11 (2H, m), 1.08 (3H, s). APCI-MS m/z: 626 [MH$^+$].

Example 43

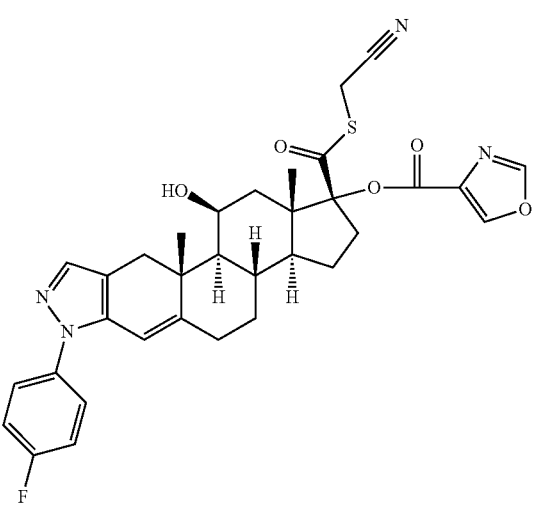

(1R,3aS,3bS,10aR,10bS,11S,12aS)-1-{[(Cyanomethyl)thio]carbonyl}-7-(4-fluoro-phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 1,3-oxazole-4-carboxylate The compound was prepared according to the procedure in Example 11, starting from intermediate 13 and 2-Bromoacetonitrile.

$^1$H NMR (400 MHz, CDCl$_3$) δ 8.32 (1H, d), 7.96 (1H, d), 7.47 (2H, m), 7.44 (1H, s), 7.17 (2H, t), 6.08 (1H, s), 4.64 (1H, bs), 3.80 (1H, d, AB), 3.57 (1H, d, AB), 3.14-2.99 (2H, m), 2.77 (1H, d), 2.53 (1H, t), 2.35-2.22 (2H, m), 2.22-2.02 (3H, m), 2.02-1.92 (1H, m), 1.92-1.81 (1H, m), 1.81-1.71 (1H, m), 1.60-1.48 (1H, m), 1.36 (1H, m), 1.34 (3H, s), 1.21-1.11 (2H, m), 1.07 (3H, s). APCI-MS m/z: 617 [MH$^+$].

144

Example 44

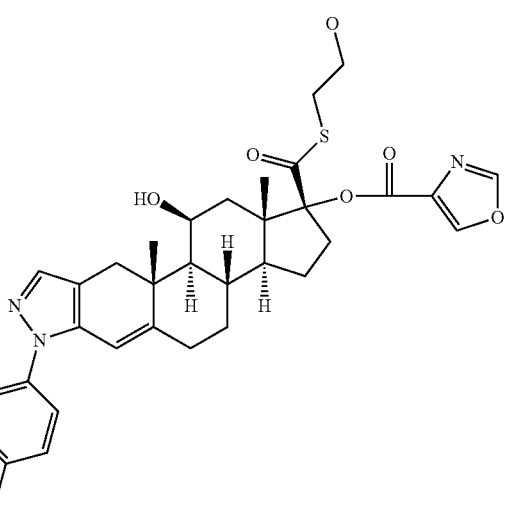

(1R,3aS,3bS,10aR,10bS,11S,12aS)-7-(4-Fluorophenyl)-11-hydroxy-1-{[(2-hydroxy-ethyl)thio]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl 1,3-oxazole-4-carboxylate The compound was prepared according to the procedure in Example 11, starting from intermediate 13 and 2-Bromoethanol.

$^1$H NMR (400 MHz, CDCl$_3$) δ 8.29 (1H, d), 7.96 (1H, d), 7.47 (2H, m), 7.44 (1H, s), 7.17 (2H, t), 6.08 (1H, s), 4.63 (1H, bs), 3.77 (2H, t), 3.24-3.15 (1H, m), 3.15-2.98 (3H, m), 2.77 (1H, d), 2.52 (1H, t), 2.34-2.22 (2H, m), 2.18-2.02 (3H, m), 2.02-1.92 (1H, m), 1.92-1.71 (3H, m), 1.55-1.45 (1H, m), 1.36 (1H, m), 1.34 (3H, s), 1.22-1.08 (2H, m), 1.04 (3H, s). APCI-MS m/z: 622 [MH$^+$].

Example 45

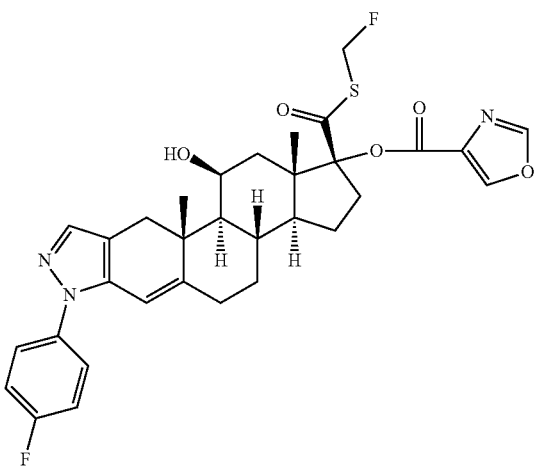

(1R,3aS,3bS,10aR,10bS,11S,12aS)-1-{[(Fluoromethyl)thio]carbonyl}-7-(4-fluoro-phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 1,3-oxazole-4-carboxylate The compound was prepared according to the procedure in Example 11, starting from intermediate 13 and Bromofluoromethane.

¹H NMR (400 MHz, CDCl₃) δ 8.31 (1H, d), 7.96 (1H, d), 7.47 (2H, m), 7.44 (1H, s), 7.17 (2H, t), 6.08 (1H, s), 6.05-5.62 (2H, m), 4.63 (1H, bs), 3.11 (1H, m), 3.03 (1H, d), 2.77 (1H, d), 2.53 (1H, t), 2.34-2.25 (2H, m), 2.21-2.03 (3H, m), 2.02-1.92 (1H, m), 1.92-1.71 (2H, m), 1.55-1.45 (1H, m), 1.37 (1H, m), 1.34 (3H, s), 1.22-1.10 (2H, m), 1.07 (3H, s). APCI-MS m/z: 610 [MH⁺].

Example 46

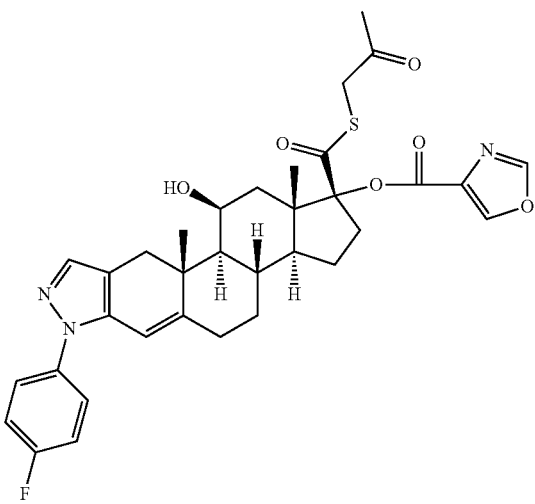

(1R,3aS,3bS,10aR,10bS,11S,12aS)-7-(4-Fluorophenyl)-11-hydroxy-10a,12a-dimethyl-1-{[(2-oxopropyl)thio]carbonyl}-1,2,3,3a,3b,4,5,7,10,10a,10b,11,12,12a-tetradecahydropcyclopenta[5,6]naphtho[1,2-f]indazol-1-yl 1,3-oxazole-4-carboxylate The compound was prepared according to the procedure in Example 11, starting from intermediate 13 and 1-Chloropropan-2-one.

¹H NMR (400 MHz, CDCl₃) δ 8.30 (1H, d), 7.95 (1H, d), 7.47 (2H, m), 7.44 (1H, s), 7.17 (2H, t), 6.08 (1H, s), 4.64 (1H, bs), 3.82 (1H, d, AB), 3.67 (1H, d, AB), 3.13-2.99 (2H, m), 2.77 (1H, d), 2.53 (1H, t), 2.34-2.24 (5H, m), 2.22-2.02 (3H, m), 2.02-1.92 (1H, m), 1.92-1.70 (2H, m), 1.55-1.45 (1H, m), 1.36 (1H, m), 1.34 (3H, s), 1.20-1.08 (2H, m), 1.04 (3H, s). APCI-MS m/z: 634 [MH⁺].

Example 47

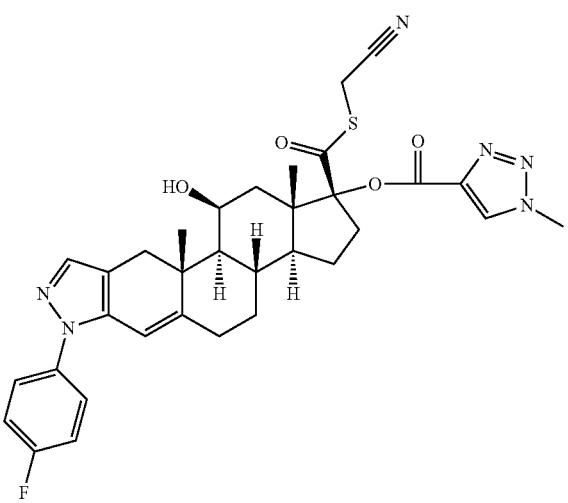

(1R,3aS,3bS,10aR,10bS,11S,12aS)-1-{[(Cyanomethyl)thio]carbonyl}-7-(4-fluoro-phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 1-methyl-1H-1,2,3-triazole-4-carboxylate The compound was prepared according to the procedure in Example 11, starting from intermediate 14 and 2-Bromoacetonitrile.

¹H NMR (400 MHz, CDCl₃) δ 8.10 (1H, d), 7.47 (2H, m), 7.44 (1H, s), 7.17 (2H, t), 6.07 (1H, s), 4.64 (1H, bs), 4.20 (3H, s), 3.78 (1H, d, AB), 3.58 (1H, d, AB), 3.14-2.99 (2H, m), 2.77 (1H, d), 2.52 (1H, t), 2.40 (1H, m), 2.29 (1H, m), 2.22-2.11 (1H, m), 2.11-2.01 (2H, m), 2.02-1.92 (1H, m), 1.92-1.79 (2H, m), 1.55-1.48 (1H, m), 1.40 (1H, m), 1.34 (3H, s), 1.20-1.10 (2H, m), 1.07 (3H, s). APCI-MS m/z: 631 [MH⁺].

Example 48

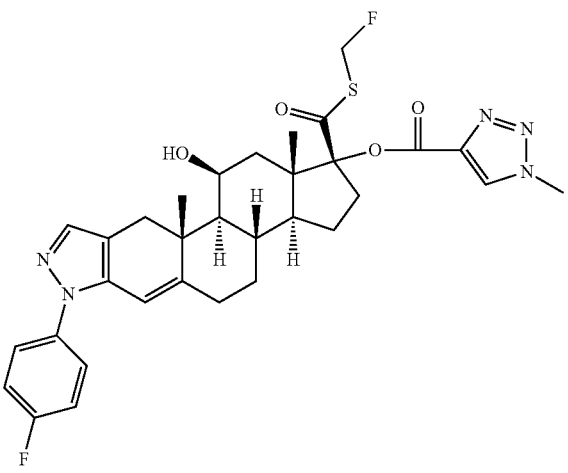

(1R,3aS,3bS,10aR,10bS,11S,12aS)-1-{[(Fluorom-
ethyl)thio]carbonyl}-7-(4-fluoro-phenyl)-11-hy-
droxy-10a,12a-dimethyl-1,2,3,3a,3b,4,5,7,10,10a,
10b,11,12,12a-tetradecahydrocyclopenta[5,6]
naphtho[1,2-f]indazol-1-yl 1-methyl-1H-1,2,3-
triazole-4-carboxylate The compound was prepared according to the procedure in Example 11, starting from intermediate 14 and Bromofluoromethane.

$^1$H NMR (400 MHz, CDCl$_3$) δ 8.09 (1H, d), 7.47 (2H, m), 7.44 (1H, s), 7.17 (2H, t), 6.07 (1H, s), 6.04-5.63 (2H, m), 4.64 (1H, bs), 4.18 (3H, s), 3.11 (1H, m), 3.03 (1H, d), 2.78 (1H, d), 2.52 (1H, t), 2.42 (1H, m), 2.29 (1H, m), 2.21-2.02 (3H, m), 2.01-1.91 (1H, m), 1.91-1.80 (2H, m), 1.55-1.48 (1H, m), 1.40 (1H, m), 1.34 (3H, s), 1.22-1.10 (2H, m), 1.07 (3H, s). APCI-MS m/z: 624 [MH$^+$].

Example 49

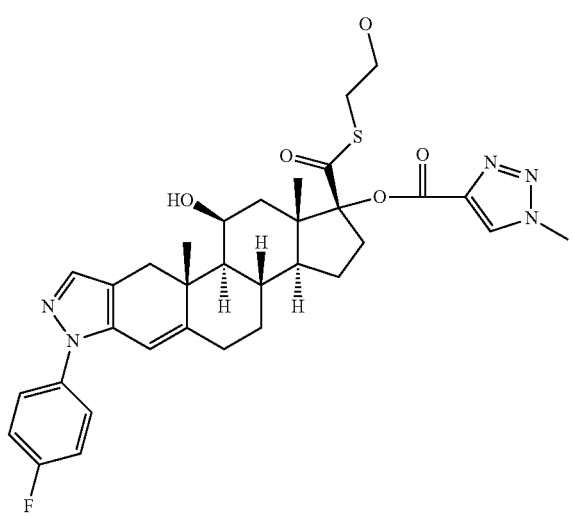

(1R,3aS,3bS,10aR,10bS,11S,12aS)-7-(4-Fluorophe-
nyl)-11-hydroxy-1-{[(2-hydroxy-ethyl)thio]carbo-
nyl}-10a,12a-dimethyl-1,2,3,3a,3b,4,5,7,10,10a,10b,
11,12,12a-tetradecahydrocyclopenta[5,6]naphtho[1,
2-f]indazol-1-yl 1-methyl-1H-1,2,3-triazole-4-
carboxylate The compound was prepared according to the procedure in Example 11, starting from intermediate 14 and 2-Bromoethanol.

$^1$H NMR (400 MHz, CDCl$_3$) δ 8.08 (1H, d), 7.47 (2H, m), 7.44 (1H, s), 7.16 (2H, t), 6.07 (1H, s), 4.64 (1H, bs), 4.18 (3H, s), 3.77 (2H, q), 3.26-3.15 (1H, m), 3.14-2.99 (3H, m), 2.78 (1H, d), 2.51 (1H, t), 2.41 (1H, m), 2.29 (1H, m), 2.18-2.00 (3H, m), 2.00-1.79 (4H, m), 1.55-1.45 (1H, m), 1.40 (1H, m), 1.34 (3H, s), 1.20-1.08 (2H, m), 1.04 (3H, s). APCI-MS m/z: 636 [MH$^+$].

Example 50

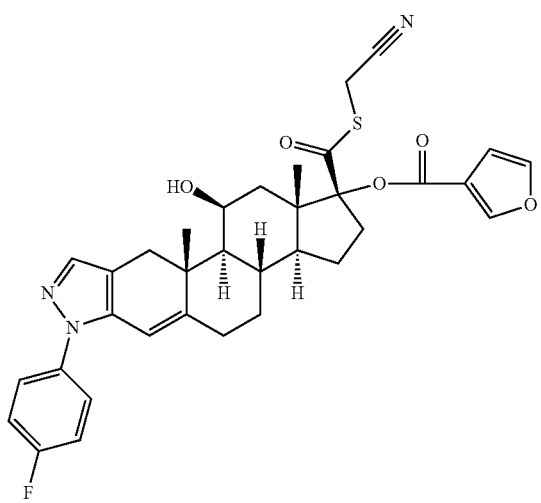

(1R,3aS,3bS,10aR,10bS,11S,12aS)-1-{[(Cyanom-
ethyl)thio]carbonyl}-7-(4-fluoro-phenyl)-11-hy-
droxy-10a,12a-dimethyl-1,2,3,3a,3b,4,5,7,10,10a,
10b,11,12,12a-tetradecahydrocyclopenta[5,6]
naphtho[1,2-f]indazol-1-yl furan-3-carboxylate The compound was prepared according to the procedure in Example 11, starting from intermediate 15 and 2-Bromoacetonitrile.

$^1$H NMR (400 MHz, CDCl$_3$) δ 8.05 (1H, d), 7.49-7.44 (4H, m), 7.17 (2H, t), 6.73 (1H, d), 6.09 (1H, s), 4.63 (1H, bs), 3.81 (1H, d, AB), 3.55 (1H, d, AB), 3.11-2.99 (2H, m), 2.77 (1H, d), 2.53 (1H, t), 2.30 (1H, m), 2.21-2.03 (4H, m), 2.01-1.93 (1H, m), 1.92-1.79 (1H, m), 1.77-1.66 (1H, m), 1.55-1.47 (1H, m), 1.35 (3H, s), 1.29 (1H, m), 1.20-1.08 (2H, m), 1.07 (3H, s). APCI-MS m/z: 616 [MH$^+$].

Example 51

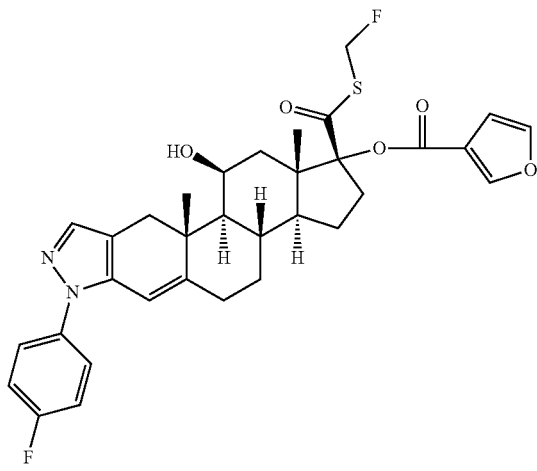

(1R,3aS,3bS,10aR,10bS,11S,12aS)-1-{[(Fluorom-ethyl)thio]carbonyl}-7-(4-fluoro-phenyl)-11-hy-droxy-10a,12a-dimethyl-1,2,3,3a,3b,4,5,7,10,10a,10b,11,12,12a-tetradecahydrocyclopenta[5,6]naphtho[1,2-f]indazol-1-yl furan-3-carboxylate The compound was prepared according to the procedure in Example 11, starting from intermediate 15 and Bromofluoromethane.

$^1$H NMR (400 MHz, CDCl$_3$) δ 8.05 (1H, d), 7.50-7.43 (4H, m), 7.17 (2H, t), 6.74 (1H, m), 6.09 (1H, s), 6.07-5.63 (1H, m), 4.63 (1H, bs), 3.13-3.01 (2H, m), 2.77 (1H, d), 2.53 (1H, t), 2.30 (1H, m), 2.23-2.04 (4H, m), 2.04-1.91 (1H, m), 1.90-1.80 (1H, m), 1.78-1.67 (1H, m), 1.55-1.45 (1H, m), 1.35 (3H, s), 1.30 (1H, m), 1.20-1.09 (2H, m), 1.06 (3H, s). APCI-MS m/z: 609 [MH$^+$].

Example 52

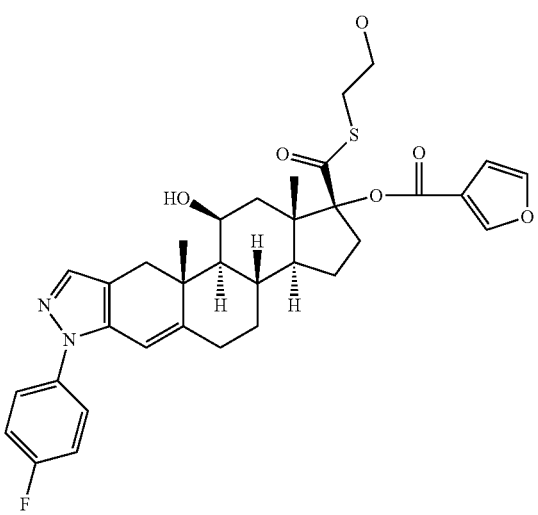

(1R,3aS,3bS,10aR,10bS,11S,12aS)-7-(4-Fluorophe-nyl)-11-hydroxy-1-{[(2-hydroxy-ethyl)thio]carbo-nyl}-10a,12a-dimethyl-1,2,3,3a,3b,4,5,7,10,10a,10b,11,12,12a-tetradecahydrocyclopenta[5,6]naphtho[1,2-f]indazol-1-yl furan-3-carboxylate The compound was prepared according to the procedure in Example 11, starting from intermediate 15 and 2-Bromoethanol.

$^1$H NMR (400 MHz, CDCl$_3$) δ 8.05 (1H, d), 7.50-7.42 (4H, m), 7.17 (2H, t), 6.74 (1H, m), 6.09 (1H, s), 4.63 (1H, bs), 3.78 (2H, m), 3.26-3.16 (1H, m), 3.14-3.00 (3H, m), 2.77 (1H, d), 2.53 (1H, t), 2.30 (1H, m), 2.19 (1H, m), 2.15-2.03 (3H, m), 2.03-1.94 (1H, m), 1.94-1.78 (2H, m), 1.78-1.67 (1H, m), 1.55-1.44 (1H, m), 1.35 (3H, s), 1.30 (1H, m), 1.21-1.05 (2H, m), 1.03 (3H, s). APCI-MS m/z: 621 [MH$^+$].

Example 53

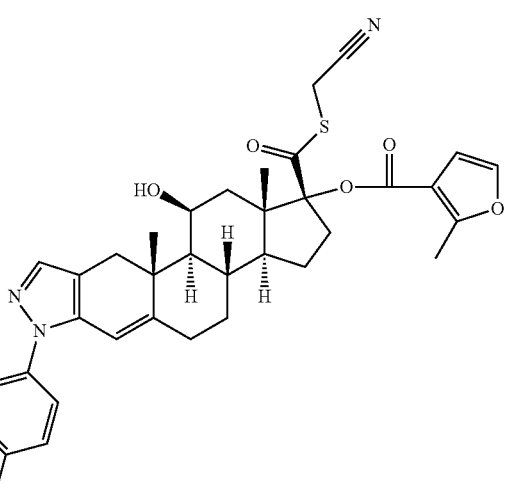

(1R,3aS,3bS,10aR,10bS,11S,12aS)-1-{[(Cyanom-ethyl)sulfanyl]carbonyl}-7-(4-fluoro-phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 2-methylfuran-3-carboxylate The compound was prepared according to the procedure in Example 11, starting from intermediate 16 and 2-Bromoacetonitrile.

$^1$H NMR (400 MHz, CDCl$_3$) δ 7.47 (2H, m), 7.44 (1H, s), 7.27 (1H, m), 7.17 (2H, t), 6.61 (1H, d), 6.09 (1H, s), 4.63 (1H, bs), 3.81 (1H, d, AB), 3.57 (1H, d, AB), 3.12-3.00 (2H, m), 2.75 (1H, d), 2.58 (3H, s), 2.53 (1H, t), 2.29 (1H, m), 2.20 (1H, m), 2.16-2.04 (3H, m), 2.04-1.93 (1H, m), 1.91-1.79 (1H, m), 1.79-1.68 (1H, m), 1.55-1.46 (1H, m), 1.35 (3H, s), 1.30-1.25 (1H, m), 1.20-1.08 (2H, m), 1.06 (3H, s). APCI-MS m/z: 630 [MH$^+$].

Example 54

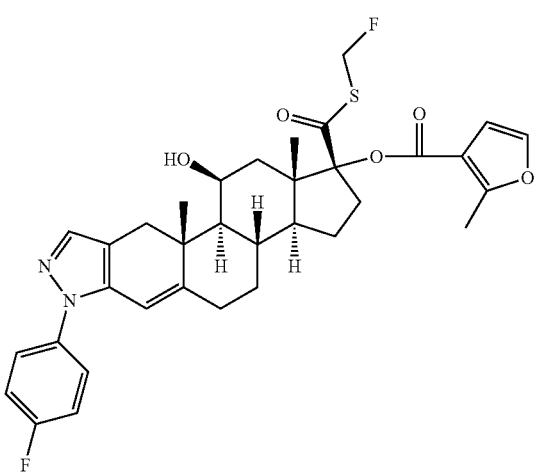

151

(1R,3aS,3bS,10aR,10bS,11S,12aS)-1-{[(Fluoromethyl)thio]carbonyl}-7-(4-fluorophenyl)-11-hydroxy-10a,12a-dimethyl-1,2,3,3a,3b,4,5,7,10,10a,10b,11,12,12a-tetradecahydropcyclopenta[5,6]naphtho[1,2-]indazol-1-yl 2-methylfuran-3-carboxylate The compound was prepared according to the procedure in Example 11, starting from intermediate 16 and Bromofluoromethane.

$^1$H NMR (400 MHz, CDCl$_3$) δ 7.46 (2H, m), 7.44 (1H, s), 7.26 (1H, m), 7.17 (2H, t), 6.62 (1H, d), 6.09 (1H, s), 6.09-5.63 (2H, m), 4.62 (1H, bs), 3.15-3.01 (2H, m), 2.75 (1H, d), 2.58 (3H, s), 2.53 (1H, t), 2.35-2.18 (2H, m), 2.18-2.03 (3H, m), 2.03-1.94 (1H, m), 1.90-1.80 (1H, m), 1.80-1.68 (1H, m), 1.56-1.44 (1H, m), 1.35 (3H, s), 1.28 (1H, m), 1.20-1.07 (2H, m), 1.06 (3H, s). APCI-MS m/z: 623 [MH$^+$].

Example 55

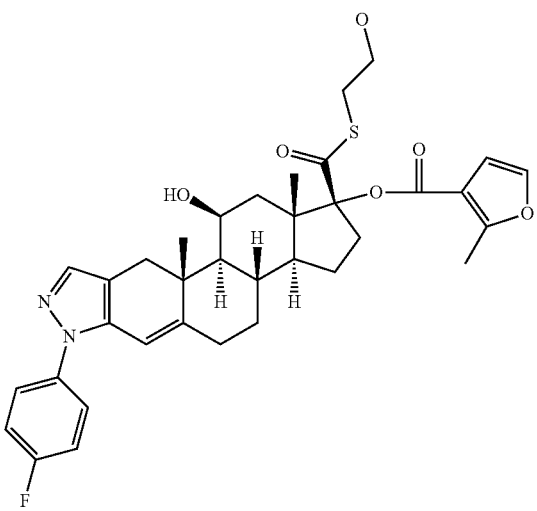

(1R,3aS,3bS,10aR,10bS,11S,12aS)-7-(4-Fluorophenyl)-11-hydroxy-1-{[(2-hydroxy-ethyl)thio]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl 2-methylfuran-3-carboxylate The compound was prepared according to the procedure in Example 11, starting from intermediate 16 and 2-Bromoethanol.

$^1$H NMR (400 MHz, CDCl$_3$) δ 7.47 (2H, m), 7.44 (1H, s), 7.26 (1H, m), 7.17 (2H, t), 6.62 (1H, d), 6.09 (1H, s), 4.62 (1H, bs), 3.78 (2H, bs), 3.28-3.19 (1H, m), 3.13-3.01 (3H, m), 2.75 (1H, d), 2.58 (3H, s), 2.53 (1H, t), 2.35-2.18 (2H, m), 2.16-1.91 (5H, m), 1.89-1.69 (2H, m), 1.56-1.44 (1H, m), 1.35 (3H, s), 1.28 (1H, m), 1.17-1.05 (2H, m), 1.03 (3H, s). APCI-MS m/z: 635 [MH$^+$].

Example 56

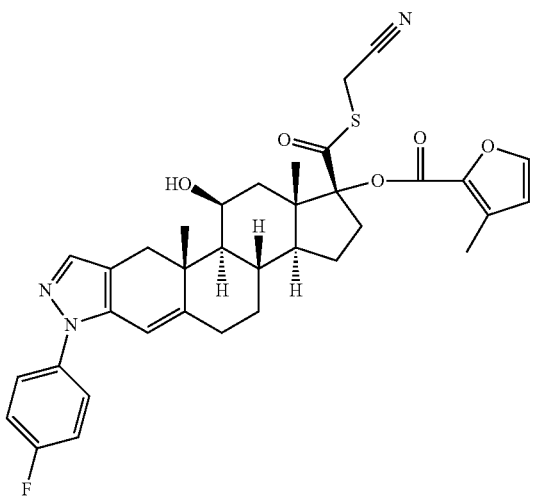

(1R,3aS,3bS,10aR,10bS,11S,12aS)-1-{[(Cyanomethyl)thio]carbonyl}-7-(4-fluorophenyl)-11-hydroxy-10a,12a-dimethyl-1,2,3,3a,3b,4,5,7,10,10a,10b,11,12,12a-tetradecahydropcyclopenta[5,6]naphtho[1,2-f]indazol-1-yl 3-methylfuran-2-carboxylate The compound was prepared according to the procedure in Example 11, starting from intermediate 17 and 2-Bromoacetonitrile.

$^1$H NMR (400 MHz, CDCl$_3$) δ 7.50-7.41 (4H, m), 7.17 (2H, t), 6.40 (1H, d), 6.09 (1H, s), 4.63 (1H, bs), 3.82 (1H, d, AB), 3.57 (1H, d, AB), 3.12-3.00 (2H, m), 2.76 (1H, d), 2.53 (1H, t), 2.37 (3H, s), 2.29 (1H, m), 2.22-1.93 (5H, m), 1.92-1.74 (2H, m), 1.57-1.47 (1H, m), 1.35 (3H, s), 1.32 (1H, m), 1.21-1.08 (2H, m), 1.07 (3H, s). APCI-MS m/z: 630 [MH$^+$].

Example 57

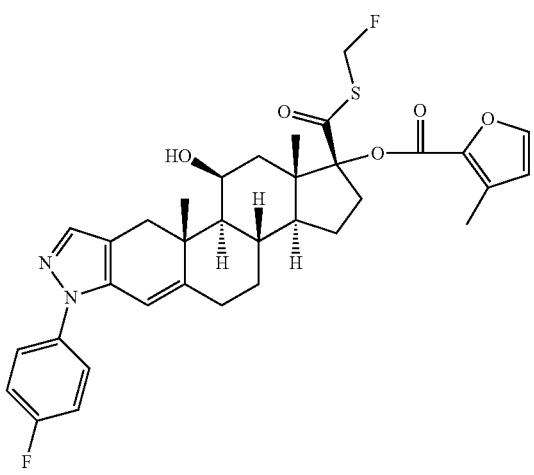

153

(1R,3aS,3bS,10aR,10bS,11S,12aS)-1-{[(Fluoromethyl)thio]carbonyl}-7-(4-fluorophenyl)-11-hydroxy-10a,12a-dimethyl-1,2,3,3a,3b,4,5,7,10,10a,10b,11,12,12a-tetradecaphydrocyclopenta[5,6]naphtho[1,2-f]indazol-1-yl 3-methylfuran-2-carboxylate The compound was prepared according to the procedure in Example 11, starting from intermediate 17 and Bromofluoromethane.

$^1$H NMR (400 MHz, CDCl$_3$) δ 7.50-7.41 (4H, m), 7.17 (2H, t), 6.39 (1H, d), 6.08 (1H, s), 6.08-5.62 (2H, m), 4.63 (1H, bs), 3.15-3.01 (2H, m), 2.77 (1H, d), 2.53 (1H, t), 2.37 (3H, s), 2.37-2.24 (2H, m), 2.18-2.03 (3H, m), 2.03-1.94 (1H, m), 1.90-1.78 (2H, m), 1.56-1.44 (1H, m), 1.35 (3H, s), 1.33 (1H, m), 1.20-1.07 (2H, m), 1.06 (3H, s). APCI-MS m/z: 623 [MH$^+$].

Example 58

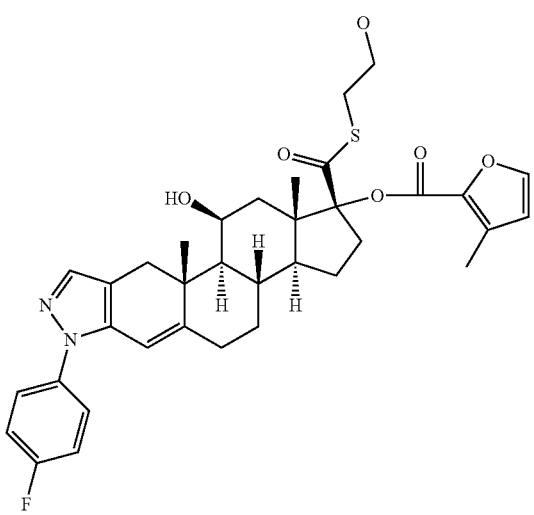

(1R,3aS,3bS,10aR,10bS,11S,12aS)-7-(4-Fluorophenyl)-11-hydroxy-1-{[(2-hydroxy-ethyl)thio]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl 3-methylfuran-2-carboxylate The compound was prepared according to the procedure in Example 11, starting from intermediate 17 and 2-Bromoethanol.

$^1$H NMR (400 MHz, CDCl$_3$) δ 7.50-7.42 (4H, m), 7.17 (2H, t), 6.39 (1H, d), 6.09 (1H, s), 4.62 (1H, bs), 3.78 (2H, bs), 3.28-3.19 (1H, m), 3.16-3.01 (3H, m), 2.77 (1H, d), 2.52 (1H, t), 2.37 (3H, s), 2.36-2.25 (2H, m), 2.15-1.92 (5H, m), 1.90-1.77 (2H, m), 1.55-1.44 (1H, m), 1.35 (3H, s), 1.33 (1H, m), 1.21-1.10 (2H, m), 1.04 (3H, s). APCI-MS m/z: 635 [MH$^+$].

Example 59

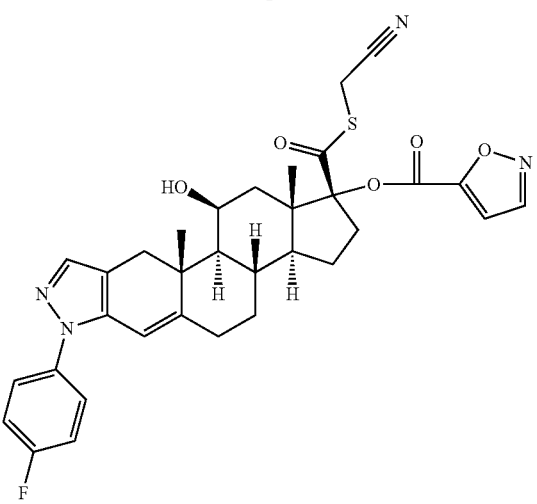

(1R,3aS,3bS,10aR,10bS,11S,12aS)-1-{[(Cyanomethyl)thio]carbonyl}-7-(4-fluorophenyl)-11-hydroxy-10a,12a-dimethyl-1,2,3,3a,3b,4,5,7,10,10a,10b,11,12,12a-tetradecahydropcyclopenta[5,6]naphtho[1,2-f]indazol-1-yl isoxazole-5-carboxylate The compound was prepared according to the procedure in Example 11, starting from intermediate 18 and 2-Bromoacetonitrile.

$^1$H NMR (400 MHz, CDCl$_3$) δ 8.42 (1H, d), 7.52-7.45 (3H, m), 7.18 (2H, t), 7.05 (1H, d), 6.09 (1H, s), 4.64 (1H, bs), 3.79 (1H, d, AB), 3.61 (1H, d, AB), 3.19-3.00 (2H, m), 2.78 (1H, d), 2.53 (1H, t), 2.30 (1H, m), 2.20-2.01 (3H, m), 2.00-1.92 (1H, m), 1.92-1.84 (1H, m), 1.84-1.73 (1H, m), 1.65-1.46 (2H, m), 1.40-1.30 (4H, m), 1.22-1.11 (2H, m), 1.09 (3H, s). APCI-MS m/z: 617 [MH$^+$].

Example 60

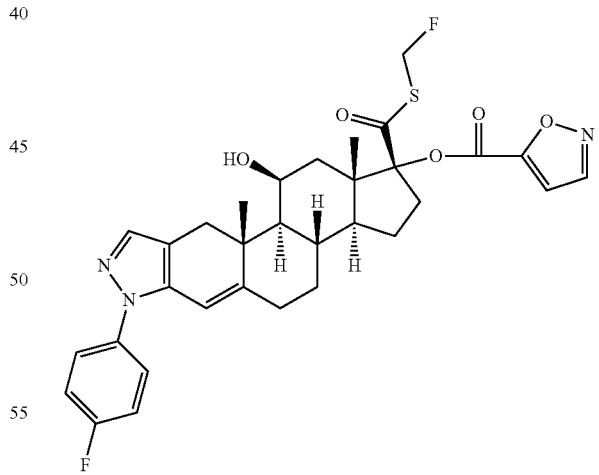

(1R,3aS,3bS,10aR,10bS,11S,12aS)-1-{[(Fluoromethyl)thio]carbonyl}-7-(4-fluorophenyl)-11-hydroxy-10a,12a-dimethyl-1,2,3,3a,3b,4,5,7,10,10a,10b,11,12,12a-tetradecahydropcyclopenta[5,6]naphtho[1,2]-indazol-1-yl isoxazole-5-carboxylate The compound was prepared according to the procedure in Example 11, starting from intermediate 18 and Bromofluoromethane.

¹H NMR (400 MHz, CDCl₃) δ 8.41 (1H, d), 7.51-7.44 (3H, m), 7.17 (2H, t), 7.03 (1H, d), 6.09 (1H, s), 6.03-5.65 (2H, m), 4.63 (1H, bs), 3.12 (1H, m), 3.04 (1H, d), 2.77 (1H, d), 2.52 (1H, t), 2.37-2.25 (2H, m), 2.19-2.02 (3H, m), 2.02-1.93 (1H, m), 1.93-1.75 (2H, m), 1.59-1.49 (1H, m), 1.36 (1H, m), 1.34 (3H, s), 1.22-1.10 (2H, m), 1.07 (3H, s). APCI-MS m/z: 610 [MH⁺].

Example 61

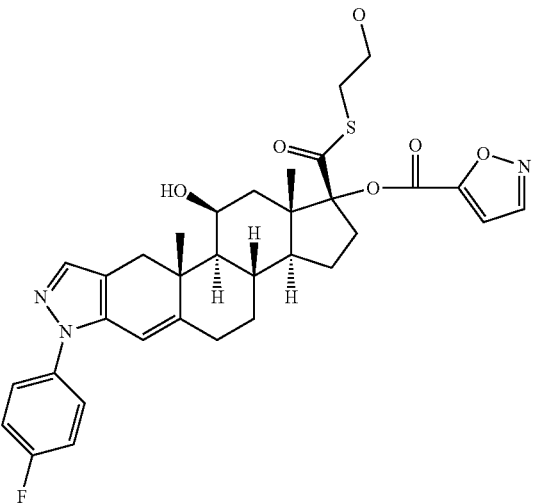

(1R,3aS,3bS,10aR,10bS,11S,12aS)-7-(4-Fluorophenyl)-11-hydroxy-1-{[(2-hydroxy-ethyl)thio]carbonyl}-10a,12a-dimethyl-1,2,3,3a,3b,4,5,7,10,10a,10b.1,12,12a-tetradecahydrocyclopenta[5,6]naphtho[1,2-f]indazol-1-yl isoxazole-5-carboxylate The compound was prepared according to the procedure in Example 11, starting from intermediate 18 and 2-Bromoethanol.

¹H NMR (400 MHz, CDCl₃) δ 8.40 (1H, d), 7.53-7.46 (3H, m), 7.18 (2H, t), 7.02 (1H, d), 6.09 (1H, s), 4.64 (1H, bs), 3.79 (2H, t), 3.25-3.01 (4H, m), 2.79 (1H, d), 2.53 (1H, t), 2.32 (1H, m), 2.18-1.93 (4H, m), 1.93-1.73 (2H, m), 1.70-1.46 (3H, m), 1.36 (1H, m), 1.35 (3H, s), 1.23-1.10 (2H, m), 1.05 (3H, s). APCI-MS m/z: 622 [MH⁺].

Example 62

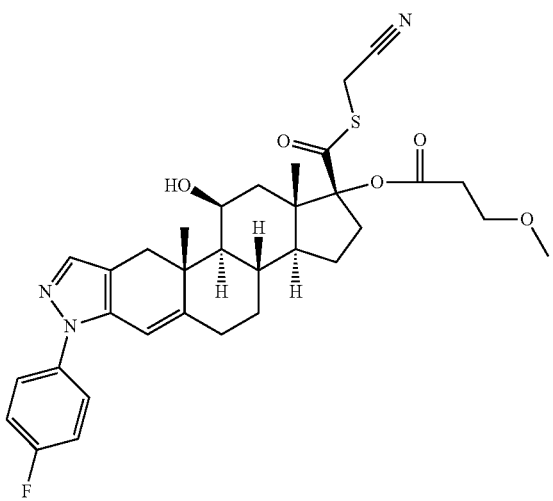

(1R,3aS,3bS,10aR,10bS,11S,12aS)-1-{[(Cyanomethyl)thio]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 3-methoxypropanoate The compound was prepared according to the procedure in Example 11, starting from intermediate 19 and 2-Bromoacetonitrile.

¹H NMR (400 MHz, CDCl₃) δ 7.47 (2H, m), 7.43 (1H, s), 7.17 (2H, t), 6.08 (1H, bs), 4.58 (1H, bs), 3.78 (1H, d, AB), 3.66 (2H, t), 3.58 (1H, d, AB), 3.35 (3H, s), 3.03 (1H, d), 2.97 (1H, m), 2.72 (1H, d), 2.61 (2H, dt), 2.51 (1H, t), 2.29 (1H, d), 2.11 (1H, m), 2.07-1.92 (4H, m), 1.89-1.76 (1H, m), 1.71-1.61 (1H, m), 1.55-1.43 (1H, m), 1.33 (3H, s), 1.26 (1H, m), 1.18-1.04 (2H, m), 1.01 (3H, s). APCI-MS m/z: 608 [MH⁺].

Example 63

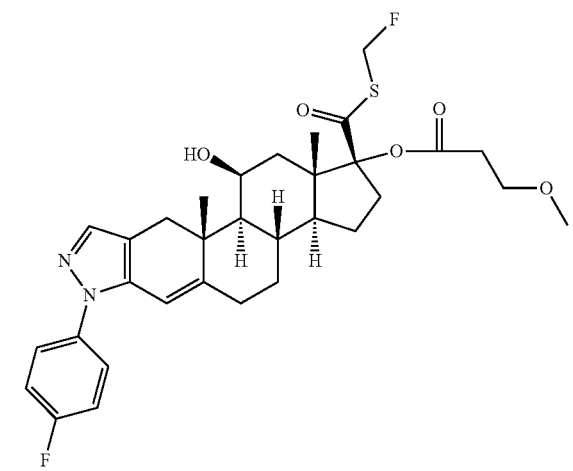

(1R,3aS,3bS,10aR,10bS,11S,12aS)-1-{[(Fluoromethyl)thio]carbonyl}-7-(4-fluorophenyl)-11-hydroxy-10a,12a-dimethyl-1,2,3,3a,3b,4,5,7,10,10a,10b,11,12,12a-tetradecahydropcyclopenta[5,6]naphtho[1,2-f]indazol-1-yl 3-methoxypropanoate The compound was prepared according to the procedure in Example 11, starting from intermediate 19 and Bromofluoromethane.

¹H NMR (400 MHz, CDCl₃) δ 7.47 (2H, m), 7.43 (1H, s), 7.17 (2H, t), 6.08 (1H, m), 6.04-5.64 (2H, m), 4.57 (1H, bs), 3.66 (2H, dt), 3.35 (3H, s), 3.06-2.94 (2H, m), 2.72 (1H, d), 2.62 (2H, dt), 2.51 (1H, t), 2.29 (1H, d), 2.14 (1H, m), 2.07-1.92 (4H, m), 1.88-1.76 (1H, m), 1.73-1.63 (1H, m), 1.52-1.41 (1H, m), 1.33 (3H, s), 1.27 (1H, d), 1.20-1.04 (2H, m), 1.00 (3H, s). APCI-MS m/z: 601 [MH⁺].

Example 64

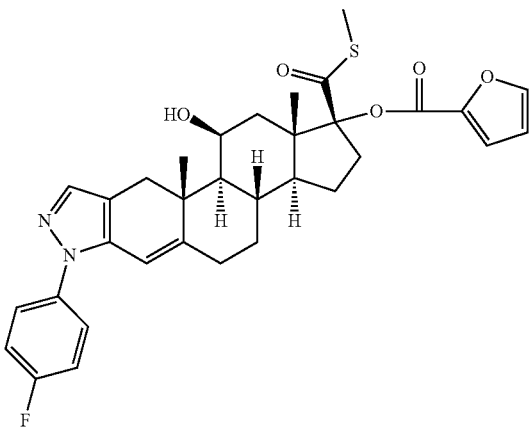

(1R,3aS,3bS,10aR,10bS,11S,12aS)-7-(4-Fluorophenyl)-11-hydroxy-10a,12a-dimethyl-1-[(methylthio)carbonyl]-1,2,3,3a,3b,4,5,7,10,10a,10b,11,12,12a-tetradecahydropcyclopenta[5,6]naphtho[1,2-f]indazol-1-yl furan-2-carboxylate The compound was prepared according to the procedure in Example 1, starting from intermediate 5 and Iodomethane.

$^1$H NMR (400 MHz, CDCl$_3$) δ 7.61 (1H, bs), 7.47 (2H, m), 7.44 (1H, s), 7.21 (1H, d), 7.17 (2H, t), 6.53 (1H, m), 6.08 (1H, m), 4.63 (1H, bs), 3.14-3.02 (2H, m), 2.78 (1H, d), 2.52 (1H, t), 2.33 (3H, s), 2.28 (2H, m), 2.20-1.93 (4H, m), 1.90-1.70 (2H, m), 1.55-1.45 (1H, m), 1.35 (3H, s), 1.34-1.25 (1H, m), 1.20-1.04 (2H, m), 1.02 (3H, s). APCI-MS m/z: 591 [MH$^+$].

Example 65

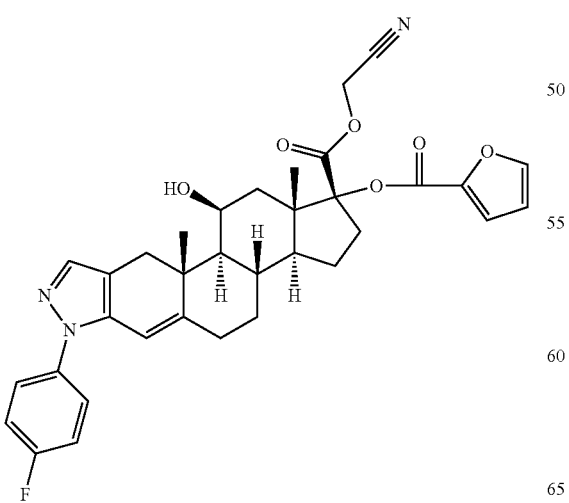

Cyanomethyl(1R,3aS,3bS,10aR,10bS,11S,12aS)-7-(4-fluorophenyl)-1-[(furan-2-ylcarbonyl)oxy]-11-hydroxy-10a,12a-dimethyl-1,2,3,3a,3b,4,5,7,10,10a,10b,11,12,12a-tetradecahydrocyclopenta[5,6]naphtho[1,2-f]indazole-1-carboxylate The compound was prepared according to the procedure in Example 9, starting from intermediate 20 and 2-Bromoacetonitrile.

$^1$H NMR (400 MHz, CDCl$_3$) δ 7.61 (1H, bs), 7.47 (2H, m), 7.45 (1H, s), 7.21 (1H, d), 7.17 (2H, t), 6.54 (1H, m), 6.09 (1H, m), 4.90 (1H, d, AB), 4.67 (1H, d, AB), 4.61 (1H, bs), 3.09-2.98 (2H, m), 2.78 (1H, d), 2.54 (1H, t), 2.36-2.19 (2H, m), 2.14-1.94 (3H, m), 1.92-1.76 (3H, m), 1.58-1.48 (1H, m), 1.36 (3H, s), 1.34-1.25 (1H, m), 1.23-1.13 (2H, m), 1.11 (3H, s). APCI-MS m/z: 600 [MH$^+$].

Example 66

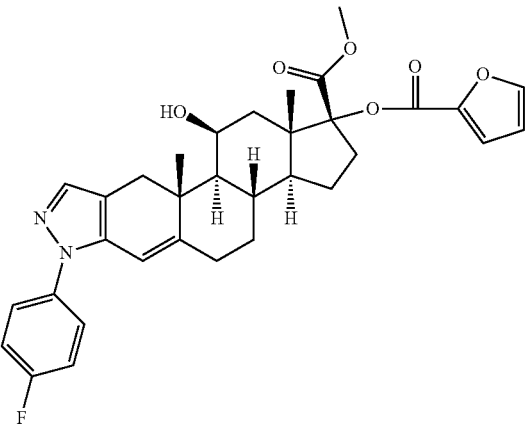

Methyl (1R,3aS,3bS,10aR,10bS,11S,12aS)-7-(4-fluorophenyl)-1-[(furan-2-yl-carbonyl)oxy]-11-hydroxy-10a,12a-dimethyl-1,2,3,3a,3b,4,5,7,10,10a,10b,11,12,12a-tetradecahydrocyclopenta[5,6]naphtho[1,2-f]indazole-1-carboxylate The compound was prepared according to the procedure in Example 9, starting from intermediate 20 and iodomethane.

$^1$H NMR (400 MHz, CDCl$_3$) δ 7.59 (1H, m), 7.47 (2H, m), 7.44 (1H, s), 7.20-7.14 (3H, d), 6.52 (1H, m), 6.09 (1H, s), 4.60 (1H, bs), 3.75 (3H, s), 3.11-3.00 (2H, m), 2.79 (1H, d), 2.53 (1H, t), 2.35-2.20 (2H, m), 2.12-1.92 (3H, m), 1.90-1.74 (3H, m), 1.56-1.46 (1H, m), 1.36 (3H, s), 1.34 (1H, m), 1.22-1.08 (2H, m), 1.06 (3H, s). APCI-MS m/z: 575 [MH$^+$].

Example 67

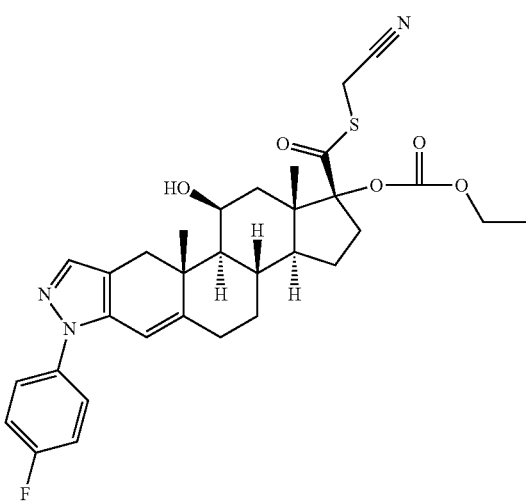

S-(Cyanomethyl)(1R,3aS,3bS,10aR,10bS,11S,12aS)-1-[(ethoxycarbonyl)oxy]-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazole-1-carbothioate The compound was prepared according to the procedure in Example 1, starting from intermediate 21 and 2-Bromoacetonitrile.

$^1$H NMR (400 MHz, CDCl$_3$) δ 7.47 (2H, m), 7.43 (1H, s), 7.16 (2H, t), 6.07 (1H, s), 4.56 (1H, bs), 4.21 (2H, m), 3.78 (1H, d, AB), 3.63 (1H, d, AB), 3.05-2.92 (2H, m), 2.69 (1H, d), 2.50 (1H, t), 2.29 (1H, d), 2.18-2.00 (3H, m), 2.00-1.91 (2H, m), 1.91-1.81 (1H, m), 1.77-1.67 (1H, m), 1.56-1.43 (1H, m), 1.33 (3H, t), 1.31 (3H, s), 1.29 (1H, m), 1.19-1.09 (2H, m), 1.01 (3H, s). APCI-MS m/z: 594 [MH$^+$].

Example 68

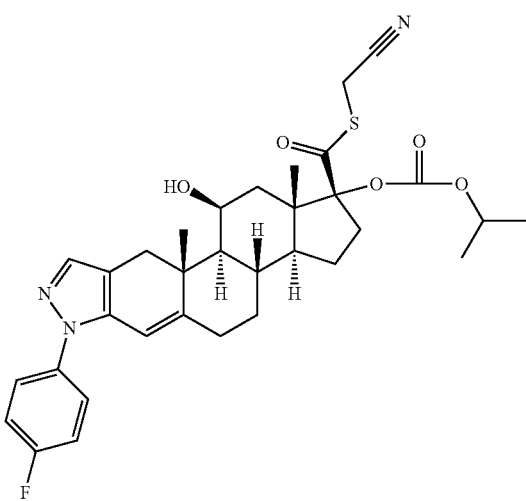

S-(Cyanomethyl)(1R,3aS,3bS,10aR,10bS,11S,12aS)-7-(4-fluorophenyl)-11-hydroxy-10a,12a-dimethyl-1-{[(1-methylethoxy)carbonyl]oxy}-1,2,3,3a,3b,4,5,7,10,10a,10b,11,12,12a-tetradecahydrocyclopenta[5,6]naphtho[1,2-f]indazole-1-carbothioate The compound was prepared according to the procedure in Example 1, starting from intermediate 22 and 2-Bromoacetonitrile.

$^1$H NMR (400 MHz, CDCl$_3$) δ 7.47 (2H, m), 7.43 (1H, s), 7.16 (2H, t), 6.07 (1H, s), 4.87 (1H, m), 4.55 (1H, bs), 3.78 (1H, d, AB), 3.63 (1H, d, AB), 3.03-2.92 (2H, m), 2.68 (1H, d), 2.50 (1H, t), 2.28 (1H, d), 2.14 (1H, m), 2.09-1.91 (4H, m), 1.91-1.81 (1H, m), 1.79-1.67 (1H, m), 1.56-1.43 (1H, m), 1.33-1.30 (9H, 3s), 1.29 (1H, m), 1.19-1.09 (2H, m), 1.00 (3H, s). APCI-MS m/z: 608 [MH$^+$].

Example 69

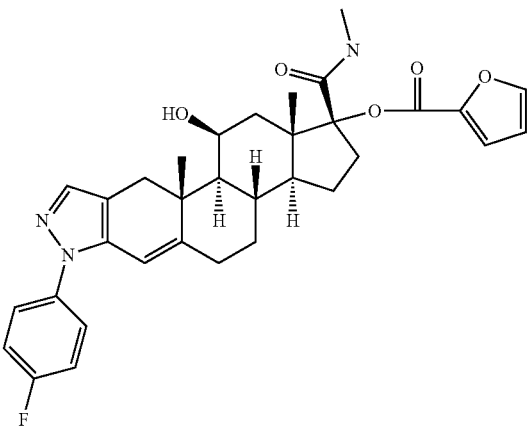

(1R,3aS,3bS,10aR,10bS,11S,12aS)-7-(4-Fluorophenyl)-11-hydroxy-10a,12a-dimethyl-1-(methylcarbamoyl)-1,2,3,3a,3b,4,5,7,10,10a,10b,11,12,12a-tetradecahydropcyclopenta[5,6]naphtho[1,2-f]indazol-1-yl furan-2-carboxylate In a 50 mL round-bottomed flask was dissolved the compound obtained in Example 7 (0.13 g, 0.21 mmol) in acetonitrile (2.5 mL) to give a yellow solution. 33% methanamine (2.5 ml, 18.59 mmol) in ethanol was added, and the obtained solution was allowed to stand in a sealed flask at room temperature, monitoring the reaction by LC-MS. After approximately 3 hours, the reaction was complete and all starting material was consumed giving two main products (P1 and P2). The volatiles were carefully removed in vacuo, leaving a yellow dry film. The material was purified on preparative HPLC, isolating the two products, which were freeze-dried to give 13 mg of P1 and 10 mg of P2 as white solids. P1 is described as Example 69, and P2 as Example 70.

$^1$H NMR (400 MHz, CDCl$_3$) δ 7.60 (1H, s), 7.47 (2H, m), 7.44 (1H, s), 7.20-7.14 (3H, m), 6.53 (1H, m), 6.09 (1H, s), 5.56 (1H, m), 4.61 (1H, bs), 3.11 (1H, m), 3.05 (1H, d), 2.85 (3H, d), 2.79 (1H, d), 2.52 (1H, t), 2.30 (1H, d), 2.23 (1H, m), 2.14-1.95 (3H, m), 1.88-1.71 (3H, m), 1.55-1.45 (1H, m), 1.35 (3H, s), 1.34 (1H, m), 1.19-1.09 (2H, m), 1.07 (3H, s). APCI-MS m/z: 574 [MH+].

Example 70

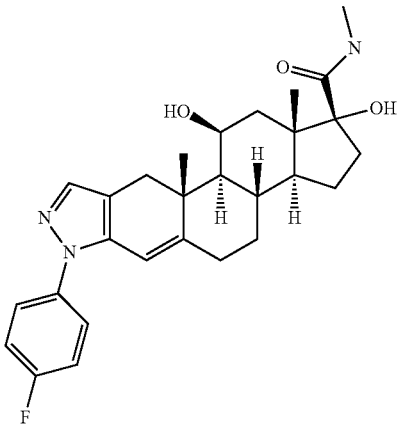

(1R,3aS,3bS,10aR,10bS,11S,12aS)-7-(4-Fluorophenyl)-1,11-dihydroxy-N,10a,12a-trimethyl-1,2,3,3a,3b,4,5,7,10,10a,10b,11,12,12a-tetradecahydrocyclopenta[5,6]naphtho[1,2-f]indazole-1-carboxamide The compound was obtained as P2 in Example 69.

$^1$H NMR (400 MHz, CDCl$_3$) δ 7.47 (2H, m), 7.41 (1H, s), 7.16 (2H, t), 6.38 (1H, bs), 6.07 (1H, s), 4.51 (1H, bs), 3.01 (1H, d), 2.87 (3H, d), 2.80 (1H, m), 2.70 (1H, d), 2.51 (1H, t), 2.28 (1H, d), 2.21 (1H, s), 2.05-1.93 (3H, m), 1.92-1.82 (1H, m), 1.77-1.69 (1H, m), 1.61 (2H, m), 1.57-1.45 (1H, m), 1.33 (3H, s), 1.24 (1H, m), 1.16-1.05 (2H, m), 1.05 (3H, s). APCI-MS m/z: 480 [MH+].

Example 71

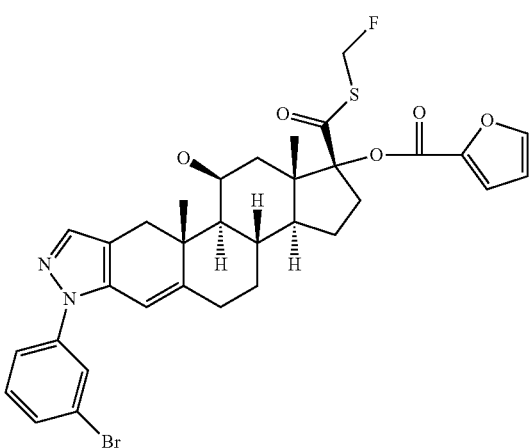

(1R,3aS,10aR,10bS,11S,12aS)-7-(3-Bromophenyl)-1-{[(fluoromethyl)thio]carbonyl}-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate The compound was prepared according to the procedure in Example 1, starting from intermediate 23 and Bromofluoromethane.

$^1$H NMR (400 MHz, CDCl$_3$) δ 7.71 (1H, t), 7.63 (1H, m), 7.50-7.43 (3H, m), 7.34 (1H, t), 7.24 (1H, d), 6.55 (1H, m), 6.15 (1H, bs), 6.07-5.60 (1H, m), 4.63 (1H, bs), 3.15-3.00 (2H, m), 2.78 (1H, d), 2.54 (1H, t), 2.39-2.23 (2H, m), 2.19-2.04 (3H, m), 2.04-1.93 (1H, m), 1.92-1.71 (2H, m), 1.57-1.47 (1H, m), 1.35 (3H, s), 1.34-1.25 (1H, m), 1.22-1.10 (2H, m), 1.06 (3H, s). APCI-MS m/z: 669 and 671 [MH+].

Example 72

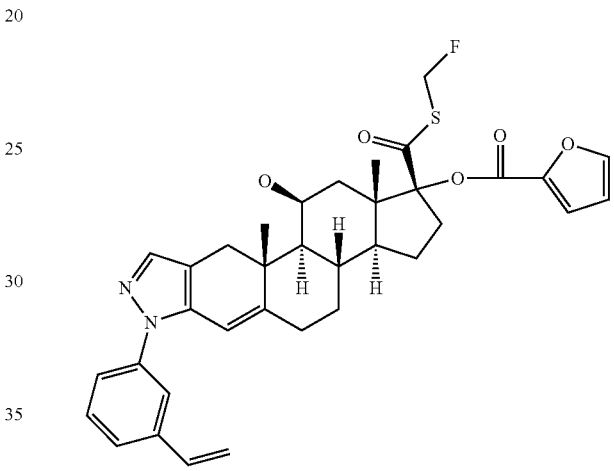

(1R,10aR,11S,12aS)-7-(3-Ethenylphenyl)-1-{[(fluoromethyl)thio]carbonyl}-11-hydroxy-10a,12a-dimethyl-1,2,3,3a,3b,4,5,7,10a,10b,11,12,12a-tetradecahydrocyclopenta[5,6]naphtho[1,2-f]indazol-1-yl furan-2-carboxylate In a 5 ml microwave vial was added the product obtained in Example 71 (0.025 g, 0.04 mmol) and vinyltributylstannane (0.023 mL, 0.08 mmol) in DME (4 mL) to give a colorless solution. The solution was degassed with nitrogen. Bis(tri-t-butylphosphine)palladium(0) (0.01 g, 0.02 mmol) was added, and the obtained mixture was degassed again and the sealed with a suitable lid. The mixture was heated in a Biotage synthesis microwave at 120° C. for 10 minutes, and was then allowed to cool. The solvent was removed in vacuo, and the residue was purified in silica gel (Heptane:EtOAc=3:1), obtaining 20 mg of a white solid which was further purified on a preparative HPLC column (acetonitrile/water). The product containing fractions were freeze-dried to give 11 mg (48%) of a white solid.

$^1$H NMR (400 MHz, CDCl$_3$) δ 7.63 (1H, s), 7.57 (1H, s), 7.46 (1H, s), 7.45-7.34 (3H, m), 7.24 (1H, d), 6.77 (1H, m), 6.55 (1H, bs), 6.16 (1H, bs), 6.07-5.90 (1H, m), 5.83 (1H, d), 5.78-5.60 (1H, m), 5.33 (1H, d), 4.64 (1H, bs), 3.15-3.00 (2H, m), 2.79 (1H, d), 2.53 (1H, t), 2.36-2.23 (2H, m), 2.21-2.04 (3H, m), 2.04-1.93 (1H, m), 1.93-1.72 (2H, m), 1.57-1.47 (1H, m), 1.35 (3H, s), 1.34 (1H, m), 1.22-1.10 (2H, m), 1.06 (3H, s). APCI-MS m/z: 617 [MH+].

Example 73

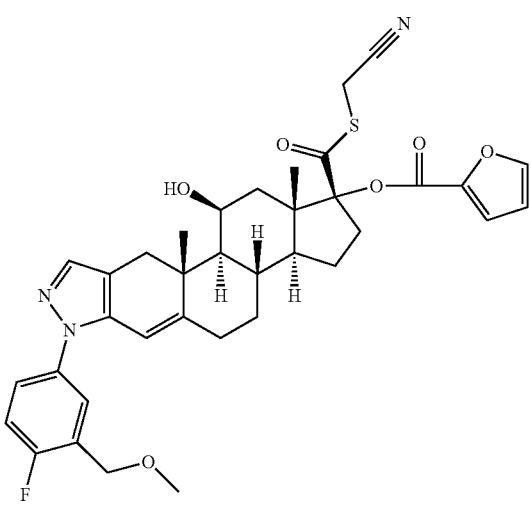

(1R,3aS,3bS,10aR,10bS,11S,12aS)-1-{[(Cyanomethyl)thio]carbonyl}-7-[4-fluoro-3-(methoxymethyl)phenyl]-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate The compound was prepared according to the procedure in Example 1, starting from intermediate 29 and 2-Bromoacetonitrile.

$^1$H NMR (400 MHz, CDCl$_3$) δ 7.64 (1H, s), 7.58 (1H, m), 7.45 (1H, s), 7.42-7.37 (1H, m), 7.24 (1H, d), 7.15 (1H, t), 6.56 (1H, m), 6.09 (1H, s), 4.64 (1H, bs), 4.58 (2H, s), 3.82 (1H, d, AB), 3.55 (1H, d, AB), 3.45 (3H, s), 3.12-3.00 (2H, m), 2.78 (1H, d), 2.52 (1H, t), 2.34-2.21 (2H, m), 2.20-2.02 (3H, m), 2.02-1.93 (1H, m), 1.93-1.81 (1H, m), 1.81-1.70 (1H, m), 1.57-1.47 (1H, m), 1.35 (3H, s), 1.33 (1H, m), 1.20-1.09 (2H, m), 1.07 (3H, s). APCI-MS m/z: 660 [MH$^+$].

Example 74

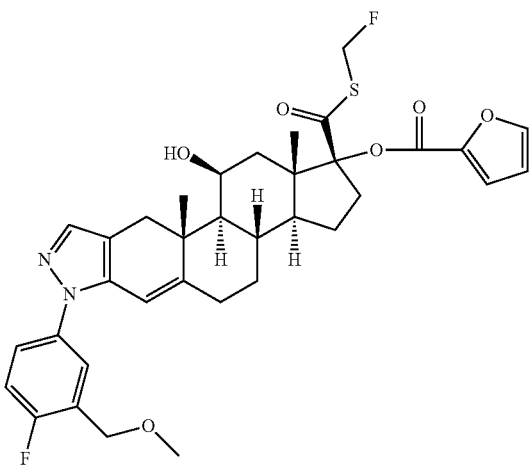

(1R,3aS,3bS,10aR,10bS,11S,12aS)-7-[4-Fluoro-3-(methoxymethyl)phenyl]-1-{[(fluoromethyl)thio]carbonyl}-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate The compound was prepared according to the procedure in Example 1, starting from intermediate 29 and Bromofluoromethane.

$^1$H NMR (400 MHz, CDCl$_3$) δ 7.63 (1H, s), 7.58 (1H, m), 7.45 (1H, s), 7.42-7.37 (1H, m), 7.24 (1H, d), 7.15 (1H, t), 6.55 (1H, m), 6.09 (1H, s), 6.07-5.60 (2H, m), 4.64 (1H, bs), 4.58 (2H, s), 3.45 (3H, s), 3.14-3.00 (2H, m), 2.78 (1H, d), 2.52 (1H, t), 2.34-2.24 (2H, m), 2.20-2.04 (3H, m), 2.04-1.92 (1H, m), 1.92-1.72 (2H, m), 1.57-1.47 (1H, m), 1.35 (3H, s), 1.33 (1H, m), 1.20-1.09 (2H, m), 1.06 (3H, s). APCI-MS m/z: 653 [MH$^+$].

Example 75

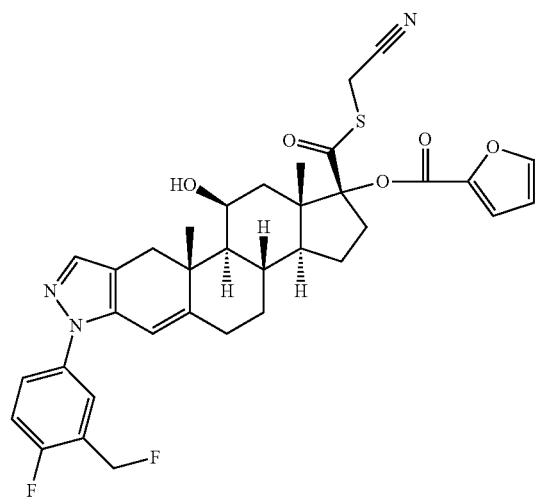

(1R,3aS,3bS,10aR,10bS,11S,12aS)-1-{[(Cyanomethyl)thio]carbonyl}-7-[4-fluoro-3-(fluoromethyl)phenyl]-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate The compound was prepared according to the procedure in Example 1, starting from intermediate 31 and 2-Bromoacetonitrile.

$^1$H NMR (400 MHz, CDCl$_3$) δ 7.63 (1H, s), 7.60 (1H, m), 7.51-7.43 (2H, m), 7.24 (1H, d), 7.20 (1H, t), 6.56 (1H, m), 6.09 (1H, s), 5.59 (1H, s), 5.47 (1H, s), 4.64 (1H, bs), 3.82 (1H, d, AB), 3.55 (1H, d, AB), 3.12-3.00 (2H, m), 2.78 (1H, d), 2.53 (1H, t), 2.34-2.22 (2H, m), 2.20-2.04 (3H, m), 2.03-1.93 (1H, m), 1.92-1.81 (1H, m), 1.81-1.71 (1H, m), 1.57-1.47 (1H, m), 1.35 (3H, s), 1.33 (1H, m), 1.21-1.10 (2H, m), 1.08 (3H, s). APCI-MS m/z: 648 [MH$^+$].

Example 76

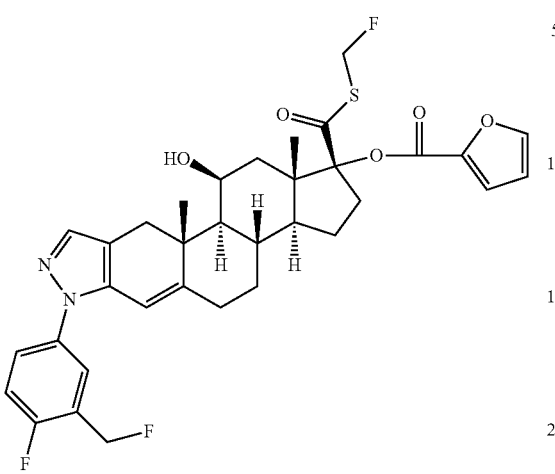

(1R,3aS,3bS,10aR,10bS,11S,12aS)-7-[4-Fluoro-3-(fluoromethyl)phenyl]-1-{[(fluoromethyl)thio]carbonyl}-11-hydroxy-10a,12a-dimethyl-1,2,3,3a,3b,4,5,7,10,10a,10b,11,12,12a-tetradecahydrocyclopenta[5,6]naphtho[1,2]-indazol-1-yl furan-2-carboxylate The compound was prepared according to the procedure in Example 1, starting from intermediate 31 and Bromofluoromethane.

$^1$H NMR (400 MHz, CDCl$_3$) δ 7.63 (1H, s), 7.60 (1H, m), 7.51-7.44 (2H, m), 7.24 (1H, d), 7.20 (1H, t), 6.56 (1H, m), 6.09 (1H, s), 6.07-5.60 (2H, m), 5.58 (1H, s), 5.46 (1H, s), 4.63 (1H, bs), 3.14-3.01 (2H, m), 2.78 (1H, d), 2.53 (1H, t), 2.35-2.25 (2H, m), 2.20-2.04 (3H, m), 2.03-1.93 (1H, m), 1.92-1.71 (2H, m), 1.57-1.47 (1H, m), 1.35 (3H, s), 1.33 (1H, m), 1.21-1.10 (2H, m), 1.06 (3H, s). APCI-MS m/z: 641 [MH$^+$].

Example 77

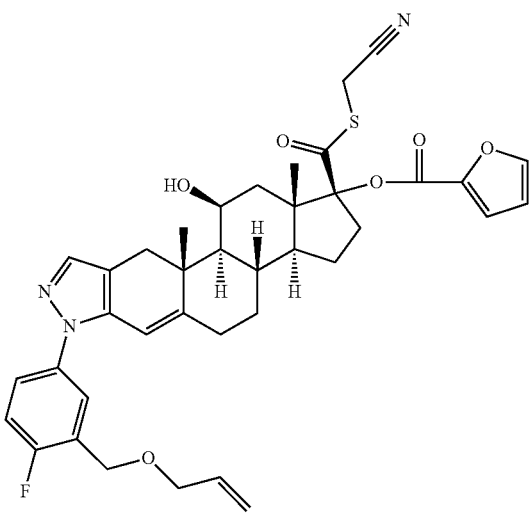

(1R,3aS,3bS,10aR,10bS,11S,12aS)-1-{[(Cyanomethyl)thio]carbonyl}-7-{4-fluoro-3-[(prop-2-en-1-yloxy)methyl]phenyl}-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate The compound was prepared according to the procedure in Example 1, starting from intermediate 33 and 2-Bromoacetonitrile.

$^1$H NMR (400 MHz, CDCl$_3$) δ 7.63 (1H, s), 7.60 (1H, m), 7.44 (1H, s), 7.43-7.36 (1H, m), 7.25 (1H, d), 7.15 (1H, t), 6.56 (1H, m), 6.09 (1H, s), 6.02-5.91 (1H, m), 5.34 (1H, m), 5.23 (1H, m), 4.64 (3H, bs), 4.10 (2H, d), 3.82 (1H, d, AB), 3.55 (1H, d, AB), 3.11-3.00 (2H, m), 2.78 (1H, d), 2.53 (1H, t), 2.36-2.21 (2H, m), 2.20-2.02 (3H, m), 2.03-1.93 (1H, m), 1.92-1.71 (2H, m), 1.56-1.47 (1H, m), 1.35 (3H, s), 1.33-1.24 (1H, m), 1.21-1.10 (2H, m), 1.07 (3H, s). APCI-MS m/z: 686 [MH$^+$].

Example 78

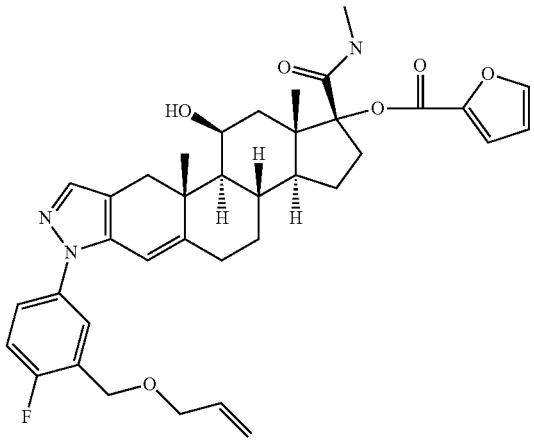

(1R,3aS,3bS,10aR,10bS,11S,12aS)-7-{4-Fluoro-3-[(prop-2-en-1-yloxy)methyl]phenyl}-11-hydroxy-10a,12a-dimethyl-1-(methylcarbamoyl)-1,2,3,3a,3b,4,5,7,10,10a,10b,11,12,12a-tetradecahydrocyclopenta[5,6]naphtho[1,2-f]indazol-1-yl furan-2-carboxylate In a 100 mL round-bottomed flask was dissolved the product obtained in Example 77 (75 mg, 0.11 mmol) in acetonitrile (2.5 mL) to give a yellow solution. 33% methanamine (2.5 mL, 20.19 mmol) in ethanol was added. The mixture was stirred in a closed flask for 3 hours, monitoring the reaction by LC-MS. When almost all of the starting material had been consumed, the volatiles were removed in vacuo. The crude mixture was purified on preparative HPLC (acetonitrile/water), and 15 mg (25%) was obtained of the desired product as a white solid after freeze-drying the pure fractions.

$^1$H NMR (400 MHz, CDCl$_3$) δ 7.63-7.58 (2H, m), 7.44 (1H, s), 7.42-7.36 (1H, m), 7.19 (1H, d), 7.14 (1H, t), 6.53 (1H, m), 6.09 (1H, s), 6.02-5.90 (1H, m), 5.56 (1H, m), 5.34 (1H, m), 5.23 (1H, m), 4.64 (2H, bs), 4.61 (1H, bs), 4.10 (2H, d), 3.16-3.00 (2H, m), 2.85 (3H, d), 2.79 (1H, d), 2.53 (1H, t), 2.34-2.19 (2H, m), 2.16-1.94 (3H, m), 1.89-1.71 (3H, m), 1.54-1.44 (1H, m), 1.36 (3H, s), 1.33 (1H, m), 1.21-1.10 (2H, m), 1.07 (3H, s). APCI-MS m/z: 644 [MH$^+$].

Example 79

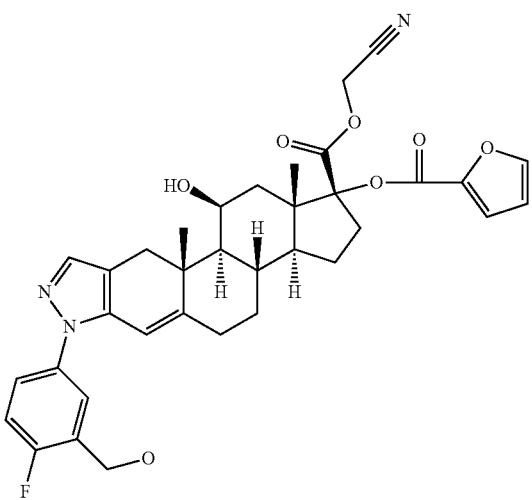

Cyanomethyl(1R,3aS,3bS,10aR,10bS,11S,12aS)-7-
[4-fluoro-3-(hydroxymethyl)phenyl]-1-[(furan-2-
ylcarbonyl)oxy]-11-hydroxy-10a,12a-dimethyl-1,2,
3,3a,3b,4,5,7,10,10a,10b,11,12,12a-
tetradecahydrocyclopenta[5,6]naphtho[1,2-f]
indazole-1-carboxylate The compound was prepared according to the procedure in Example 9, starting from intermediate 35 and 2-Bromoacetonitrile.

$^1$H NMR (400 MHz, CDCl$_3$) δ 7.64-7.59 (2H, m), 7.44 (1H, s), 7.42-7.36 (1H, m), 7.21 (1H, d), 7.16 (1H, t), 6.54 (1H, m), 6.10 (1H, s), 4.90 (1H, d, AB), 4.83 (2H, d), 4.67 (1H, d, AB), 4.61 (1H, bs), 3.09-2.98 (2H, m), 2.78 (1H, d), 2.53 (1H, t), 2.36-2.19 (2H, m), 2.14-1.95 (3H, m), 1.90 (1H, t), 1.89-1.76 (3H, m), 1.60-1.50 (1H, m), 1.35 (3H, s), 1.33 (1H, m), 1.22-1.13 (2H, m), 1.11 (3H, s). APCI-MS m/z: 630 [MH$^+$].

Example 80

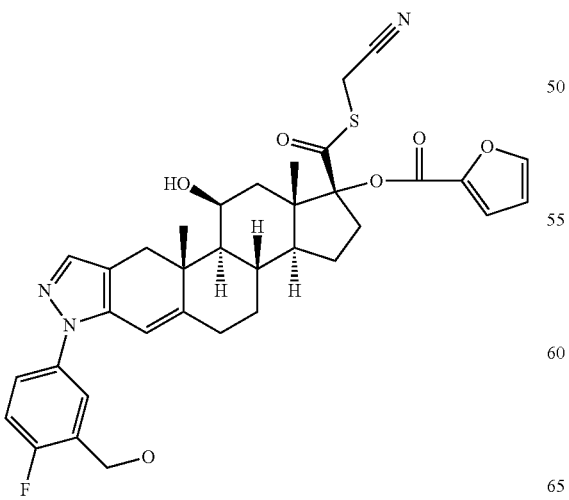

(1R,3aS,3bS,10aR,10bS,11S,12aS)-1-{[(Cyanomethyl)thio]carbonyl}-7-[4-fluoro-3-(hydroxymethyl)phenyl]-11-hydroxy-10a,12a-dimethyl-1,2,3,3a,3b,4,5,7,10,10a,10b,11,12,12a-tetradecahydrocyclopenta[5,6]naphtho[1,2]-indazol-1-yl furan-2-carboxylate In a 50 mL round-bottomed flask was dissolved Intermediate 37 (0.136 g, 0.19 mmol) in DMF (3 mL) to give an orange solution. Sodium hydrogencarbonate (0.076 mg, 1.94 mmol) and 2-bromoacetonitrile (0.032 mL, 0.49 mmol) were added, and the mixture was stirred in a sealed flask for 30 minutes. The mixture was partitioned between EtOAc (20 ml) and water (20 ml). The organic phase was collected, and the aqueous phase was extracted with another portion of EtOAc (15 ml). The organic phases were combined and were washed with water (2 times 15 ml) and brine (15 ml), and were finally dried over Na$_2$SO$_4$. Filtration and evaporation of the solvent gave 116 mg of the crude product as an orange semi-solid which was redissolved in acetonitrile (2.5 mL), and methylamine (33% in EtOH, 2.5 ml, 20.19 mmol) was added. The mixture was allowed to stand in a sealed flask at 20° C., monitoring the progress of the reaction by LC-MS. After 30 minutes, all starting material was consumed and the solvent was carefully removed in vacuo. The obtained material was purified on preparative HPLC (acetonitrile/water) and the product containing fractions were freeze-dried to give 19 mg (19%) of the desired product as a white solid.

$^1$H NMR (400 MHz, CDCl$_3$) δ 7.64 (1H, s), 7.64-7.59 (1H, m), 7.44 (1H, s), 7.42-7.36 (1H, m), 7.24 (1H, d), 7.16 (1H, t), 6.56 (1H, m), 6.09 (1H, s), 4.83 (2H, s), 4.64 (1H, bs), 3.82 (1H, d, AB), 3.55 (1H, d, AB), 3.11-3.01 (2H, m), 2.78 (1H, d), 2.53 (1H, t), 2.35-2.22 (2H, m), 2.21-2.03 (3H, m), 2.03-1.93 (1H, m), 1.93-1.70 (3H, m), 1.58-1.48 (1H, m), 1.35 (3H, s), 1.34 (1H, m), 1.20-1.09 (2H, m), 1.07 (3H, s). APCI-MS m/z: 646 [MH$^+$].

Example 81

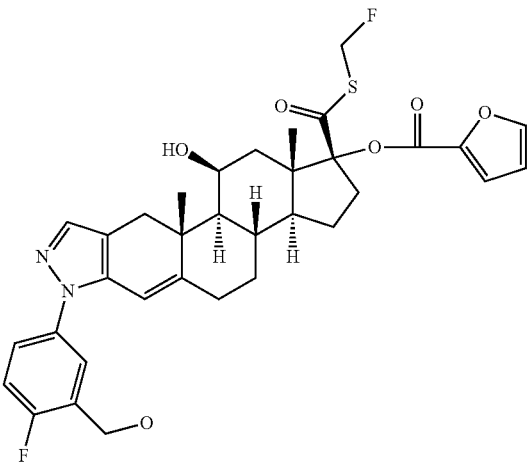

(1R,3aS,3bS,10aR,10bS,11S,12aS)-7-[4-Fluoro-3-
(hydroxymethyl)phenyl]-1-{[(fluoromethyl)thio]
carbonyl}-11-hydroxy-10a,12a-dimethyl-1,2,3,3a,
3b,4,5,7,10,10a,10b,11,12,12a-
tetradecahydrocyclopenta[5,6]naphtho[1,2-f]indazol-
1-yl furan-2-carboxylate The compound was prepared analogous to Example 80, starting from Intermediate 37.

$^1$H NMR (400 MHz, CDCl$_3$) δ 7.63 (1H, s), 7.63-7.59 (1H, m), 7.45 (1H, s), 7.41-7.36 (1H, m), 7.24 (1H, d), 7.16 (1H, t), 6.55 (1H, m), 6.09 (1H, s), 6.06-5.62 (2H, m), 4.83 (2H, s), 4.64 (1H, bs), 3.13-3.01 (2H, m), 2.78 (1H, d), 2.53 (1H, t), 2.35-2.25 (2H, m), 2.19-2.04 (3H, m), 2.03-1.94 (1H, m), 1.93-1.73 (3H, m), 1.58-1.48 (1H, m), 1.35 (3H, s), 1.34 (1H, m), 1.18-1.09 (2H, m), 1.06 (3H, s). APCI-MS m/z: 639 [MH$^+$].

Example 82

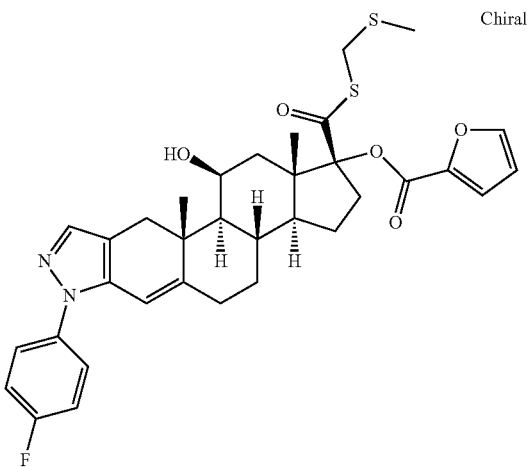

(1R,3aS,3bS,10aR,10bS,11S,12aS)-7-(4-Fluorophenyl)-11-hydroxy-10a,12a-dimethyl-1-({[(methylsulfanyl)methyl]sulfanyl}carbonyl)-1,2,3,3a,3b,4,5,7,10,10a,10b,11,12,12a-tetradecahydrocyclopenta[5,6]naphtho[1,2-f]indazol-1-yl furan-2-carboxylate Intermediate 5 (30 mg, 50 mmol) was dissolved in dichloromethane (2 ml) to give a yellow solution. Then triethylamine (100 μl) was added, followed by (chloromethyl)(methyl)mercaptane (15 mg, 13 μl, 150 μmol). The mixture was stirred overnight at room temperature, the solvents were removed under reduced pressure and the product was purified by preparative HPLC (acetonitrile/water) to give 14 mg (42%) of the title compound.

$^1$H NMR (400 MHz, CDCl$_3$) δ 7.65 (s, 1H), 7.62 (d, 1H), 7.55 (dd, 2H), 7.26-7.20 (m, 3H), 6.55 (dd, 1H), 6.04 (s, 1H), 4.62 (d, 1H), 4.08 (s, 2H), 3.11 (d, 1H), 3.08 (dq, 1H), 2.81 (d, 1H), 2.64-2.51 (m, 1H), 2.34 (d, 1H), 2.29 (dd, 1H), 2.20-1.96 (m, 4H), 2.17 (s, 3H), 1.88-1.70 (m, 2H), 1.50 (m, 1H), 1.37 (s, 3H), 1.34 (dd, 1H), 1.15 (m, H), 1.04 (s, 1H). APCI-MS m/z: 637 [MH$^+$].

Example 83

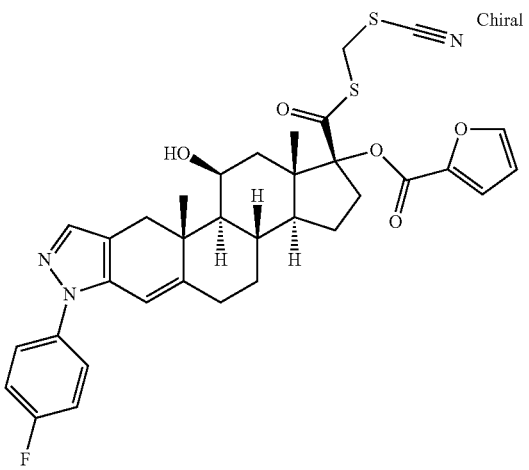

(1R,3aS,3bS,10aR,10bS,11S,12aS)-7-(4-Fluorophenyl)-11-hydroxy-10a,12a-dimethyl-1-{[(thiocyanatomethyl)sulfanyl]carbonyl}-1,2,3,3a,3b,4,5,7,10,10a,10b,11,12,12a-tetradecahydrocyclopenta[5,6]naphtho[1,2-f]indazol-1-yl furan-2-carboxylate The compound was prepared from Intermediate 5 and chloro(thiocyanato)methane according to the procedure described in Example 82.

$^1$H NMR (400 MHz, CDCl$_3$) δ 7.64 (d, 1H), 7.50 (m, 3H), 7.25 (d, 1H), 7.19 (t, 2H), 6.56 (dd, 1H), 6.07 (d, 1H), 4.64 (d, 1H), 4.44 (d, 1H), 4.27 (d, 1H), 3.05 (m, 2H), 2.79 (d, 1H), 2.55 (m, 1H), 2.36-1.95 (m, 7H), 1.91-1.71 (m, 3H), 1.59-1.42 (m, 1H), 1.36 (s, 3H), 1.34 (m, 1H), 1.21-1.02 (m, 1H), 1.07 (s, 3H). APCI-MS m/z: 648 [MH$^+$].

Example 84

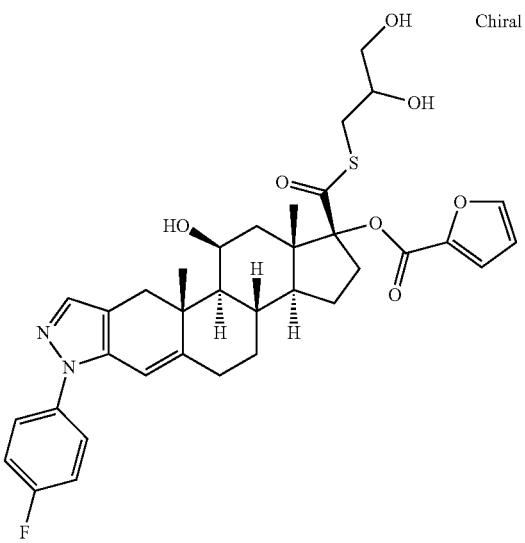

(1R,3aS,3bS,10aR,10bS,11S,12aS)-1-{[(2,3-Dihydroxypropyl)sulfanyl]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate The compound was prepared from Intermediate 5 and 3-bromopropane-1,2-diol according to the procedure described in Example 82.

$^1$H NMR (400 MHz, CDCl$_3$) δ 7.61 (m, 1H), 7.48 (m, 3H), 7.19 (m, 3H), 6.54 (dd, 1H), 6.07 (d, 1H), 4.63 (m, 1H), 3.82 (m, 1H), 3.67 (dt, 1H), 3.57 (dd, 1H), 3.22-2.95 (m, 5H), 2.78 (d, 1H), 2.52 (m, 1H), 2.34-1.92 (m, 9H), 1.88-1.71 (m, 3H), 1.56-1.38 (m, 2H), 1.35 (s, 3H), 1.31 (d, 1H), 1.13 (m, 2H), 1.02 (s, 3H), 0.98 (m, 1H). APCI-MS m/z: 651 [MH$^+$].

Example 85

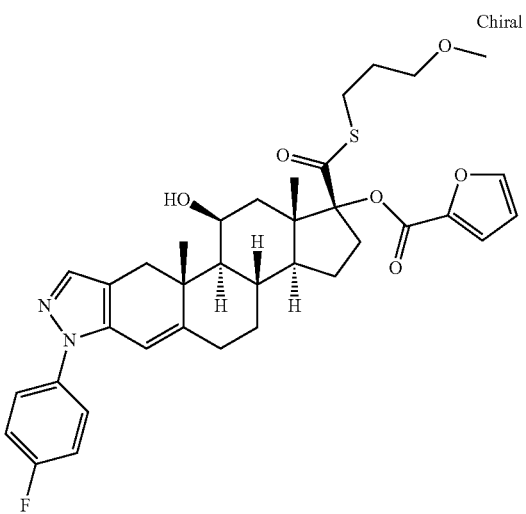

(1R,3aS,3bS,10aR,10bS,11S,12aS)-7-(4-Fluorophenyl)-11-hydroxy-{[(3-methoxypropyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate The compound was prepared from Intermediate 5 and 1-bromo-3-methoxypropane according to the procedure described in Example 82.

$^1$H NMR (400 MHz, CDCl$_3$) δ 7.61 (d, 1H), 7.50-7.45 (m, 3H), 7.21-7.14 (m, 3H), 6.53 (dd, 1H), 6.08 (d, 1H), 4.62 (d, 1H), 3.41 (t, 2H), 3.32 (s, 3H), 3.14-2.90 (m, 4H), 2.78 (d, 1H), 2.52 (m, 1H), 2.28 (m, 2H), 2.17-1.94 (m, 5H), 1.90-1.70 (m, 6H), 1.47 (m, 2H), 1.35 (s, 1H), 1.32 (m, 1H), 1.13 (mu, 1H), 1.02 (s, 3H), 0.99 (m, 1H). APCI-MS m/z: 649 [MH$^+$].

Example 86

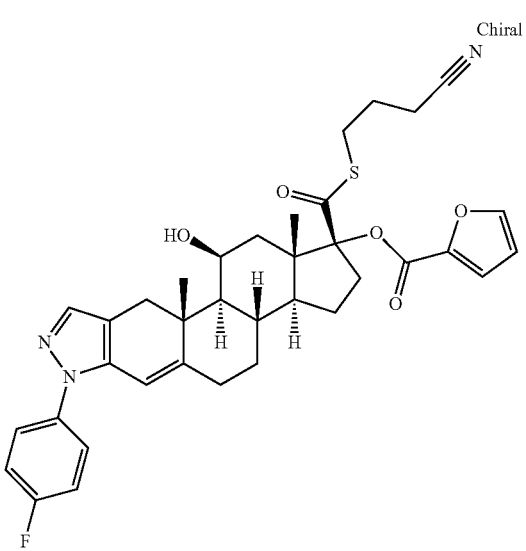

(1R,3aS,3bS,10aR,10bS,11S,12aS)-1-{[(3-Cyanopropyl)sulfanyl]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate The compound was prepared from Intermediate 5 and 4-bromobutyronitrile according to the procedure described in Example 82.

$^1$H NMR (400 MHz, CDCl$_3$) δ 7.62 (dt, 1H), 7.49-7.44 (m, 3H), 7.22 (dd, 1H), 7.17 (m, 2H), 6.55 (dd, 1H), 6.08 (d, 1H), 4.62 (d, 1H), 3.16-2.91 (m, 4H), 2.78 (d, 1H), 2.52 (m, 1H), 2.43 (t, 2H), 2.27 (m, 2H), 2.14-1.91 (m, 6H), 1.88-1.60 (m, 4H), 1.47 (m, 2H), 1.35 (s, 3H), 1.29 (m, 1H), 1.12 (m, 1H), 1.02 (s, 3H), 0.99 (m, 1H). APCI-MS m/z: 644 [MH$^+$].

Example 87

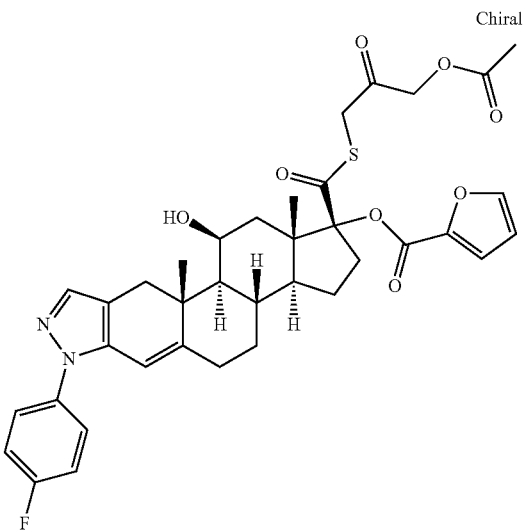

(1R,3aS,3bS,10aR,10bS,11S,12aS)-1-({[3-(Acetyloxy)-2-oxopropyl]sulfanyl}carbonyl)-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate The compound was prepared from Intermediate 5 and 3-chloro-2-oxopropyl acetate according to the procedure described in Example 82.

$^1$H NMR (400 MHz, CDCl$_3$) δ 7.62 (d, 1H), 7.47 (m, 3H), 7.23 (dd, 1H), 7.17 (t, 2H), 6.55 (dd, 1H), 6.08 (d, 1H), 4.82 (s, 2H), 4.63 (d, 1H), 3.88 (d, 1H), 3.60 (d, 1H), 3.07 (d, 1H), 3.03 (m, 1H), 2.79 (d, 1H), 2.53 (m, 1H), 2.29 (m, 1H), 2.21 (m, 1H), 2.18 (s, 3H), 2.16-1.93 (m, 4H), 1.88-1.70 (m, 4H), 1.55-1.40 (m, 2H), 1.35 (s, 3H), 1.32 (m, 1H), 1.12 (m, 1H), 1.02 (s, 3H), 1.00 (m, 1H). APCI-MS m/z: 691 [MH$^+$].

Example 88

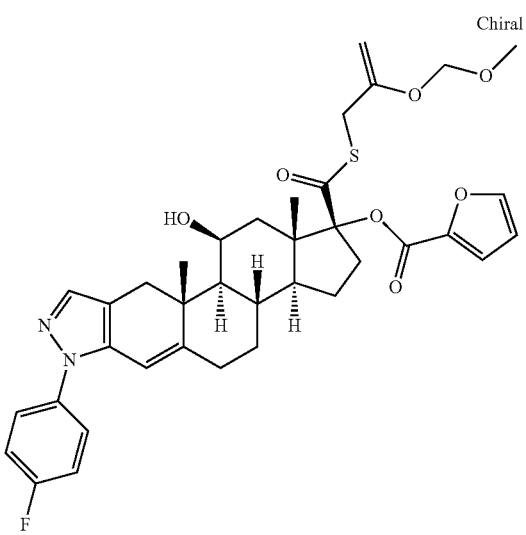

(1R,3aS,3bS,10aR,10bS,11S,12aS)-7-(4-fluorophenyl)-11-hydroxy-1-({[2-(methoxymethoxy)prop-2-en-1-yl]sulfanyl}carbonyl)-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate The compound was prepared from Intermediate 5 and 3-chloro-2-(methoxymethoxy)prop-1-ene according to the procedure described in Example 82.

$^1$H NMR (400 MHz, CDCl$_3$) δ 7.61 (m, 1H), 7.47 (m, 3H), 7.23-7.13 (m, 3H), 6.53 (dd, 1H), 6.08 (s, 1H), 4.93 (q, 2H), 4.61 (br.s, 1H), 4.31 (d, 1H), 4.23 (d, 1H), 3.73 (d, 1H), 3.56 (d, 1H), 3.45 (s, 1H), 3.41 (s, 2H), 3.12-3.01 (m, 2H), 2.78 (d, 1H), 2.52 (m, 1H), 2.27 (m, 2H), 2.20-1.93 (m, 4H), 1.89 (s, 1H), 1.87-1.68 (m, 2H), 1.58 (s, 2H), 1.48 (m, 2H), 1.34 (s, 3H), 1.33-1.03 (m, 3H), 1.02 (s, 3H). APCI-MS m/z: 677 [MH$^+$].

Example 89

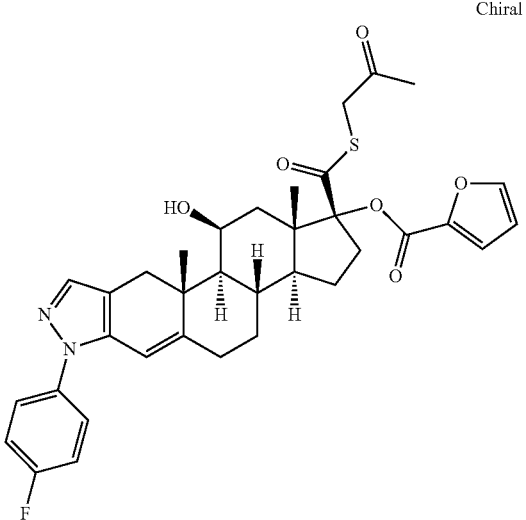

(1R,3aS,3bS,10aR,10bS,11S,12aS)-7-(4-Fluorophenyl)-11-hydroxy-10a,12a-dimethyl-1-{[(2-oxopropyl)sulfanyl]carbonyl}-1,2,3,3a,3b,4,5,7,10,10a,10b,11,12,12a-tetradecahydrocyclopenta[5,6]naphtho[1,2-f]indazol-1-yl furan-2-carboxylate The compound was prepared from Intermediate 5 and 1-chloropropan-2-one according to the procedure described in Example 82.

$^1$H NMR (400 MHz, CDCl$_3$) δ 7.62 (t, 1H), 7.47 (m, 3H), 7.22 (dd, 1H), 7.17 (m, 3H), 6.54 (dd, 1H), 6.08 (d, 1H), 4.63 (d, 1H), 3.83 (d, 1H), 3.67 (d, 1H), 3.04 (m, 2H), 2.78 (d, 1H), 2.53 (m, 1H), 2.28 (m, 2H), 2.29 (s, 3H), 2.20-1.94 (m, 5H), 1.88-1.71 (m, 3H), 1.56-1.39 (m, 2H), 1.35 (s, 3H), 1.32 (m, 1H), 1.27-0.98 (m, 3H), 1.03 (s, 3H). APCI-MS m/z: 633 [MH$^+$].

Example 90

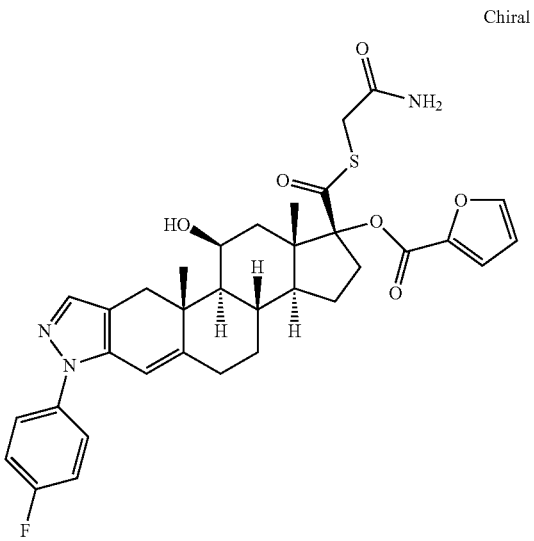

(1R,3aS,3bS,10aR,10bS,11S,12aS)-1-{[(2-Amino-2-oxoethyl)sulfanyl]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate The compound was prepared from Intermediate 5 and 2-bromoacetamide according to the procedure described in Example 82.

$^1$H NMR (400 MHz, CDCl$_3$) δ 7.64 (d, 1H), 7.49-7.44 (m, 3H), 7.24 (dd, 1H), 7.17 (m, 2H), 6.56 (dd, 1H), 6.34 (br.s, 1H), 6.09 (d, 1H), 5.35 (br.s, 1H), 4.63 (d, 1H), 3.77 (d, 1H), 3.50 (d, 1H), 3.08 (m, 1H), 3.05 (d, 2H), 2.78 (d, 1H), 2.53 (m, 1H), 2.28 (m, 2H), 2.16-1.39 (m, 10H), 1.35 (s, 3H), 1.31 (m, 1H), 1.13 (m, 1H), 1.03 (s, 3H), 1.00 (m, 1H). APCI-MS m/z: 634 [MH$^+$].

Example 91

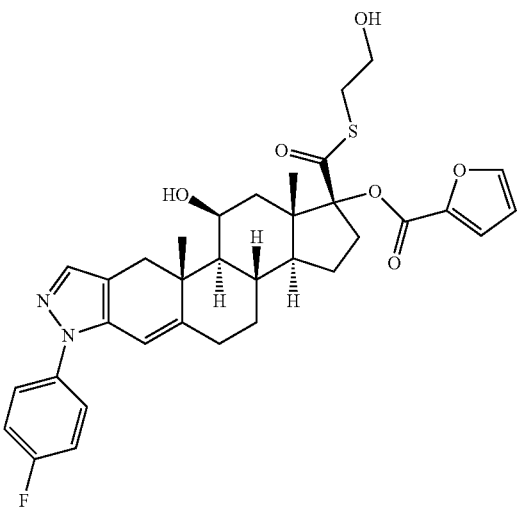

(1R,3aS,3bS,10aR,10bS,11S,12aS)-7-(4-fluorophenyl)-11-hydroxy-1-{[(2-hydroxyethyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate The compound was prepared from Intermediate 5 and 2-bromoethanol according to the procedure described in Example 82.

¹H NMR (400 MHz, CDCl₃) δ 7.61 (t, 1H), 7.52-7.45 (m, 3H), 7.22 (dd, 1H), 7.18 (m, 2H), 6.54 (dd, 1H), 6.07 (d, 1H), 4.62 (d, 1H), 3.77 (t, 2H), 3.21-3.02 (m, 4H), 2.78 (d, 1H), 2.53 (m, 1H), 2.28 (m, 3H), 2.17-1.72 (m, 10H), 1.47 (m, 2H), 1.35 (s, 3H), 1.33 (m, 1H), 1.13 (m, 1H), 1.03 (s, 3H), 0.99 (m, 1H). APCI-MS m/z: 621 [MH⁺].

Example 92

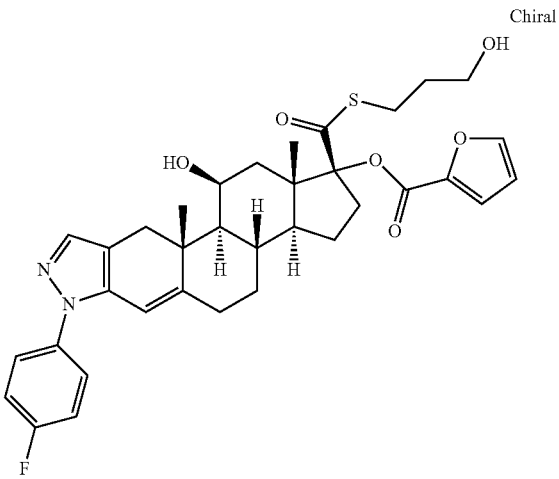

(1R,3aS,3bS,10aR,10bS,11S,12aS)-7-(4-Fluorophenyl)-11-hydroxy-1-{[(3-hydroxypropyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate The compound was prepared from Intermediate 5 and 3-bromopropan-1-ol according to the procedure described in Example 82.

¹H NMR (400 MHz, CDCl₃) δ 7.61 (dd, 1H), 7.50-7.45 (m, 3H), 7.21 (dd, 1H), 7.17 (m, 2H), 6.53 (dd, 1H), 6.08 (d, 1H), 4.62 (d, 1H), 3.66 (t, 2H), 3.15-2.96 (m, 4H), 2.78 (d, 1H), 2.52 (m, 1H), 2.34-1.70 (m, 10H), 1.46 (m, 2H), 1.35 (s, 3H), 1.32 (m, 1H), 1.13 (m, 1H), 1.03 (s, 3H), 1.01 (m, 1H). APCI-MS m/z: 635 [MH⁺].

Example 93

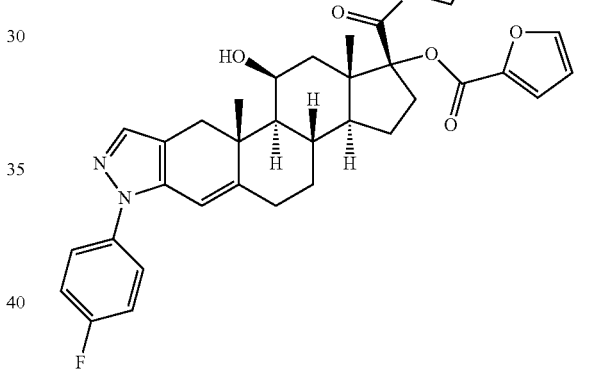

(1R,3aS,3bS,10aR,10bS,11S,12aS)-7-(4-Fluorophenyl)-11-hydroxy-1-{[(methoxymethyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate The compound was prepared from Intermediate 5 and bromo(methoxy)methane according to the procedure described in Example 82.

¹H NMR (400 MHz, CDCl₃) δ 7.61 (q, 1H), 7.50-7.45 (m, 3H), 7.21 (dt, 1H), 7.17 (t, 2H), 6.54 (dt, 1H), 6.08 (s, 1H), 5.13 (m, 2H), 4.65 (s, 1H), 3.40 (d, 1H), 3.33 (s, 2H), 3.09 (m, 1H), 3.05 (d, 1H), 2.78 (d, 1H), 2.52 (m, 1H), 2.29 (m, 3H), 2.19-1.70 (m, 8H), 1.48 (m, 2H), 1.35 (s, 3H), 1.33 (m, 1H), 1.13 (m, 1H), 1.04 (s, 3H), 1.02 (m, 1H). APCI-MS m/z: 621 [MH⁺].

Example 94

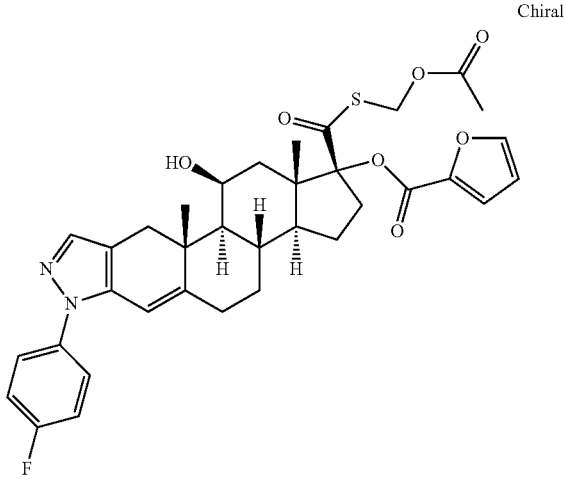

(1R,3aS,3bS,10aR,10bS,11S,12aS)-1-({[(Acetyloxy)methyl]sulfanyl}carbonyl)-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate The compound was prepared from Intermediate 5 and bromomethyl acetate according to the procedure described in Example 82.

$^1$H NMR (400 MHz, CDCl$_3$) δ 7.61 (q, 1H), 7.49-7.44 (m, 3H), 7.21 (dd, 1H), 7.17 (m, 2H), 6.54 (dd, 1H), 6.08 (d, 1H), 5.48 (q, 2H), 4.61 (d, 1H), 3.08 (m, 1H), 3.05 (d, 1H), 2.78 (d, 1H), 2.52 (m, 1H), 2.28 (m, 2H), 2.17-1.94 (m, 4H), 2.08 (s, 3H), 1.90-1.41 (m, 5H), 1.34 (s, 3H), 1.32 (m, 1H), 1.15 (m, 2H), 1.03 (s, 3H), 1.01 (m, 1H). APCI-MS m/z: 649 [MH$^+$].

Example 95

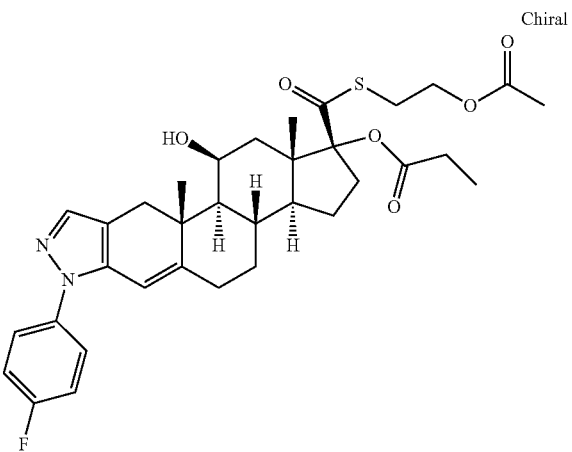

(1R,3aS,3bS,10aR,10bS,11S,12aS)-1-({[2-(Acetyloxy)ethyl]sulfanyl}carbonyl)-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl propanoate The compound was prepared from Intermediate 7 and 2-bromoethyl acetate according to the procedure described in Example 82.

$^1$H NMR (400 MHz, CDCl$_3$) δ 7.49-7.43 (m, 3H), 7.17 (m, 2H), 6.08 (d, 1H), 4.56 (d, 1H), 4.26 (m, 1H), 4.13 (m, 1H), 3.26-2.93 (m, 4H), 2.73 (d, 1H), 2.51 (m, 1H), 2.45-2.26 (m, 3H), 2.10 (m, 1H), 2.08 (s, 3H), 1.98 (m, 4H), 1.84-1.37 (m, 8H), 1.33 (s, 3H), 1.27 (m, 1H), 1.19 (m, 1H), 1.16 (t, 3H), 1.10 (m, 1H), 0.97 (s, 3H), 0.95 (m, 1H). APCI-MS m/z: 625 [MH$^+$].

Example 96

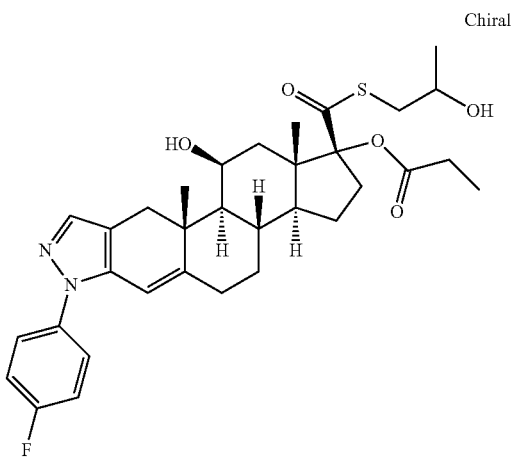

(1R,3aS,3bS,10aR,10bS,11S,2aS)-7-(4-Fluorophenyl)-11-hydroxy-1-{[(2-hydroxypropyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl propanoate The compound was prepared from Intermediate 7 and racemic 2-methyloxirane according to the procedure described in Example 82.

$^1$H NMR (400 MHz, CDCl$_3$) δ 7.49-7.44 (m, 3H), 7.17 (m, 2H), 6.08 (d, 1H), 4.56 (d, 1H), 3.94 (m, 1H), 3.21 (dd, 1H), 3.11-2.95 (m, 3H), 2.84 (dd, 1H), 2.73 (d, 1H), 2.57-2.26 (m, 4H), 2.14 (dd, 2H), 2.08-1.38 (m, 4H), 1.33 (s, 3H), 1.27 (m, 4H), 1.16 (t, 3H), 1.21-1.05 (m, 2H), 0.97 (s, 3H), 0.96 (m, 1H). APCI-MS m/z: 597 [MH$^+$].

Example 97

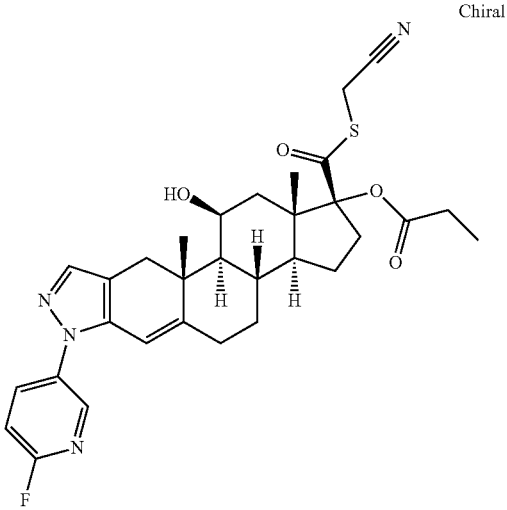

(1R,3aS,3bS,10aR,10bS,11S,12aS)-1-{[(Cyanomethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl propanoate The compound was prepared from Intermediate 43 and 2-bromoacetonitrile according to the procedure described in Example 82.

$^1$H NMR (400 MHz, CDCl$_3$) δ 8.35 (d, 1H), 8.04 (m, 1H), 7.65 (s, 1H), 7.14 (dd, 1H), 6.02 (d, 1H), 4.85 (br.s, 2H), 4.57 (d, 1H), 3.79 (d, 1H), 3.57 (d, 1H), 3.08 (d, 1H), 2.98 (ddd, 1H), 2.74 (d, 1H), 2.55 (m, 1H), 2.39 (qd, 2H), 2.32 (m, 1H), 2.13 (dd, 2H), 2.08-1.93 (m, 5H), 1.83 (m, 1H), 1.65 (m, 1H), 1.54-1.41 (m, 1H), 1.35 (s, 3H), 1.27 (dd, 1H), 1.16 (t, 3H), 1.13 (m, 1H), 1.01 (s, 3H), 1.00 (m, 1H). APCI-MS m/z: 579 [MH$^+$].

Example 98

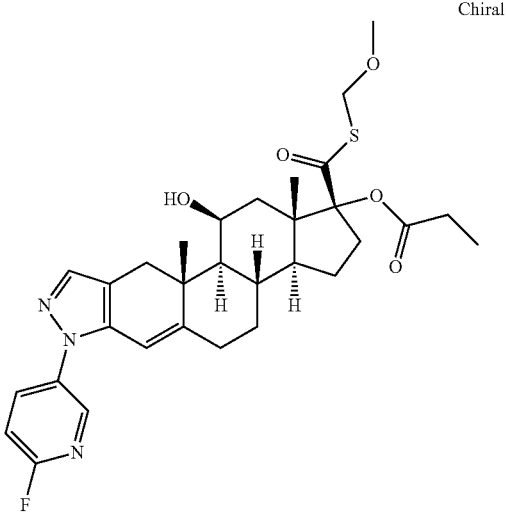

(1R,3aS,3bS,10aR,10bS,11S,12aS)-7-(6-Fluoropyridin-3-yl)-11-hydroxy-1-{[(methoxymethyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl propanoate The compound was prepared from Intermediate 43 and bromo(methoxy)methane according to the procedure described in Example 82.

$^1$H NMR (400 MHz, CDCl$_3$) δ 8.35 (d, 1H), 8.04 (td, 1H), 7.65 (s, 1H), 7.14 (dd, 1H), 6.01 (s, 1H), 5.12 (s, 1H), 4.56 (m, 1H), 3.41 (m, 1H), 3.33 (s, 3H), 3.07 (d, 1H), 3.00 (m, 1H), 2.75 (d, 1H), 2.54 (m, 1H), 2.44-2.29 (m, 3H), 2.20-1.92 (m, 5H), 1.81 (m, 1H), 1.66 (m, 1H), 1.45 (m, 2H), 1.34 (s, 3H), 1.28 (m, 1H), 1.20-1.10 (m, 4H), 0.98 (s, 3H), 0.96 (m, 1H). APCI-MS m/z: 584 [MH$^+$].

Example 99

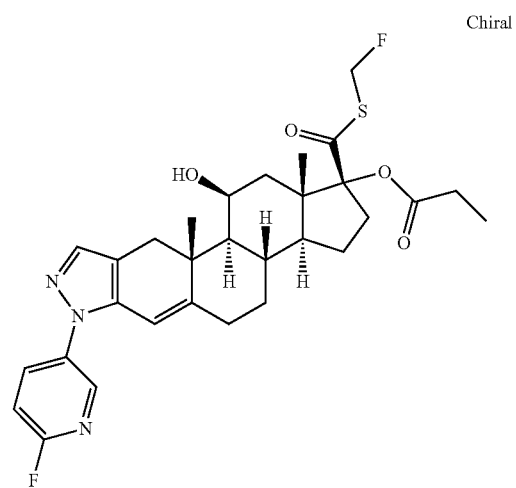

(1R,3aS,3bS,10aR,10bS,11S,12aS)-1-{[(Fluoromethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl propanoate The compound was prepared from Intermediate 43 and bromofluoromethane according to the procedure described in Example 82.

$^1$H NMR (400 MHz, CDCl$_3$) δ 8.36 (d, 1H), 8.04 (m, 1H), 7.62 (s, 1H), 7.12 (dd, 1H), 6.03 (d, 1H), 5.83 (qd, 2H), 4.56 (d, 1H), 3.07 (d, 1H), 3.00 (m, 1H), 2.74 (d, 1H), 2.55 (m, 1H), 2.39 (qd, 2H), 2.37 (m, 1H), 2.15 (dd, 1H), 2.11-1.92 (m, 4H), 1.82 (m, 1H), 1.66 (m, 1H), 1.46 (m, 1H), 1.34 (s, 3H), 1.28 (dd, 1H), 1.16 (t, 1H), 1.11 (m, 1H), 1.00 (s, 3H), 0.97 (m, 1H). APCI-MS m/z: 572 [MH$^+$].

Example 100

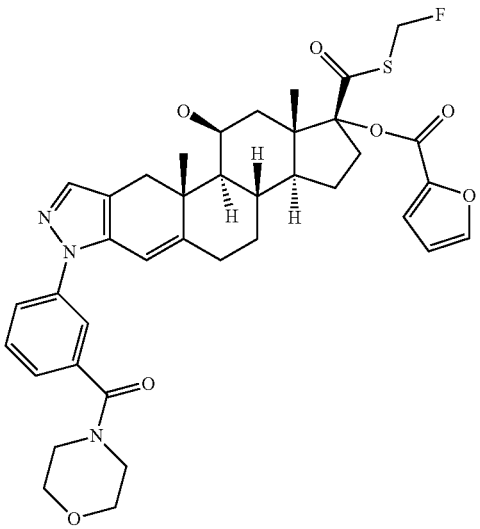

(1R,3aS,3bS,10aR,10bS,11S,12aS)-1-{[(Fluoromethyl)thio]carbonyl}-11-hydroxy-10a,12a-dimethyl-7-[3-(morpholin-4-ylcarbonyl)phenyl]-1,2,3,3a,3b,4,5,7,10,10a,10b,11,12,12a-tetradecahydrocyclopenta[5,6]naphtho[1,2-f]indazol-1-yl furan-2-carboxylate The compound was prepared from Intermediate 49 and bromofluoromethane according to the procedure for Example 1.

$^{1}$H NMR (400 MHz, CDCl$_3$) δ 7.62 (1H, s); 7.59-7.52 (3H, m); 7.49 (1H, m); 7.39 (1H, d); 7.24 (1H, d); 6.55 (1H, m); 6.13 (1H, s); 6.05-5.61 (2H, m); 4.63 (1H, m); 3.78-3.50 (4H, m); 3.11-3.03 (2H, m); 2.77 (1H, d); 2.53 (1H, t); 2.32-2.25 (2H, m); 2.16-2.05 (3H, m); 2.01-1.94 (2H, m); 1.86-1.73 (2H, m); 1.55-1.48 (1H, m); 1.37-1.31 (4H, m); 1.17-1.12 (1H, m); 1.05 (3H, s). APCI-MS m/z: 704 [MH$^+$].

Example 101

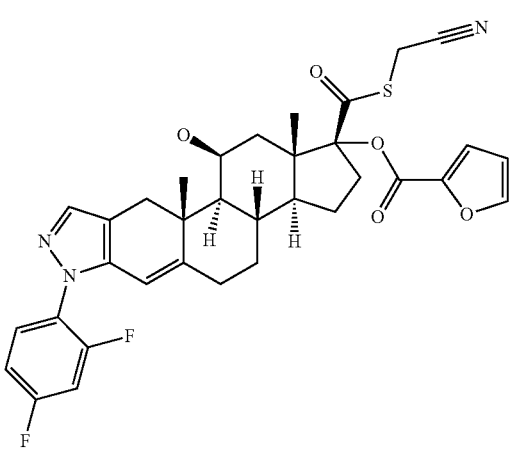

(1R,3aS,3bS,10aR,10bS,11S,12aS)-1-{[(Cyanomethyl)thio]carbonyl}-7-(2,4-difluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate The compound was prepared from Intermediate 54 and bromoacetonitrile according to the procedure for Example 1.

$^{1}$H NMR (400 MHz, CDCl$_3$) δ 7.62 (2H, d); 7.52-7.46 (1H, m); 7.24 (1H, d); 7.03 (2H, t); 6.57 (1H, m); 5.80 (1H, s); 4.63 (1H, m); 3.82 (1H, d); 3.55 (1H, d), 3.09-3.02 (2H, m); 2.80 (2H, d); 2.62-2.37 (2H, m); 2.31-2.23 (5H, m); 2.20-1.92 (2H, m); 1.87-1.71 (2H, m); 1.55-1.48 (1H, m); 1.37-1.33 (4H, m); 1.26 (1H, s); 1.19-1.12 (1H, m); 1.07 (3H, s). APCI-MS m/z: 634 [MH$^+$].

Example 102

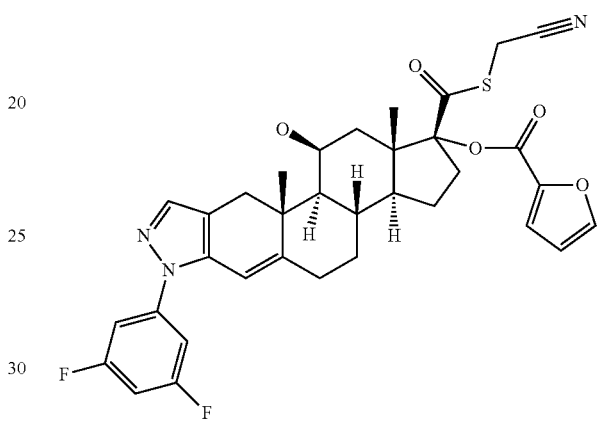

(1R,3aS,3bS,10aR,10bS,11S,12aS)-1-{[(Cyanomethyl)thio]carbonyl}-7-(3,5-difluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate The compound was prepared from Intermediate 59 and bromoacetonitrile according to the procedure for Example 1

$^{1}$H NMR (400 MHz, CDCl$_3$) δ 7.63 (1H, s); 7.47 (1H, s); 7.24 (1H, d); 7.11 (2H, d); 6.79 (1H, t); 6.56 (1H, s); 6.20 (1H, s); 5.32 (1H, s); 4.64 (1H, m); 3.82 (1H, d), 3.71 (1H, s) 3.55 (2H, d); 3.12-3.03 (2H, m); 2.76 (1H, d); 2.74 (1H, d); 2.60-2.51 (1H, t); 2.34 (1H, d); 2.26 (1H, d); 2.19-1.96 (3H, m); 1.90-1.83 (1H, m); 1.80-1.73 (2H, m); 1.55-1.43 (2H, m); 1.34-1.25 (7H, m); 1.20-1.12 (1H, m); 1.07 (3H, s). APCI-MS m/z: 634 [MH$^+$].

Example 103

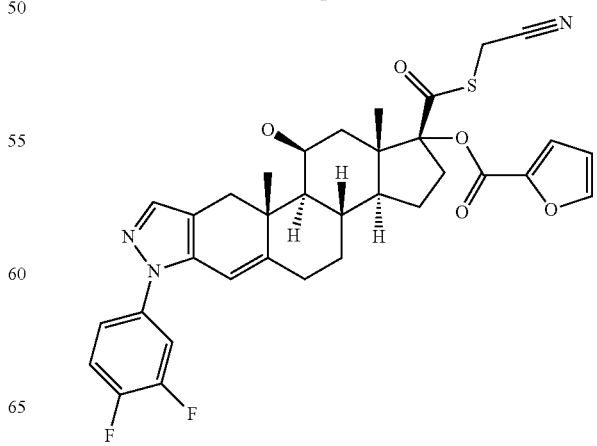

(1R,3aS,3bS,10aR,10bS,11S,12aS)-1-{[(Cyanomethyl)thio]carbonyl}-7-(3,4-difluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate The compound was prepared from Intermediate 64 and bromoacetonitrile according to the procedure for Example 1.

$^1$H NMR (400 MHz, CDCl$_3$) δ 7.63 (1H, s); 7.45 (1H, s); 7.41-7.36 (1H, m); 7.26-7.24 (2H, m); 6.56 (1H, m); 6.11 (1H, s); 4.64 (1H, m); 3.81 (1H, d); 3.55 (1H, d); 3.05 (2H, m); 2.78 (1H, d); 2.57-2.50 (1H, m); 2.34-2.22 (2H, m); 2.19-1.95 (5H, m); 1.90-1.83 (1H, m); 1.80-1.71 (1H, m); 1.56-1.47 (1H, m); 1.34-1.30 (4H, m); 1.20-1.17 (2H, m); 1.07 (3H, s). APCI-MS m/z: 634 [MH$^+$].

Example 104

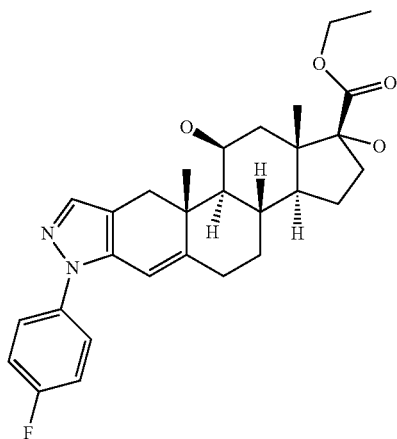

Ethyl (1R,3aS,3bS,10aR,10bS,11S,12aS)-7-(4-fluorophenyl)-1,11-dihydroxy-10a,12a-dimethyl-1,2,3,3a,3b,4,5,7,10,10a,10b,11,12,12a-tetradecahydrocyclopenta[5,6]naphtho[1,2-f]indazole-1-carboxylate To a solution of intermediate 68 (70 mg. 0.17 mmol) in ethanol (3 ml) and water (1 ml) 4-fluorophenylhydrazine hydrochloride (33 mg, 0.2 mmol) and potassium acetate (33.4 mg, 0.34 mmol)) were added and the mixture was stirred at 80° C. for 30 minutes. The crude product was purified using a HPLC Kromasil® column (CH$_3$CN/water) and the product containing fractions were freeze-dried, giving 20 mg of the desired compound.

$^1$H NMR (400 MHz, CDCl$_3$) δ 7.48-7.45 (2H, m), 7.41 (1H, s), 7.16 (1H, t), 6.07 (1H, s), 4.55-4.53 (1H, m), 4.28-4.23 (2H, m), 3.73 (1H, m), 2.99 (1H, d), 2.74-2.66 (2H, m), 2.50 (1H, t), 2.29 (1H, d), 2.02-1.93 (2H, m), 1.90-1.82 (2H, m), 1.76-1.68 (2H, m), 1.66 (1H, d), 1.62 (1H, d), 1.48-1.39 (2H, m), 1.34 (3H, d), 1.32 (3H, s), 1.27-1.23 (2H, m), 1.18-1.06 (2H, m), 1.02 (3H, s). APCI-MS m/z: 495 [MH$^+$].

Example 105

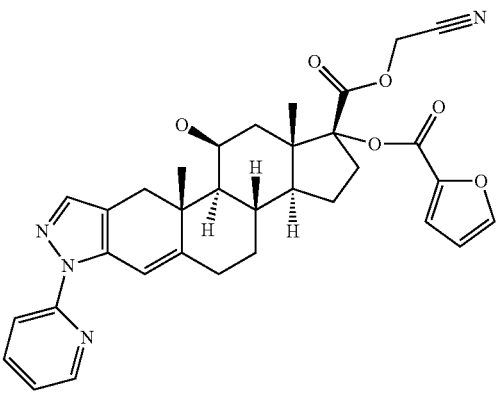

Cyanomethyl(1R,3aS,3bS,10aR,10bS,11S,12aS)-1-[(furan-2-ylcarbonyl)oxy]-11-hydroxy-10a,12a-dimethyl-7-pyridin-2-yl-1,2,3,3a,3b,4,5,7,10,10a,10b,11,12,12a-tetradecahydrocyclopenta[5,6]naphtho[1,2-f]indazole-1-carboxylate The compound was prepared from Intermediate 72 and bromoacetonitrile according to the procedure for Example 9.

$^1$H NMR (400 MHz, CDCl$_3$) δ 8.45 (1H, d); 7.91 (1H, d); 7.80 (1H, m); 7.61 (1H, s); 7.47 (1H, s); 7.22-7.15 (2H, m); 6.54 (1H, m); 4.89 (1H, d); 4.67 (1H, d); 4.61-4.60 (1H, m); 3.10-3.00 (2H, m); 2.78 (1H, d); 2.61-2.53 (1H, m); 2.44 (1H, d); 2.38-2.20 (1H, m); 2.10-1.96 (3H, m); 1.91-1.73 (3H, m); 1.60-1.47 (1H, m); 1.44 (3H, s); 1.37-1.3 (4H, m); 1.27 (2H, s); 1.20-1.15 (2H, m); 1.11 (3H, s). APCI-MS m/z: 583 [MH$^+$].

Example 106

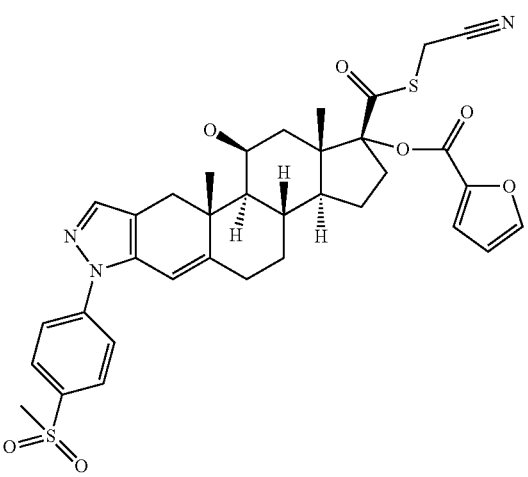

(1R,3aS,3bS,10aR,10bS,11S,12aS)-1-{[(Cyanomethyl)sulfanyl]carbonyl}-11-hydroxy-10a,12a-dimethyl-7-[4-(methylsulfonyl)phenyl]-1,2,3,3a,3b,4,5,7,10,10a,10b,11,12,12a-tetradecahydrocyclopenta[5,6]naphtho[1,2-f]indazol-1-yl furan-2-carboxylate The compound was prepared from Intermediate 75 and bromoacetonitrile according to the procedure for Example 1.

$^1$H NMR (400 MHz, CDCl$_3$) δ 8.10 (2H, d); 7.72 (2H, d); 7.63 (2H, d); 7.24 (1H, m); 6.56 (1H, m); 6.15 (1H, s); 4.64 (1H, m); 3.82 (1H, d); 3.55 (1H, d); 3.12 (3H, s); 3.08-3.03 (2H, m); 2.79 (1H, d); 2.61-2.53 (1H, m); 2.37-2.25 (2H, m); 2.20-1.99 (5H, m); 1.91-1.73 (2H, m); 1.60-1.47 (1H, m); 1.37 (3H, s); 1.34 (2H, m); 1.20-1.17 (1H, m); 1.08 (3H, s). APCI-MS m/z: 676 [MH$^+$].

Example 107

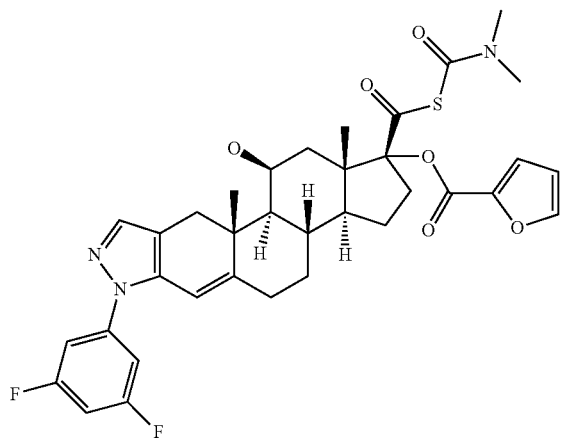

(1R,3aS,3bS,10aR,10bS,11S,12aS)-7-(3,5-Difluorophenyl)-1-{[(dimethylcarbamoyl)sulfanyl]carbonyl}-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate The compound was prepared from Intermediate 76 according to the procedure for intermediate 74.

$^1$H NMR (400 MHz, CDCl$_3$) δ 7.64 (1H, s); 7.54 (1H, s); 7.24 (1H, d); 7.08 (2H, d); 6.82 (1H, t); 6.57 (1H, s); 6.15 (1H, s); 4.61 (1H, s); 3.13 (3H, s); 3.10 (3H, s); 3.07 (2H, d); 3.02-2.98 (2H, m); 2.76 (2H, d); 2.60-2.51 (1H, t); 2.34 (1H, d); 2.20 (2H, d); 2.02-1.97 (2H, m); 1.87-1.80 (2H, m); 1.77-1.69 (1H, m); 1.55-1.47 (2H, m); 1.35 (3H, s); 1.32-1.27 (3H, m); 1.16-1.11 (4H, m). APCI-MS m/z: 666 [MH$^+$].

Example 108

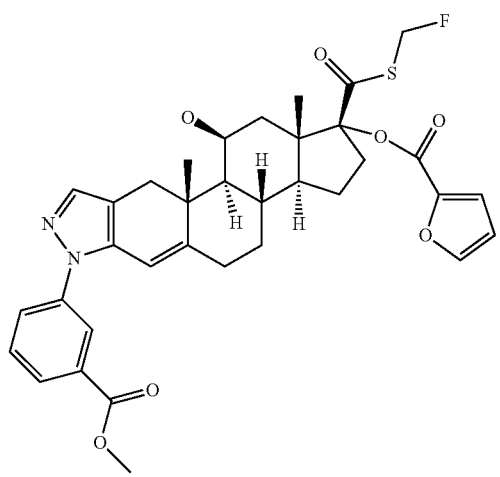

(1R,3aS,3bS,10aR,10bS,11S,12aS)-1-{[(Fluoromethyl)sulfanyl]carbonyl}-11-hydroxy-7-[3-(methoxycarbonyl)phenyl]-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate The compound was prepared from Intermediate 82 and bromoacetonitrile according to the procedure for Example 1.

$^1$H NMR (400 MHz, CDCl$_3$) δ 8.18 (1H, s); 8.02 (1H, d); 7.73 (1H, d); 7.63 (1H, s); 7.56 (1H, m); 7.48 (1H, m); 7.24 (1H, d); 6.56-6.54 (1H, m); 6.16 (1H, s); 6.06-5.61 (2H, m); 4.62 (1H, m); 3.95 (3H, s); 3.49 (1H, s); 3.12-3.03 (2H, m); 2.79 (1H, d); 2.56-2.49 (1H, t); 2.33-2.25 (2H, m); 2.18-2.05 (3H, m); 2.01-1.95 (2H, m); 1.88-1.74 (2H, m); 1.55-1.45 (1H, m); 1.36-1.31 (4H, m); 1.27-1.12 (2H, m); 1.06 (3H, s). APCI-MS m/z: 649 [MH$^+$].

Example 109

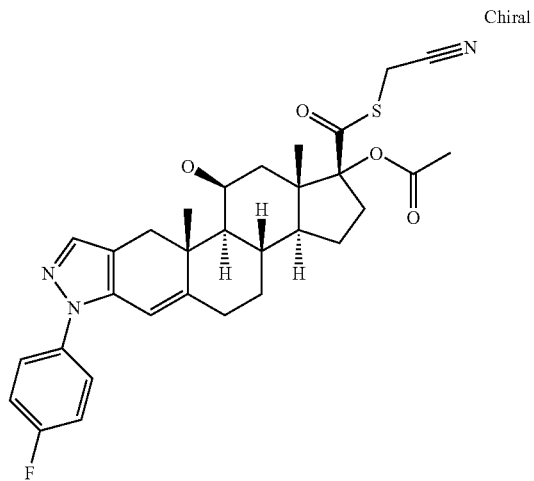

(1R,3aS,3bS,10aR,10bS,11S,12aS)-1-{[(Cyanomethyl)sulfanyl]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl acetate Intermediate 83 (0.094 g, 0.18 mmol) was dissolved in DMF (3 ml), sodium hydrogen carbonate (0.105 g, 1.25 mmol) was added and the mixture was stirred for 5 min. before 2-bromoacetonitrile (0.024 ml, 0.36 mmol) was added. The mixture was stirred for 20 min. and was subsequently partitioned between EtOAc (15 ml) and water (15 ml). The organic phase was washed with water (2 times 15 ml), brine (10 ml), and dried over $Na_2SO_4$. After filtration and evaporation of the solvent under reduced pressure, the crude product was purified on a preparative HPLC column ($CH_3CN$/water) and the product containing fractions were freeze-dried to give 40 mg of the title compound.

$^1$H NMR (400 MHz, DMSO-$d_6$) δ 7.51 (m, 2H), 7.47 (s, 1H), 7.34 (m, 2H), 6.16 (s, 1H), 4.40 (s, 1H), 4.00 (d, 2H), 2.93 (d, 1H), 2.77 (m, 1H), 2.63 (m, 1H), 2.41 (d, 1H), 2.30 (m, 1H), 2.06 (s, 4H), 1.89 (m, 5H), 1.74 (m, 1H), 1.60 (m, 1H), 1.37 (m, 1H), 1.25 (s, 3H), 1.14 (m, 1H), 1.02 (m, 1H), 0.93 (s, 3H). APCI-MS m/z: 564 [MH$^+$].

Example 110

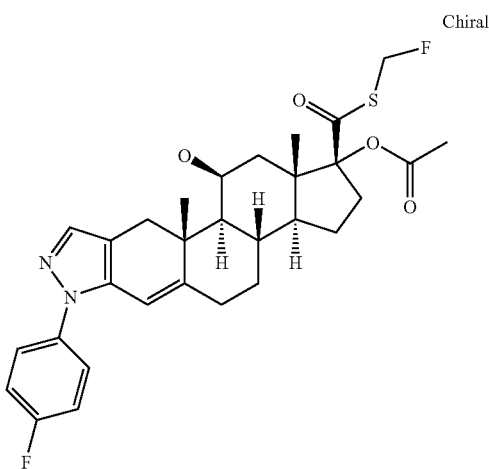

(1R,3aS,3bS,10aR,10bS,11S,12aS)-1-{[(Fluoromethyl)sulfanyl]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl acetate The compound was prepared from Intermediate 83 and bromofluoromethane according to the procedure for Example 109.

$^1$H NMR (400 MHz, DMSO-$d_6$) δ 7.51 (t, 2H), 7.47 (s, 1H), 7.34 (m, 2H), 6.16 (s, 1H), 5.96 (m, 1H), 5.84 (m, 1H), 4.40 (s, 1H), 2.93 (d, 1H), 2.77 (m, 1H), 2.63 (m, 1H), 2.41 (d, 1H), 2.30 (m, 1H), 2.06 (s, 4H), 1.89 (m, 5H), 1.74 (m, 1H), 1.60 (m, 1H), 1.37 (m, 1H), 1.25 (s, 3H), 1.14 (m, 1H), 1.02 (m, 1H), 0.93 (s, 3H). APCI-MS m/z: 557 [MH$^+$].

Example 111

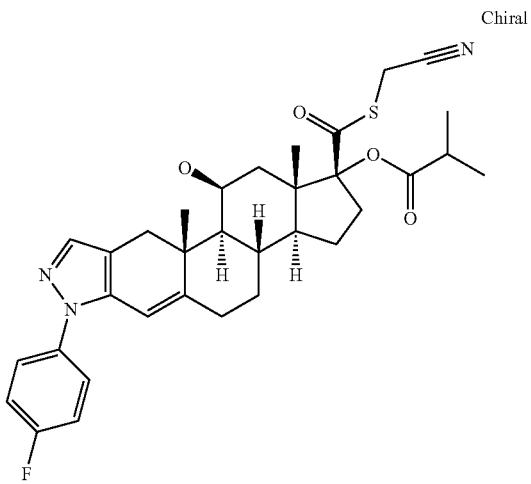

(1R,3aS,3bS,10aR,10bS,11S,12aS)-1-{[(Cyanomethyl)sulfanyl]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 2-methylpropanoate The compound was prepared from Intermediate 84 and 2-bromoacetonitrile according to the procedure described in Example 109.

$^1$H NMR (400 MHz, DMSO-d6) δ 7.52 (m, 2H), 7.49 (s, 1H), 7.35 (m, 2H), 6.15 (s, 1H), 4.59 (d, 1H), 4.41 (d, 1H), 4.00 (d, 2H), 2.98 (d, 1H), 2.86 (m, 1H), 2.70 (d, 1H), 2.59 (m, 1H), 2.42 (m 1H), 2.29 (m 1H), 2.06 (m, 2H), 1.91 (m, 3H), 1.78 (m 1H), 1.69 (m 1H), 1.42 (m, 1H), 1.29 (d, 1H), 1.23 (s, 3H), 1.12 (d, 3H), 1.09 (d, 3H), 0.90 (m, 1H), 0.98 (s, 3H). APCI-MS m/z: 592 [MH$^+$].

Example 112

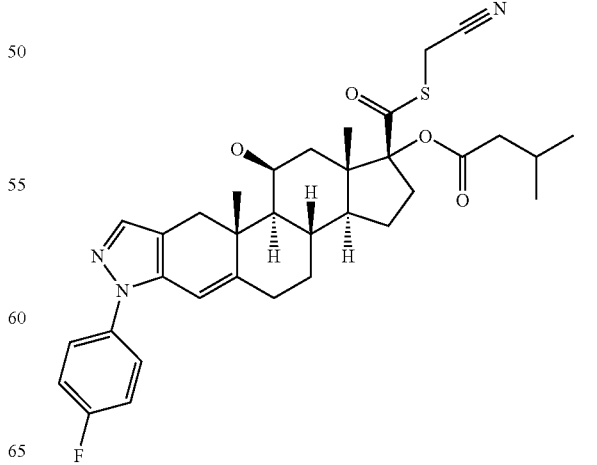

(1R,3aS,3bS,10aR,10bS,11S,12aS)-1-{[(Cyanom-
ethyl)sulfanyl]carbonyl}-7-(4-fluorophenyl)-11-hy-
droxy-10a,12a-dimethyl-1,2,3,3a,3b,4,5,7,10,10a,
10b,11,12,12a-tetradecahydrocyclopenta[5,6]
naphtho[1,2-f]indazol-1-yl 3-methylbutanoate The compound was prepared from Intermediate 85 and 2-bromoacetonitrile according to the procedure described in Example 109.

$^1$H NMR (400 MHz, DMSO-d$_6$) δ 7.51 (m, 2H), 7.47 (s, 1H), 7.35 (m, 2H), 6.14 (s, 1H), 4.60 (s, 1H), 4.40 (s, 1H), 4.05 (d, 1H), 3.96 (d, 1H), 2.94 (d, 1H), 2.79 (m, 1H), 2.64 (m, 1H), 2.24 (m, 5H), 1.95 (m, 5H), 1.73 (m, 1H), 1.59 (m, 1H), 1.37 (m, 1H), 1.27 (s, 3H), 1.12 (m, 1H), 1.00 (m, 1H), 0.92 (d, 3H), 0.91 (d, 3H), 0.90 (s, 3H). APCI-MS m/z: 606 [MH$^+$].

Example 113

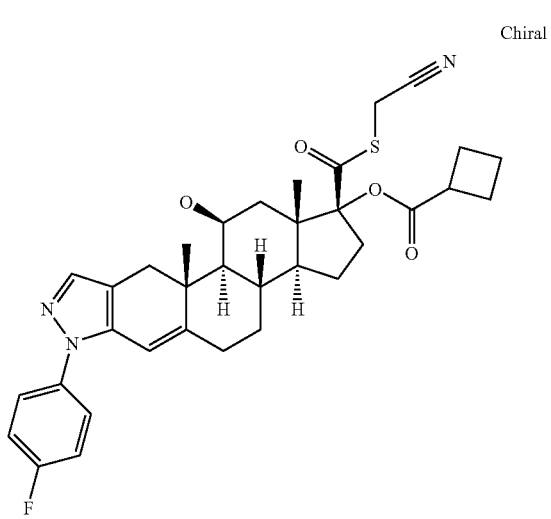

(1R,3aS,3bS,10aR,10bS,11S,12aS)-1-{[(Cyanom-
ethyl)sulfanyl]carbonyl}-7-(4-fluorophenyl)-11-hy-
droxy-10a,12a-dimethyl-1,2,3,3a,3b,4,5,7,10,10a,
10b,11,12,12a-tetradecahydrocyclopenta[5,6]
naphtho[1,2-f]indazol-1-yl cyclobutanecarboxylate The compound was prepared from Intermediate 86 and 2-bromoacetonitrile according to the procedure described in Example 109.

$^1$H NMR (400 MHz, CDCl$_3$) δ 7.69 (s, 1H), 7.51 (m, 2H), 7.24 (m, 2H), 6.00 (d, 1H), 4.56 (d, 1H), 3.80 (d, 3H), 3.57 (d, 2H), 3.20 (m, 1H), 2.98 (m, 1H), 2.75 (m, 1H), 3.09 (1, 1H), 2.56 (t, 1H), 2.39-1.78 (m, 7H), 1.76-1.55 (m, 3H), 1.56-1.43 (m, 2H), 1.38 (s, 3H), 1.30-1.08 (m, 2H), 1.04 (s, 3H). APCI-MS m/z: 604 [MH$^+$].

Example 114

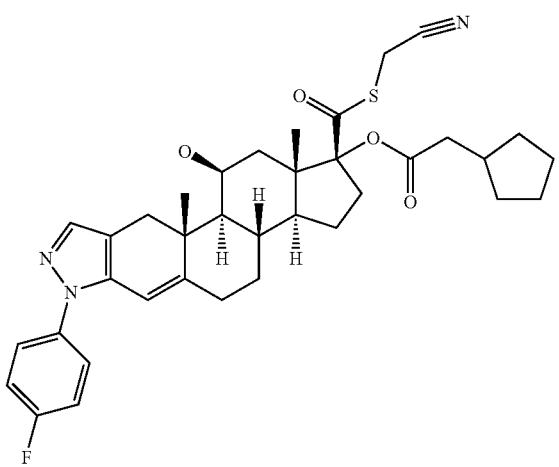

(1R,3aS,3bS,10aR,10bS,11S,12aS)-1-{[(Cyanom-
ethyl)sulfanyl]carbonyl}-7-(4-fluorophenyl)-11-hy-
droxy-10a,12a-dimethyl-1,2,3,3a,3b,4,5,7,10,10a,
10b,11,12,12a-tetradecahydrocyclopenta[5,6]
naphtho[1,2-f]indazol-1-yl cyclopentylacetate The compound was prepared from Intermediate 87 and 2-bromoacetonitrile according to the procedure described in Example 109
APCI-MS m/z: 632 [MH$^+$].

Example 115

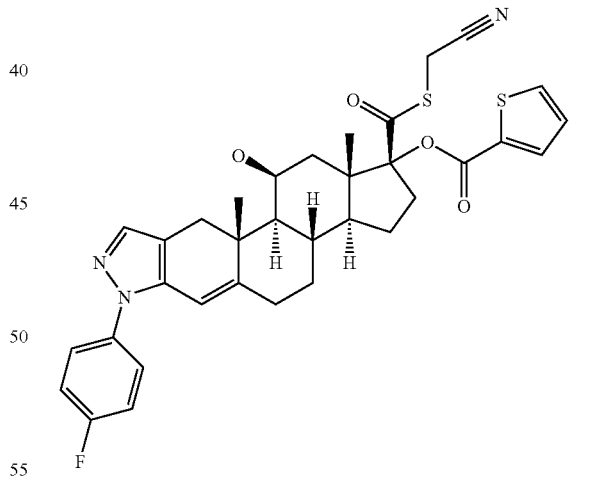

(1R,3aS,3bS,10aR,10bS,11S,12aS)-1-{[(Cyanom-
ethyl)sulfanyl]carbonyl}-7-(4-fluorophenyl)-11-hy-
droxy-10a,12a-dimethyl-1,2,3,3a,3b,4,5,7,10,10a,
10b,11,12,12a-tetradecahydrocyclopenta[5,6]
naphtho[1,2-f]indazol-1-yl thiophene-2-carboxylate The compound was prepared from Intermediate 88 and 2-bromoacetonitrile according to the procedure described in Example 109.
APCI-MS m/z: 632 [MH$^+$].

Example 116

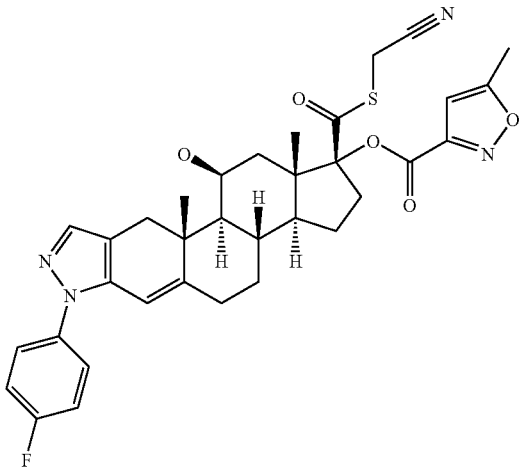

(1R,3aS,3bS,10aR,10bS,11S,12aS)-1-{[(Cyanomethyl)sulfanyl]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 5-methylisoxazole-3-carboxylate The compound was prepared from Intermediate 89 and 2-bromoacetonitrile according to the procedure described in Example 109.

$^1$H NMR (400 MHz, DMSO-d6) δ 7.51 (m, 2H), 7.47 (s, 1H), 7.34 (m, 2H), 6.76 (s 1H), 6.16 (s, 1H), 4.40 (s, 1H), 4.00 (d, 2H), 2.93 (d, 1H), 2.77 (m, 1H), 2.63 (m, 1H), 2.48, (s, 3H), 2.41 (d, 1H), 2.30 (m, 1H), 2.06 (s, 4H), 1.89 (m, 5H), 1.74 (m, 1H), 1.60 (m, 1H), 1.37 (m, 1H), 1.23 (s, 3H), 1.13 (m, 1H), 1.02 (m, 1H), 0.89 (s, 3H). APCI-MS m/z: 631 [MH$^+$].

Example 117

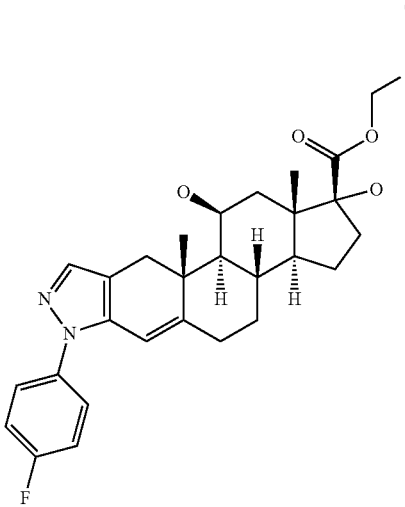

(Methylsulfanyl)methyl(1R,3aS,3bS,10aR,10bS,11S,12aS)-7-(4-fluorophenyl)-1,11-dihydroxy-10a,12a-dimethyl-1,2,3,3a,3b,4,5,7,10,10a,10b,11,12,12a-tetradecahydrocyclopenta[5,6]naphtho[1,2-f]indazole-1-carboxylate Intermediate 1 (0.2 g, 0.43 mmol) was dissolved in acetonitrile (10 ml) and triethylamine (0.178 ml, 1.29 mmol) was added followed by (chloromethyl)(methyl)sulfane (0.106 ml, 1.29 mmol). The resulting solution was heated under reflux for 16 hours. The solvent was removed under reduced pressure and the mixture was dissolved in EtOAc (15 ml), washed with 1N HCl (15 ml) and brine (10 ml) and dried over Na$_2$SO$_4$. After filtration and removal of the solvent under reduced pressure, the mixture was purified on a preparative HPLC column (CH$_3$CN/water) and the product containing fractions were freeze-dried to give 41 mg of the title compound.

$^1$H NMR (400 MHz, CDCl$_3$) δ 7.48 (m, 3H), 7.17 (m, 2H), 6.10 (s, 1H), 5.25 (dd, 2H), 4.59 (s, 1H), 3.01 (d, 1H), 2.71 (m, 3H), 2.51 (m, 1H), 2.29 (m, 4H), 2.03-1.64 (m, 6H), 1.45 (m, 3H), 1.35 (s, 3H), 1.24 (dd, 1H), 1.14 (m, 1H), 1.09 (s, 3H). APCI-MS m/z: 627 [MH$^+$].

Example 118

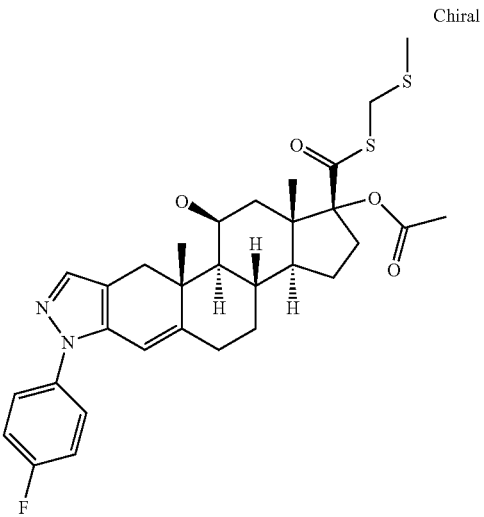

(1R,3aS,3bS,10aR,10bS,11S,12aS)-7-(4-Fluorophenyl)-11-hydroxy-10a,12a-dimethyl-1-({[(methylsulfanyl)methyl]sulfanyl}carbonyl)-1,2,3,3a,3b,4,5,7,10,10a,10b,11,12,12a-tetradecahydrocyclopenta[5,6]naphtho[1,2-f]indazol-1-yl acetate To a solution of intermediate 83 (0.1 g, 0.19 mmol) in dioxane (1 ml) N-ethyl-N-isopropylpropan-2-amine (0.095 ml, 0.57 mmol) was added with stirring. After 5 min. (chloromethyl)(methyl)sulfane (0.031 ml, 0.38 mmol) was added and the mixture was stirred for 60 min. Acetonitrile (1 ml) and water (200 μl) were added, the mixture was purified on a preparative HPLC column (CH$_3$CN/water) and the product containing fractions were freeze-dried to give 5 mg of the title compound.

$^1$H NMR (400 MHz, DMSO-d6) δ 7.51 (m, 2H), 7.47 (s, 1H), 7.34 (m, 2H), 6.16 (s, 1H), 4.40 (s, 1H), 4.08 (s 2H), 2.93 (d, 1H), 2.77 (m, 1H), 2.63 (m, 1H), 2.41 (d, 1H), 2.30 (m, 1H), 2.1 (s, 3H) 2.06 (m, 4H), 1.89 (m, 5H), 1.74 (m, 1H), 1.60 (m, 1H), 1.37 (m, 1H), 1.22 (s, 3H), 1.12 (m, 1H), 1.00 (m, 1H), 0.89 (s, 3H). APCI-MS m/z: 585 [MH$^+$].

Example 119

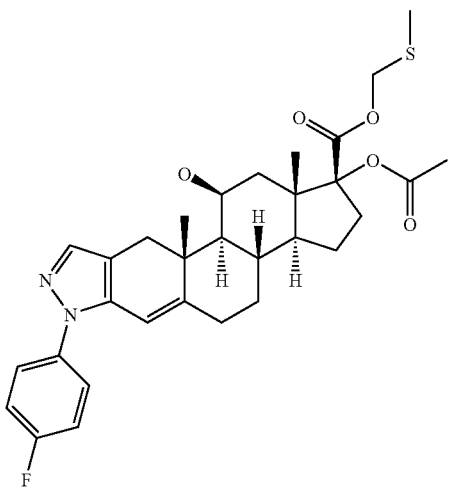

(Methylsulfanyl)methyl(1R,3aS,3bS,10aR,10bS,11S,12aS)-1-(acetyloxy)-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazole-1-carboxylate The compound was prepared from Intermediate 83 and (chloromethyl)methylsulfane according to the procedure for Example 118.

$^1$H NMR (400 MHz, CDCl$_3$) δ 7.64 (s, 1H), 7.53 (m, 2H), 7.22 (m, 2H), 6.07 (s, 1H), 5.20 (dd, 1H), 5.20 (dd, 2H), 4.62 (s, 1H), 3.07 (d, 1H), 2.97 (m, 1H), 2.75 (d, 1H), 2.75 (d, 1H), 2.66 (d, 1H), 2.54 (m, 1H), 2.34 (d, 1H), 2.29 (s, 3H), 2.18-1.63 (m, 8H), 1.48 (m, 1H), 1.37 (s, 3H), 1.29 (dd, 1H), 1.15 (m, 1H), 1.09 (s, 3H). APCI-MS m/z: 569 [MH$^+$].

Example 120

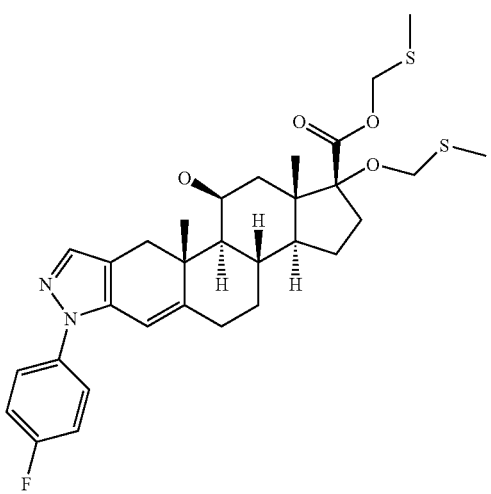

(Methylsulfanyl)methyl(1R,3aS,3bS,10aR,10bS,11S,12aS)-7-(4-fluorophenyl)-11-hydroxy-10a,12a-dimethyl-1-[(methylsulfanyl)methoxy]-1,2,3,3a,3b,4,5,7,10,10a,10b,11,12,12a-tetradecahydrocyclopenta[5,6]naphtho[1,2-f]indazole-1-carboxylate Intermediate 91 (0.1 g, 0.15 mmol) was dissolved in methanol (8 ml). Sodium hydrogen carbonate (0.018 g, 0.22 mmol) and 3 drops of water were added while stirring and the mixture was heated to 60° C. for 4 hours. After removal of the solvent in vacuo, acetonitrile (1 ml) and water (200 µl) were added and the mixture was purified on a preparative HPLC column (CH$_3$CN/water) to give after freeze-drying of the product containing fractions 70 mg of the title compound.

$^1$H NMR (400 MHz, CDCl$_3$) δ 7.48 (m, 2H), 7.45 (s, 1H), 7.17 (m, 2H), 6.08 (s, 1H), 5.23 (m, 2H), 4.52 (d, 1H), 4.43 (m, 2H), 2.98 (d, 1H), 2.69 (d, 1H), 2.51 (m, 2H), 2.32 (s, 3H), 2.24 (m, 1H), 2.20 (s, 3H), 2.04-1.69 (m, 4H), 2.04-1.69 (m, 4H), 1.46 (m, 1H), 1.35 (s, 3H), 1.27 (m, 1H), 1.10 (m, 1H), 1.04 (s, 3H). APCI-MS m/z: 587 [MH$^+$].

Example 121

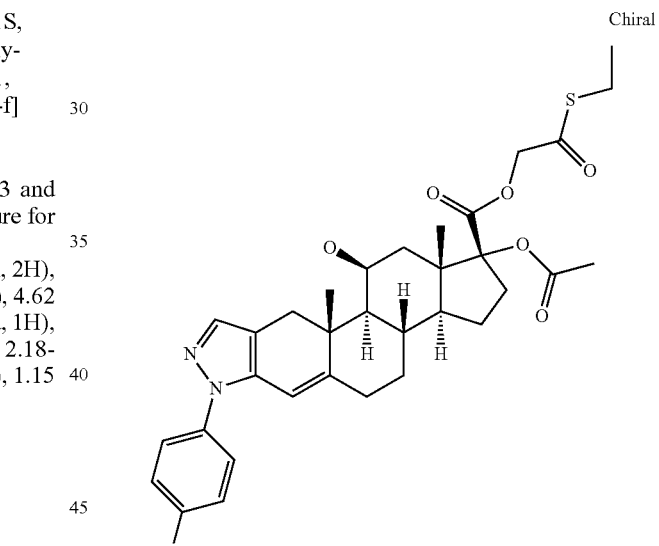

2-(Ethylsulfanyl)-2-oxoethyl(1R,3aS,3bS,10aR,10bS,11S,12aS)-1-(acetyloxy)-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazole-1-carboxylate To a stirred solution of 2-bromoacetyl bromide (0.052 ml, 0.59 mmol) in diethyl ether (12 ml) was added ethanethiol (0.015 ml, 0.20 mmol) at −25° C. under argon and warmed up to room temperature. The reaction mixture was stirred at 25° C. for another 4 hours, washed with sat. NaHCO$_3$ (20 ml) and the organic phase was separated, dried over sodium sulfate, filtered and the solvent was removed in vacuo and the obtained liquid residue was used immediately without further purification.

To Intermediate 92 (0.1 g, 0.20 mmol) in dioxane (2 ml) N-ethyl-N-isopropyl propan-2-amine (0.098 ml, 0.59 mmol) was added with stirring. After 10 min. the crude S-ethyl bromoethanethiolate (prepared above) in dioxane (0.5 ml) was added and the mixture was stirred at room temperature overnight. Acetonitrile (2 ml) and water (100 µl) were added and the mixture was purified on a preparative XBridge column (CH₃CN/water/NH₃ 0.1%) to give after freeze-drying of the product containing fractions 15 mg of the title compound.

¹H NMR (400 MHz, DMSO-d6) δ 7.52 (m, 2H), 7.49 (s, 1H), 7.35 (m, 2H), 6.15 (s, 1H), 4.75 (m, 2H), 4.59 (d, 1H), 4.41 (d, 1H), 2.98 (m, 3H), 2.86 (m, 1H), 2.70 (d, 1H), 2.42 (m, 1H), 2.29 (m, 1H), 2.20 (s, 3H), 2.06 (m, 2H), 1.91 (m, 3H), 1.78 (m 1H), 1.69 (m 1H), 1.42 (m, 1H), 1.29 (d, 1H), 1.23 (s, 3H), 1.12 (t, 3H), 1.04 (m, 1H), 0.90 (s, 3H). APCI-MS m/z: 611 [MH⁺].

Example 122

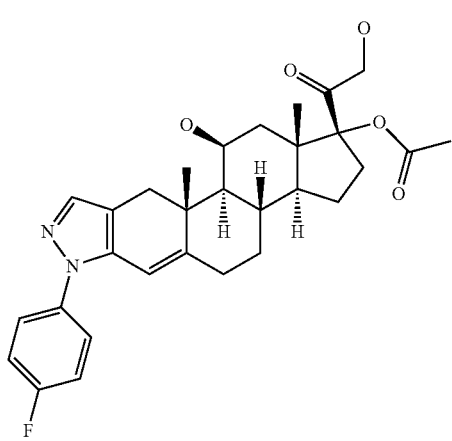

(1R,3aS,3bS,10aR,10bS,11S,12aS)-7-(4-Fluorophenyl)-11-hydroxy-1-(hydroxyacetyl)-10a,12a-dimethyl-1,2,3,3a,3b,4,5,7,10,10a,10b,11,12,12a-tetradecahydrocyclopenta[5,6]naphtho[1,2-f]indazol-1-yl acetate According to the literature (*Chem. Pharm. Bull.* 2006, 54(11), 1567-1570) pyridine 4-methylbenzenesulfonate (0.034 g, 0.14 mmol) and 1,1,1-trimethoxyethane (0.136 ml, 1.06 mmol) were added to a solution of 1-[(1R,3aS,3bS,10aR,10bS,11S,12aS)-7-(4-fluorophenyl)-1,11-dihydroxy-10a,12a-dimethyl-1,2,3,3a,3b,4,5,7,10,10a,10b,11,12,12a-tetradecahydrocyclopenta[5,6]naphtho[1,2-f]indazol-1-yl]-2-hydroxyethanone (*Steroids* 2003 (68) 177-191) (0.34 g, 0.71 mmol) in DCM (15 ml). The mixture was stirred at room temperature for 4 hours, concentrated under reduced pressure, the obtained residue was dissolved in acetone (10 ml) and 4-methyl benzenesulfonic acid hydrate (0.21 g, 1.10 mmol) dissolved in water (10 ml) was added while cooling in an ice-bath. The mixture was stirred for 60 min. at the same temperature followed by the addition of sat. NaHCO₃ solution (15 ml) and subsequent extraction with EtOAc (30 ml). The organic layer was washed with brine, dried and purified on a preparative HPLC column (CH₃CN/water) and the product containing fractions were freeze-dried to give 60 mg of the title compound.

¹H NMR (400 MHz, DMSO-d₆) δ 7.51 (m, 2H), 7.47 (s, 1H), 7.34 (m, 2H), 6.11 (s, 1H), 4.99 (t, 1H), 4.42 (d, 1H), 4.10 (dd, 1H), 2.94 (d, 1H), 2.77 (s, 1H), 2.64 (d, 1H), 2.43 (d, 2H), 2.28 (m, 1H), 2.04 (s, 3H), 1.90 (2, 2H), 1.77-1.54 (m, 6H), 1.35 (m, 1H), 1.25 (s, 3H), 1.13 (m, 1H), 1.00 (m, 1H), 0.87 (s, 3H). APCI-MS m/z: 523 [MH⁺].

Example 123

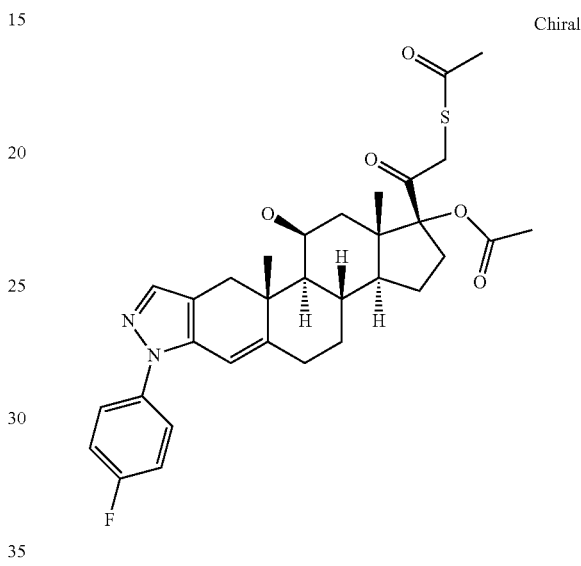

(1R,3aS,3bS,10aR,10bS,11S,12aS)-1-[(Acetylsulfanyl)acetyl]-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl acetate Potassium ethanethioate (0.019 g, 0.17 mmol) was added to a solution of Intermediate 93 (0.05 g, 0.08 mmol) in acetone (5 ml) and MeOH (1 ml). The mixture was heated under reflux for 150 min. After cooling to room temperature the solvents were removed in vacuo and the residue was redissolved in EtOAc (15 ml) and washed with a saturated solution of NaHCO₃, 1N HCl and brine. After drying over sodium sulfate the mixture was purified on a preparative HPLC column (CH₃CN/water) to give after freeze-drying of the product containing fractions 5 mg of the title compound.

¹H NMR (400 MHz, DMSO-d6) δ 7.52 (m, 2H), 7.49 (s, 1H), 7.35 (m, 2H), 6.15 (s, 1H), 4.59 (d, 1H), 4.41 (d, 1H), 3.83 (dd, 2H), 2.98 (d, 1H), 2.86 (m, 1H), 2.70 (d, 1H), 2.42 (m, 1H), 2.49, (s 3H), 2.29 (m, 1H), 2.06 (s, 3H) 2.03 (m, 2H), 1.91 (m, 3H), 1.78 (m, 1H), 1.69 (m, 1H), 1.42 (m, 1H), 1.29 (d, 1H), 1.26 (s, 3H), 1.04 (m, 1H), 0.98 (s, 3H). APCI-MS m/z: 581 [MH⁺].

Example 124

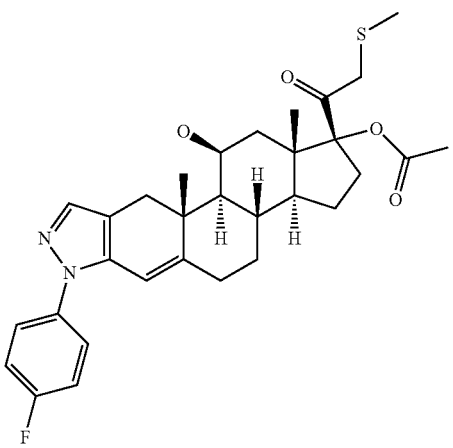

(1R,3aS,3bS,10aR,10bS,11S,12aS)-7-(4-Fluorophenyl)-11-hydroxy-10a,12a-dimethyl-1-[(methylsulfanyl)acetyl]-1,2,3,3a,3b,4,5,7,10,10a,10b,11,12,12a-tetradecahydrocyclopenta[5,6]naphtho[1,2-f]indazol-1-yl acetate The compound was prepared from Intermediate 93 and sodium methane thiolate according to the procedure for Example 123.

$^1$H NMR (400 MHz, DMSO-d$_6$) δ 7.52 (m, 2H), 7.49 (s, 1H), 7.35 (m, 2H), 6.15 (s, 1H), 4.59 (d, 1H), 4.41 (d, 1H), 3.42 (dd, 2H), 2.98 (d, 1H), 2.86 (m, 1H), 2.70 (d, 1H), 2.42 (m, 1H), 2.29 (m, 1H), 2.08 (s, 3H), 2.05 (s, 3H) 2.01 (m, 2H), 1.91 (m, 3H), 1.78 (m, 1H), 1.69 (m, 1H), 1.42 (m, 1H), 1.29 (d, 1H), 1.26 (s, 3H), 1.04 (m, 1H), 0.98 (s, 3H). APCI-MS m/z: 553 [MH$^+$].

Example 125

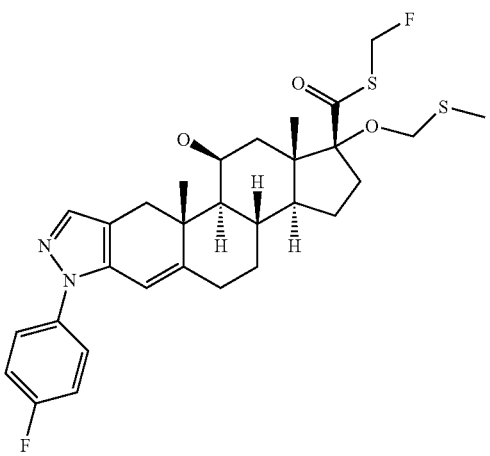

S-(Fluoromethyl)(1R,3aS,3bS,10aR,10bS,11S,12aS)-7-(4-fluorophenyl)-11-hydroxy-10a,12a-dimethyl-1-[(methylsulfanyl)methoxy]1,2,3,3a,3b,4,5,7,10,10a,10b,11,12,12a-tetradecahydrocyclopenta[5,6]naphtho[1,2-f]indazole-1-carbothioate Intermediate 96 (0.005 g, 7.45 μmol) was dissolved in methanol (2 ml) and sodium hydrogencarbonate (0.689 mg, 8.20 μmol) was added. The mixture was stirred at 40° C. for 6 hours and the solvent was evaporated under reduced pressure. The obtained residue was dissolved in EtOAc (10 ml) and washed with 1N HCl (5 ml). The organic phase was dried, evaporated under reduced pressure and purified on a preparative HPLC column (CH$_3$CN/water) and the product containing fractions were freeze-dried to give 4 mg of the title compound.

$^1$H NMR (400 MHz, DMSO-d6) δ 7.52 (m, 2H), 7.49 (s, 1H), 7.35 (m, 2H), 6.15 (s, 1H), 4.59 (d, 1H), 4.41 (d, 1H), 2.98 (d, 1H), 2.86 (m, 1H), 2.70 (d, 1H), 2.42 (m, 1H), 2.29 (m, 1H), 2.06 (m, 2H), 1.91 (m, 3H), 1.78 (m, 1H), 1.69 (m, 1H), 1.42 (m, 1H), 1.29 (d, 1H), 1.26 (s, 3H), 1.04 (m, 1H), 0.98 (s, 3H). APCI-MS m/z: 575 [MH$^+$].

Example 126

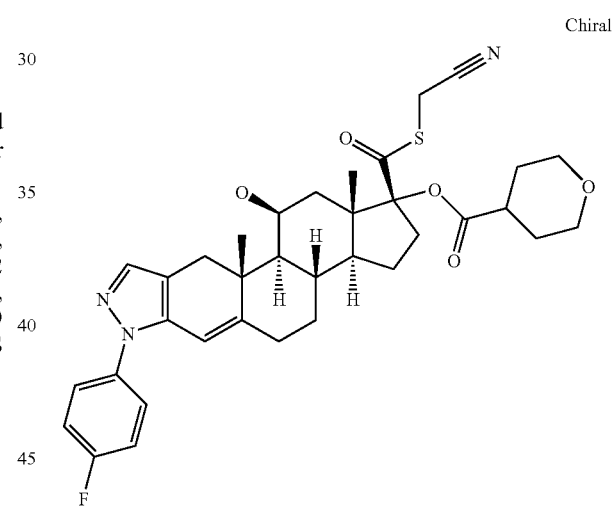

(1R,3aS,3bS,10aR,10bS,11S,12aS)-1-{[(Cyanomethyl)sulfanyl]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl tetrahydro-2H-pyran-4-carboxylate The compound was prepared from Intermediate 97 and 2-bromoacetonitrile according to the procedure described in Example 109.

$^1$H NMR (400 MHz, DMSO-d$_6$) δ 7.52 (m, 2H), 7.49 (s, 1H), 7.35 (m, 2H), 6.15 (s, 1H), 4.59 (d, 1H), 4.41 (d, 1H), 4.00 (d, 2H), 3.82 (m, 2H), 3.36 (m, 2H), 2.98 (d, 1H), 2.86 (m, 1H), 2.70 (m, 2H), 2.42 (m, 1H), 2.29 (m, 1H), 2.06 (m, 2H), 1.91 (m, 3H), 1.78 (m, 5H), 1.69 (m, 1H), 1.42 (m, 1H), 1.29 (d, 1H), 1.26 (s, 3H), 1.04 (m, 1H), 0.98 (s, 3H). APCI-MS m/z: 634 [MH$^+$].

Example 127

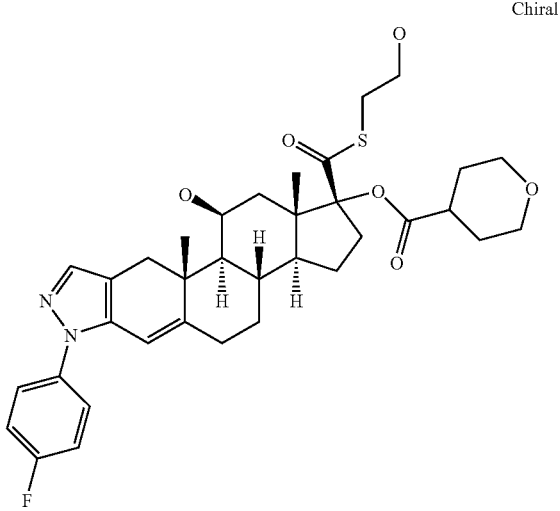

(1R,3aS,3bS,10aR,10bS,11S,12aS)-7-(4-Fluorophenyl)-11-hydroxy-1-{[(2-hydroxyethyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl tetrahydro-2H-pyran-4-carboxylate The compound was prepared from Intermediate 97 and 2-bromoethanol according to the procedure described in Example 109.

$^1$H NMR (400 MHz, DMSO-d$_6$) δ 7.52 (m, 2H), 7.49 (s, 1H), 7.35 (m, 2H), 6.15 (s, 1H), 4.93 (m, 1H), 4.59 (d, 1H), 4.41 (d, 1H), 3.82 (m, 2H), 3.43 (m, 2H), 3.35 (m, 2H), 2.93 (m, 3H), 2.79 (m, 1H), 2.64 (m, 2H), 2.42 (m, 1H), 2.29 (m, 1H), 2.06-1.66 (m, 8H), 1.58 (m, 3H), 1.34 (d, 1H), 1.22 (s, 3H), 1.15 (m, 1H) 1.03 (m, 1H), 0.85 (s, 3H). APCI-MS m/z: 639 [MH$^+$].

Example 128

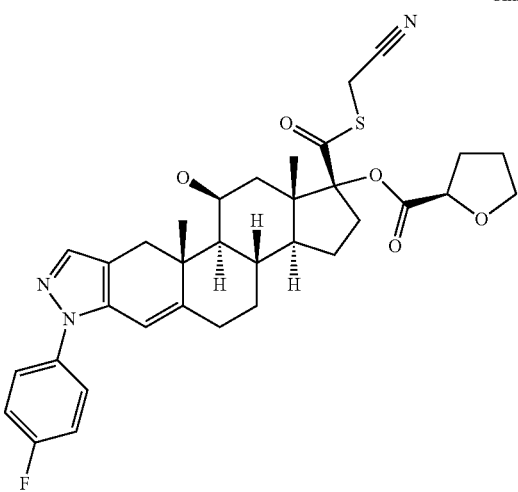

(1R,3aS,3bS,10aR,10bS,11S,12aS)-1-{[(Cyanomethyl)sulfanyl]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl (2R)-tetrahydrofuran-2-carboxylate The compound was prepared from Intermediate 98 and 2-bromoacetonitrile according to the procedure described in Example 109. The two isomers were separated on a Kromasil® C$_{18}$ HPLC column and the first eluting peak was analyzed.

$^1$H NMR (500 MHz, DMSO-d$_6$) δ 7.51 (m, 2H), 7.47 (s, 1H), 7.34 (m, 2H), 6.12 (d, 1H), 4.59 (s, 1H), 4.47 (dd, 1H), 4.36 (d, 1H), 4.06 (d, 1H), 3.97 (d, 1H), 3.81 (t, 1H), 2.95 (d, 1H), 2.79 (dd, 1H), 2.64 (m, 1H), 2.52 (m, 1H), 2.43 (m, 1H), 2.29 (m, 1H), 2.19 (m, 2H), 2.01-1.69 (m, 8H), 1.56 (m, 1H), 1.39 (m, 1H), 1.26 (s, 3H), 1.12 (m, 1H), 1.02 (m, 1H), 0.94 (s, 3H). APCI-MS m/z: 620 [MH$^+$].

Example 129

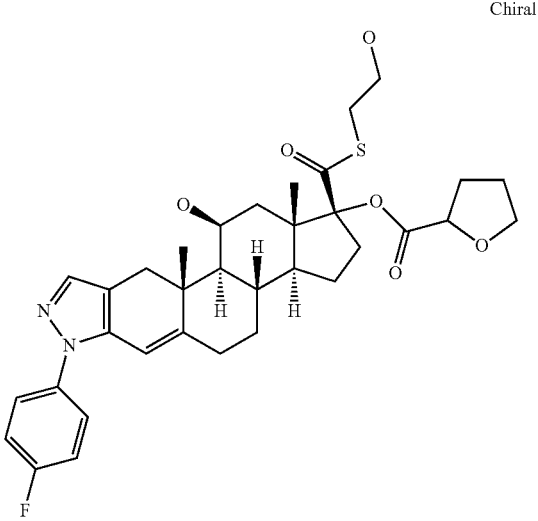

(1R,3aS,3bS,10aR,10bS,11S,12aS)-7-(4-Fluorophenyl)-11-hydroxy-1-{[(2-hydroxyethyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl tetrahydrofuran-2-carboxylate The compound was prepared from Intermediate 98 and 2-bromoethanol according to the is procedure described in Example 109.

$^1$H NMR (400 MHz, DMSO-d$_6$) δ 7.52 (m, 2H), 7.49 (s, 1H), 7.35 (m, 2H), 6.15 (s, 1H), 4.46 (m, 2H), 4.36 (d, 1H), 3.79 (m, 2H), 3.43 (m, 2H), 2.93 (m, 3H), 2.79 (m, 1H), 2.64 (m, 1H), 2.42 (m, 1H), 2.29 (m, 1H), 2.14 (m, 3H), 2.00-1.70 (m, 7H), 1.58 (m, 1H), 1.34 (m, 1H), 1.22 (s, 3H), 1.11 (m, 1H) 1.00 (m, 1H), 0.86 (s, 3H). APCI-MS m/z: 625 [MH$^+$].

Example 130

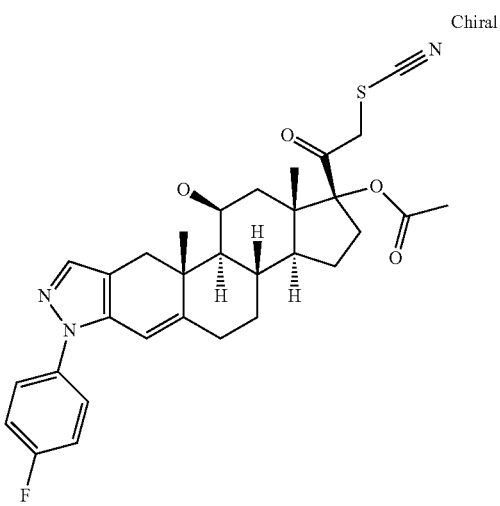

(1R,3aS,3bS,10aR,10bS,11S,12aS)-7-(4-Fluorophenyl)-11-hydroxy-10a,12a-dimethyl-1-(thiocyanatoacetyl)-1,2,3,3a,3b,4,5,7,10,10a,10b,11,12,12a-tetradecahydrocyclopenta[5,6]naphtho[1,2-f]indazol-1-yl acetate To a solution of Intermediate 93 (0.05 g, 0.08 mmol) in DMF (2 ml), potassium thiocyanate (0.053 ml, 1.03 mmol) was added and the mixture was stirred at 105° C. overnight. After cooling acetonitrile (1 ml) and water (1 ml) were added and the mixture was purified on a preparative HPLC column (CH₃CN/water) and the product containing fractions were freeze-dried to give 22 mg of the title compound.
$^1$H NMR (400 MHz, CDCl$_3$) δ 7.68 (s, 1H), 7.49 (m, 2H), 7.23 (m, 2H), 6.03 (s, 1H), 4.59 (s, 1H), 4.23 (d, 1H), 4.06 (d, 1H), 3.07 (d, 1H), 2.88 (m, 1H), 2.73 (m, 1H), 2.55 (t, 1H), 2.33 (d, 1H), 2.17 (m, 2H), 2.14 (s, 3H), 2.09-1.65 (m, 6H), 1.50 (m, 1H), 1.38 (s, 3H), 1.28 (m, 1H), 1.14 (m, 1H), 1.02 (s, 3H). APCI-MS m/z: 564 [MH⁺].

Example 131

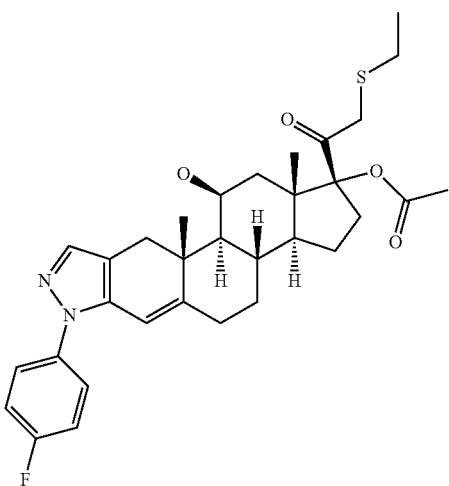

(1R,3aS,3bS,10aR,10bS,11S,12aS)-1-[(Ethylsulfanyl)acetyl]-7-(4-fluoro phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl acetate To ethanethiol (50 µl, 0.68 mmol) in dry THF (1 ml) under argon at 4° C. sodium (0.015 g, 0.67 mmol) was added and the reaction was stirred for 60 min. The obtained solution was then added at room temperature to a solution of Intermediate 93 (0.025 g, 0.04 mmol) in acetone (2 ml) and stirred for 60 min. The solvent was evaporated under reduced pressure and acetonitrile (1 ml) and water (1 ml) were added followed by purification on a preparative HPLC column (CH₃CN/water). The product containing fractions were freeze-dried to give 10 mg of the title compound.
$^1$H NMR (300 MHz, CDCl$_3$) δ 7.75 (s, 1H), 7.52 (m, 2H), 7.24 (m, 2H), 6.02 (s, 1H), 4.58 (s, 1H), 3.43 (d, 1H), 3.31 (d, 1H), 3.09 (d, 1H), 2.97 (dd, 1H), 2.72 (m, 5H), 2.56 (d, 1H), 2.34 (m, 1H), 2.09 (m, 7H), 1.78 (m, 3H), 1.46 (m, 1H), 1.38 (s, 3H), 1.28 (t, 2H), 1.12 (m, 1H), 1.04 (s, 3H). APCI-MS m/z: 567 [MH⁺].

Example 132

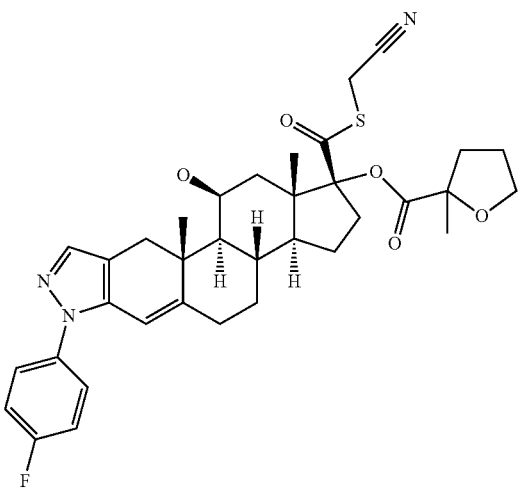

(1R,3aS,3bS,10aR,10bS,11S,12aS)-1-{[(Cyanomethyl)sulfanyl]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2]-indazol-1-yl 2-methyltetrahydrofuran-2-carboxylate The compound was prepared from Intermediate 99 and 2-bromoacetonitrile according to the procedure described in Example 109. The isomers were separated on a chiralpak IA column (i-hexane/EtOH=4:1) and the first eluting peak was analyzed.
$^1$H NMR (400 MHz, DMSO-d$_6$) δ 7.51 (m, 2H), 7.40 (s, 1H), 7.34 (m, 2H), 6.10 (s, 1H), 4.64 (s, 1H), 4.41 (s, 1H), 4.07 (d, 1H), 3.97 (d, 1H), 3.83 (m, 2H), 2.96 (d, 1H), 2.80 (t, 1H), 2.80 (m, 1H), 2.80 (m, 1H), 2.42 (m, 1H), 2.33-2.15 (m, 3H), 1.97-1.73 (m, 6H), 1.56 (m, 1H), 1.39 (m, 5H), 1.25 (s, 3H), 1.14 (d, 1H), 1.01 (m, 1H), 0.93 (s, 3H). APCI-MS m/z: 620 [MH⁺].

Example 133

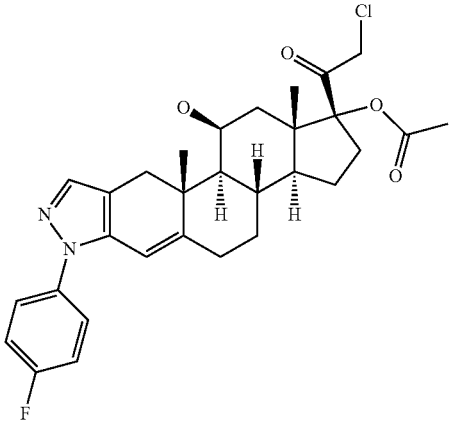

(1R,3aS,3bS,10aR,10bS,11S,12aS)-1-(Chloro-acetyl)-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl acetate According to *Chem. Pharm. Bull.* 1990, 38(3) 692-697 anhydrous lithium chloride (0.020 ml, 1.00 mmol) was added to a solution of Intermediate 93 (0.06 g, 0.10 mmol) in DMF (2 ml) and acetonitrile (1.5 ml). The mixture was heated under reflux for 6 hours then poured into ice-water and extracted with EtOAc. The organic extracts were combined, dried and concentrated in vacuo. The obtained residue was purified on a preparative HPLC column (CH₃CN/water) and the product containing fractions were freeze-dried to give 48 mg of the title compound.

¹H NMR (500 MHz, DMSO-d₆) δ 7.51 (m, 2H), 7.47 (s, 1H), 7.35 (m, 2H), 6.11 (s, 1H), 4.50 (d, 1H), 4.40 (s, 1H), 4.33 (m, 2H), 2.94 (d, 1H), 2.80 (m, 1H), 2.64 (m, 1H), 2.44 (m, 1H), 2.29 (m, 1H), 2.03 (s, 3H), 1.96 (m, 2H), 1.88 (m, 2H), 1.78-1.59 (m, 3H), 1.36 (m, 1H), 1.25 (s, 3H), 1.13 (m, 1H), 1.01 (m, 1H), 0.79 (s, 3H). APCI-MS m/z: 541 and 543 [MH⁺].

Example 134

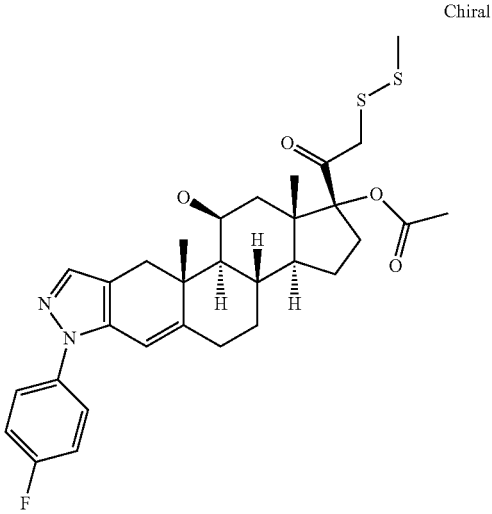

(1R,3aS,3bS,10aR,10bS,11S,12aS)-7-(4-Fluorophenyl)-11-hydroxy-10a,12a-dimethyl-1-[(methyldisulfanyl)acetyl]-1,2,3,3a,3b,4,5,7,10,10a,10b,11,12,12a-tetradecahydrocyclopenta[5,6]naphtho[1,2-f]indazol-1-yl acetate To Intermediate 100 (0.005 g, 9.28 mmol) in DCM (2 ml), 2-(methylthio)isoindoline-1,3-dione (*Tetrahedron*, 1997, 53(42) 14411-14416) (5 mg, 0.03 mmol) was added and the mixture was stirred at room temperature for 8 hours. The solvent was evaporated under reduced pressure, acetonitrile (1 ml) and water (1 ml) were added and the mixture was purified on a preparative HPLC column (CH₃CN/water) and the product containing fractions were freeze-dried to give 2 mg of the title compound.

¹H NMR (500 MHz, DMSO-d₆) δ 7.52 (m, 2H), 7.47 (s, 1H), 7.35 (m, 2H), 6.11 (s, 1H), 4.44 (s, 1H), 4.34 (s, 1H), 3.88 (d, 1H), 3.76 (d, 1H), 2.94 (d, 1H), 2.80 (t, 1H), 2.64 (m, 3H), 2.46 (s, 2H), 2.41 (m, 1H), 2.29 (m, 1H), 2.09 (s, 3H), 2.00 (m, 1H), 1.87 (m, 1H), 1.68 (m, 3H), 1.32 (m, 2H), 1.20 (s, 3H), 1.05 (m, 2H), 0.88 (s, 3H). APCI-MS m/z: 585 [MH⁺].

Example 135

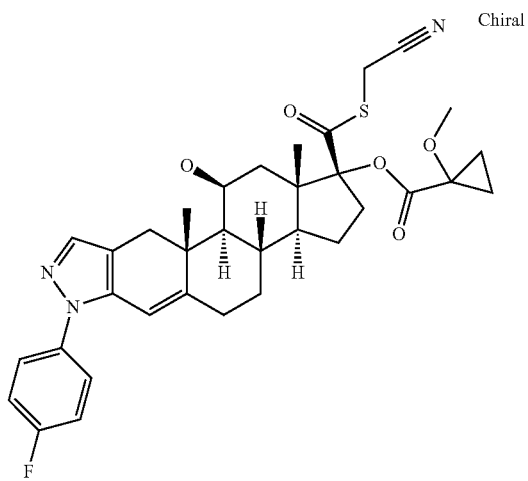

(1R,3aS,3bS,10aR,10bS,11S,12aS)-1-{[(Cyanomethyl)sulfanyl]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 1-methoxycyclopropanecarboxylate The compound was prepared from Intermediate 103 and bromoacetonitrile according to the procedure for Example 109.

¹H NMR (500 MHz, DMSO-d₆) δ 7.51 (m, 2H), 7.46 (s, 2H), 7.34 (m, 2H), 6.11 (s, 1H), 4.59 (s, 1H), 4.36 (d, 2H), 4.08 (1, 3H), 3.98 (d, 4H), 3.33 (d, 4H), 2.95 (d, 1H), 2.81 (dd, 1H), 2.65 (m, 2H), 2.43 (m, 2H), 2.28 (m, 1H), 1.96-1.83 (m, 6H), 1.82-1.73 (m, 3H), 1.52 (m, 1H), 1.38 (m, 1H), 1.29-1.18 (m, 9H), 1.14 (dd, 2H), 0.89 (s, 3H). APCI-MS m/z: 620 [MH⁺].

Example 136

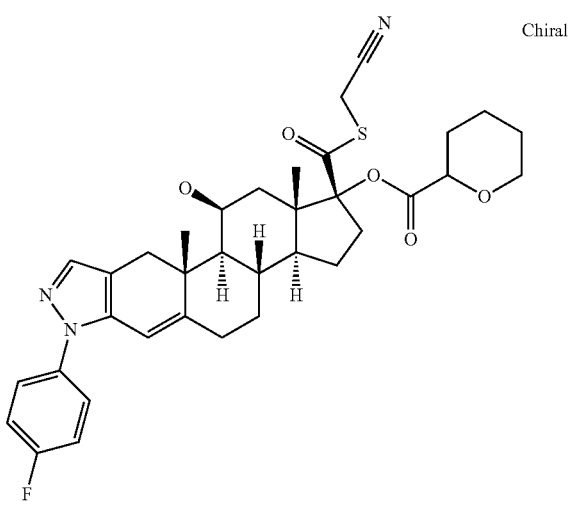

(1R,3aS,3bS,10aR,10bS,11S,12aS)-1-{[(Cyanomethyl)sulfanyl]carbonyl}-7-(4-fluorophenyl)-11-hydroxy-10a,12a-dimethyl 1,2,3,3a,3b,4,5,7,10,10a,10b,11,12,12a-tetradecahydrocyclopenta[5,6]naphtho[1,2-f]indazol-1-yl tetrahydro-2H-pyran-2-carboxylate The compound was prepared from Intermediate 104 and 2-bromoacetonitrile according to the procedure described in Example 109. The isomers were separated on a Kromasil® $C_{18}$ HPLC column and the first eluting peak was analyzed.

$^1$H NMR (500 MHz, DMSO-$d_6$) δ 7.51 (m, 2H), 7.46 (s, 1H), 7.35 (m, 2H), 6.12 (d, 1H), 4.57 (s, 1H), 4.36 (m, 1H), 4.11 (m, 1H), 4.06 (d, 1H), 3.96 (d, 1H), 3.86 (m, 1H), 3.43 (m, 1H), 2.94 (d, 1H), 2.80 (dd, 1H), 2.65 (d, 1H), 2.51 (m, 1H), 2.43 (m, 1H), 2.29 (m, 1H), 1.94-1.84 (m, 5H), 1.82-1.71 (m, 2H), 1.63-1.53 (m, 3H), 1.49-1.43 (m, 2H), 1.37 (m, 1H), 1.22 (s, 3H), 1.15 (dd, 1H), 1.03 (m, 1H), 0.89 (s, 3H) APCI-MS m/z: 634 [MH$^+$].

Example 137

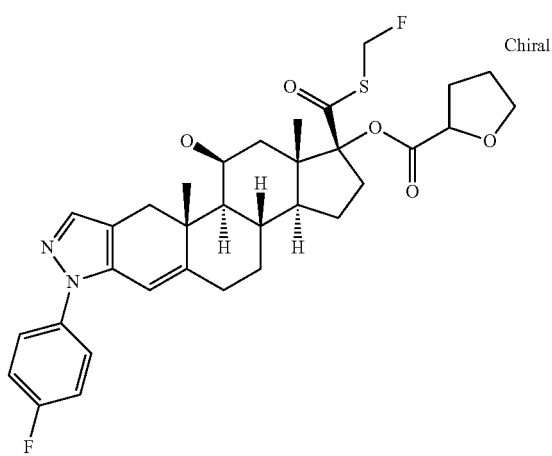

(1R,3aS,3bS,10aR,10bS,11S,12aS)-1-{[(Fluoromethyl)sulfanyl]carbonyl}-7-(4-fluorophenyl)-11-hydroxy-10a,12a-dimethyl-1,2,3,3a,3b,4,5,7,10a,10b,11,12,12a-tetradecahydrocyclopenta[5,6]naphtho[1,2-f]indazol-1-yl (2R)-tetrahydrofuran-2-carboxylate The compound was prepared from intermediate 98 and bromofluoromethane according to the procedure for Example 109.

$^1$H NMR (400 MHz, DMSO-$d_6$) δ 7.52 (m, 2H), 7.49 (s, 1H), 7.35 (m, 2H), 6.15 (s, 1H), 5.94 (d, 2H), 4.52 (m, 2H), 4.36 (d, 1H), 3.79 (m, 2H), 2.93 (m, 1H), 2.80 (m, 1H), 2.64 (m, 1H), 2.41 (m, 1H), 2.35 (m, 1H), 2.06 (m, 1H), 1.98-1.69 (m, 8H), 1.62 (m, 1H), 1.38 (m, 1H), 1.22 (s, 3H), 1.13 (m, 1H) 1.02 (m, 1H), 0.88 (s, 3H). APCI-MS m/z: 613 [MH$^+$].

Example 138

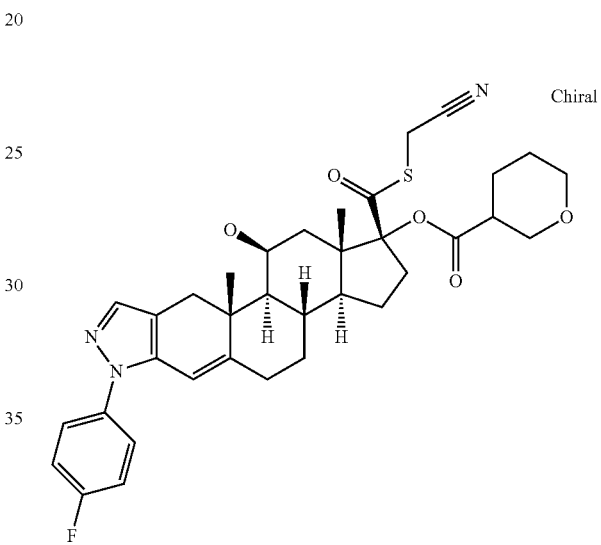

(1R,3aS,3bS,10aR,10bS,11S,12aS)-1-{[(Cyanomethyl)sulfanyl]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl tetrahydro-2H-pyran-3-carboxylate The compound was prepared from Intermediate 105 and 2-bromoacetonitrile according to the procedure described in Example 109. The isomers were separated on a chiralpak IA column (i-hexane/EtOH=3:1) and the first eluting peak was analyzed.

$^1$H NMR (400 MHz, DMSO-$d_6$) δ 7.51 (2H, dd), 7.46 (1H, s), 7.35 (2H, m), 6.11 (1H, s), 4.56 (1H, s), 4.37 (1H, s), 4.05 (1H, dd), 3.95 (1H, d), 3.88 (1H, m), 3.67 (1H, m), 3.51 (1H, m), 3.37 (1H, t), 2.95 (1H, d), 2.78 (1H, m), 2.70-2.59 (2H, m), 2.43 (1H, m), 2.29 (1H, m), 2.02-1.80 (6H, m), 1.79-1.44 (5H, m), 1.37 (1H, m), 1.22 (3H, s), 1.18 (1H, dd), 1.03 (1H, m), 0.89 (3H, s). APCI-MS m/z: 634 [MH$^+$].

Example 139

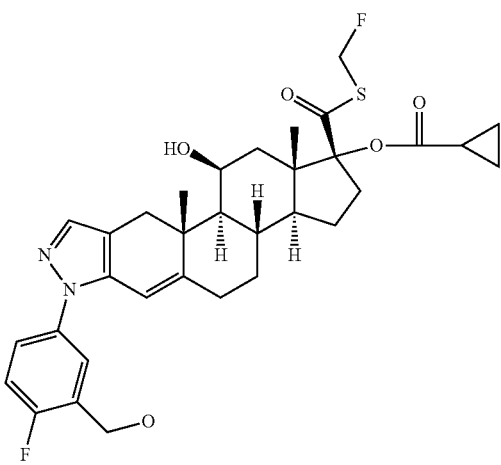

(1R,3aS,3bS,10aR,10bS,11S,12aS)-7-[4-Fluoro-3-(hydroxymethyl)phenyl]-1-{[(fluoromethyl)thio]carbonyl}-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl cyclopropanecarboxylate In a 10 mL vial was dissolved Intermediate 106 (130 mg, 0.11 mmol) in dioxane (1 mL) to give a orange solution. N-ethyl-N-isopropylpropan-2-amine (0.056 mL, 0.34 mmol) and bromofluoromethane (28.1 mg, 0.11 mmol) (45% in DMF) were added, and the mixture was allowed to stand at room temperature for 10 minutes. The solution was diluted with CH$_3$CN (1 ml) and water (1 ml), and was purified on a preparative HPLC column (CH$_3$CN/water). The product containing fractions were freeze-dried, to give 20 mg of the desired compound as a white solid.

$^1$H NMR (400 MHz, CDCl$_3$) δ 7.61 (1H, m), 7.43 (1H, s), 7.41-7.36 (1H, m), 7.15 (1H, t), 6.09 (1H, s); 6.05-5.62 (2H, m), 4.83 (2H, s), 4.58 (1H, bs), 3.07-2.92 (2H, m), 2.73 (1H, d); 2.53 (1H, t), 2.38-2.25 (1H, m), 2.15 (1H, m); 2.07-1.91 (4H, m), 1.91-1.77 (1H, m), 1.75-1.62 (2H, m), 1.52-1.40 (1H, m), 1.33 (3H, s), 1.31-1.24 (1H, m), 1.21-1.12 (1H, m), 1.12-1.02 (3H, m), 1.00 (3H, s), 0.97-0.86 (3H, m). APCI-MS m/z: 613 [MH$^+$].

Example 140

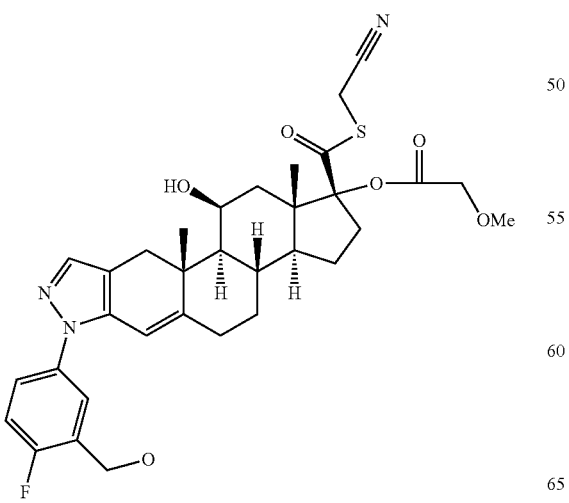

(1R,3aS,3bS,10R,10bS,11S,12aS)-1-{[(Cyanomethyl)thio]carbonyl}-7-[4-fluoro-3-(hydroxymethyl)phenyl]-11a,12a-dimethyl-1,2,3,3a,3b,4,5,7,10,10a,10b,11,12,12a-tetradecahydrocyclopenta[5,6]naphtho[1,2-f]indazol-1-yl Methoxyacetate In a 10 mL Vial was dissolved Intermediate 107 (0.27 g, 0.23 mmol) in dioxane (1 mL) to give an orange solution. N-ethyl-N-isopropylpropan-2-amine (0.153 mL, 0.92 mmol) and 2-bromoacetonitrile (0.069 g, 0.58 mmol) were added, and the mixture was allowed to stand for 10 minutes at room temperature. The obtained solution was concentrated in vacuo and the residue was purified on a preparative HPLC column (CH$_3$CN/water). The product containing fractions were freeze-dried to give 24 mg of the desired compound as a white solid.

$^1$H NMR (400 MHz, CDCl$_3$) δ 7.61 (1H, m), 7.43 (1H, s), 7.41-7.35 (1H, m), 7.15 (1H, t), 6.08 (1H, m), 4.83 (2H, d), 4.57 (1H, bs), 4.07 (2H, s), 3.89 (1H, d), 3.58 (1H, d), 3.47 (3H, s), 3.06-2.96 (2H, m), 2.71 (1H, d), 2.52 (1H, t), 2.30 (1H, d), 2.12-1.79 (6H, m), 1.69-1.58 (1H, m), 1.53-1.42 (1H, m), 1.33 (3H, s), 1.26 (1H, dd), 1.18-1.06 (2H, m), 1.02 (3H, s). APCI-MS m/z: 624 [MH$^+$].

Example 141

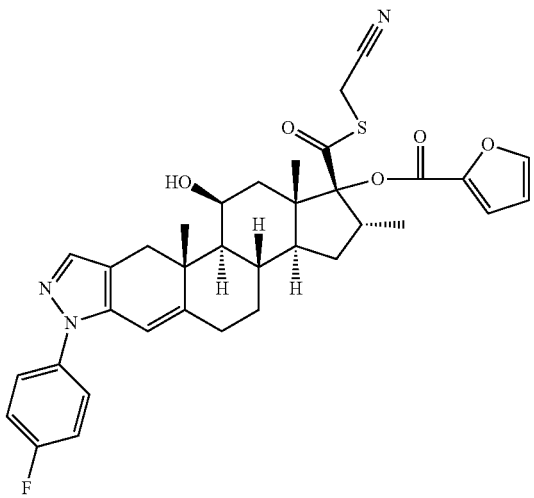

(1R,2R,3aS,3bS,10aR,10bS,11S,12aS)-1-{[(Cyanomethyl)thio]carbonyl}-7-(4-fluorophenyl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl furan-2-carboxylate The compound was prepared from Intermediate 108 and bromoacetonitrile according to the procedure for Example 1.

$^1$H NMR (400 MHz, CDCl$_3$) δ 7.62 (1H, m), 7.47 (2H, m), 7.44 (1H, s), 7.20 (1H, d), 7.17 (1H, t), 6.55 (1H, m), 6.10 (1H, s); 4.60 (1H, bs), 3.74 (2H, m), 3.46-3.36 (1H, m), 3.05 (1H, d), 2.77 (1H, d); 2.53 (1H, t), 2.30 (1H, d), 2.20 (1H, m); 2.09-1.80 (6H, m), 1.50-1.40 (1H, m), 1.34 (3H, s), 1.31 (1H, m), 1.21-1.11 (5H, m), 1.07 (3H, d). APCI-MS m/z: 630 [MH$^+$].

Example 142

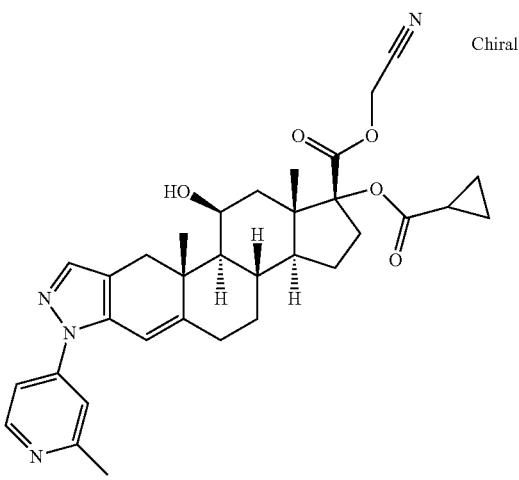

Cyanomethyl(1R,3aS,3bS,10aR,10bS,11S,12aS)-1-[(cyclopropylcarbonyl)oxy]-11-hydroxy-10a,12a-dimethyl-7-(2-methylpyridin-4-yl)-1,2,3,3a,3b,4,5,7,10,10a,10b,11,12,12a-tetradecahydrocyclopenta[5,6]naphtho[1,2-]indazole-1-carboxylate The compound was prepared from Intermediate 132 and 2-bromoacetonitrile according to the procedure described in Example 9.

$^1$H NMR (400 MHz, DMSO-d$_6$) δ 8.51 (d, 1H), 7.58 (s, 1H), 7.44 (s, 1H), 7.38 (d, 1H), 6.39 (s, 1H), 5.04 (d, 1H), 4.96 (d, 1H), 4.54 (s, 1H), 4.34 (s, 1H), 2.96 (d, 1H), 2.76 (m, 1H), 2.67 (m, 1H), 2.54 (s, 3H), 2.41 (m, 1H), 1.90 (m 3H), 1.82-1.57 (m, 6H), 1.48 (m, 1H), 1.22 (s, 3H), 1.15 (m, 1H), 1.06 (m, 1H), 0.92 (m, 5H), 0.83 (m, 2H).

APCI-MS m/z: 571 [MH$^+$].

Example 143

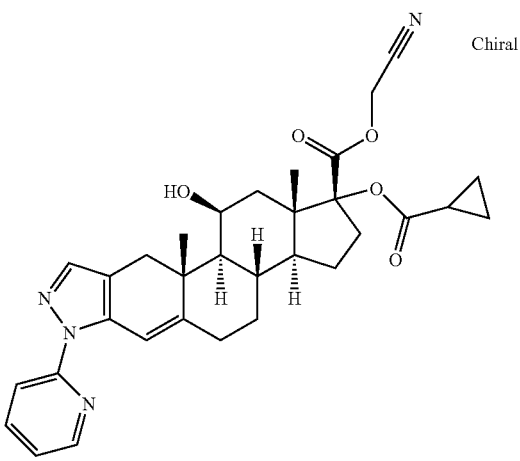

Cyanomethyl(1R,3aS,3bS,10aR,10bS,11S,12aS)-1-[(cyclopropylcarbonyl)oxy]-11-hydroxy-10a,12a-dimethyl-7-pyridin-2-yl-1,2,3,3a,3b,4,5,7,10,11a,10b,11,12,12a-tetradecahydrocyclopenta[5,6]naphtho[1,2-f]indazole-1-carboxylate The compound was prepared from Intermediate 134 and 2-bromoacetonitrile according to the procedure described in Example 9.

$^1$H NMR (400 MHz, DMSO-d$_6$) δ 8.76 (d, 1H), 8.59 (dd, 1H), 7.94 (d, 1H), 7.58 (m, 2H), 6.39 (s, 1H), 5.04 (d, 1H), 4.96 (d, 1H), 4.54 (s, 1H), 4.34 (s, 1H), 2.96 (d, 1H), 2.76 (m, 1H), 2.67 (m, 1H), 2.41 (m, 1H), 1.90 (m, 3H), 1.82-1.57 (m, 6H), 1.48 (m, 1H), 1.22 (s, 3H), 1.15 (m, 1H), 1.06 (m, 1H), 0.92 (m, 5H), 0.83 (m, 2H).

APCI-MS m/z: 557 [MH$^+$].

Example 144

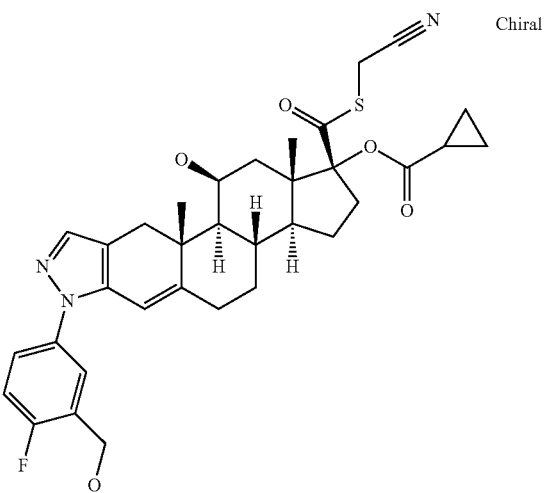

(1R,3aS,3bS,10aR,10bS,11S,12aS)-1-{[(Cyanomethyl)sulfanyl]carbonyl}-7-[4-fluoro-3-(hydroxymethyl)phenyl-]-11-hydroxy-10a,12a-dimethyl-1,2,3,3a,3b, 4,5,7,10,10a,11,12,12a-tetradecahydrocyclopenta[5,6]naphtho[1,2-f]indazol-1-yl Cyclopropanecarboxylate The compound was prepared from Intermediate 34 using the procedure for intermediate 36 and intermediate 37, using cyclopropanecarbonyl chloride and example 80. The purification of the final compound was done using a Kromasil® Phenyl HPLC column (CH$_3$CN/water).

$^1$H NMR (400 MHz, CDCl$_3$) δ 7.60 (1H, m), 7.44 (1H, s), 7.38 (1H, m), 7.15 (1H, t), 6.09 (1H, s); 4.82 (2H, s), 4.58 (1H, m), 3.78 (1H, d), 3.58 (1H, d), 3.02 (1H, d), 2.96 (1H, m); 2.73 (1H, d), 2.52 (1H, m), 2.32 (1H, m), 2.18-1.91 (5H, m), 1.84 (1H, m), 1.72-1.55 (3H, m), 1.48 (1H, m), 1.32 (3H, s), 1.28 (1H, m), 1.19-1.02 (5H, m), 1.01 (3H, s), 0.95 (2H, m). APCI-MS m/z: 620 [MH$^+$].

Example 145

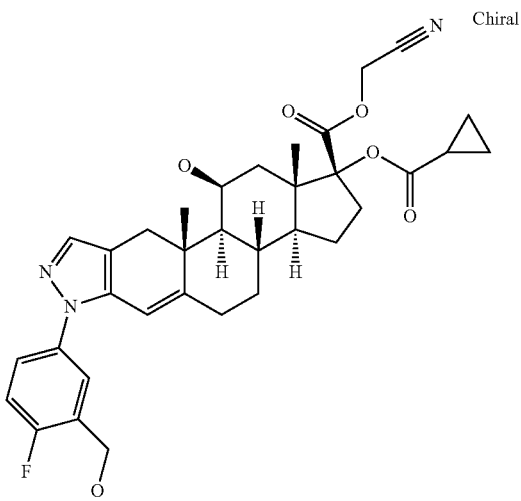

Cyanomethyl(1R,3aS,3bS,10aR,10bS,11S,12aS)-1-
[(cyclopropylcarbonyl)oxy]-7-[4-fluoro-3-(hy-
droxymethyl)phenyl]-11-hydroxy-10a,12a-dimethyl-
1,2,3,3a,3b,4,5,7,10,10a,10b,11,12,12a-
tetradecahydrocyclopenta[5,6]naphtho[1,2-f]
indazole-1-carboxylate The compound was isolated as a biproduct during the formation of Example 144. The purification of the final compound was done using a Kromasil® Phenyl HPLC column (CH₃CN/water).

$^1$H NMR (400 MHz, CDCl₃) δ 7.60 (1H, m), 7.44 (1H, s), 7.38 (1H, m), 7.15 (1H, t), 6.09 (1H, s); 4.83 (3H, m), 4.70 (1H, d), 3.02 (1H, d), 2.96 (1H, m); 2.73 (1H, d), 2.52 (1H, m), 2.32 (1H, m), 2.18-1.91 (5H, m), 1.84 (1H, m), 1.72-1.55 (3H, m), 1.48 (1H, m), 1.32 (3H, s), 1.28 (1H, m), 1.19-1.02 (5H, m), 1.01 (3H, s), 0.95 (2H, m). APCI-MS m/z: 604 [MH⁺].

Example 146

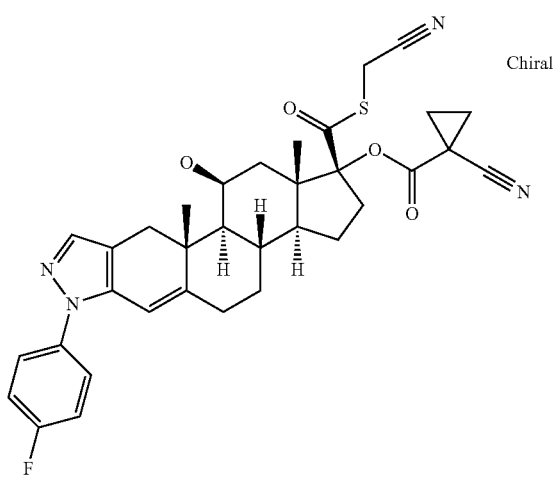

(1R,3aS,3bS,10aR,10bS,11S,12aS)-1-{[(Cyanom-
ethyl)sulfanyl]carbonyl}-7-(4-fluorophenyl)-11-hy-
droxy-10a,12a-dimethyl-1,2,3,3a,3b,4,5,7,10,10a,
10b,11,12,12a-tetradecahydrocyclopenta[5,6]
naphtho[1,2-f]indazol-1-yl 1-cyanocyclopropane
Carboxylate The compound was prepared from Intermediate 111 and bromoacetonitrile according to the procedure for Example 1.

$^1$H NMR (500 MHz, DMSO-d₆) δ 7.51 (m, 2H), 7.46 (s, 1H), 7.34 (m, 2H), 6.11 (s, 1H), 4.62 (b, 1H), 4.39 (b, 1H), 4.1 (d, 1H), 3.99 (d, 1H), 2.99 (d, 1H), 2.75 (m, 1H), 2.58 (d, 1H), 2.41 (m, 1H), 2.30 (m, 1H), 2.05-1.73 (m, 7H), 1.63 (m, 3H), 1.42 (m, 1H), 1.22 (s, 3H), 1.12 (m, 1H), 1.04 (m, 1H), 0.89 (s, 3H). APCI-MS m/z: 615 [MH⁺].

Example 147

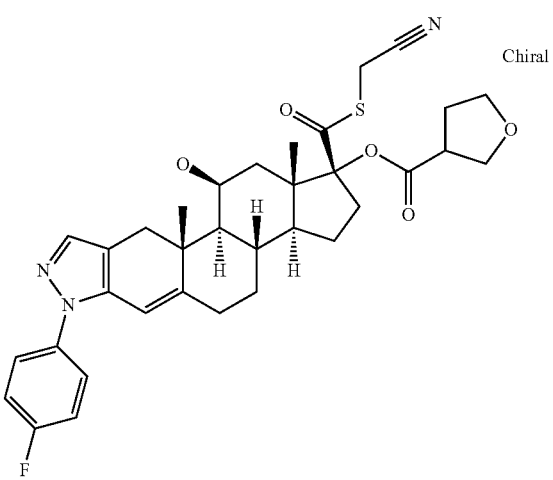

(1R,3aS,3bS,10aR,10bS,11S,12aS)-1-{[(Cyanom-
ethyl)sulfanyl]carbonyl}-7-(4-fluorophenyl)-11-hy-
droxy-10a,12a-dimethyl-1,2,3,3a,3b,4,5,7,10,10a,
10b,11,12,12a-tetradecahydrocyclopenta[5,6]
naphtho[1,2-f]indazol-1-yl tetrahydrofuran-3-
carboxylate The compound was prepared from Intermediate 112 and bromoacetonitrile according to the procedure for Example 1.

$^1$H NMR (500 MHz, DMSO-d₆) δ 7.51 (m, 2H), 7.46 (s, 1H), 7.34 (m, 2H), 6.11 (s, 1H), 4.58 (d, 1H), 4.36 (b, 1H), 4.1 (d, 1H), 3.98 (d, 1H), 3.85 (m 2H), 3.73 (m, 1H), 3.67 (m, 1H), 3.02 (m, 1H), 2.99 (d, 1H), 2.77 (m, 1H), 2.63 (m, 1H), 2.41 (m, 1H), 2.30 (m, 1H), 2.05-1.73 (m, 7H), 1.75 (m, 1H), 1.60 (m, 1H), 1.37 (m, 1H), 1.22 (s, 3H), 1.15 (m, 1H), 1.03 (m, 1H), 0.89 (s, 3H). APCI-MS m/z: 620 [MH⁺].

Example 148

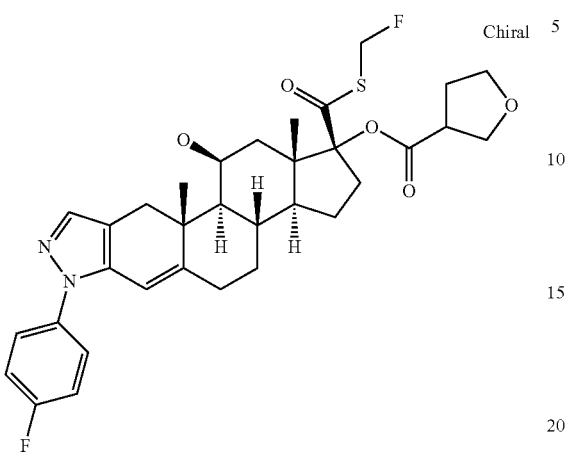

(1R,3aS,3bS,10aR,10bS,11S,12aS)-1-{[(Fluoromethyl)sulfanyl]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl tetrahydrofuran-3-carboxylate The compound was prepared from Intermediate 112 and bromofluoromethane according to the procedure for Example 1.

¹H NMR (500 MHz, DMSO-d₆) δ 7.51 (m, 2H), 7.46 (s, 1H), 7.34 (m, 2H), 6.11 (s, 1H), 5.98-5.82 (d, 2H), 4.58 (d, 1H), 4.36 (b, 1H), 3.85 (m 2H), 3.73 (m, 1H), 3.67 (m, 1H), 3.02 (m, 1H), 2.99 (d, 1H), 2.77 (m, 1H), 2.63 (m, 1H), 2.41 (m, 1H), 2.30 (m, 1H), 2.05-1.73 (m, 7H), 1.75 (m, 1H), 1.60 (m, 1H), 1.37 (m, 1H), 1.22 (s, 3H), 1.15 (m, 1H), 1.03 (m, 1H), 0.89 (s, 3H). APCI-MS m/z: 613 [MH⁺].

Example 149

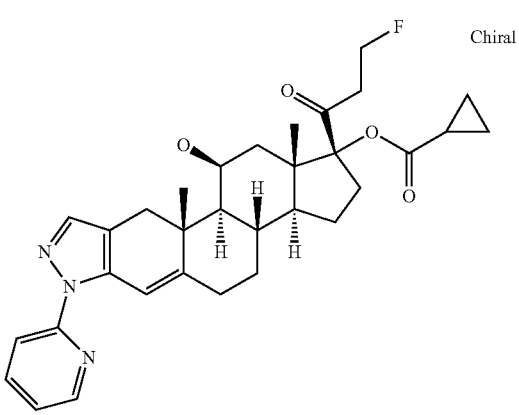

(1R,3aS,3bS,10aR,10bS,11S,12aS)-1-{[(Fluoromethyl)sulfanyl]carbonyl}-11-hydroxy-10a,12a-dimethyl-7-pyridin-2-yl-1,2,3,3a,3b,4,5,7,10,10a,10b,11,12,12a-tetradecahydrocyclopenta[5,6]naphtho[1,2-f]indazol-1-yl cyclopropane Carboxylate The compound was prepared from Intermediate 114 and bromofluoromethane according to the procedure for Example 1.

¹H NMR (500 MHz, DMSO-d₆) δ 8.46 (dd, 1H), 7.95 (t, 1H), 7.84 (d, 1H), 7.52 (s, 1H), 7.30 (m, 1H), 7.09 (s, 1H), 5.96-5.82 (d, 2H), 4.53 (b, 1H), 4.36 (s, 1H), 2.94 (d, 1H), 2.77 (m, 1H), 2.64 (m, 1H), 2.35 (m, 1H), 2.31 (m, 1H), 1.95-1.68 (m, 8H), 1.61 (m, 1H), 1.38 (m, 1H), 1.27-1.13 (m, 5H), 1.08 (m, 1H), 0.98-0.81 (s, 7H). APCI-MS m/z: 566 [MH⁺].

Example 150

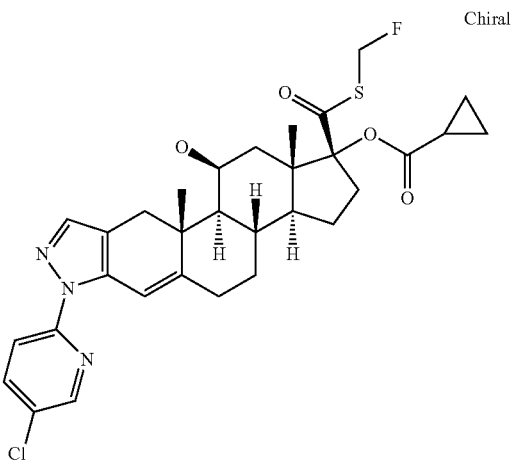

(1R,3aS,3bS,10aR,10bS,11S,12aS)-7-(5-Chloropyridin-2-yl)-1-{[(fluoromethyl)sulfanyl]carbonyl}-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl cyclopropane Carboxylate The compound was prepared from Intermediate 118 and bromofluoromethane according to the procedure for Example 1.

¹H NMR (500 MHz, DMSO-d₆) δ 8.52 (d, 1H), 8.06 (dd, 1H), 7.86 (d, 1H), 7.57 (s, 1H), 7.02 (m, 1H), 5.96-5.82 (d, 2H), 2.94 (d, 1H), 2.77 (m, 1H), 2.64 (m, 1H), 2.35 (m, 1H), 2.31 (m, 1H), 1.95-1.68 (m, 8H), 1.61 (m, 1H), 1.38 (m, 1H), 1.27-1.13 (m, 5H), 1.08 (m, 1H), 0.98-0.81 (s, 7H). APCI-MS m/z: 600 [MH⁺].

Example 151

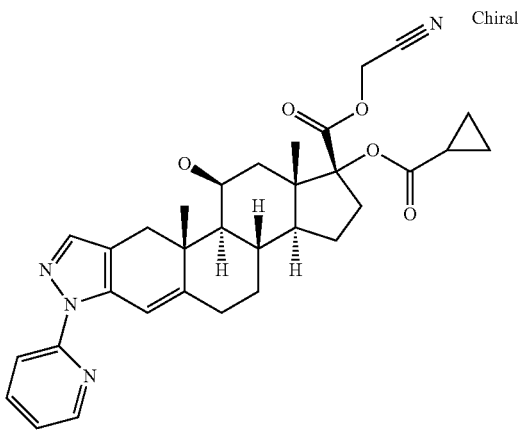

Cyanomethyl(1R,3aS,3bS,10aR,10bS,11S,12aS)-1-
[(cyclopropylcarbonyl)oxy]-11-hydroxy-10a,12a-
dimethyl-7-pyridin-2-yl-1,2,3,3a,3b,4,5,7,10,10a,
10b,11,12,12a-tetradecahydrocyclopenta[5,6]
naphtho[1,2-f]indazole-1-carboxylate The compound was prepared from Intermediate 117 and bromoacetonitrile according to the procedure for Example 9.

¹H NMR (500 MHz, DMSO-d₆) δ 8.76 (d, 1H), 8.58 (d, 1H), 7.97 (d, 1H), 7.56 (m, 2H), 6.20 (s, 1H), 5.04 (d, 1H), 4.97 (d, 1H), 4.53 (b, 1H), 4.34 (s, 1H), 2.94 (d, 1H), 2.77 (m, 1H), 2.64 (m, 1H), 2.35 (m, 1H), 2.31 (m, 1H), 1.95-1.68 (m, 8H), 1.61 (m, 1H), 1.38 (m, 1H), 1.27-1.13 (m, 5H), 1.08 (m, 1H), 0.98-0.81 (s, 7H). APCI-MS m/z: 557 [MH⁺].

Example 152

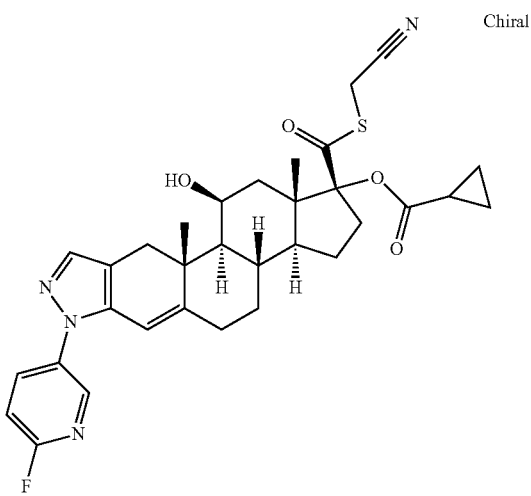

(1R,3aS,3bS,10aR,10bS,11S,12aS)-1-{[(Cyanomethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl cyclopropanecarboxylate The compound was prepared from Intermediate 119 and chloro(thiocyanato)methane according to the procedure described in Example 82.

¹H NMR (400 MHz, CDCl₃) δ 8.36 (d, 1H), 8.00 (ddd, 1H), 7.50 (s, 1H), 7.08 (dd, 1H), 6.08 (d, 1H), 4.58 (d, 1H), 3.78 (d, 1H), 3.56 (d, 1H), 3.04 (d, 1H), 2.96 (m, 1H), 2.73 (d, 1H), 2.53 (m, 1H), 2.31 (d, 1H), 2.13 (dd, 1H), 2.08-1.92 (m, 4H), 1.84 (m, 1H), 1.73-1.40 (m, 7H), 1.33 (s, 3H), 1.28 (dd, 1H), 1.21-0.91 (m, 8H). APCI-MS m/z: 591 [MH⁺].

Example 153

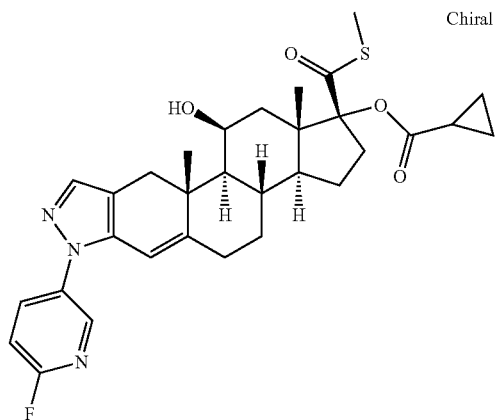

(1R,3aS,3bS,10aR,10bS,11S,12aS)-7-(6-Fluoropyridin-3-yl)-11-hydroxy-10a,12a-dimethyl-1-[(methylsulfanyl)carbonyl]-1,2,3,3a,3b,4,5,7,10,10a,10b,11,12,12a-tetradecahydrocyclopenta[5,6]naphtho[1,2-f]indazol-1-yl cyclopropanecarboxylate The compound was prepared from Intermediate 119 and iodomethane according to the procedure described in Example 82.

¹H NMR (400 MHz, CDCl₃) δ 8.37 (d, 1H), 8.00 (dddd, 1H), 7.49 (s, 1H), 7.08 (dd, 1H), 6.08 (d, 1H), 4.57 (d, 1H), 3.04 (d, 1H), 2.98 (m, 1H), 2.74 (d, 1H), 2.53 (m, 1H), 2.31 (m, 1H), 2.31 (s, 3H), 2.13 (dd, 1H), 2.08-1.91 (m, 4H), 1.82 (m, 1H), 1.71-1.38 (m, 8H), 1.33 (s, 3H), 1.28 (dd, 2H), 1.20-0.99 (m, 4H), 0.96 (s, 3H), 0.91 (m, 2H). APCI-MS m/z: 566 [MH⁺].

Example 154

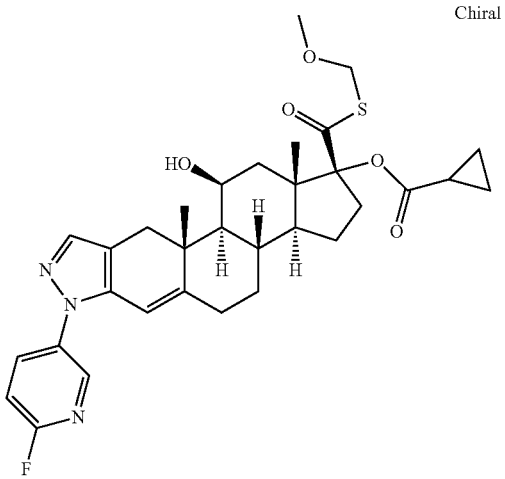

(1R,3aS,3bS,10aR,10bS,11S,12aS)-7-(6-Fluoropyridin-3-yl)-11-hydroxy-1-{[(methoxymethyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl cyclopropanecarboxylate The compound was prepared from Intermediate 119 and bromo(methoxy)methane according to the procedure described in Example 82.
APCI-MS m/z: 596 [MH⁺].

Example 155

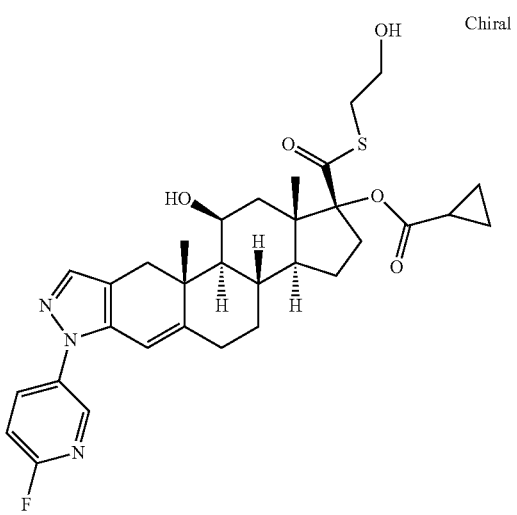

(1R,3aS,3bS,10aR,10bS,11S,12aS)-7-(6-Fluoropyridin-3-yl)-11-hydroxy-1-{[(2-hydroxyethyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl cyclopropanecarboxylate The compound was prepared from Intermediate 119 and 2-bromoethanol according to the procedure described in Example 82.

¹H NMR (400 MHz, CDCl₃) δ 8.36 (d, 1H), 8.00 (ddd, 1H), 7.50 (s, 1H), 7.08 (dd, 1H), 6.08 (d, 1H), 4.57 (d, 1H), 3.75 (dd, 2H), 3.19 (m, 1H), 3.11-2.93 (m, 3H), 2.74 (d, 1H), 2.53 (m, 1H), 2.31 (d, 1H), 2.14 (dd, 2H), 2.10-1.63 (m, 12H), 1.51-1.38 (m, 2H), 1.33 (s, 3H), 1.28 (dd, 1H), 1.19-0.99 (m, 2H), 0.98 (s, 3H), 0.96-0.86 (m, 2H). APCI-MS m/z: 596 [MH⁺].

Example 156

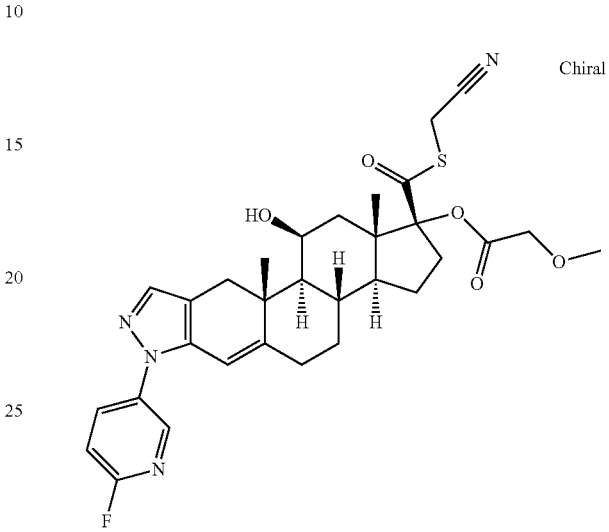

(1R,3aS,3bS,10aR,10bS,11S,12aS)-1-{[(Cyanomethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl methoxyacetate The compound was prepared from Intermediate 120 and 2-bromoacetonitrile according to the procedure described in Example 82.
¹H NMR (400 MHz, CDCl₃) δ 8.36 (d, 1H), 8.00 (m, 1H), 7.49 (s, 1H), 7.08 (dd, 1H), 6.07 (d, 1H), 4.56 (d, 1H), 4.07 (s, 2H), 3.79 (d, 1H), 3.58 (d, 1H), 3.46 (s, 3H), 3.01 (m, 2H), 2.71 (d, 1H), 2.52 (m, 1H), 2.30 (d, 1H), 2.11-1.78 (m, 6H), 1.68-1.39 (m, 4H), 1.32 (s, 3H), 1.26 (dd, 1H), 1.12 (m, 1H), 1.02 (s, 3H). APCI-MS m/z: 595 [MH⁺].

Example 157

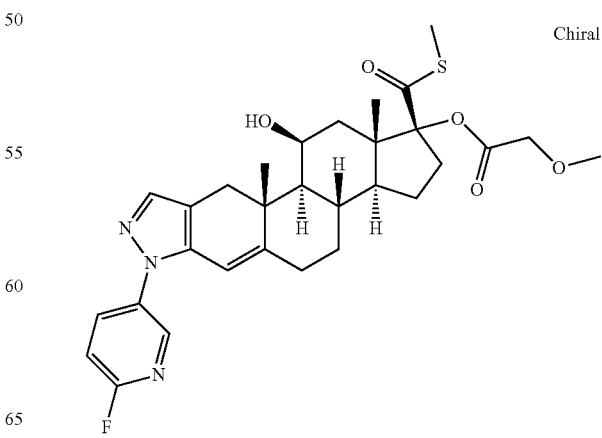

(1R,3aS,3bS,10aR,10bS,11S,12aS)-7-(6-Fluoropyridin-3-yl)-11-hydroxy-10a,12a-dimethyl-1-[(methylsulfanyl)carbonyl]-1,2,3,3a,3b,4,5,7,10,10a,10b,11,12,12a-tetradecahydrocyclopenta[5,6]naphtho[1,2-f]indazol-1-yl Methoxyacetate The compound was prepared from Intermediate 120 and iodomethane according to the procedure described in Example 82.

$^1$H NMR (400 MHz, CDCl$_3$) δ 8.36 (d, 1H), 7.99 (m, 1H), 7.48 (s, 1H), 7.07 (dd, 1H), 6.07 (d, 1H), 4.55 (d, 1H), 4.05 (s, 2H), 3.46 (s, 3H), 3.06 (m, 2H), 2.72 (d, 1H), 2.52 (m, 1H), 2.33 (s, 3H), 2.29 (m, 1H), 2.13-1.94 (m, 5H), 1.86-1.57 (m, 4H), 1.52-1.40 (m, 1H), 1.33 (s, 1H), 1.27 (dd, 1H), 1.11 (m, 1H), 0.97 (s, 3H), 0.94 (m, 1H). APCI-MS m/z: 570 [MH$^+$]

Example 158

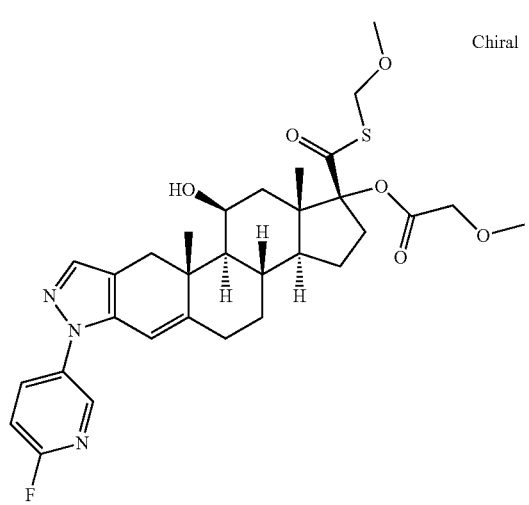

(1R,3aS,3bS,10aR,10bS,11S,12aS)-7-(6-Fluoropyridin-3-yl)-11-hydroxy-1-{[(methoxymethyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl methoxyacetate The compound was prepared from Intermediate 120 and bromo(methoxy)methane according to the procedure described in Example 82.

$^1$H NMR (400 MHz, CDCl$_3$) δ 8.36 (d, 1H), 7.99 (ddd, 1H), 7.48 (s, 1H), 7.07 (dd, 1H), 6.07 (s, 1H), 5.13 (s, 1H), 4.55 (d, 1H), 4.06 (m, 2H), 3.47 (s, 3H), 3.40 (m, 2H), 3.32 (s, 2H), 3.05 (m, 1H), 3.02 (d, 1H), 2.72 (d, 1H), 2.52 (m, 1H), 2.30 (m, 1H), 2.15-1.93 (m, 5H), 1.82 (m, 1H), 1.72-1.39 (m, 3H), 1.32 (s, 3H), 1.26 (m, 1H), 1.18-1.06 (m, 1H), 0.99 (s, 3H), 0.97 (m, 1H). APCI-MS m/z: 600 [MH$^+$].

Example 159

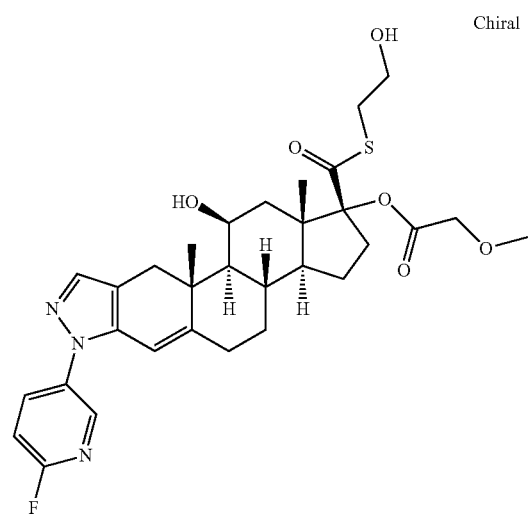

(1R,3aS,3bS,10aR,10bS,11S,12aS)-7-(6-Fluoropyridin-3-yl)-11-hydroxy-1-{[(2-hydroxyethyl)sulfanyl]carbonyl}-10a,12a-dimethyl-1,2,3,3a,3b,4,5,7,10,10b,11,12,12a-tetradecahydrocyclopenta[5,6]naphtho[1,2-f]indazol-1-yl methoxyacetate The compound was prepared from Intermediate 120 and 2-bromoethanol according to the procedure described in Example 82.

$^1$H NMR (400 MHz, CDCl$_3$) δ 8.36 (d, 1H), 7.99 (ddd, 1H), 7.48 (s, 1H), 7.07 (dd, 1H), 6.07 (d, 1H), 4.55 (d, 1H), 4.06 (dd, 2H), 3.75 (dt, 2H), 3.46 (s, 3H), 3.20-2.97 (m, 5H), 2.71 (d, 1H), 2.52 (td, 1H), 2.30 (d, 1H), 2.12-1.92 (m, 6H), 1.81 (m, 1H), 1.63 (m, 1H), 1.51-1.36 (m, 3H), 1.32 (s, 3H), 1.26 (dd, 1H), 1.09 (m, 1H), 0.98 (s, 3H). APCI-MS m/z: 600 [MH$^+$].

Example 160

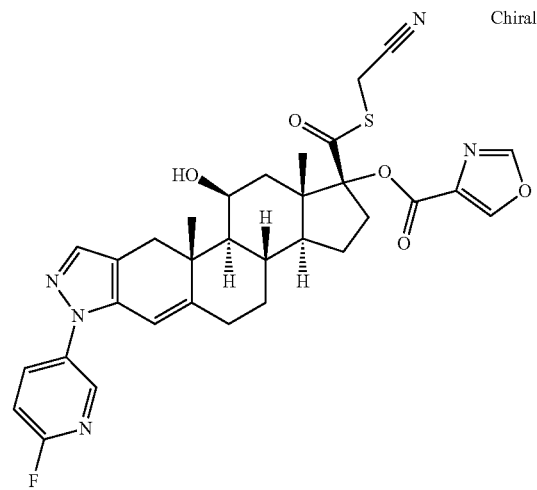

221

(1R,3aS,3bS,10aR,10bS,11S,12aS)-1-{[(Cyanomethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 1,3-oxazole-4-carboxylate The compound was prepared from Intermediate 121 and 2-bromoacetonitrile according to the procedure described in Example 82.

$^1$H NMR (400 MHz, CDCl$_3$) δ 8.36 (d, 1H), 8.31 (d, 1H), 7.99 (ddd, 1H), 7.96 (d, 1H), 7.50 (s, 1H), 7.07 (dd, 1H), 6.07 (d, 1H), 4.62 (d, 1H), 3.80 (d, 1H), 3.57 (d, 1H), 3.07 (m, 1H), 3.04 (d, 1H), 2.76 (d, 1H), 2.53 (dt, 1H), 2.34-1.70 (m, 10H), 1.59-1.45 (m, 1H), 1.34 (m, 1H), 1.34 (s, 3H), 1.15 (m, 1H), 1.07 (s, 3H). APCI-MS m/z: 618 [MH$^+$].

Example 161

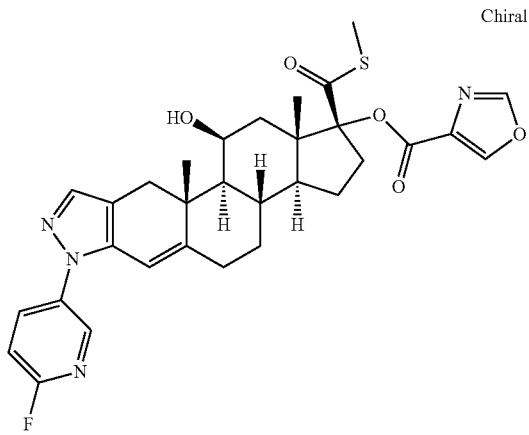

(1R,3aS,3bS,10aR,10bS,11S,12aS)-7-(6-Fluoropyridin-3-yl)-11-hydroxy-10a,12a-dimethyl-1-[(methylsulfanyl)carbonyl]-1,2,3,3a,3b,4,5,7,10,10a,10b,11,12,12a-tetradecahydrocyclopenta[5,6]naphtho[1,2-f]indazol-1-yl 1,3-oxazole-4-carboxylate The compound was prepared from Intermediate 121 and iodomethane according to the procedure described in Example 82.

$^1$H NMR (400 MHz, CDCl$_3$) δ 8.36 (d, 1H), 8.29 (d, 1H), 7.99 (ddd, 2H), 7.95 (d, 2H), 7.49 (s, 1H), 7.07 (dd, 1H), 6.07 (d, 1H), 4.62 (d, 1H), 3.11 (ddd, 1H), 3.04 (d, 1H), 2.77 (d, 1H), 2.53 (m, 1H), 2.33 (s, 3H), 2.28 (dd, 2H), 2.21-1.94 (m, 4H), 1.90-1.42 (m, 6H), 1.37 (d, 1H), 1.34 (s, 3H), 1.13 (m, 2H), 1.02 (s, 3H). APCI-MS m/z: 593 [MH$^+$].

222

Example 162

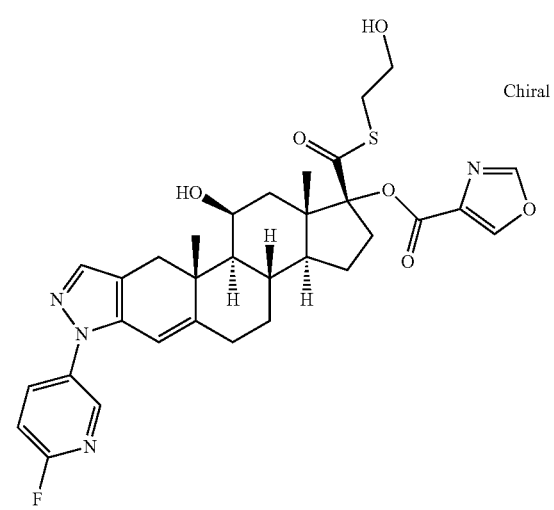

(1R,3aS,3bS,10aR,10bS,11S,12aS)-7-(6-Fluoropyridin-3-yl)-11-hydroxy-1-{[(2-hydroxyethyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl 1,3-oxazole-4-carboxylate The compound was prepared from Intermediate 121 and 2-bromoethanol according to the procedure described in Example 82.

$^1$H NMR (400 MHz, CDCl$_3$) δ 8.36 (d, 1H), 8.30 (d, 1H), 8.00 (ddd, 1H), 7.96 (d, 1H), 7.50 (s, 1H), 7.08 (dd, 1H), 6.06 (d, 1H), 4.61 (d, 1H), 3.75 (t, 2H), 3.19-3.07 (m, 3H), 3.04 (d, 1H), 2.76 (d, 1H), 2.54 (td, 1H), 2.27 (m, 2H), 2.17-1.69 (m, 10H), 1.55-1.35 (m, 3H), 1.34 (s, 3H), 1.13 (m, 1H), 1.03 (s, 3H). APCI-MS m/z: 623 [MH$^+$].

Example 163

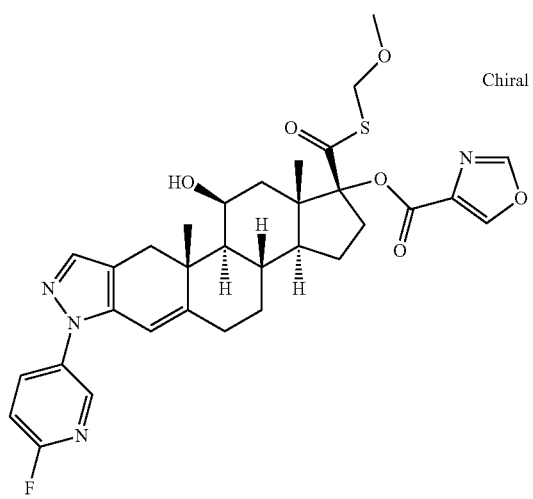

(1R,3aS,3bS,10aR,10bS,11S,12aS)-7-(6-Fluoropyridin-3-yl)-11-hydroxy-1-{[(methoxymethyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl 1,3-oxazole-4-carboxylate The compound was prepared from Intermediate 121 and bromo(methoxy)methane according to the procedure described in Example 82.

$^1$H NMR (400 MHz, CDCl$_3$) δ 8.36 (d, 1H), 8.29 (dd, 1H), 7.99 (ddd, 1H), 7.95 (t, 1H), 7.49 (s, 1H), 7.07 (dd, 1H), 6.07 (s, 1H), 5.13 (d, 1H), 4.61 (m, 1H), 3.39 (m, 1H), 3.32 (s, 2H), 3.11 (m, 1H), 3.04 (d, 1H), 2.77 (d, 1H), 2.53 (m, 1H), 2.28 (m, 2H), 2.21-1.36 (m, 13H), 1.34 (s, 3H), 1.13 (m, 1H), 1.04 (s, 3H), 1.01 (m, 1H). APCI-MS m/z: 623 [MH$^+$].

Example 164

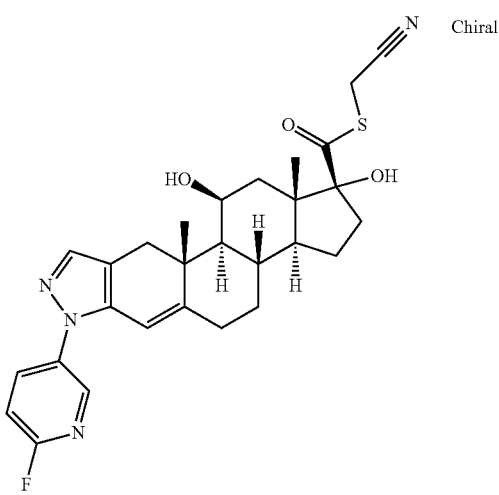

S-(Cyanomethyl)(1R,3aS,3bS,10aR,10bS,11S,12aS)-7-(6-fluoropyridin-3-yl)-1,11-dihydroxy-10a,12a-dimethyl-1,2,3,3a,3b,4,5,7,10,10a,10b,11,12,12a-tetradecahydrocyclopenta[5,6]naphtho[1,2-f]indazole-1-carbothioate The compound was prepared from Intermediate 42 and 2-bromoacetonitrile according to the procedure described in Example 82.

$^1$H NMR (400 MHz, CDCl$_3$) δ 8.36 (d, 1H), 7.99 (m, 1H), 7.48 (s, 1H), 7.07 (dd, 1H), 6.06 (d, 1H), 4.53 (d, 1H), 3.60 (dd, 2H), 3.02 (d, 1H), 2.78 (dd, 1H), 2.69 (d, 1H), 2.52 (m, 1H), 2.30 (m, 1H), 2.10-1.40 (m, 14H), 1.32 (s, 3H), 1.24 (dd, 1H), 1.12 (m, 1H), 1.03 (s, 3H). APCI-MS m/z: 523 [MH$^+$].

Example 165

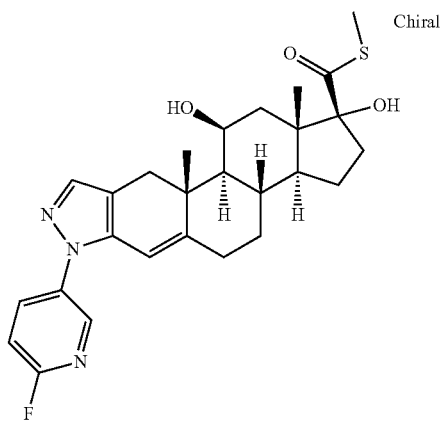

S-Methyl(1R,3aS,3bS,10aR,10bS,11S,12aS)-7-(6-fluoropyridin-3-yl)-1,11-dihydroxy-10a,12a-dimethyl-1,2,3,3a,3b,4,5,7,10,10a,10b,11,12,12a-tetradecahydrocyclopenta[5,6]naphtho[1,2-f]indazole-1-carbothioate The compound was prepared from Intermediate 42 and iodomethane according to the procedure described in Example 82.

$^1$H NMR (400 MHz, CDCl$_3$) δ 8.36 (d, 1H), 7.99 (m, 1H), 7.47 (s, 1H), 7.07 (dd, 1H), 6.06 (d, 1H), 4.53 (d, 1H), 3.02 (d, 1H), 2.78 (ddd, 1H), 2.69 (d, 1H), 2.51 (m, 1H), 2.31 (m, 1H), 2.30 (s, 3H), 2.07-1.40 (m, 13H), 1.32 (s, 3H), 1.25 (dd, 1H), 1.12 (m, 1H), 1.01 (s, 3H). APCI-MS m/z: 498 [MH$^+$].

Example 166

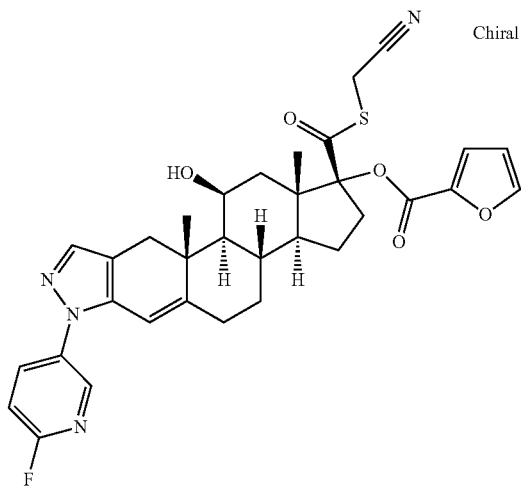

(1R,3aS,3bS,10aR,10bS,11S,12aS)-1-{[(Cyanomethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate The compound was prepared from Intermediate 122 and 2-bromoacetonitrile according to the procedure described in Example 82.

¹H NMR (400 MHz, CDCl₃) δ 8.37 (d, 1H), 8.01 (ddd, 1H), 7.63 (d, 1H), 7.52 (s, 1H), 7.24 (d, 1H), 7.08 (dd, 1H), 6.56 (dd, 1H), 6.08 (d, 1H), 4.63 (d, 1H), 3.82 (d, 1H), 3.55 (d, 1H), 3.07 (d, 1H), 3.04 (m, 1H), 2.78 (d, 1H), 2.53 (m, 1H), 2.34-1.42 (m, 12H), 1.35 (s, 3H), 1.29 (m, 1H), 1.14 (m, 2H), 1.07 (s, sH). APCI-MS m/z: 617 [MH⁺].

Example 167

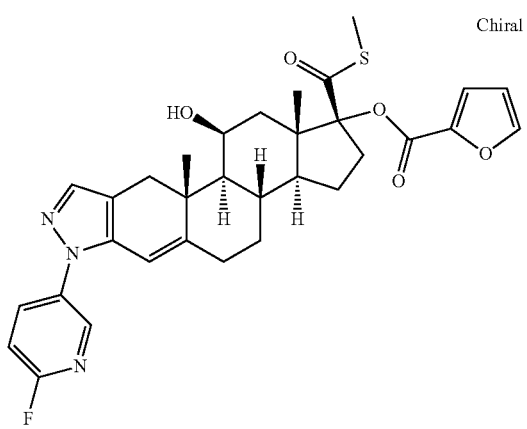

(1R,3aS,3bS,10aR,10bS,11S,12aS)-7-(6-Fluoropyridin-3-yl)-11-hydroxy-10a,12a-dimethyl-1-[(methylsulfanyl)carbonyl]-1,2,3,3a,3b,4,5,7,10,10a,10b,11,12,12a-tetradecahydrocyclopenta[5,6]naphtho[1,2-f]indazol-1-yl furan-2-carboxylate The compound was prepared from intermediate 122 and iodomethane according to the procedure described in Example 82.

¹H NMR (400 MHz, CDCl₃) δ 8.37 (d, 1H), 8.00 (ddd, 1H), 7.61 (dd, 1H), 7.51 (s, H), 7.21 (dd, 1H), 7.08 (dd, 1H), 6.53 (dd, 1H), 6.08 (d, 1H), 4.62 (d, 1H), 3.09 (m, 1H), 3.07 (d, 1H), 2.79 (d, 1H), 2.54 (m, 1H), 2.33 (s, 3H), 2.28 (dd, 1H), 2.21-1.94 (m, 4H), 1.88-1.70 (m, 2H), 1.54-1.41 (m, 1H), 1.35 (s, 3H), 1.33 (m, 1H), 1.21-1.06 (m, 23H), 1.02 (s, 3H). APCI-MS m/z: 592 [MH⁺].

Example 168

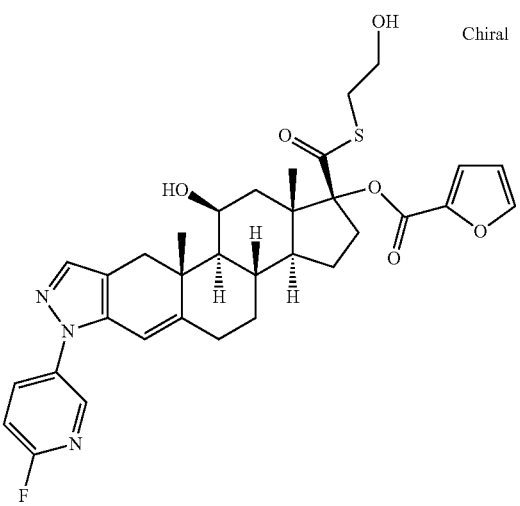

(1R,3aS,3bS,10aR,10bS,11S,12aS)-7-(6-Fluoropyridin-3-yl)-11-hydroxy-1-{[(2-hydroxyethyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate The compound was prepared from Intermediate 122 and 2-bromoethanol according to the procedure described in Example 82.

¹H NMR (400 MHz, CDCl₃) δ 8.37 (d, 1H), 8.01 (m, 1H), 7.61 (d, 1H), 7.53 (s, 1H), 7.22 (dd, 1H), 7.09 (dd, 1H), 6.54 (dd, 1H), 6.08 (d, 1H), 4.62 (d, 1H), 3.77 (t, 2H), 3.24-3.02 (m, 5H), 2.79 (d, 1H), 2.54 (m, 1H), 2.30 (m, 2H), 2.16-1.94 (m, 6H), 1.88-1.70 (m, 2H), 1.48 (m, 1H), 1.35 (s, 3H), 1.32 (m, 1H), 1.14 (m, 1H), 1.03 (s, 3H), 1.01 (m, 1H). APCI-MS m/z: 622 [MH⁺].

Example 169

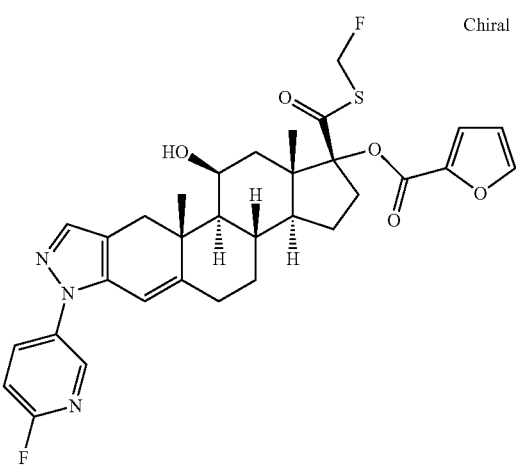

227

(1R,3aS,3bS,10aR,10bS,11S,12aS)-1-{[(Fluoromethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate The compound was prepared from Intermediate 122 and bromofluoromethane according to the procedure described in Example 82.

$^1$H NMR (400 MHz, CDCl$_3$) δ 8.37 (d, 1H), 8.01 (ddd, 1H), 7.62 (dd, 1H), 7.51 (s, 1H), 7.24 (dd, 1H), 7.08 (dd, 1H), 6.55 (dd, 1H), 6.08 (d, 1H), 5.99 (dd, 1H), 5.68 (dd, 1H), 4.63 (d, 1H), 3.10 (m, 1H), 3.06 (d, 1H), 2.78 (d, 1H), 2.54 (m, 1H), 2.29 (m, 2H), 2.18-1.95 (m, 4H), 1.90-1.72 (m, 2H), 1.58-1.42 (m, 1H), 1.35 (s, 3H), 1.32 (m, 1H), 1.14 (m, 1H), 1.06 (s, 3H), 1.04 (m, 1H). APCI-MS m/z: 610 [MH$^+$].

Example 170

228

Example 171

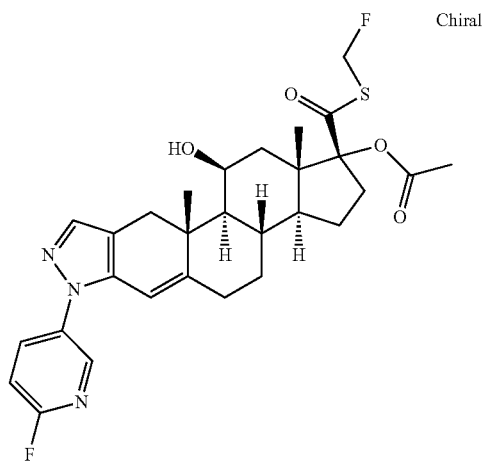

(1R,3aS,3bS,10aR,10bS,11S,12aS)-1-{[(Fluoromethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl acetate The compound was prepared from Intermediate 123 and bromofluoromethane according to the procedure described in Example 82.

$^1$H NMR (400 MHz, CDCl$_3$) δ 8.36 (d, 1H), 8.00 (ddd, 1H), 7.49 (s, 1H), 7.08 (dd, 1H), 6.08 (d, 1H), 5.95 (dd, 1H), 5.72 (dd, 1H), 4.56 (d, 1H), 3.03 (d, 1H), 3.00 (m, 1H), 2.73 (d, 1H), 2.53 (m, 1H), 2.31 (m, 1H), 2.13 (m, 1H), 2.11 (s, 3H), 2.09-1.94 (m, 5H), 1.82 (m, 1H), 1.66 (m, 1H), 1.52-1.40 (m, 2H), 1.33 (s, 3H), 1.28 (dd, 1H), 1.12 (m, 1H), 1.00 (s, 3H), 0.97 (m, 1H). APCI-MS m/z: 558 [MH$^+$].

Example 172

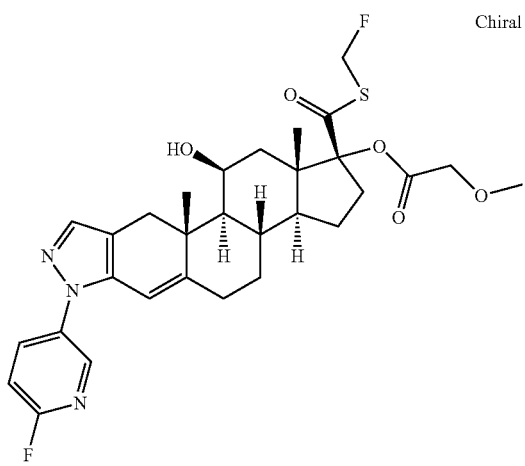

(1R,3aS,3bS,10aR,10bS,11S,12aS)-1-{[(Fluoromethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl methoxyacetate The compound was prepared from Intermediate 120 and bromofluoromethane according to the procedure described in Example 82.

$^1$H NMR (400 MHz, CDCl$_3$) δ 8.36 (d, 1H), 8.00 (ddd, 1H), 7.50 (s, 1H), 7.08 (dd, 1H), 6.08 (d, 1H), 5.96 (dd, 1H), 5.72 (dd, 1H), 4.56 (d, 1H), 4.07 (s, 2H), 3.46 (s, 3H), 3.05 (m, 1H), 3.02 (d, 1H), 2.72 (d, 1H), 2.53 (m, 1H), 2.31 (d, 1H), 2.15-1.93 (m, 6H), 1.88-1.40 (m, 4H), 1.33 (s, 3H), 1.27 (dd, 1H), 1.12 (m, 1H), 1.00 (s, 3H), 0.99 (m, 1H). APCI-MS m/z: 588 [MH$^+$].

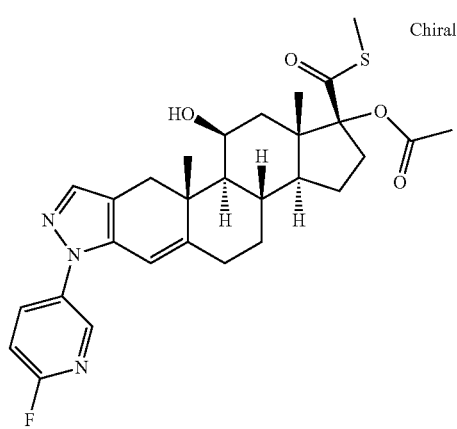

(1R,3aS,3bS,10aR,10bS,11S,12aS)-7-(6-Fluoropyridin-3-yl)-11-hydroxy-10a,12a-dimethyl-1-[(methylsulfanyl)carbonyl]-1,2,3,3a,3b,4,5,7,10,10a,10b,11,12,12a-tetradecahydrocyclopenta[5,6]naphtho[1,2-f]indazol-1-yl acetate The compound was prepared from Intermediate 123 and iodomethane according to the procedure described in Example 82.

$^1$H NMR (400 MHz, CDCl$_3$) δ 8.36 (d, 1H), 8.00 (ddd, 1H), 7.49 (s, 1H), 7.07 (dd, 1H), 6.07 (d, 1H), 4.56 (d, 1H), 3.03 (d, 1H), 3.00 (m, 1H), 2.73 (d, 1H), 2.52 (m, 1H), 2.32 (s, 3H), 2.30 (m, 1H), 2.11 (m, 1H), 2.08 (s, 3H), 2.07-1.93 (m, 4H), 1.81-1.64 (m, 3H), 1.51-1.36 (m, 1H), 1.33 (s, 13), 1.28 (dd, 1H), 1.12 (m, 2H), 0.95 (s, 3H), 0.92 (m, 1H). APCI-MS m/z: 540 [MH$^+$].

Example 173

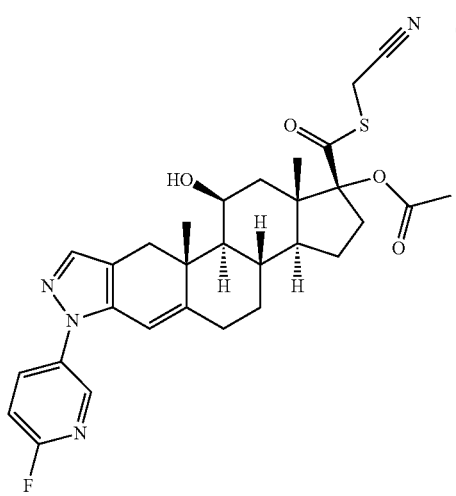

(1R,3aS,3bS,10aR,10bS,11S,12aS)-1-{[(Cyanomethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl acetate The compound was prepared from Intermediate 123 and 2-bromoacetonitrile according to the procedure described in Example 82.

$^1$H NMR (400 MHz, CDCl$_3$) δ 8.36 (d, 1H), 8.00 (ddd, 1H), 7.50 (s, 1H), 7.08 (dd, 1H), 6.07 (d, 1H), 4.56 (d, 1H), 3.78 (d, 1H), 3.57 (d, 1H), 3.03 (d, 1H), 2.96 (m, 1H), 2.72 (d, 1H), 2.53 (m, 1H), 2.31 (d, 1H), 2.11 (m, 1H), 2.10 (s, 3H), 2.07-1.93 (m, 4H), 1.82 (m, 1H), 1.65 (m, 1H), 1.53-1.40 (m, 2H), 1.33 (s, 3H), 1.28 (dd, 1H), 1.19-1.06 (m, 1H), 1.01 (s, 3H), 0.98 (m, 1H). APCI-MS m/z: 565 [MH$^+$].

Example 174

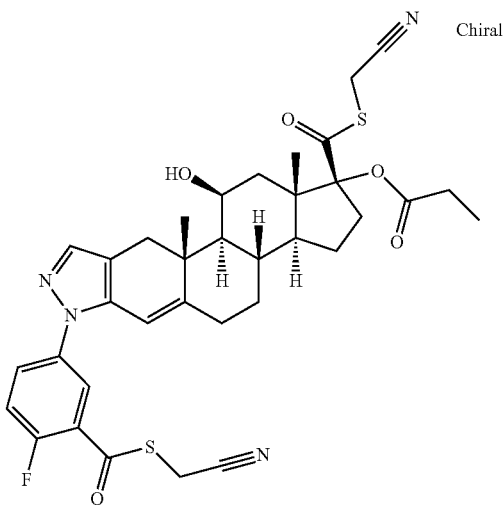

(1R,3aS,3bS,10aR,10bS,11S,12aS)-1-{[(Cyanomethyl)sulfanyl]carbonyl}-7-(3-{[(cyanomethyl)sulfanyl]carbonyl}-4-fluorophenyl)-11-hydroxy-10a,12a-dimethyl-1,2,3,3a,3b,4,5,7,10,10a,10,12,12a-tetradecahydrocyclopenta[5,6]naphtho[1,2-f]indazol-1-yl propanoate The compound was prepared from Intermediate 129 and 2-bromoacetonitrile according to the procedure described in Example 82.

$^1$H NMR (400 MHz, CDCl$_3$) δ 8.02 (dd, 1H), 7.80 (ddd, 1H), 7.48 (s, 1H), 7.34 (dd, 1H), 6.09 (d, 1H), 4.57 (d, 1H), 3.89 (s, 2H), 3.79 (d, 1H), 3.57 (d, 1H), 3.03 (d, 1H), 2.97 (m, 1H), 2.73 (d, 1H), 2.53 (m, 1H), 2.45-2.28 (m, 3H), 2.15-1.93 (m, 5H), 1.83 (m, 1H), 1.65 (m, 2H), 1.54-1.39 (m, 2H), 1.33 (s, 3H), 1.27 (dd, 1H), 1.21-1.05 (m, 4H), 1.01 (s, 3H), 0.99 (m, 1H). APCI-MS m/z: 677 [MH$^+$].

Example 175

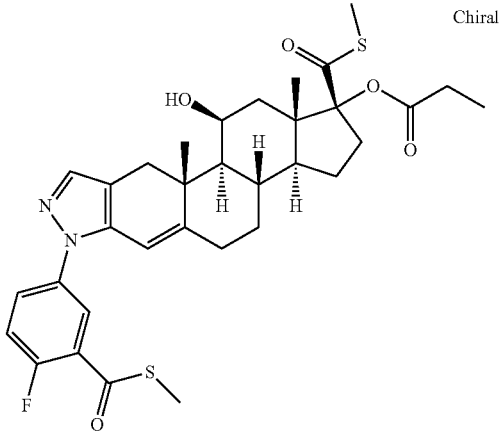

231

(1R,3aS,3bS,10aR,10bS,11S,12aS)-7-{4-Fluoro-3-[(methylsulfanyl)carbonyl]phenyl}-11-hydroxy-10a,12a-dimethyl-1-[(methylsulfanyl)carbonyl]-1,2,3,3a,3b,4,5,7,10,10a,10b,11,12,12a-tetradecahydrocyclopenta[5,6]naphtho[1,2-f]indazol-1-yl propanoate The compound was prepared from Intermediate 129 and iodomethane according to the procedure described in Example 82.

$^1$H NMR (400 MHz, CDCl$_3$) δ 7.96 (dd, 1H), 7.70 (ddd, 1H), 7.46 (s, 1H), 7.28 (t, 1H), 6.09 (d, 1H), 4.56 (d, 1H), 3.02 (d, 1H), 3.00 (m, 1H), 2.73 (d, 1H), 2.50 (d, 5H), 2.52 (s, 3H), 2.50 (m, 1H), 2.41-2.28 (m, 6H), 2.13 (dd, 1H), 2.07-1.93 (m, 4H), 1.80 (m, 2H), 1.64 (m, 1H), 1.50-1.37 (m, 2H), 1.32 (s, 3H), 1.27 (dd, 1H), 1.16 (t, 3H), 1.15-1.06 (m, 1H), 0.95 (s, 3H). APCI-MS m/z: 627 [MH$^+$].

Example 176

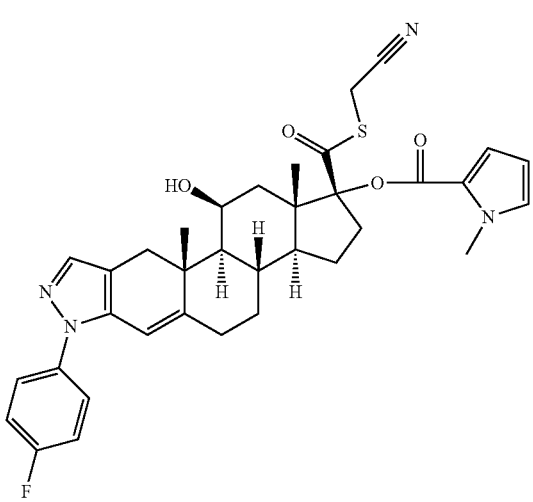

(1R,3aS,3bS,10aR,10bS,11S,12aS)-1-{[(Cyanomethyl)thio]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 1-methyl-1H-pyrrole-2-carboxylate The compound was prepared from Intermediate 130 and bromoacetonitrile according to the procedure described in Example 1.

$^1$H NMR (400 MHz, CDCl$_3$) δ 7.50-7.43 (3H, m), 7.17 (2H, t), 6.97 (1H, m), 6.86 (1H, s), 6.16 (1H, m), 6.09 (1H, s), 4.64 (1H, m), 3.89 (3H, s), 3.79 (1H, d, AB), 3.59 (1H, d, AB), 3.11-2.99 (2H, m), 2.77 (1H, d), 2.53 (1H, t), 2.35-2.19 (2H, d), 2.19-2.02 (3H, m), 2.02-1.91 (1H, m), 1.89-1.70 (2H, m), 1.56-1.43 (1H, m), 1.34 (3H, s), 1.31 (1H, m), 1.21 (1H, m), 1.17-1.07 (1H, m), 1.05 (3H, s). APCI-MS m/z: 629 [MH$^+$].

232

Example 177

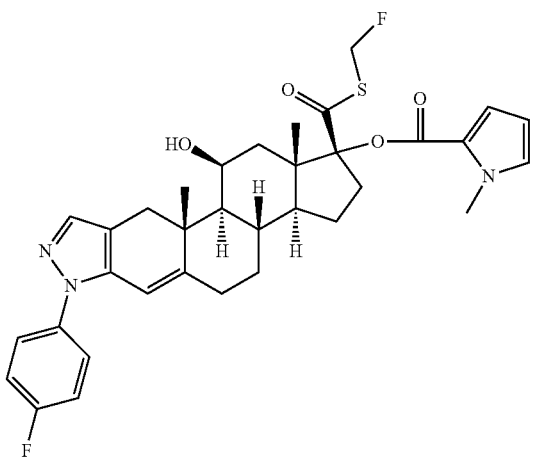

(1R,3aS,3bS,10aR,10bS,11S,12aS)-1-{[(Fluoromethyl)thio]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 1-methyl-1H-pyrrole-2-carboxylate The compound was prepared from Intermediate 130 and bromofluoromethane according to the procedure described in Example 1.

$^1$H NMR (400 MHz, CDCl$_3$) δ 7.50-7.43 (3H, m), 7.17 (2H, t), 6.98 (1H, m), 6.85 (1H, m), 6.16 (1H, m), 6.09 (1H, m), 6.07-5.63 (2H, m), 4.63 (1H, m), 3.89 (3H, s), 3.11-3.01 (2H, m), 2.77 (1H, d), 2.52 (1H, t), 2.35-2.22 (2H, d), 2.16-2.01 (3H, m), 2.01-1.93 (1H, m), 1.88-1.73 (2H, m), 1.53-1.44 (1H, m), 1.34 (3H, s), 1.31 (1H, m), 1.19-1.01 (2H, m), 1.05 (3H, s). APCI-MS m/z: 622 [MH$^+$].

Example 178

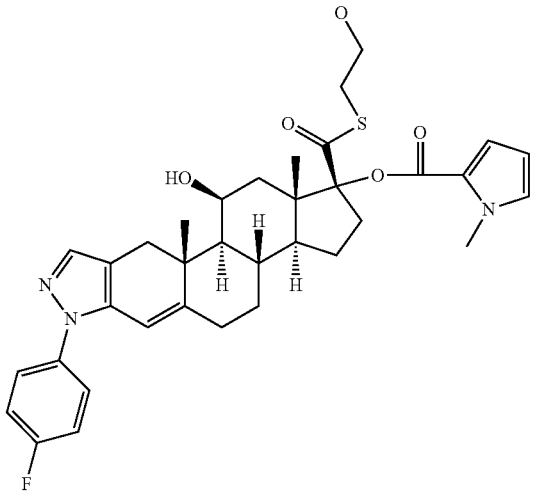

(1R,3aS,3bS,10aR,10bS,11S,12aS)-7-(4-Fluorophenyl)-11-hydroxy-1-{[(2-hydroxyethyl)thio]carbonyl}-10a,12a-dimethyl-1,2,3,3a,3b,4,5,7,10a,10b,11,12,12a-tetradecahydrocyclopenta[5,6]naphtho[1,2-]-indazol-1-yl 1-methyl-1H-pyrrole-2-carboxylate The compound was prepared from Intermediate 130 and 2-bromoethanol according to the procedure described in Example 1.

¹H NMR (400 MHz, CDCl₃) δ 7.50-7.43 (3H, m), 7.17 (2H, t), 6.98 (1H, m), 6.85 (1H, m), 6.16 (1H, m), 6.09 (1H, m), 4.63 (1H, m), 3.89 (3H, s), 3.84-3.71 (2H, m), 3.29-3.20 (1H, m) 3.11-3.01 (3H, m), 2.77 (1H, d), 2.52 (1H, t), 2.35-2.22 (2H, d), 2.15-1.92 (5H, m), 1.88-1.73 (2H, m), 1.53-1.42 (1H, m), 1.34 (3H, s), 1.31 (1H, m), 1.19 (1H, m), 1.15-1.05 (1H, m), 1.03 (3H, s). APCI-MS m/z: 634 [MH⁺].

Example 179

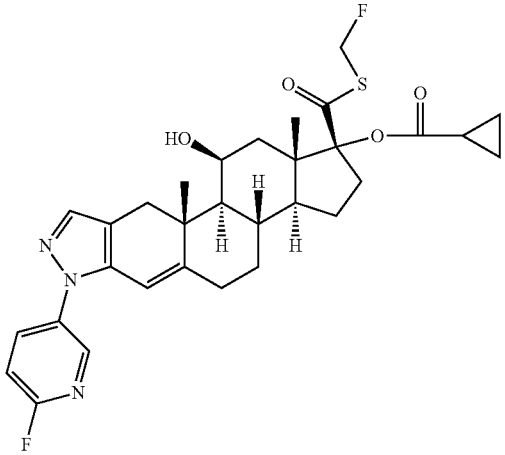

(1R,3aS,3bS,10aR,10bS,11S,12aS)-1-{[(Fluoromethyl)thio]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl cyclopropanecarboxylate The compound was prepared from Intermediate 119 and bromofluoromethane according to the procedure for Example 82.

¹H NMR (400 MHz, CDCl₃) δ 8.37 (1H, s), 8.00 (1H, m), 7.49 (1H, s), 7.08 (1H, dd), 6.08 (1H, bs); 6.05-5.62 (2H, m), 4.58 (1H, bs), 3.04 (1H, d), 2.98 (1H, m), 2.73 (1H, d), 2.54 (1H, t), 2.31 (1H, d), 2.16 (1H, m), 2.09-1.91 (5H, m), 1.89-1.79 (1H, m), 1.74-1.63 (2H, m), 1.53-1.41 (1H, m), 1.33 (3H, s), 1.31-1.25 (1H, m), 1.21-1.10 (1H, m), 1.11-1.02 (2H, m), 1.00 (3H, s), 0.96-0.90 (2H, m). APCI-MS m/z: 584 [MH⁺].

Example 180

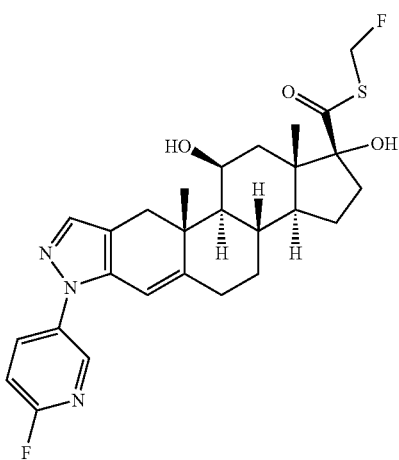

S-(Fluoromethyl)(1R,3aS,3bS,10aR,10bS,11S,12aS)-7-(6-fluoropyridin-3-yl)-1,11-dihydroxy-10a,12a-dimethyl-1,2,3,3a,3b,4,5,7,10,10a,10b,11,12,12a-tetradecahydrocyclopenta[5,6]naphtho[1,2-f]indazole-1-carbothioate The compound was prepared from Intermediate 42 and bromofluoromethane according to the procedure for Example 82.

¹H NMR (400 MHz, CDCl₃) δ 8.36 (1H, s), 7.99 (1H, m), 7.47 (1H, s), 7.07 (1H, dd), 6.07 (1H, bs); 5.93-5.68 (2H, m), 4.54 (1H, bs), 3.02 (1H, d), 2.87-2.77 (1H, m), 2.69 (1H, d), 2.52 (1H, t), 2.30 (1H, d), 2.11 (1H, s), 2.09-1.93 (3H, m), 1.93-1.86 (1H, m), 1.86-1.72 (2H, m), 1.64-1.46 (2H, m), 1.33 (3H, s), 1.25 (1H, dd), 1.20-1.10 (1H, m), 1.05-1.00 (4H, m). APCI-MS m/z: 516 [MH⁺].

Example 181

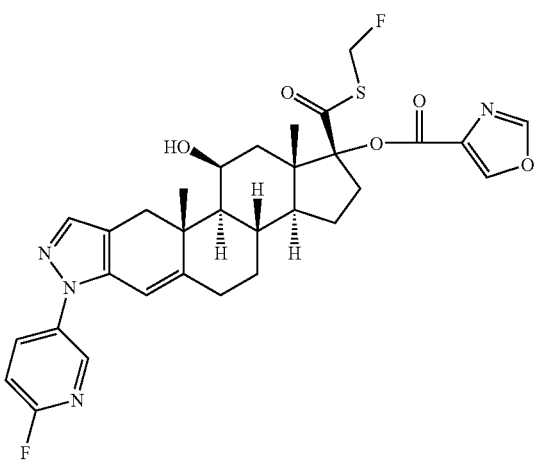

(1R,3aS,3bS,10aR,10bS,11S,12aS)-1-{[(Fluoromethyl)thio]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 1,3-oxazole-4-carboxylate The compound was prepared from Intermediate 121 and bromofluoromethane according to the procedure for Example 82.

¹H NMR (400 MHz, CDCl₃) δ 8.37 (1H, s), 8.31 (1H, d), 8.00 (1H, m), 7.96 (1H, d), 7.50 (1H, s), 7.08 (1H, dd), 6.08 (1H, bs); 6.05-5.62 (2H, m), 4.63 (1H, bs), 3.17-2.99 (2H, m), 2.77 (1H, d), 2.54 (1H, t), 2.35-2.24 (2H, m), 2.22-2.04 (3H, m), 2.04-1.93 (1H, m), 1.93-1.84 (1H, m), 1.84-1.72 (1H, m), 1.57-1.47 (1H, m), 1.37 (1H, m), 1.35 (3H, s), 1.22-1.10 (2H, m), 1.07 (3H, s). APCI-MS m/z: 611 [MH⁺].

Example 182

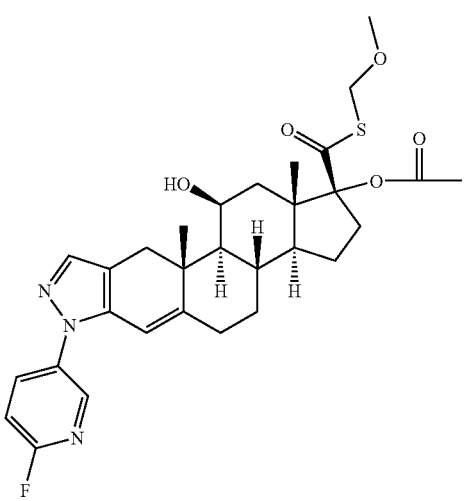

(1R,3aS,3bS,10aR,10bS,11S,12aS)-7-(6-Fluoropyridin-3-yl)-11-hydroxy-1-{[(methoxymethyl)thio]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl acetate The compound was prepared from Intermediate 123 and Bromomethyl methylether according to the procedure for Example 82.

$^1$H NMR (400 MHz, CDCl$_3$) δ 8.36 (1H, s), 7.99 (1H, m), 7.49 (1H, s), 7.07 (1H, dd), 6.08 (1H, bs); 5.12 (2H, s), 4.56 (1H, bs), 3.33 (3H, s), 3.07-2.95 (2H, m), 2.74 (1H, d), 2.53 (1H, t), 2.31 (1H, d), 2.19-2.08 (4H, m), 2.06-1.93 (4H, m), 1.88-1.75 (1H, m), 1.72-1.61 (1H, m), 1.52-1.40 (1H, m), 1.33 (3H, s), 1.29 (1H, d), 1.20-1.05 (2H, m), 0.98 (3H, s). APCI-MS m/z: 570 [MH$^+$].

Example 183

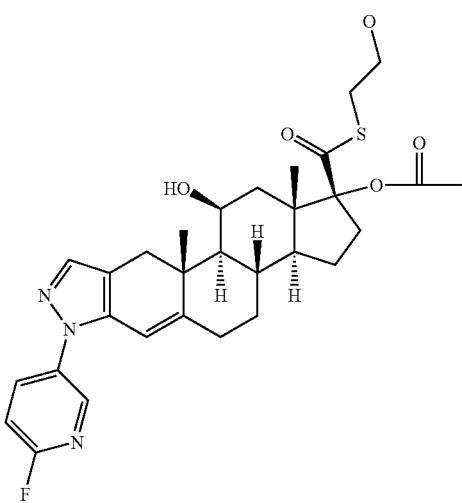

(1R,3aS,3bS,10aR,10bS,11S,12aS)-7-(6-Fluoropyridin-3-yl)-11-hydroxy-1-{[(2-hydroxyethyl)thio]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl acetate The compound was prepared from Intermediate 123 and 2-Bromoethanol according to the procedure for Example 82.

$^1$H NMR (400 MHz, CDCl$_3$) δ 8.36 (1H, s), 7.99 (1H, m), 7.49 (1H, s), 7.07 (1H, dd), 6.08 (1H, bs); 4.57 (1H, bs), 3.78 (2H, m), 3.26-3.14 (1H, m), 3.13-2.94 (3H, m), 2.73 (1H, d), 2.52 (1H, t), 2.31 (1H, d), 2.17-2.07 (4H, m), 2.07-1.92 (4H, m), 1.91-1.85 (1H, m), 1.85-1.76 (1H, m), 1.72-1.61 (1H, m), 1.51-1.40 (1H, m), 1.33 (3H, s), 1.29 (1H, d), 1.20-1.06 (2H, m), 0.97 (3H, s). APCI-MS m/z: 570 [MH$^+$].

Example 184

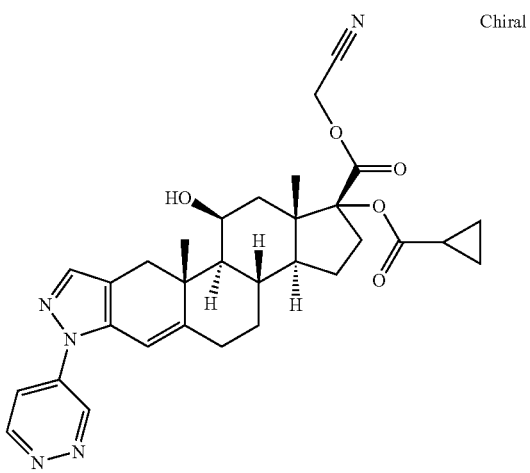

Cyanomethyl(1R,3aS,3bS,10aR,10bS,11S,12aS)-1-[(cyclopropylcarbonyl)oxy]-11-hydroxy-10a,12a-dimethyl-7-pyridazin-4-yl-1,2,3,3a,3b,4,5,7,10,10a,10b,11,12,12a-tetradecahydrocyclopenta[5,6]naphtho[1,2-f]indazole-1-carboxylate The compound was prepared from Intermediate 136 and 2-bromoacetonitrile according to the procedure described in Example 9.

$^1$H NMR (400 MHz, DMSO-d$_6$) δ 9.60 (d, 1H), 9.27 (dd, 1H), 7.89 (dd, 1H), 7.72 (s, 1H), 6.39 (s, 1H), 5.04 (d, 1H), 4.96 (d, 1H), 4.54 (s, 1H), 4.34 (s, 1H), 2.96 (d, 1H), 2.76 (m, 1H), 2.67 (m, 1H), 2.41 (m, 1H), 1.90 (m, 3H), 1.82-1.57 (m, 6H), 1.48 (m, 1H), 1.22 (s, 3H), 1.15 (m, 1H), 1.06 (m, 1H), 0.92 (m, 5H), 0.83 (m, 2H). APCI-MS m/z: 558 [MH$^+$].

Example 185

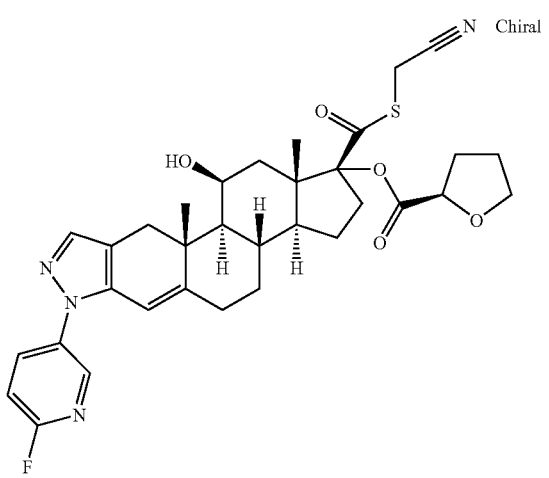

(1R,3aS,3bS,10aR,10bS,11S,12aS)-1-{[(Cyanomethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl (2R)-tetrahydrofuran-2-carboxylate The compound was prepared from Intermediate 137 and 2-bromoacetonitrile according to the procedure described in Example 1.

$^1$H NMR (500 MHz, DMSO-d$_6$) δ 8.39 (s, 1H), 8.14 (m, 1H), 7.55 (s, 1H), 7.36 (dd, 1H), 6.16 (d, 1H), 4.59 (b, 1H), 4.49 (dd, 1H), 4.36 (b, 1H), 3.80 (m, 2H), 2.95 (d, 1H), 2.79 (m, 1H), 2.64 (m, 1H), 2.43 (m, 1H), 2.31 (m, 1H), 2.19 (m, 2H), 2.05 (m, 1H), 1.98-1.69 (m, 9H), 1.60 (m, 1H), 1.39 (m, 1H), 1.23 (s, 3H), 1.12 (m, 1H), 1.02 (m, 1H), 0.89 (s, 3H). APCI-MS m/z: 621 [MH$^+$].

Example 186

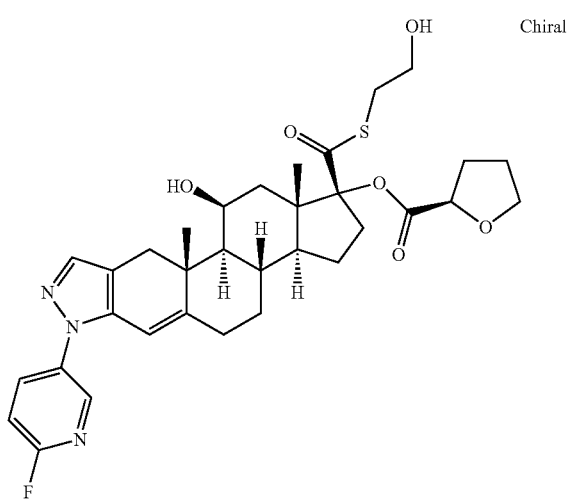

Example 187

(1R,3aS,3bS,10aR,10bS,11S,12aS)-7-(6-Fluoropyridin-3-yl)-11-hydroxy-1-{[(2-hydroxyethyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl (2R)-tetrahydrofuran-2-carboxylate The compound was prepared from Intermediate 137 and 2-bromoethanol according to the procedure described in Example 1.

$^1$H NMR (400 MHz, DMSO-d$_6$) δ 8.39 (s, 1H), 8.14 (m, 1H), 7.55 (s, 1H), 7.36 (dd, 1H), 6.16 (d, 1H), 4.50 (b, 3H), 4.75 (b, 1H), 3.80 (m, 2H), 2.95 (m, 3H), 2.79 (m, 1H), 2.64 (m, 1H), 2.43 (m, 1H), 2.31 (m, 1H), 2.11 (m, 3H), 1.98-1.78 (m, 8H), 1.72 (m, 1H), 1.57 (m, 1H), 1.34 (m, 1H), 1.21 (s, 3H), 1.12 (m, 1H), 1.02 (m, 1H), 0.8s (s, 3H).

APCI-MS m/z: 626 [MH$^+$].

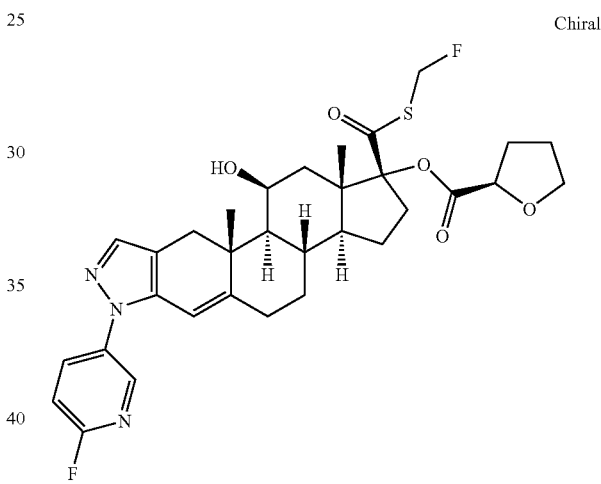

(1R,3aS,3bS,10aR,10bS,11S,12aS)-1-{[(Fluoromethyl)sulfanyl]carbonyl}-7-(6-fluoropyridin-3-yl)-11-hydroxy-10a,12a-dimethyl-1,2,3,3a,3b,4,5,10,10a,10b,11,12,12a-tetradecahydrocyclopenta[5,6]naphtho[1,2-f]indazol-1-yl (2R)-tetrahydrofuran-2-carboxylate The compound was prepared from Intermediate 137 and bromofluoromethane according to the procedure described in Example 1.

$^1$H NMR (400 MHz, DMSO-d$_6$) δ 8.39 (s, 1H), 8.14 (m, 1H), 7.55 (s, 1H), 7.36 (dd, 1H), 6.16 (d, 1H), 5.98 (m, 1H), 5.84 (m 1H), 4.55 (d, 1H), 4.35 (b, 1H), 3.80 (m, 1H), 2.95 (m, 3H), 2.79 (m, 1H), 2.64 (m, 1H), 2.43 (m, 1H), 2.31 (m, 1H), 2.11 (m, 3H), 1.98-1.78 (m, 8H), 1.72 (m, 1H), 1.57 (m, 1H), 1.34 (m, 1H), 1.21 (s, 3H), 1.12 (m, 1H), 1.02 (m, 1H), 0.8s (s, 3H). APCI-MS m/z: 614 [MH$^+$].

Example 188

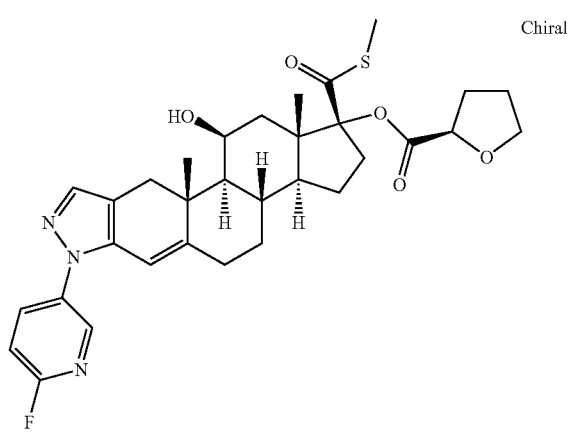

(1R,3aS,3bS,10aR,10bS,11S,12aS)-7-(6-Fluoropyridin-3-yl)-11-hydroxy-10a,12a-dimethyl-1-[(methylsulfanyl)carbonyl]-1,2,3,3a,3b,4,5,7,10,10a,10b,11,12,12a-tetradecahydrocyclopenta[5,6]naphtho[1,2]-indazol-1-yl (2R)-tetrahydrofuran-2-carboxylate The compound was prepared from Intermediate 137 and iodomethane according to the procedure described in Example 82.

$^1$H NMR (500 MHz, DMSO-d$_6$) δ 8.39 (s, 1H), 8.14 (m, 1H), 7.55 (s, 1H), 7.36 (dd, 1H), 6.16 (d, 1H), 4.49 (b, 2H), 4.36 (b, 1H), 3.80 (m, 2H), 2.95 (d, 1H), 2.79 (m, 1H), 2.64 (m, 1H), 2.43 (m, 1H), 2.31 (m, 1H), 2.24 (s, 3H), 2.19 (m, 2H), 2.05 (m, 1H), 1.98-1.69 (m, 7H), 1.60 (m, 1H), 1.39 (m, 1H), 1.23 (s, 3H), 1.12 (m, 1H), 1.02 (m, 1H), 0.89 (s, 3H). APCI-MS m/z: 596 [MH$^+$].

Example 189

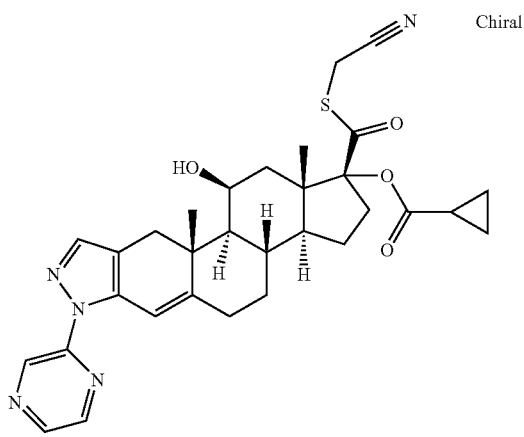

(1R,3aS,3bS,10aR,10bS,11S,12aS)-1-{[(Cyanomethyl)sulfanyl]carbonyl}-11-hydroxy-10a,12a-dimethyl-7-pyrazin-2-yl-1,2,3,3a,3b,4,5,7,10,10a,10b,11,12,12a-tetradecahydrocyclopenta[5,6]naphtho[1,2-f]indazol-1-yl cyclopropanecarboxylate The compound was prepared from Intermediate 140 and 2-bromoacetonitrile according to the procedure described in Example 1.

$^1$H NMR (400 MHz, DMSO-d$_6$) δ 9.15 (s, 1H), 8.54 (m, 2H), 7.65 (s, 1H), 7.00 (s, 1H), 4.56 (b, 1H), 4.34 (s, 1H), 4.04 (d, 1H), 3.93 (d, 1H), 2.96 (d, 1H), 2.76 (m, 1H), 2.67 (m, 1H), 2.45 (m, 1H), 2.41 (m, 1H), 1.97-1.65 (m, 8H), 1.59 (m, 1H), 1.38 (m, 1H), 1.28 (m, 4H), 1.02 (m, 1H), 0.92 (m, 6H).
APCI-MS m/z: 574 [MH$^+$].

Example 190

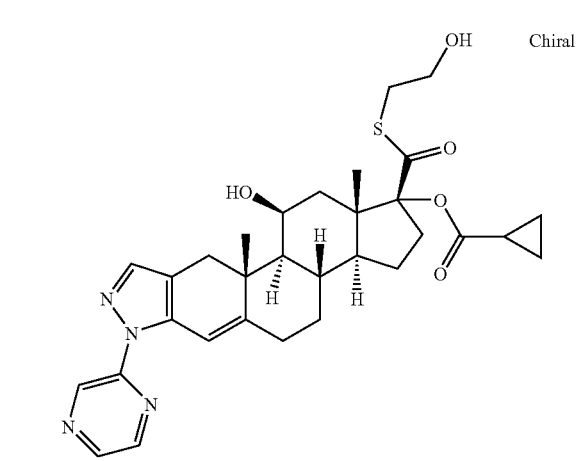

(1R,3aS,3bS,10aR,10bS,11S,12aS)-11-Hydroxy-{[(2-hydroxyethyl)sulfanyl]carbonyl}-10a,12a-dimethyl-7-pyrazin-2-yl-1,2,3,3a,3b,4,5,7,10,10a,10b,11,12,12a-tetradecahydrocyclopenta[5,6]naphtho[1,2-f]indazol-1-yl cyclopropane carboxylate The compound was prepared from Intermediate 140 and 2-bromoethanol according to the procedure described in Example 1.

$^1$H NMR (400 MHz, DMSO-d$_6$) δ 9.15 (s, 1H), 8.54 (m, 2H), 7.65 (s, 1H), 7.00 (s, 1H), 4.56 (b, 1H), 4.34 (s, 1H), 4.04 (d, 1H), 3.93 (d, 1H), 2.96 (d, 1H), 2.76 (m, 1H), 2.67 (m, 1H), 2.45 (m, 1H), 2.41 (m, 1H), 1.97-1.65 (m, 8H), 1.59 (m, 1H), 1.38 (m, 1H), 1.28 (m, 4H), 1.02 (m, 1H), 0.92 (m, 6H).
APCI-MS m/z: 579 [MH$^+$].

Example 191

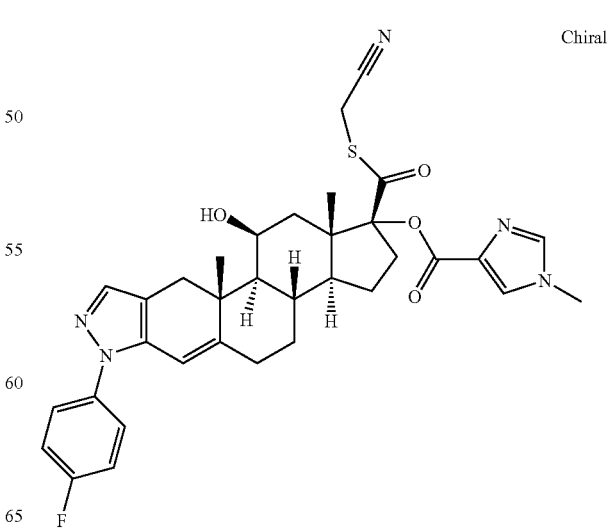

(1R,3aS,3bS,10aR,10bS,11S,12aS)-1-{[(Cyanomethyl)sulfanyl]carbonyl}-7-(4-fluorophenyl)-11-hydroxy-10a,12a-dimethyl-1,2,3,3a,3b,4,5,7,10,11a,10b,11,12,12a-tetradecahydrocyclopenta[5,6]naphtho[1,2-f]indazol-1-yl 1-methyl-1H-imidazole-4-carboxylate The compound was prepared from Intermediate 141 and 2-bromoacetonitrile according to the procedure described in Example 1.

$^{1}$H NMR (400 MHz, DMSO-d6) δ 8.01 (s, 1H), 7.79 (s, 1H), 7.51 (m, 3H), 7.35 (m, 2H), 6.13 (s, 1H), 4.58 (b, 1H), 4.42 (s, 1H), 4.00 (d, 2H), 3.72 (s, 3H), 3.00 (d, 1H), 2.85 (m, 1H), 2.68 (m, 2H), 2.11 (d, 1H), 2.03-1.61 (m, 6H), 1.42 (m, 1H), 1.26 (m, 4H), 1.11 (m, 1H), 0.89 (s, 3H).

APCI-MS m/z: 630 [MH$^{+}$].

Example 192

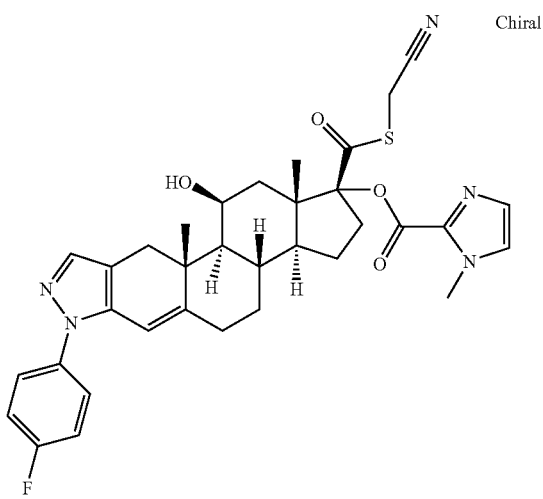

(1R,3aS,3bS,10aR,10bS,11S,12aS)-1-{[(Cyanomethyl)sulfanyl]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 1-methyl-1H-imidazole-2-carboxylate The compound was prepared from Intermediate 142 and 2-bromoacetonitrile according to the procedure described in Example 1.

$^{1}$H NMR (400 MHz, DMSO-d$_{6}$) δ 7.51 (m, 4H), 7.33 (m, 2H), 7.13 (m, 1H), 6.13 (s, 1H), 4.58 (b, 1H), 4.42 (s, 1H), 4.00 (d, 2H), 3.88 (s, 3H), 3.00 (d, 1H), 2.85 (m, 1H), 2.68 (m, 2H), 2.11 (d, 1H), 2.03-1.61 (m, 6H), 1.42 (m, 1H), 1.26 (m, 4H), 1.11 (m, 1H), 0.89 (s, 3H).

APCI-MS m/z: 630 [MH$^{+}$].

Example 193

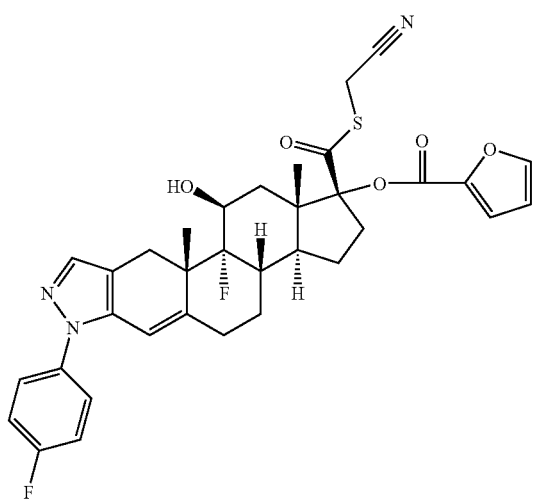

(1R,3aS,3bS,10aS,10bR,11S,12aS)-1-{[(Cyanomethyl)sulfanyl]carbonyl}-10b-fluoro-7-(4-fluorophenyl)-11-hydroxy-10a,12a-dimethyl-1,2,3,3a,3b,4,5,7,10,10a,11,12,12a-tetradecahydrocyclopenta[5,6]naphtho[1,2-f]indazol-1-yl furan-2-carboxylate The compound was prepared according to the procedure for Example 11, starting from Intermediate 147 and 2-Bromoacetonitrile.

$^{1}$H NMR (400 MHz, CDCl$_{3}$) δ 7.64 (1H, bs), 7.49-7.44 (3H, m), 7.24 (1H, d), 7.17 (2H, t), 6.55 (1H, m), 6.19 (1H, bs), 4.55 (1H, bs), 3.85 (1H, d, AB), 3.53 (1H, d, AB), 3.38 (1H, d), 3.06 (1H, m), 2.83 (1H, d), 2.69-2.56 (2H, m), 2.46-2.28 (3H, m), 2.25-2.12 (1H, m), 1.93 (1H, d), 1.89-1.72 (2H, m), 1.66-1.50 (2H, m), 1.44 (3H, s), 1.38 (1H, m), 1.07 (3H, d). APCI-MS m/z: 634 [MH$^{+}$].

Example 194

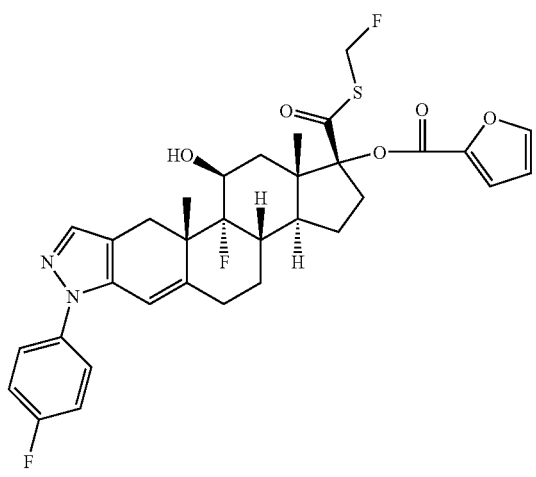

243

(1R,3aS,3bS,10aS,10bR,11S,12aS)-1-{[(Fluoromethyl)sulfanyl]carbonyl}-10b-fluoro-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate The compound was prepared according to the procedure for Example 11, starting from Intermediate 147 and Bromofluoromethane.

$^1$H NMR (400 MHz, CDCl$_3$) δ 7.63 (1H, m), 7.50-7.44 (3H, m), 7.24 (1H, d), 7.17 (2H, t), 6.54 (1H, m), 6.19 (1H, bs), 6.11-5.58 (2H, m), 4.55 (1H, bs), 3.38 (1H, d), 3.08 (1H, m), 2.82 (1H, d), 2.71-2.55 (2H, m), 2.44-2.29 (3H, m), 2.24-2.10 (1H, m), 1.97 (1H, d), 1.88-1.71 (2H, m), 1.66-1.48 (2H, m), 1.44 (3H, s), 1.35 (1H, m), 1.05 (3H, d). APCI-MS m/z: 627 [MH$^+$].

Example 195

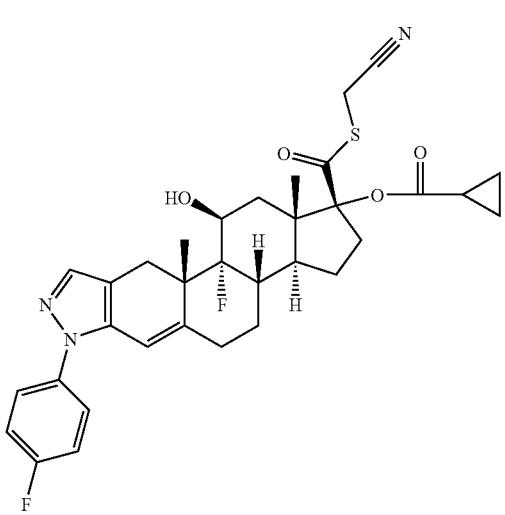

(1R,3aS,3bS,10aS,10bR,11S,12aS)-1-{[(Cyanomethyl)sulfanyl]carbonyl}-10b-fluoro-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2]-indazol-1-yl cyclopropanecarboxylate The compound was prepared according to the procedure for Example 11, starting from Intermediate 148 and 2-Bromoacetonitrile.

$^1$H NMR (400 MHz, CDCl$_3$) δ 7.50-7.44 (3H, m), 7.17 (2H, t), 6.18 (1H, bs), 4.48 (1H, bs), 3.80 (1H, d, AB), 3.55 (1H, d, AB), 3.33 (1H, d), 2.97 (1H, m), 2.80 (1H, d), 2.60 (1H, t), 2.48 (1H, d), 2.40-2.14 (3H, m), 2.07-1.97 (1H, m), 1.87 (1H, d), 1.83-1.72 (2H, m), 1.72-1.65 (1H, m), 1.63-1.57 (1H, m), 1.52-1.44 (1H, m), 1.41 (3H, s), 1.12-1.03 (2H, m), 1.00 (3H, s), 0.98-0.92 (2H, m). APCI-MS m/z: 608 [MH$^+$].

244

Example 196

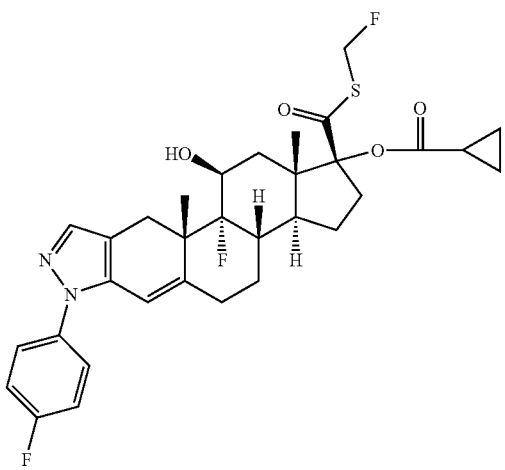

(1R,3aS,3bS,10aS,10bR,11S,12aS)-1-{[(Fluoromethyl)sulfanyl]carbonyl}-10b-fluoro-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl cyclopropanecarboxylate The compound was prepared according to the procedure for Example 11, starting from Intermediate 148 and Bromofluoromethane.

$^1$H NMR (400 MHz, CDCl$_3$) δ 7.50-7.42 (3H, m), 7.17 (2H, t), 6.19 (1H, bs), 6.08-5.60 (2H, m), 4.48 (1H, bs), 3.34 (1H, d), 2.99 (1H, m), 2.80 (1H, d), 2.61 (1H, t), 2.50 (1H, d), 2.41-2.30 (2H, m), 2.30-2.15 (2H, m), 2.06-1.94 (1H, m), 1.90 (1H, d), 1.85-1.72 (2H, m), 1.72-1.65 (1H, m), 1.60-1.52 (1H, m), 1.41 (3H, s), 1.35-1.30 (1H, m), 1.13-1.01 (2H, m), 0.99 (3H, s), 0.96-0.91 (2H, m). APCI-MS m/z: 601 [MH$^+$].

Example 197

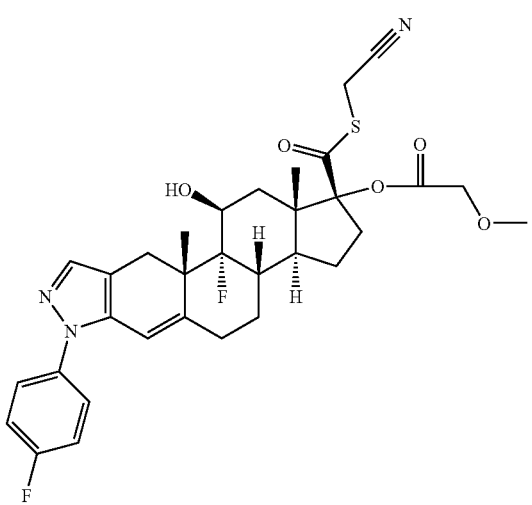

(1R,3aS,3bS,10aS,10bR,11S,12aS)-1-{[(Cyanomethyl)sulfanyl]carbonyl}-10b-fluoro-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl methoxyacetate The compound was prepared according to the procedure for Example 11, starting from Intermediate 149 and 2-Bromoacetonitrile.

$^1$H NMR (400 MHz, CDCl$_3$) δ 7.50-7.42 (3H, m), 7.16 (2H, t), 6.18 (1H, bs), 4.48 (1H, bs), 4.09 (2H, m), 3.82 (1H, d, AB), 3.57 (1H, d, AB), 3.46 (3H, s), 3.32 (1H, d), 3.03 (1H, m), 2.79 (1H, d), 2.61 (1H, t), 2.46 (1H, d), 2.40-2.24 (2H, m), 2.24-2.01 (2H, m), 1.89-1.68 (3H, m), 1.65-1.53 (2H, m), 1.44 (1H, m), 1.41 (3H, s), 1.02 (3H, s). APCI-MS m/z: 612 [MH$^+$].

Example 198

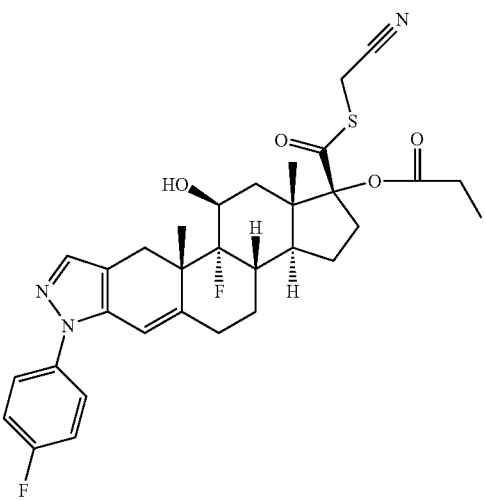

Example 199

(1R,3aS,3bS,10aS,10bR,11S,12aS)-1-{[(Cyanomethyl)sulfanyl]carbonyl}-10b-fluoro-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl propanoate The compound was prepared according to the procedure for Example 11, starting from Intermediate 150 and 2-Bromoacetonitrile.

$^1$H NMR (400 MHz, CDCl$_3$) δ 7.51-7.42 (3H, m), 7.16 (2H, t), 6.18 (1H, bs), 4.49 (1H, bs), 3.81 (1H, d, AB), 3.55 (1H, d, AB), 3.33 (1H, d), 2.99 (1H, m), 2.80 (1H, d), 2.61 (1H, t), 2.51 (1H, d), 2.46-2.29 (4H, m), 2.24-2.13 (1H, m), 2.09-1.97 (1H, m), 1.86 (1H, d), 1.83-1.71 (2H, m), 1.66-1.50 (2H, m), 1.41 (3H, s), 1.36 (1H, m), 1.16 (3H, t), 1.00 (3H, s). APCI-MS m/z: 596 [MH$^+$].

Example 200

(1R,3aS,3bS,10aS,10bR,11S,12aS)-1-{[(Fluoromethyl)sulfanyl]carbonyl}-10b-fluoro-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl methoxyacetate The compound was prepared according to the procedure for Example 11, starting from Intermediate 149 and Bromofluoromethane.

$^1$H NMR (400 MHz, CDCl$_3$) δ 7.50-7.42 (3H, m), 7.16 (2H, t), 6.18 (1H, bs), 6.08-5.61 (2H, m), 4.48 (1H, bs), 4.09 (2H, m), 3.47 (3H, s), 3.32 (1H, d), 3.05 (1H, m), 2.79 (1H, d), 2.60 (1H, t), 2.48 (1H, d), 2.40-2.24 (2H, m), 2.24-2.01 (2H, m), 1.88 (1H, d), 1.84-1.70 (2H, m), 1.60-1.43 (2H, m), 1.44 (1H, m), 1.41 (3H, s), 1.34 (1H, m), 1.00 (3H, s). APCI-MS m/z: 605 [MH$^+$].

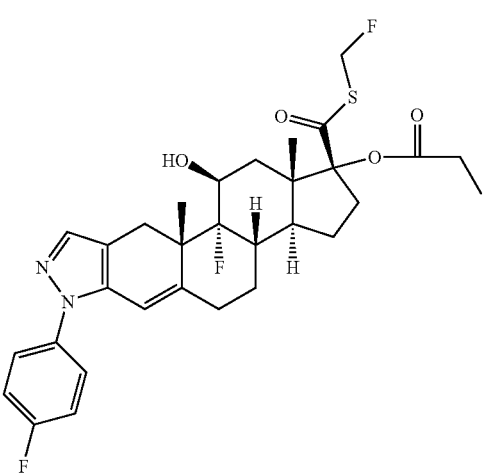

(1R,3aS,3bS,10aS,10bR,11S,12aS)-1-{[(Fluorom-
ethyl)sulfanyl]carbonyl}-10b-fluoro-7-(4-fluorophe-
nyl)-11-hydroxy-10a,12a-dimethyl-1,2,3,3a,3b,4,5,7,
10,10a,10b,11,12,12a-tetradecahydrocyclopenta[5,6]
naphtho[1,2-f]indazol-1-yl propanoate The compound was prepared according to the procedure for Example 11, starting from Intermediate 150 and Bromofluoromethane.

$^1$H NMR (400 MHz, CDCl$_3$) δ 7.50-7.42 (3H, m), 7.17 (2H, t), 6.18 (1H, bs), 6.09-5.60 (2H, m), 4.48 (1H, bs), 3.33 (1H, d), 3.02 (1H, m), 2.80 (1H, d), 2.65-2.48 (2H, m), 2.46-2.29 (4H, m), 2.30-2.15 (1H, m), 2.10-1.95 (1H, m), 1.89 (1H, d), 1.85-1.70 (2H, m), 1.66-1.50 (2H, m), 1.42 (3H, s), 1.28 (1H, m), 1.17 (3H, t), 0.99 (3H, s). APCI-MS m/z: 589 [MH$^+$].

Example 201

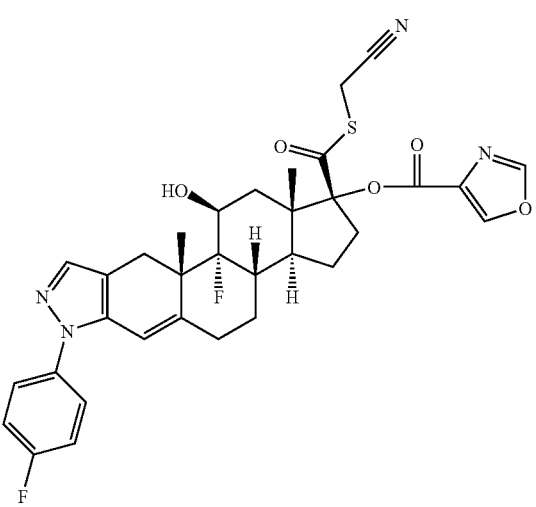

(1R,3aS,3bS,10aS,10bR,11S,12aS)-1-{[(Cyanom-
ethyl)sulfanyl]-carbonyl}-10b-fluoro-7-(4-fluorophe-
nyl)-11-hydroxy-10a,12a-dimethyl-1,2,3,3a,3b,4,5,7,
10,10a,10b,11,12,12a-tetradecahydrocyclopenta[5,6]
naphtho[1,2-f]indazol-1-yl 1,3-oxazole-4-
carboxylate The compound was prepared according to the procedure for Example 11, starting from Intermediate 151 and 2-Bromoacetonitrile.

$^1$H NMR (400 MHz, CDCl$_3$) δ 8.28 (1H, d), 7.96 (1H, d), 7.50-7.42 (3H, m), 7.17 (2H, t), 6.19 (1H, bs), 4.55 (1H, bs), 3.84 (1H, d, AB), 3.54 (1H, d, AB), 3.36 (1H, d), 3.08 (1H, m), 2.82 (1H, d), 2.69-2.55 (2H, m), 2.44-2.13 (4H, m), 1.94 (1H, d), 1.89-1.71 (2H, m), 1.63-1.48 (2H, m), 1.46 (1H, m), 1.44 (3H, s), 1.07 (3H, s). APCI-MS m/z: 635 [MH$^+$].

Example 202

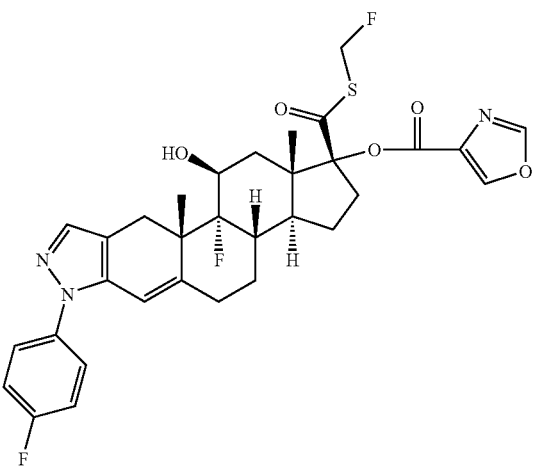

(1R,3aS,3bS,10aS,10bR,11S,12aS)-1-{[(Fluorom-
ethyl)sulfanyl]carbonyl}-10b-fluoro-7-(4-fluorophe-
nyl)-11-hydroxy-10a,12a-dimethyl-1,2,3,3a,3b,4,5,7,
10,10a,10b,11,12,12a-tetradecahydrocyclopenta[5,6]
naphtho[1,2-f]indazol-1-yl 1,3-oxazole-4-
carboxylate The compound was prepared according to the procedure for Example 11, starting from Intermediate 151 and Bromofluoromethane.

$^1$H NMR (400 MHz, CDCl$_3$) δ 8.28 (1H, d), 7.95 (1H, d), 7.50-7.42 (3H, m), 7.17 (2H, t), 6.19 (1H, bs), 6.10-5.58 (2H, m), 4.55 (1H, bs), 3.36 (1H, d), 3.11 (1H, m), 2.82 (1H, d), 2.68-2.54 (2H, m), 2.45-2.26 (3H, m), 2.25-2.13 (1H, m), 1.98 (1H, d), 1.89-1.71 (2H, m), 1.65-1.48 (2H, m), 1.43 (3H, s), 1.38 (1H, m), 1.06 (3H, s). APCI-MS m/z: 628 [MH$^+$].

Example 203

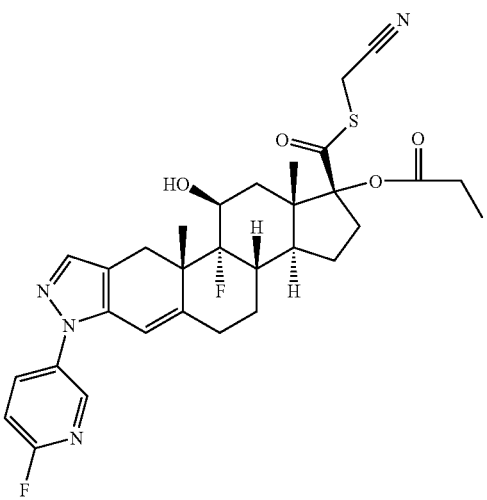

249

(1R,3aS,3bS,10aS,10bR,11S,12aS)-1-{[(Cyanom-
ethyl)sulfanyl]carbonyl}-10b-fluoro-7-(6-fluoropyri-
din-3-yl)-11-hydroxy-10a,12a-dimethyl-1,2,3,3a,3b,
4,5,7,10,10a,10b,11,12,12a-
tetradecahydrocyclopenta[5,6]naphtho[1,2-f]indazol-
1-yl propanoate The compound was prepared according to the procedure in Example 11, starting from Intermediate 153 and 2-Bromoacetonitrile.

$^1$H NMR (400 MHz, CDCl$_3$) δ 8.37 (1H, s), 7.99 (1H, m), 7.51 (1H, s), 7.07 (1H, m), 6.18 (1H, s), 4.48 (1H, bs), 3.81 (1H, d, AB), 3.55 (1H, d, AB), 3.33 (1H, d), 3.00 (1H, m), 2.82 (1H, d), 2.63 (1H, t), 2.50 (1H, d), 2.45-2.24 (5H, m), 2.25-2.13 (1H, m), 2.10-1.97 (1H, m), 1.86 (1H, d), 1.83-1.71 (2H, m), 1.66-1.50 (1H, m), 1.42 (3H, s), 1.35 (1H, bs), 1.16 (3H, t), 1.01 (3H, s). APCI-MS m/z: 597 [MH$^+$].

Example 204

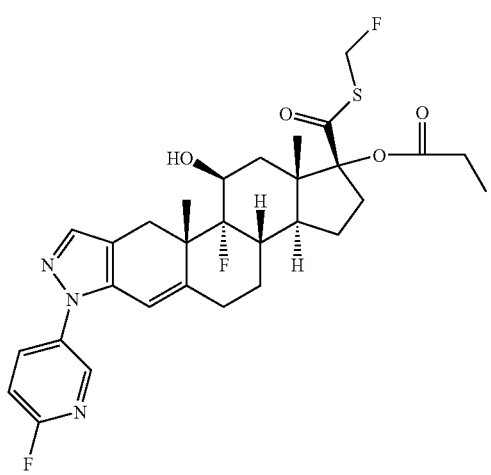

(1R,3aS,3bS,10aS,10bR,11S,12aS)-1-{[(Fluorom-
ethyl)sulfanyl]carbonyl}-10b-fluoro-7-(6-fluoropyri-
din-3-yl)-11-hydroxy-10a,12a-dimethyl-1,2,3,3a,3b,
4,5,7,10,10a,10b,11,12,12a-
tetradecahydrocyclopenta[5,6]naphtho[1,2-f]indazol-
1-yl propanoate The compound was prepared according to the procedure for Example 11, starting from Intermediate 153 and Bromofluoromethane.

$^1$H NMR (400 MHz, CDCl$_3$) δ 8.37 (1H, s), 7.99 (1H, m), 7.51 (1H, s), 7.07 (1H, m), 6.18 (1H, s), 6.10-5.60 (2H, m), 4.47 (1H, bs), 3.33 (1H, d), 3.03 (1H, m), 2.81 (1H, d), 2.62 (1H, t), 2.52 (1H, d), 2.45-2.14 (6H, m), 2.07-10.96 (1H, m), 1.89 (1H, d), 1.84-1.71 (2H, m), 1.66-1.54 (1H, m), 1.42 (3H, s), 1.35 (1H, bs), 1.17 (3H, t), 0.99 (3H, s). APCI-MS m/z: 590 [MH$^+$].

Example 205

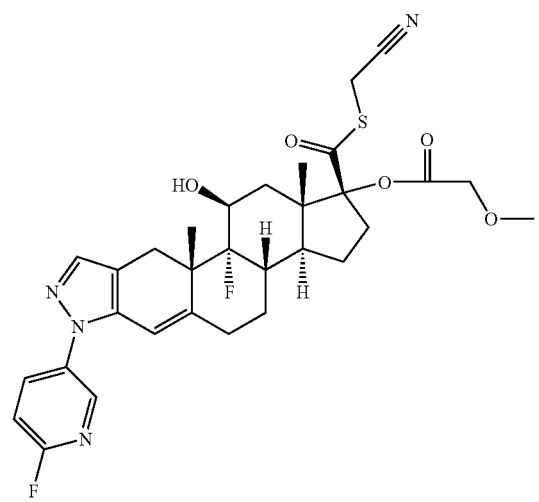

(1R,3aS,3bS,10aS,10bR,11S,12aS)-1-{[(Cyanom-
ethyl)sulfanyl]carbonyl}-10b-fluoro-7-(6-fluoropyri-
din-3-yl)-11-hydroxy-10a,12a-dimethyl-1,2,3,3a,3b,
4,5,7,10,10a,10b,11,12,12a-
tetradecahydrocyclopenta[5,6]naphtho[1,2-f]indazol-
1-yl methoxyacetate The compound was prepared according to the procedure for Example 11, starting from Intermediate 154 and 2-Bromoacetonitrile.

$^1$H NMR (400 MHz, CDCl$_3$) δ 8.36 (1H, s), 7.99 (1H, m), 7.51 (1H, s), 7.07 (1H, m), 6.18 (1H, s), 4.48 (1H, bs), 4.08 (2H, m, AB), 3.82 (1H, d), 3.56 (1H, d), 3.46 (3H, s), 3.33 (1H, d), 3.03 (1H, m), 2.81 (1H, d), 2.62 (1H, t), 2.47 (1H, d), 2.42-2.24 (2H, m), 2.24-2.01 (2H, m), 1.92-1.71 (3H, m), 1.68-1.45 (2H, m), 1.42 (3H, s), 1.37 (1H, bs), 1.02 (3H, s). APCI-MS m/z: 613 [MH$^+$].

Example 206

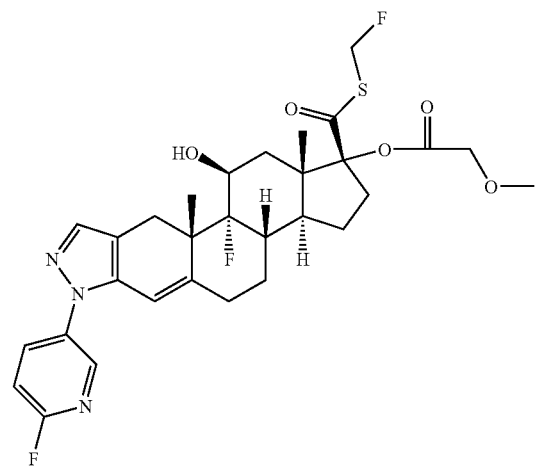

(1R,3aS,3bS,10aS,10bR,11S,12aS)-1-{[(Fluorom-ethyl)sulfanyl]carbonyl}-10b-fluoro-7-(6-fluoropyri-din-3-yl)-11-hydroxyl-1,2,3,3a,3b,4,5,7,10,10a,10b,11,12,12a-tetradecahydrocyclopenta[5,6]naphtho[1,2-f]indazol-1-yl methoxyacetate The compound was prepared according to the procedure for Example 11, starting from Intermediate 154 and Bromofluoromethane.

$^1$H NMR (400 MHz, CDCl$_3$) δ 8.36 (1H, s), 7.99 (1H, m), 7.51 (1H, s), 7.07 (1H, m), 6.18 (1H, s), 6.10-5.61 (2H, m), 4.48 (1H, bs), 4.08 (2H, m, AB), 3.47 (3H, s), 3.33 (1H, d), 3.06 (1H, m), 2.81 (1H, d), 2.62 (1H, t), 2.49 (1H, d), 2.42-2.24 (2H, m), 2.24-2.14 (1H, m), 2.14-2.01 (1H, m), 1.95-1.71 (3H, m), 1.66-1.44 (2H, m), 1.42 (3H, s), 1.30 (1H, bs), 1.01 (3H, s). APCI-MS m/z: 606 [MH$^+$].

Example 207

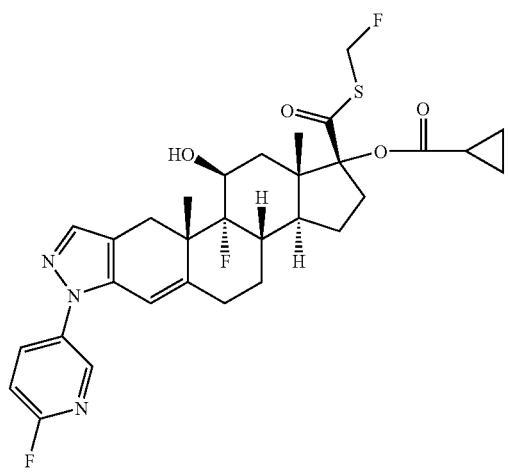

(1R,3aS,3bS,10aS,10bR,11S,12aS)-1-{[(Cyanom-ethyl)sulfanyl]carbonyl}-10b-fluoro-7-(6-fluoropyri-din-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl cyclopropanecarboxylate The compound was prepared according to the procedure for Example 11, starting from Intermediate 155 and 2-Bromoacetonitrile.

$^1$H NMR (400 MHz, CDCl$_3$) δ 8.36 (1H, s), 7.99 (1H, m), 7.51 (1H, s), 7.08 (1H, m), 6.18 (1H, s), 4.49 (1H, bs), 3.80 (1H, d, AB), 3.54 (1H, d, AB), 3.34 (1H, d), 2.97 (1H, m), 2.82 (1H, d), 2.62 (1H, t), 2.49 (1H, d), 2.41-2.25 (2H, m), 2.24-2.14 (1H, m), 2.09-1.96 (1H, m), 1.91-1.73 (3H, m), 1.73-1.64 (1H, m), 1.61-1.45 (2H, m), 1.42 (4H, m), 1.12-1.02 (2H, m), 1.00 (3H, s), 0.98-0.93 (2H, m). APCI-MS m/z: 609 [MH$^+$].

Example 208

(1R,3aS,3bS,10aS,10bR,11S,12aS)-1-{[(Fluorom-ethyl)sulfanyl]carbonyl}-10b-fluoro-7-(6-fluoropyri-din-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl cyclopropanecarboxylate The compound was prepared according to the procedure for Example 11, starting from Intermediate 155 and Bromofluoromethane.

$^1$H NMR (400 MHz, CDCl$_3$) δ 8.37 (1H, s), 7.99 (1H, m), 7.51 (1H, s), 7.07 (1H, m), 6.18 (1H, s), 6.08-5.60 (2H, m), 4.48 (1H, bs), 3.34 (1H, d), 3.00 (1H, m), 2.82 (1H, d), 2.63 (1H, t), 2.51 (1H, d), 2.43-2.14 (3H, m), 2.07-1.95 (1H, m), 1.91 (1H, d), 1.87-1.73 (2H, m), 1.73-1.64 (1H, m), 1.61-1.45 (2H, m), 1.42 (3H, s), 1.31 (1H, m), 1.14-1.01 (2H, m), 0.99 (3H, s), 0.97-0.90 (2H, m). APCI-MS m/z: 602 [MH$^+$].

Example 209

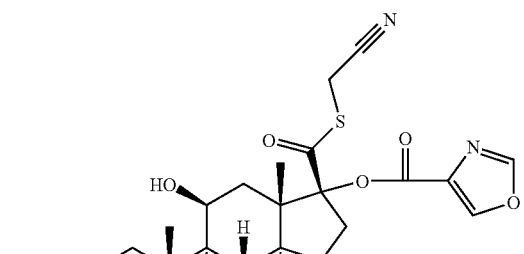

(1R,3aS,3bS,10aS,10bR,11S,12aS)-1-{[(Cyanomethyl)sulfanyl]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 1,3-oxazole-4-carboxylate The compound was prepared according to the procedure for Example 11, starting from Intermediate 156 and 2-Bromoacetonitrile.

$^1$H NMR (400 MHz, CDCl$_3$) δ 8.37 (1H, s), 8.28 (1H, s), 7.99 (1H, m), 7.96 (1H, s), 7.52 (1H, s), 7.08 (1H, m), 6.18 (1H, s), 4.55 (1H, bs), 3.84 (1H, d, AB), 3.54 (1H, d, AB), 3.37 (1H, d), 3.08 (1H, m), 2.83 (1H, d), 2.71-2.56 (2H, m), 2.48-2.26 (3H, m), 2.26-2.14 (1H, m), 1.95 (1H, d), 1.89-1.72 (2H, m), 1.67-1.48 (2H, m), 1.46 (1H, m), 1.44 (3H, s), 1.07 (3H, s). APCI-MS m/z: 636 [MH$^+$].

Example 210

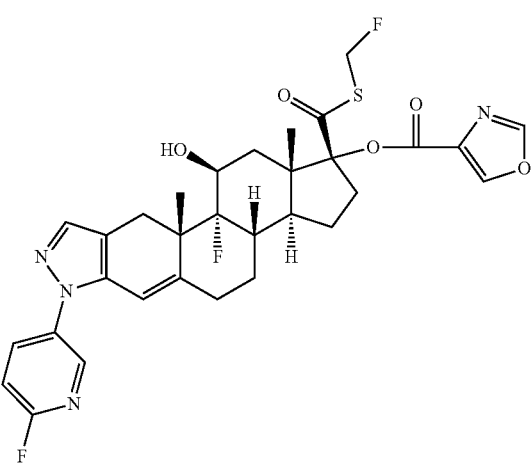

(1R,3aS,3bS,10aS,10bR,11S,12aS)-1-{[(Fluoromethyl)sulfanyl]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 1,3-oxazole-4-carboxylate The compound was prepared according to the procedure for Example 11, starting from Intermediate 156 and Bromofluoromethane.

$^1$H NMR (400 MHz, CDCl$_3$) δ 8.36 (1H, s), 8.28 (1H, s), 7.99 (1H, m), 7.95 (1H, s), 7.52 (1H, s), 7.08 (1H, m), 6.19 (1H, s), 6.11-5.56 (2H, m), 4.55 (1H, bs), 3.36 (1H, d), 3.10 (1H, m), 2.83 (1H, d), 2.71-2.56 (2H, m), 2.48-2.26 (3H, m), 2.25-2.12 (1H, m), 1.99 (1H, d), 1.90-1.72 (2H, m), 1.70-1.48 (2H, m), 1.44 (3H, s), 1.37 (1H, m), 1.06 (3H, s). APCI-MS m/z: 629 [MH$^+$].

Example 211

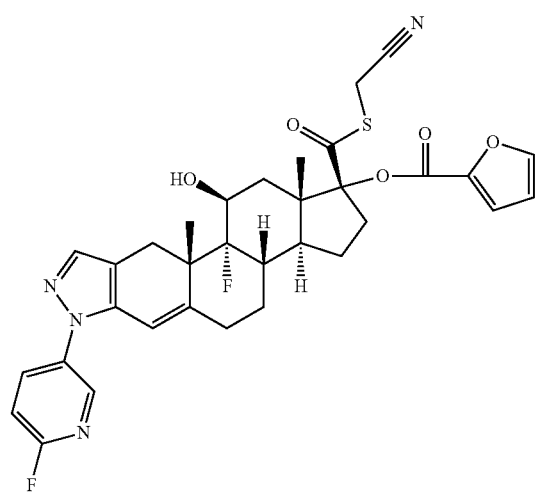

(1R,3aS,3bS,10aS,10bR,11S,12aS)-1-{[(Cyanomethyl)sulfanyl]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate The compound was prepared according to the procedure for Example 11, starting from Intermediate 157 and 2-Bromoacetonitrile.

$^1$H NMR (400 MHz, CDCl$_3$) δ 8.37 (1H, s), 7.99 (1H, m), 7.64 (1H, s), 7.52 (1H, s), 7.24 (1H, d), 7.08 (1H, dd), 6.55 (1H, m), 6.19 (1H, s), 4.55 (1H, bs), 3.85 (1H, d, AB), 3.53 (1H, d, AB), 3.38 (1H, d), 3.07 (1H, m), 2.84 (1H, d), 2.70-2.56 (2H, m), 2.48-2.26 (3H, m), 2.25-2.12 (1H, m), 1.94 (1H, d), 1.89-1.73 (2H, m), 1.69-1.50 (2H, m), 1.46 (1H, m), 1.44 (3H, s), 1.07 (3H, s). APCI-MS m/z: 635 [MH$^+$].

Example 212

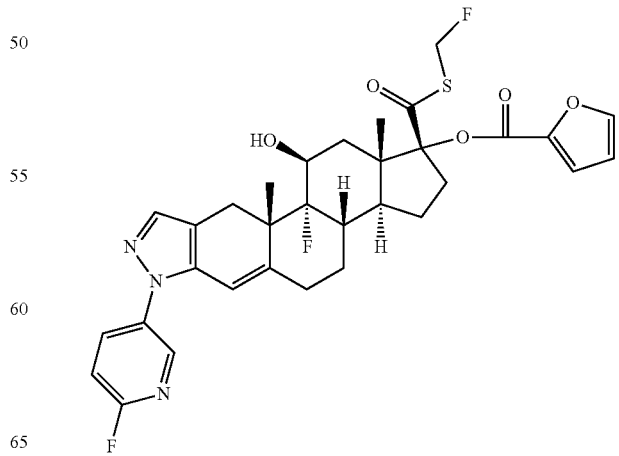

(1R,3aS,3bS,10aS,10bR,11S,12aS)-1-{[(Fluorom-
ethyl)sulfanyl]carbonyl}-10b-fluoro-7-(6-fluoropyri-
din-3-yl)-11-hydroxy-10a,12a-dimethyl-1,2,3,3a,3b,
4,5,7,10a,10b,11,12,12a-tetradecahydrocyclopenta[5,
6]naphtho[1,2-f]indazol-1-yl furan-2-carboxylate The compound was prepared according to the procedure for Example 11, starting from Intermediate 157 and Bromofluoromethane.

$^1$H NMR (400 MHz, CDCl$_3$) δ 8.37 (1H, s), 7.99 (1H, m), 7.63 (1H, s), 7.52 (1H, s), 7.24 (1H, d), 7.07 (1H, dd), 6.54 (1H, m), 6.19 (1H, s), 6.12-5.58 (2H, m), 4.54 (1H, bs), 3.38 (1H, d), 3.09 (1H, m), 2.84 (1H, d), 2.71-2.56 (2H, m), 2.45-2.28 (3H, m), 2.24-2.10 (1H, m), 1.97 (1H, d), 1.89-1.72 (2H, m), 1.69-1.47 (2H, m), 1.44 (3H, s), 1.37 (1H, m), 1.06 (3H, s). APCI-MS m/z: 628 [MH$^+$].

Example 213

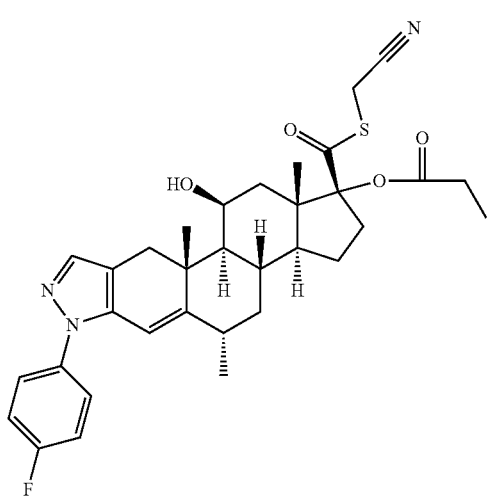

(1R,3aS,3bS,5S,10aR,10bS,11S,12aS)-1-{[(Cya-
nomethyl)sulfanyl]carbonyl}-7-(4-fluorophenyl)-11-
hydroxy-5,10a,12a-trimethyl-1,2,3,3a,3b,4,5,7,10,
10a,10b,11,12,12a-tetradecahydrocyclopenta[5,6]
naphtho[1,2-f]indazol-1-yl propanoate The compound was prepared according to the procedure for Example 11, starting from Intermediate 160 and 2-Bromoacetonitrile.

$^1$H NMR (400 MHz, CDCl$_3$) δ 7.50-7.42 (3H, m), 7.18 (2H, t), 6.13 (1H, s), 4.58 (1H, bs), 3.79 (1H, d, AB), 3.56 (1H, d, AB), 3.05-2.92 (2H, m), 2.77 (1H, d), 2.52 (1H, bs), 2.37 (2H, q), 2.17-2.05 (2H, m), 2.02-1.91 (3H, m), 1.88-1.76 (1H, m), 1.67-1.57 (1H, m), 1.54-1.42 (1H, m), 1.34 (3H, s), 1.25 (1H, d), 1.19-1.13 (4H, m), 1.11 (3H, d), 1.01 (3H, s), 0.86 (1H, q). APCI-MS m/z: 592 [MH$^+$].

Example 214

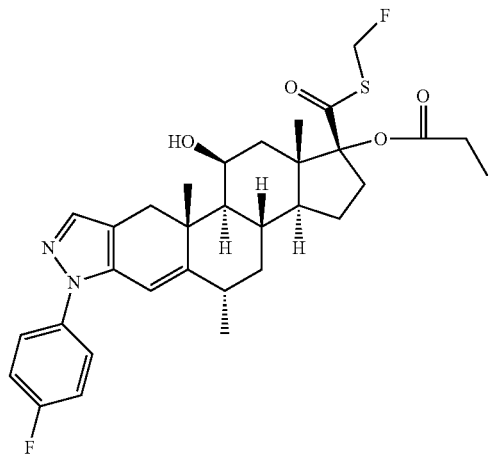

(1R,3aS,3bS,5S,10aR,10bS,11S,12aS)-1-{[(Fluo-
romethyl)sulfanyl]carbonyl}-7-(4-fluorophenyl)-11-
hydroxy-5,10a,12a-trimethyl-1,2,3,3a,3b,4,5,7,10,
10a,10b,11,12,12a-tetradecahydrocyclopenta[5,6]
naphtho[1,2-f]indazol-1-yl propanoate The compound was prepared according to the procedure for Example 11, starting from Intermediate 160 and Bromofluoromethane.

$^1$H NMR (400 MHz, CDCl$_3$) δ 7.50-7.45 (2H, m), 7.44 (1H, s), 7.18 (2H, t), 6.13 (1H, s), 6.06-5.61 (2H, m), 4.57 (1H, bs), 3.07-2.95 (2H, m), 2.77 (1H, d), 2.52 (1H, bs), 2.37 (2H, q), 2.17-2.05 (2H, m), 2.02-1.91 (3H, m), 1.88-1.76 (1H, m), 1.69-1.57 (1H, m), 1.54-1.42 (1H, m), 1.34 (3H, s), 1.26 (1H, d), 1.20-1.07 (7H, m), 1.00 (3H, s), 0.86 (1H, q). APCI-MS m/z: 585 [MH$^+$].

Example 215

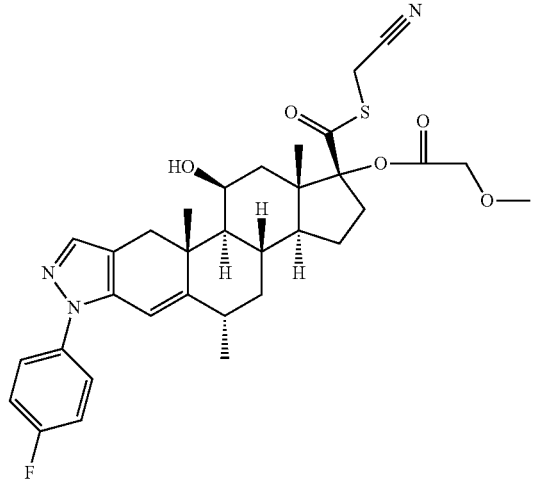

(1R,3aS,3bS,5S,10aR,10bS,11S,12aS)-1-{[(Cyanomethyl)sulfanyl]carbonyl}-7-(4-fluorophenyl)-11-hydroxy-5,10a,12a-trimethyl-1,2,3,3a,3b,4,5,7,10,10a,10b,11,12,12a-tetradecahydrocyclopenta[5,6]naphtho[1,2-f]indazol-1-yl methoxyacetate The compound was prepared according to the procedure for Example 11, starting from Intermediate 161 and 2-Bromoacetonitrile.

$^1$H NMR (400 MHz, CDCl$_3$) δ 7.50-7.45 (2H, m), 7.44 (1H, s), 7.18 (2H, t), 6.13 (1H, s), 4.57 (1H, bs), 4.06 (2H, s), 3.79 (1H, d, AB), 3.58 (1H, d, AB), 3.45 (3H, s), 3.07-2.95 (2H, m), 2.76 (1H, d), 2.52 (1H, bs), 2.17-1.91 (5H, m), 1.90-1.77 (1H, m), 1.65-1.45 (2H, m), 1.33 (3H, s), 1.25 (1H, d), 1.17 (1H, m), 1.11 (3H, d), 1.02 (3H, s), 0.85 (1H, q). APCI-MS m/z: 608 [MH$^+$].

Example 216

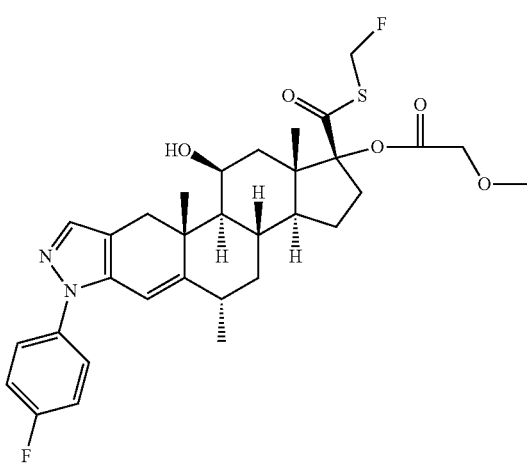

(1R,3aS,3bS,5S,10aR,10bS,11S,12aS)-1-{[(Fluoromethyl)sulfanyl]carbonyl}-7-(4-fluorophenyl)-11-hydroxy-5,10a,12a-trimethyl-1,2,3,3a,3b,4,5,7,10,10a,10b,11,12,12a-tetradecahydrocyclopenta[5,6]naphtho[1,2]-indazol-1-yl methoxyacetate The compound was prepared according to the procedure for Example 11, starting from Intermediate 161 and Bromofluoromethane.

$^1$H NMR (400 MHz, CDCl$_3$) δ 7.51-7.44 (2H, m), 7.43 (1H, s), 7.18 (2H, t), 6.13 (1H, s), 6.05-5.62 (2H, m), 4.56 (1H, bs), 4.07 (2H, s), 3.46 (3H, s), 3.09-2.94 (2H, m), 2.76 (1H, d), 2.52 (1H, bs), 2.17-1.90 (5H, m), 1.89-1.75 (1H, m), 1.67-1.55 (1H, m), 1.54-1.43 (1H, m), 1.33 (3H, s), 1.25 (1H, d), 1.15 (1H, d), 1.11 (3H, d), 1.01 (3H, s), 0.85 (1H, q). APCI-MS m/z: 601 [MH$^+$].

Example 217

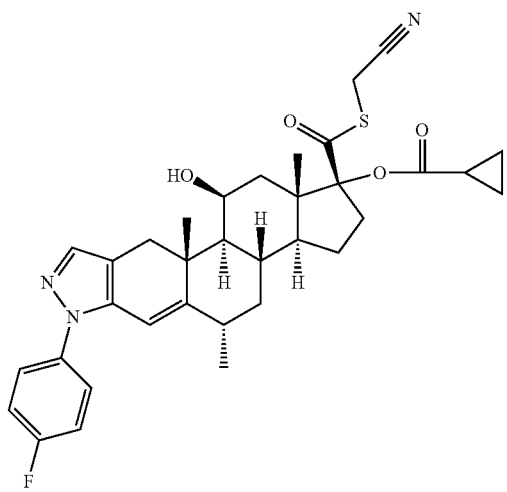

(1R,3aS,3bS,5S,10aR,10bS,11S,12aS)-1-{[(Cyanomethyl)sulfanyl]carbonyl}-7-(4-fluorophenyl)-11-hydroxy-5,10a,12a-trimethyl-1,2,3,3a,3b,4,5,7,10,10a,10b,11,12,12a-tetradecahydrocyclopenta[5,6]naphtho[1,2-f]indazol-1-yl cyclopropanecarboxylate The compound was prepared according to the procedure for Example 11, starting from Intermediate 162 and 2-Bromoacetonitrile.

$^1$H NMR (400 MHz, CDCl$_3$) δ 7.51-7.42 (3H, m), 7.18 (2H, t), 6.13 (1H, s), 4.59 (1H, bs), 3.77 (1H, d, AB), 3.56 (1H, d, AB), 3.05-2.89 (2H, m), 2.77 (1H, d), 2.52 (1H, bs), 2.19-2.05 (2H, m), 2.02-1.91 (3H, m), 1.88-1.76 (1H, m), 1.71-1.60 (2H, m), 1.54-1.40 (1H, m), 1.34 (3H, s), 1.26 (1H, d), 1.18 (1H, bs), 1.11 (3H, d), 1.07-0.99 (5H, m), 0.97-0.81 (3H, m). APCI-MS m/z: 604 [MH$^+$].

Example 218

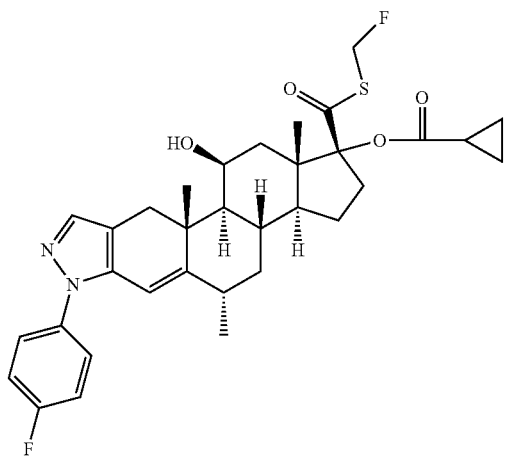

(1R,3aS,3bS,5S,10aR,10bS,11S,12aS)-1-{[(Fluoromethyl)sulfanyl]carbonyl}-7-(4-fluorophenyl)-11-hydroxy-5,10a,12a-trimethyl-1,2,3,3a,3b,4,5,7,10,10a,10b,11,12,12a-tetradecahydrocyclopenta[5,6]naphtho[1,2-f]indazol-1-yl cyclopropanecarboxylate The compound was prepared according to the procedure for Example 11, starting from Intermediate 162 and Bromofluoromethane.

¹H NMR (400 MHz, CDCl₃) δ 7.51-7.45 (2H, m), 7.44 (1H, s), 7.18 (2H, t), 6.13 (1H, s), 6.06-5.61 (2H, m), 4.58 (1H, bs), 3.05-2.93 (2H, m), 2.77 (1H, d), 2.52 (1H, bs), 2.19-2.05 (2H, m), 2.04-1.90 (3H, m), 1.90-1.77 (1H, m), 1.72-1.59 (2H, m), 1.53-1.42 (1H, m), 1.34 (3H, s), 1.26 (1H, d), 1.14-1.09 (4H, m), 1.07-0.98 (5H, m), 0.96-0.82 (3H, m). APCI-MS m/z: 597 [MH⁺].

Example 219

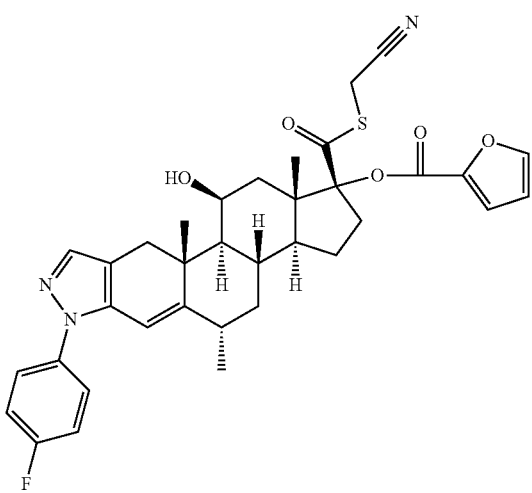

(1R,3aS,3bS,5S,10aR,10bS,11S,12aS)-1-{[(Cyanomethyl)sulfanyl]carbonyl}-7-(4-fluorophenyl)-11-hydroxy-5,10a,12a-trimethyl-1,2,3,3a,3b,4,5,7,10,10a,10b,11,12,12a-tetradecahydrocyclopenta[5,6]naphtho[1,2-f]indazol-1-yl furan-2-carboxylate The compound was prepared according to the procedure for Example 11, starting from Intermediate 163 and 2-Bromoacetonitrile.

¹H NMR (400 MHz, CDCl₃) δ 7.63 (1H, s), 7.52-7.42 (3H, s), 7.24 (1H, d), 7.18 (2H, t), 6.55 (1H, s), 6.13 (1H, s), 4.64 (1H, bs), 3.81 (1H, d, AB), 3.54 (1H, d, AB), 3.12-2.99 (2H, m), 2.82 (1H, d), 2.54 (1H, bs), 2.25 (1H, d), 2.20-2.09 (2H, m), 2.05 (1H, d), 2.00-1.91 (1H, m), 1.90-1.79 (1H, m), 1.78-1.67 (1H, m), 1.60-1.48 (1H, m), 1.36 (3H, s), 1.32 (1H, d), 1.22 (1H, bs), 1.11 (3H, d), 1.07 (3H, s), 0.88 (1H, q). APCI-MS m/z: 630 [MH⁺].

Example 220

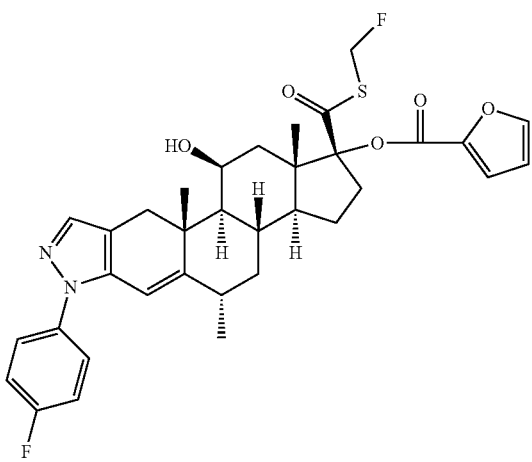

(1R,3aS,3bS,5S,10aR,10bS,11S,12aS)-{[(Fluoromethyl)sulfanyl]carbonyl}-7-(4-fluorophenyl)-11-hydroxy-5,10a,12a-trimethyl-1,2,3,3a,3b,4,5,7,10,10a,10b,11,12,12a-tetradecahydrocyclopenta[5,6]naphtho[1,2-f]indazol-1-yl furan-2-carboxylate The compound was prepared according to the procedure for Example 11, starting from Intermediate 163 and Bromofluoromethane.

¹H NMR (400 MHz, CDCl₃) δ 7.62 (1H, s), 7.50-7.44 (3H, s), 7.23 (1H, d), 7.18 (2H, t), 6.54 (1H, m), 6.14 (1H, s), 6.08-4.54 (2H, m), 4.64 (1H, bs), 3.14-2.99 (2H, m), 2.82 (1H, d), 2.53 (1H, bs), 2.27 (1H, d), 2.20-2.04 (3H, m), 2.01-1.90 (1H, m), 1.90-1.80 (1H, m), 1.80-1.68 (1H, m), 1:57-1.46 (1H, m), 1.36 (3H, s), 1.32 (1H, d), 1.17 (1H, bs), 1.11 (3H, d), 1.06 (3H, s), 0.88 (1H, q). APCI-MS m/z: 623 [MH⁺].

Human Glucocorticoid Receptor (GR) Assay

The assay is based on a commercial kit from Panvera/Invitrogen (Part number P2893). The assay technology is fluorescence polarization. The kit utilises recombinant human GR (Panvera, Part number P2812), a Fluoromone™ labelled tracer (GS Red, Panvera, Part number P2894) and a Stabilizing Peptide 10× (Panvera, Part number P2815). The GR and Stabilizing Peptide reagents are stored at −70° C. while the GS Red is stored at −20° C. Also included in the kit are 1M DTT (Panvera, Part number P2325, stored at −20° C.) and GR Screening buffer 10× (Panvera, Part number P2814, stored at −70° C. initially but once thawed stored at room temperature). Avoid repeated freeze/thaws for all reagents. The GR Screening buffer 10× comprises 100 mM potassium phosphate, 200 mM sodium molybdate, 1 mM EDTA and 20% DMSO.

Test compounds (1 μL) and controls (1 μL) in 100% DMSO were added to black polystyrene 384-well plates (Greiner low volume black flat-bottom, part number 784076). 0% control was 100% DMSO and 100% control was 10 μM Dexamethasone. Background solution (8 μL; assay buffer 10×, Stabilizing Peptide, DTT and ice cold MQ water) was added to the background wells. GS Red solution (7 μL; assay buffer 10×, Stabilizing Peptide, DTT, GS Red and ice cold water) was added to all wells except background wells. GR solution (7 μL; assay buffer 10×, Stabilizing Peptide, DTT, GR and ice cold water) was added to all wells. The plate was sealed and incubated in a dark at room temperature for 2 hours. The plate was read in an Analyst plate reader (LJL Biosystems/Molecular Devices Corporation) or other similar plate reader capable of recording fluorescence polarization (excitation wavelength 530 nm, emission wavelength 590 nm and a dichroic mirror at 561 nm). The IC₅₀ values were calculated using XLfit model 205 and are shown in Table 1.

TABLE 1

| Example No. | Inhibition of GR binding, IC₅₀ (nM) | Example No. | Inhibition of GR binding, IC₅₀ (nM) |
|---|---|---|---|
| 1 | 7.6 | 2 | 7.4 |
| 3 | 15 | 4 | 5.9 |
| 5 | 15 | 6 | 5.9 |
| 7 | 5.6 | 8 | 4.7 |
| 9 | 9.4 | 10 | 3.2 |
| 11 | 3.8 | 12 | 5.8 |
| 13 | 3.1 | 14 | 3.6 |
| 15 | 3.7 | 16 | 3.4 |
| 17 | 4.8 | 18 | 4.1 |
| 19 | 3.7 | 20 | 7.7 |
| 21 | 2.7 | 22 | 3.9 |
| 23 | 13 | 24 | 5.1 |

TABLE 1-continued

| Example No. | Inhibition of GR binding, IC$_{50}$ (nM) | Example No. | Inhibition of GR binding, IC$_{50}$ (nM) |
|---|---|---|---|
| 25 | 10 | 26 | 4.3 |
| 27 | 3 | 28 | 4.2 |
| 29 | 5.7 | 30 | 3.1 |
| 31 | 4.5 | 32 | 1.6 |
| 33 | 2.7 | 34 | 1.7 |
| 35 | 5 | 36 | 2.5 |
| 37 | 5.7 | 38 | 5.7 |
| 39 | 3.3 | 40 | 2.9 |
| 41 | 4.1 | 42 | 3.2 |
| 43 | 2.7 | 44 | 2.9 |
| 45 | 3.4 | 46 | 3.9 |
| 47 | 2.5 | 48 | 4.9 |
| 49 | 3.5 | 50 | 5.8 |
| 51 | 6.9 | 52 | 6.4 |
| 53 | 9 | 54 | 7.3 |
| 55 | 7 | 56 | 6.5 |
| 57 | 3.8 | 58 | 5.5 |
| 59 | 3.9 | 60 | 4.5 |
| 61 | 8.3 | 62 | 2.2 |
| 63 | 3.3 | 64 | 5.8 |
| 65 | 2.6 | 66 | 3.3 |
| 67 | 38 | 68 | 12 |
| 69 | 3 | 70 | 3.8 |
| 71 | 13 | 72 | 17 |
| 73 | 6.4 | 74 | 22 |
| 75 | 7.2 | 76 | 35 |
| 77 | 22 | 78 | 12 |
| 79 | 4.2 | 80 | 4.2 |
| 81 | 4.5 | 82 | 8.5 |
| 83 | 18 | 84 | 5 |
| 85 | 6.3 | 86 | 3.5 |
| 87 | 5.3 | 88 | 13 |
| 89 | 6.9 | 90 | 4.6 |
| 91 | 3.7 | 92 | 4 |
| 93 | 5.6 | 94 | 5.9 |
| 95 | 4.7 | 96 | — |
| 97 | 2.1 | 98 | 3.1 |
| 99 | 2.1 | 100 | 2.7 |
| 101 | 29 | 102 | 8.2 |
| 103 | 6.4 | 104 | 4.2 |
| 105 | 6.1 | 106 | 160 |
| 107 | 59 | 108 | 6.6 |
| 109 | 4.1 | 110 | 6.7 |
| 111 | 6.3 | 112 | 18 |
| 113 | 11 | 114 | 16 |
| 115 | 10 | 116 | 6.9 |
| 117 | 7 | 118 | 18 |
| 119 | 4.6 | 120 | 7 |
| 121 | 6.6 | 122 | 1.3 |
| 123 | 5.4 | 124 | 2.4 |
| 125 | 4.7 | 126 | 2.7 |
| 127 | 3.7 | 128 | 3.8 |
| 129 | — | 130 | 5.9 |
| 131 | 4.1 | 132 | 4 |
| 133 | 3.4 | 134 | 2.9 |
| 135 | 7.6 | 136 | 4.5 |
| 137 | 2.8 | 138 | 3.8 |
| 139 | 3.5 | 140 | 2.3 |
| 141 | 13 | 142 | 1.6 |
| 143 | 1.5 | 144 | 3.8 |
| 145 | 3.2 | 146 | 3.4 |
| 147 | — | 148 | — |
| 149 | 5 | 150 | 21 |
| 151 | 1.5 | 152 | 7 |
| 153 | 2.4 | 154 | 5.9 |
| 155 | 1.9 | 156 | 1.3 |
| 157 | 1.1 | 158 | 2.4 |
| 159 | 3.6 | 160 | 2.1 |
| 161 | 1.3 | 162 | 1.8 |
| 163 | 1.7 | 164 | 1.4 |
| 165 | 3.8 | 166 | 5.8 |
| 167 | 5.6 | 168 | 5.3 |
| 169 | — | 170 | — |
| 171 | — | 172 | — |
| 173 | — | 174 | 34 |
| 175 | 18 | 176 | 11 |
| 177 | 7.5 | 178 | 7.6 |
| 179 | — | 180 | — |
| 181 | — | 182 | — |
| 183 | — | 184 | 1.7 |
| 185 | 2.7 | 186 | 2.3 |
| 187 | 2.3 | 188 | 1.2 |
| 189 | 5 | 190 | 3.7 |
| 191 | — | 192 | — |
| 193 | 3.3 | 194 | 2.3 |
| 195 | 4.7 | 196 | 14 |
| 197 | 3.3 | 198 | 2.6 |
| 199 | 4.6 | 200 | 14 |
| 201 | 5.3 | 202 | 5.8 |
| 203 | 2.3 | 204 | 3.3 |
| 205 | 1.4 | 206 | 2.5 |
| 207 | 3.3 | 208 | 3.4 |
| 209 | 3.6 | 210 | 2 |
| 211 | 2.2 | 212 | 2.1 |
| 213 | 11 | 214 | 49 |
| 215 | 51 | 216 | 8.8 |
| 217 | — | 218 | — |
| 219 | — | 220 | — |

The invention claimed is:

1. A compound of formula

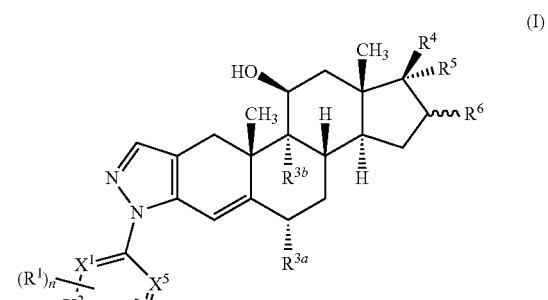

(I)

wherein $X^1$, $X^2$, $X^3$, $X^4$ and $X^5$
each independently represent CH or a nitrogen atom, provided that no more than two of $X^1$, $X^2$, $X^3$, $X^4$ and $X^5$ may simultaneously represent a nitrogen atom;

n and p
each independently represent 0 or 1;

$R^1$ represents a halogen atom or a methyl or a methoxy group;

$R^2$ represents a halogen atom, —C(O)OCH$_3$, —C(O)—S—CH$_2$CN, —C(O)—S—CH$_3$, —C(O)-heterocyclyl, —SO$_2$CH$_3$, a C$_2$-C$_6$ alkenyl group, or a methyl group optionally substituted by halogen, hydroxyl, methoxy, —OCH$_2$CH=CH$_2$ or —NR$^7$R$^8$;

$R^{3a}$ represents a hydrogen atom or methyl group and $R^{3b}$ represents a hydrogen or fluorine atom;

$R^4$ represents —C(O)—S—C(O)N(CH$_3$)$_2$ or, —C(O)—Y—CH(R$^{11}$)—R$^9$;

$R^5$ represents hydroxyl, —OCH$_2$SCH$_3$, —O—C(O)—R$^{10}$, —O—C(O)—NH—R$^{10}$, —O—C(O)—O—R$^{10}$ or —O—C(O)—S—R$^{10}$;

$R^6$ represents a hydrogen or a halogen atom or a methyl group, and when $R^5$ is other than a hydroxyl group, $R^6$ may additionally represent a hydroxyl group;

R⁷ and R⁸
each independently represent a hydrogen atom, or a $C_1$-$C_3$ alkyl or a $C_1$-$C_3$ hydroxyalkyl group, or R⁷ and R⁸
together with the nitrogen atom to which they are attached form a 3- to 8-membered saturated or partially saturated heterocyclic ring optionally containing a further ring heterogroup selected from nitrogen, $S(O)_m$ and oxygen, the heterocyclic ring being optionally substituted by at least one substituent selected from hydroxyl, $C_1$-$C_3$ alkyl and $C_1$-$C_3$ hydroxyalkyl;

m is 0, 1 or 2;

Y represents an oxygen or sulphur atom or a group>NH;

R⁹ represents hydrogen, halogen, cyano, —S—CN, —C(O)N(R¹²)₂, $C_1$-$C_6$ alkoxycarbonyl, $C_1$-$C_6$ alkylcarbonyl (optionally substituted by —OC(O)CH₃), $C_1$-$C_6$ alkylcarbonyloxy, $C_1$-$C_6$ alkoxy, $C_1$-$C_6$ alkylthio, —C(O)—S—$C_1$-$C_6$ alkyl, —C(=CH₂)—O—CH₂OCH₃, $C_1$-$C_6$ alkyl, $C_2$-$C_6$ alkenyl, $C_2$-$C_6$ alkynyl or $C_3$-$C_7$ cycloalkyl, the latter four groups being optionally substituted by one or more substituents independently selected from halogen, hydroxyl, cyano, hydroxymethyl, $C_1$-$C_4$ alkoxy and $C_1$-$C_4$ alkylcarbonyloxy;

R¹⁰ represents $C_1$-$C_6$ alkyl (optionally substituted by halogen, $C_1$-$C_4$ alkoxy, $C_1$-$C_4$ alkylcarbonyloxy or $C_3$-$C_7$ cycloalkyl) or a 3- to 10-membered saturated or unsaturated carbocyclic or heterocyclic ring system which ring system may be optionally substituted by at least one substituent selected from halogen, carboxyl, hydroxyl, oxo, nitro, cyano, mercapto, $C_1$-$C_6$ alkyl, $C_2$-$C_6$ alkenyl, $C_1$-$C_6$ haloalkyl, $C_1$-$C_6$ hydroxyalkyl, $C_1$-$C_6$ alkoxy, $C_1$-$C_6$ haloalkoxy, $C_1$-$C_6$ alkylthio, $C_1$-$C_6$ alkylsulphinyl, $C_1$-$C_6$ alkylsulphonyl, $C_1$-$C_6$ alkylcarbonyl, $C_1$-$C_6$ alkylcarbonyloxy, $C_1$-$C_6$ alkoxycarbonyl, amino (—NH₂), carboxamido (—CONH₂), (mono) $C_1$-$C_6$ alkylamino, (di) $C_1$-$C_6$ alkylamino and phenyl;

R¹¹ represents a hydrogen atom or a methyl group; and each R¹²
independently represents a hydrogen atom or a methyl group;

or a pharmaceutically acceptable salt thereof.

2. A compound according to claim 1, wherein $X^1$, $X^2$, $X^3$, $X^4$ and $X^5$ each represent CH.

3. A compound according to claim 1, wherein n is 1 and R¹ represents a halogen atom.

4. A compound according to claim 1, wherein $R^{3a}$ represents a hydrogen atom and $R^{3b}$ represents a hydrogen atom.

5. A compound according to claim 1, wherein R⁴ represents —C(O)—Y—CH(R¹¹)—R⁹.

6. A compound according to claim 1, wherein Y represents an oxygen or sulphur atom.

7. A compound according to claim 1, wherein R⁹ represents hydrogen, halogen, cyano, —S—CN, —C(O)N(R¹²)₂, $C_1$-$C_2$ alkoxycarbonyl, $C_1$-$C_2$ alkylcarbonyl (optionally substituted by —OC(O)CH₃), $C_1$-$C_2$ alkylcarbonyloxy, $C_1$-$C_2$ alkoxy, $C_1$-$C_2$ alkylthio, —C(O)—S—$C_1$-$C_2$ alkyl, —C(=CH₂)—O—CH₂OCH₃, $C_1$-$C_6$ alkyl, $C_2$-$C_4$ alkenyl, $C_2$-$C_4$ alkynyl or $C_3$-$C_6$ cycloalkyl, the latter four groups being optionally substituted by one or more substituents independently selected from halogen, hydroxyl, cyano, hydroxymethyl, $C_1$-$C_4$ alkoxy and $C_1$-$C_4$ alkylcarbonyloxy.

8. A compound according to claim 1, wherein R⁹ represents hydrogen, halogen, cyano, methyl and hydroxymethyl.

9. A compound according to claim 1, wherein R⁵ represents hydroxyl, —OCH₂SCH₃, —O—C(O)—R¹⁰ or —O—C(O)—O—R¹⁰.

10. A compound according to claim 1, wherein R¹⁰ represents a 3- to 6-membered saturated or unsaturated carbocyclic or heterocyclic ring system, the ring system being optionally substituted by at least one substituent selected from cyano, $C_1$-$C_4$ alkyl and $C_1$-$C_4$ alkoxy.

11. A compound of formula (Ia)

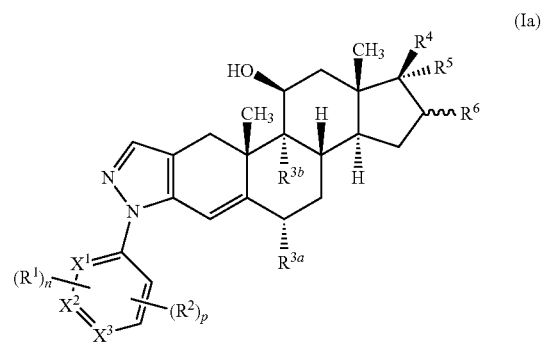

(Ia)

wherein
$X^1$, $X^2$ and $X^3$
each represent CH, wherein one of $X^1$, $X^2$ and $X^3$ optionally alternatively represents a nitrogen atom;

n and p
each independently represent 0 or 1;

R¹ represents a halogen atom or a methyl or a methoxy group;

R² represents —CO₂CH₃, a halogen atom, or a methyl group optionally substituted by a hydroxyl or a —NR⁷R⁸ group;

$R^{3a}$ represents a hydrogen atom and $R^{3b}$ represents a hydrogen or fluorine atom;

R⁴ represents —C(O)CH₂OH or —C(O)—Y—CH₂R⁹;

R⁵ represents a group —O—C(O)—R¹⁰, —O—C(O)—NH—R¹⁰, —O—C(O)—O—R¹⁰ or —O—C(O)—S—R¹⁰;

R⁶ represents a hydrogen or a halogen atom or a hydroxyl or a methyl group;

R⁷ and R⁸
each independently represent a hydrogen atom, or a $C_1$-$C_3$ alkyl or a $C_1$-$C_3$ hydroxyalkyl group, or R⁷ and R⁸ together with the nitrogen atom to which they are attached form a 3- to 8-membered saturated or partially saturated heterocyclic ring optionally containing a further ring heterogroup selected from nitrogen, $S(O)_m$ and oxygen, the heterocyclic ring being optionally substituted by at least one substituent selected from hydroxyl, $C_1$-$C_3$ alkyl and $C_1$-$C_3$ hydroxyalkyl;

m is 0, 1 or 2;

Y represents an oxygen or sulphur atom or a group>NH;

R⁹ represents a hydrogen or a halogen atom or a methyl or a cyano group; and

R¹⁰ represents a 5- to 10-membered saturated or unsaturated carbocyclic or heterocyclic ring system optionally substituted by at least one substituent selected from halogen, carboxyl, hydroxyl, oxo, nitro, cyano, mercapto, $C_1$-$C_6$ alkyl, $C_2$-$C_6$ alkenyl, $C_1$-$C_6$ haloalkyl, $C_1$-$C_6$ hydroxyalkyl, $C_1$-$C_6$ alkoxy, $C_1$-$C_6$ haloalkoxy, $C_1$-$C_6$ alkylthio, $C_1$-$C_6$ alkylsulphinyl, $C_1$-$C_6$ alkylsulphonyl, $C_1$-$C_6$ alkylcarbonyl, $C_1$-$C_6$ alkylcarbonyloxy, $C_1$-$C_6$ alkoxycarbonyl, amino, carboxamido, (mono) $C_1$-$C_6$ alkylamino, (di) $C_1$-$C_6$ alkylamino and phenyl.

12. A compound according to claim 1 selected from:
- (1R,3aS,3bS,10aR,10bS,11S,12aS)-1-{[(Fluoromethyl)thio]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 4-methyl-1,3-thiazole-5-carboxylate;
- (1R,3aS,3bS,10aR,10bS,11S,12aS)-1-{[(Cyanomethyl)thio]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 4-methyl-1,3-thiazole-5-carboxylate;
- (1R,3aS,3bS,10aR,10bS,11S,12aS)-1-[(Ethylthio)carbonyl]-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 4-methyl-1,3-thiazole-5-carboxylate;
- (1R,3aS,3bS,10aR,10bS,11S,12aS)-1-{[(Fluoromethyl)thio]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 4-methyl-1,2,3-thiadiazole-5-carboxylate;
- (1R,3aS,3bS,10aR,10bS,11S,12aS)-1-[(Ethylthio)carbonyl]-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 4-methyl-1,2,3-thiadiazole-5-carboxylate;
- (1R,3aS,3bS,10aR,10bS,11S,12aS)-1-{[(Cyanomethyl)thio]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 4-methyl-1,2,3-thiadiazole-5-carboxylate;
- (1R,3aS,3bS,10aR,10bS,11S,12aS)-1-{[(Fluoromethyl)thio]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 2-furoate;
- Cyanomethyl (1R,3aS,3bS,10aR,10bS,11S,12aS)-7-(4-fluorophenyl)-11-hydroxy-10a,12a-dimethyl-1-{[(4-methyl-1,3-thiazol-5-yl)carbonyl]oxy}-1,2,3,3a,3b,4,5,7,10,10a,10b,11,12,12a-tetradecahydrocyclopenta[5,6]naphtho[1,2-f]indazole-1-carboxylate;
- (1R,3aS,3bS,10aR,10bS,11S,12aS)-1-{[(Cyanomethyl)thio]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl propionate;
- (1R,3aS,3bS,10aR,10bS,11S,12aS)-7-(4-Fluorophenyl)-11-hydroxy-1-{[(2-methoxy-2-oxoethyl)thio]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl propanoate;
- (1R,3aS,3bS,10aR,10bS,11S,12aS)-1-{[(1-Cyanoethyl)thio]carbonyl}-7-(4-fluoro-phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl propanoate;
- (1R,3aS,3bS,10aR,10bS,11S,12aS)-1-{[(2-Amino-2-oxoethyl)thio]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl propanoate;
- (1R,3aS,3bS,10aR,10bS,11S,12aS)-7-(4-Fluorophenyl)-11-hydroxy-1-{[(methoxy-methyl)thio]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl propanoate;
- (1R,3aS,3bS,10aR,10bS,11S,12aS)-7-(4-Fluorophenyl)-11-hydroxy-1-{[(2-hydroxyethyl)thio]carbonyl}-10a,12a-dimethyl-1,2,3,3a,3b,4,5,7,10,10a,10b,11,12,12a-tetradecahydro-cyclopenta[5,6]naphtho[1,2-f]indazol-1-yl propanoate;
- (1R,3aS,3bS,10aR,10bS,11S,12aS)-1-{[(2-Cyanoethyl)thio]carbonyl}-7-(4-fluoro-phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl propanoate;
- (1R,3aS,3bS,10aR,10bS,11S,12aS)-7-(4-Fluorophenyl)-11-hydroxy-10a,12a-dimethyl-1-{[(2-oxopropyl)thio]carbonyl}-1,2,3,3a,3b,4,5,7,10,10a,10b,11,12,12a-tetradeca-hydrocyclopenta[5,6]naphtho[1,2-f]indazol-1-yl propanoate;
- (1R,3aS,3bS,10aR,10bS,11S,12aS)-7-(4-Fluorophenyl)-11-hydroxy-1-{[(4-hydroxy-but-2-yn-1-yl)thio]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl propanoate;
- (1R,3aS,3bS,10aR,10bS,11S,12aS)-1-{[(Fluoromethyl)thio]carbonyl}-7-(4-fluoro-phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl propanoate;
- (1R,3aS,3bS,10aR,10bS,11S,12aS)-7-(4-fluorophenyl)-11-hydroxy-10a,12a-dimethyl-1-[(prop-2-yn-1-ylthio)carbonyl]-1,2,3,3a,3b,4,5,7,10,10a,10b,11,12,12a-tetradeca-hydrocyclopenta[5,6]naphtho[1,2-f]indazol-1-yl propanoate;
- (1R,3aS,3bS,10aR,10bS,11S,12aS)-7-(4-Fluorophenyl)-11-hydroxy-10a,12a-dimethyl-1-[(methylthio)carbonyl]-1,2,3,3a,3b,4,5,7,10,10a,10b,11,12,12a-tetradecahydro-cyclopenta[5,6]naphtho[1,2-f]indazol-1-yl propanoate;
- (1R,3aS,3bS,10aR,10bS,11S,12aS)-1-({[2-(Dimethylamino)-2-oxoethyl]thio}carbonyl)-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl propanoate;
- (1R,3aS,3bS,10aR,10bS,11S,12aS)-7-(4-Fluorophenyl)-11-hydroxy-10a,12a-dimethyl-1-[(prop-2-en-1-ylthio)carbonyl]-1,2,3,3a,3b,4,5,7,10,10a,10b,11,12,12a-tetradecahydro-cyclopenta[5,6]naphtho[1,2-f]indazol-1-yl propanoate;
- (1R,3aS,3bS,10aR,10bS,11S,12aS)-7-(4-Fluorophenyl)-11-hydroxy-1-{[(3-hydroxy-propyl)thio]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl propanoate;
- (1R,3aS,3bS,10aR,10bS,11S,12aS)-1-{[(Cyclopropylmethyl)thio]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl propanoate;
- (1R,3aS,3bS,10aR,10bS,11S,12aS)-1-{[(2-Fluoroethyl)thio]carbonyl}-7-(4-fluoro-phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl propanoate;
- (1R,3aS,3bS,10aR,10bS,11S,12aS)-1-{[(Cyanomethyl)thio]carbonyl}-7-(4-fluoro-phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl fluoroacetate;
- (1R,3aS,3bS,10aR,10bS,11S,12aS)-1-{[(Fluoromethyl)thio]carbonyl}-7-(4-fluoro-phenyl)-11-hydroxy-10a, 12a-dimethyl-1,2,3,3a,3b,4,5,7,10,10a,10b,11,12,12a-tetradecahydrocyclopenta[5,6]naphtho[1,2-f]indazol-1-yl fluoroacetate;

(1R,3aS,3bS,10aR,10bS,11S,12aS)-1-{[(Cyanomethyl)thio]carbonyl}-7-(4-fluoro-phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl (acetyloxy)acetate;

(1R,3aS,3bS,10aR,10bS,11S,12aS)-1-{[(Cyanomethyl)thio]carbonyl}-7-(4-fluoro-phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl methoxyacetate;

(1R,3aS,3bS,10aR,10bS,11S,12aS)-7-(4-Fluorophenyl)-11-hydroxy-1-{[(4-hydroxy-but-2-yn-1-yl)thio]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl methoxyacetate;

(1R,3aS,3bS,10aR,10bS,11S,12aS)-7-(4-Fluorophenyl)-11-hydroxy-1-{[(2-hydroxy-ethyl)thio]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl methoxyacetate;

(1R,3aS,3bS,10aR,10bS,11S,12aS)-7-(4-Fluorophenyl)-11-hydroxy-10a,12a-dimethyl-1-{[(2-oxopropyl)thio]carbonyl}-1,2,3,3a,3b,4,5,7,10,10a,10b,11,12,12a-tetradecahydro cyclopenta[5,6]naphtho[1,2-f]indazol-1-yl methoxyacetate;

(1R,3aS,3bS,10aR,10bS,11S,12aS)-1-{[(Fluoromethyl)thio]carbonyl}-7-(4-fluoro-phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl methoxyacetate;

(1R,3aS,3bS,10aR,10bS,11S,12aS)-1-{[(Cyanomethyl)thio]carbonyl}-7-(4-fluoro-phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl cyclopropanecarboxylate;

(1R,3aS,3bS,10aR,10bS,11S,12aS)-7-(4-Fluorophenyl)-11-hydroxy-1-{[(2-hydroxy-ethyl)thio]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl cyclopropanecarboxylate;

(1R,3aS,3bS,10aR,10bS,11S,12aS)-7-(4-Fluorophenyl)-11-hydroxy-1-{[(4-hydroxybut-2-yn-1-yl)thio]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl cyclopropanecarboxylate;

(1R,3aS,3bS,10aR,10bS,11S,12aS)-1-{[(Fluoromethyl)thio]carbonyl}-7-(4-fluoro-phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl cyclopropanecarboxylate;

(1R,3aS,3bS,10aR,10bS,11S,12aS)-1-{[(Cyanomethyl)thio]carbonyl}-7-(4-fluorophenyl)-11-hydroxy-10a,12a-dimethyl-1,2,3,3a,3b,4,5,7,10,10a,10b,11,12,12a-tetradecahydro-cyclopenta[5,6]naphtho[1,2-f]indazol-1-yl 1,3-thiazole-2-carboxylate;

(1R,3aS,3bS,10aR,10bS,11S,12aS)-7-(4-Fluorophenyl)-11-hydroxy-1-{[(2-hydroxy-ethyl)thio]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl 1,3-thiazole-2-carboxylate;

(1R,3aS,3bS,10aR,10bS,11S,12aS)-7-(4-Fluorophenyl)-11-hydroxy-1-{[(4-hydroxy-but-2-yn-1-yl)thio]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl 1,3-thiazole-2-carboxylate;

(1R,3aS,3bS,10aR,10bS,11S,12aS)-1-{[(Fluoromethyl)thio]carbonyl}-7-(4-fluoro-phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 1,3-thiazole-2-carboxylate;

(1R,3aS,3bS,10aR,10bS,11S,12aS)-1-{[(Cyanomethyl)thio]carbonyl}-7-(4-fluoro-phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 1,3-oxazole-4-carboxylate;

(1R,3aS,3bS,10aR,10bS,11S,12aS)-7-(4-Fluorophenyl)-11-hydroxy-1-{[(2-hydroxy-ethyl)thio]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl 1,3-oxazole-4-carboxylate;

(1R,3aS,3bS,10aR,10bS,11S,12aS)-1-{[(Fluoromethyl)thio]carbonyl}-7-(4-fluoro-phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 1,3-oxazole-4-carboxylate;

(1R,3aS,3bS,10aR,10bS,11S,12aS)-7-(4-Fluorophenyl)-11-hydroxy-10a,12a-dimethyl-1-{[(2-oxopropyl)thio]carbonyl}-1,2,3,3a,3b,4,5,7,10,10a,10b,11,12,12a-tetradecahydro-cyclopenta[5,6]naphtho[1,2-f]indazol-1-yl 1,3-oxazole-4-carboxylate;

(1R,3aS,3bS,10aR,10bS,11S,12aS)-1-{[(Cyanomethyl)thio]carbonyl}-7-(4-fluoro-phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 1-methyl-1H-1,2,3-triazole-4-carboxylate;

(1R,3aS,3bS,10aR,10bS,11S,12aS)-1-{[(Fluoromethyl)thio]carbonyl}-7-(4-fluoro-phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 1-methyl-1H-1,2,3-triazole-4-carboxylate;

(1R,3aS,3bS,10aR,10bS,11S,12aS)-7-(4-Fluorophenyl)-11-hydroxy-1-{[(2-hydroxy-ethyl)thio]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl 1-methyl-1H-1,2,3-triazole-4-carboxylate;

(1R,3aS,3bS,10aR,10bS,11S,12aS)-1-{[(Cyanomethyl)thio]carbonyl}-7-(4-fluoro-phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-3-carboxylate;

(1R,3aS,3bS,10aR,10bS,11S,12aS)-1-{[(Fluoromethyl)thio]carbonyl}-7-(4-fluoro-phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-3-carboxylate;

(1R,3aS,3bS,10aR,10bS,11S,12aS)-7-(4-Fluorophenyl)-11-hydroxy-1-{[(2-hydroxy-ethyl)thio]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl furan-3-carboxylate;

(1R,3aS,3bS,10aR,10bS,11S,12aS)-1-{[(Cyanomethyl)sulfanyl]carbonyl}-7-(4-fluoro-phenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 2-methylfuran-3-carboxylate;

(1R,3aS,3bS,10aR,10bS,11S,12aS)-1-{[(Fluoromethyl)thio]carbonyl}-7-(4-fluorophenyl)-11-hydroxy-10a,12a-dimethyl-1,2,3,3a,3b,4,5,7,10,10a,10b,11,12,12a-tetradecahydro-cyclopenta[5,6]naphtho[1,2-f]indazol-1-yl 2-methylfuran-3-carboxylate;

(1R,3aS,3bS,10aR,10bS,11S,12aS)-7-(4-Fluorophenyl)-11-hydroxy-1-{[(2-hydroxy-ethyl)thio]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl 2-methylfuran-3-carboxylate;

(1R,3aS,3bS,10aR,10bS,11S,12aS)-1-{[(Cyanomethyl)thio]carbonyl}-7-(4-fluorophenyl)-11-hydroxy-10a,12a-dimethyl-1,2,3,3a,3b,4,5,7,10,10a,10b,11,12,12a-tetradecahydro-cyclopenta[5,6]naphtho[1,2-f]indazol-1-yl 3-methylfuran-2-carboxylate;

(1R,3aS,3bS,10aR,10bS,11S,12aS)-1-{[(Fluoromethyl)thio]carbonyl}-7-(4-fluorophenyl)-11-hydroxy-10a,12a-dimethyl-1,2,3,3a,3b,4,5,7,10,10a,10b,11,12,12a-tetradeca-hydrocyclopenta[5,6]naphtho[1,2-f]indazol-1-yl 3-methylfuran-2-carboxylate;

(1R,3aS,3bS,10aR,10bS,11S,12aS)-7-(4-Fluorophenyl)-11-hydroxy-1-{[(2-hydroxy-ethyl)thio]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl 3-methylfuran-2-carboxylate;

(1R,3aS,3bS,10aR,10bS,11S,12aS)-1-{[(Cyanomethyl)thio]carbonyl}-7-(4-fluorophenyl)-11-hydroxy-10a,12a-dimethyl-1,2,3,3a,3b,4,5,7,10,10a,10b,11,12,12a-tetradecahydro-cyclopenta[5,6]naphtho[1,2-f]indazol-1-yl isoxazole-5-carboxylate;

(1R,3aS,3bS,10aR,10bS,11S,12aS)-1-{[(Fluoromethyl)thio]carbonyl}-7-(4-fluorophenyl)-11-hydroxy-10a,12a-dimethyl-1,2,3,3a,3b,4,5,7,10,10a,10b,11,12,12a-tetradecahydro-cyclopenta[5,6]naphtho[1,2-f]indazol-1-yl isoxazole-5-carboxylate;

(1R,3aS,3bS,10aR,10bS,11S,12aS)-7-(4-Fluorophenyl)-11-hydroxy-1-{[(2-hydroxy-ethyl)thio]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl isoxazole-5-carboxylate;

(1R,3aS,3bS,10aR,10bS,11S,12aS)-1-{[(Cyanomethyl)thio]carbonyl}-7-(4-fluorophenyl)-11-hydroxy-10a,12a-dimethyl-1,2,3,3a,3b,4,5,7,10,10a,10b,11,12,12a-tetradecahydro-cyclopenta[5,6]naphtho[1,2-f]indazol-1-yl 3-methoxypropanoate;

(1R,3aS,3bS,10aR,10bS,11S,12aS)-1-{[(Fluoromethyl)thio]carbonyl}-7-(4-fluorophenyl)-11-hydroxy-10a,12a-dimethyl-1,2,3,3a,3b,4,5,7,10,10a,10b,11,12,12a-tetradecahydro-cyclopenta[5,6]naphtho[1,2-f]indazol-1-yl 3-methoxypropanoate;

(1R,3aS,3bS,10aR,10bS,11S,12aS)-7-(4-Fluorophenyl)-11-hydroxy-10a,12a-dimethyl-1-[(methylthio)carbonyl]-1,2,3,3a,3b,4,5,7,10,10a,10b,11,12,12a-tetradecahydro-cyclopenta[5,6]naphtho[1,2-f]indazol-1-yl furan-2-carboxylate;

Cyanomethyl (1R,3aS,3bS,10aR,10bS,11S,12aS)-7-(4-fluorophenyl)-1-[(furan-2-ylcarbonyl)oxy]-11-hydroxy-10a,12a-dimethyl-1,2,3,3a,3b,4,5,7,10,10a,10b,11,12,12a-tetradecahydrocyclopenta[5,6]naphtho[1,2-f]indazole-1-carboxylate;

Methyl (1R,3aS,3bS,10aR,10bS,11S,12aS)-7-(4-fluorophenyl)-1-[(furan-2-yl-carbonyl)oxy]-11-hydroxy-10a,12a-dimethyl-1,2,3,3a,3b,4,5,7,10,10a,10b,11,12,12a-tetradecahydrocyclopenta[5,6]naphtho[1,2-f]indazole-1-carboxylate;

S-(Cyanomethyl)(1R,3aS,3bS,10aR,10bS,11S,12aS)-1-[(ethoxycarbonyl)oxy]-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazole-1-carbothioate;

S-(Cyanomethyl)(1R,3aS,3bS,10aR,10bS,11S,12aS)-7-(4-fluorophenyl)-11-hydroxy-10a,12a-dimethyl-1-{[(1-methylethoxy)carbonyl]oxy}-1,2,3,3a,3b,4,5,7,10,10a,10b,11,12,12a-tetradecahydrocyclopenta[5,6]naphtho[1,2-f]indazole-1-carbothioate;

(1R,3aS,3bS,10aR,10bS,11S,12aS)-7-(4-Fluorophenyl)-11-hydroxy-10a,12a-dimethyl-1-(methylcarbamoyl)-1,2,3,3a,3b,4,5,7,10,10a,10b,11,12,12a-tetradecahydro-cyclopenta[5,6]naphtho[1,2-f]indazol-1-yl furan-2-carboxylate;

(1R,3aS,3bS,10aR,10bS,11S,12aS)-7-(4-Fluorophenyl)-1,11-dihydroxy-N,10a,12a-trimethyl-1,2,3,3a,3b,4,5,7,10,10a,10b,11,12,12a-tetradecahydrocyclopenta[5,6]naphtho[1,2-f]indazole-1-carboxamide;

(1R,3aS,10aR,10bS,11S,12aS)-7-(3-Bromophenyl)-1-{[(fluoromethyl)thio]carbonyl}-11-hydroxy-10a,12a-dimethyl-1,2,3,3a,3b,4,5,7,10,10a,10b,11,12,12a-tetradeca-hydrocyclopenta[5,6]naphtho[1,2-f]indazol-1-yl furan-2-carboxylate;

(1R,10aR,11S,12aS)-7-(3-Ethenylphenyl)-1-{[(fluoromethyl)thio]carbonyl}-11-hydroxy-10a,12a-dimethyl-1,2,3,3a,3b,4,5,7,10,10a,10b,11,12,12a-tetradecahydro-cyclopenta[5,6]naphtho[1,2-f]indazol-1-yl furan-2-carboxylate;

(1R,3aS,3bS,10aR,10bS,11S,12aS)-1-{[(Cyanomethyl)thio]carbonyl}-7-[4-fluoro-3-(methoxymethyl)phenyl]-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-7-[4-Fluoro-3-(methoxymethyl)phenyl]-1-{[(fluoromethyl)thio]carbonyl}-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-1-{[(Cyanomethyl)thio]carbonyl}-7-[4-fluoro-3-(fluoromethyl)phenyl]-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-7-[4-Fluoro-3-(fluoromethyl)phenyl]-1-{[(fluoromethyl)thio]carbonyl}-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-1-{[(Cyanomethyl)thio]carbonyl}-7-{4-fluoro-3-[(prop-2-en-1-yloxy)methyl]phenyl}-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-7-{4-Fluoro-3-[(prop-2-en-1-yloxy)methyl]phenyl}-11-hydroxy-10a,12a-dimethyl-1-(methylcarbamoyl)-1,2,3,3a,3b,4,5,7,10,10a,10b,11,12,12a-tetradecahydrocyclopenta[5,6]naphtho[1,2-f]indazol-1-yl furan-2-carboxylate;

Cyanomethyl (1R,3aS,3bS,10aR,10bS,11 S,12aS)-7-[4-fluoro-3-(hydroxymethyl)phenyl]-1-[(furan-2-ylcarbonyl)oxy]-11-hydroxy-10a,12a-dimethyl-1,2,3,3a,3b,4,5,7,10,10a,10b,11,12,12a-tetradecahydrocyclopenta[5,6]naphtho[1,2-f]indazole-1-carboxylate;

(1R,3aS,3bS,10aR,10bS,11S,12aS)-1-{[(Cyanomethyl)thio]carbonyl}-7-[4-fluoro-3-(hydroxymethyl)phenyl]-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-7-[4-Fluoro-3-(hydroxymethyl)phenyl]-1-{[(fluoromethyl)thio]carbonyl}-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-7-(4-Fluorophenyl)-11-hydroxy-10a,12a-dimethyl-1-({[(methylsulfanyl)methyl]sulfanyl}carbonyl)-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-7-(4-Fluorophenyl)-11-hydroxy-10a,12a-dimethyl-1-{[(thiocyanatomethyl)sulfanyl]carbonyl}-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-1-{[(2,3-Dihydroxypropyl)sulfanyl]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-7-(4-Fluorophenyl)-11-hydroxy-1-{[(3-methoxypropyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-1-{[(3-Cyanopropyl)sulfanyl]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-1-({[3-(Acetyloxy)-2-oxopropyl]sulfanyl}carbonyl)-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-7-(4-fluorophenyl)-11-hydroxy-1-({[2-(methoxymethoxy)prop-2-en-1-yl]sulfanyl}carbonyl)-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-7-(4-Fluorophenyl)-11-hydroxy-10a,12a-dimethyl-1-{[(2-oxopropyl)sulfanyl]carbonyl}-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-1-{[(2-Amino-2-oxoethyl)sulfanyl]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-7-(4-fluorophenyl)-11-hydroxy-1-{[(2-hydroxyethyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-7-(4-Fluorophenyl)-11-hydroxy-1-{[(3-hydroxypropyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-7-(4-Fluorophenyl)-11-hydroxy-1-{[(methoxymethyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-1-({[(Acetyloxy)methyl]sulfanyl}carbonyl)-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-1-({[2-(Acetyloxy)ethyl]sulfanyl}carbonyl)-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl propanoate;

(1R,3aS,3bS,10aR,10bS,11S,12aS)-7-(4-Fluorophenyl)-11-hydroxy-1-{[(2-hydroxypropyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl propanoate;

(1R,3aS,3bS,10aR,10bS,11S,12aS)-1-{[(Cyanomethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl propanoate;

(1R,3aS,3bS,10aR,10bS,11S,12aS)-7-(6-Fluoropyridin-3-yl)-11-hydroxy-1-{[(methoxymethyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl propanoate;

(1R,3aS,3bS,10aR,10bS,11S,12aS)-1-{[(Fluoromethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl propanoate;

(1R,3aS,3bS,10aR,10bS,11S,12aS)-1-{[(Fluoromethyl)thio]carbonyl}-11-hydroxy-10a,12a-dimethyl-7-[3-(morpholin-4-ylcarbonyl)phenyl]-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-1-{[(Cyanomethyl)thio]carbonyl}-7-(2,4-difluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-1-{[(Cyanomethyl)thio]carbonyl}-7-(3,5-difluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-1-{[(Cyanomethyl)thio]carbonyl}-7-(3,4-difluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

Ethyl (1R,3aS,3bS,10aR,10bS,11S,12aS)-7-(4-fluorophenyl)-1,11-dihydroxy-10a,12a-dimethyl-1,2,3,3a,3b,4,5,7,10,10a,10b,11,12,12a-tetradecahydrocyclopenta[5,6]naphtho[1,2-f]indazole-1-carboxylate;

Cyanomethyl (1R,3aS,3bS,10aR,10bS,11S,12aS)-1-[(furan-2-ylcarbonyl)oxy]-11-hydroxy-10a,12a-dimethyl-7-pyridin-2-yl-1,2,3,3a,3b,4,5,7,10,10a,10b,11,12,12a-tetradecahydrocyclopenta[5,6]naphtho[1,2-f]indazole-1-carboxylate;

(1R,3aS,3bS,10aR,10bS,11S,12aS)-1-{[(Cyanomethyl)sulfanyl]carbonyl}-11-hydroxy-10a,12a-dimethyl-7-[4-(methylsulfonyl)phenyl]-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-7-(3,5-Difluorophenyl)-1-{[(dimethylcarbamoyl)sulfanyl]carbonyl}-11-hydroxy-10a,12a-dimethyl-1,2,3,3a,3b,4,5,7,10,10a, 10b,11,12,12a-tetradecahydrocyclopenta[5,6]naphtho[1,2-f]indazol-1-yl furan-2-carboxylate;

(1R,3aS,3bS,10aR,10bS,11S,12aS)-1-{[(Fluoromethyl)sulfanyl]carbonyl}-11-hydroxy-7-[3-(methoxycarbonyl)phenyl]-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-1-{[(Cyanomethyl)sulfanyl]carbonyl}-7-(4-fluorophenyl)-11-hydroxy-10a,12a-dimethyl-1,2,3,3a,3b,4,5,7,10,10a, 10b,11,12,12a-tetradecahydrocyclopenta[5,6]naphtho[1,2-f]indazol-1-yl acetate;

(1R,3aS,3bS,10aR,10bS,11S,12aS)-1-{[(Fluoromethyl)sulfanyl]carbonyl}-7-(4-fluorophenyl)-11-hydroxy-10a,12a-dimethyl-1,2,3,3a,3b,4,5,7,10,10a, 10b,11,12,12a-tetradecahydrocyclopenta[5,6]naphtho[1,2-f]indazol-1-yl acetate;

(1R,3aS,3bS,10aR,10bS,11S,12aS)-1-{[(Cyanomethyl)sulfanyl]carbonyl}-7-(4-fluorophenyl)-11-hydroxy-10a,12a-dimethyl-1,2,3,3a,3b,4,5,7,10,10a, 10b,11,12,12a-tetradecahydrocyclopenta[5,6]naphtho[1,2-f]indazol-1-yl 2-methylpropanoate;

(1R,3aS,3bS,10aR,10bS,11S,12aS)-1-{[(Cyanomethyl)sulfanyl]carbonyl}-7-(4-fluorophenyl)-11-hydroxy-10a,12a-dimethyl-1,2,3,3a,3b,4,5,7,10,10a, 10b,11,12,12a-tetradecahydrocyclopenta[5,6]naphtho[1,2-f]indazol-1-yl 3-methylbutanoate;

(1R,3aS,3bS,10aR,10bS,11S,12aS)-1-{[(Cyanomethyl)sulfanyl]carbonyl}-7-(4-fluorophenyl)-11-hydroxy-10a,12a-dimethyl-1,2,3,3a,3b,4,5,7,10,10a, 10b,11,12,12a-tetradecahydrocyclopenta[5,6]naphtho[1,2-f]indazol-1-yl cyclobutanecarboxylate;

(1R,3aS,3bS,10aR,10bS,11S,12aS)-1-{[(Cyanomethyl)sulfanyl]carbonyl}-7-(4-fluorophenyl)-11-hydroxy-10a,12a-dimethyl-1,2,3,3a,3b,4,5,7,10,10a, 10b,11,12,12a-tetradecahydrocyclopenta[5,6]naphtho[1,2-f]indazol-1-yl cyclopentylacetate;

(1R,3aS,3bS,10aR,10bS,11S,12aS)-1-{[(Cyanomethyl)sulfanyl]carbonyl}-7-(4-fluorophenyl)-11-hydroxy-10a,12a-dimethyl-1,2,3,3a,3b,4,5,7,10,10a, 10b,11,12,12a-tetradecahydrocyclopenta[5,6]naphtho[1,2-f]indazol-1-yl thiophene-2-carboxylate;

(1R,3aS,3bS,10aR,10bS,11S,12aS)-1-{[(Cyanomethyl)sulfanyl]carbonyl}-7-(4-fluorophenyl)-11-hydroxy-10a,12a-dimethyl-1,2,3,3a,3b,4,5,7,10,10a, 10b,11,12,12a-tetradecahydrocyclopenta[5,6]naphtho[1,2-f]indazol-1-yl 5-methylisoxazole-3-carboxylate;

(Methylsulfanyl)methyl (1R,3aS,3bS,10aR,10bS,11S,12aS)-7-(4-fluorophenyl)-1,11-dihydroxy-10a,12a-dimethyl-1,2,3,3a,3b,4,5,7,10,10a, 10b,11,12,12a-tetradecahydrocyclopenta[5,6]naphtho[1,2-f]indazole-1-carboxylate;

(1R,3aS,3bS,10aR,10bS,11S,12aS)-7-(4-Fluorophenyl)-11-hydroxy-10a,12a-dimethyl-1-({[(methylsulfanyl)methyl]sulfanyl}carbonyl)-1,2,3,3a,3b,4,5,7,10,10a, 10b,11,12,12a-tetradecahydrocyclopenta[5,6]naphtho[1,2-f]indazol-1-yl acetate;

(Methylsulfanyl)methyl (1R,3aS,3bS,10aR,10bS,11S,12aS)-1-(acetyloxy)-7-(4-fluorophenyl)-11-hydroxy-10a,12a-dimethyl-1,2,3,3a,3b,4,5,7,10,10a, 10b,11,12,12a-tetradecahydrocyclopenta[5,6]naphtho[1,2-f]indazole-1-carboxylate;

(Methylsulfanyl)methyl (1R,3aS,3bS,10aR,10bS,11S,12aS)-7-(4-fluorophenyl)-11-hydroxy-10a,12a-dimethyl-1-[(methylsulfanyl)methoxy]-1,2,3,3a,3b,4,5,7,10,10a,10b,11,12,12a-tetradecahydrocyclopenta[5,6]naphtho[1,2-f]indazole-1-carboxylate;

2-(Ethylsulfanyl)-2-oxoethyl (1R,3aS,3bS,10aR,10bS,11S,12aS)-1-(acetyloxy)-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazole-1-carboxylate;

S-(Fluoromethyl)(1R,3aS,3bS,10aR,10bS,11S,12aS)-7-(4-fluorophenyl)-11-hydroxy-10a,12a-dimethyl-1-[(methylsulfanyl)methoxy]1,2,3,3a,3b,4,5,7,10,10a,10b,11,12,12a-tetradecahydrocyclopenta[5,6]naphtho[1,2-f]indazole-1-carbothioate;

(1R,3aS,3bS,10aR,10bS,11S,12aS)-1-{[(Cyanomethyl)sulfanyl]carbonyl}-7-(4-fluorophenyl)-11-hydroxy-10a,12a-dimethyl-1,2,3,3a,3b,4,5,7,10,10a, 10b,11,12,12a-tetradecahydrocyclopenta[5,6]naphtho[1,2-f]indazol-1-yl tetrahydro-2H-pyran-4-carboxylate;

(1R,3aS,3bS,10aR,10bS,11S,12aS)-7-(4-Fluorophenyl)-11-hydroxy-1-{[(2-hydroxyethyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl tetrahydro-2H-pyran-4-carboxylate;

(1R,3aS,3bS,10aR,10bS,11S,12aS)-1-{[(Cyanomethyl)sulfanyl]carbonyl}-7-(4-fluorophenyl)-11-hydroxy-10a,12a-dimethyl-1,2,3,3a,3b,4,5,7,10,10a, 10b,11,12,12a-tetradecahydrocyclopenta[5,6]naphtho[1,2-f]indazol-1-yl (2R)-tetrahydrofuran-2-carboxylate;

(1R,3aS,3bS,10aR,10bS,11S,12aS)-7-(4-Fluorophenyl)-11-hydroxy-1-{[(2-hydroxyethyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl tetrahydrofuran-2-carboxylate;

(1R,3aS,3bS,10aR,10bS,11S,12aS)-1-{[(Cyanomethyl)sulfanyl]carbonyl}-7-(4-fluorophenyl)-11-hydroxy-10a,12a-dimethyl-1,2,3,3a,3b,4,5,7,10,10a, 10b,11,12,12a-tetradecahydrocyclopenta[5,6]naphtho[1,2-f]indazol-1-yl 2-methyltetrahydrofuran-2-carboxylate;

(1R,3aS,3bS,10aR,10bS,11S,12aS)-1-{[(Cyanomethyl)sulfanyl]carbonyl}-7-(4-fluorophenyl)-11-hydroxy-10a,12a-dimethyl-1,2,3,3a,3b,4,5,7,10,10a, 10b,11,12,12a-tetradecahydrocyclopenta[5,6]naphtho[1,2-f]indazol-1-yl 1-methoxycyclopropanecarboxylate;

(1R,3aS,3bS,10aR,10bS,11S,12aS)-1-{[(Cyanomethyl)sulfanyl]carbonyl}-7-(4-fluorophenyl)-11-hydroxy-10a,12a-dimethyl 1,2,3,3a,3b,4,5,7,10,10a, 10b,11,12,12a-tetradecahydrocyclopenta[5,6]naphtho[1,2-f]indazol-1-yl tetrahydro-2H-pyran-2-carboxylate;

(1R,3aS,3bS,10aR,10bS,11S,12aS)-1-{[(Fluoromethyl)sulfanyl]carbonyl}-7-(4-fluorophenyl)-11-hydroxy-10a,12a-dimethyl-1,2,3,3a,3b,4,5,7,10,10a, 10b,11,12,12a-tetradecahydrocyclopenta[5,6]naphtho[1,2-f]indazol-1-yl (2R)-tetrahydrofuran-2-carboxylate;

(1R,3aS,3bS,10aR,10bS,11S,12aS)-1-{[(Cyanomethyl)sulfanyl]carbonyl}-7-(4-fluorophenyl)-11-hydroxy-10a,12a-dimethyl-1,2,3,3a,3b,4,5,7,10,10a, 10b,11,12,12a-tetradecahydrocyclopenta[5,6]naphtho[1,2-f]indazol-1-yl tetrahydro-2H-pyran-3-carboxylate;

(1R,3aS,3bS,10aR,10bS,11S,12aS)-7-[4-Fluoro-3-(hydroxymethyl)phenyl]-1-{[(fluoromethyl)thio]carbonyl}-11-hydroxy-10a,12a-dimethyl-1,2,3,3a,3b, 4,5,7,10,10a,10b,11,12,12a-tetradecahydrocyclopenta[5,6]naphtho[1,2-f]indazol-1-yl cyclopropanecarboxylate;

(1R,3aS,3bS,10aR,10bS,11S,12aS)-1-{[(Cyanomethyl)thio]carbonyl}-7-[4-fluoro-3-(hydroxymethyl)phenyl]-11-hydroxy-10a,12a-dimethyl-1,2,3,3a,3b,4,5,7,10,10a, 10b,11,12,12a-tetradecahydrocyclopenta[5,6]naphtho[1,2-f]indazol-1-yl methoxyacetate;

(1R,2R,3aS,3bS,10aR,10bS,11S,12aS)-1-{[(Cyanomethyl)thio]carbonyl}-7-(4-fluorophenyl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-1-{[(Cyanomethyl)sulfanyl]carbonyl}-7-[4-fluoro-3-(hydroxymethyl)phenyl]-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl cyclopropanecarboxylate;

Cyanomethyl (1R,3aS,3bS,10aR,10bS,11S,12aS)-1-[(cyclopropylcarbonyl)oxy]-7-[4-fluoro-3-(hydroxymethyl)phenyl]-11-hydroxy-10a,12a-dimethyl-1,2,3,3a,3b,4,5,7,10,10a,10b,11,12,12a-tetradecahydrocyclopenta[5,6]naphtho[1,2-f]indazole-1-carboxylate;

(1R,3aS,3bS,10aR,10bS,11S,12aS)-1-{[(Cyanomethyl)sulfanyl]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 1-cyanocyclopropane carboxylate;

(1R,3aS,3bS,10aR,10bS,11S,12aS)-1-{[(Cyanomethyl)sulfanyl]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl tetrahydrofuran-3-carboxylate;

(1R,3aS,3bS,10aR,10bS,11S,12aS)-1-{[(Fluoromethyl)sulfanyl]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl tetrahydrofuran-3-carboxylate;

(1R,3aS,3bS,10aR,10bS,11S,12aS)-1-{[(Fluoromethyl)sulfanyl]carbonyl}-11-hydroxy-10a,12a-dimethyl-7-pyridin-2-yl-1,2,3,3a,3b,4,5,7,10,10a,10b,11,12,12a-tetradecahydrocyclopenta[5,6]naphtho[1,2-f]indazol-1-yl cyclopropane carboxylate;

(1R,3aS,3bS,10aR,10bS,11S,12aS)-7-(5-Chloropyridin-2-yl)-1-{[(fluoromethyl)sulfanyl]carbonyl}-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl cyclopropane carboxylate;

Cyanomethyl (1R,3aS,3bS,10aR,10bS,11S,12aS)-1-[(cyclopropylcarbonyl)oxy]-11-hydroxy-10a,12a-dimethyl-7-pyridin-2-yl-1,2,3,3a,3b,4,5,7,10,10a,10b,11,12,12a-tetradecahydrocyclopenta[5,6]naphtho[1,2-f]indazole-1-carboxylate;

(1R,3aS,3bS,10aR,10bS,11S,12aS)-1-{[(Cyanomethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl cyclopropanecarboxylate;

(1R,3aS,3bS,10aR,10bS,11S,12aS)-7-(6-Fluoropyridin-3-yl)-11-hydroxy-10a,12a-dimethyl-1-[(methylsulfanyl)carbonyl]-1,2,3,3a,3b,4,5,7,10,10a,10b,11,12,12a-tetradecahydrocyclopenta[5,6]naphtho[1,2-f]indazol-1-yl cyclopropanecarboxylate;

(1R,3aS,3bS,10aR,10bS,11S,12aS)-7-(6-Fluoropyridin-3-yl)-11-hydroxy-1-{[(methoxymethyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl cyclopropanecarboxylate;

(1R,3aS,3bS,10aR,10bS,11S,12aS)-7-(6-Fluoropyridin-3-yl)-11-hydroxy-1-{[(2-hydroxyethyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl cyclopropanecarboxylate;

(1R,3aS,3bS,10aR,10bS,11S,12aS)-1-{[(Cyanomethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl methoxyacetate;

(1R,3aS,3bS,10aR,10bS,11S,12aS)-7-(6-Fluoropyridin-3-yl)-11-hydroxy-10a,12a-dimethyl-1-[(methylsulfanyl)carbonyl]-1,2,3,3a,3b,4,5,7,10,10a,10b,11,12,12a-tetradecahydrocyclopenta[5,6]naphtho[1,2-f]indazol-1-yl methoxyacetate;

(1R,3aS,3bS,10aR,10bS,11S,12aS)-7-(6-Fluoropyridin-3-yl)-11-hydroxy-1-{[(methoxymethyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl methoxyacetate;

(1R,3 aS,3bS,10aR,10bS,11S,12aS)-7-(6-Fluoropyridin-3-yl)-11-hydroxy-1-{[(2-hydroxyethyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl methoxyacetate;

(1R,3aS,3bS,10aR,10bS,11S,12aS)-1-{[(Cyanomethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 1,3-oxazole-4-carboxylate;

(1R,3aS,3bS,10aR,10bS,11S,12aS)-7-(6-Fluoropyridin-3-yl)-11-hydroxy-10a,12a-dimethyl-1-[(methylsulfanyl)carbonyl]-1,2,3,3a,3b,4,5,7,10,10a,10b,11,12,12a-tetradecahydrocyclopenta[5,6]naphtho[1,2-f]indazol-1-yl 1,3-oxazole-4-carboxylate;

(1R,3aS,3bS,10aR,10bS,11S,12aS)-7-(6-Fluoropyridin-3-yl)-11-hydroxy-1-{[(2-hydroxyethyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl 1,3-oxazole-4-carboxylate;

(1R,3aS,3bS,10aR,10bS,11S,12aS)-7-(6-Fluoropyridin-3-yl)-11-hydroxy-1-{[(methoxymethyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl 1,3-oxazole-4-carboxylate;

S-(Cyanomethyl)(1R,3aS,3bS,10aR,10bS,11S,12aS)-7-(6-fluoropyridin-3-yl)-1,11-dihydroxy-10a,12a-dimethyl-1,2,3,3a,3b,4,5,7,10,10a,10b,11,12,12a-tetradecahydrocyclopenta[5,6]naphtho[1,2-f]indazole-1-carbothioate;

S-Methyl (1R,3aS,3bS,10aR,10bS,11S,12aS)-7-(6-fluoropyridin-3-yl)-1,11-dihydroxy-10a,12a-dimethyl-1,2,3,3a,3b,4,5,7,10,10a,10b,11,12,12a-tetradecahydrocyclopenta[5,6]naphtho[1,2-f]indazole-1-carbothioate;

(1R,3aS,3bS,10aR,10bS,11S,12aS)-1-{[(Cyanomethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-7-(6-Fluoropyridin-3-yl)-11-hydroxy-10a,12a-dimethyl-1-[(methylsulfanyl)carbonyl]-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-7-(6-Fluoropyridin-3-yl)-11-hydroxy-1-{[(2-hydroxyethyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aR,10bS,11S,12aS)-1-{[(Fluoromethyl)sulfanyl]carbonyl}-7-(6-fluoropyridin-3-yl)-11-hydroxy-10a,12a-dimethyl-1,2,3,3a,3b,4,5,7,10,10a,10b, 11,12,12a-tetradecahydrocyclopenta[5,6]naphtho[1,2-f]indazol-1-yl furan-2-carboxylate;

(1R,3aS,3bS,10aR,10bS,11S,12aS)-1-{[(Fluoromethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl methoxyacetate;

(1R,3aS,3bS,10aR,10bS,11S,12aS)-1-{[(Fluoromethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl acetate;

(1R,3aS,3bS,10aR,10bS,11S,12aS)-7-(6-Fluoropyridin-3-yl)-11-hydroxy-10a,12a-dimethyl-1-[(methylsulfanyl)carbonyl]-1,2,3,3a,3b,4,5,7,10,10a,10b,11,12,12a-tetradecahydrocyclopenta[5,6]naphtho[1,2-f]indazol-1-yl acetate;

(1R,3aS,3bS,10aR,10bS,11S,12aS)-1-{[(Cyanomethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl acetate;

(1R,3aS,3bS,10aR,10bS,11S,12aS)-1-{[(Cyanomethyl)sulfanyl]carbonyl}-7-(3-{[(cyanomethyl)sulfanyl]carbonyl}-4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl propanoate;

(1R,3aS,3bS,10aR,10bS,11S,12 aS)-7-{4-Fluoro-3-[(methylsulfanyl)carbonyl]phenyl}-11-hydroxy-10a,12a-dimethyl-1-[(methylsulfanyl)carbonyl]-1,2,3,3a,3b,4,5,7,10,10a,10b,11,12,12a-tetradecahydrocyclopenta[5,6]naphtho[1,2-f]indazol-1-yl propanoate;

(1R,3aS,3bS,10aR,10bS,11S,12aS)-1-{[(Cyanomethyl)thio]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 1-methyl-1H-pyrrole-2-carboxylate;

(1R,3aS,3bS,10aR,10bS,11S,12aS)-1-{[(Fluoromethyl)thio]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 1-methyl-1H-pyrrole-2-carboxylate;

(1R,3aS,3bS,10aR,10bS,11S,12aS)-7-(4-Fluorophenyl)-11-hydroxy-1-{[(2-hydroxyethyl)thio]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl 1-methyl-1H-pyrrole-2-carboxylate;

(1R,3aS,3bS,10aR,10bS,11S,12aS)-1-{[(Fluoromethyl)thio]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl cyclopropanecarboxylate;

S-(Fluoromethyl)(1R,3 aS,3bS,10aR,10bS,11S,12aS)-7-(6-fluoropyridin-3-yl)-1,11-dihydroxy-10a,12a-dimethyl-1,2,3,3a,3b,4,5,7,10,10a,10b,11,12,12a-tetradecahydrocyclopenta[5,6]naphtho[1,2-f]indazole-1-carbothioate;

(1R,3aS,3bS,10aR,10bS,11S,12aS)-1-{[(Fluoromethyl)thio]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 1,3-oxazole-4-carboxylate;

(1R,3aS,3bS,10aR,10bS,11S,12aS)-7-(6-Fluoropyridin-3-yl)-11-hydroxy-1-{[(methoxymethyl)thio]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl acetate; (1R,3aS,3bS,10aR,10bS,11S,12aS)-7-(6-Fluoropyridin-3-yl)-11-hydroxy-1-{[(2-hydroxyethyl)thio]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl acetate;

Cyanomethyl (1R,3aS,3bS,10aR,10bS,11S,12aS)-1-[(cyclopropylcarbonyl)oxy]-11-hydroxy-10a,12a-dimethyl-7-(2-methylpyridin-4-yl)-1,2,3,3a,3b,4,5,7,10,10a,10b,11,12,12a-tetradecahydrocyclopenta[5,6]naphtho[1,2-f]indazole-1-carboxylate;

Cyanomethyl (1R,3aS,3bS,10aR,10bS,11S,12aS)-1-[(cyclopropylcarbonyl)oxy]-11-hydroxy-10a,12a-dimethyl-7-pyridin-2-yl-1,2,3,3a,3b,4,5,7,10,10a,10b,11,12,12a-tetradecahydrocyclopenta[5,6]naphtho[1,2-f]indazole-1-carboxylate;

Cyanomethyl (1R,3aS,3bS,10aR,10bS,11S,12aS)-1-[(cyclopropylcarbonyl)oxy]-11-hydroxy-10a,12a-dimethyl-7-pyridazin-4-yl-1,2,3,3a,3b,4,5,7,10,10a,10b,11,12,12a-tetradecahydrocyclopenta[5,6]naphtho[1,2-f]indazole-1-carboxylate;

(1R,3aS,3bS,10aR,10bS,11S,12aS)-1-{[(Cyanomethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl (2R)-tetrahydrofuran-2-carboxylate;

(1R,3aS,3bS,10aR,10bS,11S,12aS)-7-(6-Fluoropyridin-3-yl)-11-hydroxy-1-{[(2-hydroxyethyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl (2R)-tetrahydrofuran-2-carboxylate;

(1R,3aS,3bS,10aR,10bS,11S,12aS)-1-{[(Fluoromethyl)sulfanyl]carbonyl}-7-(6-fluoropyridin-3-yl)-11-hydroxy-10a,12a-dimethyl-1,2,3,3a,3b,4,5,7,10,10a, 10b,11,12,12a-tetradecahydrocyclopenta[5,6]naphtho[1,2-f]indazol-1-yl (2R)-tetrahydrofuran-2-carboxylate;

(1R,3aS,3bS,10aR,10bS,11S,12aS)-7-(6-Fluoropyridin-3-yl)-11-hydroxy-10a,12a-dimethyl-1-[(methylsulfanyl)carbonyl]-1,2,3,3a,3b,4,5,7,10,10a,10b,11,12,12a-tetradecahydrocyclopenta[5,6]naphtho[1,2-f]indazol-1-yl (2R)-tetrahydrofuran-2-carboxylate;

(1R,3aS,3bS,10aR,10bS,11S,12aS)-1-{[(Cyanomethyl)sulfanyl]carbonyl}-11-hydroxy-10a,12a-dimethyl-7-pyrazin-2-yl-1,2,3,3a,3b,4,5,7,10,10a,10b,11,12,12a-tetradecahydrocyclopenta[5,6]naphtho[1,2-f]indazol-1-yl cyclopropanecarboxylate;

(1R,3aS,3bS,10aR,10bS,11S,12aS)-11-Hydroxy-1-{[(2-hydroxyethyl)sulfanyl]carbonyl}-10a,12a-dimethyl-7-pyrazin-2-yl-1,2,3,3a,3b,4,5,7,10,10a,10b,11,12,12a-tetradecahydrocyclopenta[5,6]naphtho[1,2-f]indazol-1-yl cyclopropane carboxylate;

(1R,3aS,3bS,10aR,10bS,11S,12aS)-1-{[(Cyanomethyl)sulfanyl]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 1-methyl-1H-imidazole-4-carboxylate;

(1R,3aS,3bS,10aR,10bS,11S,12aS)-1-{[(Cyanomethyl)sulfanyl]carbonyl}-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 1-methyl-1H-imidazole-2-carboxylate;

(1R,3aS,3bS,10aS,10bR,11S,12aS)-1-{[(Cyanomethyl)sulfanyl]carbonyl}-10b-fluoro-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aS,10bR,11S,12aS)-1-{[(Fluoromethyl)sulfanyl]carbonyl}-10b-fluoro-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aS,10bR,11S,12aS)-1-{[(Cyanomethyl)sulfanyl]carbonyl}-10b-fluoro-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl cyclopropanecarboxylate;

(1R,3aS,3bS,10aS,10bR,11S,12aS)-1-{[(Fluoromethyl)sulfanyl]carbonyl}-10b-fluoro-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl cyclopropanecarboxylate;

(1R,3aS,3bS,10aS,10bR,11S,12aS)-1-{[(Cyanomethyl)sulfanyl]carbonyl}-10b-fluoro-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl methoxyacetate;

(1R,3aS,3bS,10aS,10bR,11S,12aS)-1-{[(Fluoromethyl)sulfanyl]carbonyl}-10b-fluoro-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl methoxyacetate;

(1R,3aS,3bS,10aS,10bR,11S,12aS)-1-{[(Cyanomethyl)sulfanyl]carbonyl}-10b-fluoro-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl propanoate;

(1R,3aS,3bS,10aS,10bR,11S,12aS)-1-{[(Fluoromethyl)sulfanyl]carbonyl}-10b-fluoro-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl propanoate;

(1R,3aS,3bS,10aS,10bR,11S,12aS)-1-{[(Cyanomethyl)sulfanyl]carbonyl}-10b-fluoro-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 1,3-oxazole-4-carboxylate;

(1R,3aS,3bS,10aS,10bR,11S,12aS)-1-{[(Fluoromethyl)sulfanyl]carbonyl}-10b-fluoro-7-(4-fluorophenyl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 1,3-oxazole-4-carboxylate;

(1R,3aS,3bS,10aS,10bR,11S,12aS)-1-{[(Cyanomethyl)sulfanyl]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl propanoate;

(1R,3aS,3bS,10aS,10bR,11S,12aS)-1-{[(Fluoromethyl)sulfanyl]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl propanoate;

(1R,3aS,3bS,10aS,10bR,11S,12aS)-1-{[(Cyanomethyl)sulfanyl]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl methoxyacetate;

(1R,3aS,3bS,10aS,10bR,11S,12aS)-1-{[(Fluoromethyl)sulfanyl]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl methoxyacetate;

(1R,3aS,3bS,10aS,10bR,11S,12aS)-1-{[(Cyanomethyl)sulfanyl]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl cyclopropanecarboxylate;

(1R,3aS,3bS,10aS,10bR,11S,12aS)-1-{[(Fluoromethyl)sulfanyl]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl cyclopropanecarboxylate;

(1R,3aS,3bS,10aS,10bR,11S,12aS)-1-{[(Cyanomethyl)sulfanyl]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 1,3-oxazole-4-carboxylate;

(1R,3aS,3bS,10aS,10bR,11S,12aS)-1-{[(Fluoromethyl)sulfanyl]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl 1,3-oxazole-4-carboxylate;

(1R,3aS,3bS,10aS,10bR,11S,12aS)-1-{[(Cyanomethyl)sulfanyl]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,10aS,10bR,11S,12aS)-1-{[(Fluoromethyl)sulfanyl]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl furan-2-carboxylate;

(1R,3aS,3bS,5S,10aR,10bS,11S,12aS)-1-{[(Cyanomethyl)sulfanyl]carbonyl}-7-(4-fluorophenyl)-11-hydroxy-5,10a,12a-trimethyl-1,2,3,3a,3b,4,5,7,10,10a,10b,11,12,12a-tetradecahydrocyclopenta[5,6]naphtho[1,2-f]indazol-1-yl propanoate;

(1R,3aS,3bS,5S,10aR,10bS,11S,12aS)-1-{[(Fluoromethyl)sulfanyl]carbonyl}-7-(4-fluorophenyl)-11-hydroxy-5,10a,12a-trimethyl-1,2,3,3a,3b,4,5,7,10,10a,10b,11,12,12a-tetradecahydrocyclopenta[5,6]naphtho[1,2-f]indazol-1-yl propanoate;

(1R,3aS,3bS,5S,10aR,10bS,11S,12aS)-1-{[(Cyanomethyl)sulfanyl]carbonyl}-7-(4-fluorophenyl)-11-hydroxy-5,10a,12a-trimethyl-1,2,3,3a,3b,4,5,7,10,10a,10b,11,12,12a-tetradecahydrocyclopenta[5,6]naphtho[1,2-f]indazol-1-yl methoxyacetate;

(1R,3aS,3bS,5S,10aR,10bS,11S,12aS)-1-{[(Fluoromethyl)sulfanyl]carbonyl}-7-(4-fluorophenyl)-11-hydroxy-5,10a,12a-trimethyl-1,2,3,3a,3b,4,5,7,10,10a,10b,11,12,12a-tetradecahydrocyclopenta[5,6]naphtho[1,2-f]indazol-1-yl methoxyacetate;

(1R,3aS,3bS,5S,10aR,10bS,11S,12aS)-1-{[(Cyanomethyl)sulfanyl]carbonyl}-7-(4-fluorophenyl)-11-hydroxy-5,10a,12a-trimethyl-1,2,3,3a,3b,4,5,7,10,10a,10b,11,12,12a-tetradecahydrocyclopenta[5,6]naphtho[1,2-f]indazol-1-yl cyclopropanecarboxylate;

(1R,3aS,3bS,5S,10aR,10bS,11S,12aS)-1-[(Fluoromethyl)sulfanyl]carbonyl-7-(4-fluorophenyl)-11-hydroxy-5,10a,12a-trimethyl-1,2,3,3a,3b,4,5,7,10,10a,10b,11,12,12a-tetradecahydrocyclopenta[5,6]naphtho[1,2-f]indazol-1-yl cyclopropanecarboxylate;

(1R,3aS,3bS,5S,10aR,10bS,11S,12aS)-1-{[(Cyanomethyl)sulfanyl]carbonyl}-7-(4-fluorophenyl)-11-hydroxy-5,10a,12a-trimethyl-1,2,3,3a,3b,4,5,7,10,10a,10b,11,12,12a-tetradecahydrocyclopenta[5,6]naphtho[1,2-f]indazol-1-yl furan-2-carboxylate;

or
(1R,3aS,3bS,5S,10aR,10bS,11S,12aS)-1-{[(Fluoromethyl)sulfanyl]carbonyl}-7-(4-fluorophenyl)-11-hydroxy-5,10a,12a-trimethyl-1,2,3,3a,3b,4,5,7,10,10a,10b,11,12,12a-tetradecahydrocyclopenta[5,6]naphtho[1,2-f]indazol-1-yl furan-2-carboxylate;
or a pharmaceutically acceptable salt thereof.

13. A process for the preparation of a compound of formula (I) or a pharmaceutically acceptable salt thereof as defined in claim 1 which comprises reacting a compound of formula (II)

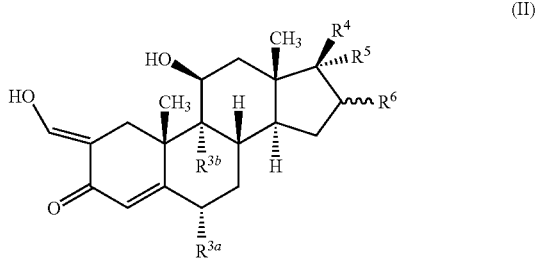

(II)

wherein $R^{3a}$, $R^{3b}$, $R^4$, $R^5$ and $R^6$ are as defined in formula (I), with a compound of formula (III) or an acid addition salt thereof

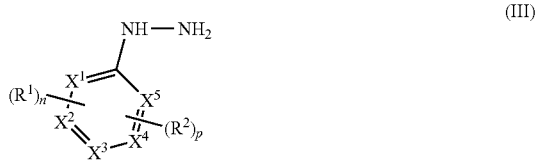

(III)

wherein n, p, $R^1$, $R^2$, $X^1$, $X^2$, $X^3$, $X^4$ and $X^5$ are as defined in formula (I), and optionally thereafter carrying out one or more of the following procedures:

converting a compound of formula (I) into another compound of formula (I)

removing any protecting groups forming a pharmaceutically acceptable salt.

14. A pharmaceutical composition comprising a compound of formula (I) as claimed in any one of claims 1, 11 and 12 or a pharmaceutically acceptable salt thereof in association with a pharmaceutically acceptable adjuvant, diluent or carrier.

15. A method of treating asthma, chronic obstructive pulmonary disease or allergic rhinitis, said method comprising administering to a patient in need thereof a therapeutically effective amount for treatment of asthma, chronic obstructive pulmonary disease or allergic rhinitis of a compound of formula (I) as claimed in any one of claims 1, 11 and 12 or a pharmaceutically acceptable salt thereof.

16. A compound according to claim 1, wherein one of $X^1$, $X^2$, $X^3$, $X^4$, and $X^5$ represents a nitrogen atom and the others represent CH.

17. A compound according to claim 1, wherein $R^{3a}$ represents a hydrogen atom and $R^{3b}$ represents a flourine atom.

18. A compound according to claim 1, wherein $R^5$ represents —O-C(O)-$R^{10}$.

19. A compound according to claim 1, wherein $R^{10}$ represents either $C_1$-$C_4$ alkyl optionally substituted by $C_1$-$C_2$ alkoxy, or a cyclopropyl or furanyl ring.

* * * * *